United States Patent
Beattie et al.

(10) Patent No.: US 9,763,957 B2
(45) Date of Patent: Sep. 19, 2017

(54) AUTOTAXIN INHIBITORS

(71) Applicant: Novartis AG, Basel (CH)

(72) Inventors: David Beattie, Horsham (GB); Urs Baettig, Reinach (CH); Darren Mark Legrand, Horsham (GB); Andrew Stuart Lister, Broadbridge Heath (GB); Jeffrey McKenna, Carlisle, MA (US); David William Pearce, Horsham (GB); David Andrew Sandham, Horsham (GB); Oliver Ross Steward, Horsham (GB); Christopher Thomson, Belmont, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/906,161

(22) PCT Filed: Jul. 16, 2014

(86) PCT No.: PCT/IB2014/063143
§ 371 (c)(1),
(2) Date: Jan. 19, 2016

(87) PCT Pub. No.: WO2015/008230
PCT Pub. Date: Jan. 22, 2015

(65) Prior Publication Data
US 2016/0184318 A1 Jun. 30, 2016

(30) Foreign Application Priority Data

Jul. 18, 2013 (EP) .................................. 13177061

(51) Int. Cl.
| | | |
|---|---|---|
| *A61K 31/445* | (2006.01) | |
| *A61K 31/551* | (2006.01) | |
| *C07D 403/12* | (2006.01) | |
| *C07D 401/14* | (2006.01) | |
| *C07D 413/14* | (2006.01) | |
| *A61K 31/41* | (2006.01) | |
| *A61K 31/4245* | (2006.01) | |
| *A61K 31/427* | (2006.01) | |
| *A61K 31/5377* | (2006.01) | |
| *A61K 31/5513* | (2006.01) | |
| *C07D 401/10* | (2006.01) | |
| *C07D 401/12* | (2006.01) | |
| *C07D 403/10* | (2006.01) | |
| *C07D 403/14* | (2006.01) | |

(Continued)

(52) U.S. Cl.
CPC ............ *A61K 31/551* (2013.01); *A61K 31/41* (2013.01); *A61K 31/427* (2013.01); *A61K 31/4245* (2013.01); *A61K 31/439* (2013.01); *A61K 31/445* (2013.01); *A61K 31/45* (2013.01); *A61K 31/454* (2013.01); *A61K 31/4545* (2013.01); *A61K 31/496* (2013.01); *A61K 31/504* (2013.01); *A61K 31/506* (2013.01); *A61K 31/5377* (2013.01); *A61K 31/5513* (2013.01); *A61K 45/06* (2013.01); *C07D 257/04* (2013.01); *C07D 401/10* (2013.01); *C07D 401/12* (2013.01); *C07D 401/14* (2013.01); *C07D 403/10* (2013.01); *C07D 403/12* (2013.01); *C07D 403/14* (2013.01); *C07D 405/12* (2013.01); *C07D 407/12* (2013.01); *C07D 413/10* (2013.01); *C07D 413/12* (2013.01); *C07D 413/14* (2013.01); *C07D 417/10* (2013.01); *C07D 417/14* (2013.01); *C07D 471/08* (2013.01)

(58) Field of Classification Search
USPC .................................... 514/317; 546/268.1
See application file for complete search history.

(56) References Cited

U.S. PATENT DOCUMENTS

| | | | | |
|---|---|---|---|---|
| 7,645,760 B2 * | 1/2010 | Bollbuck | ............. | C07D 207/14 514/255.03 |
| 7,799,782 B2 * | 9/2010 | Munson | ............... | C07D 231/56 514/234.5 |

(Continued)

FOREIGN PATENT DOCUMENTS

| | | |
|---|---|---|
| EP | 1604981 A1 | 12/2005 |
| EP | 1760071 A1 | 3/2007 |

(Continued)

OTHER PUBLICATIONS

International Search Report and Written Opinion for International Application No. PCT/IB2014/063143, mailed Nov. 7, 2014, 11 pages.

(Continued)

*Primary Examiner* — Rei-Tsang Shiao
(74) *Attorney, Agent, or Firm* — Shawn D. Britt

(57) ABSTRACT

The present invention relates to novel compounds that are autotaxin inhibitors, processes for their preparation, pharmaceutical compositions and medicaments containing them and to their use in diseases and disorders mediated by autotaxin.

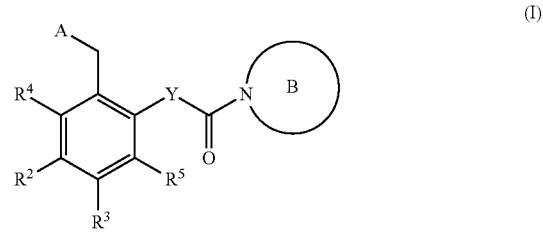

7 Claims, No Drawings

(51) Int. Cl.

| | | |
|---|---|---|
| C07D 407/12 | (2006.01) | |
| C07D 413/10 | (2006.01) | |
| C07D 413/12 | (2006.01) | |
| C07D 417/10 | (2006.01) | |
| C07D 417/14 | (2006.01) | |
| C07D 257/04 | (2006.01) | |
| A61K 45/06 | (2006.01) | |
| A61K 31/45 | (2006.01) | |
| A61K 31/496 | (2006.01) | |
| A61K 31/504 | (2006.01) | |
| A61K 31/439 | (2006.01) | |
| A61K 31/454 | (2006.01) | |
| A61K 31/4545 | (2006.01) | |
| A61K 31/506 | (2006.01) | |
| C07D 405/12 | (2006.01) | |
| C07D 471/08 | (2006.01) | |

(56) References Cited

U.S. PATENT DOCUMENTS

2004/0167188 A1   8/2004   Xin et al.
2004/0214870 A1*  10/2004   Xin ..................... C07D 261/18
                                               514/362

FOREIGN PATENT DOCUMENTS

| EP | 1864971 | A1 | 12/2007 |
|---|---|---|---|
| GB | 2041363 | A | 9/1980 |
| WO | 9856771 | A2 | 12/1998 |
| WO | 9908697 | A1 | 2/1999 |
| WO | 9908699 | A1 | 2/1999 |
| WO | 0105782 | A1 | 1/2001 |
| WO | 03032916 | A2 | 4/2003 |
| WO | 2004009533 | A1 | 1/2004 |
| WO | 2004009588 | A1 | 1/2004 |
| WO | 2004037796 | A2 | 5/2004 |
| WO | 2004063169 | A1 | 7/2004 |
| WO | 2005018642 | A1 | 3/2005 |
| WO | 2005077372 | A1 | 8/2005 |
| WO | 2005079769 | A2 | 9/2005 |
| WO | 2005103054 | A2 | 11/2005 |
| WO | 2006066948 | A1 | 6/2006 |
| WO | 2006078941 | A2 | 7/2006 |
| WO | 2007044804 | A2 | 4/2007 |
| WO | 2008144933 | A1 | 12/2008 |
| WO | 2009046804 | A1 | 4/2009 |
| WO | 2010112116 | A1 | 10/2010 |
| WO | 2010115491 | A2 | 10/2010 |
| WO | 2012024559 | A1 | 2/2012 |
| WO | 2012088438 | A1 | 6/2012 |
| WO | 2012145737 | A1 | 10/2012 |
| WO | 2013019561 | A1 | 2/2013 |
| WO | 2015008229 | A1 | 1/2015 |

OTHER PUBLICATIONS

International Search Report and Written Opinion for International Application No. PCT/IB2014/063142, mailed Oct. 23, 2014, 8 pages.

* cited by examiner

AUTOTAXIN INHIBITORS

RELATED APPLICATIONS

This application is a U.S. National Phase filing of International Application No. PCT/IB2014/063143 filed 16 Jul. 2014, which claims priority to EP Application No. EP13177061.2 filed 18 Jul. 2013, the contents of which are incorporated herein by reference in their entirety.

TECHNICAL FIELD

The present invention relates to novel compounds that are autotaxin inhibitors, processes for their preparation, pharmaceutical compositions and medicaments containing them and to their use in diseases and disorders mediated by autotaxin.

BACKGROUND

Autotaxin (ATX), also known as ectonucleotide pyrophosphatase/phosphodiesterase (ENPP2), is a secreted ectoenzyme known to possess lysophospholipase D activity (Umezu-Goto et al., 2002), and is responsible for producing the bioactive lipid mediator lysophosphatidic acid (LPA) by the hydrolysis of lysophosphatidylcholine (LPC) (Tokumura et al., 2002). LPA is highly implicated in the pathogenesis of a number of physio-pathological diseases, including cancer (Liu et al., 2009; Mills & Moolenaar, 2003), neuropathic pain (Inoue et al., 2004) and fibrosis (Tager et al., 2008). Following the production of LPA, the lipid binds to specific G protein-coupled receptors of which there are seven known isoforms (Noguchi et al., 2009). Binding of LPA activates multiple signalling pathways (Mills & Moolenaar, 2003) including cell migration (van Dijk et al., 1998), proliferation and survival (Brindley, 2004). Other cellular responses include smooth muscle contraction, apoptosis and platelet aggregation (Tigyi & Parrill, 2003).

ATX was originally identified as a cell motility-stimulating factor following isolation from human A2058 melanoma cells (Stracke et al., 1992). Subsequent work on the enzyme was focused towards its role as a motility factor due to its aberrant expression in many cancer types including breast and renal cancer (Stassar et al., 2001), Hodgkin's lymphoma (Baumforth et al., 2005), follicular lymphoma (Masuda et al., 2008), as well as fibrosis of the lung and kidney (Hama et al., 2004). Ten years following its discovery, ATX was characterised as a secreted lysophospholipase (lysoPLD) (Tokumura et al., 2002; Gesta et al., 2002). Since then ATX gene knockout mice have shown that the ATX-LPA signalling axis plays a vital role during embryonic development of the cardiovascular and neural system (Tanaka et al., 2006; van Meeteren et al., 2006), resulting in early embryonic lethality (Bachner et al., 1999).

ATX belongs to a family of proteins called nucleotide pyrophosphatase/phosphodiesterase (NPP), encoded for by the gene ENPP. The family consists of seven structurally related enzymes (ENPP 1-7) conserved within vertebrates which are numbered according to their discovery. They were originally defined by their ability to hydrolyse pyrophosphate or phosphodiester bonds of various nucleotides and nucleotides derivatives in vitro (Stefan et al., 1999; Goding et al., 1998; Gijsbers et al., 2001), though ENPP2 and choline phosphate esters (ENPP6 & 7) have specific activity for other extracellular non-nucleotide molecules. ENPP2 (ATX) is unique within the family as it is the only secreted protein, whereas other ENPP members are transmembrane proteins (Stefan et al., 2005).

Hence, there is a need for potent inhibitors of ATX.

WO2004/009588 (Pfizer) relates to bicyclic piperidine compounds for use as CCR1 antagonists.

WO2006/066948 (Schering) relates to piperidine derivatives for use as CCR1 antagonists.

WO2005/079769 (Schering) relates to piperazine derivatives for use as CCR1 antagonists.

WO2004/037796 (Novartis) relates to 1-(4-benzylpiperazin-1-yl)-3-phenylpropenone derivatives for use as CCR1 antagonists.

WO1998/56771 (Schering) relates to N-benzylpiperazine derivates for use as chemokine antagonists.

SUMMARY OF THE INVENTION

In a first aspect, the invention relates to a compound according to formula (I)

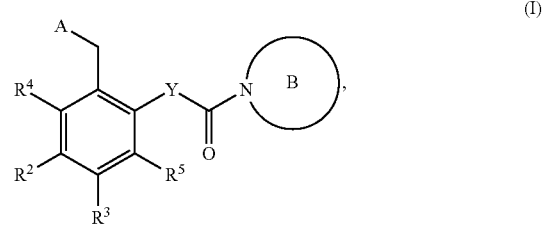

or a pharmaceutically acceptable salt thereof, wherein
A is selected from the group consisting of

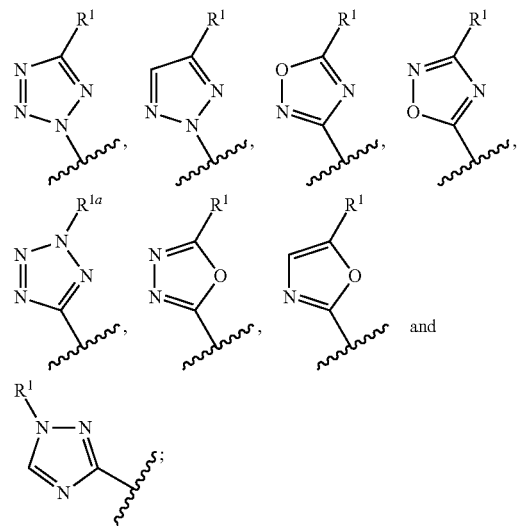

$R^1$ is selected from the group consisting of H and $C_{1-4}$ alkyl;
$R^{1a}$ is $C_{1-4}$ alkyl;
$R^2$ is halogen, $-CF_3$, $-CF_2H$, $-OCF_3$, $-OCF_2H$, $-OCH_3$, $-CH_3$ or CN, and $R^3$, $R^4$ and $R^5$ are H; or
$R^3$ is halogen and $R^2$, $R^4$ and $R^5$ are H; or
$R^4$ is halogen and $R^2$, $R^3$ and $R^5$ are H; or
$R^2$ is halogen, $-CF_3$, $-CF_2H$, $-OCF_3$, $-OCF_2H$, $-OCH_3$, $-CH_3$ or CN, $R^3$ is halogen and $R^4$ and $R^5$ are H;

Y is selected from the group consisting of —CH=CH—, —CH$_2$—CH$_2$—, —O—CH$_2$—, —CH$_2$—O—, —C(CH$_3$)=CH— and —C=C(CH$_3$)—;

B is a 4 to 8 membered nitrogen-containing heterocyclic ring or a bridged 4 to 8 membered nitrogen-containing heterocyclic ring system which 4 to 8 membered nitrogen-containing heterocyclic ring or bridged 4 to 8 membered nitrogen-containing heterocyclic ring system is unsubstituted or substituted with 1 to 3 substituents independently selected from the group consisting of Q;

Q is selected from the group consisting of
(i) —(CR$^{Ba}$R$^{Bb}$)$_n$-5 or 6 membered heteroaryl or —(CR$^{Ba}$R$^{Bb}$)$_{n1}$—O—(CR$^{Ba}$R$^{Bb}$)$_n$-5 or 6 membered heteroaryl which heteroaryl is unsubstituted or substituted with 1 to 3 substituents independently selected from the group consisting of X;
(ii) —(CR$^{Ba}$R$^{Bb}$)$_n$-phenyl or —(CR$^{Ba}$R$^{Bb}$)$_{n1}$—O—(CR$^{Ba}$R$^{Bb}$)$_n$-phenyl which phenyl is unsubstituted or substituted with 1 to 3 substituents independently selected from the group consisting of X;
(iii) —(CR$^{Ba}$R$^{Bb}$)$_n$-9 to 10 membered fused bicyclic ring system or —(CR$^{Ba}$R$^{Bb}$)$_{n1}$—O—(CR$^{Ba}$R$^{Bb}$)$_n$-9 to 10 membered fused bicyclic ring system which 9 to 10 membered fused bicyclic ring system is unsubstituted or substituted with 1 to 3 substituents independently selected from the group consisting of X;
(iv) —(CR$^{Ba}$R$^{Bb}$)$_n$-5 or 6 membered heterocyclyl or —(CR$^{Ba}$R$^{Bb}$)$_{n1}$—O—(CR$^{Ba}$R$^{Bb}$)$_n$-5 or 6 membered heterocyclyl which heterocyclyl is unsubstituted or substituted with 1 to 3 substituents independently selected from the group consisting of X;
(v) C$_{1-4}$ alkyl;
(vi) C$_{1-4}$ alkoxy;
(vii) C$_{1-4}$ alkoxy C$_{1-4}$ alkyl;
(viii) C$_{1-4}$ haloalkyl;
(ix) hydroxy C$_{1-4}$ alkyl;
(x) —(CR$^{Ba}$R$^{Bb}$)$_n$C$_{3-6}$cycloalkyl;
(xi) —(CR$^{Ba}$R$^{Bb}$)$_n$—C(=O)R$^{Bc}$ or —(CR$^{Ba}$R$^{Bb}$)$_{n1}$—O—(CR$^{Ba}$R$^{Bb}$)$_n$—C(O)R$^{Bc}$;
(xii) —(CR$^{Ba}$R$^{Bb}$)$_n$—C(=O)OR$^{Be}$ or —(CR$^{Ba}$R$^{Bb}$)$_{n1}$—O—(CR$^{Ba}$R$^{Bb}$)$_n$—C(=O)OR$^{Be}$;
(xiii) —(CR$^{Ba}$R$^{Bb}$)$_n$NR$^{Bd}$—C(=O)R$^{Bc}$ or —(CR$^{Ba}$R$^{Bb}$)$_{n1}$—O—(CR$^{Ba}$R$^{Bb}$)$_n$—NR$^{Bd}$—C(=O)R$^{Bc}$;
(xiv) —(CR$^{Ba}$R$^{Bb}$)$_n$NR$^{Bd}$—C(=O)OR$^{Bc}$ or —(CR$^{Ba}$R$^{Bb}$)$_{n1}$—O—(CR$^{Ba}$R$^{Bb}$)$_n$—NR$^{Bd}$—C(=O)OR$^{Bc}$;
(xv) —(CR$^{Ba}$R$^{Bb}$)$_n$—C(=O)NR$^{Bc}$R$^{Bd}$ or —(CR$^{Ba}$R$^{Bb}$)$_{n1}$—O—(CR$^{Ba}$R$^{Bb}$)$_n$—C(=O)NR$^{Bc}$R$^{Bd}$;
(xvi) —(CR$^{Ba}$R$^{Bb}$)$_n$—NR$^{Bd}$R$^{Be}$ or —(CR$^{Ba}$R$^{Bb}$)$_{n1}$—O—(CR$^{Ba}$R$^{Bb}$)$_n$—NR$^{Bd}$R$^{Be}$;
(xvii) —(CR$^{Ba}$R$^{Bb}$)$_n$—NR$^{Bd}$—S(O)$_2$—R$^{Bf}$;
(xviii) —(CR$^{Ba}$R$^{Bb}$)$_n$—S(O)$_2$—NR$^{Bd}$R$^{Be}$ or —(CR$^{Ba}$R$^{Bb}$)$_{n1}$—O—(CR$^{Ba}$R$^{Bb}$)$_n$—S(O)$_2$—NR$^{Bd}$R$^{Be}$;
(xix) —(CR$^{Ba}$R$^{Bb}$)$_n$—S(O)$_2$—R$^{Bf}$;
(xx) halogen;
(xxi) OH;
(xxii) oxo; and
(xxiii) CN;

R$^{Ba}$, R$^{Bb}$, R$^{Xa}$, R$^{Xb}$ are independently selected from the group consisting of H, OH, C$_{1-4}$ alkyl and C$_{1-4}$ alkoxy;

R$^{Bc}$, R$^{Be}$ and R$^{Bf}$ are independently selected from the group consisting of H, C$_{1-4}$alkyl, —(CR$^{Ba}$R$^{Bb}$)$_{n1}$—C$_{3-6}$cycloalkyl, —(CR$^{Ba}$R$^{Bb}$)$_{n1}$—C$_{3-6}$cycloalkenyl, hydroxyC$_{1-4}$alkyl, C$_{1-4}$haloalkyl, C$_{1-4}$alkoxyC$_{1-4}$alkyl, OH, —(CR$^{Ba}$R$^{Bb}$)$_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;

R$^{Bd}$ is selected from the group consisting of H and C$_{1-4}$alkyl; or

R$^{Bc}$ and R$^{Bd}$ or R$^{Bd}$ and R$^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$ cycloalkyl, —(CR$^{Ba}$R$^{Bb}$)$_{n1}$—C$_{3-6}$cycloalkenyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^a$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xc}$, R$^{Xd}$ and R$^{Xe}$ are independently selected from the group consisting of H, C$_{1-4}$alkyl, —(CR$^{Xa}$R$^{Xb}$)$_{q1}$—C$_{3-6}$ cycloalkyl, hydroxyC$_{1-4}$alkyl, C$_{1-4}$haloalkyl, C$_{1-4}$alkoxy C$_{1-4}$alkyl, OH—(CR$^{Xa}$R$^{Xb}$)$_{q1}$-5 or 6 membered heterocyclyl and —(CR$^{Xa}$R$^{Xb}$)$_{q1}$-5 or 6 membered heteroaryl; wherein the C$_{3-6}$ cycloalkyl, heterocyclyl and heteroaryl are unsubstituted or substituted by 1 to 3 substituents independently selected from the group consisting of C$_{1-4}$ alkyl, C$_{1-4}$ alkoxy, —(CR$^{Xa}$R$^{Xb}$)$_{q1}$—C$_{3-6}$ cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_{q1}$—C$_{3-6}$ cycloalkyl, hydroxy C$_{1-4}$alkyl, C$_{1-4}$haloalkyl, C$_{1-4}$alkoxyC$_{1-4}$alkyl, halogen and OH;

n and n1 are independently selected from the group consisting of 0, 1, 2, 3, 4 and 5;

q and q1 are independently selected from the group consisting of 0, 1 and 2;

with the proviso that the compound is not 2-[4-chloro-2-(1H-tetrazol-5-ylmethyl)-phenoxy]-1-[(cis)-3-(4-fluoro-phenoxy)-8-aza-bicyclo[3.2.1]oct-8-yl]-ethanone.

In another aspect, the invention relates to processes for preparing compounds of the first aspect.

In another aspect, the invention relates to the use of compounds of the first aspect in the treatment of a disease or condition selected from fibrosis, pruritus, cirrhosis, cancer, diabetes, kidney diseases and pain.

In a further aspect, the invention relates to pharmaceutical compositions and combinations comprising a compound of the first aspect.

DESCRIPTION OF THE EMBODIMENTS

Embodiment 1: A Compound According to Formula (I)

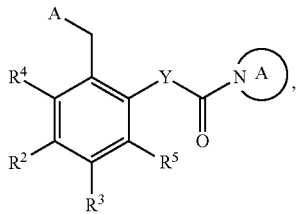

(I)

or a pharmaceutically acceptable salt thereof, wherein
A is selected from the group consisting of

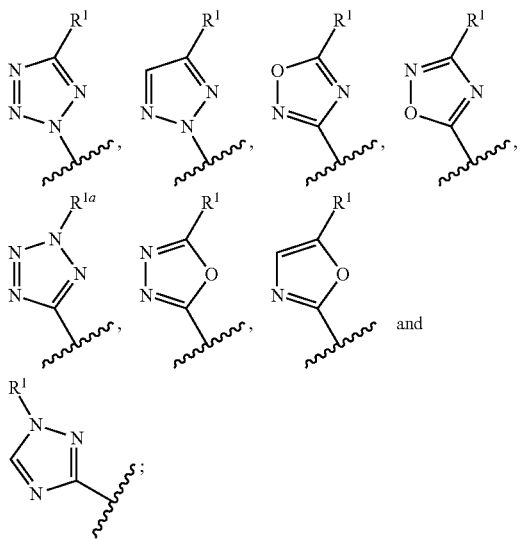

and $R^1$ is selected from the group consisting of H and $C_{1-4}$ alkyl;

$R^{1a}$ is $C_{1-4}$ alkyl;

$R^2$ is halogen, $-CF_3$, $-CF_2H$, $-OCF_3$, $-OCF_2H$, $-OCH_3$, $-CH_3$ or CN, and $R^3$, $R^4$ and $R^5$ are H; or $R^3$ is halogen and $R^2$, $R^4$ and $R^5$ are H; or $R^4$ is halogen and $R^2$, $R^3$ and $R^5$ are H; or $R^2$ is halogen, $-CF_3$, $-CF_2H$, $-OCF_3$, $-OCF_2H$, $-OCH_3$, $-CH_3$ or CN, $R^3$ is halogen and $R^4$ and $R^5$ are H;

Y is selected from the group consisting of $-CH=CH-$, $-CH_2-CH_2-$, $-O-CH_2-$, $-CH_2-O-$, $-C(CH_3)=CH-$ and $-C=C(CH_3)-$;

B is a 4 to 8 membered nitrogen-containing heterocyclic ring or a bridged 4 to 8 membered nitrogen-containing heterocyclic ring system which 4 to 8 membered nitrogen-containing heterocyclic ring or bridged 4 to 8 membered nitrogen-containing heterocyclic ring system is unsubstituted or substituted with 1 to 3 substituents independently selected from the group consisting of Q;

Q is selected from the group consisting of
(i) $-(CR^{Ba}R^{Bb})_n$-5 or 6 membered heteroaryl or $-(CR^{Ba}R^{Bb})_{n1}-O-(CR^{Ba}R^{Bb})_n$-5 or 6 membered heteroaryl which heteroaryl is unsubstituted or substituted with 1 to 3 substituents independently selected from the group consisting of X;

(ii) $-(CR^{Ba}R^{Bb})_n$-phenyl or $-(CR^{Ba}R^{Bb})_{n1}-O-(CR^{Ba}R^{Bb})_n$-phenyl which phenyl is unsubstituted or substituted with 1 to 3 substituents independently selected from the group consisting of X;

(iii) $-(CR^{Ba}R^{Bb})_n$-9 to 10 membered fused bicyclic ring system or $-(CR^{Ba}R^{Bb})_{n1}-O-(CR^{Ba}R^{Bb})_n$-9 to 10 membered fused bicyclic ring system which 9 to 10 membered fused bicyclic ring system is unsubstituted or substituted with 1 to 3 substituents independently selected from the group consisting of X;

(iv) $-(CR^{Ba}R^{Bb})_n$-5 or 6 membered heterocyclyl or $-(CR^{Ba}R^{Bb})_{n1}-O-(CR^{Ba}R^{Bb})_n$-5 or 6 membered heterocyclyl which heterocyclyl is unsubstituted or substituted with 1 to 3 substituents independently selected from the group consisting of X;

(v) $C_{1-4}$ alkyl;
(vi) $C_{1-4}$ alkoxy;
(vii) $C_{1-4}$ alkoxy $C_{1-4}$ alkyl;
(viii) $C_{1-4}$ haloalkyl;
(ix) hydroxy $C_{1-4}$ alkyl;
(x) $-(CR^{Ba}R^{Bb})_n C_{3-6}$cycloalkyl;
(xi) $-(CR^{Ba}R^{Bb})_n-C(=O)R^{Bc}$ or $-(CR^{Ba}R^{Bb})_{n1}-O-(CR^{Ba}R^{Bb})_n-C(=O)R^{Bc}$;
(xii) $-(CR^{Ba}R^{Bb})_n-C(=O)OR^{Be}$ or $-(CR^{Ba}R^{Bb})_{n1}-O-(CR^{Ba}R^{Bb})_n-C(=O)OR^{Be}$;
(xiii) $-(CR^{Ba}R^{Bb})_n NR^{Bd}-C(=O)R^{Bc}$ or $-(CR^{Ba}R^{Bb})_{n1}-O-(CR^{Ba}R^{Bb})_n-NR^{Bd}-C(=O)R^{Bc}$;
(xiv) $-(CR^{Ba}R^{Bb})_n NR^{Bd}-C(=O)OR^{Bc}$ or $-(CR^{Ba}R^{Bb})_{n1}-O-(CR^{Ba}R^{Bb})_{n1}-NR^{Bd}-C(=O)OR^{Bc}$;
(xv) $-(CR^{Ba}R^{Bb})_n-C(=O)NR^{Bc}R^{Bd}$ or $-(CR^{Ba}R^{Bb})_{n1}-O-(CR^{Ba}R^{Bb})_n-C(=O)NR^{Bc}R^{Bd}$;
(xvi) $-(CR^{Ba}R^{Bb})_n-NR^{Bd}R^{Be}$ or $-(CR^{Ba}R^{Bb})_{n1}-O-(CR^{Ba}R^{Bb})_n-NR^{Bd}R^{Be}$;
(xvii) $-(CR^{Ba}R^{Bb})_n-NR^{Bd}-S(O)_2-R^{Bf}$;
(xviii) $-(CR^{Ba}R^{Bb})_n-S(O)_2-NR^{Bd}R^{Be}$ or $-(CR^{Ba}R^{Bb})_{n1}-O-(CR^{Ba}R^{Bb})_n-S(O)_2-NR^{Bd}R^{Be}$;
(xix) $-(CR^{Ba}R^{Bb})_n-S(O)_2-R^{Bf}$;
(xx) halogen;
(xxi) OH;
(xxii) oxo; and
(xxiii) CN;

$R^{Ba}$, $R^{Bb}$, $R^{Xa}$, $R^{Xb}$ are independently selected from the group consisting of H, OH, $C_{1-4}$ alkyl and $C_{1-4}$ alkoxy;

$R^{Bc}$, $R^{Be}$ and $R^{Bf}$ are independently selected from the group consisting of H, $C_{1-4}$alkyl, $-(CR^{Ba}R^{Bb})_{n1}-C_{3-6}$cycloalkyl, $-(CR^{Ba}R^{Bb})_{n1}-C_{3-6}$cycloalkenyl, hydroxy$C_{1-4}$alkyl, $C_{1-4}$haloalkyl, $C_{1-4}$alkoxy$C_{1-4}$alkyl, OH, $-(CR^{Ba}R^{Bb})_{n1}$-5 or 6 membered heteroaryl, $-(CR^{Ba}R^{Bb})_{n1}$-phenyl and $-(CR^{Ba}R^{Bb})_{n1}$-5 or 6 membered heterocyclyl, wherein the $C_{3-6}$cycloalkyl, heteroaryl, phenyl and heterocyclyl are unsubstituted or substituted by 1 to 3 substituents selected from the group consisting of X;

$R^{Bd}$ is selected from the group consisting of H and $C_{1-4}$alkyl; or $R^{Bc}$ and $R^{Bd}$ or $R^{Bd}$ and $R^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, $-(CR^{Xa}R^{Xb})_q-C_{3-6}$ cycloalkyl, $-(CR^{Ba}R^{Bb})_{n1}-C_{3-6}$cycloalkenyl, halogen, CN, $-(CR^{Xa}R^{Xb})_q$-5 or 6 membered heterocyclyl, $-(CR^{Xa}R^{Xb})_q$-5 or 6 membered heteroaryl, $-(CR^{Xa}R^{Xb})_q$-phenyl, oxo, OH, $-(CR^{Xa}R^{Xb})_q-C(=O)R^{Xc}$, $-(CR^{Xa}R^{Xb})_q-C(=O)OR^{Xc}$, $-(CR^{Xa}R^{Xb})_q-NR^{Xd}R^{Xe}$ and $-(CR^{Xa}$ $R^{Xb})_q$—C(=O)$NR^{Xd}R^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —($CR^{Xa}R^{Xb})_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;

$R^{Xc}$, $R^{Xd}$ and $R^{Xe}$ are independently selected from the group consisting of H, $C_{1-4}$alkyl, —($CR^{Xa}R^{Xb})_{q1}$—$C_{3-6}$cycloalkyl, hydroxy$C_{1-4}$alkyl, $C_{1-4}$haloalkyl, $C_{1-4}$alkoxy $C_{1-4}$alkyl, OH—($CR^{Xa}R^{Xb})_{q1}$-5 or 6 membered heterocyclyl and —($CR^{Xa}R^{Xb})_{q1}$-5 or 6 membered heteroaryl; wherein the $C_{3-6}$ cycloalkyl, heterocyclyl and heteroaryl are unsubstituted or substituted by 1 to 3 substituents independently selected from the group consisting of $C_{1-4}$ alkyl, $C_{1-4}$ alkoxy, —($CR^{Xa}R^{Xb})_{q1}$—$C_{3-6}$ cycloalkyl, $C_{1-4}$ haloalkyl, hydroxy$C_{1-4}$alkyl, $C_{1-4}$alkoxy$C_{1-4}$alkyl, halogen and OH; or $R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —($CR^{Xa}R^{Xb})_{q1}$—$C_{3-6}$ cycloalkyl, hydroxy $C_{1-4}$alkyl, $C_{1-4}$haloalkyl, $C_{1-4}$alkoxy$C_{1-4}$alkyl, halogen and OH;

n and n1 are independently selected from the group consisting of 0, 1, 2, 3, 4 and 5;

q and q1 are independently selected from the group consisting of 0, 1 and 2;

with the proviso that the compound is not 2-[4-chloro-2-(1H-tetrazol-5-ylmethyl)-phenoxy]-1-[(cis)-3-(4-fluorophenoxy)-8-aza-bicyclo[3.2.1]oct-8-yl]-ethanone.

Embodiment 1.1: A Compound According to Formula (I)

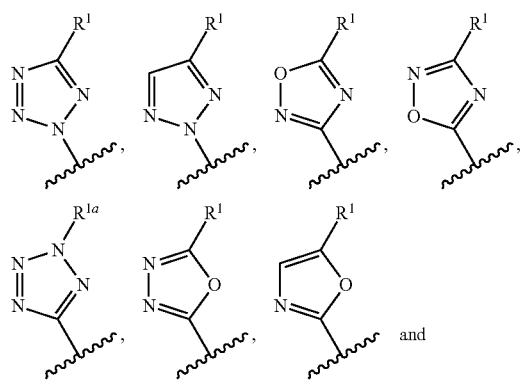

(I)

or a pharmaceutically acceptable salt thereof, wherein

A is selected from the group consisting of

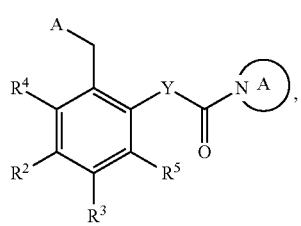

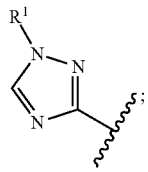

$R^1$ is selected from the group consisting of H and $C_{1-4}$ alkyl;

$R^{1a}$ is $C_{1-4}$ alkyl;

$R^2$ is halogen, —$CF_3$, —$CF_2H$, —$OCF_3$, —$OCF_2H$, —$OCH_3$, —$CH_3$ or CN, and $R^3$, $R^4$ and $R^5$ are H; or $R^3$ is halogen and $R^2$, $R^4$ and $R^5$ are H; or $R^4$ is halogen and $R^2$, $R^3$ and $R^5$ are H; or $R^2$ is halogen, —$CF_3$, —$CF_2H$, —$OCF_3$, —$OCF_2H$, —$OCH_3$, —$CH_3$ or CN, $R^3$ is halogen and $R^4$ and $R^5$ are H;

Y is selected from the group consisting of —CH=CH—, —$CH_2$—$CH_2$—, —O—$CH_2$—, —$CH_2$—O—, —C($CH_3$)=CH— and —C=C($CH_3$)—;

B is a 4 to 8 membered nitrogen-containing heterocyclic ring or a bridged 4 to 8 membered nitrogen-containing heterocyclic ring system which 4 to 8 membered nitrogen-containing heterocyclic ring or bridged 4 to 8 membered nitrogen-containing heterocyclic ring system is unsubstituted or substituted with 1 to 3 substituents independently selected from the group consisting of Q;

Q is selected from the group consisting of (i) —($CR^{Ba}R^{Bb})_n$-5 or 6 membered heteroaryl or —O—($CR^{Ba}R^{Bb})_n$-5 or 6 membered heteroaryl which heteroaryl is unsubstituted or substituted with 1 to 3 substituents independently selected from the group consisting of X;

(ii) —($CR^{Ba}R^{Bb})_n$-phenyl or —O—($CR^{Ba}R^{Bb})_n$-phenyl which phenyl is unsubstituted or substituted with 1 to 3 substituents independently selected from the group consisting of X;

(iii) —($CR^{Ba}R^{Bb})_n$-9 to 10 membered fused bicyclic ring system or —O—($CR^{Ba}R^{Bb})_n$-9 to 10 membered fused bicyclic ring system which 9 to 10 membered fused bicyclic ring system is unsubstituted or substituted with 1 to 3 substituents independently selected from the group consisting of X;

(iv) —($CR^{Ba}R^{Bb})_n$-5 or 6 membered heterocyclyl or —O—($CR^{Ba}R^{Bb})_n$-5 or 6 membered heterocyclyl which heterocyclyl is unsubstituted or substituted with 1 to 3 substituents independently selected from the group consisting of X;

(v) $C_{1-4}$ alkyl;

(vi) $C_{1-4}$ alkoxy;

(vii) $C_{1-4}$ alkoxy $C_{1-4}$ alkyl;

(viii) $C_{1-4}$ haloalkyl;

(ix) hydroxy $C_{1-4}$ alkyl;

(x) —($CR^{Ba}R^{Bb})_n$$C_{3-6}$cycloalkyl;

(xi) —($CR^{Ba}R^{Bb})_n$—C(=O)RB or —O—($CR^{Ba}R^{Bb})_n$—C(=O)$R^{Bc}$;

(xii) —($CR^{Ba}R^{Bb})_n$—C(=O)$OR^{Be}$ or —O—($CR^{Ba}R^{Bb})_n$C(=O)$OR^{Be}$;

(xiii) —($CR^{Ba}R^{Bb})_n$$NR^{Bd}$—C(=O)$R^{Bc}$ or —O—($CR^{Ba}R^{Bb})_n$$NR^{Bd}$—C(=O)$R^{Bc}$;

(xiv) —($CR^{Ba}R^{Bb})_n$$NR^{Bd}$—C(=O)$OR^{Bc}$ or —O—($CR^{Ba}R^{Bb})_n$$NR^{Bd}$—C(=O)$OR^{Bc}$;

(xv) —($CR^{Ba}R^{Bb})_n$—C(=O)$NR^{Bc}R^{Bd}$ or —O—($CR^{Ba}R^{Bb})_n$—C(=O)$NR^{Bc}R^{Bd}$;

(xvi) —($CR^{Ba}R^{Bb})_n$—$NR^{Bd}R^{Be}$ or —O—($CR^{Ba}R^{Bb})_n$—$NR^{Bd}R^{Be}$;

(xvii) —($CR^{Ba}R^{Bb})_n$—$NR^{Bd}$—S(O)$_2$—$R^{Bf}$;

(xviii) —(CR$^{Ba}$R$^{Bb}$)$_n$—S(O)$_2$—NR$^{Bd}$R$^{Be}$ or —O—(CR$^{Ba}$R$^{Bb}$)$_n$—S(O)$_2$—NR$^{Bd}$R$^{Be}$;
(xix) —(CR$^{Ba}$R$^{Bb}$)$_n$—S(O)$_2$—R$^{Bf}$;
(xx) halogen;
(xxi) OH;
(xxii) oxo; and
(xxiii) CN;

R$^{Ba}$, R$^{Bb}$, R$^{Xa}$, R$^{Xb}$ are independently selected from the group consisting of H, OH, C$_{1-4}$ alkyl and C$_{1-4}$ alkoxy;

R$^{Bc}$, R$^{Be}$ and R$^{Bf}$ are independently selected from the group consisting of H, C$_{1-4}$alkyl, —(CR$^{Ba}$R$^{Bb}$)$_n$—C$_{3-6}$cycloalkyl, hydroxyC$_{1-4}$alkyl, C$_{1-4}$haloalkyl, C$_{1-4}$alkoxyC$_{1-4}$alkyl, OH, —(CR$^{Ba}$R$^{Bb}$)$_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;

R$^{Bd}$ is selected from the group consisting of H and C$_{1-4}$alkyl; or

R$^{Bc}$ and R$^{Bd}$ or R$^{Bd}$ and R$^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xc}$, R$^{Xd}$ and R$^{Xe}$ are independently selected from the group consisting of H, C$_{1-4}$alkyl, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxy C$_{1-4}$alkyl, OH and —(CR$^{Xa}$R$^{Xb}$)$_q$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_q$—C$_{3-6}$cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_q$—C$_{3-6}$cycloalkyl, hydroxy C$_{1-4}$alkyl, C$_{1-4}$haloalkyl, C$_{1-4}$alkoxyC$_{1-4}$alkyl, halogen and OH;

n and n1 are independently selected from the group consisting of 0, 1, 2, 3 and 4;
q is selected from the group consisting of 0, 1 and 2;
wherein when Q or R$^{Bc}$ is a 5 membered heteroaryl selected from the group consisting of
1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;
then said heteroaryl is substituted with 1 or 2 substituents independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-phenyl, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$;

and wherein when Q or R$^{Bc}$ is a 5 membered heteroaryl selected from the group consisting of
1H-1,2,3-triazol-4-yl;
2H-1,2,3-triazol-4-yl;
1H-1,2,3-triazol-5-yl;
then said triazolyl is substituted with 1 or 2 substituents independently selected from the group consisting of C$_{1-4}$ alkoxy, C$_{1-4}$ haloalkyl, hydroxyC$_{1-4}$alkyl, C$_{1-4}$alkoxy C$_{1-4}$alkyl, —(CR$^{Xa}$R$^{Xb}$)$_q$—C$_{3-6}$cycloalkyl, CN, —(CR$^{Xa}$R$^{Xb}$)$_q$-5 or 6 membered heterocyclyl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$;

with the proviso that the compound is not 2-[4-chloro-2-(1H-tetrazol-5-ylmethyl)-phenoxy]-1-[(cis)-3-(4-fluoro-phenoxy)-8-aza-bicyclo[3.2.1]oct-8-yl]-ethanone.

Compound 2-[4-chloro-2-(1H-tetrazol-5-ylmethyl)-phenoxy]-1-[(cis)-3-(4-fluoro-phenoxy)-8-aza-bicyclo[3.2.1] oct-8-yl]-ethanone is disclosed in WO2004/009588 (Pfizer) which relates to bicyclic piperidine compounds for use as CCR1 antagonists.

Embodiment 2: A compound or salt according to embodiment 1, wherein
A is selected from the group consisting of

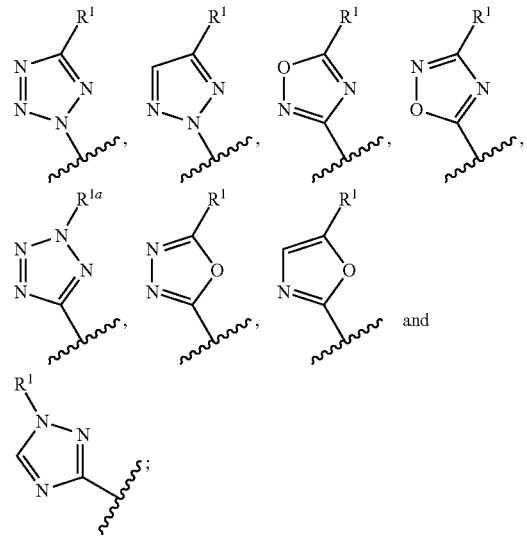

R$^1$ is selected from the group consisting of H and C$_{1-4}$ alkyl;
R$^{1a}$ is C$_{1-4}$ alkyl;
R$^2$ is halogen, —CF$_3$, —CF$_2$H, —OCF$_3$, —OCF$_2$H, —OCH$_3$, —CH$_3$ or CN, and R$^3$, R$^4$ and R$^5$ are H; or
R$^3$ is halogen and R$^2$, R$^4$ and R$^5$ are H; or
R$^4$ is halogen and R$^2$, R$^3$ and R$^5$ are H; or R² is halogen, —CF₃, —CF₂H, —OCF₃, —OCF₂H, —OCH₃, —CH₃ or CN, R³ is halogen and R⁴ and R⁵ are H;

Y is selected from the group consisting of —CH=CH—, —CH₂—CH₂—, —O—CH₂—, —CH₂—O—, —C(CH₃)=CH— and —C≡C(CH₃)—;

B is a 4 to 8 membered nitrogen-containing heterocyclic ring or a bridged 4 to 8 membered nitrogen-containing heterocyclic ring system which 4 to 8 membered nitrogen-containing heterocyclic ring or bridged 4 to 8 membered nitrogen-containing heterocyclic ring system is unsubstituted or substituted with 1 to 3 substituents independently selected from the group consisting of Q;

Q is selected from the group consisting of
(i) —(CR$^{Ba}$R$^{Bb}$)$_n$-5 or 6 membered heteroaryl or —(CR$^{Ba}$R$^{Bb}$)$_{n1}$—O—(CR$^{Ba}$R$^{Bb}$)$_n$-5 or 6 membered heteroaryl which heteroaryl is unsubstituted or substituted with 1 to 3 substituents independently selected from the group consisting of X;
(ii) —(CR$^{Ba}$R$^{Bb}$)$_n$-9 to 10 membered fused bicyclic ring system or —(CR$^{Ba}$R$^{Bb}$)$_{n1}$—O—(CR$^{Ba}$R$^{Bb}$)$_n$-9 to 10 membered fused bicyclic ring system which 9 to 10 membered fused bicyclic ring system is unsubstituted or substituted with 1 to 3 substituents independently selected from the group consisting of X;
(iii) —(CR$^{Ba}$R$^{Bb}$)$_n$-5 or 6 membered heterocyclyl or —(CR$^{Ba}$R$^{Bb}$)$_{n1}$—O—(CR$^{Ba}$R$^{Bb}$)$_n$-5 or 6 membered heterocyclyl which heterocyclyl is unsubstituted or substituted with 1 to 3 substituents independently selected from the group consisting of X;
(iv) C$_{1-4}$ alkyl;
(v) C$_{1-4}$ alkoxy;
(vi) C$_{1-4}$ alkoxy C$_{1-4}$ alkyl;
(vii) C$_{1-4}$ haloalkyl;
(viii) hydroxy C$_{1-4}$ alkyl;
(ix) —(CR$^{Ba}$R$^{Bb}$)$_n$C$_{3-6}$ cycloalkyl;
(x) —(CR$^{Ba}$R$^{Bb}$)$_n$—C(=O)R$^{Bc}$ or —(CR$^{Ba}$R$^{Bb}$)$_n$—O—(CR$^{Ba}$R$^{Bb}$)$_n$—C(=O)R$^{Bc}$;
(xi) —(CR$^{Ba}$R$^{Bb}$)$_n$—C(=O)OR$^{Be}$ or —(CR$^{Ba}$R$^{Bb}$)$_{n1}$—O—(CR$^{Ba}$R$^{Bb}$)$_n$—C(=O)OR$^{Be}$;
(xii) —(CR$^{Ba}$R$^{Bb}$)$_n$NR$^{Bd}$—C(=O)R$^{Bc}$ or —(CR$^{Ba}$R$^{Bb}$)$_{n1}$—O—(CR$^{Ba}$R$^{Bb}$)$_n$—NR$^{Bd}$—C(=O)R$^{Bc}$;
(xiii) —(CR$^{Ba}$R$^{Bb}$)$_n$NR$^{Bd}$—C(=O)OR$^{Bc}$ or —(CR$^{Ba}$R$^{Bb}$)$_{n1}$—O—(CR$^{Ba}$R$^{Bb}$)$_n$—NR$^{Bd}$—C(=O)OR$^{Bc}$;
(xiv) —(CR$^{Ba}$R$^{Bb}$)$_n$—C(=O)NR$^{Bc}$R$^{Bd}$ or —(CR$^{Ba}$R$^{Bb}$)$_{n1}$—O—(CR$^{Ba}$R$^{Bb}$)$_n$—C(=O)NR$^{Bc}$R$^{Bd}$;
(xv) —(CR$^{Ba}$R$^{Bb}$)$_n$—NR$^{Bd}$R$^{Be}$ or —(CR$^{Ba}$R$^{Bb}$)$_{n1}$—O—(CR$^{Ba}$R$^{Bb}$)$_n$—NR$^{Bd}$R$^{Be}$;
(xvi) —(CR$^{Ba}$R$^{Bb}$)$_n$—NR$^{Bd}$—S(O)₂—R$^{Bf}$;
(xvii) —(CR$^{Ba}$R$^{Bb}$)$_n$—S(O)₂—NR$^{Bd}$R$^{Be}$ or —(CR$^{Ba}$R$^{Bb}$)$_{n1}$—O—(CR$^{Ba}$R$^{Bb}$)$_n$—S(O)₂—NR$^{Bd}$R$^{Be}$;
(xviii) —(CR$^{Ba}$R$^{Bb}$)$_n$—S(O)₂—R$^{Bf}$;
(xix) halogen;
(xx) OH;
(xxi) oxo; and
(xxii) CN;

R$^{Ba}$, R$^{Bb}$, R$^{Xa}$, R$^{Xb}$ are independently selected from the group consisting of H, OH, C$_{1-4}$ alkyl and C$_{1-4}$ alkoxy;

R$^{Bc}$, R$^{Be}$ and R$^{Bf}$ are independently selected from the group consisting of H, C$_{1-4}$alkyl, —(CR$^{Ba}$R$^{Bb}$)$_{n1}$—C$_{3-6}$cycloalkyl, —(CR$^{Ba}$R$^{Bb}$)$_{n1}$—C$_{3-6}$cycloalkenyl, hydroxyC$_{1-4}$alkyl, C$_{1-4}$haloalkyl, C$_{1-4}$alkoxyC$_{1-4}$alkyl, OH, —(CR$^{Ba}$R$^{Bb}$)$_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;

R$^{Bd}$ is selected from the group consisting of H and C$_{1-4}$alkyl; or

R$^{Bc}$ and R$^{Bd}$ or R$^{Bd}$ and R$^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$ cycloalkyl, —(CR$^{Ba}$R$^{Bb}$)$_{n1}$—C$_{3-6}$cycloalkenyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xc}$, R$^{Xd}$ and R$^{Xe}$ are independently selected from the group consisting of H, C$_{1-4}$alkyl, —(CR$^{Xa}$R$^{Xb}$)$_{q1}$—C$_{3-6}$ cycloalkyl, hydroxyC$_{1-4}$alkyl, C$_{1-4}$haloalkyl, C$_{1-4}$alkoxy C$_{1-4}$alkyl, OH—(CR$^{Xa}$R$^{Xb}$)$_{q1}$-5 or 6 membered heterocyclyl and —(CR$^{Xa}$R$^{Xb}$)$_{q1}$-5 or 6 membered heteroaryl;

wherein the C$_{3-6}$ cycloalkyl, heterocyclyl and heteroaryl are unsubstituted or substituted by 1 to 3 substituents independently selected from the group consisting of C$_{1-4}$ alkyl, C$_{1-4}$ alkoxy, —(CR$^{Xa}$R$^{Xb}$)$_{q1}$—C$_{3-6}$ cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_{q1}$—C$_{3-6}$ cycloalkyl, hydroxy C$_{1-4}$alkyl, C$_{1-4}$haloalkyl, C$_{1-4}$alkoxyC$_{1-4}$alkyl, halogen and OH;

n and n1 are independently selected from the group consisting of 0, 1, 2, 3, 4 and 5;

q and q1 are independently selected from the group consisting of 0, 1 and 2;

with the proviso that the compound is not 2-[4-chloro-2-(1H-tetrazol-5-ylmethyl)-phenoxy]-1-[(cis)-3-(4-fluoro-phenoxy)-8-aza-bicyclo[3.2.1]oct-8-yl]-ethanone.

Embodiment 2.1: A compound or salt according to embodiment 1, wherein
A is selected from the group consisting of

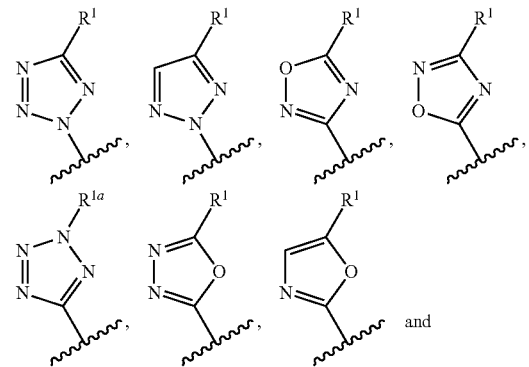

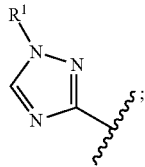

R$^1$ is selected from the group consisting of H and C$_{1-4}$ alkyl;

R$^{1a}$ is C$_{1-4}$ alkyl;

R$^2$ is halogen, —CF$_3$, —CF$_2$H, —OCF$_3$, —OCF$_2$H, —OCH$_3$, —CH$_3$ or CN, and R$^3$, R$^4$ and R$^5$ are H; or R$^3$ is halogen and R$^2$, R$^4$ and R$^5$ are H; or R$^4$ is halogen and R$^2$, R$^3$ and R$^5$ are H; or R$^2$ is halogen, —CF$_3$, —CF$_2$H, —OCF$_3$, —OCF$_2$H, —OCH$_3$, —CH$_3$ or CN, R$^3$ is halogen and R$^4$ and R$^5$ are H;

Y is selected from the group consisting of —CH=CH—, —CH$_2$—CH$_2$—, —O—CH$_2$—, —CH$_2$—O—, —C(CH$_3$)=CH— and —C=C(CH$_3$)—;

B is a 4 to 8 membered nitrogen-containing heterocyclic ring or a bridged 4 to 8 membered nitrogen-containing heterocyclic ring system which 4 to 8 membered nitrogen-containing heterocyclic ring or bridged 4 to 8 membered nitrogen-containing heterocyclic ring system is unsubstituted or substituted with 1 to 3 substituents independently selected from the group consisting of Q;

Q is selected from the group consisting of (i) —(CR$^{Ba}$R$^{Bb}$)$_n$-5 or 6 membered heteroaryl or —O—(CR$^{Ba}$R$^{Bb}$)$_n$-5 or 6 membered heteroaryl which heteroaryl is unsubstituted or substituted with 1 to 3 substituents independently selected from the group consisting of X;

(ii) —(CR$^{Ba}$R$^{Bb}$)$_n$-9 to 10 membered fused bicyclic ring system or —O—(CR$^{Ba}$R$^{Bb}$)$_n$-9 to 10 membered fused bicyclic ring system which 9 to 10 membered fused bicyclic ring system is unsubstituted or substituted with 1 to 3 substituents independently selected from the group consisting of X;

(iii) —(CR$^{Ba}$R$^{Bb}$)$_n$-5 or 6 membered heterocyclyl or —O—(CR$^{Ba}$R$^{Bb}$)$_n$-5 or 6 membered heterocyclyl which heterocyclyl is unsubstituted or substituted with 1 to 3 substituents independently selected from the group consisting of X;

(iv) C$_{1-4}$ alkyl;

(v) C$_{1-4}$ alkoxy;

(vi) C$_{1-4}$ alkoxy C$_{1-4}$ alkyl;

(vii) C$_{1-4}$ haloalkyl;

(viii) hydroxy C$_{1-4}$ alkyl;

(ix) —(CR$^{Ba}$R$^{Bb}$)$_n$C$_{3-6}$ cycloalkyl;

(x) —(CR$^{Ba}$R$^{Bb}$)$_n$—C(=O)R$^{Bc}$ or —O—(CR$^{Ba}$R$^{Bb}$)$_n$—C(=O)R$^{Bc}$;

(xi) —(CR$^{Ba}$R$^{Bb}$)$_n$—C(=O)OR$^{Be}$ or —O—(CR$^{Ba}$R$^{Bb}$)$_n$C(=O)OR$^{Be}$;

(xii) —(CR$^{Ba}$R$^{Bb}$)$_n$NR$^{Bd}$—C(=O)R$^{Bc}$ or —O—(CR$^{Ba}$R$^{Bb}$)$_n$NR$^{Bd}$—C(=O)R$^{Bc}$;

(xiii) —(CR$^{Ba}$R$^{Bb}$)$_n$NR$^{Bd}$—C(=O)OR$^{Bc}$ or —O—(CR$^{Ba}$R$^{Bb}$)$_n$NR$^{Bd}$—C(=O)OR$^{Bc}$;

(xiv) —(CR$^{Ba}$R$^{Bb}$)$_n$—C(=O)NR$^{Bc}$R$^{Bd}$ or —O—(CR$^{Ba}$R$^{Bb}$)$_n$—C(=O)NR$^{Bc}$R$^{Bd}$;

(xv) —(CR$^{Ba}$R$^{Bb}$)$_n$—NR$^{Bd}$R$^{Be}$ or —O—(CR$^{Ba}$R$^{Bb}$)$_n$—NR$^{Bd}$R$^{Be}$;

(xvi) —(CR$^{Ba}$R$^{Bb}$)$_n$—NR$^{Bd}$—S(O)$_2$—R$^{Bf}$;

(xvii) —(CR$^{Ba}$R$^{Bb}$)$_n$—S(O)$_2$—NR$^{Bd}$R$^{Be}$ or —O—(CR$^{Ba}$R$^{Bb}$)$_n$—S(O)$_2$—NR$^{Bd}$R$^{Be}$;

(xviii) —(CR$^{Ba}$R$^{Bb}$)$_n$—S(O)$_2$—R$^{Bf}$;

(xix) halogen;

(xx) OH;

(xxi) oxo; and (xxii) CN;

R$^{Ba}$, R$^{Bb}$, R$^{Xa}$, R$^{Xb}$ are independently selected from the group consisting of H, OH, C$_{1-4}$ alkyl and C$_{1-4}$ alkoxy;

R$^{Bc}$, R$^{Be}$ and R$^{Bf}$ are independently selected from the group consisting of H, C$_{1-4}$alkyl, —(CR$^{Ba}$R$^{Bb}$)$_{n1}$—C$_{3-6}$cycloalkyl, hydroxyC$_{1-4}$alkyl, C$_{1-4}$haloalkyl, C$_{1-4}$alkoxy C$_{1-4}$alkyl, OH, —(CR$^{Ba}$R$^{Bb}$)$_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;

R$^{Bd}$ is selected from the group consisting of H and C$_{1-4}$alkyl; or

R$^{Bc}$ and R$^{Bd}$ or R$^{Bd}$ and R$^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xc}$, R$^{Xd}$ and R$^{Xe}$ are independently selected from the group consisting of H, C$_{1-4}$alkyl, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxy C$_{1-4}$alkyl, OH and —(CR$^{Xa}$R$^{Xb}$)$_q$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_q$—C$_{3-6}$cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_q$—C$_{3-6}$cycloalkyl, hydroxy C$_{1-4}$alkyl, C$_{1-4}$haloalkyl, C$_{1-4}$alkoxyC$_{1-4}$alkyl, halogen and OH;

n and n1 are independently selected from the group consisting of 0, 1, 2, 3 and 4;

q is selected from the group consisting of 0, 1 and 2;

wherein when Q or R$^{Bc}$ is a 5 membered heteroaryl selected from the group consisting of 1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;

then said heteroaryl is substituted with 1 or 2 substituents independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-phenyl, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—$NR^{Xd}R^{Xe}$ and —$(CR^{Xa}R^{Xb})_q$—C(=O)$NR^{Xd}R^{Xe}$;

and wherein when Q or $R^{Bc}$ is a 5 membered heteroaryl selected from the group consisting of 1H-1,2,3-triazol-4-yl;
2H-1,2,3-triazol-4-yl;
1H-1,2,3-triazol-5-yl;

then said triazolyl is substituted with 1 or 2 substituents independently selected from the group consisting of $C_{1-4}$ alkoxy, $C_{1-4}$ haloalkyl, hydroxy$C_{1-4}$alkyl, $C_{1-4}$alkoxy $C_{1-4}$alkyl, —$(CR^{Xa}R^{Xb})_q$—$C_{3-6}$cycloalkyl, CN, —$(CR^{Xa}R^{Xb})_q$-5 or 6 membered heterocyclyl, —$(CR^{Xa}R^{Xb})_q$-phenyl, oxo, OH, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—$NR^{Xd}R^{Xe}$ and —$(CR^{Xa}R^{Xb})_q$—C(=O)$NR^{Xd}R^{Xe}$;

with the proviso that the compound is not 2-[4-chloro-2-(1H-tetrazol-5-ylmethyl)-phenoxy]-1-[(cis)-3-(4-fluoro-phenoxy)-8-aza-bicyclo[3.2.1]oct-8-yl]-ethanone.

Embodiment 3: A compound or salt according to embodiment 1, wherein
A is selected from the group consisting of

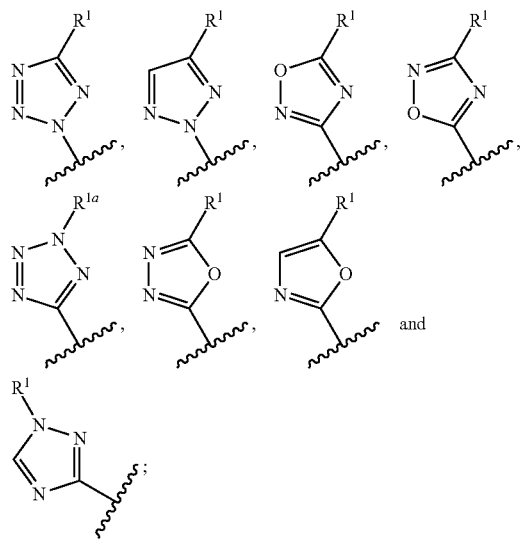

$R^1$ is selected from the group consisting of H and $C_{1-4}$ alkyl;
$R^{1a}$ is $C_{1-4}$ alkyl;
$R^2$ is halogen, —$CF_3$, —$CF_2H$, —$OCF_3$, —$OCF_2H$, —$OCH_3$, —$CH_3$ or CN, and $R^3$, $R^4$ and $R^5$ are H; or
$R^3$ is halogen and $R^2$, $R^4$ and $R^5$ are H; or
$R^4$ is halogen and $R^2$, $R^3$ and $R^5$ are H; or
$R^2$ is halogen, —$CF_3$, —$CF_2H$, —$OCF_3$, —$OCF_2H$, —$OCH_3$, —$CH_3$ or CN, $R^3$ is halogen and $R^4$ and $R^5$ are H;
Y is selected from the group consisting of —CH=CH—, —$CH_2$—$CH_2$—, —O—$CH_2$—, —$CH_2$—O—, —C($CH_3$)=CH— and —C=C($CH_3$)—;
B is selected from the group consisting of
(1) piperidin-1-yl,
(2) piperazin-1-yl,
(3) azetidin-1-yl,
(4) pyrrolidin-1-yl,
(5) morpholin-4-yl,
(6) 1,4-diazepan-1-yl,
(7) thiazolidin-3-yl, and
(8) 2,5-diazabicyclo[2.2.2]octan-2-yl;
wherein each of the rings (1) to (8) is unsubstituted or substituted with 1 to 3 substituents independently selected from the group consisting of Q;
Q is selected from the group consisting of
(i) —$(CR^{Ba}R^{Bb})_n$-5 or 6 membered heteroaryl or —$(CR^{Ba}R^{Bb})_{n1}$—O—$(CR^{Ba}R^{Bb})_n$-5 or 6 membered heteroaryl which heteroaryl is unsubstituted or substituted with 1 to 3 substituents independently selected from the group consisting of X;
(ii) —$(CR^{Ba}R^{Bb})_n$-phenyl or —$(CR^{Ba}R^{Bb})_{n1}$—O—$(CR^{Ba}R^{Bb})_n$-phenyl which phenyl is unsubstituted or substituted with 1 to 3 substituents independently selected from the group consisting of X;
(iii) —$(CR^{Ba}R^{Bb})_n$-9 to 10 membered fused bicyclic ring system or —$(CR^{Ba}R^{Bb})_{n1}$—O—$(CR^{Ba}R^{Bb})_n$-9 to 10 membered fused bicyclic ring system which 9 to 10 membered fused bicyclic ring system is unsubstituted or substituted with 1 to 3 substituents independently selected from the group consisting of X;
(iv) —$(CR^{Ba}R^{Bb})_n$-5 or 6 membered heterocyclyl or —$(CR^{Ba}R^{Bb})_{n1}$—O—$(CR^{Ba}R^{Bb})_n$-5 or 6 membered heterocyclyl which heterocyclyl is unsubstituted or substituted with 1 to 3 substituents independently selected from the group consisting of X;
(v) $C_{1-4}$ alkyl;
(vi) $C_{1-4}$ alkoxy;
(vii) $C_{1-4}$ alkoxy $C_{1-4}$ alkyl;
(viii) $C_{1-4}$ haloalkyl;
(ix) hydroxy $C_{1-4}$ alkyl;
(x) —$(CR^{Ba}R^{Bb})_n$$C_{3-6}$cycloalkyl;
(xi) —$(CR^{Ba}R^{Bb})_n$—C(=O)$R^{Bc}$ or —$(CR^{Ba}R^{Bb})_n$—O—$(CR^{Ba}R^{Bb})_n$—C(=O)$R^{Bc}$;
(xii) —$(CR^{Ba}R^{Bb})_n$—C(=O)O$R^{Be}$ or —$(CR^{Ba}R^{Bb})_{n1}$—O—$(CR^{Ba}R^{Bb})_n$—C(=O)O$R^{Be}$;
(xiii) —$(CR^{Ba}R^{Bb})_n$$NR^{Bd}$—C(=O)$R^{Bc}$ or —$(CR^{Ba}R^{Bb})_n$—O—$(CR^{Ba}R^{Bb})_n$—$NR^{Bd}$—C(=O)$R^{Bc}$;
(xiv) —$(CR^{Ba}R^{Bb})_n$$NR^{Bd}$—C(=O)O$R^{Bc}$ or —$(CR^{Ba}R^{Bb})_{n1}$—O—$(CR^{Ba}R^{Bb})_{n1}$—$NR^{Bd}$—C(=O)O$R^{Bc}$;
(xv) —$(CR^{Ba}R^{Bb})_n$—C(=O)$NR^{Bc}R^{Bd}$ or —$(CR^{Ba}R^{Bb})_{n1}$—O—$(CR^{Ba}R^{Bb})_n$—C(=O)$NR^{Bc}R^{Bd}$;
(xvi) —$(CR^{Ba}R^{Bb})_n$—$NR^{Bd}R^{Be}$ or —$(CR^{Ba}R^{Bb})_{n1}$—O—$(CR^{Ba}R^{Bb})_n$—$NR^{Bd}R^{Be}$;
(xvii) —$(CR^{Ba}R^{Bb})_n$—$NR^{Bd}$—S(O)$_2$—$R^{Bf}$;
(xviii) —$(CR^{Ba}R^{Bb})_n$—S(O)$_2$—$NR^{Bd}R^{Be}$ or —$(CR^{Ba}R^{Bb})_{n1}$—O—$(CR^{Ba}R^{Bb})_n$—S(O)$_2$—$NR^{Bd}R^{Be}$;
(xix) —$(CR^{Ba}R^{Bb})_n$—S(O)$_2$—$R^{Bf}$;
(xx) halogen;
(xxi) OH;
(xxii) oxo; and
(xxiii) CN;
$R^{Ba}$, $R^{Bb}$, $R^{Xa}$, $R^{Xb}$ are independently selected from the group consisting of H, OH, $C_{1-4}$ alkyl and $C_{1-4}$ alkoxy;
$R^{Bc}$, $R^{Be}$ and $R^{Bf}$ are independently selected from the group consisting of H, $C_{1-4}$alkyl, —$(CR^{Ba}R^{Bb})_{n1}$—$C_{3-6}$cycloalkyl, —$(CR^{Ba}R^{Bb})_{n1}$—$C_{3-6}$cycloalkenyl, hydroxy $C_{1-4}$alkyl, $C_{1-4}$haloalkyl, $C_{1-4}$alkoxy$C_{1-4}$alkyl, OH, —$(CR^{Ba}R^{Bb})_{n1}$-5 or 6 membered heteroaryl, —$(CR^{Ba}R^{Bb})_{n1}$-phenyl and —$(CR^{Ba}R^{Bb})_{n1}$-5 or 6 membered heterocyclyl, wherein the $C_{3-6}$cycloalkyl, heteroaryl, phenyl and heterocyclyl are unsubstituted or substituted by 1 to 3 substituents selected from the group consisting of X;

$R^{Bd}$ is selected from the group consisting of H and $C_{1-4}$alkyl; or $R^{Bc}$ and $R^{Bd}$ or $R^{Bd}$ and $R^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, $-(CR^{Xa}R^{Xb})_q-C_{3-6}$ cycloalkyl, $-(CR^{Ba}R^{Bb})_{n1}-C_{3-6}$cycloalkenyl, halogen, CN, $-(CR^{Xa}R^{Xb})_q$-5 or 6 membered heterocyclyl, $-(CR^{Xa}R^{Xb})_q$-5 or 6 membered heteroaryl, $-(CR^{Xa}R^{Xb})_q$-phenyl, oxo, OH, $-(CR^{Xa}R^{Xb})_q-C(=O)R^{Xc}$, $-(CR^{Xa}R^{Xb})_q-C(=O)OR^{Xc}$, $-(CR^{Xa}R^{Xb})_q-NR^{Xd}R^{Xe}$ and $-(CR^{Xa}R^{Xb})_q-C(=O)NR^{Xd}R^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, $-(CR^{Xa}R^{Xb})_q-C_{3-6}$cycloalkyl, hydroxy$C_{1-4}$alkyl, $C_{1-4}$haloalkyl, $C_{1-4}$alkoxy$C_{1-4}$alkyl, halogen and OH;

$R^{Xc}$, $R^{Xd}$ and $R^{Xe}$ are independently selected from the group consisting of H, $C_{1-4}$alkyl, $-(CR^{Xa}R^{Xb})_{q1}-C_{3-6}$ cycloalkyl, hydroxy$C_{1-4}$alkyl, $C_{1-4}$haloalkyl, $C_{1-4}$alkoxy $C_{1-4}$alkyl, OH $-(CR^{Xa}R^{Xb})_q$-5 or 6 membered heterocyclyl and $-(CR^{Xa}R^{Xb})_{q1}$-5 or 6 membered heteroaryl;

wherein the $C_{3-6}$ cycloalkyl, heterocyclyl and heteroaryl are unsubstituted or substituted by 1 to 3 substituents independently selected from the group consisting of $C_{1-4}$ alkyl, $C_{1-4}$ alkoxy, $-(CR^{Xa}R^{Xb})_{q1}-C_{3-6}$ cycloalkyl, $C_{1-4}$ haloalkyl, hydroxy$C_{1-4}$alkyl, $C_{1-4}$alkoxy$C_{1-4}$alkyl, halogen and OH; or $R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, $-(CR^{Xa}R^{Xb})_{q1}-C_{3-6}$ cycloalkyl, hydroxy $C_{1-4}$alkyl, $C_{1-4}$haloalkyl, $C_{1-4}$alkoxy$C_{1-4}$alkyl, halogen and OH;

n and n1 are independently selected from the group consisting of 0, 1, 2, 3, 4 and 5;

q and q1 are independently selected from the group consisting of 0, 1 and 2.

Embodiment 3.1: A compound or salt according to embodiment 1, wherein

A is selected from the group consisting of

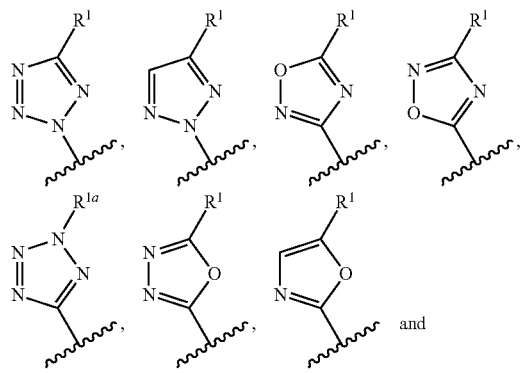

-continued

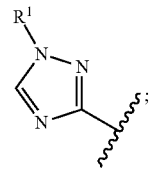

$R^1$ is selected from the group consisting of H and $C_{1-4}$ alkyl;

$R^{1a}$ is $C_{1-4}$ alkyl;

$R^2$ is halogen, $-CF_3$, $-CF_2H$, $-OCF_3$, $-OCF_2H$, $-OCH_3$, $-CH_3$ or CN, and $R^3$, $R^4$ and $R^5$ are H; or $R^3$ is halogen and $R^2$, $R^4$ and $R^5$ are H; or $R^4$ is halogen and $R^2$, $R^3$ and $R^5$ are H; or $R^2$ is halogen, $-CF_3$, $-CF_2H$, $-OCF_3$, $-OCF_2H$, $-OCH_3$, $-CH_3$ or CN, $R^3$ is halogen and $R^4$ and $R^5$ are H;

Y is selected from the group consisting of $-CH=CH-$, $-CH_2-CH_2-$, $-O-CH_2-$, $-CH_2-O-$, $-C(CH_3)=CH-$ and $-C=C(CH_3)-$;

B is selected from the group consisting of
(1) piperidin-1-yl,
(2) piperazin-1-yl,
(3) azetidin-1-yl,
(4) pyrrolidin-1-yl,
(5) morpholin-4-yl,
(6) 1,4-diazepan-1-yl,
(7) thiazolidin-3-yl, and
(8) 2,5-diazabicyclo[2.2.2]octan-2-yl;

wherein each of the rings (1) to (8) is unsubstituted or substituted with 1 to 3 substituents independently selected from the group consisting of Q;

Q is selected from the group consisting of
(i) $-(CR^{Ba}R^{Bb})_n$-5 or 6 membered heteroaryl or $-O-(CR^{Ba}R^{Bb})_n$-5 or 6 membered heteroaryl which heteroaryl is unsubstituted or substituted with 1 to 3 substituents independently selected from the group consisting of X;
(ii) $-(CR^{Ba}R^{Bb})_n$-phenyl or $-O-(CR^{Ba}R^{Bb})_n$-phenyl which phenyl is unsubstituted or substituted with 1 to 3 substituents independently selected from the group consisting of X;
(iii) $-(CR^{Ba}R^{Bb})_n$-9 to 10 membered fused bicyclic ring system or $-O-(CR^{Ba}R^{Bb})_n$-9 to 10 membered fused bicyclic ring system which 9 to 10 membered fused bicyclic ring system is unsubstituted or substituted with 1 to 3 substituents independently selected from the group consisting of X;
(iv) $-(CR^{Ba}R^{Bb})_n$-5 or 6 membered heterocyclyl or $-O-(CR^{Ba}R^{Bb})_n$-5 or 6 membered heterocyclyl which heterocyclyl is unsubstituted or substituted with 1 to 3 substituents independently selected from the group consisting of X;
(v) $C_{1-4}$ alkyl;
(vi) $C_{1-4}$ alkoxy;
(vii) $C_{1-4}$ alkoxy $C_{1-4}$ alkyl;
(viii) $C_{1-4}$ haloalkyl;
(ix) hydroxy $C_{1-4}$ alkyl;
(x) $-(CR^{Ba}R^{Bb})_n C_{3-6}$cycloalkyl;
(xi) $-(CR^{Ba}R^{Bb})_n-C(=O)R^{Bc}$ or $-O-(CR^{Ba}R^{Bb})_n-C(=O)R^{Bc}$;
(xii) $-(CR^{Ba}R^{Bb})_n-C(=O)OR^{Be}$ or $-O-(CR^{Ba}R^{Bb})_n C(=O)OR^{Be}$;
(xiii) $-(CR^{Ba}R^{Bb})_n NR^{Bd}-C(=O)R^{Bc}$ or $-O-(CR^{Ba}R^{Bb})_n NR^{Bd}-C(=O)R^{Bc}$;
(xiv) $-(CR^{Ba}R^{Bb})_n NR^{Bd}-C(=O)OR^{Bc}$ or $-O-(CR^{Ba}R^{Bb})_n NR^{Bd}-C(=O)OR^{Bc}$;

(xv) —(CR^{Ba}R^{Bb})_n—C(=O)NR^{Bc}R^{Bd} or —O—(CR^{Ba}R^{Bb})_n—C(=O)NR^{Bc}R^{Bd};
(xvi) —(CR^{Ba}R^{Bb})_n—NR^{Bd}R^{Be} or —O—(CR^{Ba}R^{Bb})_n—NR^{Bd}R^{Be};
(xvii) —(CR^{Ba}R^{Bb})_n—NR^{Bd}—S(O)_2—R^{Bf};
(xviii) —(CR^{Ba}R^{Bb})_n—S(O)_2—NR^{Bd}R^{Be} or —O—(CR^{Ba}R^{Bb})_n—S(O)_2—NR^{Bd}R^{Be};
(xix) —(CR^{Ba}R^{Bb})_n—S(O)_2—R^{Bf};
(xx) halogen;
(xxi) OH;
(xxii) oxo; and
(xxiii) CN;
$R^{Ba}$, $R^{Bb}$, $R^{Xa}$, $R^{Xb}$ are independently selected from the group consisting of H, OH, $C_{1-4}$ alkyl and $C_{1-4}$ alkoxy;
$R^{Bc}$, $R^{Be}$ and $R^{Bf}$ are independently selected from the group consisting of H, $C_{1-4}$alkyl, —(CR^{Ba}R^{Bb})_{n1}—C_{3-6}cycloalkyl, hydroxyC_{1-4}alkyl, $C_{1-4}$haloalkyl, $C_{1-4}$alkoxy $C_{1-4}$alkyl, OH, —(CR^{Ba}R^{Bb})_{n1}-5 or 6 membered heteroaryl, —(CR^{Ba}R^{Bb})_{n1}-phenyl and —(CR^{Ba}R^{Bb})_{n1}-5 or 6 membered heterocyclyl, wherein the $C_{3-6}$cycloalkyl, heteroaryl, phenyl and heterocyclyl are unsubstituted or substituted by 1 to 3 substituents selected from the group consisting of X;
$R^{Bd}$ is selected from the group consisting of H and $C_{1-4}$alkyl; or
$R^{Bc}$ and $R^{Bd}$ or $R^{Bd}$ and $R^{Be}$ together with the nitrogen atom to which they are attached form a 5 to 6 membered heterocyclyl which heterocyclyl is unsubstituted or substituted by 1 to 3 substituents selected from the group consisting of X;
X is independently selected from the group consisting of $C_{1-4}$ alkyl, $C_{1-4}$ alkoxy, $C_{1-4}$ haloalkyl, hydroxyC_{1-4}alkyl, $C_{1-4}$alkoxyC_{1-4}alkyl, —(CR^{Xa}R^{Xb})_q—C_{1-6} cycloalkyl, halogen, CN, —(CR^{Xa}R^{Xb})_q-5 or 6 membered heterocyclyl, —(CR^{Xa}R^{Xb})_q-5 or 6 membered heteroaryl, —(CR^{Xa}R^{Xb})_q-phenyl, oxo, OH, —(CR^{Xa}R^{Xb})_q—C(=O)R^{Xc}, —(CR^{Xa}R^{Xb})_q—C(=O)OR^{Xc}, —(CR^{Xa}R^{Xb})_q—NR^{Xd}R^{Xe} and —(CR^{Xa}R^{Xb})_q—C(=O)NR^{Xd}R^{Xe}; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —(CR^{Xa}R^{Xb})_q—C_{3-6}cycloalkyl, hydroxyC_{1-4}alkyl, $C_{1-4}$haloalkyl, $C_{1-4}$alkoxyC_{1-4}alkyl, halogen and OH;
$R^{Xc}$, $R^{Xd}$ and $R^{Xe}$ are independently selected from the group consisting of H, $C_{1-4}$alkyl, —(CR^{Xa}R^{Xb})_q—C_{3-6}cycloalkyl, hydroxyC_{1-4}alkyl, $C_{1-4}$haloalkyl, $C_{1-4}$alkoxy $C_{1-4}$alkyl, OH and —(CR^{Xa}R^{Xb})_q-5 or 6 membered heterocyclyl; wherein the $C_{3-6}$cycloalkyl and heterocyclyl are unsubstituted or substituted by 1 to 3 substituents independently selected from the group consisting of $C_{1-4}$ alkyl, $C_{1-4}$ alkoxy, —(CR^{Xa}R^{Xb})_q—C_{3-6}cycloalkyl, $C_{1-4}$ haloalkyl, hydroxyC_{1-4}alkyl, $C_{1-4}$alkoxyC_{1-4}alkyl, halogen and OH; or
$R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —(CR^{Xa}R^{Xb})_q—C_{3-6}cycloalkyl, hydroxy $C_{1-4}$alkyl, $C_{1-4}$haloalkyl, $C_{1-4}$alkoxyC_{1-4}alkyl, halogen and OH;
n and n1 are independently selected from the group consisting of 0, 1, 2, 3 and 4;
q is selected from the group consisting of 0, 1 and 2;
wherein when Q or $R^{Bc}$ is a 5 membered heteroaryl selected from the group consisting of
1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;
then said heteroaryl is substituted with 1 or 2 substituents independently selected from the group consisting of $C_{1-4}$ alkyl, $C_{1-4}$ alkoxy, $C_{1-4}$ haloalkyl, hydroxyC_{1-4}alkyl, $C_{1-4}$alkoxyC_{1-4}alkyl, —(CR^{Xa}R^{Xb})_q—C_{1-6} cycloalkyl, halogen, CN, —(CR^{Xa}R^{Xb})_q-5 or 6 membered heterocyclyl, —(CR^aR^{Xb})_q-phenyl, —(CR^{Xa}R^{Xb})_q—C(=O)R^{Xc}, —(CR^{Xa}R^{Xb})_q—C(=O)OR^{Xc}, —(CR^{Xa}R^{Xb})_q—NR^{Xd}R^{Xe} and —(CR^{Xa}R^{Xb})_q—C(=O)NR^{Xd}R^{Xe};
and wherein when Q or $R^{Bc}$ is a 5 membered heteroaryl selected from the group consisting of
1H-1,2,3-triazol-4-yl;
2H-1,2,3-triazol-4-yl;
1H-1,2,3-triazol-5-yl;
then said triazolyl is substituted with 1 or 2 substituents independently selected from the group consisting of $C_{1-4}$ alkoxy, $C_{1-4}$ haloalkyl, hydroxyC_{1-4}alkyl, $C_{1-4}$alkoxy $C_{1-4}$alkyl, —(CR^{Xa}R^{Xb})_qC_{1-6}cycloalkyl, CN, —(CR^{Xa}R^{Xb})_q-5 or 6 membered heterocyclyl, —(CR^{Xa}R^{Xb})_q-phenyl, oxo, OH, —(CR^{Xa}R^{Xb})_q—C(=O)R^{Xc}, —(CR^{Xa}R^{Xb})_q—C(=O)OR^{Xc}, —(CR^{Xa}R^{Xb})_q—NR^{Xd}R^{Xe} and —(CR^{Xa}R^{Xb})_q—C(=O)NR^{Xd}R^{Xe}.
Embodiment 4: A compound or salt according to embodiment 1, wherein
A is selected from the group consisting of

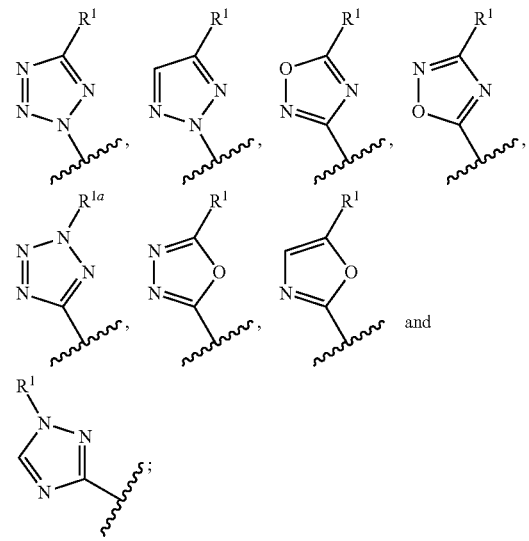

$R^1$ is selected from the group consisting of H and $C_{1-4}$ alkyl;
$R^{1a}$ is $C_{1-4}$ alkyl;
$R^2$ is halogen, —CF_3, —CF_2H, —OCF_3, —OCF_2H, —OCH_3, —CH_3 or CN, and $R^3$, $R^4$ and $R^5$ are H; or
$R^3$ is halogen and $R^2$, $R^4$ and $R^5$ are H; or
$R^4$ is halogen and $R^2$, $R^3$ and $R^5$ are H; or
$R^2$ is halogen, —CF_3, —CF_2H, —OCF_3, —OCF_2H, —OCH_3, —CH_3 or CN, $R^3$ is halogen and $R^4$ and $R^5$ are H;

Y is selected from the group consisting of —CH=CH—, —CH$_2$—CH$_2$—, —O—CH$_2$—, —CH$_2$—O—, —C(CH$_3$)=CH— and —C=C(CH$_3$)—;

B is selected from the group consisting of
(1) piperidin-1-yl,
(2) piperazin-1-yl,
(3) azetidin-1-yl,
(4) pyrrolidin-1-yl,
(5) morpholin-4-yl,
(6) 1,4-diazepan-1-yl,
(7) thiazolidin-3-yl, and
(8) 2,5-diazabicyclo[2.2.2]octan-2-yl;
wherein each of the rings (1) to (8) is unsubstituted or substituted with 1 to 3 substituents independently selected from the group consisting of Q;

Q is selected from the group consisting of
(i) —(CR$^{Ba}$R$^{Bb}$)$_n$-5 or 6 membered heteroaryl or —O—(CR$^{Ba}$R$^{Bb}$)$_n$-5 or 6 membered heteroaryl which heteroaryl is unsubstituted or substituted with 1 to 3 substituents independently selected from the group consisting of X;
(ii) —(CR$^{Ba}$R$^{Bb}$)$_n$-9 to 10 membered fused bicyclic ring system or —O—(CR$^{Ba}$R$^{Bb}$)$_n$-9 to 10 membered fused bicyclic ring system which 9 to 10 membered fused bicyclic ring system is unsubstituted or substituted with 1 to 3 substituents independently selected from the group consisting of X;
(iii) —(CR$^{Ba}$R$^{Bb}$)$_n$-5 or 6 membered heterocyclyl or —O—(CR$^{Ba}$R$^{Bb}$)$_n$-5 or 6 membered heterocyclyl which heterocyclyl is unsubstituted or substituted with 1 to 3 substituents independently selected from the group consisting of X;
(iv) C$_{1-4}$ alkyl;
(v) C$_{1-4}$ alkoxy;
(vi) C$_{1-4}$ alkoxy C$_{1-4}$ alkyl;
(vii) C$_{1-4}$ haloalkyl;
(viii) hydroxy C$_{1-4}$ alkyl;
(ix) —(CR$^{Ba}$R$^{Bb}$)$_n$C$_{3-6}$ cycloalkyl;
(x) —(CR$^{Ba}$R$^{Bb}$)$_n$—C(=O)R$^{Bc}$ or —O—(CR$^{Ba}$R$^{Bb}$)$_n$—C(=O)R$^{Bc}$;
(xi) —(CR$^{Ba}$R$^{Bb}$)$_n$—C(=O)OR$^{Be}$ or —O—(CR$^{Ba}$R$^{Bb}$)$_n$C(=O)OR$^{Be}$;
(xii) —(CR$^{Ba}$R$^{Bb}$)$_n$NR$^{Bd}$—C(=O)R$^{Bc}$ or —O—(CR$^{Ba}$R$^{Bb}$)$_n$NR$^{Bd}$—C(=O)R$^{Bc}$;
(xiii) —(CR$^{Ba}$R$^{Bb}$)$_n$NR$^{Bd}$—C(=O)OR$^{Bc}$ or —O—(CR$^{Ba}$R$^{Bb}$)$_n$NR$^{Bd}$—C(=O)OR$^{Bc}$;
(xiv) —(CR$^{Ba}$R$^{Bb}$)$_n$—C(=O)NR$^{Bc}$R$^{Bd}$ or —O—(CR$^{Ba}$R$^{Bb}$)$_n$—C(=O)NR$^{Bc}$R$^{Bd}$;
(xv) —(CR$^{Ba}$R$^{Bb}$)$_n$—NR$^{Bd}$R$^{Be}$ or —O—(CR$^{Ba}$R$^{Bb}$)$_n$—NR$^{Bd}$R$^{Be}$;
(xvi) —(CR$^{Ba}$R$^{Bb}$)$_n$—NR$^{Bd}$—S(O)$_2$—R$^{Bf}$;
(xvii) —(CR$^{Ba}$R$^{Bb}$)$_n$—S(O)$_2$—NR$^{Bd}$R$^{Be}$ or —O—(CR$^{Ba}$R$^{Bb}$)$_n$—S(O)$_2$—NR$^{Bd}$R$^{Be}$;
(xviii) —(CR$^{Ba}$R$^{Bb}$)$_n$—S(O)$_2$—R$^{Bf}$;
(xix) halogen;
(xx) OH;
(xxi) oxo; and
(xxii) CN;

R$^{Ba}$, R$^{Bb}$, R$^{Xa}$, R$^{Xb}$ are independently selected from the group consisting of H, OH, C$_{1-4}$ alkyl and C$_{1-4}$ alkoxy;

R$^{Bc}$, R$^{Be}$ and R$^{Bf}$ are independently selected from the group consisting of H, C$_{1-4}$alkyl, —(CR$^{Ba}$R$^{Bb}$)$_{n1}$—C$_{3-6}$cycloalkyl, —(CR$^{Ba}$R$^{Bb}$)$_{n1}$—C$_{3-6}$cycloalkenyl, hydroxy C$_{1-4}$alkyl, C$_{1-4}$haloalkyl, C$_{1-4}$alkoxyC$_{1-4}$alkyl, OH, —(CR$^{Ba}$R$^{Bb}$)$_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;

R$^{Bd}$ is selected from the group consisting of H and C$_{1-4}$alkyl; or

R$^{Bc}$ and R$^{Bd}$ or R$^{Bd}$ and R$^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$ cycloalkyl, —(CR$^{Ba}$R$^{Bb}$)$_{n1}$—C$_{3-6}$cycloalkenyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xc}$, R$^{Xd}$ and R$^{Xe}$ are independently selected from the group consisting of H, C$_{1-4}$alkyl, —(CR$^{Xa}$R$^{Xb}$)$_{q1}$—C$_{3-6}$ cycloalkyl, hydroxyC$_{1-4}$alkyl, C$_{1-4}$haloalkyl, C$_{1-4}$alkoxy C$_{1-4}$alkyl, OH —(CR$^{Xa}$R$^{Xb}$)$_{q1}$-5 or 6 membered heterocyclyl and —(CR$^{Xa}$R$^{Xb}$)$_{q1}$-5 or 6 membered heteroaryl;

wherein the C$_{3-6}$ cycloalkyl, heterocyclyl and heteroaryl are unsubstituted or substituted by 1 to 3 substituents independently selected from the group consisting of C$_{1-4}$ alkyl, C$_{1-4}$ alkoxy, —(CR$^{Xa}$R$^{Xb}$)$_{q1}$—C$_{3-6}$ cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_{q1}$—C$_{3-6}$ cycloalkyl, hydroxy C$_{1-4}$alkyl, C$_{1-4}$haloalkyl, C$_{1-4}$alkoxyC$_{1-4}$alkyl, halogen and OH;

n and n1 are independently selected from the group consisting of 0, 1, 2, 3, 4 and 5;

q and q1 are independently selected from the group consisting of 0, 1 and 2.

Embodiment 4.1: A compound or salt according to embodiment 1, wherein

A is selected from the group consisting of

-continued

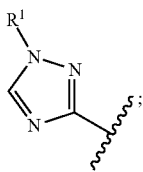

R¹ is selected from the group consisting of H and C$_{1-4}$ alkyl;
R$^{1a}$ is C$_{1-4}$ alkyl;
R² is halogen, —CF$_3$, —CF$_2$H, —OCF$_3$, —OCF$_2$H, —OCH$_3$, —CH$_3$ or CN, and R³, R⁴ and R⁵ are H; or
R³ is halogen and R², R⁴ and R⁵ are H; or
R⁴ is halogen and R², R³ and R⁵ are H; or
R² is halogen, —CF$_3$, —CF$_2$H, —OCF$_3$, —OCF$_2$H, —OCH$_3$, —CH$_3$ or CN, R³ is halogen and R⁴ and R⁵ are H;
Y is selected from the group consisting of —CH=CH—, —CH$_2$—CH$_2$—, —O—CH$_2$—, —CH$_2$—O—, —C(CH$_3$)=CH— and —C=C(CH$_3$)—;
B is selected from the group consisting of
(1) piperidin-1-yl,
(2) piperazin-1-yl,
(3) azetidin-1-yl,
(4) pyrrolidin-1-yl,
(5) morpholin-4-yl,
(6) 1,4-diazepan-1-yl,
(7) thiazolidin-3-yl, and
(8) 2,5-diazabicyclo[2.2.2]octan-2-yl;
wherein each of the rings (1) to (8) is unsubstituted or substituted with 1 to 3 substituents independently selected from the group consisting of Q;
Q is selected from the group consisting of
(i) —(CR$^{Ba}$R$^{Bb}$)$_n$-5 or 6 membered heteroaryl or —O—(CR$^{Ba}$R$^{Bb}$)$_n$-5 or 6 membered heteroaryl which heteroaryl is unsubstituted or substituted with 1 to 3 substituents independently selected from the group consisting of X;
(ii) —(CR$^{Ba}$R$^{Bb}$)$_n$-9 to 10 membered fused bicyclic ring system or —O—(CR$^{Ba}$R$^{Bb}$)$_n$-9 to 10 membered fused bicyclic ring system which 9 to 10 membered fused bicyclic ring system is unsubstituted or substituted with 1 to 3 substituents independently selected from the group consisting of X;
(iii) —(CR$^{Ba}$R$^{Bb}$)$_n$-5 or 6 membered heterocyclyl or —O—(CR$^{Ba}$R$^{Bb}$)$_n$-5 or 6 membered heterocyclyl which heterocyclyl is unsubstituted or substituted with 1 to 3 substituents independently selected from the group consisting of X;
(iv) C$_{1-4}$ alkyl;
(v) C$_{1-4}$ alkoxy;
(vi) C$_{1-4}$ alkoxy C$_{1-4}$ alkyl;
(vii) C$_{1-4}$ haloalkyl;
(viii) hydroxy C$_{1-4}$ alkyl;
(ix) —(CR$^{Ba}$R$^{Bb}$)$_n$C$_{3-6}$cycloalkyl;
(x) —(CR$^{Ba}$R$^{Bb}$)$_n$—C(=O)R$^{Bc}$ or —O—(CR$^{Ba}$R$^{Bb}$)$_n$—C(=O)R$^{Bc}$;
(xi) —(CR$^{Ba}$R$^{Bb}$)$_n$—C(=O)OR$^{Be}$ or —O—(CR$^{Ba}$R$^{Bb}$)$_n$C(=O)OR$^{Be}$;
(xii) —(CR$^{Ba}$R$^{Bb}$)$_n$NR$^{Bd}$—C(=O)R$^{Bc}$ or —O—(CR$^{Ba}$R$^{Bb}$)$_n$NR$^{Bd}$—C(=O)R$^{Bc}$;
(xiii) —(CR$^{Ba}$R$^{Bb}$)$_n$NR$^{Bd}$—C(=O)OR$^{Bc}$ or —O—(CR$^{Ba}$R$^{Bb}$)$_n$NR$^{Bd}$—C(=O)OR$^{Bc}$;
(xiv) —(CR$^{Ba}$R$^{Bb}$)$_n$—C(=O)NR$^{Bc}$R$^{Bd}$ or —O—(CR$^{Ba}$R$^{Bb}$)$_n$—C(=O)NR$^{Bc}$R$^{Bd}$;
(xv) —(CR$^{Ba}$R$^{Bb}$)$_n$—NR$^{Bd}$R$^{Be}$ or —O—(CR$^{Ba}$R$^{Bb}$)$_n$—NR$^{Bd}$R$^{Be}$;
(xvi) —(CR$^{Ba}$R$^{Bb}$)$_n$—NR$^{Bd}$—S(O)$_2$—R$^{Bf}$;
(xvii) —(CR$^{Ba}$R$^{Bb}$)$_n$—S(O)$_2$—NR$^{Bd}$R$^{Be}$ or —O—(CR$^{Ba}$R$^{Bb}$)$_n$—S(O)$_2$—NR$^{Bd}$R$^{Be}$;
(xviii) —(CR$^{Ba}$R$^{Bb}$)$_n$—S(O)$_2$—R$^{Bf}$;
(xix) halogen;
(xx) OH;
(xxi) oxo; and
(xxii) CN;
R$^{Ba}$, R$^{Bb}$, R$^{Xa}$, R$^{Xb}$ are independently selected from the group consisting of H, OH, C$_{1-4}$ alkyl and C$_{1-4}$ alkoxy;
R$^{Bc}$, R$^{Be}$ and R$^{Bf}$ are independently selected from the group consisting of H, C$_{1-4}$alkyl, —(CR$^{Ba}$R$^{Bb}$)$_{n1}$—C$_{3-6}$cycloalkyl, hydroxyC$_{1-4}$alkyl, C$_{1-4}$haloalkyl, C$_{1-4}$alkoxyC$_{1-4}$alkyl, OH, —(CR$^{Ba}$R$^{Bb}$)$_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;
R$^{Bd}$ is selected from the group consisting of H and C$_{1-4}$alkyl; or
R$^{Bc}$ and R$^{Bd}$ or R$^{Bd}$ and R$^{Be}$ together with the nitrogen atom to which they are attached form a 5 to 6 membered heterocyclyl which heterocyclyl is unsubstituted or substituted by 1 to 3 substituents selected from the group consisting of X;
X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$ cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;
R$^{Xc}$, R$^{Xd}$ and R$^{Xe}$ are independently selected from the group consisting of H, C$_{1-4}$alkyl, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, OH and —(CR$^{Xa}$R$^{Xb}$)$_q$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_q$—C$_{3-6}$cycloalkyl, C$_{1-4}$ haloalkyl, hydroxyC$_{1-4}$alkyl, C$_{1-4}$alkoxyC$_{1-4}$alkyl, halogen and OH; or
R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_q$—C$_{3-6}$cycloalkyl, hydroxy C$_{1-4}$alkyl, C$_{1-4}$haloalkyl, C$_{1-4}$alkoxyC$_{1-4}$alkyl, halogen and OH;
n and n1 are independently selected from the group consisting of 0, 1, 2, 3 and 4;
q is selected from the group consisting of 0, 1 and 2;
wherein when Q or R$^{Bc}$ is a 5 membered heteroaryl selected from the group consisting of
1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;

isoxazol-5-yl;
isothiazol-5-yl;
pyrazol-3-yl; and
pyrazol-5-yl;
then said heteroaryl is substituted with 1 or 2 substituents independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-phenyl, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—N$R^{Xd}R^{Xe}$ and —$(CR^{Xa}R^{Xb})_q$—C(=O)N$R^{Xd}R^{Xe}$;

and wherein when Q or $R^{Bc}$ is a 5 membered heteroaryl selected from the group consisting of
1H-1,2,3-triazol-4-yl;
2H-1,2,3-triazol-4-yl;
1H-1,2,3-triazol-5-yl;
then said triazolyl is substituted with 1 or 2 substituents independently selected from the group consisting of $C_{1-4}$ alkoxy, $C_{1-4}$ haloalkyl, hydroxy$C_{1-4}$alkyl, $C_{1-4}$alkoxy $C_{1-4}$alkyl, —$(CR^{Xa}R^{Xb})_q$—$C_{3-6}$cycloalkyl, CN, —$(CR^{Xa}R^{Xb})_q$-5 or 6 membered heterocyclyl, —$(CR^{Xa}R^{Xb})_q$-phenyl, oxo, OH, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—N$R^{Xd}R^{Xe}$ and —$(CR^{Xa}R^{Xb})_q$—C(=O)N$R^{Xd}R^{Xe}$.

Embodiment 5: A compound or salt according to embodiment 1, wherein
A is selected from the group consisting of

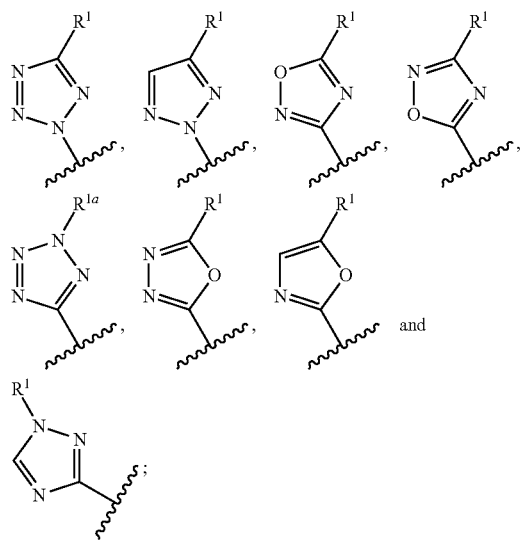

$R^1$ is selected from the group consisting of H and $C_{1-4}$ alkyl;
$R^{1a}$ is $C_{1-4}$ alkyl;
$R^2$ is halogen, —$CF_3$, —$CF_2H$, —$OCF_3$, —$OCF_2H$, —$OCH_3$, —$CH_3$ or CN, and $R^3$, $R^4$ and $R^5$ are H; or
$R^3$ is halogen and $R^2$, $R^4$ and $R^5$ are H; or
$R^4$ is halogen and $R^2$, $R^3$ and $R^5$ are H; or
$R^2$ is halogen, —$CF_3$, —$CF_2H$, —$OCF_3$, —$OCF_2H$, —$OCH_3$, —$CH_3$ or CN, $R^3$ is halogen and $R^4$ and $R^5$ are H;
Y is selected from the group consisting of —CH=CH—, —$CH_2$—$CH_2$—, —O—$CH_2$—, —$CH_2$—O—, —C($CH_3$)=CH— and —C=C($CH_3$)—;

B is selected from the group consisting of

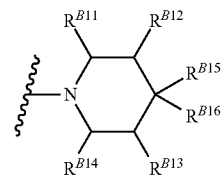

(1)

wherein
(1.1) $R^{B11}$, $R^{B12}$, $R^{B13}$ and $R^{B14}$ are H; $R^{B15}$ is selected from the group consisting of Q; and
$R^{B16}$ is selected from the group consisting of H, OH and $C_{1-4}$ alkyl; or
(1.2) $R^{B12}$, $R^{B13}$, $R^{B14}$, $R^{B15}$ and $R^{B16}$ are H; and $R^{B11}$ is selected from the group consisting of Q; or
(1.3) $R^{B11}$, $R^{B13}$, $R^{B14}$, $R^{B15}$ and $R^{B16}$ are H; and $R^{B12}$ is selected from the group consisting of Q; or
(1.4) $R^{B12}$, $R^{B13}$, $R^{B14}$, $R^{B16}$ are H; $R^{B11}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; and $R^{B15}$ is selected from the group consisting of Q;

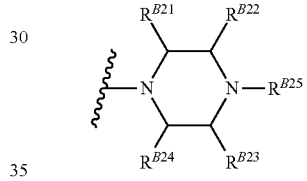

(2)

wherein
(2.1) $R^{B21}$, $R^{B22}$, $R^{B23}$ and $R^{B24}$ are H; and $R^{B25}$ is selected from the group consisting of Q; or
(2.2) $R^{B22}$, $R^{B23}$, $R^{B24}$, $R^{B25}$ are H; and $R^{B21}$ is selected from the group consisting of Q; or
(2.3) $R^{B21}$, $R^{B23}$, $R^{B24}$, $R^{B25}$ are H; and $R^{B22}$ is selected from the group consisting of Q; or
(2.4) $R^{B22}$, $R^{B23}$ and $R^{B24}$ are H; $R^{B21}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; and $R^{B25}$ is selected from the group consisting of Q;

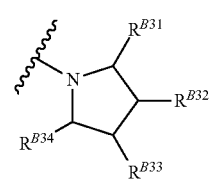

(3)

wherein
(3.1) $R^{B32}$, $R^{B33}$ and $R^{B34}$ are H; $R^{B31}$ is selected from a group consisting of Q; or
(3.2) $R^{B31}$, $R^{B33}$ and $R^{B34}$ are H; $R^{B32}$ is selected from a group consisting of Q; or
(3.3) $R^{B32}$ and $R^{B34}$ are H; $R^{B33}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; $R^{B31}$ is selected from a group consisting of Q;

(4)

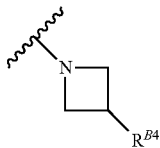

wherein
R$^{B4}$ is selected from a group consisting of Q;

(5)

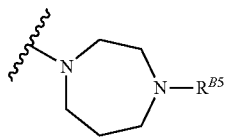

wherein
R$^{B5}$ is selected from a group consisting of Q;

(6)

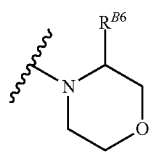

wherein
R$^{B6}$ is selected from a group consisting of Q;

(7)

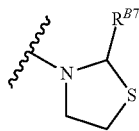

wherein
R$^{B7}$ is selected from a group consisting of Q;

(8)

wherein
R$^{B8}$ is selected from a group consisting of Q;
Q is selected from the group consisting of
(i) —(CR$^{Ba}$R$^{Bb}$)$_n$-5 or 6 membered heteroaryl or —(CR$^{Ba}$R$^{Bb}$)$_{n1}$—O—(CR$^{Ba}$R$^{Bb}$)$_n$-5 or 6 membered heteroaryl which heteroaryl is unsubstituted or substituted with 1 to 3 substituents independently selected from the group consisting of X;
(ii) —(CR$^{Ba}$R$^{Bb}$)$_n$-phenyl or —(CR$^{Ba}$R$^{Bb}$)$_{n1}$—O—(CR$^{Ba}$R$^{Bb}$)$_n$-phenyl which phenyl is unsubstituted or substituted with 1 to 3 substituents independently selected from the group consisting of X;
(iii) —(CR$^{Ba}$R$^{Bb}$)$_n$-9 to 10 membered fused bicyclic ring system or —(CR$^{Ba}$R$^{Bb}$)$_{n1}$—O—(CR$^{Ba}$R$^{Bb}$)$_n$-9 to 10 membered fused bicyclic ring system which 9 to 10 membered fused bicyclic ring system is unsubstituted or substituted with 1 to 3 substituents independently selected from the group consisting of X;
(iv) —(CR$^{Ba}$R$^{Bb}$)$_n$-5 or 6 membered heterocyclyl or —(CR$^{Ba}$R$^{Bb}$)$_{n1}$—O—(CR$^{Ba}$R$^{Bb}$)$_n$-5 or 6 membered heterocyclyl which heterocyclyl is unsubstituted or substituted with 1 to 3 substituents independently selected from the group consisting of X;
(v) C$_{1-4}$ alkyl;
(vi) C$_{1-4}$ alkoxy;
(vii) C$_{1-4}$ alkoxy C$_{1-4}$ alkyl;
(viii) C$_{1-4}$ haloalkyl;
(ix) hydroxy C$_{1-4}$ alkyl;
(x) —(CR$^{Ba}$R$^{Bb}$)$_n$C$_{3-6}$cycloalkyl;
(xi) —(CR$^{Ba}$R$^{Bb}$)$_n$—C(=O)R$^{Bc}$ or —(CR$^{Ba}$R$^{Bb}$)$_{n1}$—O—(CR$^{Ba}$R$^{Bb}$)$_n$—C(=O)R$^{Bc}$;
(xii) —(CR$^{Ba}$R$^{Bb}$)$_n$—C(=O)OR$^{Be}$ or —(CR$^{Ba}$R$^{Bb}$)$_{n1}$—O—(CR$^{Ba}$R$^{Bb}$)$_n$—C(=O)OR$^{Be}$;
(xiii) —(CR$^{Ba}$R$^{Bb}$)$_n$NR$^{Bd}$—C(=O)R$^{Bc}$ or —(CR$^{Ba}$R$^{Bb}$)$_{n1}$—O—(CR$^{Ba}$R$^{Bb}$)$_n$—NR$^{Bd}$—C(=O)R$^{Bc}$;
(xiv) —(CR$^{Ba}$R$^{Bb}$)$_n$NR$^{Bd}$—C(=O)OR$^{Bc}$ or —(CR$^{Ba}$R$^{Bb}$)$_{n1}$—O—(CR$^{Ba}$R$^{Bb}$)$_n$—NR$^{Bd}$—C(=O)OR$^{Bc}$;
(xv) —(CR$^{Ba}$R$^{Bb}$)$_n$—C(=O)NR$^{Bc}$R$^{Bd}$ or —(CR$^{Ba}$R$^{Bb}$)$_{n1}$—O—(CR$^{Ba}$R$^{Bb}$)$_n$—C(=O)NR$^{Bc}$R$^{Bd}$;
(xvi) —(CR$^{Ba}$R$^{Bb}$)$_n$—NR$^{Bd}$R$^{Be}$ or —(CR$^{Ba}$R$^{Bb}$)$_{n1}$—O—(CR$^{Ba}$R$^{Bb}$)$_n$—NR$^{Bd}$R$^{Be}$;
(xvii) —(CR$^{Ba}$R$^{Bb}$)$_n$—NR$^{Bd}$—S(O)$_2$—R$^{Bf}$;
(xviii) —(CR$^{Ba}$R$^{Bb}$)$_n$—S(O)$_2$—NR$^{Bd}$R$^{Be}$ or —(CR$^{Ba}$R$^{Bb}$)$_{n1}$—O—(CR$^{Ba}$R$^{Bb}$)$_n$—S(O)$_2$—NR$^{Bd}$R$^{Be}$;
(xix) —(CR$^{Ba}$R$^{Bb}$)$_n$—S(O)$_2$—R$^{Bf}$;
(xx) halogen;
(xxi) OH;
(xxii) oxo; and
(xxiii) CN;
R$^{Ba}$, R$^{Bb}$, R$^{Xa}$, R$^{Xb}$ are independently selected from the group consisting of H, OH, C$_{1-4}$ alkyl and C$_{1-4}$ alkoxy;
R$^{Bc}$, R$^{Be}$ and R$^{Bf}$ are independently selected from the group consisting of H, C$_{1-4}$alkyl, —(CR$^{Ba}$R$^{Bb}$)$_{n1}$—C$_{3-6}$cycloalkyl, —(CR$^{Ba}$R$^{Bb}$)$_{n1}$—C$_{3-6}$cycloalkenyl, hydroxyC$_{1-4}$alkyl, C$_{1-4}$haloalkyl, C$_{1-4}$alkoxyC$_{1-4}$alkyl, OH, —(CR$^{Ba}$R$^{Bb}$)$_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;
R$^{Bd}$ is selected from the group consisting of H and C$_{1-4}$alkyl; or
R$^{Bc}$ and R$^{Bd}$ or R$^{Bd}$ and R$^{Be}$ together with the nitrogen atom to which they are attached form a 5 to 6 membered heterocyclyl which heterocyclyl is unsubstituted or substituted by 1 to 3 substituents selected from the group consisting of X;
X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$ cycloalkyl, —(CR$^{Ba}$R$^{Bb}$)$_{n1}$—C$_{3-6}$cycloalkenyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

$R^{Xc}$, $R^{Xd}$ and $R^{Xe}$ are independently selected from the group consisting of H, $C_{1-4}$alkyl, $-(CR^{Xa}R^{Xb})_{q1}-C_{3-6}$ cycloalkyl, hydroxy$C_{1-4}$alkyl, $C_{1-4}$haloalkyl, $C_{1-4}$alkoxy $C_{1-4}$alkyl, OH $-(CR^{Xa}R^{Xb})_{q1}$-5 or 6 membered heterocyclyl and $-(CR^{Xa}R^{Xb})_{q1}$-5 or 6 membered heteroaryl;

wherein the $C_{3-6}$ cycloalkyl, heterocyclyl and heteroaryl are unsubstituted or substituted by 1 to 3 substituents independently selected from the group consisting of $C_{1-4}$ alkyl, $C_{1-4}$ alkoxy, $-(CR^{Xa}R^{Xb})_{q1}-C_{3-6}$ cycloalkyl, $C_{1-4}$ haloalkyl, hydroxy$C_{1-4}$alkyl, $C_{1-4}$alkoxy$C_{1-4}$alkyl, halogen and OH; or $R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, $-(CR^{Xa}R^{Xb})_{q1}-C_{3-6}$ cycloalkyl, hydroxy $C_{1-4}$alkyl, $C_{1-4}$haloalkyl, $C_{1-4}$alkoxy$C_{1-4}$alkyl, halogen and OH;

n and n1 are independently selected from the group consisting of 0, 1, 2, 3, 4 and 5;

q and q1 are independently selected from the group consisting of 0, 1 and 2.

Embodiment 5.1: A compound or salt according to embodiment 1, wherein

A is selected from the group consisting of

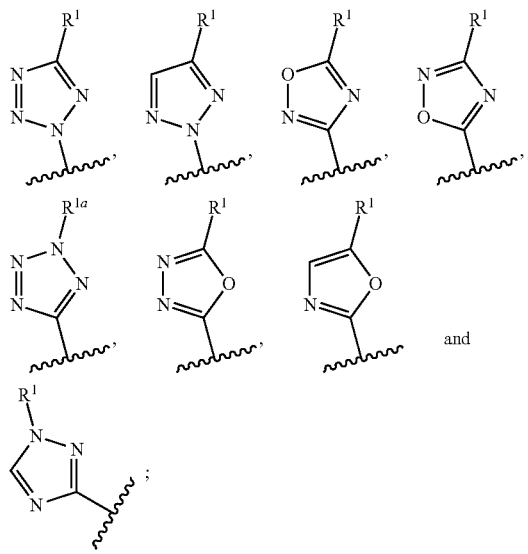

$R^1$ is selected from the group consisting of H and $C_{1-4}$ alkyl;

$R^{1a}$ is $C_{1-4}$ alkyl;

$R^2$ is halogen, $-CF_3$, $-CF_2H$, $-OCF_3$, $-OCF_2H$, $-OCH_3$, $-CH_3$ or CN, and $R^3$, $R^4$ and $R^5$ are H; or $R^3$ is halogen and $R^2$, $R^4$ and $R^5$ are H; or $R^4$ is halogen and $R^2$, $R^3$ and $R^5$ are H; or $R^2$ is halogen, $-CF_3$, $-CF_2H$, $-OCF_3$, $-OCF_2H$, $-OCH_3$, $-CH_3$ or CN, $R^3$ is halogen and $R^4$ and $R^5$ are H;

Y is selected from the group consisting of $-CH=CH-$, $-CH_2-CH_2-$, $-O-CH_2-$, $-CH_2-O-$, $-C(CH_3)=CH-$ and $-C=C(CH_3)-$;

B is selected from the group consisting of

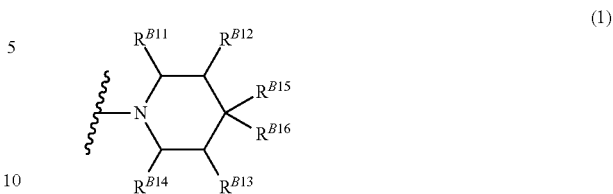

(1)

wherein
(1.1) $R^{B11}$, $R^{B12}$, $R^{B13}$ and $R^{B14}$ are H; $R^{B15}$ is selected from the group consisting of Q; and
$R^{B16}$ is selected from the group consisting of H, OH and $C_{1-4}$ alkyl; or
(1.2) $R^{B12}$, $R^{B13}$, $R^{B14}$, $R^{B15}$ and $R^{B16}$ are H; and $R^{B11}$ is selected from the group consisting of Q; or
(1.3) $R^{B11}$, $R^{B13}$, $R^{B14}$, $R^{B15}$ and $R^{B16}$ are H; and $R^{B12}$ is selected from the group consisting of Q; or
(1.4) $R^{B12}$, $R^{B13}$, $R^{B14}$, $R^{B16}$ are H; $R^{B11}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; and $R^{B15}$ is selected from the group consisting of Q;

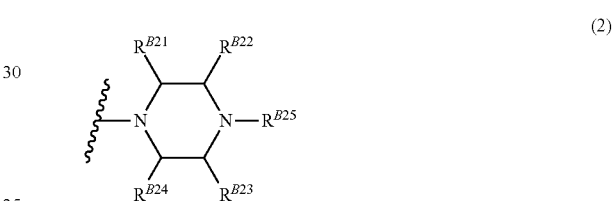

(2)

wherein
(2.1) $R^{B21}$, $R^{B22}$, $R^{B23}$ and $R^{B24}$ are H; and $R^{B25}$ is selected from the group consisting of Q; or
(2.2) $R^{B22}$, $R^{B23}$, $R^{B24}$, $R^{B25}$ are H; and $R^{B21}$ is selected from the group consisting of Q; or
(2.3) $R^{B21}$, $R^{B23}$, $R^{B24}$, $R^{B25}$ are H; and $R^{B22}$ is selected from the group consisting of Q; or
(2.4) $R^{B22}$, $R^{B23}$ and $R^{B24}$ are H; $R^{B21}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; and $R^{B25}$ is selected from the group consisting of Q;

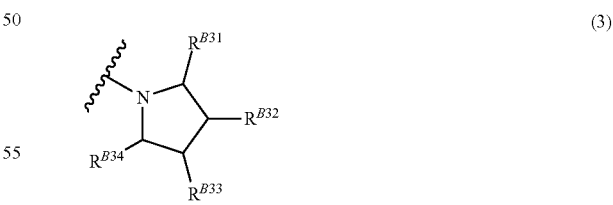

(3)

wherein
(3.1) $R^{B32}$, $R^{B33}$ and $R^{B34}$ are H; $R^{B31}$ is selected from a group consisting of Q; or
(3.2) $R^{B31}$, $R^{B33}$ and $R^{B34}$ are H; $R^{B32}$ is selected from a group consisting of Q; or
(3.3) $R^{B32}$ and $R^{B34}$ are H; $R^{B33}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; $R^{B31}$ is selected from a group consisting of Q;

(4)

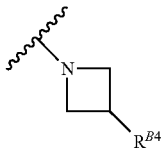

wherein
R$^{B4}$ is selected from a group consisting of Q;

(5)

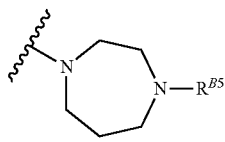

wherein
R$^{B5}$ is selected from a group consisting of Q;

(6)

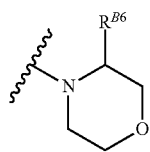

wherein
R$^{B6}$ is selected from a group consisting of Q;

(7)

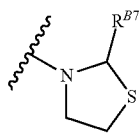

wherein
R$^{B7}$ is selected from a group consisting of Q;

(8)

wherein
R$^{B8}$ is selected from a group consisting of Q;
Q is selected from the group consisting of
(i) —(CR$^{Ba}$R$^{Bb}$)$_n$-5 or 6 membered heteroaryl or —O—(CR$^{Ba}$R$^{Bb}$)$_n$-5 or 6 membered heteroaryl which heteroaryl is unsubstituted or substituted with 1 to 3 substituents independently selected from the group consisting of X;
(ii) —(CR$^{Ba}$R$^{Bb}$)$_n$-phenyl or —O—(CR$^{Ba}$R$^{Bb}$)$_n$-phenyl which phenyl is unsubstituted or substituted with 1 to 3 substituents independently selected from the group consisting of X;
(iii) —(CR$^{Ba}$R$^{Bb}$)$_n$-9 to 10 membered fused bicyclic ring system or —O—(CR$^{Ba}$R$^{Bb}$)$_n$-9 to 10 membered fused bicyclic ring system which 9 to 10 membered fused bicyclic ring system is unsubstituted or substituted with 1 to 3 substituents independently selected from the group consisting of X;
(iv) —(CR$^{Ba}$R$^{Bb}$)$_n$-5 or 6 membered heterocyclyl or —O—(CR$^{Ba}$R$^{Bb}$)$_n$-5 or 6 membered heterocyclyl which heterocyclyl is unsubstituted or substituted with 1 to 3 substituents independently selected from the group consisting of X;
(v) C$_{1-4}$ alkyl;
(vi) C$_{1-4}$ alkoxy;
(vii) C$_{1-4}$ alkoxy C$_{1-4}$ alkyl;
(viii) C$_{1-4}$ haloalkyl;
(ix) hydroxy C$_{1-4}$ alkyl;
(x) —(CR$^{Ba}$R$^{Bb}$)$_n$C$_{3-6}$cycloalkyl;
(xi) —(CR$^{Ba}$R$^{Bb}$)$_n$—C(=O)R$^{Bc}$ or —O—(CR$^{Ba}$R$^{Bb}$)$_n$—C(=O)R$^{Bc}$;
(xii) —(CR$^{Ba}$R$^{Bb}$)$_n$—C(=O)OR$^{Be}$ or —O—(CR$^{Ba}$R$^{Bb}$)$_n$C(=O)OR$^{Be}$;
(xiii) —(CR$^{Ba}$R$^{Bb}$)$_n$NR$^{Bd}$—C(=O)R$^{Bc}$ or —O—(CR$^{Ba}$R$^{Bb}$)$_n$NR$^{Bd}$—C(=O)R$^{Bc}$;
(xiv) —(CR$^{Ba}$R$^{Bb}$)$_n$NR$^{Bd}$—C(=O)OR$^{Bc}$ or —O—(CR$^{Ba}$R$^{Bb}$)$_n$NR$^{Bd}$—C(=O)OR$^{Bc}$;
(xv) —(CR$^{Ba}$R$^{Bb}$)$_n$—C(=O)NR$^{Bc}$R$^{Bd}$ or —O—(CR$^{Ba}$R$^{Bb}$)$_n$—C(=O)NR$^{Bc}$R$^{Bd}$;
(xvi) —(CR$^{Ba}$R$^{Bb}$)$_n$—NR$^{Bd}$R$^{Be}$ or —O—(CR$^{Ba}$R$^{Bb}$)$_n$—NR$^{Bd}$R$^{Be}$;
(xvii) —(CR$^{Ba}$R$^{Bb}$)$_n$—NR$^{Bd}$—S(O)$_2$—R$^{Bf}$;
(xviii) —(CR$^{Ba}$R$^{Bb}$)$_n$—S(O)$_2$—NR$^{Bd}$R$^{Be}$ or —O—(CR$^{Ba}$R$^{Bb}$)$_n$—S(O)$_2$—NR$^{Bd}$R$^{Be}$;
(xix) —(CR$^{Ba}$R$^{Bb}$)$_n$—S(O)$_2$—R$^{Bf}$;
(xx) halogen;
(xxi) OH;
(xxii) oxo; and
(xxiii) CN;
R$^{Ba}$, R$^{Bb}$, R$^{Xa}$, R$^{Xb}$ are independently selected from the group consisting of H, OH, C$_{1-4}$ alkyl and C$_{1-4}$ alkoxy;
R$^{Bc}$, R$^{Be}$ and R$^{Bf}$ are independently selected from the group consisting of H, C$_{1-4}$alkyl, —(CR$^{Ba}$R$^{Bb}$)$_{n1}$'C$_{3-6}$cycloalkyl, hydroxyC$_{1-4}$alkyl, C$_{1-4}$haloalkyl, C$_{1-4}$alkoxy C$_{1-4}$alkyl, OH, —(CR$^{Ba}$R$^{Bb}$)$_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;
R$^{Bd}$ is selected from the group consisting of H and C$_{1-4}$alkyl; or
R$^{Bc}$ and R$^{Bd}$ or R$^{Bd}$ and R$^{Be}$ together with the nitrogen atom to which they are attached form a 5 to 6 membered heterocyclyl which heterocyclyl is unsubstituted or substituted by 1 to 3 substituents selected from the group consisting of X;
X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;
R$^{Xc}$, R$^{Xd}$ and R$^{Xe}$ are independently selected from the group consisting of H, C$_{1-4}$alkyl, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxy C$_{1-4}$alkyl, OH and —(CR$^{Xa}$R$^{Xb}$)$_q$-5 or 6 membered heterocyclyl; wherein the $C_{3-6}$cycloalkyl and heterocyclyl are unsubstituted or substituted by 1 to 3 substituents independently selected from the group consisting of $C_{1-4}$ alkyl, $C_{1-4}$ alkoxy, —$(CR^{Xa}R^{Xb})_q$—$C_{3-6}$cycloalkyl, $C_{1-4}$ haloalkyl, hydroxy$C_{1-4}$alkyl, $C_{1-4}$alkoxy$C_{1-4}$alkyl, halogen and OH; or $R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —$(CR^{Xa}R^{Xb})_q$—$C_{3-6}$cycloalkyl, hydroxy $C_{1-4}$alkyl, $C_{1-4}$haloalkyl, $C_{1-4}$alkoxy$C_{1-4}$alkyl, halogen and OH;

n and n1 are independently selected from the group consisting of 0, 1, 2, 3 and 4;

q is selected from the group consisting of 0, 1 and 2;

wherein when Q or $R^{Bc}$ is a 5 membered heteroaryl selected from the group consisting of 1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;

then said heteroaryl is substituted with 1 or 2 substituents independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-phenyl, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—N$R^{Xd}R^{Xe}$ and —$(CR^{Xa}R^{Xb})_q$—C(=O)N$R^{Xd}R^{Xe}$;

and wherein when Q or $R^{Bc}$ is a 5 membered heteroaryl selected from the group consisting of 1H-1,2,3-triazol-4-yl;
2H-1,2,3-triazol-4-yl;
1H-1,2,3-triazol-5-yl;

then said triazolyl is substituted with 1 or 2 substituents independently selected from the group consisting of $C_{1-4}$ alkoxy, $C_{1-4}$ haloalkyl, hydroxy$C_{1-4}$alkyl, $C_{1-4}$alkoxy $C_{1-4}$alkyl, —$(CR^{Xa}R^{Xb})_q$—$C_{3-6}$cycloalkyl, CN, —$(CR^{Xa}R^{Xb})_q$-5 or 6 membered heterocyclyl, —$(CR^{Xa}R^{Xb})_q$-phenyl, oxo, OH, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—N$R^{Xd}R^{Xe}$ and —$(CR^{Xa}R^{Xb})_q$—C(=O)N$R^{Xd}R^{Xe}$.

Embodiment 6: A compound or salt according to embodiment 1, wherein

A is selected from the group consisting of

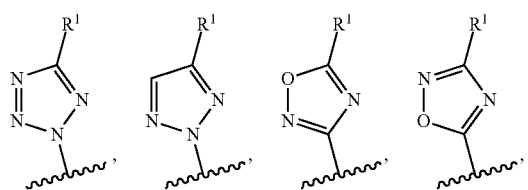

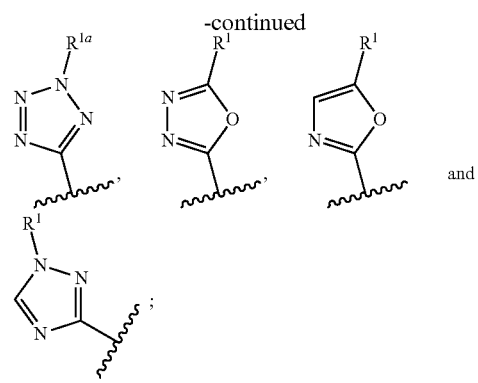

$R^1$ is selected from the group consisting of H and $C_{1-4}$ alkyl;

$R^{1a}$ is $C_{1-4}$ alkyl;

$R^2$ is halogen, —$CF_3$, —$CF_2H$, —$OCF_3$, —$OCF_2H$, —$OCH_3$, —$CH_3$ or CN, and $R^3$, $R^4$ and $R^5$ are H; or $R^3$ is halogen and $R^2$, $R^4$ and $R^5$ are H; or $R^4$ is halogen and $R^2$, $R^3$ and $R^5$ are H; or $R^2$ is halogen, —$CF_3$, —$CF_2H$, —$OCF_3$, —$OCF_2H$, —$OCH_3$, —$CH_3$ or CN, $R^3$ is halogen and $R^4$ and $R^5$ are H;

Y is selected from the group consisting of —CH=CH—, —$CH_2$—$CH_2$—, —O—$CH_2$—, —$CH_2$—O—, —C($CH_3$)=CH— and —C=C($CH_3$)—;

B is selected from the group consisting of

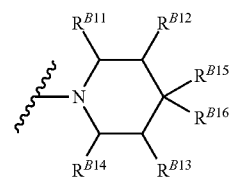

(1)

wherein (1.1) $R^{B11}$, $R^{B12}$, $R^{B13}$ and $R^{B14}$ are H; $R^{B15}$ is selected from the group consisting of Q; and $R^{B16}$ is selected from the group consisting of H, OH and $C_{1-4}$ alkyl; or (1.2) $R^{B12}$, $R^{B13}$, $R^{B14}$, $R^{B15}$ and $R^{B16}$ are H; and $R^{B11}$ is selected from the group consisting of Q; or (1.3) $R^{B11}$, $R^{B13}$, $R^{B14}$, $R^{B15}$ and $R^{B16}$ are H; and $R^{B12}$ is selected from the group consisting of Q; or (1.4) $R^{B12}$, $R^{B13}$, $R^{B14}$, $R^{B16}$ are H; $R^{B11}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; and $R^{B15}$ is selected from the group consisting of Q;

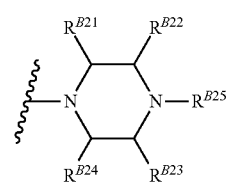

(2)

wherein (2.1) $R^{B21}$, $R^{B22}$, $R^{B23}$ and $R^{B24}$ are H; and $R^{B25}$ is selected from the group consisting of Q; or (2.2) $R^{B22}$, $R^{B23}$, $R^{B24}$, $R^{B25}$ are H; and $R^{B21}$ is selected from the group consisting of Q; or (2.3) $R^{B21}$, $R^{B23}$, $R^{B24}$, $R^{B25}$ are H; and $R^{B22}$ is selected from the group consisting of Q; or (2.4) $R^{B22}$, $R^{B23}$ and $R^{B24}$ are H; $R^{B21}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; and $R^{B25}$ is selected from the group consisting of Q;

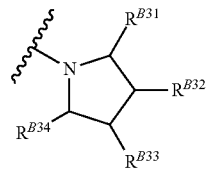

(3)

wherein (3.1) $R^{B32}$, $R^{B33}$ and $R^{B34}$ are H; $R^{B31}$ is selected from a group consisting of Q; or (3.2) $R^{B31}$, $R^{B33}$ and $R^{B34}$ are H; $R^{B32}$ is selected from a group consisting of Q; or (3.3) $R^{B32}$ and $R^{B34}$ are H; $R^{B33}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; $R^{B31}$ is selected from a group consisting of Q;

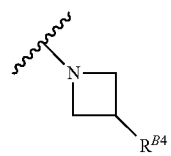

(4)

wherein
$R^{B4}$ is selected from a group consisting of Q;

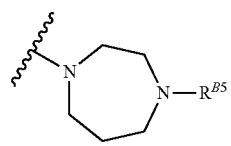

(5)

wherein
$R^{B5}$ is selected from a group consisting of Q;

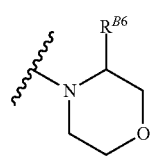

(6)

wherein
$R^{B6}$ is selected from a group consisting of Q;

(7)

wherein
$R^{B7}$ is selected from a group consisting of Q;

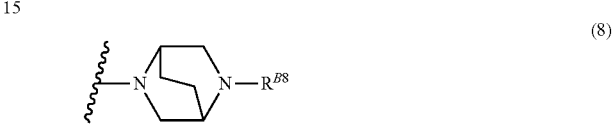

(8)

wherein
$R^{B8}$ is selected from a group consisting of Q;
Q is selected from the group consisting of
(i) —$(CR^{Ba}R^{Bb})_n$-5 or 6 membered heteroaryl or —$(CR^{Ba}R^{Bb})_{n1}$—O—$(CR^{Ba}R^{Bb})_n$-5 or 6 membered heteroaryl which heteroaryl is unsubstituted or substituted with 1 to 3 substituents independently selected from the group consisting of X;
(ii) —$(CR^{Ba}R^{Bb})_n$-9 to 10 membered fused bicyclic ring system or —$(CR^{Ba}R^{Bb})_{n1}$—O—$(CR^{Ba}R^{Bb})_n$-9 to 10 membered fused bicyclic ring system which 9 to 10 membered fused bicyclic ring system is unsubstituted or substituted with 1 to 3 substituents independently selected from the group consisting of X;
(iii) —$(CR^{Ba}R^{Bb})_n$-5 or 6 membered heterocyclyl or —$(CR^{Ba}R^{Bb})_{n1}$—O—$(CR^{Ba}R^{Bb})_n$-5 or 6 membered heterocyclyl which heterocyclyl is unsubstituted or substituted with 1 to 3 substituents independently selected from the group consisting of X;
(iv) $C_{1-4}$ alkyl;
(v) $C_{1-4}$ alkoxy;
(vi) $C_{1-4}$ alkoxy $C_{1-4}$ alkyl;
(vii) $C_{1-4}$ haloalkyl;
(viii) hydroxy $C_{1-4}$ alkyl;
(ix) —$(CR^{Ba}R^{Bb})_n C_{3-6}$cycloalkyl;
(x) —$(CR^{Ba}R^{Bb})_n$—C(=O)$R^{Bc}$ or —$(CR^{Ba}R^{Bb})_{n1}$—O—$(CR^{Ba}R^{Bb})_n$—C(=O)$R^{Bc}$;
(xi) —$(CR^{Ba}R^{Bb})_n$—C(=O)O$R^{Be}$ or —$(CR^{Ba}R^{Bb})_{n1}$—O—$(CR^{Ba}R^{Bb})_n$—C(=O)O$R^{Be}$;
(xii) —$(CR^{Ba}R^{Bb})_n$NR$^{Bd}$—C(=O)$R^{Bc}$ or —$(CR^{Ba}R^{Bb})_{n1}$—O—$(CR^{Ba}R^{Bb})_n$—NR$^{Bd}$—C(=O)$R^{Bc}$;
(xiii) —$(CR^{Ba}R^{Bb})_n$NR$^{Bd}$—C(=O)O$R^{Bc}$ or —$(CR^{Ba}R^{Bb})_{n1}$—O—$(CR^{Ba}R^{Bb})_n$—NR$^{Bd}$—C(=O)ORB;
(xiv) —$(CR^{Ba}R^{Bb})_n$—C(=O)NR$^{Bc}$R$^{Bd}$ or —$(CR^{Ba}R^{Bb})_{n1}$—O—$(CR^{Ba}R^{Bb})_n$—C(=)NR$^{Bc}$R$^{Bd}$;
(xv) —$(CR^{Ba}R^{Bb})_n$—NR$^{Bd}$R$^{Be}$ or —$(CR^{Ba}R^{Bb})_{n1}$—O—$(CR^{Ba}R^{Bb})_n$—NR$^{Bd}$R$^{Be}$;
(xvi) —$(CR^{Ba}R^{Bb})_n$—NR$^{Bd}$—S(O)$_2$—R$^{Bf}$;
(xvii) —$(CR^{Ba}R^{Bb})_n$—S(O)$_2$—NR$^{Bd}$R$^{Be}$ or —$(CR^{Ba}R^{Bb})_{n1}$—O—$(CR^{Ba}R^{Bb})_n$—S(O)$_2$—NR$^{Bd}$R$^{Be}$;
(xviii) —$(CR^{Ba}R^{Bb})_n$—S(O)$_2$—R$^{Bf}$;
(xix) halogen;
(xx) OH;
(xxi) oxo; and
(xxii) CN;
$R^{Ba}$, $R^{Bb}$, $R^{Xa}$, $R^{Xb}$ are independently selected from the group consisting of H, OH, $C_{1-4}$ alkyl and $C_{1-4}$ alkoxy;
$R^{Bc}$, $R^{Be}$ and $R^{Bf}$ are independently selected from the group consisting of H, $C_{1-4}$alkyl, —$(CR^{Ba}R^{Bb})_{n1}$—$C_{3-6}$cycloalkyl, —(CR$^{Ba}$R$^{Bb}$)$_{n1}$—C$_{3-6}$cycloalkenyl, hydroxy C$_{1-4}$alkyl, C$_{1-4}$haloalkyl, C$_{1-4}$alkoxyC$_{1-4}$alkyl, OH, —(CR$^{Ba}$R$^{Bb}$)$_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;

R$^{Bd}$ is selected from the group consisting of H and C$_{1-4}$alkyl; or

R$^{Bc}$ and R$^{Bd}$ or R$^{Bd}$ and R$^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$ cycloalkyl, —(CR$^{Ba}$R$^{Bb}$)$_{n1}$—C$_{3-6}$cycloalkenyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$Cycloalkyl, hydroxyC$_{1-4}$alkyl, C$_{1-4}$haloalkyl, C$_{1-4}$alkoxyC$_{1-4}$alkyl, halogen and OH;

R$^{Xc}$, R$^{Xd}$ and R$^{Xe}$ are independently selected from the group consisting of H, C$_{1-4}$alkyl, —(CR$^{Xa}$R$^{Xb}$)$_{q1}$—C$_{3-6}$cycloalkyl, hydroxyC$_{1-4}$alkyl, C$_{1-4}$haloalkyl, C$_{1-4}$alkoxyC$_{1-4}$alkyl, OH —(CR$^{Xa}$R$^{Xb}$)$_{q1}$-5 or 6 membered heterocyclyl and —(CR$^{Xa}$R$^{Xb}$)$_{q1}$-5 or 6 membered heteroaryl;

wherein the C$_{3-6}$ cycloalkyl, heterocyclyl and heteroaryl are unsubstituted or substituted by 1 to 3 substituents independently selected from the group consisting of C$_{1-4}$ alkyl, C$_{1-4}$ alkoxy, —(CR$^{Xa}$R$^{Xb}$)$_{q1}$—C$_{3-6}$ cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_{q1}$—C$_{3-6}$ cycloalkyl, hydroxy C$_{1-4}$alkyl, C$_{1-4}$haloalkyl, C$_{1-4}$alkoxyC$_{1-4}$alkyl, halogen and OH;

n and n1 are independently selected from the group consisting of 0, 1, 2, 3, 4 and 5;

q and q1 are independently selected from the group consisting of 0, 1 and 2.

Embodiment 6.1: A compound or salt according to embodiment 1, wherein

A is selected from the group consisting of

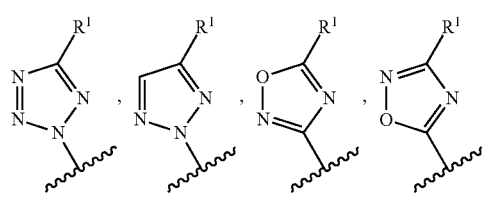

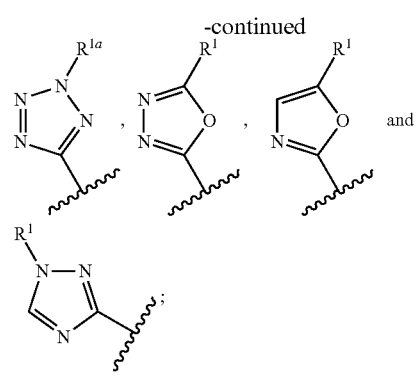

R$^1$ is selected from the group consisting of H and C$_{1-4}$ alkyl;

R$^{1a}$ is C$_{1-4}$ alkyl;

R$^2$ is halogen, —CF$_3$, —CF$_2$H, —OCF$_3$, —OCF$_2$H, —OCH$_3$, —CH$_3$ or CN, and R$^3$, R$^4$ and R$^5$ are H; or R$^3$ is halogen and R$^2$, R$^4$ and R$^5$ are H; or R$^4$ is halogen and R$^2$, R$^3$ and R$^5$ are H; or R$^2$ is halogen, —CF$_3$, —CF$_2$H, —OCF$_3$, —OCF$_2$H, —OCH$_3$, —CH$_3$ or CN, R$^3$ is halogen and R$^4$ and R$^5$ are H;

Y is selected from the group consisting of —CH=CH—, —CH$_2$—CH$_2$—, —O—CH$_2$—, —CH$_2$—O—, —C(CH$_3$)=CH— and —C=C(CH$_3$)—;

B is selected from the group consisting of

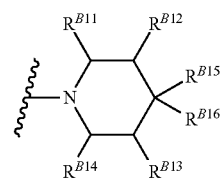

(1)

wherein (1.1) R$^{B11}$, R$^{B12}$, R$^{B13}$ and R$^{B14}$ are H; R$^{B15}$ is selected from the group consisting of Q; and R$^{B16}$ is selected from the group consisting of H, OH and C$_{1-4}$ alkyl; or (1.2) R$^{B12}$, R$^{B13}$, R$^{B14}$, R$^{B15}$ and R$^{B16}$ are H; and R$^{B11}$ is selected from the group consisting of Q; or (1.3) R$^{B11}$, R$^{B13}$, R$^{B14}$, R$^{B15}$ and R$^{B16}$ are H; and R$^{B12}$ is selected from the group consisting of Q; or (1.4) R$^{B12}$, R$^{B13}$, R$^{B14}$, R$^{B16}$ are H; R$^{B11}$ is selected from the group consisting of C$_{1-4}$ alkyl, C$_{1-4}$ alkoxy, C$_{1-4}$ alkoxy C$_{1-4}$ alkyl, C$_{1-4}$ haloalkyl, hydroxy C$_{1-4}$ alkyl and halogen; and R$^{B15}$ is selected from the group consisting of Q;

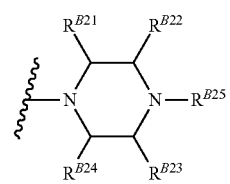

(2)

wherein (2.1) R$^{B21}$, R$^{B22}$, R$^{B23}$ and R$^{B24}$ are H; and R$^{B25}$ is selected from the group consisting of Q; or (2.2) $R^{B22}$, $R^{B23}$, $R^{B24}$, $R^{B25}$ are H; and $R^{B21}$ is selected from the group consisting of Q; or (2.3) $R^{B21}$, $R^{B23}$, $R^{B24}$, $R^{B25}$ are H; and $R^{B22}$ is selected from the group consisting of Q; or (2.4) $R^{B22}$, $R^{B23}$ and $R^{B24}$ are H; $R^{B21}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; and $R^{B25}$ is selected from the group consisting of Q;

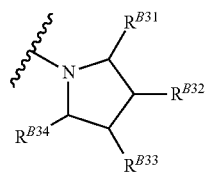
(3)

wherein (3.1) $R^{B32}$, $R^{B33}$ and $R^{B34}$ are H; $R^{B31}$ is selected from a group consisting of Q; or (3.2) $R^{B31}$, $R^{B33}$ and $R^{B34}$ are H; $R^{B32}$ is selected from a group consisting of Q; or (3.3) $R^{B32}$ and $R^{B34}$ are H; $R^{B33}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; $R^{B31}$ is selected from a group consisting of Q;

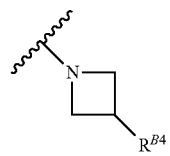
(4)

wherein
$R^{B4}$ is selected from a group consisting of Q;

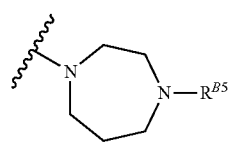
(5)

wherein
$R^{B5}$ is selected from a group consisting of Q;

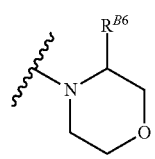
(6)

wherein
$R^{B6}$ is selected from a group consisting of Q;

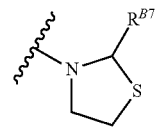
(7)

wherein
$R^{B7}$ is selected from a group consisting of Q;

(8)

wherein
$R^{B8}$ is selected from a group consisting of Q;
Q is selected from the group consisting of
(i) —$(CR^{Ba}R^{Bb})_n$-5 or 6 membered heteroaryl or —O—$(CR^{Ba}R^{Bb})_n$-5 or 6 membered heteroaryl which heteroaryl is unsubstituted or substituted with 1 to 3 substituents independently selected from the group consisting of X;
(ii) —$(CR^{Ba}R^{Bb})_n$-9 to 10 membered fused bicyclic ring system or —O—$(CR^{Ba}R^{Bb})_n$-9 to 10 membered fused bicyclic ring system which 9 to 10 membered fused bicyclic ring system is unsubstituted or substituted with 1 to 3 substituents independently selected from the group consisting of X;
(iii) —$(CR^{Ba}R^{Bb})_n$-5 or 6 membered heterocyclyl or —O—$(CR^{Ba}R^{Bb})_n$-5 or 6 membered heterocyclyl which heterocyclyl is unsubstituted or substituted with 1 to 3 substituents independently selected from the group consisting of X;
(iv) $C_{1-4}$ alkyl;
(v) $C_{1-4}$ alkoxy;
(vi) $C_{1-4}$ alkoxy $C_{1-4}$ alkyl;
(vii) $C_{1-4}$ haloalkyl;
(viii) hydroxy $C_{1-4}$ alkyl;
(ix) —$(CR^{Ba}R^{Bb})_n C_{3-6}$cycloalkyl;
(x) —$(CR^{Ba}R^{Bb})_n$—C(=O)$R^{Bc}$ or —O—$(CR^{Ba}R^{Bb})_n$—C(=O)$R^{Bc}$;
(xi) —$(CR^{Ba}R^{Bb})_n$—C(=O)O$R^{Be}$ or —O—$(CR^{Ba}R^{Bb})_n$C(=O)O$R^{Be}$;
(xii) —$(CR^{Ba}R^{Bb})_n NR^{Bd}$—C(=O)$R^{Bc}$ or —O—$(CR^{Ba}R^{Bb})_n NR^{Bd}$—C(=O)$R^{Bc}$;
(xiii) —$(CR^{Ba}R^{Bb})_n NR^{Bd}$—C(=O)O$R^{Bc}$ or —O—$(CR^{Ba}R^{Bb})_n NR^{Bd}$—C(=O)O$R^{Bc}$;
(xiv) —$(CR^{Ba}R^{Bb})_n$—C(=O)N$R^{Bc}R^{Bd}$ or —O—$(CR^{Ba}R^{Bb})_n$—C(=O)N$R^{Bc}R^{Bd}$;
(xv) —$(CR^{Ba}R^{Bb})_n$—N$R^{Bd}R^{Be}$ or —O—$(CR^{Ba}R^{Bb})_n$—N$R^{Bd}R^{Be}$;
(xvi) —$(CR^{Ba}R^{Bb})_n$—N$R^{Bd}$—S(O)$_2$—$R^{Bf}$;
(xvii) —$(CR^{Ba}R^{Bb})_n$—S(O)$_2$—N$R^{Bd}R^{Be}$ or —O—$(CR^{Ba}R^{Bb})_n$—S(O)$_2$—N$R^{Bd}R^{Be}$;
(xviii) —$(CR^{Ba}R^{Bb})_n$—S(O)$_2$—$R^{Bf}$;
(xix) halogen;
(xx) OH;
(xxi) oxo; and
(xxii) CN;
$R^{Ba}$, $R^{Bb}$, $R^{Xa}$, $R^{Xb}$ are independently selected from the group consisting of H, OH, $C_{1-4}$ alkyl and $C_{1-4}$ alkoxy;
$R^{Bc}$, $R^{Be}$ and $R^{Bf}$ are independently selected from the group consisting of H, $C_{1-4}$alkyl, —$(CR^{Ba}R^{Bb})_{n1}$'$C_{3-6}$cycloalkyl, hydroxy$C_{1-4}$alkyl, $C_{1-4}$haloalkyl, $C_{1-4}$alkoxy$C_{1-4}$alkyl, OH, —$(CR^{Ba}R^{Bb})_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;

R$^{Bd}$ is selected from the group consisting of H and C$_{1-4}$alkyl; or

R$^{Bc}$ and R$^{Bd}$ or R$^{Bd}$ and R$^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$Cycloalkyl, hydroxyC$_{1-4}$alkyl, C$_{1-4}$haloalkyl, C$_{1-4}$alkoxyC$_{1-4}$alkyl, halogen and OH;

R$^{Xc}$, R$^{Xd}$ and R$^{Xe}$ are independently selected from the group consisting of H, C$_{1-4}$alkyl, —(CR$^{Xa}$R$^{Xb}$)$_q$—C$_{3-6}$Cycloalkyl, hydroxyC$_{1-4}$alkyl, C$_{1-4}$haloalkyl, C$_{1-4}$alkoxy C$_{1-4}$alkyl, OH and —(CR$^{Xa}$R$^{Xb}$)$_q$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_q$—C$_{3-6}$Cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_q$—C$_{3-6}$cycloalkyl, hydroxy C$_{1-4}$alkyl, C$_{1-4}$haloalkyl, C$_{1-4}$alkoxyC$_{1-4}$alkyl, halogen and OH;

n and n1 are independently selected from the group consisting of 0, 1, 2, 3 and 4;

q is selected from the group consisting of 0, 1 and 2;

wherein when Q or R$^{Bc}$ is a 5 membered heteroaryl selected from the group consisting of 1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;

then said heteroaryl is substituted with 1 or 2 substituents independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-phenyl, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$;

and wherein when Q or R$^{Bc}$ is a 5 membered heteroaryl selected from the group consisting of 1H-1,2,3-triazol-4-yl;
2H-1,2,3-triazol-4-yl;
1H-1,2,3-triazol-5-yl;

then said triazolyl is substituted with 1 or 2 substituents independently selected from the group consisting of C$_{1-4}$ alkoxy, C$_{1-4}$ haloalkyl, hydroxyC$_{1-4}$alkyl, C$_{1-4}$alkoxy C$_{1-4}$alkyl, —(CR$^{Xa}$R$^{Xb}$)$_q$—C$_{3-6}$cycloalkyl, CN, —(CR$^{Xa}$R$^{Xb}$)$_q$-5 or 6 membered heterocyclyl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$.

Embodiment 7: A compound or salt according to embodiment 1, wherein

A is selected from the group consisting of

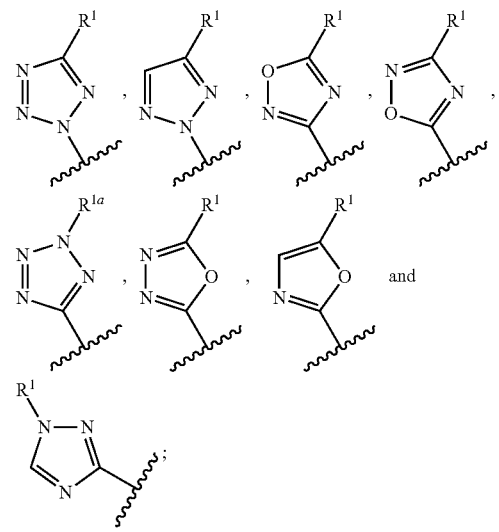

R$^1$ is selected from the group consisting of H and C$_{1-4}$ alkyl;

R$^{1a}$ is C$_{1-4}$ alkyl;

R$^2$ is halogen, —CF$_3$, —CF$_2$H, —OCF$_3$, —OCF$_2$H, —OCH$_3$, —CH$_3$ or CN, and R$^3$, R$^4$ and R$^5$ are H; or R$^3$ is halogen and R$^2$, R$^4$ and R$^5$ are H; or R$^4$ is halogen and R$^2$, R$^3$ and R$^5$ are H; or R$^2$ is halogen, —CF$_3$, —CF$_2$H, —OCF$_3$, —OCF$_2$H, —OCH$_3$, —CH$_3$ or CN, R$^3$ is halogen and R$^4$ and R$^5$ are H;

Y is selected from the group consisting of —CH=CH—, —CH$_2$—CH$_2$—, —O—CH$_2$—, —CH$_2$—O—, —C(CH$_3$)=CH— and —C=C(CH$_3$)—;

B is selected from the group consisting of

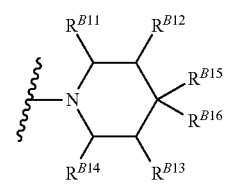

(1)

wherein (1.1) R$^{B11}$, R$^{B12}$, R$^{B13}$ and R$^{B14}$ are H; R$^{B15}$ is selected from the group consisting of Q1; and $R^{B16}$ is selected from the group consisting of H, OH, $C_{1-4}$ alkyl and $C_{1-4}$ alkoxy; or (1.2) $R^{B12}$, $R^{B13}$, $R^{B14}$, $R^{B15}$ and $R^{B16}$ are H; and $R^{B11}$ is selected from the group consisting of Q1; or (1.3) $R^{B11}$, $R^{B13}$, $R^{B14}$, $R^{B15}$ and $R^{B16}$ are H; and $R^{B12}$ is selected from the group consisting of Q1; or (1.4) $R^{B12}$, $R^{B13}$, $R^{B14}$, $R^{B16}$ are H; $R^{B11}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; and $R^{B15}$ is selected from the group consisting of Q1;

Q1 is selected from the group consisting of
(i) —$(CR^{Ba}R^{Bb})_n$-5 or 6 membered heteroaryl or —O—$(CR^{Ba}R^{Bb})_n$-5 or 6 membered heteroaryl which heteroaryl is unsubstituted or substituted with 1 to 3 substituents independently selected from the group consisting of X;

(ii) —$(CR^{Ba}R^{Bb})_n$-phenyl or —O—$(CR^{Ba}R^{Bb})_n$-phenyl which phenyl is unsubstituted or substituted with 1 to 3 substituents independently selected from the group consisting of X;

(iii) —$(CR^{Ba}R^{Bb})_n$-9 to 10 membered fused bicyclic ring system or —O—$(CR^{Ba}R^{Bb})_n$-9 to 10 membered fused bicyclic ring system which 9 to 10 membered fused bicyclic ring system is unsubstituted or substituted with 1 to 3 substituents independently selected from the group consisting of X;

(iv) —$(CR^{Ba}R^{Bb})_n$-5 or 6 membered heterocyclyl or —O—$(CR^{Ba}R^{Bb})_n$-5 or 6 membered heterocyclyl which heterocyclyl is unsubstituted or substituted with 1 to 3 substituents independently selected from the group consisting of X;

(v) $C_{1-4}$ haloalkyl;

(vi) —$(CR^{Ba}R^{Bb})_n$—C(=O)OR$^{Bc}$ or —O—$(CR^{Ba}R^{Bb})_n$C(=O)OR$^{Bc}$;

(vii) —$(CR^{Ba}R^{Bb})_n$NR$^{Bd}$—C(=O)R$^{Bc}$ or —O—$(CR^{Ba}R^{Bb})$NR$^{Bd}$—C(=O) R$^{Bc}$;

(viii) —$(CR^{Ba}R^{Bb})_n$—C(=O)NR$^{Bd}$R$^{Bc}$ or —O—$(CR^{Ba}R^{Bb})_n$—C(=O)NR$^{Bd}$R$^{Bc}$; and (ix) halogen;

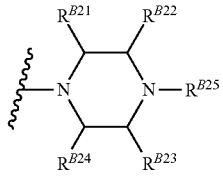

(2)

wherein (2.1) $R^{B21}$, $R^{B22}$, $R^{B23}$ and $R^{B24}$ are H; and $R^{B25}$ is selected from the group consisting of Q2; or (2.2) $R^{B22}$, $R^{B23}$, $R^{B24}$, $R^{B25}$ are H; and $R^{B21}$ is selected from the group consisting of Q2; or (2.3) $R^{B21}$, $R^{B23}$, $R^{B24}$, $R^{B25}$ are H; and $R^{B22}$ is selected from the group consisting of Q2; or (2.4) $R^{B22}$, $R^{B23}$ and $R^{B24}$ are H; $R^{B21}$ is selected from the group consisting of $C_{1-4}$ alkyl, $C_{1-4}$ alkoxy, $C_{1-4}$ alkoxy $C_{1-4}$ alkyl, $C_{1-4}$ haloalkyl, hydroxy $C_{1-4}$ alkyl and halogen; and $R^{B25}$ is selected from the group consisting of Q2;

Q2 is selected from the group consisting of
(i) —$(CR^{Ba}R^{Bb})_n$-5 or 6 membered heteroaryl or —O—$(CR^{Ba}R^{Bb})_n$-5 or 6 membered heteroaryl which heteroaryl is unsubstituted or substituted with 1 to 3 substituents independently selected from the group consisting of X;

(ii) $C_{1-4}$ haloalkyl;

(iii) —$(CR^{Ba}R^{Bb})_n$—C(=O)OR$^{Bc}$ or —O—$(CR^{Ba}R^{Bb})_n$C(=O)OR$^{Bc}$;

(iv) —$(CR^{Ba}R^{Bb})_n$NR$^{Bd}$—C(=O)R$^{Bc}$ or —O—$(CR^{Ba}R^{Bb})_n$NR$^{Bd}$—C(=O)R$^{Bc}$;

(v) —$(CR^{Ba}R^{Bb})_n$—C(=O)NR$^{Bd}$R$^{Bc}$ or —O—$(CR^{Ba}R^{Bb})_n$—C(=O)NR$^{Bd}$R$^{Bc}$; and (vi) halogen;

$R^{Ba}$, $R^{Bb}$, $R^{Xa}$, $R^{Xb}$ are independently selected from the group consisting of H, OH, $C_{1-4}$ alkyl and $C_{1-4}$ alkoxy;

$R^{Bc}$, $R^{Be}$ and $R^{Bf}$ are independently selected from the group consisting of H, $C_{1-4}$alkyl, —$(CR^{Ba}R^{Bb})_{n1}$—$C_{3-6}$cycloalkyl, —$(CR^{Ba}R^{Bb})_{n1}$—$C_{3-6}$cycloalkenyl, hydroxy$C_{1-4}$alkyl, $C_{1-4}$haloalkyl, $C_{1-4}$alkoxy$C_{1-4}$alkyl, OH, —$(CR^{Ba}R^{Bb})_{n1}$-5 or 6 membered heteroaryl, —$(CR^{Ba}R^{Bb})_{n1}$-phenyl and —$(CR^{Ba}R^{Bb})_{n1}$-5 or 6 membered heterocyclyl, wherein the $C_{3-6}$cycloalkyl, heteroaryl, phenyl and heterocyclyl are unsubstituted or substituted by 1 to 3 substituents selected from the group consisting of X;

$R^{Bd}$ is selected from the group consisting of H and $C_{1-4}$alkyl; or $R^{Bc}$ and $R^{Bd}$ or $R^{Bd}$ and $R^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$ cycloalkyl, —$(CR^{Ba}R^{Bb})_{n1}$—$C_{3-6}$cycloalkenyl, halogen, CN, —$(CR^{Xa}R^{Xb})_q$-5 or 6 membered heterocyclyl, —$(CR^{Xa}R^{Xb})_q$-5 or 6 membered heteroaryl, —$(CR^{Xa}R^{Xb})_q$-phenyl, oxo, OH, —$(CR^{Xa}R^{Xb})_q$—C(=O)R$^{Xc}$, —$(CR^{Xa}R^{Xb})_q$—C(=O)OR$^{Xc}$, —$(CR^{Xa}R^{Xb})_q$—NR$^{Xd}$R$^{Xe}$ and —$(CR^{Xa}R^{Xb})_q$—C(=O)NR$^{Xd}$R$^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —$(CR^{Xa}R^{Xb})_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;

$R^{Xc}$, $R^{Xd}$ and $R^{Xe}$ are independently selected from the group consisting of H, $C_{1-4}$alkyl, —$(CR^{Xa}R^{Xb})_{q1}$—$C_{3-6}$ cycloalkyl, hydroxy$C_{1-4}$alkyl, $C_{1-4}$haloalkyl, $C_{1-4}$alkoxy $C_{1-4}$alkyl, OH —$(CR^{Xa}R^{Xb})_q$-5 or 6 membered heterocyclyl and —$(CR^{Xa}R^{Xb})_q$-5 or 6 membered heteroaryl;

wherein the $C_{3-6}$ cycloalkyl, heterocyclyl and heteroaryl are unsubstituted or substituted by 1 to 3 substituents independently selected from the group consisting of $C_{1-4}$ alkyl, $C_{1-4}$ alkoxy, —$(CR^{Xa}R^{Xb})_{q1}$—$C_{3-6}$ cycloalkyl, $C_{1-4}$ haloalkyl, hydroxy$C_{1-4}$alkyl, $C_{1-4}$alkoxy$C_{1-4}$alkyl, halogen and OH; or $R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —$(CR^{Xa}R^{Xb})_{q1}$—$C_{3-6}$ cycloalkyl, hydroxy $C_{1-4}$alkyl, $C_{1-4}$haloalkyl, $C_{1-4}$alkoxy$C_{1-4}$alkyl, halogen and OH;

n and n1 are independently selected from the group consisting of 0, 1, 2, 3, 4 and 5;

q and q1 are independently selected from the group consisting of 0, 1 and 2.

Embodiment 7.1: A compound or salt according to embodiment 1, wherein

A is selected from the group consisting of

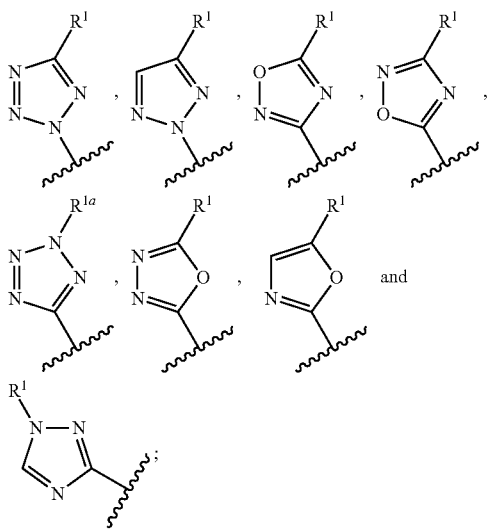

R$^1$ is selected from the group consisting of H and C$_{1-4}$ alkyl;
R$^{1a}$ is C$_{1-4}$ alkyl;
R$^2$ is halogen, —CF$_3$, —CF$_2$H, —OCF$_3$, —OCF$_2$H, —OCH$_3$, —CH$_3$ or CN, and R$^3$, R$^4$ and R$^5$ are H; or
R$^3$ is halogen and R$^2$, R$^4$ and R$^5$ are H; or
R$^4$ is halogen and R$^2$, R$^3$ and R$^5$ are H; or
R$^2$ is halogen, —CF$_3$, —CF$_2$H, —OCF$_3$, —OCF$_2$H, —OCH$_3$, —CH$_3$ or CN, R$^3$ is halogen and R$^4$ and R$^5$ are H;
Y is selected from the group consisting of —CH=CH—, —CH$_2$—CH$_2$—, —O—CH$_2$—, —CH$_2$—O—, —C(CH$_3$)=CH— and —C=C(CH$_3$)—;
B is selected from the group consisting of

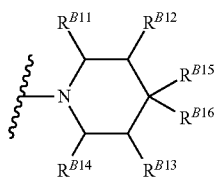

(1)

wherein
(1.1) R$^{B11}$, R$^{B12}$, R$^{B13}$ and R$^{B14}$ are H; R$^{B15}$ is selected from the group consisting of Q1; and
R$^{B16}$ is selected from the group consisting of H, OH, C$_{1-4}$ alkyl and C$_{1-4}$ alkoxy; or
(1.2) R$^{B12}$, R$^{B13}$, R$^{B14}$, R$^{B15}$ and R$^{B16}$ are H; and R$^{B11}$ is selected from the group consisting of Q1; or
(1.3) R$^{B11}$, R$^{B13}$, R$^{B14}$, R$^{B15}$ and R$^{B16}$ are H; and R$^{B12}$ is selected from the group consisting of Q1; or
(1.4) R$^{B12}$, R$^{B13}$, R$^{B14}$, R$^{B16}$ are H; R$^{B11}$ is selected from the group consisting of C$_{1-4}$ alkyl, C$_{1-4}$ alkoxy, C$_{1-4}$ alkoxy C$_{1-4}$ alkyl, C$_{1-4}$ haloalkyl, hydroxy C$_{1-4}$ alkyl and halogen; and R$^{B15}$ is selected from the group consisting of Q1;
Q1 is selected from the group consisting of
(i) —(CR$^{Ba}$R$^{Bb}$)$_n$-5 or 6 membered heteroaryl or —O—(CR$^{Ba}$R$^{Bb}$)$_n$-5 or 6 membered heteroaryl which heteroaryl is unsubstituted or substituted with 1 to 3 substituents independently selected from the group consisting of X;

(ii) —(CR$^{Ba}$R$^{Bb}$)$_n$-phenyl or —O—(CR$^{Ba}$R$^{Bb}$)$_n$-phenyl which phenyl is unsubstituted or substituted with 1 to 3 substituents independently selected from the group consisting of X;
(iii) —(CR$^{Ba}$R$^{Bb}$)$_n$-9 to 10 membered fused bicyclic ring system or —O—(CR$^{Ba}$R$^{Bb}$)$_n$-9 to 10 membered fused bicyclic ring system which 9 to 10 membered fused bicyclic ring system is unsubstituted or substituted with 1 to 3 substituents independently selected from the group consisting of X;
(iv) —(CR$^{Ba}$R$^{Bb}$)$_n$-5 or 6 membered heterocyclyl or —O—(CR$^{Ba}$R$^{Bb}$)$_n$-5 or 6 membered heterocyclyl which heterocyclyl is unsubstituted or substituted with 1 to 3 substituents independently selected from the group consisting of X;
(v) C$_{1-4}$ haloalkyl;
(vi) —(CR$^{Ba}$R$^{Bb}$)$_n$—C(=O)OR$^{Bc}$ or —O—(CR$^{Ba}$R$^{Bb}$)$_n$C(=O)OR$^{Bc}$;
(vii) —(CR$^{Ba}$R$^{Bb}$)$_n$NR$^{Bd}$—C(=O)R$^{Bc}$ or —O—(CR$^{Ba}$R$^{Bb}$)$_n$NR$^{Bd}$—C(=O)R$^{Bc}$;
(viii) —(CR$^{Ba}$R$^{Bb}$)$_n$—C(=O)NR$^{Bd}$R$^{Bc}$ or —O—(CR$^{Ba}$R$^{Bb}$)$_n$—C(=O)NR$^{Bd}$R$^{Bc}$; and
(ix) halogen;

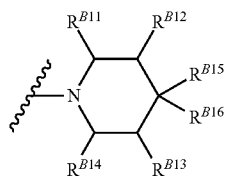

(2)

wherein
(2.1) R$^{B21}$, R$^{B22}$, R$^{B23}$ and R$^{B24}$ are H; and R$^{B25}$ is selected from the group consisting of Q2; or
(2.2) R$^{B22}$, R$^{B23}$, R$^{B24}$, R$^{B25}$ are H; and R$^{B21}$ is selected from the group consisting of Q2; or
(2.3) R$^{B21}$, R$^{B23}$, R$^{B24}$, R$^{B25}$ are H; and R$^{B22}$ is selected from the group consisting of Q2; or
(2.4) R$^{B22}$, R$^{B23}$ and R$^{B24}$ are H; R$^{B21}$ is selected from the group consisting of C$_{1-4}$ alkyl, C$_{1-4}$ alkoxy, C$_{1-4}$ alkoxy C$_{1-4}$ alkyl, C$_{1-4}$ haloalkyl, hydroxy C$_{1-4}$ alkyl and halogen; and R$^{B25}$ is selected from the group consisting of Q2;
Q2 is selected from the group consisting of
(i) —(CR$^{Ba}$R$^{Bb}$)$_n$-5 or 6 membered heteroaryl or —O—(CR$^{Ba}$R$^{Bb}$)$_n$-5 or 6 membered heteroaryl which heteroaryl is unsubstituted or substituted with 1 to 3 substituents independently selected from the group consisting of X;
(ii) C$_{1-4}$ haloalkyl;
(iii) —(CR$^{Ba}$R$^{Bb}$)$_n$—C(=O)OR$^{Bc}$ or —O—(CR$^{Ba}$R$^{Bb}$)$_n$C(=O)OR$^{Bc}$;
(iv) —(CR$^{Ba}$R$^{Bb}$)$_n$NR$^{Bd}$—C(=O)R$^{Bc}$ or —O—(CR$^{Ba}$R$^{Bb}$)$_n$NR$^{Bd}$—C(=O)R$^{Bc}$;
(v) —(CR$^{Ba}$R$^{Bb}$)$_n$—C(=O)NR$^{Bd}$R$^{Bc}$ or —O—(CR$^{Ba}$R$^{Bb}$)$_n$—C(=O)NR$^{Bd}$R$^{Bc}$; and
(vi) halogen;
R$^{Ba}$, R$^{Bb}$, R$^{Xa}$, R$^{Xb}$ are independently selected from the group consisting of H, OH, C$_{1-4}$ alkyl and C$_{1-4}$ alkoxy;
R$^{Bc}$, R$^{Be}$ and R$^{Bf}$ are independently selected from the group consisting of H, C$_{1-4}$alkyl, —(CR$^{Ba}$R$^{Bb}$)$_{n1}$—C$_{3-6}$cycloalkyl, hydroxyC$_{1-4}$alkyl, C$_{1-4}$haloalkyl, C$_{1-4}$alkoxyC$_{1-4}$alkyl, OH, —(CR$^{Ba}$R$^{Bb}$)$_{n1}$-5 or 6 membered heteroaryl, —(CR$^{Ba}$R$^{Bb}$)$_{n1}$-phenyl and —(CR$^{Ba}$R$^{Bb}$)$_{n1}$-5 or 6 membered heterocyclyl, wherein the C$_{3-6}$cycloalkyl, heteroaryl, phenyl and heterocyclyl are unsubstituted or substituted by 1 to 3 substituents selected from the group consisting of X;

$R^{Bd}$ is selected from the group consisting of H and $C_{1-4}$alkyl; or $R^{Bd}$ and $R^{Be}$ together with the nitrogen atom to which they are attached form a 5 to 6 membered heterocyclyl which heterocyclyl is unsubstituted or substituted by 1 to 3 substituents selected from the group consisting of X;

X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-5 or 6 membered heteroaryl, —$(CR^{Xa}R^{Xb})_q$-phenyl, oxo, OH, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—N$R^{Xd}R^{Xe}$ and —$(CR^{Xa}R^{Xb})_q$—C(=O)N$R^{Xd}R^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —$(CR^{Xa}R^{Xb})_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;

$R^{Xc}$, $R^{Xd}$ and $R^{Xe}$ are independently selected from the group consisting of H, $C_{1-4}$alkyl, —$(CR^{Xa}R^{Xb})_q$—$C_{3-6}$cycloalkyl, hydroxy$C_{1-4}$alkyl, $C_{1-4}$haloalkyl, $C_{1-4}$alkoxy$C_{1-4}$alkyl, OH and —$(CR^{Xa}R^{Xb})_q$-5 or 6 membered heterocyclyl; wherein the $C_{3-6}$cycloalkyl and heterocyclyl are unsubstituted or substituted by 1 to 3 substituents independently selected from the group consisting of $C_{1-4}$ alkyl, $C_{1-4}$ alkoxy, —$(CR^{Xa}R^{Xb})_q$—$C_{3-6}$cycloalkyl, $C_{1-4}$ haloalkyl, hydroxy$C_{1-4}$alkyl, $C_{1-4}$alkoxy$C_{1-4}$alkyl, halogen and OH; or $R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —$(CR^{Xa}R^{Xb})_q$—$C_{3-6}$cycloalkyl, hydroxy $C_{1-4}$alkyl, $C_{1-4}$haloalkyl, $C_{1-4}$alkoxy$C_{1-4}$alkyl, halogen and OH;

n and n1 are independently selected from the group consisting of 0, 1, 2, 3 and 4;

q is selected from the group consisting of 0, 1 and 2;

wherein when Q1, Q2 or $R^{Bc}$ is a 5 membered heteroaryl selected from the group consisting of
1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;

then said heteroaryl is substituted with 1 or 2 substituents independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-phenyl, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—N$R^{Xd}R^{Xe}$ and —$(CR^{Xa}R^{Xb})_q$—C(=O)N$R^{Xd}R^{Xe}$;

and wherein when Q1, Q2 or $R^{Bc}$ is a 5 membered heteroaryl selected from the group consisting of
1H-1,2,3-triazol-4-yl;
2H-1,2,3-triazol-4-yl;
1H-1,2,3-triazol-5-yl;

then said triazolyl is substituted with 1 or 2 substituents independently selected from the group consisting of $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, CN, —$(CR^{Xa}R^{Xb})_q$-5 or 6 membered heterocyclyl, —$(CR^{Xa}R^{Xb})_q$-phenyl, oxo, OH, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—N$R^{Xd}R^{Xe}$ and —$(CR^{Xa}R^{Xb})_q$—C(=O)N$R^{Xd}R^{Xe}$.

Embodiment 8: A compound or salt according to embodiment 1, of formula (Ia)

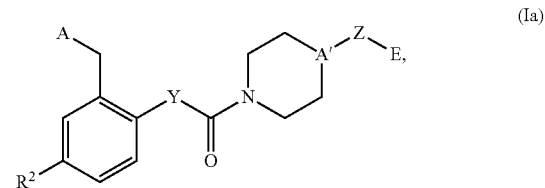

(Ia)

or a pharmaceutically acceptable salt thereof,
wherein
A is selected from the group consisting of

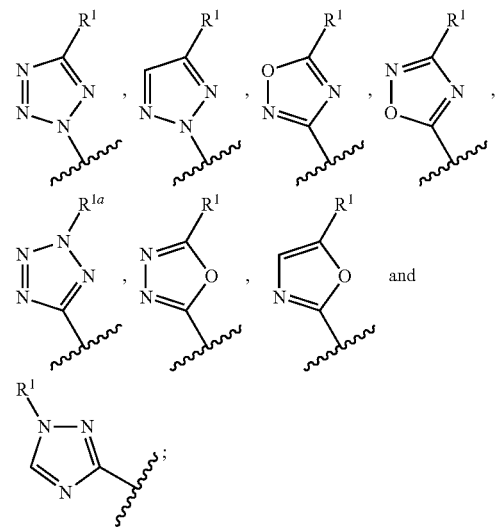

$R^1$ is selected from the group consisting of H and $C_{1-4}$ alkyl;

$R^{1a}$ is $C_{1-4}$ alkyl;

$R^2$ is halogen, —$CF_3$, —$CF_2H$, —$OCF_3$, —$OCF_2H$, —$OCH_3$, —$CH_3$ or CN;

Y is selected from the group consisting of —CH=CH—, —$CH_2$—$CH_2$—, —O—$CH_2$—, —$CH_2$—O—, —C($CH_3$)=CH— and —C=C($CH_3$)—;

A' is $CR^6$ or N;

$R^6$ is selected from H, OH and $C_{1-4}$ alkoxy;

Z is selected from the group consisting of —$(CR^{7a}R^{7b})_m$—, —$(CH_2)_{m1}$—C(=O)—$(CH_2)_{m2}$—, —$(CH_2)_{m1}$—O—$(CH_2)_{m2}$—, —$(CH_2)_{m1}$—N$R^8$C(=O)—$(CH_2)_{m2}$—, —$(CH_2)_{m1}$—C(=O)N$R^8$—$(CH_2)_{m2}$— and —$(CH_2)_{m1}$—N$R^8$—$(CH_2)_{m2}$—;

$R^{7a}$ and $R^{7b}$ is independently selected from H, OH, $C_{1-4}$ alkyl and $C_{1-4}$ alkoxy;

$R^8$ is selected from H and $C_{1-4}$ alkyl;

m, m1 and m2 are independently selected from the group consisting of 0, 1, 2, 3, 4 and 5;

E is selected from the group consisting of (i) 5 or 6 membered heteroaryl which is unsubstituted or substituted with 1 to 3 substituents independently selected from the group consisting of X;

(ii) phenyl which is unsubstituted or substituted with 1 to 3 substituents independently selected from the group consisting of X;

(iii) 9 to 10 membered fused bicyclic ring system which is unsubstituted or substituted with 1 to 3 substituents independently selected from the group consisting of X;

(iv) 5 or 6 membered heterocyclyl which heterocyclyl is unsubstituted or substituted with 1 to 3 substituents independently selected from the group consisting of X;

X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-5 or 6 membered heteroaryl, —$(CR^{Xa}R^{Xb})_q$-phenyl, oxo, OH, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—N$R^{Xd}R^{Xe}$ and —$(CR^{Xa}R^{Xb})_q$—C(=O)N$R^{Xd}R^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —$(CR^{Xa}R^{Xb})_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;

$R^{Xa}$ and $R^{Xb}$ are independently selected from the group consisting of H, OH, $C_{1-4}$ alkyl and $C_{1-4}$ alkoxy;

$R^{Xc}$, $R^{Xd}$ and $R^{Xe}$ are independently selected from the group consisting of H, $C_{1-4}$alkyl, —$(CR^{Xa}R^{Xb})_{q1}$—$C_{3-6}$cycloalkyl, hydroxy$C_{1-4}$alkyl, $C_{1-4}$haloalkyl, $C_{1-4}$alkoxy $C_{1-4}$alkyl, OH, —$(CR^{Xa}R^{Xb})_{q1}$-5 or 6 membered heterocyclyl and —$(CR^{Xa}R^{Xb})_{q1}$-5 or 6 membered heteroaryl; wherein the $C_{3-6}$cycloalkyl and heterocyclyl are unsubstituted or substituted by 1 to 3 substituents independently selected from the group consisting of $C_{1-4}$ alkyl, $C_{1-4}$ alkoxy, —$(CR^{Xa}R^{Xb})_{q1}$—$C_{3-6}$cycloalkyl, $C_{1-4}$ haloalkyl, hydroxy$C_{1-4}$alkyl, $C_{1-4}$alkoxy$C_{1-4}$alkyl, halogen and OH; or $R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —$(CR^{Xa}R^{Xb})_{q1}$—$C_{3-6}$cycloalkyl, hydroxy $C_{1-4}$alkyl, $C_{1-4}$haloalkyl, $C_{1-4}$alkoxy$C_{1-4}$alkyl, halogen and OH;

q and q1 are selected from the group consisting of 0, 1 and 2.

Embodiment 8.1: A compound or salt according to embodiment 1, of formula (Ia)

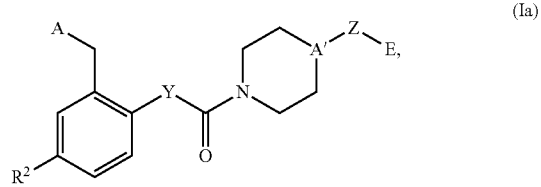

(Ia)

or a pharmaceutically acceptable salt thereof, wherein

A is selected from the group consisting of

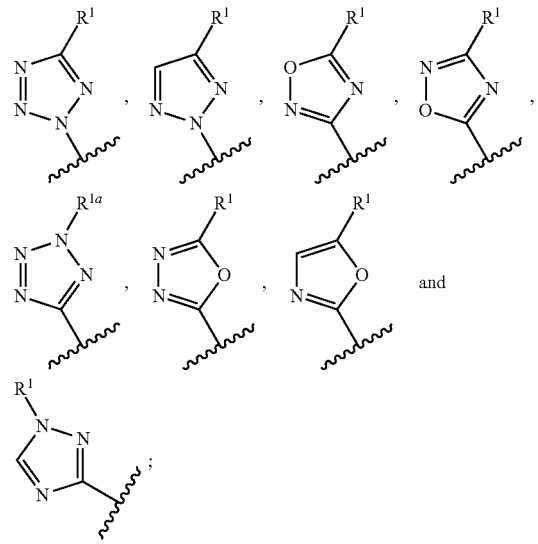

$R^1$ is selected from the group consisting of H and $C_{1-4}$ alkyl;

$R^{1a}$ is $C_{1-4}$ alkyl;

$R^2$ is halogen, —$CF_3$, —$CF_2H$, —$OCF_3$, —$OCF_2H$, —$OCH_3$, —$CH_3$ or CN;

Y is selected from the group consisting of —CH=CH—, —$CH_2$—$CH_2$—, —O—$CH_2$—, —$CH_2$—O—, —C($CH_3$)=CH— and —C=C($CH_3$)—;

A' is $CR^6$ or N;

$R^6$ is selected from H, OH and $C_{1-4}$ alkoxy;

Z is selected from the group consisting of —$(CR^{7a}R^{7b})_m$—, —C(=O)— and —O—;

$R^{7a}$ and $R^{7b}$ is independently selected from H, OH, $C_{1-4}$ alkyl and $C_{1-4}$ alkoxy;

m is selected from the group consisting of 0, 1, 2, 3 and 4;

E is selected from the group consisting of (i) 5 or 6 membered heteroaryl which is unsubstituted or substituted with 1 to 3 substituents independently selected from the group consisting of X;

(ii) phenyl which is unsubstituted or substituted with 1 to 3 substituents independently selected from the group consisting of X;

(iii) 9 to 10 membered fused bicyclic ring system which is unsubstituted or substituted with 1 to 3 substituents independently selected from the group consisting of X;

(iv) 5 or 6 membered heterocyclyl which heterocyclyl is unsubstituted or substituted with 1 to 3 substituents independently selected from the group consisting of X;

X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-5 or 6 membered heteroaryl, —$(CR^{Xa}R^{Xb})_q$-phenyl, oxo, OH, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—N$R^{Xd}R^{Xe}$ and —$(CR^{Xa}R^{Xb})_q$—C(=O)N$R^{Xd}R^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xa}$ and R$^{Xb}$ are independently selected from the group consisting of H, OH, C$_{1-4}$ alkyl and C$_{1-4}$ alkoxy;

R$^{Xc}$, R$^{Xd}$ and R$^{Xe}$ are independently selected from the group consisting of H, C$_{1-4}$alkyl, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxy C$_{1-4}$alkyl, OH and —(CR$^{Xa}$R$^{Xb}$)$_q$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_q$—C$_{3-6}$cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_q$—C$_{3-6}$cycloalkyl, hydroxy C$_{1-4}$alkyl, C$_{1-4}$haloalkyl, C$_{1-4}$alkoxyC$_{1-4}$alkyl, halogen and OH;

q is selected from the group consisting of 0, 1 and 2;

wherein when E is a 5 membered heteroaryl selected from the group consisting of 1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;

then said heteroaryl is substituted with 1 or 2 substituents independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-phenyl, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$;

and wherein when E is a 5 membered heteroaryl selected from the group consisting of 1H-1,2,3-triazol-4-yl;
2H-1,2,3-triazol-4-yl;
1H-1,2,3-triazol-5-yl;

then said triazolyl is substituted with 1 or 2 substituents independently selected from the group consisting of C$_{1-4}$ alkoxy, C$_{1-4}$ haloalkyl, hydroxyC$_{1-4}$alkyl, C$_{1-4}$alkoxy C$_{1-4}$alkyl, —(CR$^{Xa}$R$^{Xb}$)$_q$—C$_{3-6}$cycloalkyl, CN, —(CR$^{Xa}$R$^{Xb}$)$_q$-5 or 6 membered heterocyclyl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$.

Embodiment 9: A compound or salt according to embodiment 1, of formula (Ia)

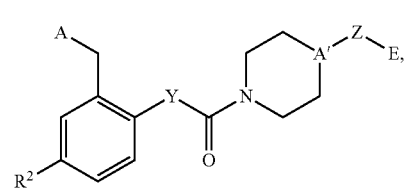

or a pharmaceutically acceptable salt thereof,
wherein
A is selected from the group consisting of

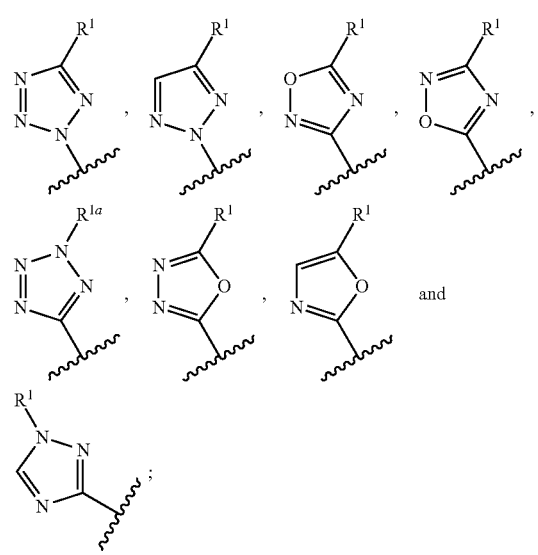

R$^1$ is selected from the group consisting of H and C$_{1-4}$ alkyl;
R$^{1a}$ is C$_{1-4}$ alkyl;
R$^2$ is halogen, —CF$_3$, —CF$_2$H, —OCF$_3$, —OCF$_2$H, —OCH$_3$, —CH$_3$ or CN;
Y is selected from the group consisting of —CH=CH—, —CH$_2$—CH$_2$—, —O—CH$_2$—, —CH$_2$—O—, —C(CH$_3$)=CH— and —C=C(CH$_3$)—;
A' is CR$^6$ or N;
R$^6$ is selected from H, OH and C$_{1-4}$ alkoxy;
Z is selected from the group consisting of —(CR$^{7a}$R$^{7b}$)$_m$—, —C(=O)— and —O—;
R$^{7a}$ and R$^{7b}$ is independently selected from H, OH, C$_{1-4}$ alkyl and C$_{1-4}$ alkoxy;
m is selected from 0, 1, 2, 3 and 4;
E is selected from the group consisting of
(i) 5 or 6 membered heteroaryl which is unsubstituted or substituted with 1 to 3 substituents independently selected from the group consisting of X;
(ii) phenyl which is unsubstituted or substituted with 1 to 3 substituents independently selected from the group consisting of X;
(iii) 9 to 10 membered fused bicyclic ring system which is unsubstituted or substituted with 1 to 3 substituents independently selected from the group consisting of X; and
(iv) 5 or 6 membered heterocyclyl which heterocyclyl is unsubstituted or substituted with 1 to 3 substituents independently selected from the group consisting of X;
X is independently selected from the group consisting of C$_{1-4}$ alkyl, C$_{1-4}$ alkoxy, C$_{1-4}$ haloalkyl, hydroxyC$_{1-4}$alkyl, C₁₋₄alkoxyC₁₋₄alkyl, —(CR$^{Xa}$R$^{Xb}$)$_q$—C₃₋₆cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C₃₋₆cycloalkyl, heteroaryl, phenyl and heterocyclyl are unsubstituted or substituted by 1 to 3 substituents independently selected from the group consisting of C₁₋₄alkyl, C₁₋₄alkoxy, —(CR$^{Xa}$R$^{Xb}$)$_q$—C₃₋₆cycloalkyl, hydroxyC₁₋₄alkyl, C₁₋₄haloalkyl, C₁₋₄alkoxyC₁₋₄alkyl, halogen and OH;

R$^{Xa}$ and R$^{Xb}$ are independently selected from the group consisting of H, OH, C₁₋₄ alkyl and C₁₋₄ alkoxy;

R$^{Xc}$, R$^{Xd}$ and R$^{Xe}$ are independently selected from the group consisting of H, C₁₋₄alkyl, —(CR$^{Xa}$R$^{Xb}$)$_q$—C₃₋₆cycloalkyl, hydroxyC₁₋₄alkyl, C₁₋₄haloalkyl, C₁₋₄alkoxyC₁₋₄alkyl, OH and —(CR$^{Xa}$R$^{Xb}$)$_q$-5 or 6 membered heterocyclyl; wherein the C₃₋₆cycloalkyl and heterocyclyl are unsubstituted or substituted by 1 to 3 substituents independently selected from the group consisting of C₁₋₄ alkyl, C₁₋₄ alkoxy, —(CR$^{Xa}$R$^{Xb}$)$_q$—C₃₋₆cycloalkyl, C₁₋₄ haloalkyl, hydroxyC₁₋₄alkyl, C₁₋₄alkoxyC₁₋₄alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C₁₋₄alkyl, C₁₋₄alkoxy, —(CR$^{Xa}$R$^{Xb}$)$_q$—C₃₋₆cycloalkyl, hydroxy C₁₋₄alkyl, C₁₋₄haloalkyl, C₁₋₄alkoxyC₁₋₄alkyl, halogen and OH;

q is selected from the group consisting of 0, 1 and 2;

wherein when E is a 5 membered heteroaryl selected from the group consisting of
1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;

then said heteroaryl is substituted with 1 or 2 substituents independently selected from the group consisting of C₁₋₄ alkyl, C₁₋₄ alkoxy, C₁₋₄ haloalkyl, hydroxyC₁₋₄alkyl, C₁₋₄alkoxyC₁₋₄alkyl, —(CR$^{Xa}$R$^{Xb}$)$_q$—C₃₋₆cycloalkyl, halogen, CN, —(CR$^{Xa}$R$^{Xb}$)$_q$-5 or 6 membered heterocyclyl, —(CR$^{Xa}$R$^{Xb}$)$_q$-phenyl, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$;

and wherein when E is a 5 membered heteroaryl selected from the group consisting of
1H-1,2,3-triazol-4-yl;
2H-1,2,3-triazol-4-yl;
1H-1,2,3-triazol-5-yl;

then said triazolyl is substituted with 1 or 2 substituents independently selected from the group consisting of C₁₋₄ alkoxy, C₁₋₄ haloalkyl, hydroxyC₁₋₄alkyl, C₁₋₄alkoxy C₁₋₄alkyl, —(CR$^{Xa}$R$^{Xb}$)$_q$—C₃₋₆cycloalkyl, CN, —(CR$^{Xa}$R$^{Xb}$)$_q$-5 or 6 membered heterocyclyl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$;

and wherein if A' is N, E is not phenyl.

Embodiment 9.1: A compound or salt according to embodiment 1, of formula (Ia)

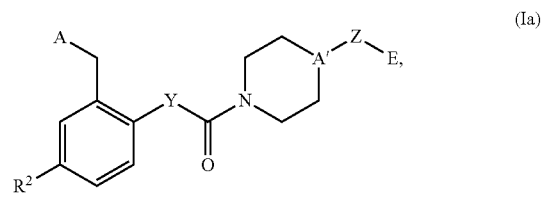

(Ia)

or a pharmaceutically acceptable salt thereof,
wherein
A is selected from the group consisting of

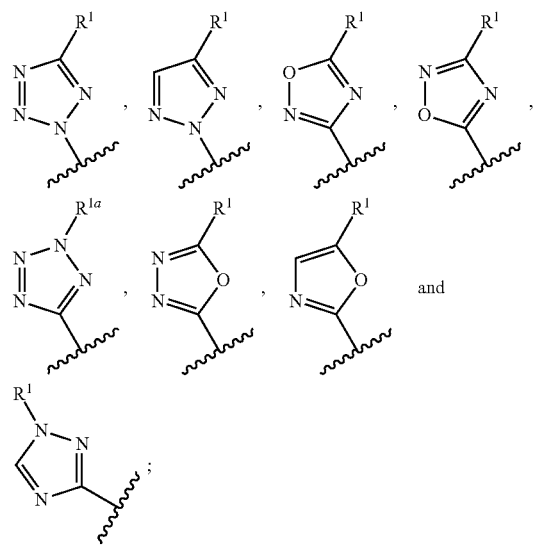

R¹ is selected from the group consisting of H and C₁₋₄ alkyl;
R$^{1a}$ is C₁₋₄ alkyl;
R² is halogen, —CF₃, —CF₂H, —OCF₃, —OCF₂H, —OCH₃, —CH₃ or CN;
Y is selected from the group consisting of —CH=CH—, —CH₂—CH₂—, —O—CH₂—, —CH₂—O—, —C(CH₃)=CH— and —C=C(CH₃)—;
A' is CR⁶ or N;
R⁶ is selected from H, OH and C₁₋₄ alkoxy;
Z is selected from the group consisting of —(CR$^{7a}$R$^{7b}$)$_m$—, —C(=O)— and —O—;
R$^{7a}$ and R$^{7b}$ is independently selected from H, OH, C₁₋₄ alkyl and C₁₋₄ alkoxy;
m is selected from 0, 1, 2, 3 and 4;
E is selected from the group consisting of
(i) 5 or 6 membered heteroaryl which is unsubstituted or substituted with 1 to 3 substituents independently selected from the group consisting of X;
(ii) 9 to 10 membered fused bicyclic ring system which is unsubstituted or substituted with 1 to 3 substituents independently selected from the group consisting of X; and
(iii) 5 or 6 membered heterocyclyl which heterocyclyl is unsubstituted or substituted with 1 to 3 substituents independently selected from the group consisting of X;
X is independently selected from the group consisting of C₁₋₄ alkyl, C₁₋₄ alkoxy, C₁₋₄ haloalkyl, hydroxyC₁₋₄alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xa}$ and R$^{Xb}$ are independently selected from the group consisting of H, OH, C$_{1-4}$ alkyl and C$_{1-4}$ alkoxy;

R$^{Xc}$, R$^{Xd}$ and R$^{Xe}$ are independently selected from the group consisting of H, C$_{1-4}$alkyl, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, OH and —(CR$^{Xa}$R$^{Xb}$)$_q$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_q$—C$_{3-6}$cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_q$—C$_{3-6}$cycloalkyl, hydroxy C$_{1-4}$alkyl, C$_{1-4}$haloalkyl, C$_{1-4}$alkoxyC$_{1-4}$alkyl, halogen and OH;

q is selected from the group consisting of 0, 1 and 2;

wherein when E is a 5 membered heteroaryl selected from the group consisting of
1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;

then said heteroaryl is substituted with 1 or 2 substituents independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-phenyl, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$;

and wherein when E is a 5 membered heteroaryl selected from the group consisting of
1H-1,2,3-triazol-4-yl;
2H-1,2,3-triazol-4-yl;
1H-1,2,3-triazol-5-yl;

then said triazolyl is substituted with 1 or 2 substituents independently selected from the group consisting of C$_{1-4}$ alkyl, C$_{1-4}$ haloalkyl, hydroxyC$_{1-4}$alkyl, C$_{1-4}$alkoxy C$_{1-4}$alkyl, —(CR$^{Xa}$R$^{Xb}$)$_q$—C$_{3-6}$cycloalkyl, CN, —(CR$^{Xa}$R$^{Xb}$)$_q$-5 or 6 membered heterocyclyl, —(CR$^{Xa}$R$^{Xb}$)$_q$-phenyl, oxo, OH, —(CR$^{Xa}$R$^{Xb}$)$_q$—C(=O) R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$.

Embodiment 10: A compound or salt according to embodiment 1, of formula (Ia)

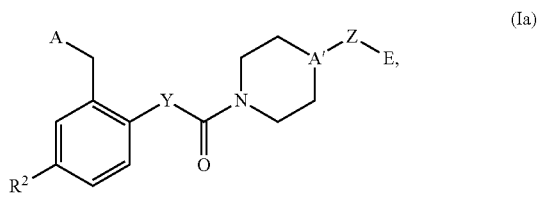

(Ia)

or a pharmaceutically acceptable salt thereof,
wherein
A is selected from the group consisting of

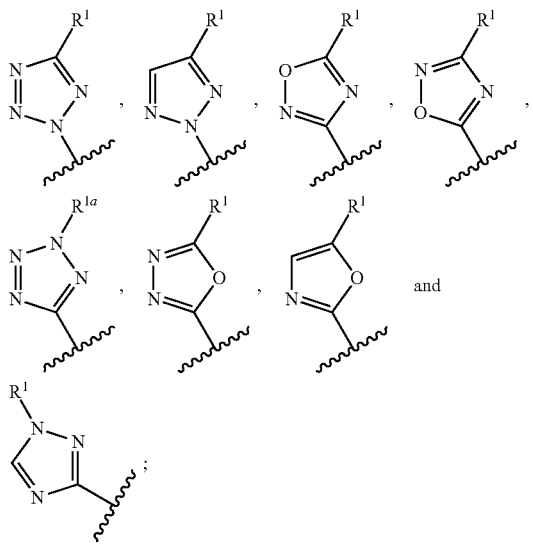

and

R$^1$ is selected from the group consisting of H and C$_{1-4}$ alkyl;
R$^{1a}$ is 01-4 alkyl;
R$^2$ is halogen, —CF$_3$, —CF$_2$H, —OCF$_3$, —OCF$_2$H, —OCH$_3$, —CH$_3$ or CN;
Y is selected from the group consisting of —CH=CH—, —CH$_2$—CH$_2$—, —O—CH$_2$—, —CH$_2$—O—, —C(CH$_3$)=CH— and —C=C(CH$_3$)—;
A' is CR$^6$ or N;
R$^6$ is selected from H, OH and C$_{1-4}$ alkoxy;
Z is selected from the group consisting of —(CR$^{7a}$R$^{7b}$)$_m$—, —(CH$_2$)$_{m1}$—C(=O)—(CH$_2$)$_{m2}$—, —(CH$_2$)$_{m1}$—O—(CH$_2$)$_{m2}$—, —(CH$_2$)$_{m1}$—NR$^8$C(=O)—(CH$_2$)$_{m2}$—, —(CH$_2$)$_{m1}$—C(=O)NR$^8$—(CH$_2$)$_{m2}$— and —(CH$_2$)$_{m1}$—NR$^8$—(CH$_2$)$_{m2}$—;
R$^{7a}$ and R$^{7b}$ is independently selected from H, OH, C$_{1-4}$ alkyl and C$_{1-4}$ alkoxy;
R$^8$ is selected from H and C$_{1-4}$ alkyl;
m, m1 and m2 are independently selected from the group consisting of 0, 1, 2, 3, 4 and 5;
E is a 5 or 6 membered heteroaryl which heteroaryl is unsubstituted or substituted with 1 to 3 substituents independently selected from the group consisting of X;
X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xc}$, R$^{Xd}$ and R$^{Xe}$ are independently selected from the group consisting of H, C$_{1-4}$alkyl, —(CR$^{Xa}$R$^{Xb}$)$_{q1}$—C$_{3-6}$cycloalkyl, hydroxyC$_{1-4}$alkyl, C$_{1-4}$haloalkyl, C$_{1-4}$alkoxyC$_{1-4}$alkyl, OH and —(CR$^{Xa}$R$^{Xb}$)$_{q1}$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_{q1}$—C$_{3-6}$cycloalkyl, C$_{1-4}$ haloalkyl, hydroxyC$_{1-4}$alkyl, C$_{1-4}$alkoxyC$_{1-4}$alkyl, halogen and OH; or R$^{Xa}$ and R$^{Xb}$ are independently selected from the group consisting of H, OH, C$_{1-4}$ alkyl and C$_{1-4}$ alkoxy;

R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_{q1}$—C$_{3-6}$cycloalkyl, hydroxy C$_{1-4}$alkyl, C$_{1-4}$haloalkyl, C$_{1-4}$alkoxyC$_{1-4}$alkyl, halogen and OH;

q and q1 are selected from the group consisting of 0, 1 and 2.

Embodiment 10.1: A compound or salt according to embodiment 1, of formula (Ia)

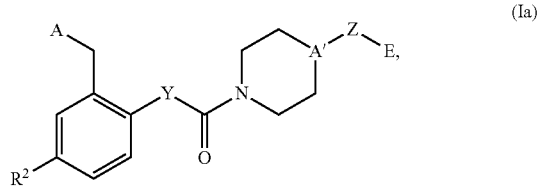

(Ia)

or a pharmaceutically acceptable salt thereof,
wherein
A is selected from the group consisting of

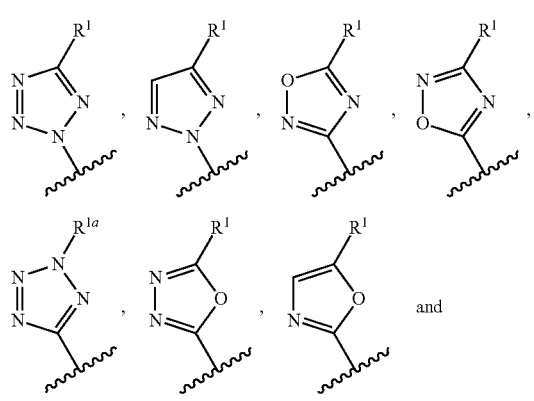

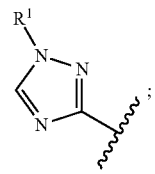

R$^1$ is selected from the group consisting of H and C$_{1-4}$ alkyl;

R$^{1a}$ is C$_{1-4}$ alkyl;

R$^2$ is halogen, —CF$_3$, —CF$_2$H, —OCF$_3$, —OCF$_2$H, —OCH$_3$, —CH$_3$ or CN;

Y is selected from the group consisting of —CH=CH—, —CH$_2$—CH$_2$—, —O—CH$_2$—, —CH$_2$—O—, —C(CH$_3$)=CH— and —C=C(CH$_3$)—;

A' is CR$^6$ or N;

R$^6$ is selected from H, OH and C$_{1-4}$ alkoxy;

Z is selected from the group consisting of —(CR$^{7a}$R$^{7b}$)$_m$—, —C(=O)— and —O—;

R$^{7a}$ and R$^{7b}$ is independently selected from H, OH, C$_{1-4}$ alkyl and C$_{1-4}$ alkoxy;

m is selected from 0, 1, 2, 3 and 4;

E is a 5 or 6 membered heteroaryl which heteroaryl is unsubstituted or substituted with 1 to 3 substituents independently selected from the group consisting of X;

X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xc}$, R$^{Xd}$ and R$^{Xe}$ are independently selected from the group consisting of H, C$_{1-4}$alkyl, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxy C$_{1-4}$alkyl, OH and —(CR$^{Xa}$R$^{Xb}$)$_q$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_q$—C$_{3-6}$cycloalkyl, C$_{1-4}$ haloalkyl, hydroxyC$_{1-4}$alkyl, C$_{1-4}$alkoxyC$_{1-4}$alkyl, halogen and OH; or R$^{Xa}$ and R$^{Xb}$ are independently selected from the group consisting of H, OH, C$_{1-4}$ alkyl and C$_{1-4}$ alkoxy;

R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_q$—C$_{3-6}$cycloalkyl, hydroxy C$_{1-4}$alkyl, C$_{1-4}$haloalkyl, C$_{1-4}$alkoxyC$_{1-4}$alkyl, halogen and OH;

q is selected from the group consisting of 0, 1 and 2;

wherein when E is a 5 membered heteroaryl selected from the group consisting of
1H-imidazol-4-yl;
1H-imidazol-5-yl;
1H-tetrazol-5-yl;
2H-tetrazol-5-yl;
1,3-oxazol-4-yl;
1,3-oxazol-5-yl;

1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;
then said heteroaryl is substituted with 1 or 2 substituents independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-phenyl, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—$NR^{Xd}R^{Xe}$ and —$(CR^{Xa}R^{Xb})_q$—C(=O)$NR^{Xd}R^{Xe}$;

and wherein when E is a 5 membered heteroaryl selected from the group consisting of
1H-1,2,3-triazol-4-yl;
2H-1,2,3-triazol-4-yl;
1H-1,2,3-triazol-5-yl;
then said triazolyl is substituted with 1 or 2 substituents independently selected from the group consisting of $C_{1-4}$ alkoxy, $C_{1-4}$ haloalkyl, hydroxy$C_{1-4}$alkyl, $C_{1-4}$alkoxy $C_{1-4}$alkyl, —$(CR^{Xa}R^{Xb})_q$—$C_{3-6}$cycloalkyl, CN, —$(CR^{Xa}R^{Xb})_q$-5 or 6 membered heterocyclyl, —$(CR^{Xa}R^{Xb})_q$-phenyl, oxo, OH, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—$NR^{Xd}R^{Xe}$ and —$(CR^{Xa}R^{Xb})_q$—C(=O)$NR^{Xd}R^{Xe}$.

Embodiment 11: A compound or salt according to embodiment 1, of formula (Ia)

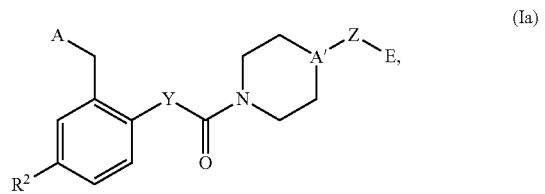

(Ia)

or a pharmaceutically acceptable salt thereof,
wherein
A is selected from the group consisting of

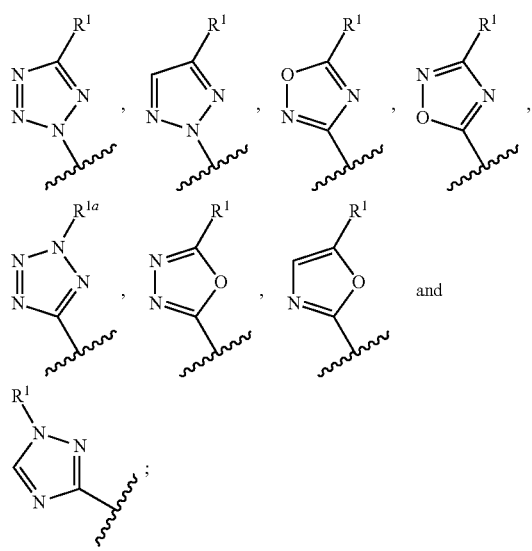

$R^1$ is selected from the group consisting of H and $C_{1-4}$ alkyl;
$R^{1a}$ is $C_{1-4}$ alkyl;
$R^2$ is halogen, —$CF_3$, —$CF_2H$, —$OCF_3$, —$OCF_2H$, —$OCH_3$, —$CH_3$ or CN;
Y is selected from the group consisting of —CH=CH—, —$CH_2$—$CH_2$—, —O—$CH_2$—, —$CH_2$—O—, —C($CH_3$)=CH— and —C=C($CH_3$)—;
A' is $CR^6$ or N;
$R^6$ is selected from H, OH and $C_{1-4}$ alkoxy;
Z is selected from the group consisting of —$(CR^{7a}R^{7b})_m$—, —$(CH_2)_{m1}$—C(=O)—$(CH_2)_{m2}$—, —$(CH_2)_{m1}$—O—$(CH_2)_{m2}$—, —$(CH_2)_{m1}$—$NR^8$C(=O)—$(CH_2)_{m2}$—, —$(CH_2)_{m1}$—C(=O)$NR^8$—$(CH_2)_{m2}$— and —$(CH_2)_{m1}$—$NR^8$—$(CH_2)_{m2}$—;
$R^{7a}$ and $R^{7b}$ is independently selected from H, OH, $C_{1-4}$ alkyl and $C_{1-4}$ alkoxy;
$R^8$ is selected from H and $C_{1-4}$ alkyl;
m, m1 and m2 are independently selected from the group consisting of 0, 1, 2, 3, 4 and 5;
E is selected from the group consisting of
(i) oxadiazolyl;
(ii) pyrazolyl;
(iii) oxazolyl;
(iv) isoxazolyl;
(v) pyridinyl;
(vi) thiazolyl;
(vii) triazolyl;
(viii) pyrimidinyl;
(ix) tetrazolyl;
(x) pyrazinyl; and
(xi) furanyl;
wherein each ring is unsubstituted or substituted with 1 to 3 substituents independently selected from the group consisting of X;
X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-5 or 6 membered heteroaryl, —$(CR^{Xa}R^{Xb})_q$-phenyl, oxo, OH, —$(CR^{Xa}R^{Xb})_q$—C(=O)Rx, —$(CR^{Xa}R^{Xb})_q$—C(=O)O$R^{Xc}$, —$(CR^{Xa}R^{Xb})_q$—$NR^{Xd}R^{Xe}$ and —$(CR^{Xa}R^{Xb})_q$—C(=O)$NR^{Xd}R^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —$(CR^{Xa}R^{Xb})_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;
$R^{Xa}$ and $R^{Xb}$ are independently selected from the group consisting of H, OH, $C_{1-4}$ alkyl and $C_{1-4}$ alkoxy;
$R^{Xc}$, $R^{Xd}$ and $R^{Xe}$ are independently selected from the group consisting of H, $C_{1-4}$alkyl, —$(CR^{Xa}R^{Xb})_{q1}$—$C_{3-6}$cycloalkyl, hydroxy$C_{1-4}$alkyl, $C_{1-4}$haloalkyl, $C_{1-4}$alkoxy $C_{1-4}$alkyl, OH and —$(CR^{Xa}R^{Xb})_{q1}$-5 or 6 membered heterocyclyl; wherein the $C_{3-6}$cycloalkyl and heterocyclyl are unsubstituted or substituted by 1 to 3 substituents independently selected from the group consisting of $C_{1-4}$ alkyl, $C_{1-4}$ alkoxy, —$(CR^{Xa}R^{Xb})_{q1}$—$C_{3-6}$cycloalkyl, $C_{1-4}$ haloalkyl, hydroxy$C_{1-4}$alkyl, $C_{1-4}$alkoxy$C_{1-4}$alkyl, halogen and OH; or
$R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —$(CR^{Xa}R^{Xb})_{q1}$—$C_{3-6}$cycloalkyl, hydroxy $C_{1-4}$alkyl, $C_{1-4}$haloalkyl, $C_{1-4}$alkoxy$C_{1-4}$alkyl, halogen and OH;

q and q1 are selected from the group consisting of 0, 1 and 2.

Embodiment 11.1: A compound or salt according to embodiment 1, of formula (Ia)

(Ia)

or a pharmaceutically acceptable salt thereof,
wherein
A is selected from the group consisting of $R^1$ is selected from the group consisting of H and $C_{1-4}$ alkyl;
$R^{1a}$ is $C_{1-4}$ alkyl;
$R^2$ is halogen, —$CF_3$, —$CF_2H$, —$OCF_3$, —$OCF_2H$, —$OCH_3$, —$CH_3$ or CN;
Y is selected from the group consisting of —CH=CH—, —$CH_2$—$CH_2$—, —O—$CH_2$—, —$CH_2$—O—, —C($CH_3$)=CH— and —C=C($CH_3$)—;
A' is $CR^6$ or N;
$R^6$ is selected from H, OH and $C_{1-4}$ alkoxy;
Z is selected from the group consisting of —($CR^{7a}R^{7b}$)$_m$—, —C(=O)— and —O—;
$R^{7a}$ and $R^{7b}$ is independently selected from H, OH, $C_{1-4}$ alkyl and $C_{1-4}$ alkoxy;
m is selected from 0, 1, 2, 3 and 4;
E is selected from the group consisting of
(i) oxadiazolyl;
(ii) pyrazolyl;
(iii) oxazolyl;
(iv) isoxazolyl;
(v) pyridinyl;
(vi) thiazolyl;
(vii) triazolyl;
(viii) pyrimidinyl;
(ix) tetrazolyl;
(x) pyrazinyl; and
(xi) furanyl;
wherein each ring is unsubstituted or substituted with 1 to 3 substituents independently selected from the group consisting of X;
X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —($CR^{Xa}R^{Xb}$)$_q$—$C_{3-6}$cycloalkyl, halogen, CN, —($CR^{Xa}R^{Xb}$)$_q$-5 or 6 membered heterocyclyl, —($CR^{Xa}R^{Xb}$)$_q$-5 or 6 membered heteroaryl, —($CR^{Xa}R^{Xb}$)$_q$-phenyl, oxo, OH, —($CR^{Xa}R^{Xb}$)$_q$—C(=O)$R^{Xc}$, —($CR^{Xa}R^{Xb}$)$_q$—C(=O)O$R^{Xc}$, —($CR^{Xa}R^{Xb}$)$_q$—$NR^{Xd}R^{Xe}$ and —($CR^{Xa}R^{Xb}$)$_q$—C(=O)$NR^{Xd}R^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —($CR^{Xa}R^{Xb}$)$_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;
$R^{Xa}$ and $R^{Xb}$ are independently selected from the group consisting of H, OH, $C_{1-4}$ alkyl and $C_{1-4}$ alkoxy;
$R^{Xc}$, $R^{Xd}$ and $R^{Xe}$ are independently selected from the group consisting of H, $C_{1-4}$alkyl, —($CR^{Xa}R^{Xb}$)$_q$—$C_{3-6}$cycloalkyl, hydroxy$C_{1-4}$alkyl, $C_{1-4}$haloalkyl, $C_{1-4}$alkoxy$C_{1-4}$alkyl, OH and —($CR^{Xa}R^{Xb}$)$_q$-5 or 6 membered heterocyclyl; wherein the $C_{3-6}$cycloalkyl and heterocyclyl are unsubstituted or substituted by 1 to 3 substituents independently selected from the group consisting of $C_{1-4}$ alkyl, $C_{1-4}$ alkoxy, —($CR^{Xa}R^{Xb}$)$_q$—$C_{3-6}$cycloalkyl, $C_{1-4}$ haloalkyl, hydroxy$C_{1-4}$alkyl, $C_{1-4}$alkoxy$C_{1-4}$alkyl, halogen and OH; or
$R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —($CR^{Xa}R^{Xb}$)$_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;
q is selected from the group consisting of 0, 1 and 2;
wherein when E is a 5 membered heteroaryl selected from the group consisting of
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
pyrazol-3-yl; and
pyrazol-5-yl;
then said heteroaryl is substituted with 1 or 2 substituents independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —($CR^{Xa}R^{Xb}$)$_q$—$C_{3-6}$cycloalkyl, halogen, CN, —($CR^{Xa}R^{Xb}$)$_q$-5 or 6 membered heterocyclyl, —($CR^{Xa}R^{Xb}$)$_q$-phenyl, —($CR^{Xa}R^{Xb}$)$_q$—C(=O)$R^{Xc}$, —($CR^{Xa}R^{Xb}$)$_q$—C(=O)O$R^{Xc}$, —($CR^{Xa}R^{Xb}$)$_q$—$NR^{Xd}R^{Xe}$ and —($CR^{Xa}R^{Xb}$)$_q$—C(=O)$NR^{Xd}R^{Xe}$;
and wherein when E is a 5 membered heteroaryl selected from the group consisting of
1H-1,2,3-triazol-4-yl;
2H-1,2,3-triazol-4-yl;
1H-1,2,3-triazol-5-yl;
then said triazolyl is substituted with 1 or 2 substituents independently selected from the group consisting of $C_{1-4}$ alkoxy, $C_{1-4}$ haloalkyl, hydroxy$C_{1-4}$alkyl, $C_{1-4}$alkoxy$C_{1-4}$alkyl, —($CR^{Xa}$ $R^{Xb})_q$-5 or 6 membered heterocyclyl, —$(CR^{Xa}R^{Xb})_q$-phenyl, oxo, OH, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—NR$^{Xd}$R$^{Xe}$ and —$(CR^{Xa}R^{Xb})_q$—C(=O)NR$^{Xd}$R$^{Xe}$ Embodiment 12: A compound or salt according to embodiment 1, of formula (Ia)

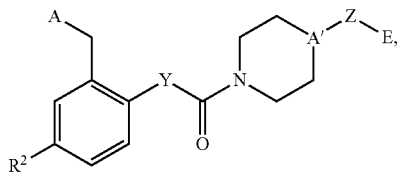

or a pharmaceutically acceptable salt thereof,
wherein
A is selected from the group consisting of

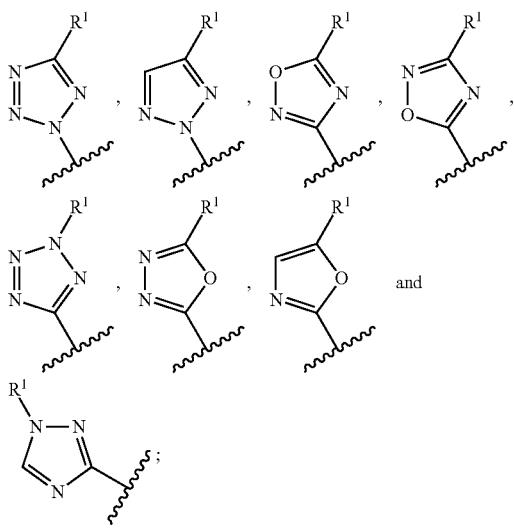

$R^1$ is selected from the group consisting of H and $C_{1-4}$ alkyl;
$R^{1a}$ is $C_{1-4}$ alkyl;
$R^2$ is halogen, —$CF_3$, —$CF_2H$, —$OCF_3$, —$OCF_2H$, —$OCH_3$, —$CH_3$ or CN;
Y is selected from the group consisting of —CH=CH—, —$CH_2$—$CH_2$—, —O—$CH_2$—, —$CH_2$—O—, —C($CH_3$)=CH— and —C=C($CH_3$)—;
A' is $CR^6$ or N;
$R^6$ is selected from H, OH and $C_{1-4}$ alkoxy;
Z is selected from the group consisting of —($CR^{7a}R^{7b})_m$—, —$(CH_2)_{m1}$—C(=O)—$(CH_2)_{m2}$—, —$(CH_2)_{m1}$—O—$(CH_2)_{m2}$—, —$(CH_2)_{m1}$—NR$^8$C(=O)—$(CH_2)_{m2}$—, —$(CH_2)_{m1}$—C(=O)NR$^8$—$(CH_2)_{m2}$— and —$(CH_2)_{m1}$—NR$^8$—$(CH_2)_{m2}$—;
$R^{7a}$ and $R^{7b}$ is independently selected from H, OH, $C_{1-4}$ alkyl and $C_{1-4}$ alkoxy;
$R^8$ is selected from H and $C_{1-4}$ alkyl;
m, m1 and m2 are independently selected from the group consisting of 0, 1, 2, 3, 4 and 5;
E is selected from the group consisting of
(i) oxadiazol-2-yl;
(ii) oxadiazol-3-yl;
(iii) oxadiazol-5-yl;
(iv) pyrazol-1-yl;
(v) pyrazol-3-yl;
(vi) pyrazol-4-yl;
(vii) pyrazol-5-yl;
(viii) oxazol-2-yl;
(ix) oxazol-4-yl;
(xi) isoxazol-3-yl;
(xii) isoxazol-5-yl;
(xiii) pyridine-2-yl;
(xiv) thiazol-2-yl;
(xv) triazol-1-yl;
(xvi) triazol-2-yl;
(xvii) triazol-3-yl;
(xviii) pyrimidin-2-yl;
(ixx) pyrimidin-5-yl;
(xx) tetrazol-1-yl;
(xxi) tetrazol-2-yl;
(xxii) pyrazin-2-yl; and
(xxiii) furan-2-yl;
wherein each ring is unsubstituted or substituted with 1 to 3 substituents independently selected from the group consisting of X;
X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-5 or 6 membered heteroaryl, —$(CR^{Xa}R^{Xb})_q$-phenyl, oxo, OH, —$(CR^{Xa}R^{Xb})_q$—C(=O)$R^{Xc}$, —$(CR^{Xa}R^{Xb})_q$—C(=O)O$R^{Xc}$, —$(CR^{Xa}R^{Xb})_q$—NR$^{Xd}$R$^{Xe}$ and —$(CR^{Xa}R^{Xb})_q$—C(=O)NR$^{Xd}$R$^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —$(CR^{Xa}R^{Xb})_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;
$R^{Xa}$ and $R^{Xb}$ are independently selected from the group consisting of H, OH, $C_{1-4}$ alkyl and $C_{1-4}$ alkoxy;
$R^{Xc}$, $R^{Xd}$ and $R^{Xe}$ are independently selected from the group consisting of H, $C_{1-4}$alkyl, —$(CR^{Xa}R^{Xb})_{q1}$—$C_{3-6}$cycloalkyl, hydroxy$C_{1-4}$alkyl, $C_{1-4}$haloalkyl, $C_{1-4}$alkoxy$C_{1-4}$alkyl, OH and —$(CR^{Xa}R^{Xb})_{q1}$-5 or 6 membered heterocyclyl; wherein the $C_{3-6}$cycloalkyl and heterocyclyl are unsubstituted or substituted by 1 to 3 substituents independently selected from the group consisting of $C_{1-4}$ alkyl, $C_{1-4}$ alkoxy, —$(CR^{Xa}R^{Xb})_{q1}$—$C_{3-6}$cycloalkyl, $C_{1-4}$ haloalkyl, hydroxy$C_{1-4}$alkyl, $C_{1-4}$alkoxy$C_{1-4}$alkyl, halogen and OH; or
$R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —$(CR^{Xa}R^{Xb})_{q1}$—$C_{3-6}$cycloalkyl, hydroxy $C_{1-4}$alkyl, $C_{1-4}$haloalkyl, $C_{1-4}$alkoxy$C_{1-4}$alkyl, halogen and OH;
q and q1 are selected from the group consisting of 0, 1 and 2.

Embodiment 12.1: A compound or salt according to embodiment 1, of formula (Ia)

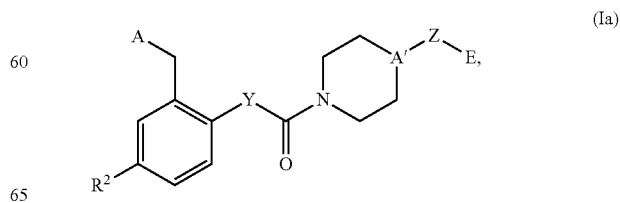

or a pharmaceutically acceptable salt thereof, wherein
A is selected from the group consisting of

[structures: seven heteroaryl ring options bearing R¹]

R¹ is selected from the group consisting of H and $C_{1-4}$ alkyl;
$R^{1a}$ is $C_{1-4}$ alkyl;
$R^2$ is halogen, —$CF_3$, —$CF_2H$, —$OCF_3$, —$OCF_2H$, —$OCH_3$, —$CH_3$ or CN;
Y is selected from the group consisting of —CH=CH—, —$CH_2$—$CH_2$—, —O—$CH_2$—, —$CH_2$—O—, —C($CH_3$)=CH— and —C=C($CH_3$)—;
A' is $CR^6$ or N;
$R^6$ is selected from H, OH and $C_{1-4}$ alkoxy;
Z is selected from the group consisting of —($CR^{7a}R^{7b}$)$_m$—, —C(=O)— and —O—;
$R^{7a}$ and $R^{7b}$ is independently selected from H, OH, $C_{1-4}$ alkyl and $C_{1-4}$ alkoxy;
m is selected from 0, 1, 2, 3 and 4;
E is selected from the group consisting of
(i) oxadiazol-2-yl;
(ii) oxadiazol-3-yl;
(iii) oxadiazol-5-yl;
(iv) pyrazol-1-yl;
(v) pyrazol-3-yl;
(vi) pyrazol-4-yl;
(vii) pyrazol-5-yl;
(viii) oxazol-2-yl;
(ix) oxazol-4-yl;
(xi) isoxazol-3-yl;
(xii) isoxazol-5-yl;
(xiii) pyridine-2-yl;
(xiv) thiazol-2-yl;
(xv) triazol-1-yl;
(xvi) triazol-2-yl;
(xvii) triazol-3-yl;
(xviii) pyrimidin-2-yl;
(ixx) pyrimidin-5-yl;
(xx) tetrazol-1-yl;
(xxi) tetrazol-2-yl;
(xxii) pyrazin-2-yl; and
(xxiii) furan-2-yl;
wherein each ring is unsubstituted or substituted with 1 to 3 substituents independently selected from the group consisting of X;

X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —($CR^{Xa}R^{Xb}$)$_q$—$C_{3-6}$cycloalkyl, halogen, CN, —($CR^{Xa}R^{Xb}$)$_q$-5 or 6 membered heterocyclyl, —($CR^{Xa}R^{Xb}$)$_q$-5 or 6 membered heteroaryl, —($CR^{Xa}R^{Xb}$)$_q$-phenyl, oxo, OH, —($CR^{Xa}R^{Xb}$)$_q$—C(=O)$R^{Xc}$, —($CR^{Xa}R^{Xb}$)$_q$—C(=O)O$R^{Xc}$, —($CR^{Xa}R^{Xb}$)$_q$—$NR^{Xd}R^{Xe}$ and —($CR^{Xa}R^{Xb}$)$_q$—C(=O)$NR^{Xd}R^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —($CR^{Xa}R^{Xb}$)$_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;
$R^{Xa}$ and $R^{Xb}$ are independently selected from the group consisting of H, OH, $C_{1-4}$ alkyl and $C_{1-4}$ alkoxy;
$R^{Xc}$, $R^{Xd}$ and $R^{Xe}$ are independently selected from the group consisting of H, $C_{1-4}$alkyl, —($CR^{Xa}R^{Xb}$)$_q$—$C_{3-6}$cycloalkyl, hydroxy$C_{1-4}$alkyl, $C_{1-4}$haloalkyl, $C_{1-4}$alkoxy $C_{1-4}$alkyl, OH and —($CR^{Xa}R^{Xb}$)$_q$-5 or 6 membered heterocyclyl; wherein the $C_{3-6}$cycloalkyl and heterocyclyl are unsubstituted or substituted by 1 to 3 substituents independently selected from the group consisting of $C_{1-4}$ alkyl, $C_{1-4}$ alkoxy, —($CR^{Xa}R^{Xb}$)$_q$—$C_{3-6}$cycloalkyl, $C_{1-4}$ haloalkyl, hydroxy$C_{1-4}$alkyl, $C_{1-4}$alkoxy$C_{1-4}$alkyl, halogen and OH; or
$R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —($CR^{Xa}R^{Xb}$)$_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;
q is selected from the group consisting of 0, 1 and 2;
wherein when E is a 5 membered heteroaryl selected from the group consisting of
1H-imidazol-4-yl;
1H-imidazol-5-yl;
1H-tetrazol-5-yl;
2H-tetrazol-5-yl;
1,3-oxazol-4-yl;
1,3-oxazol-5-yl;
1,3-thiazol-5-yl;
1,3-thiazol-4-yl;
1,2,4-oxadiazol-3-yl;
isoxazol-5-yl;
isothiazol-5-yl;
pyrazol-3-yl; and
pyrazol-5-yl;
then said heteroaryl is substituted with 1 or 2 substituents independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —($CR^{Xa}R^{Xb}$)$_q$—$C_{3-6}$cycloalkyl, halogen, CN, —($CR^{Xa}R^{Xb}$)$_q$-5 or 6 membered heterocyclyl, —($CR^{Xa}R^{Xb}$)$_q$-phenyl, —($CR^{Xa}R^{Xb}$)$_q$—C(=O)$R^{Xc}$, —($CR^{Xa}R^{Xb}$)$_q$—C(=O)O$R^{Xc}$, —($CR^{Xa}R^{Xb}$)$_q$—$NR^{Xd}R^{Xe}$ and —($CR^{Xa}R^{Xb}$)$_q$—C(=O)$NR^{Xd}R^{Xe}$.

Embodiment 13: A compound or salt according to embodiment 1, of formula (Ia)

[structure (Ia)]

or a pharmaceutically acceptable salt thereof, wherein
A is selected from the group consisting of

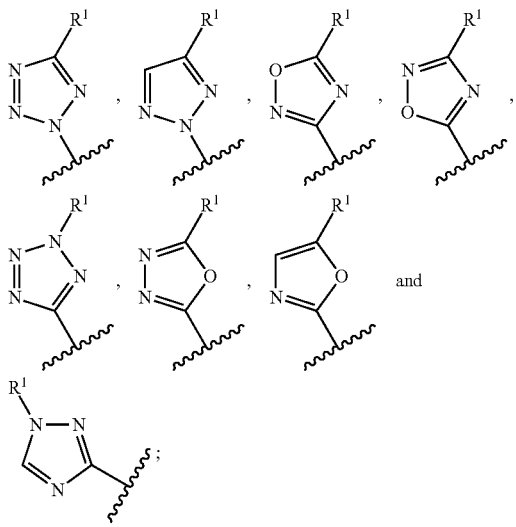

$R^1$ is selected from the group consisting of H and $C_{1-4}$ alkyl;
$R^{1a}$ is $C_{1-4}$ alkyl;
$R^2$ is halogen, —$CF_3$, —$CF_2H$, —$OCF_3$, —$OCF_2H$, —$OCH_3$, —$CH_3$ or CN;
Y is selected from the group consisting of —CH=CH—, —$CH_2$—$CH_2$—, —O—$CH_2$—, —$CH_2$—O—, —C($CH_3$)=CH— and —C=C($CH_3$)—;
A' is $CR^6$ or N;
$R^6$ is selected from H, OH and $C_{1-4}$ alkoxy;
Z is selected from the group consisting of —$(CR^{7a}R^{7b})_m$—, —$(CH_2)_{m1}$—C(=O)—$(CH_2)_{m2}$—, —$(CH_2)_{m1}$—O—$(CH_2)_{m2}$—, —$(CH_2)_{m1}$—$NR^8$C(=O)—$(CH_2)_{m2}$—, —$(CH_2)_{m1}$—C(=O)$NR^8$—$(CH_2)_{m2}$— and —$(CH_2)_{m1}$—$NR^8$—$(CH_2)_{m2}$—;
$R^{7a}$ and $R^{7b}$ is independently selected from H, OH, $C_{1-4}$ alkyl and $C_{1-4}$ alkoxy;
$R^8$ is selected from H and $C_{1-4}$ alkyl;
m, m1 and m2 are independently selected from the group consisting of 0, 1, 2, 3, 4 and 5;
E is selected from the group consisting of
(i) oxadiazol-2-yl;
(ii) oxadiazol-3-yl;
(iii) oxadiazol-5-yl;
(iv) pyrazol-1-yl;
(v) pyrazol-3-yl;
(vi) pyrazol-4-yl;
(ix) oxazol-4-yl;
(xii) isoxazol-5-yl;
(xiii) pyridine-2-yl;
(xvi) triazol-2-yl;
(ixx) pyrimidin-5-yl; and
(xxi) tetrazol-2-yl;
wherein each ring is unsubstituted or substituted with 1 to 3 substituents independently selected from the group consisting of X;
X is independently selected from the group consisting of $C_{1-4}$ alkyl, $C_{1-4}$ alkoxy, $C_{1-4}$ haloalkyl, hydroxy$C_{1-4}$alkyl, $C_{1-4}$alkoxy$C_{1-4}$alkyl, —$(CR^{Xa}R^{Xb})_q$—$C_{3-6}$cycloalkyl, halogen, CN, —$(CR^{Xa}R^{Xb})_q$-5 or 6 membered heterocyclyl, —$(CR^{Xa}R^{Xb})_q$-5 or 6 membered heteroaryl, —$(CR^{Xa}R^{Xb})_q$-phenyl, oxo, OH, —$(CR^{Xa}R^{Xb})_q$—C(=O)Rx, —$(CR^{Xa}R^{Xb})_q$—C(=O)$OR^{Xc}$, —$(CR^{Xa}R^{Xb})_q$—$NR^{Xd}R^{Xe}$ and —$(CR^{Xa}R^{Xb})_q$—C(=O)$NR^{Xd}R^{Xe}$; wherein the $C_{3-6}$cycloalkyl, heteroaryl, phenyl and heterocyclyl are unsubstituted or substituted by 1 to 3 substituents independently selected from the group consisting of $C_{1-4}$alkyl, $C_{1-4}$alkoxy, —$(CR^{Xa}R^{Xb})_q$—$C_{3-6}$cycloalkyl, hydroxy$C_{1-4}$alkyl, $C_{1-4}$haloalkyl, $C_{1-4}$alkoxy$C_{1-4}$alkyl, halogen and OH;
$R^{Xa}$ and $R^{Xb}$ are independently selected from the group consisting of H, OH, $C_{1-4}$ alkyl and $C_{1-4}$ alkoxy;
$R^{Xc}$, $R^{Xd}$ and $R^{Xe}$ are independently selected from the group consisting of H, $C_{1-4}$alkyl, —$(CR^{Xa}R^{Xb})_{q1}$—$C_{3-6}$cycloalkyl, hydroxy$C_{1-4}$alkyl, $C_{1-4}$haloalkyl, $C_{1-4}$alkoxy$C_{1-4}$alkyl, OH and —$(CR^{Xa}R^{Xb})_{q1}$-5 or 6 membered heterocyclyl; wherein the $C_{3-6}$cycloalkyl and heterocyclyl are unsubstituted or substituted by 1 to 3 substituents independently selected from the group consisting of $C_{1-4}$ alkyl, $C_{1-4}$ alkoxy, —$(CR^{Xa}R^{Xb})_{q1}$—$C_{3-6}$cycloalkyl, $C_{1-4}$ haloalkyl, hydroxy$C_{1-4}$alkyl, $C_{1-4}$alkoxy$C_{1-4}$alkyl, halogen and OH; or
$R^{Xd}$ and $R^{Xe}$ together with the nitrogen atom to which they are attached form a 5 to 6 membered heterocyclyl which heterocyclyl is unsubstituted or substituted by 1 to 3 substituents selected from the group consisting of $C_{1-4}$alkyl, $C_{1-4}$alkoxy, —$(CR^{Xa}R^{Xb})_{q1}$—$C_{3-6}$cycloalkyl, hydroxy $C_{1-4}$alkyl, $C_{1-4}$haloalkyl, $C_{1-4}$alkoxy$C_{1-4}$alkyl, halogen and OH;
q and q1 are selected from the group consisting of 0, 1 and 2.

Embodiment 13.1: A compound or salt according to embodiment 1, of formula (Ia)

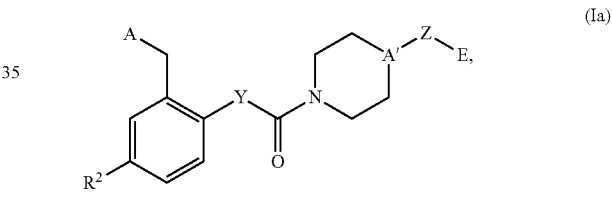

or a pharmaceutically acceptable salt thereof,
wherein
A is selected from the group consisting of

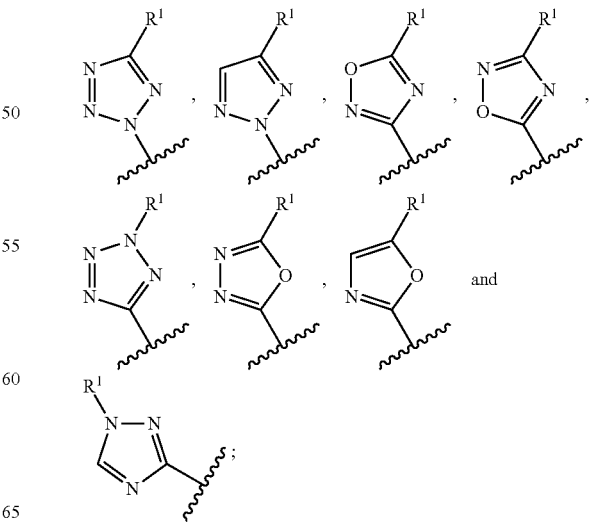

R¹ is selected from the group consisting of H and C₁₋₄ alkyl;

R¹ᵃ is C₁₋₄ alkyl;

R² is halogen, —CF₃, —CF₂H, —OCF₃, —OCF₂H, —OCH₃, —CH₃ or CN;

Y is selected from the group consisting of —CH═CH—, —CH₂—CH₂—, —O—CH₂—, —CH₂—O—, —C(CH₃)═CH— and —C═C(CH₃)—;

A' is CR⁶ or N;

R⁶ is selected from H, OH and C₁₋₄ alkoxy;

Z is selected from the group consisting of —(CR⁷ᵃR⁷ᵇ)ₘ—, —C(═O)— and —O—;

R⁷ᵃ and R⁷ᵇ is independently selected from H, OH, C₁₋₄ alkyl and C₁₋₄ alkoxy;

m is selected from 0, 1, 2, 3 and 4;

E is selected from the group consisting of
(i) oxadiazol-2-yl;
(ii) oxadiazol-3-yl;
(iii) oxadiazol-5-yl;
(iv) pyrazol-1-yl;
(v) pyrazol-3-yl;
(vi) pyrazol-4-yl;
(ix) oxazol-4-yl;
(xii) isoxazol-5-yl;
(xiii) pyridine-2-yl;
(xvi) triazol-2-yl;
(ixx) pyrimidin-5-yl; and
(xxi) tetrazol-2-yl;

wherein each ring is unsubstituted or substituted with 1 to 3 substituents independently selected from the group consisting of X;

X is independently selected from the group consisting of C₁₋₄ alkyl, C₁₋₄ alkoxy, C₁₋₄ haloalkyl, hydroxyC₁₋₄alkyl, C₁₋₄alkoxyC₁₋₄alkyl, —(CR^{Xa}R^{Xb})_q—C₃₋₆cycloalkyl, halogen, CN, —(CR^{Xa}R^{Xb})_q-5 or 6 membered heterocyclyl, —(CR^{Xa}R^{Xb})_q-5 or 6 membered heteroaryl, —(CR^{Xa}R^{Xb})_q-phenyl, oxo, OH, —(CR^{Xa}R^{Xb})_q—C(═O)R^{Xc}, —(CR^{Xa}R^{Xb})_q—C(═O)OR^{Xc}, —(CR^{Xa}R^{Xb})_q—NR^{Xd}R^{Xe} and —(CR^{Xa}R^{Xb})_q—C(═O)NR^{Xd}R^{Xe}; wherein the C₃₋₆cycloalkyl, heteroaryl, phenyl and heterocyclyl are unsubstituted or substituted by 1 to 3 substituents independently selected from the group consisting of C₁₋₄alkyl, C₁₋₄alkoxy, —(CR^{Xa}R^{Xb})_q—C₃₋₆cycloalkyl, hydroxyC₁₋₄alkyl, C₁₋₄haloalkyl, C₁₋₄alkoxyC₁₋₄alkyl, halogen and OH;

R^{Xa} and R^{Xb} are independently selected from the group consisting of H, OH, C₁₋₄ alkyl and C₁₋₄ alkoxy;

R^{Xc}, R^{Xd} and R^{Xe} are independently selected from the group consisting of H, C₁₋₄alkyl, —(CR^{Xa}R^{Xb})_q—C₃₋₆cycloalkyl, hydroxyC₁₋₄alkyl, C₁₋₄haloalkyl, C₁₋₄alkoxy C₁₋₄alkyl, OH and —(CR^{Xa}R^{Xb})_q-5 or 6 membered heterocyclyl; wherein the C₃₋₆cycloalkyl and heterocyclyl are unsubstituted or substituted by 1 to 3 substituents independently selected from the group consisting of C₁₋₄ alkyl, C₁₋₄ alkoxy, —(CR^{Xa}R^{Xb})_q—C₃₋₆cycloalkyl, C₁₋₄ haloalkyl, hydroxyC₁₋₄alkyl, C₁₋₄alkoxyC₁₋₄alkyl, halogen and OH; or R^{Xd} and R^{Xe} together with the nitrogen atom to which they are attached form a 5 to 6 membered heterocyclyl which heterocyclyl is unsubstituted or substituted by 1 to 3 substituents selected from the group consisting of C₁₋₄alkyl, C₁₋₄alkoxy, —(CR^{Xa}R^{Xb})_q—C₃₋₆cycloalkyl, hydroxy C₁₋₄alkyl, C₁₋₄haloalkyl, C₁₋₄alkoxyC₁₋₄alkyl, halogen and OH;

q is selected from the group consisting of 0, 1 and 2;

wherein when E is a 5 membered heteroaryl selected from the group consisting of
1,3-oxazol-4-yl;
1,2,4-oxadiazol-3-yl;
isoxazol-5-yl;
pyrazol-3-yl; and
pyrazol-5-yl;

then said heteroaryl is substituted with 1 or 2 substituents independently selected from the group consisting of C₁₋₄ alkyl, C₁₋₄ alkoxy, C₁₋₄ haloalkyl, hydroxyC₁₋₄alkyl, C₁₋₄alkoxyC₁₋₄alkyl, —(CR^{Xa}R^{Xb})_q—C₁₋₆ cycloalkyl, halogen, CN, —(CR^{Xa}R^{Xb})_q-5 or 6 membered heterocyclyl, —(CR^{Xa}R^{Xb})_q-phenyl, —(CR^{Xa}R^{Xb})_q—C(═O)R^{Xc}, —(CR^{Xa}R^{Xb})_q—C(═O)OR^{Xc}, —(CR^{Xa}R^{Xb})_q—NR^{Xd}R^{Xe} and —(CR^{Xa}R^{Xb})_q—C(═O)NR^{Xd}R^{Xe}.

Embodiment 14: A compound or salt according to any one of embodiments 1 to 13, wherein A is selected from the group consisting of

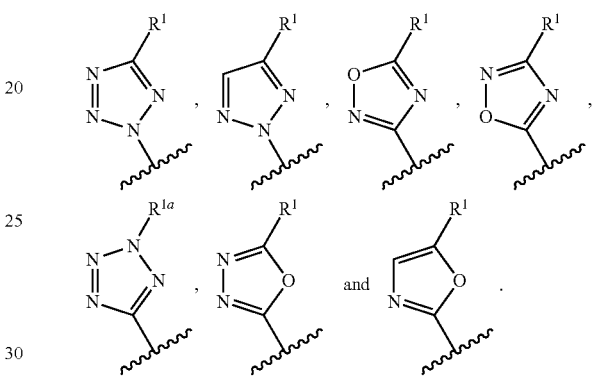

Embodiment 14.1: A compound or salt according to any one of embodiments 1 to 13, wherein A is selected from the group consisting of

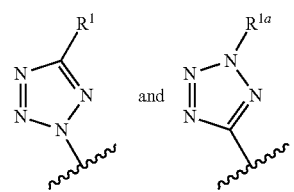

Embodiment 15: A compound or salt according to embodiment 1, of formula (Ia)

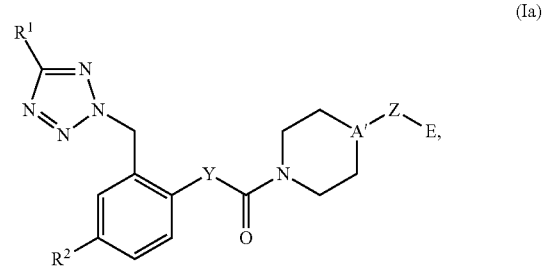

(Ia)

or a pharmaceutically acceptable salt thereof,
wherein

R¹ is selected from the group consisting of H and C₁₋₄ alkyl;

R² is halogen, —CF₃, —CF₂H, —OCF₃, —OCF₂H, —OCH₃, —CH₃ or CN;

Y is selected from the group consisting of —CH=CH—, —CH$_2$—CH$_2$—, —O—CH$_2$—, —CH$_2$—O—, —C(CH$_3$)=CH— and —C=C(CH$_3$)—;

A' is CR$^6$ or N;

R$^6$ is selected from H, OH and C$_{1-4}$ alkoxy;

Z is selected from the group consisting of —(CR$^{7a}$R$^{7b}$)$_m$—, —(CH$_2$)$_{m1}$—C(=O)—(CH$_2$)$_{m2}$—, —(CH$_2$)$_{m1}$—O—(CH$_2$)$_{m2}$—, —(CH$_2$)$_{m1}$—NR$^8$C(=O)—(CH$_2$)$_{m2}$—, —(CH$_2$)$_{m1}$—C(=O)NR$^8$—(CH$_2$)$_{m2}$— and —(CH$_2$)$_{m1}$—NR$^8$—(CH$_2$)$_{m2}$—;

R$^{7a}$ and R$^{7b}$ is independently selected from H, OH, C$_{1-4}$ alkyl and C$_{1-4}$ alkoxy;

R$^8$ is selected from H and C$_{1-4}$ alkyl;

m, m1 and m2 are independently selected from the group consisting of 0, 1, 2, 3, 4 and 5;

E is selected from the group consisting of
(i) oxadiazol-2-yl;
(ii) oxadiazol-3-yl;
(iii) oxadiazol-5-yl;
(iv) pyrazol-1-yl;
(v) pyrazol-3-yl;
(vi) pyrazol-4-yl;
(ix) oxazol-4-yl;
(xii) isoxazol-5-yl;
(xiii) pyridine-2-yl;
(xvi) triazol-2-yl;
(ixx) pyrimidin-5-yl; and
(xxi) tetrazol-2-yl;

wherein each ring is unsubstituted or substituted with 1 to 3 substituents independently selected from the group consisting of X;

X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xa}$ and R$^{Xb}$ are independently selected from the group consisting of H, OH, C$_{1-4}$ alkyl and C$_{1-4}$ alkoxy;

R$^{Xc}$, R$^{Xd}$ and R$^{Xe}$ are independently selected from the group consisting of H, C$_{1-4}$alkyl, —(CR$^{Xa}$R$^{Xb}$)$_{q1}$—C$_{3-6}$cycloalkyl, hydroxyC$_{1-4}$alkyl, C$_{1-4}$haloalkyl, C$_{1-4}$alkoxyC$_{1-4}$alkyl, OH and —(CR$^{Xa}$R$^{Xb}$)$_{q1}$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_{q1}$—C$_{3-6}$cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_{q1}$—C$_{3-6}$cycloalkyl, hydroxy C$_{1-4}$alkyl, C$_{1-4}$haloalkyl, C$_{1-4}$alkoxyC$_{1-4}$alkyl, halogen and OH;

q and q1 are selected from the group consisting of 0, 1 and 2.

Embodiment 15.1: A compound or salt according to embodiment 1, of formula (Ia)

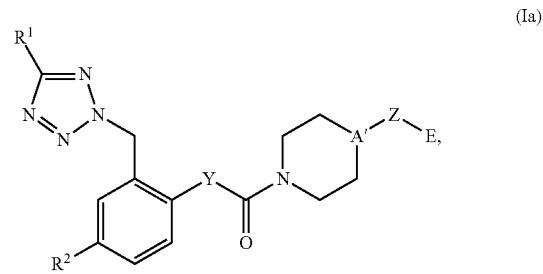

(Ia)

or a pharmaceutically acceptable salt thereof, wherein

R$^1$ is selected from the group consisting of H and C$_{1-4}$ alkyl;

R$^2$ is halogen, —CF$_3$, —CF$_2$H, —OCF$_3$, —OCF$_2$H, —OCH$_3$, —CH$_3$ or CN;

Y is selected from the group consisting of —CH=CH—, —CH$_2$—CH$_2$—, —O—CH$_2$—, —CH$_2$—O—, —C(CH$_3$)=CH— and —C=C(CH$_3$)—;

A' is CR$^6$ or N;

R$^6$ is selected from H, OH and C$_{1-4}$ alkoxy;

Z is selected from the group consisting of —(CR$^{7a}$R$^{7b}$)$_m$—, —C(=O)— and —O—;

R$^{7a}$ and R$^{7b}$ is independently selected from H, OH, C$_{1-4}$ alkyl and C$_{1-4}$ alkoxy;

m is selected from 0, 1, 2, 3 and 4;

E is selected from the group consisting of
(i) oxadiazol-2-yl;
(ii) oxadiazol-3-yl;
(iii) oxadiazol-5-yl;
(iv) pyrazol-1-yl;
(v) pyrazol-3-yl;
(vi) pyrazol-4-yl;
(ix) oxazol-4-yl;
(xii) isoxazol-5-yl;
(xiii) pyridine-2-yl;
(xvi) triazol-2-yl;
(ixx) pyrimidin-5-yl; and
(xxi) tetrazol-2-yl;

wherein each ring is unsubstituted or substituted with 1 to 3 substituents independently selected from the group consisting of X;

X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xa}$ and R$^{Xb}$ are independently selected from the group consisting of H, OH, C$_{1-4}$ alkyl and C$_{1-4}$ alkoxy;

R$^{Xc}$, R$^{Xd}$ and R$^{Xe}$ are independently selected from the group consisting of H, C$_{1-4}$alkyl, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$ alkyl, OH and —(CR$^{Xa}$R$^{Xb}$)$_q$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_q$—C$_{3-6}$cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_q$—C$_{3-6}$cycloalkyl, hydroxy C$_{1-4}$alkyl, C$_{1-4}$haloalkyl, C$_{1-4}$alkoxyC$_{1-4}$alkyl, halogen and OH;

q is selected from the group consisting of 0, 1 and 2;
wherein when E is a 5 membered heteroaryl selected from the group consisting of
1,3-oxazol-4-yl;
1,2,4-oxadiazol-3-yl;
isoxazol-5-yl; and
pyrazol-3-yl;
then said heteroaryl is substituted with 1 or 2 substituents independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-phenyl, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$ Embodiment 16: A compound or salt according to embodiment 1, of formula (Ib)

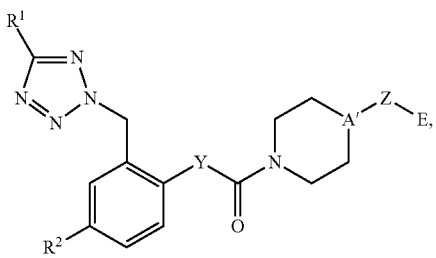

(Ib)

or a pharmaceutically acceptable salt thereof,
wherein
R$^1$ is selected from the group consisting of H and C$_{1-4}$ alkyl;
R$^{1a}$ is C$_{1-4}$ alkyl;
R$^2$ is halogen, —CF$_3$, —CF$_2$H, —OCF$_3$, —OCF$_2$H, —OCH$_3$, —CH$_3$ or CN;
Y is selected from the group consisting of —CH=CH—, —CH$_2$—CH$_2$—, —O—CH$_2$—, —CH$_2$—O—, —C(CH$_3$)=CH— and —C=C(CH$_3$)—;
A' is CR$^6$ or N;
R$^6$ is selected from H, OH and C$_{1-4}$ alkoxy;
Z is selected from the group consisting of —(CR$^{7a}$R$^{7b}$)$_m$—, —(CH$_2$)$_{m1}$—C(=O)—(CH$_2$)$_{m2}$—, —(CH$_2$)$_{m1}$—O—(CH$_2$)$_{m2}$—, —(CH$_2$)$_{m1}$—NR$^8$C(=O)—(CH$_2$)$_{m2}$—, —(CH$_2$)$_{m1}$—C(=O)NR$^8$—(CH$_2$)$_{m2}$— and —(CH$_2$)$_{m1}$—NR$^8$—(CH$_2$)$_{m2}$—;
R$^{7a}$ and R$^{7b}$ is independently selected from H, OH, C$_{1-4}$ alkyl and C$_{1-4}$ alkoxy;
R$^8$ is selected from H and C$_{1-4}$ alkyl;
m, m1 and m2 are independently selected from the group consisting of 0, 1, 2, 3, 4 and 5;
E is selected from the group consisting of
(i) oxadiazol-2-yl;
(ii) oxadiazol-3-yl;
(iii) oxadiazol-5-yl;
(iv) pyrazol-1-yl;
(v) pyrazol-3-yl;
(vi) pyrazol-4-yl;
(ix) oxazol-4-yl;
(xii) isoxazol-5-yl;
(xiii) pyridine-2-yl;
(xvi) triazol-2-yl;
(ixx) pyrimidin-5-yl; and
(xxi) tetrazol-2-yl;
wherein each ring is unsubstituted or substituted with 1 to 3 substituents independently selected from the group consisting of X;
X is independently selected from the group consisting of C$_{1-4}$ alkyl, C$_{1-4}$ alkoxy, C$_{1-4}$ haloalkyl, hydroxyC$_{1-4}$alkyl, C$_{1-4}$alkoxyC$_{1-4}$alkyl, —(CR$^{Xa}$R$^{Xb}$)$_q$—C$_{3-6}$cycloalkyl, halogen, CN, —(CR$^{Xa}$R$^{Xb}$)$_q$-5 or 6 membered heterocyclyl, —(CR$^{Xa}$R$^{Xb}$)$_q$-5 or 6 membered heteroaryl, —(CR$^{Xa}$R$^{Xb}$)$_q$-phenyl, oxo, OH, —(CR$^{Xa}$R$^{Xb}$)$_q$—C(=O)R$^{Xc}$, —(CR$^{Xa}$R$^{Xb}$)$_q$—C(=O)OR$^{Xc}$, —(CR$^{Xa}$R$^{Xb}$)$_q$—NR$^{Xd}$R$^{Xe}$ and —(CR$^{Xa}$R$^{Xb}$)$_q$—C(=O)NR$^{Xd}$R$^{Xe}$; wherein the C$_{3-6}$cycloalkyl, heteroaryl, phenyl and heterocyclyl are unsubstituted or substituted by 1 to 3 substituents independently selected from the group consisting of C$_{1-4}$alkyl, C$_{1-4}$alkoxy, —(CR$^{Xa}$R$^{Xb}$)$_q$—C$_{3-6}$cycloalkyl, hydroxyC$_{1-4}$alkyl, C$_{1-4}$haloalkyl, C$_{1-4}$alkoxyC$_{1-4}$alkyl, halogen and OH;

R$^{Xa}$ and R$^{Xb}$ are independently selected from the group consisting of H, OH, C$_{1-4}$ alkyl and C$_{1-4}$ alkoxy;

R$^{Xc}$, R$^{Xd}$ and R$^{Xe}$ are independently selected from the group consisting of H, C$_{1-4}$alkyl, —(CR$^{Xa}$R$^{Xb}$)$_{q1}$—C$_{3-6}$cycloalkyl, hydroxyC$_{1-4}$alkyl, C$_{1-4}$haloalkyl, C$_{1-4}$alkoxyC$_{1-4}$alkyl, OH and —(CR$^{Xa}$R$^{Xb}$)$_{q1}$-5 or 6 membered heterocyclyl; wherein the C$_{3-6}$cycloalkyl and heterocyclyl are unsubstituted or substituted by 1 to 3 substituents independently selected from the group consisting of C$_{1-4}$ alkyl, C$_{1-4}$ alkoxy, —(CR$^{Xa}$R$^{Xb}$)$_{q1}$—C$_{3-6}$cycloalkyl, C$_{1-4}$ haloalkyl, hydroxyC$_{1-4}$alkyl, C$_{1-4}$alkoxyC$_{1-4}$alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C$_{1-4}$alkyl, C$_{1-4}$alkoxy, —(CR$^{Xa}$R$^{Xb}$)$_{q1}$—C$_{3-6}$cycloalkyl, hydroxy C$_{1-4}$alkyl, C$_{1-4}$haloalkyl, C$_{1-4}$alkoxyC$_{1-4}$alkyl, halogen and OH;

q and q1 are selected from the group consisting of 0, 1 and 2.

Embodiment 16.1: A compound or salt according to embodiment 1, of formula (Ib)

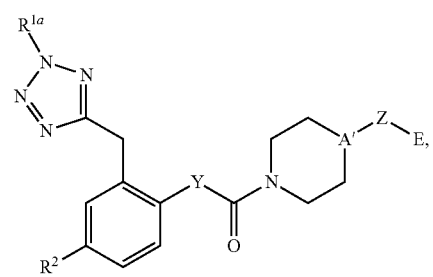

(Ib)

or a pharmaceutically acceptable salt thereof,
wherein
R$^1$ is selected from the group consisting of H and C$_{1-4}$ alkyl;
R$^{1a}$ is C$_{1-4}$ alkyl;

R² is halogen, —CF₃, —CF₂H, —OCF₃, —OCF₂H, —OCH₃, —CH₃ or CN;

Y is selected from the group consisting of —CH═CH—, —CH₂—CH₂—, —O—CH₂—, —CH₂—O—, —C(CH₃)═CH— and —C═C(CH₃)—;

A' is CR⁶ or N;

R⁶ is selected from H, OH and C₁₋₄ alkoxy;

Z is selected from the group consisting of —(CR⁷ᵃR⁷ᵇ)ₘ—, —C(═O)— and —O—;

R⁷ᵃ and R⁷ᵇ is independently selected from H, OH, C₁₋₄ alkyl and C₁₋₄ alkoxy;

m is selected from 0, 1, 2, 3 and 4;

E is selected from the group consisting of
(i) oxadiazol-2-yl;
(ii) oxadiazol-3-yl;
(iii) oxadiazol-5-yl;
(iv) pyrazol-1-yl;
(v) pyrazol-3-yl;
(vi) pyrazol-4-yl;
(ix) oxazol-4-yl;
(xii) isoxazol-5-yl;
(xiii) pyridine-2-yl;
(xvi) triazol-2-yl;
(ixx) pyrimidin-5-yl; and
(xxi) tetrazol-2-yl;

wherein each ring is unsubstituted or substituted with 1 to 3 substituents independently selected from the group consisting of X;

X is independently selected from the group consisting of C₁₋₄ alkyl, C₁₋₄ alkoxy, C₁₋₄ haloalkyl, hydroxyC₁₋₄alkyl, C₁₋₄alkoxyC₁₋₄alkyl, —(CR$^{Xa}$R$^{Xb}$)_q—C₃₋₆cycloalkyl, halogen, CN, —(CR$^{Xa}$R$^{Xb}$)_q-5 or 6 membered heterocyclyl, —(CR$^{Xa}$R$^{Xb}$)_q-5 or 6 membered heteroaryl, —(CR$^{Xa}$R$^{Xb}$)_q-phenyl, oxo, OH, —(CR$^{Xa}$R$^{Xb}$)_q—C(═O)R$^{Xc}$, —(CR$^{Xa}$R$^{Xb}$)_q—C(═O)OR$^{Xc}$, —(CR$^{Xa}$R$^{Xb}$)_q—NR$^{Xd}$R$^{Xe}$ and —(CR$^{Xa}$R$^{Xb}$)_q—C(═O)NR$^{Xd}$R$^{Xe}$; wherein the C₃₋₆cycloalkyl, heteroaryl, phenyl and heterocyclyl are unsubstituted or substituted by 1 to 3 substituents independently selected from the group consisting of C₁₋₄alkyl, C₁₋₄alkoxy, —(CR$^{Xa}$R$^{Xb}$)_q—C₃₋₆cycloalkyl, hydroxyC₁₋₄alkyl, C₁₋₄haloalkyl, C₁₋₄alkoxyC₁₋₄alkyl, halogen and OH;

R$^{Xa}$ and R$^{Xb}$ are independently selected from the group consisting of H, OH, C₁₋₄ alkyl and C₁₋₄ alkoxy;

R$^{Xc}$, R$^{Xd}$ and R$^{Xe}$ are independently selected from the group consisting of H, C₁₋₄alkyl, —(CR$^{Xa}$R$^{Xb}$)_q—C₃₋₆cycloalkyl, hydroxyC₁₋₄alkyl, C₁₋₄haloalkyl, C₁₋₄alkoxyC₁₋₄alkyl, OH and —(CR$^{Xa}$R$^{Xb}$)_q-5 or 6 membered heterocyclyl; wherein the C₃₋₆cycloalkyl and heterocyclyl are unsubstituted or substituted by 1 to 3 substituents independently selected from the group consisting of C₁₋₄ alkyl, C₁₋₄ alkoxy, —(CR$^{Xa}$R$^{Xb}$)_q—C₃₋₆cycloalkyl, C₁₋₄ haloalkyl, hydroxyC₁₋₄alkyl, C₁₋₄alkoxyC₁₋₄alkyl, halogen and OH; or R$^{Xd}$ and R$^{Xe}$ together with the nitrogen atom to which they are attached form a 5 to 6 membered heterocyclyl which heterocyclyl is unsubstituted or substituted by 1 to 3 substituents selected from the group consisting of C₁₋₄alkyl, C₁₋₄alkoxy, —(CR$^{Xa}$R$^{Xb}$)_q—C₃₋₆cycloalkyl, hydroxy C₁₋₄alkyl, C₁₋₄haloalkyl, C₁₋₄alkoxyC₁₋₄alkyl, halogen and OH;

q is selected from the group consisting of 0, 1 and 2;

wherein when E is a 5 membered heteroaryl selected from the group consisting of
1,3-oxazol-4-yl;
1,2,4-oxadiazol-3-yl;
isoxazol-5-yl; and
pyrazol-3-yl;

then said heteroaryl is substituted with 1 or 2 substituents independently selected from the group consisting of C₁₋₄ alkyl, C₁₋₄ alkoxy, C₁₋₄ haloalkyl, hydroxyC₁₋₄alkyl, C₁₋₄alkoxyC₁₋₄alkyl, —(CR$^{Xa}$R$^{Xb}$)_q—C₃₋₆cycloalkyl, halogen, CN, —(CR$^{Xa}$R$^{Xb}$)_q-5 or 6 membered heterocyclyl, —(CR$^{Xa}$R$^{Xb}$)_q-phenyl, —(CR$^{Xa}$R$^{Xb}$)_q—C(═O)R$^{Xc}$, —(CR$^{Xa}$R$^{Xb}$)_q— C(═O)OR$^{Xc}$, —(CR$^{Xa}$R$^{Xb}$)_q—NR$^{Xd}$R$^{Xe}$ and —(CR$^{Xa}$R$^{Xb}$)_q—C(═O)NR$^{Xd}$R$^{Xe}$.

Embodiment 17: A compound or salt according to any one of embodiment 1 to 16, wherein R¹ is methyl.

Embodiment 18: A compound or salt according to any one of embodiments 1 to 17, wherein R² is —CF₃, chloro, —CF₂H or —OCF₃.

Embodiment 19: A compound or salt according to embodiment 18, wherein R² is —CF₃ or chloro.

Embodiment 20: A compound or salt according to any one of embodiments 1 to 19, wherein Y is selected from the group consisting of —CH═CH—, —CH₂—CH₂— and —C(CH₃)═CH—.

Embodiment 21: A compound or salt according to any one of embodiments 1 to 19, wherein Y is selected from the group consisting of —O—CH₂—, —CH₂—O— and —C(CH₃)═CH—, more particularly —O—CH₂— and —C(CH₃)═CH—.

Embodiment 22: A compound or salt according to any one of embodiments 8 to 21, wherein A' is CR⁶ and R⁶ is H.

Embodiment 23: A compound or salt according to any one of embodiments 8 to 22, wherein Z is selected from the group consisting of —(CR⁷ᵃR⁷ᵇ)ₘ—, wherein R⁷ᵃ and R⁷ᵇ are H and m is 0 or 1.

Embodiment 24: A compound according to embodiment 1 selected from the group consisting of (S,E)-1-(2-(5-methyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one;

(E)-1-(4-(3-methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one;

(E)-1-(4-(5-methyl-1,2,4-oxadiazol-3-yl)piperidin-1-yl)-3-(2-((5-methyl-2H-tetrazol-2-yl)methyl)-4-(trifluoromethoxy)phenyl)prop-2-en-1-one;

(E)-1-(4-(5-methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one;

(E)-1-(2-(3-methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one;

(E)-1-(2-(3-methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one;

(E)-1-(2-(3-methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one;

(S,E)-N-methyl-1-(3-(2-((5-methyl-2H-tetrazol-2-yl)methyl)-4-(trifluoromethyl)phenyl)acryloyl)piperidine-2-carboxamide;

(R,E)-3-(4-chloro-2-((5-methyl-2H-tetrazol-2-yl)methyl)phenyl)-1-(3-(5-methyl-1,3,4-oxadiazol-2-yl)pyrrolidin-1-yl)prop-2-en-1-one;

(S,E)-3-(4-chloro-2-((5-methyl-2H-tetrazol-2-yl)methyl)phenyl)-1-(2-(5-methyl-1,3,4-oxadiazol-2-yl)pyrrolidin-1-yl)prop-2-en-1-one;

(E)-3-(4-chloro-2-((5-methyl-2H-tetrazol-2-yl)methyl)phenyl)-1-(4-(4-methyl-1H-1,2,3-triazol-1-yl)piperidin-1-yl)prop-2-en-1-one;

(E)-3-(4-chloro-2-((5-methyl-2H-tetrazol-2-yl)methyl) phenyl)-1-(4-(3-methyl-1H-1,2,4-triazol-1-yl)piperidin-1-yl)prop-2-en-1-one;

(E)-3-(4-chloro-2-((5-methyl-2H-tetrazol-2-yl)methyl) phenyl)-1-(4-(5-methyl-1H-1,2,4-triazol-1-yl)piperidin-1-yl)prop-2-en-1-one;

(E)-3-(4-chloro-2-((5-methyl-2H-tetrazol-2-yl)methyl) phenyl)-1-(4-(5-methyl-1H-tetrazol-1-yl)piperidin-1-yl) prop-2-en-1-one;

(E)-3-(4-chloro-2-((5-methyl-1,3,4-oxadiazol-2-yl) methyl)phenyl)-1-(4-((5-methyl-1,3,4-oxadiazol-2-yl) methyl)piperidin-1-yl)prop-2-en-1-one;

(E)-3-(4-chloro-2-((5-methyl-2H-tetrazol-2-yl)methyl) phenyl)-1-(4-hydroxy-4-((4-(morpholine-4-carbonyl)-1H-pyrazol-1-yl)methyl)piperidin-1-yl)prop-2-en-1-one;

(E)-1-((1-(3-(4-chloro-2-((5-methyl-2H-tetrazol-2-yl) methyl)phenyl)acryloyl)-4-hydroxypiperidin-4-yl)methyl)-N,N-dimethyl-1H-pyrazole-4-carboxamide;

(E)-3-(4-chloro-2-((5-methyl-2H-tetrazol-2-yl)methyl) phenyl)-1-(4-hydroxy-4-((4-(piperidine-1-carbonyl)-1H-pyrazol-1-yl)methyl)piperidin-1-yl)prop-2-en-1-one;

(E)-3-(4-chloro-2-((5-methyl-2H-tetrazol-2-yl)methyl) phenyl)-1-(4-(5-methyl-2H-tetrazol-2-yl)piperidin-1-yl) prop-2-en-1-one;

(E)-3-(4-chloro-2-((5-methyl-2H-tetrazol-2-yl)methyl) phenyl)-1-(4-hydroxy-4-((4-(trifluoromethyl)-1H-pyrazol-1-yl)methyl)piperidin-1-yl)prop-2-en-1-one;

(E)-3-(4-chloro-2-((5-methyl-2H-tetrazol-2-yl)methyl) phenyl)-1-(4-(5-methyl-1,2,4-oxadiazol-3-yl)piperidin-1-yl) prop-2-en-1-one;

(E)-3-(4-chloro-2-((5-methyl-2H-tetrazol-2-yl)methyl) phenyl)-1-(4-(2-(5-methyl-1,3,4-oxadiazol-2-yl)ethyl)piperidin-1-yl)prop-2-en-1-one;

(E)-3-(4-chloro-2-((3-methyl-1,2,4-oxadiazol-5-yl) methyl)phenyl)-1-(4-((5-methyl-1,3,4-oxadiazol-2-yl) methyl)piperidin-1-yl)prop-2-en-1-one;

(E)-1-(4-(2H-1,2,3-triazol-2-yl)piperidin-1-yl)-3-(4-chloro-2-((5-methyl-2H-tetrazol-2-yl)methyl)phenyl)prop-2-en-1-one;

(E)-3-(4-chloro-2-((5-methyl-2H-tetrazol-2-yl)methyl) phenyl)-1-(2-(3-methyl-1,2,4-oxadiazol-5-yl)piperidin-1-yl)prop-2-en-1-one;

(E)-3-(4-chloro-2-((5-methyl-2H-tetrazol-2-yl)methyl) phenyl)-1-(2-(3-methyl-1,2,4-oxadiazol-5-yl)piperidin-1-yl)prop-2-en-1-one;

(E)-3-(4-chloro-2-((5-methyl-2H-tetrazol-2-yl)methyl) phenyl)-1-(4-(5-methyloxazol-2-yl)piperidin-1-yl)prop-2-en-1-one;

(E)-3-(4-chloro-2-((5-methyl-2H-tetrazol-2-yl)methyl) phenyl)-1-(4-(4-methyl-2H-1,2,3-triazol-2-yl)piperidin-1-yl)prop-2-en-1-one;

(E)-3-(4-chloro-2-((5-methyl-2H-tetrazol-2-yl)methyl) phenyl)-1-(4-(3-(5-methyl-1,3,4-oxadiazol-2-yl)propyl)piperidin-1-yl)prop-2-en-1-one;

(E)-3-(4-chloro-2-((5-methyl-2H-tetrazol-2-yl)methyl) phenyl)-1-(4-(2-methyloxazol-4-yl)piperidin-1-yl)prop-2-en-1-one;

(E)-3-(4-chloro-2-((5-methyl-2H-tetrazol-2-yl)methyl) phenyl)-1-(4-(4-methyl-1H-pyrazol-1-yl)piperidin-1-yl) prop-2-en-1-one;

(E)-methyl 1-(3-(4-chloro-2-((5-methyl-2H-tetrazol-2-yl) methyl)phenyl)acryloyl)piperidine-2-carboxylate;

(E)-3-(4-chloro-2-((5-methyl-2H-tetrazol-2-yl)methyl) phenyl)-1-(2-(3-isopropyl-1,2,4-oxadiazol-5-yl)piperidin-1-yl)prop-2-en-1-one;

(E)-3-(4-chloro-2-((5-methyl-2H-tetrazol-2-yl)methyl) phenyl)-1-(2-(3-isopropyl-1,2,4-oxadiazol-5-yl)piperidin-1-yl)prop-2-en-1-one;

(E)-3-(4-chloro-2-((5-methyl-2H-tetrazol-2-yl)methyl) phenyl)-1-(2-(3-isopropyl-1,2,4-oxadiazol-5-yl)piperidin-1-yl)prop-2-en-1-one;

(E)-3-(4-chloro-2-((5-methyl-2H-tetrazol-2-yl)methyl) phenyl)-1-(4-((5-methyloxazol-2-yl)methyl)piperidin-1-yl) prop-2-en-1-one;

(E)-ethyl 1-((1-(3-(4-chloro-2-((5-methyl-2H-tetrazol-2-yl)methyl)phenyl)acryloyl)-4-hydroxypiperidin-4-yl) methyl)-1H-pyrazole-4-carboxylate;

(E)-3-(4-chloro-2-((5-methyl-2H-tetrazol-2-yl)methyl) phenyl)-1-(4-(2-(4-methyl-1H-pyrazol-1-yl)ethyl)piperidin-1-yl)prop-2-en-1-one;

(E)-3-(4-chloro-2-((5-methyl-2H-tetrazol-2-yl)methyl) phenyl)-1-(3-(3-isopropyl-1,2,4-oxadiazol-5-yl)piperidin-1-yl)prop-2-en-1-one;

(E)-3-(4-chloro-2-((5-methyl-2H-tetrazol-2-yl)methyl) phenyl)-1-(3-(3-isopropyl-1,2,4-oxadiazol-5-yl)piperidin-1-yl)prop-2-en-1-one;

(E)-3-(4-chloro-2-((5-methyl-2H-tetrazol-2-yl)methyl) phenyl)-1-(3-(3-isopropyl-1,2,4-oxadiazol-5-yl)piperidin-1-yl)prop-2-en-1-one;

(E)-1-((1-(3-(4-chloro-2-((5-methyl-2H-tetrazol-2-yl) methyl)phenyl)acryloyl)-4-hydroxypiperidin-4-yl)methyl)-1H-pyrazole-4-carboxylic acid;

1-(4-(5-methyl-1,2,4-oxadiazol-3-yl)piperidin-1-yl)-2-(2-((5-methyl-2H-tetrazol-2-yl)methyl)-4-(trifluoromethyl) phenoxy)ethanone;

(E)-1-(4-(3-methyl-1H-1,2,4-triazol-1-yl)piperidin-1-yl)-3-(2-((5-methyl-2H-tetrazol-2-yl)methyl)-4-(trifluoromethyl)phenyl)prop-2-en-1-one;

(E)-1-(2-(5-methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one;

(E)-1-(2-(5-methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one;

(E)-1-(2-(5-methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one;

(E)-3-(4-chloro-2-((5-methyl-2H-tetrazol-2-yl)methyl) phenyl)-1-(4-(5-methyl-1,3,4-oxadiazol-2-yl)piperidin-1-yl)but-2-en-1-one;

1-(4-(5-methyl-1,3,4-oxadiazol-2-yl)piperidin-1-yl)-3-(2-((5-methyl-2H-tetrazol-2-yl)methyl)-4-(trifluoromethyl) phenyl)propan-1-one;

(E)-3-(4-fluoro-2-((5-methyl-2H-tetrazol-2-yl)methyl) phenyl)-1-(4-((5-methyl-1,3,4-oxadiazol-2-yl)methyl)piperidin-1-yl)prop-2-en-1-one;

(E)-3-(4,5-difluoro-2-((5-methyl-2H-tetrazol-2-yl) methyl)phenyl)-1-(4-((5-methyl-1,3,4-oxadiazol-2-yl) methyl)piperidin-1-yl)prop-2-en-1-one;

(E)-3-(5-chloro-2-((5-methyl-2H-tetrazol-2-yl)methyl) phenyl)-1-(4-((5-methyl-1,3,4-oxadiazol-2-yl)methyl)piperidin-1-yl)prop-2-en-1-one;

(E)-3-(2-fluoro-6-((5-methyl-2H-tetrazol-2-yl)methyl) phenyl)-1-(4-((5-methyl-1,3,4-oxadiazol-2-yl)methyl)piperidin-1-yl)prop-2-en-1-one;

(E)-3-(4-chloro-2-((5-methyloxazol-2-yl)methyl)phenyl)-1-(4-((5-methyl-1,3,4-oxadiazol-2-yl)methyl)piperidin-1-yl)prop-2-en-1-one;

(E)-3-(2-chloro-6-((5-methyl-2H-tetrazol-2-yl)methyl) phenyl)-1-(4-((5-methyl-1,3,4-oxadiazol-2-yl)methyl)piperidin-1-yl)prop-2-en-1-one;

4-chloro-2-((5-methyl-2H-tetrazol-2-yl)methyl)benzyl 4-(5-methyl-1,3,4-oxadiazol-2-yl)piperidine-1-carboxylate;

4-chloro-2-((5-methyl-2H-tetrazol-2-yl)methyl)benzyl 4-(5-methyloxazol-2-yl)piperidine-1-carboxylate;

(E)-3-(4-chloro-2-((5-methyl-2H-tetrazol-2-yl)methyl)phenyl)-1-(4-(pyrimidin-2-yl)piperazin-1-yl)prop-2-en-1-one;

(E)-3-(4-chloro-2-((5-methyl-2H-tetrazol-2-yl)methyl)phenyl)-1-(3-(methylsulfonyl)azetidin-1-yl)prop-2-en-1-one;

(E)-1-(1-(3-(4-chloro-2-((5-methyl-2H-tetrazol-2-yl)methyl)phenyl)acryloyl)piperidin-4-yl)imidazolidin-2-one;

(E)-tert-butyl (1-(3-(4-chloro-2-((5-methyl-2H-tetrazol-2-yl)methyl)phenyl)acryloyl)azetidin-3-yl)methylcarbamate;

(E)-3-(4-chloro-2-((5-methyl-2H-tetrazol-2-yl)methyl)phenyl)-1-(3-fluoropyrrolidin-1-yl)prop-2-en-1-one;

(E)-3-(4-chloro-2-((5-methyl-2H-tetrazol-2-yl)methyl)phenyl)-1-(4-(2-hydroxyethyl)piperidin-1-yl)prop-2-en-1-one;

(E)-3-(4-chloro-2-((5-methyl-2H-tetrazol-2-yl)methyl)phenyl)-1-(3-hydroxypiperidin-1-yl) prop-2-en-1-one;

(E)-1-(3-(4-chloro-2-((5-methyl-2H-tetrazol-2-yl)methyl)phenyl)acryloyl)piperidine-3-carboxamide;

(E)-ethyl 1-(3-(4-chloro-2-((5-methyl-2H-tetrazol-2-yl)methyl)phenyl)acryloyl)piperidine-4-carboxylate;

(E)-3-(4-chloro-2-((5-methyl-2H-tetrazol-2-yl)methyl)phenyl)-1-(4-(2-oxo-2-(piperidin-1-yl)ethoxy)piperidin-1-yl)prop-2-en-1-one;

(E)-1-(4-((1H-pyrazol-1-yl)methyl)piperidin-1-yl)-3-(4-chloro-2-((5-methyl-2H-tetrazol-2-yl)methyl)phenyl)prop-2-en-1-one;

(E)-3-(4-chloro-2-((5-methyl-2H-tetrazol-2-yl)methyl)phenyl)-1-(4-(trifluoromethyl) piperidin-1-yl)prop-2-en-1-one;

(E)-2-(1-(3-(4-chloro-2-((5-methyl-2H-tetrazol-2-yl)methyl)phenyl)acryloyl)piperidin-4-yloxy)-N, N-dimethylbenzamide;

(R,E)-3-(4-chloro-2-((5-methyl-2H-tetrazol-2-yl)methyl)phenyl)-1-(2-methylpiperidin-1-yl) prop-2-en-1-one;

(E)-1-(3-acetylpiperidin-1-yl)-3-(4-chloro-2-((5-methyl-2H-tetrazol-2-yl)methyl)phenyl)prop-2-en-1-one;

(E)-3-(4-chloro-2-((5-methyl-2H-tetrazol-2-yl)methyl)phenyl)-1-(3-(4-methyl-4H-1,2,4-triazol-3-yl)piperidin-1-yl)prop-2-en-1-one;

(E)-3-(4-chloro-2-((5-methyl-2H-tetrazol-2-yl)methyl)phenyl)-1-(3-(methoxymethyl)piperidin-1-yl)prop-2-en-1-one;

(S,E)-N-(1-(3-(4-chloro-2-((5-methyl-2H-tetrazol-2-yl)methyl)phenyl)acryloyl) pyrrolidin-3-yl)-2,2,2-trifluoroacetamide;

(E)-2-(1-(3-(4-chloro-2-((5-methyl-2H-tetrazol-2-yl)methyl)phenyl)acryloyl)piperidin-4-yloxy)-N-methylacetamide;

(E)-3-(4-chloro-2-((5-methyl-2H-tetrazol-2-yl)methyl)phenyl)-1-(4-(furan-2-carbonyl)piperazin-1-yl)prop-2-en-1-one;

(E)-3-(4-chloro-2-((5-methyl-2H-tetrazol-2-yl)methyl)phenyl)-1-(4-hydroxy-2-methylpiperidin-1-yl)prop-2-en-1-one;

(E)-3-(4-chloro-2-((5-methyl-2H-tetrazol-2-yl)methyl)phenyl)-1-(4-hydroxy-2-methylpiperidin-1-yl)prop-2-en-1-one;

(R,E)-3-(4-chloro-2-((5-methyl-2H-tetrazol-2-yl)methyl)phenyl)-1-(2-methyl-4-(1-methyl-1H-pyrazol-3-yl)piperazin-1-yl)prop-2-en-1-one;

(E)-1-(3-(2-((5-methyl-2H-tetrazol-2-yl)methyl)-4-(trifluoromethyl)phenyl)acryloyl)piperidine-4-carboxylic acid;

(E)-3-(4-(difluoromethyl)-2-((5-methyl-2H-tetrazol-2-yl)methyl)phenyl)-1-(4-(5-methyl-1,3,4-oxadiazol-2-yl)piperidin-1-yl)prop-2-en-1-one;

(E)-1-(4-((1-methyl-1H-pyrazol-4-yl)methyl) piperazin-1-yl)-3-(2-((5-methyl-2H-tetrazol-2-yl)methyl)-4-(trifluoromethyl)phenyl)prop-2-en-1-one;

(E)-1-(4-(5-methyl-1,3,4-oxadiazol-2-yl)piperidin-1-yl)-3-(2-((5-methyl-2H-tetrazol-2-yl)methyl)-4-(trifluoromethoxy)phenyl)prop-2-en-1-one;

(E)-3-(4-(difluoromethyl)-2-((5-methyl-2H-tetrazol-2-yl)methyl)phenyl)-1-(4-(5-methyl-1,2,4-oxadiazol-3-yl)piperidin-1-yl)prop-2-en-1-one;

(E)-1-(4-((5-methyl-1,3,4-oxadiazol-2-yl)methyl)piperidin-1-yl)-3-(2-((5-methyl-2H-tetrazol-2-yl)methyl)-4-(trifluoromethoxy)phenyl)prop-2-en-1-one;

(E)-1-(4-(5-methyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one;

(E)-3-(4-(difluoromethoxy)-2-((5-methyl-2H-tetrazol-2-yl)methyl)phenyl)-1-(4-((5-methyl-1,3,4-oxadiazol-2-yl)methyl)piperidin-1-yl)prop-2-en-1-one;

(E)-3-(4-(difluoromethyl)-2-((5-methyl-2H-tetrazol-2-yl)methyl)phenyl)-1-(4-((5-methyl-1,3,4-oxadiazol-2-yl)methyl)piperidin-1-yl)prop-2-en-1-one;

(E)-1-(4-((3-methyl-1,2,4-oxadiazol-5-yl)methyl)piperidin-1-yl)-3-(2-((5-methyl-2H-tetrazol-2-yl)methyl)-4-(trifluoromethyl)phenyl)prop-2-en-1-one;

(E)-3-(4-chloro-2-((5-methyl-2H-tetrazol-2-yl)methyl)phenyl)-1-(5-((2-methyloxazol-4-yl)methyl)-2,5-diazabicyclo[2.2.2]octan-2-yl)prop-2-en-1-one;

(R,E)-3-(4-chloro-2-((5-methyl-2H-tetrazol-2-yl)methyl)phenyl)-1-(2-methyl-4-((2-methyloxazol-4-yl)methyl)piperazin-1-yl)prop-2-en-1-one;

(E)-3-(4-chloro-2-((5-methyl-2H-tetrazol-2-yl)methyl)phenyl)-1-(4-(hydroxy(4-methylthiazol-2-yl)methyl)piperidin-1-yl)prop-2-en-1-one;

(E)-3-(4-chloro-2-((5-methyl-2H-tetrazol-2-yl)methyl)phenyl)-1-(4-(4-fluorophenyl)piperidin-1-yl)prop-2-en-1-one;

(R,E)-tert-butyl 2-(3-methyl-4-(3-(2-((5-methyl-2H-tetrazol-2-yl)methyl)-4-(trifluoromethyl)phenyl)acryloyl)piperazin-1-yl)acetate;

(E)-3-(4-chloro-2-((5-methyl-2H-tetrazol-2-yl)methyl)phenyl)-1-(4-((4-chlorophenyl)(hydroxy)methyl)piperidin-1-yl)prop-2-en-1-one;

(E)-3-(4-chloro-2-((5-methyl-2H-tetrazol-2-yl)methyl)phenyl)-1-(4-((4-chlorophenyl)(hydroxy)methyl)piperidin-1-yl)prop-2-en-1-one;

(E)-3-(4-chloro-2-((5-methyl-2H-tetrazol-2-yl)methyl)phenyl)-1-(4-((4-chlorophenyl)(hydroxy)methyl)piperidin-1-yl)prop-2-en-1-one;

(E)-methyl 1-(3-(2-((5-methyl-2H-tetrazol-2-yl)methyl)-4-(trifluoromethyl)phenyl)acryloyl)piperidine-4-carboxylate;

(E)-tert-butyl 4-(3-(2-((5-methyl-2H-tetrazol-2-yl)methyl)-4-(trifluoromethyl)phenyl)acryloyl)piperazine-1-carboxylate;

(R,E)-3-(2-((5-methyl-2H-tetrazol-2-yl)methyl)-4-(trifluoromethyl)phenyl)-1-(2-methyl-4-((2-methyloxazol-4-yl)methyl)piperazin-1-yl)prop-2-en-1-one;

(R,E)-3-(2-((5-methyl-2H-tetrazol-2-yl)methyl)-4-(trifluoromethyl)phenyl)-1-(2-methyl-4-((1-methyl-1H-pyrazol-4-yl)methyl)piperazin-1-yl)prop-2-en-1-one;

(E)-1-(4-((5-methyl-1,2,4-oxadiazol-3-yl)methyl)piperidin-1-yl)-3-(2-((5-methyl-2H-tetrazol-2-yl)methyl)-4-(trifluoromethyl)phenyl)prop-2-en-1-one;

(E)-1-(4-((5-methyl-1,3,4-oxadiazol-2-yl)methyl)piperidin-1-yl)-3-(4-methyl-2-((5-methyl-2H-tetrazol-2-yl)methyl)phenyl)prop-2-en-1-one;

(R,E)-3-(4-chloro-2-((5-methyl-2H-tetrazol-2-yl)methyl)phenyl)-1-(2-methyl-4-((1-methyl-1H-pyrazol-4-yl)methyl)piperazin-1-yl)prop-2-en-1-one;

(E)-3-(2-((5-methyl-2H-tetrazol-2-yl)methyl)-4-(trifluoromethyl)phenyl)-1-(4-((2-methyloxazol-4-yl)methyl)piperazin-1-yl)prop-2-en-1-one;

(E)-3-(2-((2H-1,2,3-triazol-2-yl)methyl)-4-chlorophenyl)-1-(4-((5-methyl-1,3,4-oxadiazol-2-yl)methyl)piperidin-1-yl)prop-2-en-1-one;

(E)-3-(4-chloro-2-((3-methyl-1,2,4-oxadiazol-5-yl)methyl)phenyl)-1-(4-((2-methyloxazol-4-yl)methyl)piperazin-1-yl)prop-2-en-1-one;

(E)-3-(2-((2H-tetrazol-2-yl)methyl)-4-chlorophenyl)-1-(4-((5-methyl-1,3,4-oxadiazol-2-yl)methyl)piperidin-1-yl)prop-2-en-1-one;

(E)-3-(3-fluoro-2-((5-methyl-2H-tetrazol-2-yl)methyl)phenyl)-1-(4-((5-methyl-1,3,4-oxadiazol-2-yl)methyl)piperidin-1-yl)prop-2-en-1-one;

(E)-3-(5-fluoro-2-((5-methyl-2H-tetrazol-2-yl)methyl)phenyl)-1-(4-((5-methyl-1,3,4-oxadiazol-2-yl)methyl)piperidin-1-yl)prop-2-en-1-one;

(E)-3-(4-chloro-2-((4-methyl-2H-1,2,3-triazol-2-yl)methyl)phenyl)-1-(4-((5-methyl-1,3,4-oxadiazol-2-yl)methyl)piperidin-1-yl)prop-2-en-1-one;

(E)-1-(4-((5-methyl-1,3,4-oxadiazol-2-yl)methyl)piperidin-1-yl)-3-(2-((5-methyl-2H-tetrazol-2-yl)methyl)-4-(trifluoromethyl)phenyl)prop-2-en-1-one;

(E)-4-(3-(4-((5-methyl-1,3,4-oxadiazol-2-yl)methyl)piperidin-1-yl)-3-oxoprop-1-enyl)-3-((5-methyl-2H-tetrazol-2-yl)methyl)benzonitrile;

(E)-3-(4-methoxy-2-((5-methyl-2H-tetrazol-2-yl)methyl)phenyl)-1-(4-((5-methyl-1,3,4-oxadiazol-2-yl)methyl)piperidin-1-yl)prop-2-en-1-one;

(E)-2-(1-(3-(4-chloro-2-((5-methyl-2H-tetrazol-2-yl)methyl)phenyl)acryloyl)piperidin-3-yloxy)-N-ethylacetamide;

(E)-methyl 4-(3-(4-chloro-2-((5-methyl-2H-tetrazol-2-yl)methyl)phenyl)acryloyl)morpholine-3-carboxylate;

(E)-3-(4-chloro-2-((5-methyl-2H-tetrazol-2-yl)methyl)phenyl)-1-(4-(methoxymethyl)piperidin-1-yl)prop-2-en-1-one;

(E)-3-(4-chloro-2-((5-methyl-2H-tetrazol-2-yl)methyl)phenyl)-1-(4-(pyrimidin-2-yl)-1,4-diazepan-1-yl)prop-2-en-1-one;

(E)-1-(4-acetyl-1,4-diazepan-1-yl)-3-(4-chloro-2-((5-methyl-2H-tetrazol-2-yl)methyl)phenyl)prop-2-en-1-one;

(E)-methyl 3-(3-(4-chloro-2-((5-methyl-2H-tetrazol-2-yl)methyl)phenyl)acryloyl)thiazolidine-2-carboxylate;

(E)-2-(4-(3-(4-chloro-2-((5-methyl-2H-tetrazol-2-yl)methyl)phenyl)acryloyl)piperazin-1-yl)nicotinonitrile;

(E)-3-(4-chloro-2-((5-methyl-2H-tetrazol-2-yl)methyl)phenyl)-1-(4-(3-(pyrrolidine-1-carbonyl)pyridin-2-yl)piperazin-1-yl)prop-2-en-1-one;

(E)-2-(1-(3-(4-chloro-2-((5-methyl-2H-tetrazol-2-yl)methyl)phenyl)acryloyl)piperidin-4-yloxy)-N-propylacetamide;

(E)-2-methoxy-N-methyl-N-(1-(3-(2-((5-methyl-2H-tetrazol-2-yl)methyl)-4-(trifluoromethyl)phenyl)acryloyl)piperidin-4-yl)acetamide;

(E)-3-(4-chloro-2-((5-methyl-2H-tetrazol-2-yl)methyl)phenyl)-1-(3-(5-methyl-1,3,4-oxadiazol-2-yl)azetidin-1-yl)prop-2-en-1-one;

(E)-1-(4-(5-cyclopropyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one;

(E)-4-fluoro-N-methyl-N-(1-(3-(2-((5-methyl-2H-tetrazol-2-yl)methyl)-4-(trifluoromethyl)phenyl)acryloyl)piperidin-4-yl)benzamide;

(E)-1-(4-((3-methyl-1,2,4-oxadiazol-5-yl)methyl)piperazin-1-yl)-3-(2-((5-methyl-2H-tetrazol-2-yl)methyl)-4-(trifluoromethyl)phenyl)prop-2-en-1-one;

(E)-1-(4-((1-methyl-1H-pyrazol-3-yl)methyl)piperazin-1-yl)-3-(2-((5-methyl-2H-tetrazol-2-yl)methyl)-4-(trifluoromethyl)phenyl)prop-2-en-1-one;

(S,E)-N-methyl-1-(3-(2-((5-methyl-2H-tetrazol-2-yl)methyl)-4-(trifluoromethyl)phenyl)acryloyl)pyrrolidine-2-carboxamide;

(S,E)-4,4-difluoro-N-methyl-1-(3-(2-((5-methyl-2H-tetrazol-2-yl)methyl)-4-(trifluoromethyl)phenyl)acryloyl)pyrrolidine-2-carboxamide;

(E)-1-(4-(5-ethyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one;

(E)-1-(4-((5-methyl-1,2,4-oxadiazol-3-yl)methyl)piperazin-1-yl)-3-(2-((5-methyl-2H-tetrazol-2-yl)methyl)-4-(trifluoromethyl)phenyl)prop-2-en-1-one;

(E)-3-(4-chloro-2-((5-methyl-2H-tetrazol-2-yl)methyl)phenyl)-1-(4-(5-ethyl-1,3,4-oxadiazol-2-yl)piperidin-1-yl)prop-2-en-1-one;

(E)-N-methyl-N-(1-(3-(2-((5-methyl-2H-tetrazol-2-yl)methyl)-4-(trifluoromethyl)phenyl)acryloyl)piperidin-4-yl)-2-(3-methylisoxazol-5-yl)acetamide;

(E)-3-(4-chloro-2-((5-methyl-2H-tetrazol-2-yl)methyl)phenyl)-1-(4-(5-cyclopropyl-1,3,4-oxadiazol-2-yl)piperidin-1-yl)prop-2-en-1-one;

(E)-1'-(3-(2-((5-methyl-2H-tetrazol-2-yl)methyl)-4-(trifluoromethyl)phenyl)acryloyl)-1,4'-bipiperidin-2-one;

(E)-3-(4-chloro-2-((5-methyl-2H-tetrazol-2-yl)methyl)phenyl)-1-(2-methyl-4-(5-methyl-1,3,4-oxadiazol-2-yl)piperidin-1-yl)prop-2-en-1-one;

(E)-1-(4-(methoxymethyl)piperidin-1-yl)-3-(2-((5-methyl-2H-tetrazol-2-yl)methyl)-4-(trifluoromethyl)phenyl)prop-2-en-1-one;

(E)-3-(4-chloro-2-((5-methyl-2H-tetrazol-2-yl)methyl)phenyl)-1-(4-(5-isopropyl-1,3,4-oxadiazol-2-yl)piperidin-1-yl)prop-2-en-1-one;

(E)-3-(2-((5-methyl-2H-tetrazol-2-yl)methyl)-4-(trifluoromethyl)phenyl)-1-(4-((3-methylisoxazol-5-yl)methyl)piperazin-1-yl)prop-2-en-1-one;

(E)-1-(4-(ethylsulfonyl)piperazin-1-yl)-3-(2-((5-methyl-2H-tetrazol-2-yl)methyl)-4-(trifluoromethyl)phenyl)prop-2-en-1-one;

(E)-1-(4-(5-cyclobutyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one;

(R,E)-3-(4-chloro-2-((5-methyl-2H-tetrazol-2-yl)methyl)phenyl)-1-(2-methyl-4-((5-methyl-1,2,4-oxadiazol-3-yl)methyl)piperazin-1-yl)prop-2-en-1-one;

(E)-3-(2-((5-methyl-2H-tetrazol-2-yl)methyl)-4-(trifluoromethyl)phenyl)-1-(4-((5-methylisoxazol-3-yl)methyl)piperazin-1-yl)prop-2-en-1-one;

(S,E)-1-(2-(methoxymethyl)-4-((2-methyloxazol-4-yl)methyl)piperazin-1-yl)-3-(2-((5-methyl-2H-tetrazol-2-yl)methyl)-4-(trifluoromethyl)phenyl)prop-2-en-1-one;

(E)-1-(3-methoxypiperidin-1-yl)-3-(2-((5-methyl-2H-tetrazol-2-yl)methyl)-4-(trifluoromethyl)phenyl)prop-2-en-1-one;

(E)-1-(3-methoxypiperidin-1-yl)-3-(2-((5-methyl-2H-tetrazol-2-yl)methyl)-4-(trifluoromethyl)phenyl)prop-2-en-1-one;

(E)-1-(3-methoxypiperidin-1-yl)-3-(2-((5-methyl-2H-tetrazol-2-yl)methyl)-4-(trifluoromethyl)phenyl)prop-2-en-1-one;

(E)-3-(4-chloro-2-((5-methyl-2H-tetrazol-2-yl)methyl)phenyl)-1-(4-((5-methyl-2H-tetrazol-2-yl)methyl)piperidin-1-yl)prop-2-en-1-one;

(E)-3-(4-chloro-2-((5-methyl-2H-tetrazol-2-yl)methyl)phenyl)-1-(4-(5-((tetrahydro-2H-pyran-4-yl)methyl)-1,3,4-oxadiazol-2-yl)piperidin-1-yl)prop-2-en-1-one;

(S,E)-1-(2-(methoxymethyl)pyrrolidin-1-yl)-3-(2-((5-methyl-2H-tetrazol-2-yl)methyl)-4-(trifluoromethyl)phenyl)prop-2-en-1-one;

(E)-N-methyl-N-(1-(3-(2-((5-methyl-2H-tetrazol-2-yl)methyl)-4-(trifluoromethyl)phenyl)acryloyl)piperidin-4-yl)cyclopropanesulfonamide;

(E)-1-(3-fluoropiperidin-1-yl)-3-(2-((5-methyl-2H-tetrazol-2-yl)methyl)-4-(trifluoromethyl)phenyl)prop-2-en-1-one;

(R,E)-3-(4-chloro-2-((5-methyl-2H-tetrazol-2-yl)methyl)phenyl)-1-(2-methyl-4-((3-methyl-1,2,4-oxadiazol-5-yl)methyl)piperazin-1-yl)prop-2-en-1-one;

(E)-1-(3-fluoropiperidin-1-yl)-3-(2-((5-methyl-2H-tetrazol-2-yl)methyl)-4-(trifluoromethyl)phenyl)prop-2-en-1-one;

(E)-1-(3-fluoropiperidin-1-yl)-3-(2-((5-methyl-2H-tetrazol-2-yl)methyl)-4-(trifluoromethyl)phenyl)prop-2-en-1-one;

(E)-1-(4-((4-methyl-1,2,5-oxadiazol-3-yl)methyl)piperazin-1-yl)-3-(2-((5-methyl-2H-tetrazol-2-yl)methyl)-4-(trifluoromethyl)phenyl)prop-2-en-1-one;

(R,E)-3-(2-((5-methyl-2H-tetrazol-2-yl)methyl)-4-(trifluoromethyl)phenyl)-1-(2-methylpyrrolidin-1-yl)prop-2-en-1-one;

(E)-4-fluoro-N-methyl-N-(1-(3-(2-((5-methyl-2H-tetrazol-2-yl)methyl)-4-(trifluoromethyl)phenyl)acryloyl)piperidin-4-yl)benzenesulfonamide;

(E)-1-(4-((4-methoxybenzyl)(methyl)amino)piperidin-1-yl)-3-(2-((5-methyl-2H-tetrazol-2-yl)methyl)-4-(trifluoromethyl)phenyl)prop-2-en-1-one;

(E)-3-(4-chloro-2-((5-methyl-2H-tetrazol-2-yl)methyl)phenyl)-1-(4-((4-methyl-2H-1,2,3-triazol-2-yl)methyl)piperidin-1-yl)prop-2-en-1-one;

(S,E)-3-(2-((5-methyl-2H-tetrazol-2-yl)methyl)-4-(trifluoromethyl)phenyl)-1-(2-(trifluoromethyl)piperidin-1-yl)prop-2-en-1-one;

(E)-3-(4-chloro-2-((5-methyl-2H-tetrazol-2-yl)methyl)phenyl)-1-(4-(5-(piperidin-1-ylmethyl)-1,3,4-oxadiazol-2-yl)piperidin-1-yl)prop-2-en-1-one;

(R,E)-3-(4-chloro-2-((5-methyl-2H-tetrazol-2-yl)methyl)phenyl)-1-(4-((5-methoxypyridin-2-yl)methyl)-2-methylpiperazin-1-yl)prop-2-en-1-one;

(E)-3-(2-((5-methyl-2H-tetrazol-2-yl)methyl)-4-(trifluoromethyl)phenyl)-1-(2-(trifluoromethyl)piperidin-1-yl)prop-2-en-1-one;

(E)-N-(1-(3-(4-chloro-2-((5-methyl-2H-tetrazol-2-yl)methyl)phenyl)acryloyl) piperidin-4-yl)acetamide;

(E)-1-(1-(3-(2-((5-methyl-2H-tetrazol-2-yl)methyl)-4-(trifluoromethyl)phenyl)acryloyl)piperidin-4-yl)pyrrolidin-2-one;

(E)-3-(4-chloro-2-((5-methyl-2H-tetrazol-2-yl)methyl)phenyl)-1-(4-((5-methyl-1,3,4-oxadiazol-2-yl)methyl)piperidin-1-yl)prop-2-en-1-one;

(E)-methyl 1-(3-(4-chloro-2-((5-methyl-2H-tetrazol-2-yl)methyl)phenyl)acryloyl)piperidine-4-carboxylate;

(E)-3-(4-chloro-2-((5-methyl-2H-tetrazol-2-yl)methyl)phenyl)-1-(4-(2-morpholino-2-oxoethyl)piperidin-1-yl)prop-2-en-1-one;

(E)-3-(4-chloro-2-((5-methyl-2H-tetrazol-2-yl)methyl)phenyl)-1-(3-(4-fluorophenoxy)azetidin-1-yl)prop-2-en-1-one;

(E)-1-((2S,4S)-4-fluoro-2-(hydroxymethyl)pyrrolidin-1-yl)-3-(2-((5-methyl-2H-tetrazol-2-yl)methyl)-4-(trifluoromethyl)phenyl)prop-2-en-1-one;

(S,E)-1-(2-(hydroxymethyl)-4-((2-methyloxazol-4-yl)methyl)piperazin-1-yl)-3-(2-((5-methyl-2H-tetrazol-2-yl)methyl)-4-(trifluoromethyl)phenyl)prop-2-en-1-one;

(S,E)-1-(2-(hydroxymethyl)pyrrolidin-1-yl)-3-(2-((5-methyl-2H-tetrazol-2-yl)methyl)-4-(trifluoromethyl)phenyl)prop-2-en-1-one;

(E)-3-(4-chloro-2-((5-methyl-2H-tetrazol-2-yl)methyl)phenyl)-1-(4-(5-(morpholinomethyl)-1,3,4-oxadiazol-2-yl)piperidin-1-yl)prop-2-en-1-one;

(E)-3-(4-chloro-2-((5-methyl-2H-tetrazol-2-yl)methyl)phenyl)-1-(4-(5-(trifluoromethyl)pyridin-2-yloxy)piperidin-1-yl)prop-2-en-1-one;

(E)-3-(4-chloro-2-((5-methyl-2H-tetrazol-2-yl)methyl)phenyl)-1-(4-((5-(morpholinomethyl)-1,3,4-oxadiazol-2-yl)methyl)piperidin-1-yl)prop-2-en-1-one;

(S,E)-3-(2-((5-methyl-2H-tetrazol-2-yl)methyl)-4-(trifluoromethyl)phenyl)-1-(2-(trifluoromethyl)pyrrolidin-1-yl)prop-2-en-1-one;

(E)-1-(4-benzyl-4-hydroxypiperidin-1-yl)-3-(4-chloro-2-((5-methyl-2H-tetrazol-2-yl)methyl)phenyl)prop-2-en-1-one;

(E)-1-(4-benzylpiperidin-1-yl)-3-(4-chloro-2-((5-methyl-2H-tetrazol-2-yl)methyl)phenyl)prop-2-en-1-one;

(E)-3-(4-chloro-2-((5-methyl-2H-tetrazol-2-yl)methyl)phenyl)-1-(4-((5-methoxypyridin-2-yl)methyl)piperazin-1-yl)prop-2-en-1-one;

(E)-3-(4-chloro-2-((5-methyl-2H-tetrazol-2-yl)methyl)phenyl)-1-(4-((3-methylisoxazol-5-yl)methyl)piperazin-1-yl)prop-2-en-1-one;

(E)-3-(4-chloro-2-((5-methyl-2H-tetrazol-2-yl)methyl)phenyl)-1-(4-((2-methyloxazol-4-yl)methyl)piperazin-1-yl)prop-2-en-1-one;

(E)-3-(4-chloro-2-((5-methyl-2H-tetrazol-2-yl)methyl)phenyl)-1-(4-((1-methyl-1H-benzo[d]imidazol-2-yl)methyl)piperazin-1-yl)prop-2-en-1-one;

(E)-3-(4-chloro-2-((5-methyl-2H-tetrazol-2-yl)methyl)phenyl)-1-(4-((1-methyl-5-phenyl-1H-pyrazol-3-yl)methyl)piperazin-1-yl)prop-2-en-1-one;

(E)-3-(4-chloro-2-((5-methyl-2H-tetrazol-2-yl)methyl)phenyl)-1-(4-((1-methyl-3-phenyl-1H-pyrazol-5-yl)methyl)piperazin-1-yl)prop-2-en-1-one;

(E)-3-(4-chloro-2-((5-methyl-2H-tetrazol-2-yl)methyl)phenyl)-1-(4-((5-methoxypyrazin-2-yl)methyl)piperazin-1-yl)prop-2-en-1-one;

(E)-3-(4-chloro-2-((5-methyl-2H-tetrazol-2-yl)methyl)phenyl)-1-(4-((2-morpholinopyrimidin-5-yl)methyl)piperazin-1-yl)prop-2-en-1-one;

(E)-3-(4-chloro-2-((5-methyl-2H-tetrazol-2-yl)methyl)phenyl)-1-(4-((1-methyl-1H-pyrazol-4-yl)methyl)piperazin-1-yl)prop-2-en-1-one;

(E)-3-(4-chloro-2-((5-methyl-2H-tetrazol-2-yl)methyl)phenyl)-1-(4-(5-(2,2,2-trifluoroethyl)-1,3,4-oxadiazol-2-yl)piperidin-1-yl)prop-2-en-1-one;

(E)-3-(2-((5-methyl-2H-tetrazol-2-yl)methyl)-4-(trifluoromethyl)phenyl)-1-(3-(trifluoromethyl)morpholino)prop-2-en-1-one;

(R,E)-3-(4-chloro-2-((2-methyl-2H-tetrazol-5-yl)methyl)phenyl)-1-(4-(4-fluorobenzyl)-2-methylpiperazin-1-yl)prop-2-en-1-one;

(R,E)-3-(4-chloro-2-((5-methyl-1,2,4-oxadiazol-3-yl)methyl)phenyl)-1-(4-(4-fluorobenzyl)-2-methylpiperazin-1-yl)prop-2-en-1-one;

(E)-N-(2-(1-(3-(4-chloro-2-((5-methyl-2H-tetrazol-2-yl)methyl)phenyl)acryloyl)piperidin-4-yl)ethyl)-1H-1,2,3-triazole-4-carboxamide;

(E)-N-(2-(1-(3-(4-chloro-2-((5-methyl-2H-tetrazol-2-yl)methyl)phenyl)acryloyl)piperidin-4-yl)ethyl)-3-(trifluoromethyl)-1H-pyrazole-4-carboxamide;

(E)-N-((1-(3-(4-chloro-2-((5-methyl-2H-tetrazol-2-yl)methyl)phenyl)acryloyl)piperidin-4-yl)methyl)-3-(3-hydroxyisoxazol-5-yl) propanamide;

(E)-N-(2-(1-(3-(4-chloro-2-((5-methyl-2H-tetrazol-2-yl)methyl)phenyl)acryloyl)piperidin-4-yl)ethyl)-N-methyl-2-oxo-2,3-dihydrooxazole-5-carboxamide;

(E)-1-(4-(1-(1H-1,2,3-triazole-4-carbonyl)piperidin-4-yl)piperazin-1-yl)-3-(4-chloro-2-((5-methyl-2H-tetrazol-2-yl)methyl)phenyl)prop-2-en-1-one;

(E)-3-(2-(4-(3-(4-chloro-2-((5-methyl-2H-tetrazol-2-yl)methyl)phenyl)acryloyl)morpholin-2-yl)ethylamino)-4-ethoxycyclobut-3-ene-1,2-dione;

(E)-N-(1-(3-(4-chloro-2-((5-methyl-2H-tetrazol-2-yl)methyl)phenyl)acryloyl) piperidin-4-yl)-4-(1H-1,2,3-triazol-4-yl)butanamide;

(E)-N-(1-(3-(2-((5-methyl-2H-tetrazol-2-yl)methyl)-4-(trifluoromethyl)phenyl)acryloyl)piperidin-4-yl)-4-(1H-1,2,3-triazol-4-yl)butanamide;

1-(4-(5-(1H-1,2,3-triazol-4-yl)pentyl)piperidin-1-yl)-3-(2-((5-methyl-2H-tetrazol-2-yl)methyl)-4-(trifluoromethyl)phenyl)propan-1-one;

1-(4-(5-(1H-1,2,3-triazol-4-yl)pentyl)piperidin-1-yl)-2-(2-((5-methyl-2H-tetrazol-2-yl)methyl)-4-(trifluoromethyl)phenoxy)ethanone;

(E)-1-(4-(4-(1H-1,2,3-triazol-4-yl)butylamino)piperidin-1-yl)-3-(2-((5-methyl-2H-tetrazol-2-yl)methyl)-4-(trifluoromethyl)phenyl)prop-2-en-1-one;

(E)-N-(1-(3-(2-((5-methyl-2H-tetrazol-2-yl)methyl)-4-(trifluoromethyl)phenyl)acryloyl)piperidin-4-yl)-6-(1H-1,2,3-triazol-5-yl)hexanamide; and (E)-1-(4-(2-(2-(1H-1,2,3-triazol-5-yl)ethoxy)ethyl)piperidin-1-yl)-3-(2-((5-methyl-2H-tetrazol-2-yl)methyl)-4-(trifluoromethyl)phenyl)prop-2-en-1-one;

or a pharmaceutically acceptable salt thereof.

DEFINITIONS

"Halo" or "halogen", as used herein, may be fluoro, chloro, bromo or iodo.

"$C_{1-4}$ alkyl", as used herein, denotes straight chain or branched alkyl having 1-4 carbon atoms. If a different number of carbon atoms is specified, such as $C_6$ or $C_3$, then the definition is to be amended accordingly, such as "$C_1$-$C_4$ alkyl" will represent methyl, ethyl, propyl, isopropyl, butyl, isobutyl, sec-butyl and tert-butyl.

"$C_{1-4}$ haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.

"$C_{1-4}$ alkoxy", as used herein, refers to an —O—$C_{1-4}$ alkyl group wherein $C_{1-4}$ alkyl is as defined herein. Examples of such groups include methoxy, ethoxy, propoxy, butoxy, pentoxy or hexoxy and the like. As for alkyl unless a particular structure is specified the terms propoxy, butoxy etc include all straight and branched chain forms having the appropriate number of carbon atoms e.g. propoxy includes n-propoxy and isopropoxy.

"$C_{1-4}$ haloalkoxy" as used herein refers to an —O—$C_{1-4}$ alkyl group wherein $C_{1-4}$ alkyl is as defined herein and substituted with one or more halogen groups, e.g. —O—$CF_3$.

"$C_{1-4}$ alkoxy $C_{1-4}$ alkyl" as used herein refers to an —$C_{1-3}$ alkyl-O—$C_{1-3}$alkyl group wherein $C_{1-3}$ alkyl is as defined herein. Examples of such groups include methoxyethyl, methoxypropyl, ethoxypropyl.

"hydroxyl $C_{1-4}$alkyl", as used herein, denotes a straight chain or branched alkyl having 1-4 carbon atoms with at least one hydrogen substituted with a hydroxy group. If a different number of carbon atoms is specified, such as $C_6$ or $C_3$, then the definition is to be amended accordingly, such as "$C_1$-$C_4$ hydroxyalkyl" will represent methyl, ethyl, propyl, isopropyl, butyl, isobutyl, sec-butyl and tert-butyl that have at least one hydrogen substituted with hydroxy.

"$C_{3-6}$ cycloalkyl" as used herein refers to a saturated monocyclic hydrocarbon ring of 3 to 6 carbon atoms. Examples of such groups include cyclopropyl, cyclobutyl, cyclopentyl and cyclohexyl. If a different number of carbon atoms is specified, then the definition is to be amended accordingly.

"$C_{3-6}$ cycloalkenyl" as used herein refers to a partially saturated monocyclic hydrocarbon ring of 3 to 6 carbon atoms. Examples of such groups include cyclopropenyl, cyclobutenyl, cyclopentenyl, cyclohexenyl and cyclohexa-1,4-dienyl. If a different number of carbon atoms is specified, then the definition is to be amended accordingly.

"Oxo" refers to =O.

The term "4 to 8 membered nitrogen-containing heterocyclic ring" as used herein refers to a 4 to 8 membered saturated or partially saturated ring which may contain in addition to the nitrogen atom indicated in formula (I) 1 or 2 further heteroatoms independently selected from oxygen, nitrogen or sulphur. Suitable examples of such rings include pyrrolidinyl, piperidinyl, piperazinyl, morpholinyl, thiomorpholinyl and azetidinyl.

The term "bridged 4 to 8 membered nitrogen-containing heterocyclic ring system" as used herein refers to a "4 to 8 membered nitrogen-containing heterocyclic ring" as defined hereinbefore wherein two non-neighbouring carbon atoms (i.e. carbon atoms that are not directly bonded to each other) of the "4 to 8 membered nitrogen-containing heterocyclic ring" are connected via a saturated —$(CH_2)_n$— carbon chain, where n is 1, 2 or 3. In one embodiment, n is 1 or 2. In another embodiment, n is 1.

The term "5 or 6 membered heteroaryl" refers to a 5 or 6 membered aromatic ring system which contains 1 to 3 heteroatoms selected from oxygen, nitrogen or sulfur. Examples of 5-membered heteroaryl rings in this instance include furanyl, pyrrolyl, oxazolyl, thiazolyl, imidazolyl, oxadiazolyl, thiadiazolyl, triazolyl, isothiazolyl, isoxazolyl, thiophenyl, or pyrazolyl. Examples of 6-membered heteroaryl rings include pyridinyl, pyridazinyl, pyrimidinyl, pyrazinyl, or triazinyl.

The term "5 or 6 membered heterocyclyl ring" refers to a 5 or 6 membered saturated or partially unsaturated ring system which contains 1 to 3 heteroatoms selected from oxygen, nitrogen or sulphur. Suitable examples of such ring systems include pyrrolidinyl, piperidinyl, piperazinyl, morpholinyl, homomorpholinyl, thiomorpholinyl, tetrahydrofuranyl, tetrahydropyranyl, tetrahydrothiophenyl, pyrrolinyl, or oxazolinyl.

The term "9 to 10 membered fused bicyclic ring system" refers to a "5 or 6 membered heteroaryl" or a "5 or 6 membered heterocyclyl ring" as defined hereinbefore wherein two neighbouring atoms (i.e. atoms bonded directly to each other) of the "5 or 6 membered heteroaryl" or "5 or 6 membered heterocyclyl ring" form together a second ring which second ring contains 0, 1 or 2 heteroatoms selected from oxygen, nitrogen and sulphur.

The term "a," "an," "the" and similar terms used in the context of the present invention (especially in the context of the claims) are to be construed to cover both the singular and plural unless otherwise indicated herein or clearly contradicted by the context.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, when one embodiment refers to several other embodiments by using the term "according to any one of", for example "according to any one of embodiments 1 to 5", then said embodiment refers not only to embodiments indicated by the integers such as 1 and 2 but also to embodiments indicated by numbers with a decimal component such as 1.1, 1.2 or 2.1, 2.2, 2.3. For example, "according to any one of embodiments 1 to 3" means according to any one of embodiments 1, 1.1, 2, 3, 3.1, 3.2, 3.3, 3.4, 3.5, 3.6, 3.7.

Various embodiments of the invention are described herein. It will be recognized that features specified in each embodiment may be combined with other specified features to provide further embodiments.

The term "compounds of the (present) invention" or "a compound of the (present) invention" refers to a compound as defined in any one of embodiments 1 to 144.

The compounds of the present invention may be prepared by the routes described in the following Schemes or the Examples.

In the following general methods, R4, R2, R3, R5, A, B, X and Y are as previously defined in the embodiments, or limited to designations in the Schemes. Unless otherwise stated, starting materials are either commercially available or are prepared by known methods.

Compounds of formula I, where Y is —CH2—CH2—, may be prepared from compounds of formula I, where Y is —CH═CH—, by hydrogenation over a suitable catalyst, such as palladium on carbon, in a suitable solvent, such as ethanol at room temperature.

Compounds of formula I may be prepared from compounds of formula II and III as illustrated in Scheme 1, by using a suitable coupling reagent, such as T3P or HATU and an organic base such as triethylamine, in a suitable organic solvent such as DMF, ethylacetate or dichloromethane, at a temperature from 25° C. to 50° C., preferably at 25° C.

Scheme 1

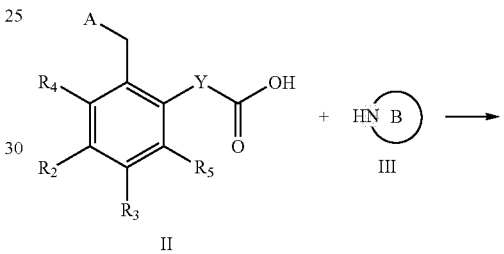

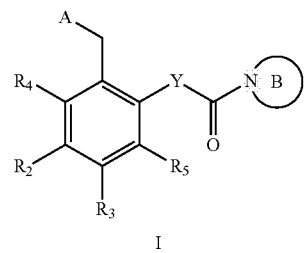

I

Alternatively, when Y is CH═CH, compounds of formula I may be prepared from compounds of formula IV and V as illustrated in Scheme 2, wherein Y1 is a halogen group, preferably a bromine. The coupling reaction requires suitable "Heck" conditions of a palladium catalyst and phosphine ligand, such as palladium II acetate and tri-o-tolyl phosphine, and a suitable organic base, such as triethylamine, in an organic solvent such as DMF, at a temperature of 60° C. to 120° C., preferably at 80° C. Those skilled in the art will appreciate that other catalyst/phosphine combinations and solvents may also be suitable.

Compounds of formula V may be prepared by compounds of formula III by reaction with acryloyl chloride in the presence of a base, such as triethylamine, in a suitable solvent such as dichloromethane at a temperature of 0° C.

Scheme 2

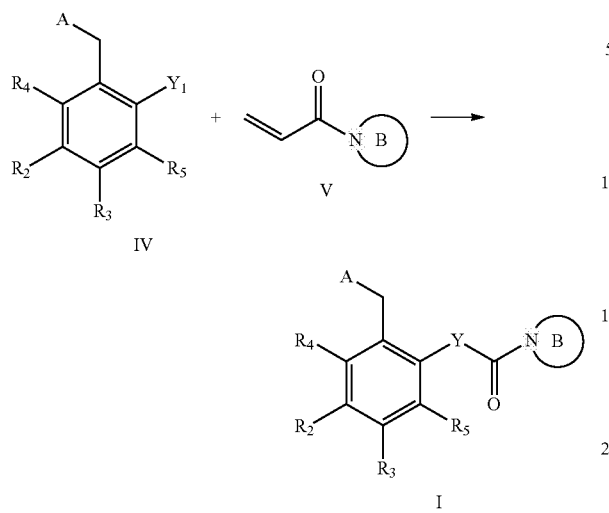

When Y is CH=CH, compounds of formula IIa can be prepared from compounds of formula IV, where Y1 is a halogen group, preferably bromine, as illustrated in Scheme 3.

Step i) Compounds of formula VI can be prepared from compounds of formula IV using "Heck" coupling conditions with ethyl acrylate, such as palladium II acetate and tri-o-tolyl phosphine, and a suitable organic base, such as triethylamine in an organic solvent such as DMF, at a temperature of 60° C. to 120° C., preferably at 80° C. Those skilled in the art will appreciate that other catalyst/phosphine combinations and solvents may also be suitable.

Step ii) Compounds of formula IIa can be prepared from compounds of formula VI using an alkaline solution, such as sodium hydroxide solution, in an organic solvent such as ethanol, at a temperature of 0° C. to 50° C., preferably at room temperature.

Scheme 3

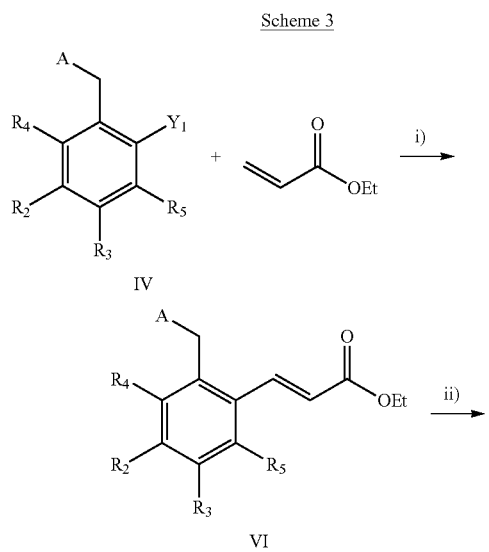

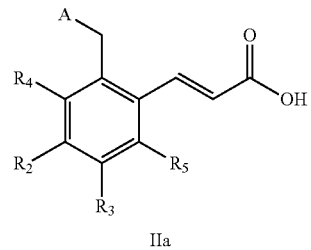

IIa

Compounds of formula II where Y is —CH$_2$—CH$_2$— can be prepared from compounds of formula IV analogously to Scheme 3 by the replacing ethyl acrylate with acrolein diethylacetal.

When A is a nitrogen linked tetrazole or triazole, compounds of formula IV can be prepared as illustrated in Scheme 4 from compounds of formula VII, where Y$_1$ is a halogen, preferably bromine or an ester group, preferably methylester, by an alkylation reaction using a suitable base, such as potassium carbonate, in a suitable solvent such as DMF at a temperature of −10° C. to 50° C., preferably 0° C. to room temperature. The heterocycle A is either commercially available or synthesized by known procedures.

Scheme 4

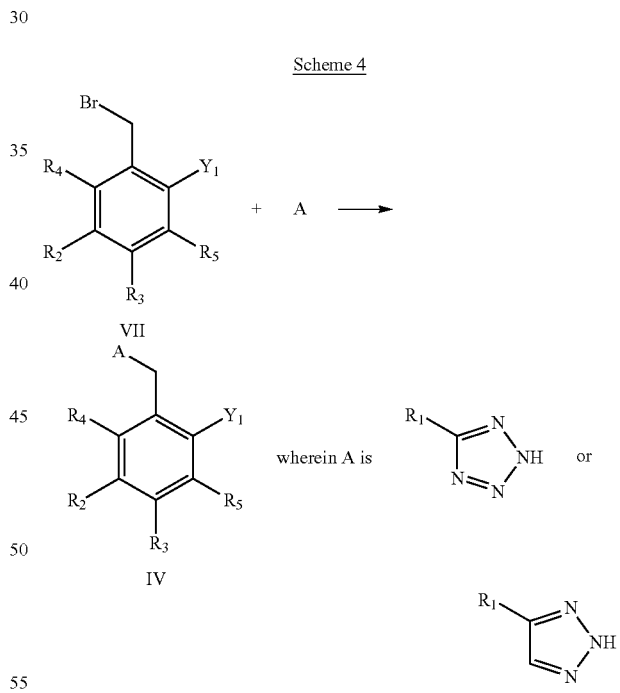

When A is 1,2,4 oxadiazole, compounds of formula IV may be prepared from compounds of formula VIII, where Y1 is a halogen, preferably bromine, and are either commercially available or synthesized by known procedures, as illustrated in Scheme 5. The procedure follows a cyclisation-condensation reaction with an hydroxyl amidine, such as hydroxyl acetamidine, and a suitable coupling reagent, such as T3P or HATU, in the presence of a base, such as triethylamine, in a suitable solvent, such as DMF at a temperature of 100° C. to 180° C. R$^{1a}$ is C$_{1-4}$alkyl.

Scheme 5

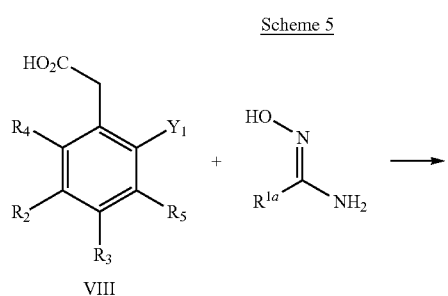

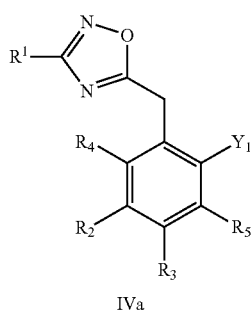

When A is oxazole compounds of formula IV may be prepared from compounds of formula VIII, where Y1 is a halogen, preferably bromine, as illustrated in Scheme 6.

Step i) Compounds of formula IX may be prepared from compounds of formula VIII by a coupling reaction with prop-2-yn-1-amine using a suitable coupling reagent such as T3P or HATU in the presence of an organic base, such as triethylamine, in a suitable solvent such as DMF, ethyl acetate or DCM at a temperature of 0° C. to 50° C., preferably at room temperature.

Step ii) Compounds of formula IVb can be prepared from compound of formula IX by a cyclisation-condensation reaction under strong acid conditions, such as triflic acid, in a suitable solvent such as 1,4 dioxane, at a temperature of 50° C. to 120° C., preferably at 90° C. Those skilled in the art would appreciate that other annulation methods are known for the synthesis of an oxazole rings.

Scheme 6

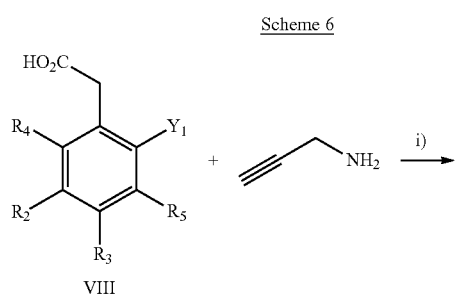

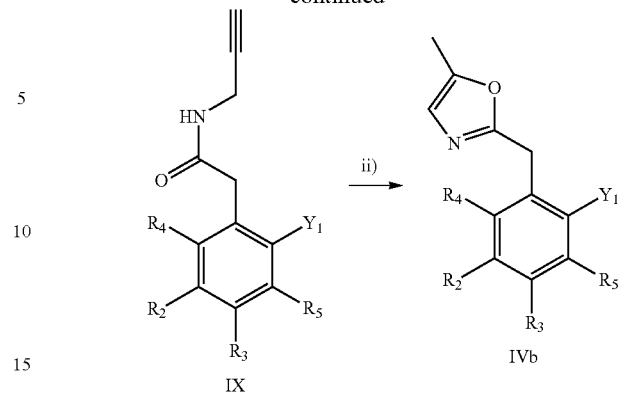

Alternatively, when A is 1,3,4 oxadiazole, compounds of formula IV may be prepared from compounds of formula VIII, where Y1 is a halogen, preferably a bromine, as illustrated in Scheme 7.

Step i) Compounds of formula X may be prepared from compounds of formula VIII by a coupling reaction with an acyl hydrazide, such as acetohydrazide, using a suitable coupling reagent such as T3P or HATU in the presence of an organic base such as triethylamine, in a suitable solvent such as DMF, ethyl acetate or DCM at a temperature of 0° C. to 50° C., preferably at room temperature.

Step ii) Compounds of formula IVc can be prepared from compounds of formula X by a cyclisation-condensation reaction with a suitable reagent such as the Burgess reagent or triphenyl phosphine with hexachloroethane and a suitable organic base such as triethylamine. The reaction is performed in a suitable solvent such as THF or DCM at a temperature between 25° C. and solvent reflux, preferably at solvent reflux.

Scheme 7

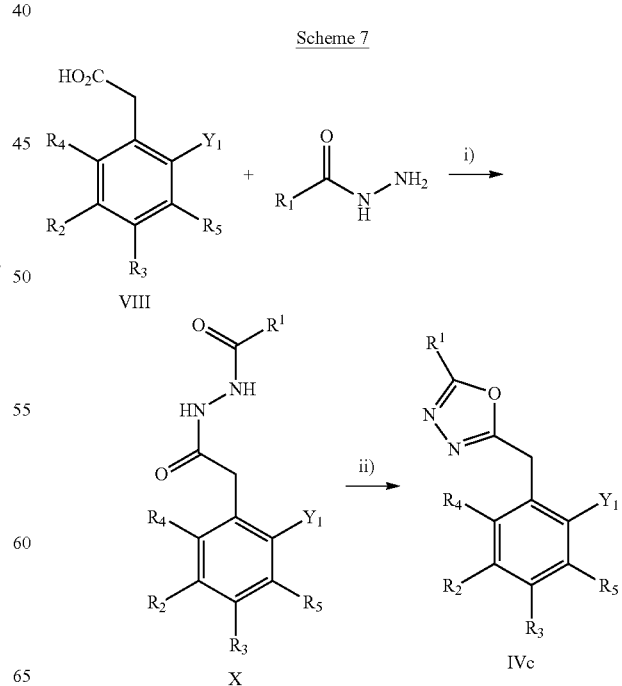

When A is the alternate 1,2,4 oxadiazole, compounds of formula IV may be prepared from compounds of formula VII where Y1 is a halogen, preferably bromine, as illustrated in Scheme 8.

Step i. Compounds of formula XI may be prepared from compounds of formula VII by a nucleophilic substitution reaction with a cyanide reagent, such as potassium cyanide, in a suitable solvent such as THF or DMF, at a temperature of 0° C. to 50° C., preferably at room temperature.

Step ii. Compounds of formula XII may be prepared from compounds of formula XI by a reaction with hydroxylamine in the presence of a base, such as potassium carbonate, in a suitable solvent such as ethanol at a temperature of 80° C. to 120° C., preferably 95° C.

Step iii. Compounds of formula XIII may be prepared from compounds of formula XII by an acylation reaction with a suitable acetylating reagent, such as acetyl chloride or a carboxylic acid together with a suitable coupling reagent, such as T3P or HATU in the presence of an organic base, such as triethylamine, in a suitable solvent such as DCM or THF, at a temperature of 0° C. to 50° C., preferably at room temperature. The acyl halide or carboxylic acid is either commercially available or synthesized from known procedures.

Step iv. Compounds of formula IVd may be prepared from compounds of formula XIII by a cyclisation-condensation reaction using a suitable reagent such as hexachloroethane in an acidic solvent such acetic acid, at a temperature of 80° C. to 120° C., preferably at 100° C.

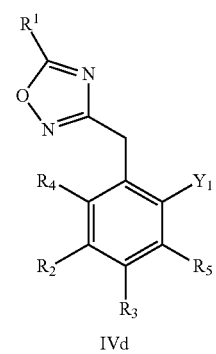

IVd

When A is a carbon linked tetrazole, compounds of formula IV may be prepared from compounds of formula XI, where Y1 is a halogen, preferably bromine, or an ester group, preferably methylester, as illustrated in Scheme 9.

Step i: Compounds of formula XV may be prepared from compounds of formula XI by reaction with an azide, such as sodium azide in a suitable solvent such as toluene at a temperature of 80° C. to 120° C., preferably at reflux temperature.

Step ii. Compounds of formula IVe may be prepared from compounds of formula XV by alkylation with a suitable alkylating agent such as methyl iodide, in the presence of a suitable base, such triethylamine, in a suitable solvent such as DMF, or MeCN, at a temperature of 25° C. to 100° C., preferably 80° C.

Scheme 8

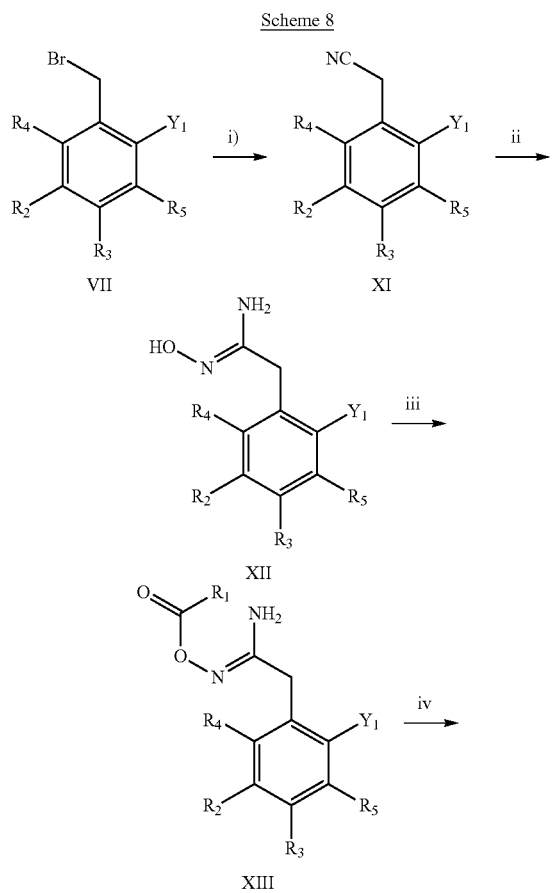

Scheme 9

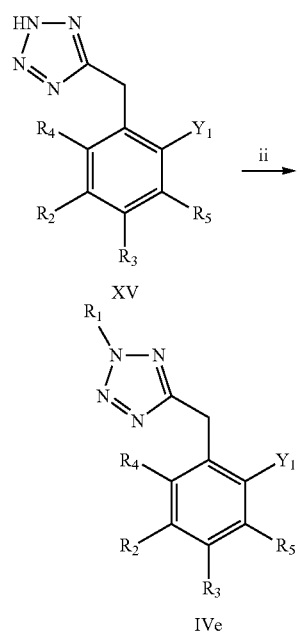

Compounds of formula VII may be prepared from compounds of formula XVI, which are either commercially available or synthesized by known procedures, where Y1 is a halogen, preferably bromine or an ester group, preferably methylester, by a bromination reaction illustrated in Scheme 10 using a suitable brominating agent, such as N-bromosuccinimide and a radical initiator such as AIBN in a suitable solvent such as tBuOAc at a temperature of 80° C. to 120° C., preferably at 90° C.

Scheme 10

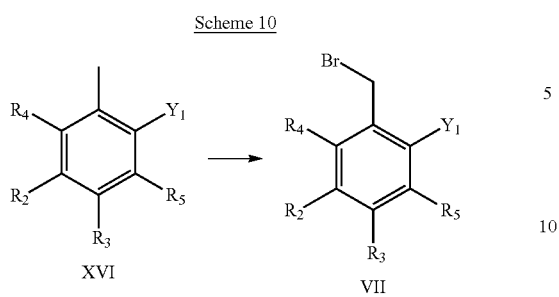

When Y1 is an ester, such as a methyl ester, compounds of formula XVI may be prepared from compounds of formula XVII as illustrated in Scheme 11.

Step 1. Compounds of formula XVIII may be prepared from compounds of formula XVII using methods described in the literature. G. P Lahm et. al. Bioorg. Med. Chem. Lett. 15 (2005) 4898-4906.

Step ii. Compounds of formula XVI may be prepared from compounds of formula XVIII by esterification in a suitable alcoholic solvent, such as methanol, in the presence of a strong acid, such as sulfuric acid, at reflux temperature.

Scheme 11

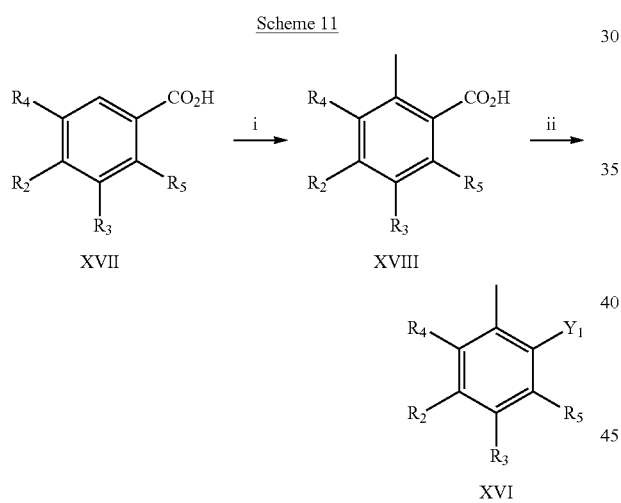

When Y is CH3CH=CH, Compounds of formula II, may be prepared from compounds of formula IV where Y1 is an ester, such as a methyl ester, as illustrated in Scheme 12.

Scheme 12

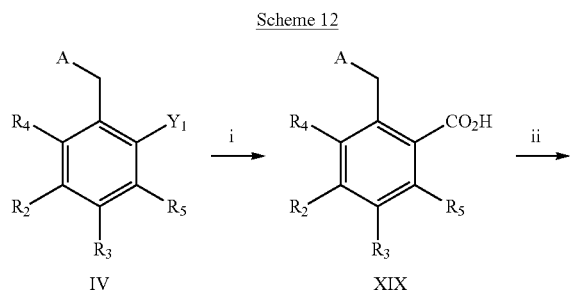

Step i. Compounds of formula XIX may be prepared from compounds of formula IV by standard saponification conditions known to those skilled in the art.

Step ii. Compounds of formula XX may be prepared from compounds of formula XIX by a coupling reaction with N,O-dimethylhydroxylamine using a suitable coupling reagent such as HATU or T3P in the presence of a suitable base, such as triethylamine, in a suitable solvent such as DMF or EtOAc, at a temperature of 0° C. to 50° C., preferably at room temperature.

Step iii. Compounds of formula XXI may be prepared from compounds of formula XX by a nucleophilic substitution reaction with a suitable Grignard reagent, such methylmagnesium bromide, in a suitable solvent such as THF or diethylether at a temperature of −78° C. to 0° C., preferably at −78° C.

Step iv. Compounds of formula XXII may be prepared from compounds of formula XXI by reaction with a suitable ylid such as triethylphosphonoacetate and sodium hydride, in a suitable solvent such as THF at a temperature of 0° C. to 60° C.

Step v. Compounds of formula II may be prepared from compounds of formula XXII by standard saponification conditions known to those skilled in the art.

When Y is —CH2-O—, Compounds of formula I, may be prepared from compounds of formula IV where Y1 is an ester, such as a methyl ester, as illustrated in Scheme 13.

Scheme 13

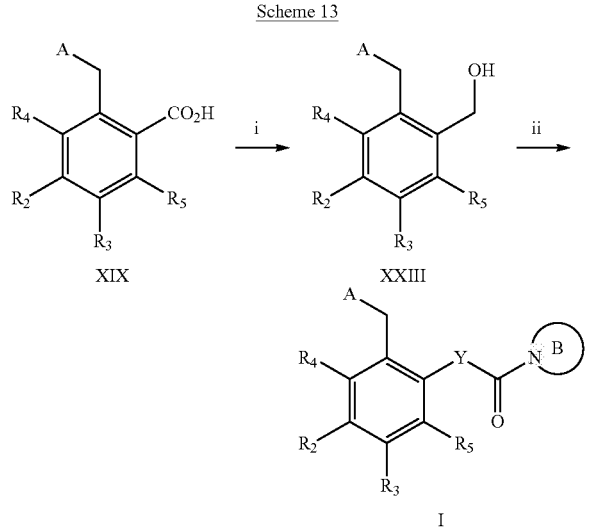

Step i. Compounds of formula XXIII may be prepared from compounds of formula XIX by reduction of the carboxylic acid group using a reducing agent such as borane. THF complex in a suitable solvent such as THF, at a temperature of 25° C. to 50° C., preferably at 50° C.

Step ii. Compounds of formula I may be prepared from compounds of formula XXIII by a coupling reaction with compounds of formula III using a phosgene equivalent, such as triphosgene or carbonyl diimidazole, preferably carbonyl diimidazole, in a suitable solvent such as DMF at a temperature of 0° C. to 25° C., preferably 25° C.

Compounds of formula III are either commercially available or synthesized by known procedures or by the following Schemes where P is a protecting group. Protection and deprotection strategies are known to those skilled in the art, examples of which can be found in the publication 'Protective Groups in Organic Synthesis' by Green et al. Unless otherwise stated, starting materials are either commercially available or synthesized by known procedures. In the following Schemes, $R^{Ba}$ and $R^{Bb}$ are independently selected from H, $C_{1-4}$ alkyl or $C_{1-4}$ alkoxy, and n is as previously defined in the embodiments.

Compounds of formula III where Q is an $-(CR^{Ba}R^{Bb})_n$-1,3,4-oxadiazole, may be prepared from compounds of formula XXIV, by a coupling-cyclisation-condensation sequence illustrated in Scheme 14.

Step i) Compounds of formula XXV may be prepared from compounds of formula XXIV by a coupling reaction with an acyl hydrazide, such as acetohydrazide and a coupling reagent such as HATU or T3P, in the presence of a suitable base such as triethylamine, in a suitable solvent such DMF or EtOAc at a temperature of 0 to 50° C., preferably at room temperature.

Step ii) Compounds of formula XXVI may be prepared from compounds of formula XXV by a cyclisation condensation step using a suitable activating agent, such as the Burgess reagent or triphenyl phosphine with hexachloroethane, and a suitable organic base, such as triethylamine or diiosopropylethylamine. The reaction is performed in a suitable solvent such as THF or DCM at a temperature between 25° C. and solvent reflux, preferably at solvent reflux.

Step iii. Compounds of formula IIIa may be prepared from compounds of formula XXVI by a deprotection step using standard deprotection chemistry known to those skilled in the art. For example if P is an tertbutoxycarbonate group then suitable deprotection reagents are strong acids such as trifluoroacetic acid.

Alternatively, Compounds of formula XXIVa may be prepared from compounds of formula XXIV by reaction with a protected form of hydrazine such as tert-butyl hydrazinecarboxylate, with a suitable coupling reagent, such as T3P or HATU, in the presence of a suitable base such as triethylamine, in a suitable solvent such as DMF or DCM at a temperature of 0° C. to 50° C., preferably at room temperature. Compounds of formula XXV may be prepared from compounds of formula XXIVa by a coupling reaction with a carboxylic acid using a suitable coupling reagent, such as T3P or HATU, in the presence of a suitable base such as triethylamine, in a suitable solvent such as DMF or DCM at a temperature of 0° C. to 50° C., preferably at room temperature.

Scheme 14

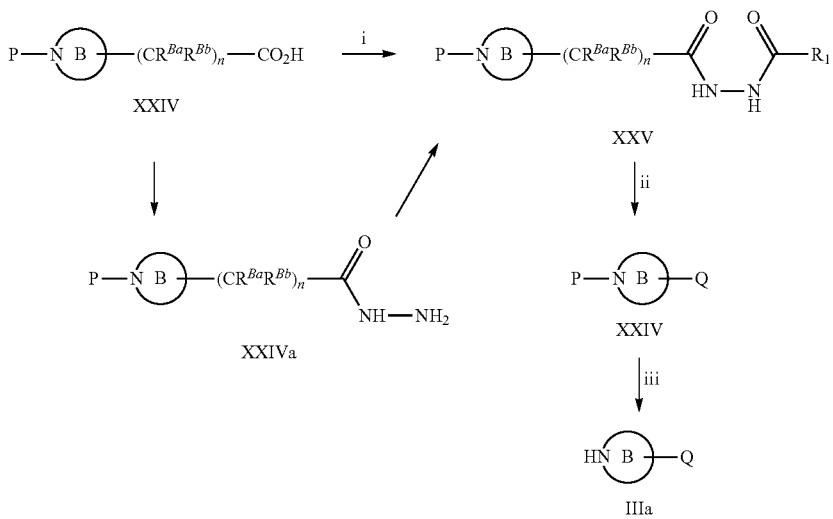

Analogous to Scheme 14, Compounds of formula III where Q is an —$(CR^{Ba}R^{Bb})_n$-1,2,4-oxadiazole ring, may be prepared from compounds of formula XXIV, by replacing the acyl hydrazide in step i with an hydroxyl amidine such as hydroxylacetamidine.

Also, Compounds of formula III may be prepared from compounds of formula XXIV by a coupling reaction with the appropriate primary or secondary amine. Suitable coupling reagents are T3P or HATU in the presence of a suitable base such as triethylamine, in a suitable solvent such as DMF or ethylacetate at 25° C. to 50° C., preferably at room temperature.

Compounds of formula III may be prepared from compounds of formula XXVII, by a reductive amination chemistry using suitable aldehydes or ketones and a reducing agent such as sodium triacetoxyborohydride or sodium cyanoborohydride or picoline borane, in a suitable solvent such as methanol or THF, at room temperature, as illustrated in Scheme 15. Alternatively, compounds of formula III may be prepared from compounds of formula XXVII by coupling reaction with the appropriate carboxylic acid. Suitable coupling reagents are T3P, or HATU, in the presence of a suitable base, such as triethylamine, in a suitable solvent, such as DMF or ethyl acetate, at a temperature of 25° C. to 50° C., preferably at room temperature.

Alternatively, Compounds of formula IIIb may be prepared from compounds of formula XXVII by reaction with a sulfonyl chloride, such as cyclopropyl sulfonyl chloride or benzene sulfonyl chloride, in the presence of a suitable base, such as triethylamine, in a suitable solvent, such as dichloromethane at a temperature of 0° C. to 25° C.

Scheme 15

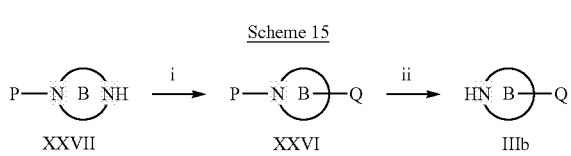

Compounds of formula IIIc may be prepared from compounds of formula XXVIII, by an activation reaction to give a leaving group L followed by an SN2 displacement reaction as illustrated in Scheme 16.

Step i. Compounds of formula XXIX may be prepared from compounds of formula XXVIII by activation to a leaving group with a suitable reagent, such as methane sulphonyl chloride or p-toluene sulfonyl chloride, in the presence of a suitable base such as triethylamine, in a suitable solvent such as THF at a temperature of 0° C. to 25° C., preferably at 0° C.

Step ii. Compounds of formula XXIV may be prepared from compounds of formula XXIX by direct displacement of the leaving group with a suitable nucleophile, such as tetrazole, triazole, pyrazole, alkoxide, and lactams such as pyrrolidinone in the presence of a suitable base such as potassium carbonate, cesium carbonate or sodium hydride, in a suitable solvent such as THF or DMF and a temperature of 0° C. to 120° C. Those skilled in the art would know that other activation reagents, nucleophiles and bases are possible. For example the 'Mitsonobu' reaction is an alternative protocol known to those skilled in the art using substituted phenols as the nucleophilic component.

Alternatively, Compounds of formula III may be prepared from compounds of formula XXVIII by an alkylation reaction with an alkyl halide using a suitable base, such as sodium hydride, in a suitable solvent such as THF or DMF at a temperature of 0° C. to 100° C., preferably at room temperature.

Scheme 16

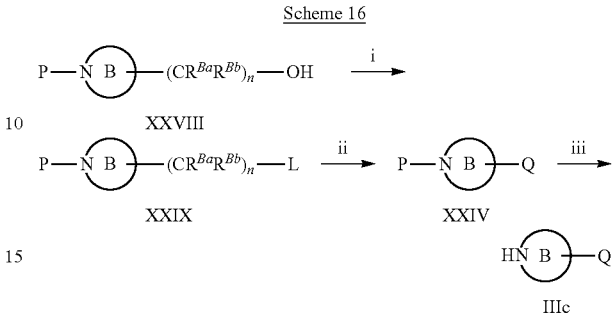

Compounds of formula IIId may be prepared from compounds of formula XXX by a nucleophilic addition reaction with a suitable electrophilic group as illustrated in Scheme 17, where E is an electrophilic group, such as an epoxide, ketone or aldehyde. Suitable nucleophiles include heterocycles such as pyrazole in the presence of a suitable base such as sodium hydride or potassium carbonate, or Grignard reagents such as phenyl magnesium bromide. The reaction is conducted in a suitable solvent, such as THF or DMF at a temperature of 0° C. to 120° C. Compounds of formula XXX are either commercially available or synthesized by known procedures.

Scheme 17

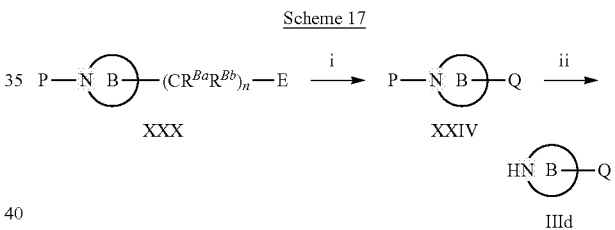

Compounds of formula IIIc may be prepared from compounds of formula XXXI, by coupling with the appropriate carboxylic acid as illustrated in Scheme 18. Suitable coupling reagents are T3P, or HATU, in the presence of a suitable base, such as triethylamine, in a suitable solvent, such as DMF or ethyl acetate, at a temperature of 25° C. to 50° C., preferably at room temperature.

Alternatively, Compounds of formula III may be prepared from compounds of formula XXXI by reaction with a sulfonyl chloride, such as cyclopropyl sulfonyl chloride or benzene sulfonyl chloride, in the presence of a suitable base, such as triethylamine, in a suitable solvent, such as dichloromethane at a temperature of 0° C. to 25° C.

Scheme 18

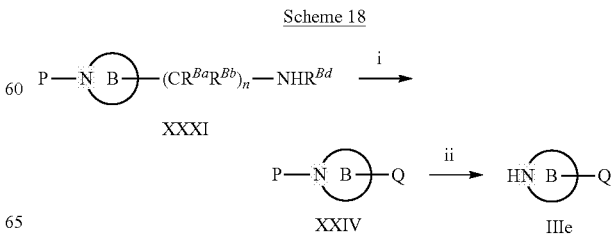

Compounds of formula IIIf may be prepared from compounds of formula XXXII by a coupling, cyclisation condensation sequence, illustrated in Scheme 19.

Step i. Compounds of formula XXXIII may be prepared from compounds of formula XXXII by reaction with hydroxylamine hydrochloride in the presence of a suitable base, such as tetramethylguanidine, in a suitable solvent such as methanol at a temperature of 50° C. to 100° C. preferably at solvent reflux.

Step ii. Compounds of formula XXXIV may be prepared from compounds of formula XXXIII by a coupling reaction with a carboxylic acid, which is either commercially available or synthesized by known procedures, using coupling reagents, such as HATU or T3P, in the presence of a suitable base, such as triethylamine, in a suitable solvent, such as DCM, DMF or EtOAc, at a temperature of 25° C. to 50° C., preferably at room temperature.

Step iii. Compounds of formula XXVI may be prepared from compounds of formula XXXIV by heating in the presence of a dehydrating reagent such as dried molecular sieves, in a suitable solvent, such as toluene, at reflux temperature.

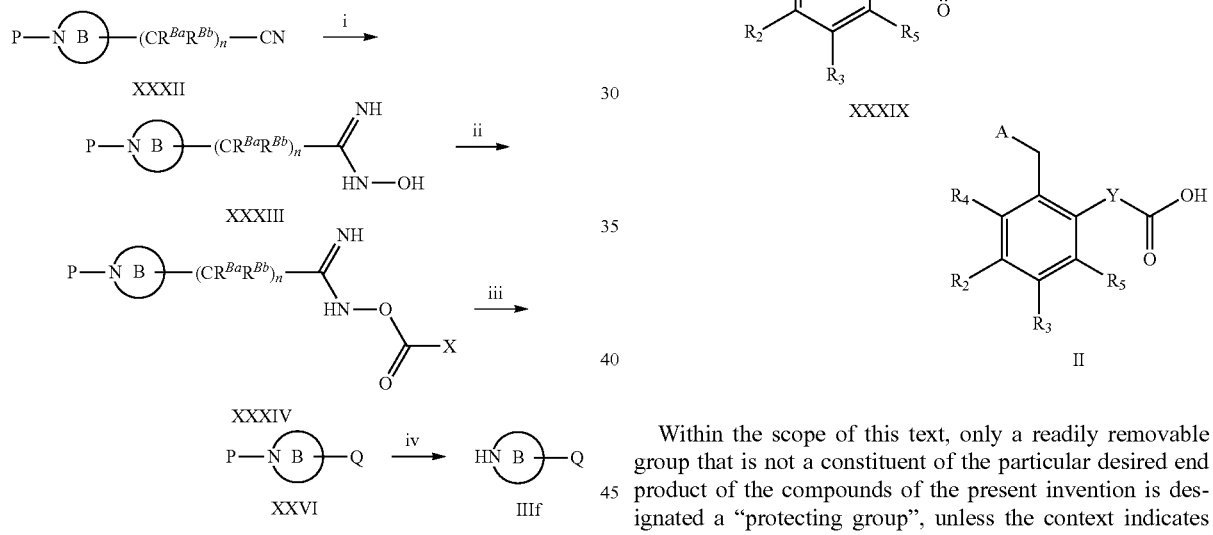

Scheme 19

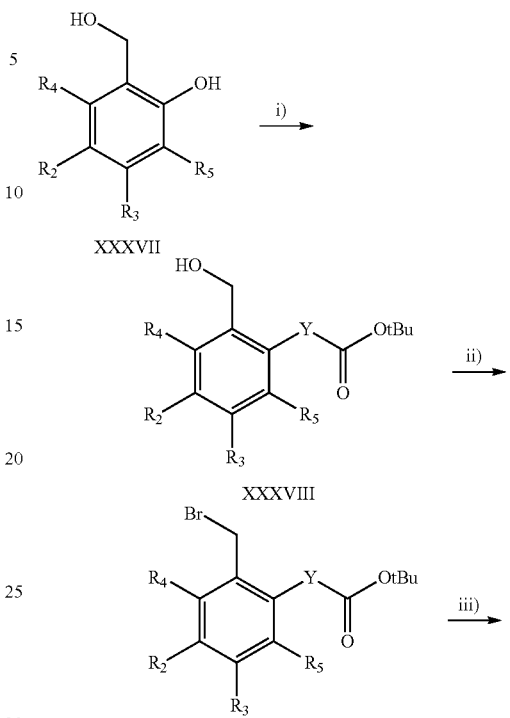

Scheme 20

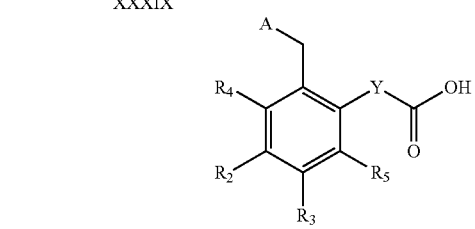

Compounds of the present invention and intermediates can also be converted into each other according to methods generally known to those skilled in the art.

When Y is —O—CH2-, Compounds of formula II may be prepared from compounds of formula XXXVII as illustrated in Scheme 20.

Step i. Compounds of formula XXXVIII may be prepared from compounds of formula XXXVII by an alkylation reaction with a halo acetate, such as tert-butyl 2-bromoacetate, in the presence of a base, such as potassium carbonate, in a suitable solvent such as THF or MeCN at 25° C. to 50° C., preferably at room temperature.

Step ii. Compounds of formula XXXIX may be prepared from compounds of formula XXXVIII by a bromination reaction with a brominating agent, such as hexabromoacetone and triphenyl phosphine, in a suitable solvent, such as MeCN, at 25° C. to 80° C., preferably at 40° C.

Step iii. Compounds of formula II may be prepared from compounds of formula XXXIX, by chemistry illustrated in Scheme 4, where Y1 is —O—CH2-CO2tBu.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter. All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60 OC, at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds of the present invention, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl $4^{th}$ Ed. 1952, Methods of Organic Synthesis, Thieme, Volume 21).

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compounds of the present invention. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds of the present invention described herein may contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds of the present invention may be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound of the present invention contains a double bond, the substituent may be E or Z configuration. If the compound of the present invention contains a disubstituted cycloalkyl, the cycloalkyl substituent may have a cis- or trans-configuration. All tautomeric forms, for example for group A in embodiment 1, are also intended to be included.

As used herein, the terms "salt" or "salts" refers to an acid addition or base addition salt of a compound of the present invention. "Salts" include in particular "pharmaceutical acceptable salts". The term "pharmaceutically acceptable salts" refers to salts that retain the biological effectiveness and properties of the compounds of the present invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the compounds of the present invention can be synthesized from a basic or acidic moiety, by conventional chemical methods. Generally, such salts can be prepared by reacting free acid forms of the compounds of the present invention with a stoichiometric amount of the appropriate base (such as Na, Ca, Mg, or K hydroxide, carbonate, bicarbonate or the like), or by reacting free base forms of the compounds of the present invention with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds of the present invention have structures depicted by the formulas given herein except that one or more atoms are replaced by an atom having a selected atomic mass or mass number. Examples of isotopes that can be incorporated into compounds of the present invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds of the present invention, for example those into which radioactive isotopes, such as $^{3}H$ and $^{14}C$, or those into which non-radioactive isotopes, such as $^{2}H$ and $^{13}C$ are present. Such isotopically labelled compounds of the present invention are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound of the present invention may be particularly desirable for PET or SPECT studies. Isotopically-labeled compounds of the present invention can generally be prepared by conventional techniques known to those skilled in the art or by processes analogous to those described in the accompanying Generic Schemes, Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of the present invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

The compounds of the present invention in free form or in salt form, exhibit valuable pharmacological properties, e.g. as indicated in in vitro tests as provided herein, and are therefore indicated for therapy or for use as research chemicals, e.g. as tool compounds.

Thus, in an embodiment 25, there is provided a compound according to any one of embodiments 1 to 24 for use in medicine.

The compounds according to any one of embodiments 1 to 24 are potent inhibitors of ATX (see $IC_{50}$ data disclosed herein). The compounds of the present invention are hence useful in the treatment of an ATX-dependent or ATX-mediated disease or condition.

Thus, in an embodiment 26, there is provided a compound according to any one of embodiments 1 to 24 for use in the treatment of an ATX-dependent or ATX-mediated disease or condition. In an embodiment 27, there is provided the use of a compound according to any one of embodiments 1 to 24 in the treatment of an ATX-dependent or ATX-mediated disease or condition. In an embodiment 28, there is provided the use of a compound according to any one of embodiments 1 to 24 in the manufacture of a medicament for the treatment of an ATX-dependent or ATX-mediated disease or condition. In an embodiment 29, there is provided a method of treating an ATX-dependent or ATX-mediated disease or condition comprising administering to the subject a therapeutically effective amount of a compound according to any one of embodiments 1 to 24.

Hence, in a further embodiment 30, the compounds of the invention are useful for the treatment of a disease or condition according to embodiments 26, 27, 28 and 29, wherein the disease or condition is selected from fibrosis, pruritus, cirrhosis, cancer, diabetes, kidney diseases and pain.

In an embodiment 31, the compounds of the invention are useful for the treatment of a disease or condition according to embodiment 30, wherein the disease or condition is selected from pulmonary fibrosis, idiopathic pulmonary fibrosis, a diffuse parenchymal interstitial lung disease including iatrogenic drug-induced fibrosis, occupational and/or environmental induced fibrosis (Farmer lung), radiation induced fibrosis, bleomycin induced pulmonary fibrosis, asbestos induced pulmonary fibrosis, acute respiratory distress syndrome (ARDS), kidney fibrosis, tubulointerstitium fibrosis, gut fibrosis, liver fibrosis, alcohol induced liver fibrosis, toxic/drug induced liver fibrosis, infection induced liver fibrosis, viral induced liver fibrosis, cutaneous fibrosis, spinal cord injury/fibrosis, myelofibrosis, renal fibrosis, skin fibrosis, ocular fibrosis, post-transplant fibrosis, hepatic fibrosis with or without cirrhosis, cardiac fibrosis, neuropathic pruritus, neurogenic pruritus, psychogenic pruritus, cholestatic pruritus, primary biliary cirrhosis, liver cirrhosis, breast cancer, pancreatic cancer, ovarian cancer, prostate cancer, glioblastoma, bone cancer, colon cancer, bowel cancer, head and neck cancer, diabetes, polycystic kidney disease, acute kidney injury, chronic kidney disease, neuropathic pain and cancer pain.

In an embodiment 32, the compounds of the invention are useful for the treatment of a disease or condition according to embodiment 31, wherein the disease or condition is selected from idiopathic pulmonary fibrosis, breast cancer, pancreatic cancer, prostate cancer, cholestatic pruritus, primary biliary cirrhosis and polycystic kidney disease, particularly idiopathic pulmonary fibrosis.

The compounds of the invention will be typically formulated as pharmaceutical compositions.

Thus, in an embodiment 33 of the invention, the present invention provides a pharmaceutical composition comprising a compound according to any one of embodiments 1 to 24, or a pharmaceutically acceptable salt thereof, and a pharmaceutically acceptable carrier.

The pharmaceutical composition can be formulated for particular routes of administration such as oral administration, parenteral administration, and rectal administration, inhaled administration etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the present invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Where the inhalable form of the active ingredient is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042 (including the BREEZHALER™ device), WO 97/20589 (including the CERTIHALER™ device), WO 97/30743 (including the TWISTHALER™ device), WO 05/37353 (including the GYROHALER™ device), U.S. Pat. No. 6,536,427 (including the DISKUS™ device), WO 97/25086 (including the DISKHALER™ device), WO 95/14089 (including the GEMINI™ device), WO 03/77979 (including the PROHALER™ device), and also the devices disclosed in WO 08/51621, WO 09/117112 and US 2005/0183724.

Hence, the invention also includes (A) a compound of the present invention, or a pharmaceutically acceptable salt thereof, in inhalable form; (B) an inhalable medicament comprising a compound of the present invention in inhalable form together with a pharmaceutically acceptable carrier in inhalable form; (C) a pharmaceutical product comprising a compound of the present invention in inhalable form in association with an inhalation device; and (D) an inhalation device containing a compound of the present invention in inhalable form.

Dosages of agents of the invention employed in practicing the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of the present invention and at least one other therapeutic agent as a combined preparation for simultaneous, separate or sequential use in therapy. Products provided as a combined preparation include a composition comprising the compound of the present invention and the other therapeutic agent(s) together in the same pharmaceutical composition, or the compound of the present invention and the other therapeutic agent(s) in separate form, e.g. in the form of a kit.

Thus, in an embodiment 34, the invention provides a pharmaceutical composition comprising a compound according to any one of embodiments 1 to 24 and one or more therapeutically active co-agent. Optionally, the pharmaceutical composition may comprise a pharmaceutically acceptable excipient, as described above.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In an embodiment 35 of the invention, there is provided a pharmaceutical combination, comprising:
a therapeutically effective amount of the compound according to any one of embodiments 1 to 24, or a pharmaceutically acceptable salt thereof, and one or more therapeutically active co-agent.

In an embodiment 36 of the invention, there is provided a pharmaceutical combination according to embodiment 35, wherein the therapeutically active co-agent is selected from immunosuppresants, analgesics, anti-cancer agent, anti-inflammatories, chemokine receptor antagonists, bronchodilators, leukotriene receptor antagonists, leukotriene formation inhibitors, monoacylglycerol kinase inhibitors, phospholipase A1 inhibitors, phospholipase A2 inhibitors, lysophospholipase D (lysoPLD) inhibitors, decongestants, antihistamines, mucolytics, anticholinergics, antitussives, expectorants, and β2 agonists.

Suitable anti-inflammatory drugs include steroids, for example corticosteroids. Suitable steroids include budesonide, beclamethasone (e.g. dipropionate), butixocort (e.g. propionate), CHF5188, ciclesonide, dexamethasone, flunisolide, fluticasone (e.g. propionate or furoate), GSK-685698, GSK-870086, LAS40369, methyl prednisolone, mometasone (e.g. furoate), prednisolone, rofleponide, and triamcinolone (e.g. acetonide). In certain preferred embodiments the steroid is long-acting corticosteroids such as budesonide, ciclesonide, fluticasone propionate, fluticasone furoate or mometasone furoate.

Suitable $\beta$2-agonists include arformoterol (e.g. tartrate), albuterol/salbutamol (e.g. racemate or single enantiomer such as the R-enantiomer, or salt thereof especially sulfate), AZD3199, bambuterol, BI-171800, bitolterol (e.g. mesylate), carmoterol, clenbuterol, etanterol, fenoterol (e.g. racemate or single enantiomer such as the R-enantiomer, or salt thereof especially hydrobromide), flerbuterol, formoterol (e.g. racemate or single diastereomer such as the R,R-diastereomer, or salt thereof especially fumarate or fumarate dihydrate), GSK-159802, GSK-597901, GSK-678007, indacaterol (e.g. racemate or single enantiomer such as the R-enantiomer, or salt thereof especially maleate, acetate or xinafoate), LAS100977, metaproterenol, milveterol (e.g. hydrochloride), naminterol, olodaterol (e.g. racemate or single enantiomer such as the R-enantiomer, or salt thereof especially hydrochloride), PF-610355, pirbuterol (e.g. acetate), procaterol, reproterol, salmefamol, salmeterol (e.g. racemate or single enantiomer such as the R-enantiomer, or salt thereof especially xinafoate), terbutaline (e.g. sulphate) and vilanterol (or a salt thereof especially trifenatate. In certain preferred embodiments the $\beta_2$-agonist is an ultra-long-acting $\beta_2$-agonist such as indacaterol, or potentially carmoterol, LAS-100977, milveterol, olodaterol, PF-610355 or vilanterol. A preferred embodiment one of the second active ingredients is indacaterol (i.e. (R)-5-[2-(5,6-diethyl-indan-2-ylamino)-1-hydroxyethyl]-8-hydroxy-1H-quinolin-2-one) or a salt thereof. This is a $\beta_2$-adrenoceptor agonist that has an especially long duration of action (i.e. over 24 hours) and a short onset of action (i.e. about 10 minutes). This compound is prepared by the processes described in international patent applications WO 2000/75114 and WO 2005/123684. It is capable of forming acid addition salts, particularly pharmaceutically acceptable acid addition salts. A preferred salt of (R)-5-[2-(5,6-diethyl-indan-2-ylamino)-1-hydroxyethyl]-8-hydroxy-1H-quinolin-2-one is the maleate salt. Another preferred salt is (R)-5-[2-(5,6-diethyl-indan-2-ylamino)-1-hydroxyethyl]-8-hydroxy-1H-quinolin-2-one acetate. Another preferred salt is (R)-5-[2-(5,6-diethyl-indan-2-ylamino)-1-hydroxyethyl]-8-hydroxy-1H-quinolin-2-one xinafoate.

Suitable bronchodilatory drugs include anticholinergic or antimuscarinic agents, such as aclidinium (e.g. bromide), BEA-2108 (e.g. bromide), BEA-2180 (e.g. bromide), CHF-5407, darifenacin (e.g. bromide), darotropium (e.g. bromide), glycopyrrolate (e.g. racemate or single enantiomer, or salt thereof especially bromide), dexpirronium (e.g. bromide), iGSK-202405, GSK-203423, GSK-573719, GSK-656398, ipratropium (e.g. bromide), LAS35201, LAS186368, otilonium (e.g. bromide), oxitropium (e.g. bromide), oxybutynin, PF-3715455, PF-3635659, pirenzepine, revatropate (e.g. hydrobromide), solifenacin (e.g. succinate), SVT-40776, TD-4208, terodiline, tiotropium (e.g. bromide), tolterodine (e.g. tartrate), and trospium (e.g. chloride). In certain preferred embodiments the muscarinic antagonists is long-acting muscarinic antagonist such as darotropium bromide, glycopyrrolate or tiotropium bromide.

Suitable dual anti-inflammatory and bronchodilatory drugs include dual beta-2 adrenoceptor agonist/muscarinic antagonists such as GSK-961081 (e.g. succinate). and those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and terenadine, as well as those disclosed in JP 2004107299, WO 03/099807 and WO 04/026841.

EXPERIMENTAL

EXAMPLES

The following examples are intended to illustrate the invention and are not to be construed as being limitations thereon.

General Conditions:

Mass spectra were acquired on LC-MS, SFC-MS, or GC-MS systems using electrospray, chemical and electron impact ionization methods from a range of instruments of the following configurations: Agilent 1100 HPLC systems with an Agilent 6110 Mass Spectrometer [M+H]+ refers to protonated molecular ion of the chemical species.

NMR spectra were run on Bruker AVANCE 400 MHz or 500 MHz NMR spectrometers using ICON-NMR, under TopSpin program control. Spectra were measured at 298 K, unless indicated otherwise, and were referenced relative to the solvent resonance.

Instrumentation:

MS Methods: Using Agilent 1100 HPLC systems with an Agilent 6110 Mass Spectrometer 2minLowpHv03:
Column: Waters Acquity CSH 1.7 µm, 2.1×50 mm
Temperature: 50° C.
Mobile Phase: A: Water +0.1% Formic Acid B: Acetonitrile +0.1% Formic Acid
Flow rate: 1.0 mL/min
Gradient: 0.0 min 5% B, 0.2-1.8 min 5-98% B, 1.8-2.1 min 98% B, 2.1-2.3 min 98% B 2minLowpHv01:
Column: Waters Acquity CSH 1.7 µm, 2.1×50 mm
Temperature: 50° C.
Mobile Phase: A: Water +0.1% Formic Acid B: Acetonitrile +0.1% Formic Acid
Flow rate: 1.0 mL/min
Gradient: 0.0 min 5% B, 0.2-1.55 min 5-98% B, 1.55-1.75 min 98% B, 1.75-1.8 min 98-5% B 8minLowpHv01:
Column: Waters Acquity CSH 1.7 µm, 2.1×100 mm
Temperature: 50° C.
Mobile Phase: A: Water +0.1% Formic Acid B: Acetonitrile +0.1% Formic Acid
Flow rate: 0.7 mL/min
Gradient: 0.0 min 2% B, 0.3-6.5 min 2-98% B, 6.5-7.5 min 98% B, 7.5-8.0 min 5-98% B 2minLowpH:
Column: Waters Acquity CSH 1.7 µm, 2.1×50 mm
Temperature: 50° C.
Mobile Phase: A: Water +0.1% Formic Acid B: Acetonitrile +0.1% Formic Acid Flow rate: 1.0 mL/min
Gradient: 0.0 min 5% B, 0.2-1.3 min 5-98% B, 1.3-1.55 min 98% B, 1.55-1.6 min 98-5% B
10minLowpH:
Column: Waters Acquity CSH 1.7 μm, 2.1×100 mm
Temperature: 50° C.
Mobile Phase: A: Water +0.1% Formic Acid B: Acetonitrile +0.1% Formic Acid
Flow rate: 0.7 mL/min
Gradient: 0.0 min 2% B, 0.5-8.0 min 2-98% B, 8.0-9.0 min 98% B, 9.0-9.1 min 98-2% B
2minLowpHv02:
Column: Waters Acquity CSH 1.7 μm, 2.1×50 mm
Temperature: 50° C.
Mobile Phase: A: Water +0.1% TFA B: Acetonitrile +0.1% TFA
Flow rate: 1.0 mL/min
Gradient: 0.0 min 5% B, 0.2-1.55 min 5-98% B, 1.55-1.75 min 98% B, 1.75-1.8 min 98-5% B
2minHighpHv03:
Column: Waters Acquity CSH 1.7 μm, 2.1×50 mm
Temperature: 50° C.
Mobile Phase: A: Water +0.1% Ammonia B: Acetonitrile +0.1% Ammonia
Flow rate: 1.0 mL/min
Gradient: 0.0 min 5% B, 0.2-1.8 min 5-98% B, 1.8-2.1 min 98% B, 2.1-2.3 min 98-5% B
8minLowpHv01:
Column: Waters Acquity CSH 1.7 μm, 2.1×100 mm
Temperature: 50° C.
Mobile Phase: A: Water +0.1% Formic Acid B: Acetonitrile +0.1% Formic Acid
Flow rate: 0.7 mL/min
Gradient: 0.0 min 2% B, 0.3-6.5 min 2-98% B, 6.5-7.5 min 98% B, 7.5-8.0 min 5-98% B
Abbreviations:
BOC tertiary butyl carboxy
br broad
d doublet
dd doublet of doublets
DCM dichloromethane
DIPEA diethylisopropylamine
DMA N,N-dimethylformamide
DME 1,4-dimethoxyethane
DMF N,N-dimethylformamide
DMSO dimethylsulfoxide
EtOAc ethyl acetate
h hour(s)
HPLC high pressure liquid chromatography
LCMS liquid chromatography and mass spectrometry
MeOH methanol
MS mass spectrometry
m or mult multiplet
mg milligram
min minutes
mL millilitre
mmol millimol
MTBE methyl tertiary-butyl ether
m/z mass to charge ratio
NMR nuclear magnetic resonance
ppm parts per million
rac racemic
Rt retention time
s singlet
t triplet
TBME methyl tert-butyl ether
TFA trifluoroacetic acid
THF tetrahydrofuran

PREPARATION OF THE EXAMPLES

Example 1

(S,E)-1-(2-(5-Methyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one

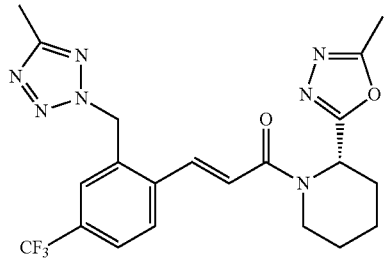 [SMILES: Cc1nnn(Cc2cc(C(F)(F)F)ccc2/C=C/C(=O)N2CCCC[C@H]2c2nnc(C)o2)n1]

(E)-3-(2-((5-Methyl-2H-tetrazol-2-yl)methyl)-4-(trifluoromethyl)phenyl)acrylic acid (Intermediate AB) (100 mg, 0.320 mmol) and (S)-2-methyl-5-(piperidin-2-yl)-1,3,4-oxadiazole (Intermediate B) (59 mg, 0.352 mmol) were placed in a flask with dry DMF (2 mL). DIPEA (0.28 mL, 1.60 mmol) was added followed by the slow addition of T3P® (50% in DMF) (0.374 mL, 0.641 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;
LC-MS Rt=1.26 mins; [M+H]$^+$ 462.4; Method 2min-LowpHv03
$^1$H NMR (400 MHz, DMSO-d6) δ 8.10 (1H, m), 7.90-7.78 (3H, m), 7.36 (1H, d), 6.11 (2H, s), 5.99 (0.6H, m), 5.89 (0.4H, m), 4.46 (0.4H, m), 4.20 (0.6H, m), 3.11 (0.4H, m), 2.49 (3H, s), 2.40 (3H, s), 2.33-2.18 (1H, m), 1.83 (1H, m), 1.75-1.60 (2H, m), 1.60-1.30 (2.6H, m).

Example 2

(E)-1-(4-(3-Methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one

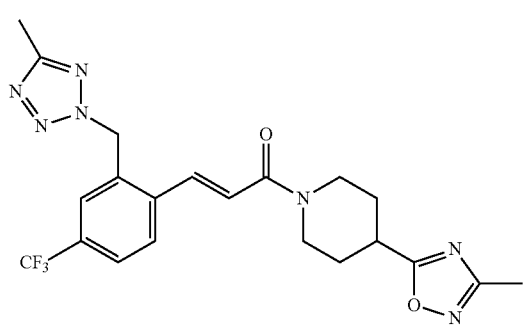 [SMILES: Cc1noc(C2CCN(C(=O)/C=C/c3ccc(C(F)(F)F)cc3Cn3nnc(C)n3)CC2)n1]

(E)-3-(2-((5-Methyl-2H-tetrazol-2-yl)methyl)-4-(trifluoromethyl)phenyl)acrylic acid (Intermediate AB) (100 mg, 0.320 mmol) and 3-methyl-5-(piperidin-4-yl)-1,2,4-oxadiazole (58.9 mg, 0.352 mmol) were placed in a flask with dry DMF (2 mL). DIPEA (0.28 mL, 1.60 mmol) was added followed by the slow addition of T3P® (50% in DMF) (0.374 mL, 0.641 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.27 mins; [M+H]$^+$ 462.3; Method 2min-LowpHv03

$^1$H NMR (400 MHz, DMSO-d6) δ 8.10 (1H, d), 7.89 (1H, s), 7.85-7.70 (2H, m), 7.29 (1H, d), 6.11 (2H, s), 4.38 (1H, m), 4.19 (1H, m), 3.32 (2H, m), 2.98 (1H, m), 2.41 (3H, s), 2.32 (3H, s), 2.09 (2H, m), 1.65 (2H, m),

Example 3

(E)-1-(4-(5-Methyl-1,2,4-oxadiazol-3-yl)piperidin-1-yl)-3-(2-((5-methyl-2H-tetrazol-2-yl)methyl)-4-(trifluoromethoxy)phenyl)prop-2-en-1-one

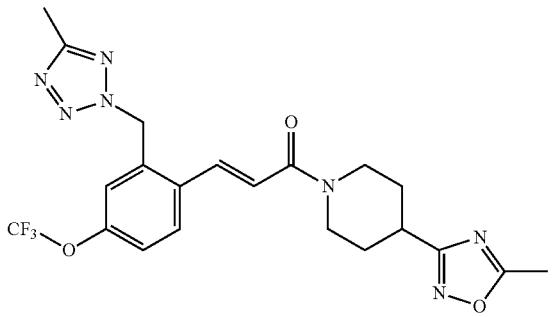 [SMILES: Cc1nnn(Cc2cc(OC(F)(F)F)ccc2/C=C/C(=O)N2CCC(c3noc(C)n3)CC2)n1]

(E)-3-(2-((5-Methyl-2H-tetrazol-2-yl)methyl)-4-(trifluoromethoxy)phenyl)acrylic acid (Intermediate AC) (100 mg, 0.305 mmol) and 5-methyl-3-(piperidin-4-yl)-1,2,4-oxadiazole (Intermediate E) (68.3 mg, 0.335 mmol) were placed in a flask with dry EtOAc (2 mL). DIPEA (0.266 mL, 1.52 mmol) was added to the suspension followed by the slow addition of T3P® (50% in EtOAc) (0.356 mL, 0.609 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.28 mins; [M+H]$^+$478.4; Method 2min-LowpHv03

$^1$H NMR (400 MHz, DMSO-d6) δ 8.00 (1H, d), 7.71 (1H, d), 7.43 (2H, m), 7.20 (1H, d), 6.08 (2H, s), 4.40 (1H, m), 4.20 (1H, m), 3.30 (H, m), 3.10 (H, m), 2.91 (1H, m), 2.58 (3H, s), 2.41 (3H, s), 1.99 (2H, m), 1.60 (2H, m),

Example 4

(E)-1-(4-(5-Methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one

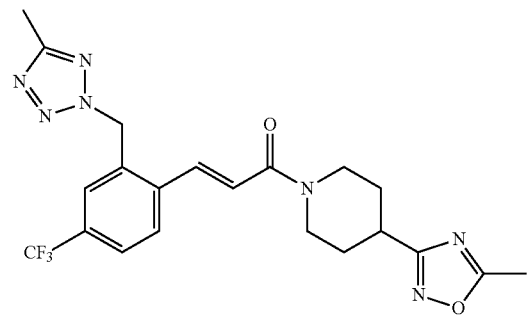 [SMILES: Cc1nnn(Cc2cc(C(F)(F)F)ccc2/C=C/C(=O)N2CCC(c3noc(C)n3)CC2)n1]

(E)-3-(2-((5-Methyl-2H-tetrazol-2-yl)methyl)-4-(trifluoromethyl)phenyl)acrylic acid (Intermediate AB) (100 mg, 0.320 mmol) and 5-methyl-3-(piperidin-4-yl)-1,2,4-oxadiazole (72 mg, 0.352 mmol) were placed in a flask with dry DMF (2 mL). DIPEA (0.28 mL, 1.60 mmol) was added followed by the slow addition of T3P® (50% in DMF) (0.374 mL, 0.641 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.21 mins; [M+H]$^+$ 462.4; Method 2min-LowpHv03

$^1$H NMR (400 MHz, DMSO-d6) δ 8.10 (1H, d), 7.89 (1H, s), 7.85-7.70 (2H, m), 7.29 (1H, d), 6.11 (2H, s), 4.40 (1H, m), 4.20 (1H, m), 3.30 (H, m), 3.10 (H, m), 2.95 (1H, m), 2.58 (3H, s), 2.41 (3H, s), 1.99 (2H, m), 1.60 (2H, m),

Example 5 rac-(E)-1-(2-(3-Methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one

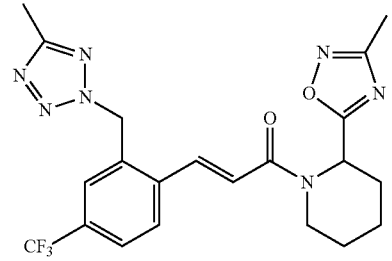 [SMILES: Cc1noc(C2CCCCN2C(=O)/C=C/c2ccc(C(F)(F)F)cc2Cn2nnc(C)n2)n1]

(E)-3-(2-((5-Methyl-2H-tetrazol-2-yl)methyl)-4-(trifluoromethyl)phenyl)acrylic acid (Intermediate AB) (200 mg, 0.641 mmol) and 3-methyl-5-(piperidin-2-yl)-1,2,4-oxadiazole hydrochloride (143 mg, 0.705 mmol) were placed in a flask with dry DMF (4 mL). DIPEA (0.559 mL, 3.20 mmol)

was added followed by the slow addition of T3P® (50% in DMF) (0.748 mL, 1.28 mmol). The reaction mixture was stirred at room temperature for 2 h and then partitioned between EtOAc (20 mL) and water (20 mL). The organic phase was washed with water and brine, dried over MgSO₄, filtered and the solvent was removed in vacuo. Purification of the crude product by chromatography on silica eluting with 0-100% (10% MeOH in EtOAc) in iso-hexane afforded the title compound;

LC-MS Rt=1.36 mins; [M+H]⁺ 462.3; Method 2min-LowpHv03

Example 5a (R,E)-1-(2-(3-methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one or Example 5b (S,E)-1-(2-(3-methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one

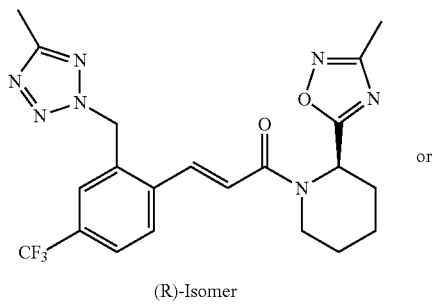

(R)-Isomer

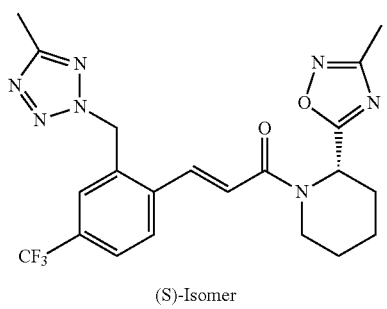

(S)-Isomer (rac)-(E)-1-(2-(3-Methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one was separated by SFC chiral chromatography (CHIRALPAK IC 250×10 mm 5 um, 50% isopropanol in CO₂);

Example 5a (R,E)-1-(2-(3-methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one or (S,E)-1-(2-(3-methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one First eluted peak: SFC Rt=3.66 mins;
LC-MS Rt=1.36 mins; [M+H]⁺ 462.3; Method 2min-LowpHv03

Example 5b (R,E)-1-(2-(3-methyl-1,2,4-oxadiazol-5-yl)piperidin-1-yl)-3-(2-((5-methyl-2H-tetrazol-2-yl)methyl)-4-(trifluoromethyl)phenyl)prop-2-en-1-one or (S,E)-1-(2-(3-methyl-1,2,4-oxadiazol-5-yl)piperidin-1-yl)-3-(2-((5-methyl-2H-tetrazol-2-yl)methyl)-4-(trifluoromethyl) phenyl)prop-2-en-1-one Second eluted peak: SFC Rt=7.63 mins;
LC-MS Rt=1.34 mins; [M+H]⁺ 462.2; Method 2min-LowpHv03

Example 6

(S,E)-N-Methyl-1-(3-(2-((5-methyl-2H-tetrazol-2-yl)methyl)-4-(trifluoromethyl) phenyl)acryloyl)piperidine-2-carboxamide

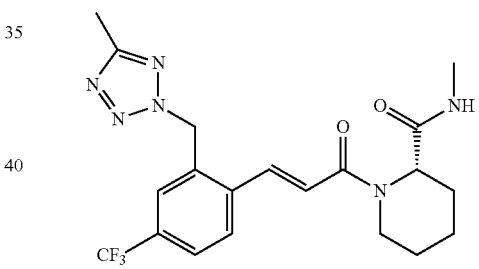

(E)-3-(2-((5-Methyl-2H-tetrazol-2-yl)methyl)-4-(trifluoromethyl)phenyl)acrylic acid (Intermediate AB) (100 mg, 0.320 mmol) and (S)—N-Methylpiperidine-2-carboxamide (Intermediate BC) (50 mg, 0.352 mmol) were placed in a flask with dry DMF (2 mL). DIPEA (0.28 mL, 1.60 mmol) was added followed by the slow addition of T3P® (50% in DMF) (0.374 mL, 0.641 mmol). The reaction mixture was stirred at room temperature for 2 h and then partitioned between EtOAc (20 mL) and water (20 mL). The organic phase was washed with water and brine, dried over MgSO₄, filtered and the solvent was removed in vacuo. Purification of the crude product by chromatography on silica eluting with 0-100% (10% MeOH in EtOAc) in iso-hexane afforded the title compound;

LC-MS Rt=1.15 mins; [M+H]⁺ No mass ion present; Method 2minLowpHv03

1H NMR (400 MHz, DMSO-d6) δ 8.10 (1H, m), 7.89-7.71 (4H, m), 7.30 (0.6H, d), 7.18 (0.4H, d), 6.10 (2H, m), 5.08 (0.6H, m), 4.87 (0.4H, m), 4.41 (0.4H, m), 4.11 (0.6H, m), 3.31 (0.4H, m), 3.22 (0.6H, m), 2.61 (3H, d), 2.41 (3H, s), 2.28-2.12 (1H, m), 1.60 (2H, m), 1.49 (1H, m), 1.32 (2H, m).

Example 7

(R,E)-3-(4-Chloro-2-((5-methyl-2H-tetrazol-2-yl)methyl)phenyl)-1-(3-(5-methyl-1,3,4-oxadiazol-2-yl)pyrrolidin-1-yl)prop-2-en-1-one

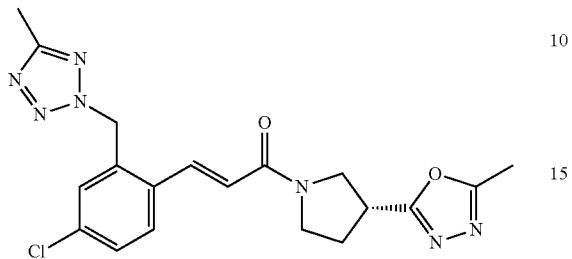

(E)-3-(4-Chloro-2-((5-methyl-2H-tetrazol-2-yl)methyl)phenyl)acrylic acid (Intermediate A) (100 mg, 0.359 mmol) and (R)-2-methyl-5-(pyrrolidin-3-yl)-1,3,4-oxadiazole (Intermediate BA) (60 mg, 0.395 mmol) were placed in a flask with dry DMF (2 mL). DIPEA (0.313 mL, 1.79 mmol) was added followed by the slow addition of T3P® (50% in DMF) (0.42 mL, 0.718 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.05 mins; [M+H]$^+$414.3; Method 2min-LowpHv03

Example 8

(S,E)-3-(4-Chloro-2-((5-methyl-2H-tetrazol-2-yl)methyl)phenyl)-1-(2-(5-methyl-1,3,4-oxadiazol-2-yl)pyrrolidin-1-yl)prop-2-en-1-one

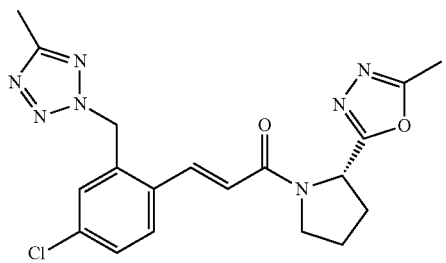 [SMILES: Cc1nnn(Cc2cc(Cl)ccc2/C=C/C(=O)N2CCC[C@H]2c2nnc(C)o2)n1]

(E)-3-(4-Chloro-2-((5-methyl-2H-tetrazol-2-yl)methyl)phenyl)acrylic acid (Intermediate A) (100 mg, 0.359 mmol) and (S)-2-methyl-5-(pyrrolidin-2-yl)-1,3,4-oxadiazole (Intermediate BB) (60 mg, 0.395 mmol) were placed in a flask with dry DMF (2 mL). DIPEA (0.313 mL, 1.79 mmol) was added followed by the slow addition of T3P® (50% in DMF) (0.42 mL, 0.718 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.09 mins; [M+H]$^+$414.4; Method 2min-LowpHv03

Example 9

(E)-3-(4-Chloro-2-((5-methyl-2H-tetrazol-2-yl)methyl)phenyl)-1-(4-(4-methyl-1H-1,2,3-triazol-1-yl)piperidin-1-yl)prop-2-en-1-one

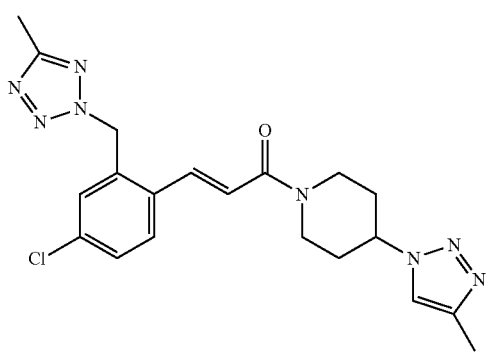 [SMILES: Cc1cn(C2CCN(C(=O)/C=C/c3ccc(Cl)cc3Cn3nnc(C)n3)CC2)nn1]

(E)-3-(4-Chloro-2-((5-methyl-2H-tetrazol-2-yl)methyl)phenyl)acrylic acid (Intermediate A) (100 mg, 0.359 mmol) and 4-(4-methyl-1H-1,2,3-triazol-1-yl)piperidine (Intermediate C) (66 mg, 0.395 mmol) were placed in a flask with dry DMF (2 mL). DIPEA (0.313 mL, 1.79 mmol) was added followed by the slow addition of T3P® (50% in DMF) (0.42 mL, 0.718 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.09 mins; [M+H]$^+$ 427.3; Method 2min-LowpHv03

Example 10

(E)-3-(4-Chloro-2-((5-methyl-2H-tetrazol-2-yl)methyl)phenyl)-1-(4-(3-methyl-1H-1,2,4-triazol-1-yl)piperidin-1-yl)prop-2-en-1-one

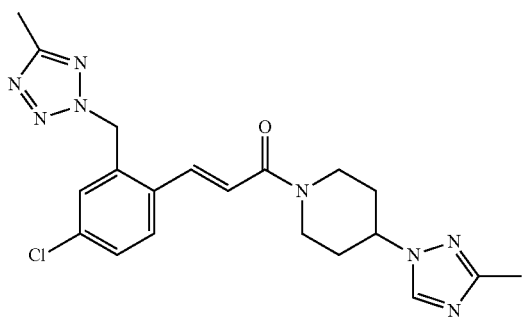 [SMILES: Cc1ncn(C2CCN(C(=O)/C=C/c3ccc(Cl)cc3Cn3nnc(C)n3)CC2)n1]

(E)-3-(4-Chloro-2-((5-methyl-2H-tetrazol-2-yl)methyl)phenyl)acrylic acid (Intermediate A) (60 mg, 0.215 mmol) and 4-(3-methyl-1H-1,2,4-triazol-1-yl)piperidine (Intermediate CA) (66 mg, 0.237 mmol) were placed in a flask with dry DMF (1 mL). DIPEA (0.188 mL, 1.08 mmol) was added followed by the slow addition of T3P® (50% in DMF) (0.25 mL, 0.431 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.03 mins; [M+H]$^+$ 427.6; Method 2min-LowpHv03

Example 11

(E)-3-(4-Chloro-2-((5-methyl-2H-tetrazol-2-yl)methyl)phenyl)-1-(4-(5-methyl-1H-1,2,4-triazol-1-yl)piperidin-1-yl)prop-2-en-1-one

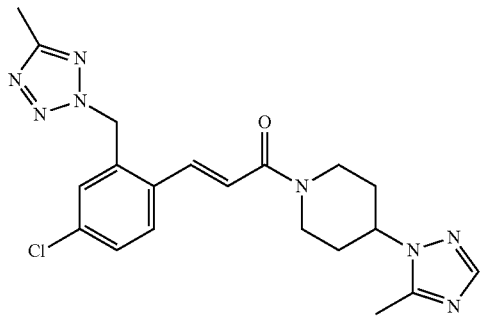 [SMILES: Cc1nnn(Cc2cc(Cl)ccc2/C=C/C(=O)N2CCC(n3ncnc3C)CC2)n1]

(E)-3-(4-Chloro-2-((5-methyl-2H-tetrazol-2-yl)methyl)phenyl)acrylic acid (Intermediate A) (80 mg, 0.287 mmol) and 4-(5-methyl-1H-1,2,4-triazol-1-yl)piperidine (Intermediate CB) (88 mg, 0.316 mmol) were placed in a flask with dry DMF (1 mL). DIPEA (0.25 mL, 1.43 mmol) was added followed by the slow addition of T3P® (50% in DMF) (0.335 mL, 0.574 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.02 mins; [M+H]$^+$ 427.5; Method 2min-LowpHv03

Example 12

(E)-3-(4-Chloro-2-((5-methyl-2H-tetrazol-2-yl)methyl)phenyl)-1-(4-(5-methyl-1H-tetrazol-1-yl)piperidin-1-yl)prop-2-en-1-one

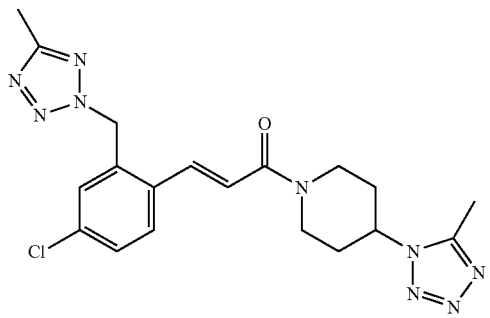 [SMILES: Cc1nnn(Cc2cc(Cl)ccc2/C=C/C(=O)N2CCC(n3nnnc3C)CC2)n1]

(E)-3-(4-Chloro-2-((5-methyl-2H-tetrazol-2-yl)methyl)phenyl)acrylic acid (Intermediate A) (50 mg, 0.179 mmol) and 4-(5-methyl-1H-tetrazol-1-yl)piperidine (Intermediate CC) (33 mg, 0.197 mmol) were placed in a flask with dry DMF (1 mL). DIPEA (0.157 mL, 0.897 mmol) was added followed by the slow addition of T3P® (50% in DMF) (0.21 mL, 0.359 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.08 mins; [M+H]$^+$ 428.6; Method 2min-LowpHv03

Example 13

(E)-3-(4-Chloro-2-((5-methyl-1,3,4-oxadiazol-2-yl)methyl)phenyl)-1-(4-((5-methyl-1,3,4-oxadiazol-2-yl)methyl)piperidin-1-yl)prop-2-en-1-one

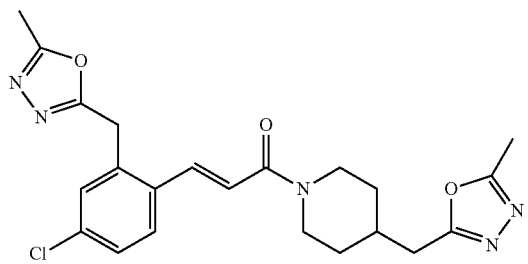 [SMILES: Cc1nnc(Cc2cc(Cl)ccc2/C=C/C(=O)N2CCC(Cc3nnc(C)o3)CC2)o1]

(E)-3-(4-Chloro-2-((5-methyl-1,3,4-oxadiazol-2-yl)methyl)phenyl)acrylic acid (Intermediate AD) (113 mg, 0.406 mmol) and 2-methyl-5-(piperidin-4-ylmethyl)-1,3,4-oxadiazole (Intermediate BD) (120 mg, 0.406 mmol) were placed in a flask with dry DMF (2 mL). DIPEA (0.355 mL, 2.03 mmol) was added followed by the slow addition of T3P® (50% in DMF) (0.475 mL, 0.813 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=0.95 mins; [M+H]$^+$ 442.2; Method 2min-LowpHv03

Example 14

(E)-3-(4-Chloro-2-((5-methyl-2H-tetrazol-2-yl)methyl)phenyl)-1-(4-hydroxy-4-((4-(morpholine-4-carbonyl)-1H-pyrazol-1-yl)methyl)piperidin-1-yl)prop-2-en-1-one

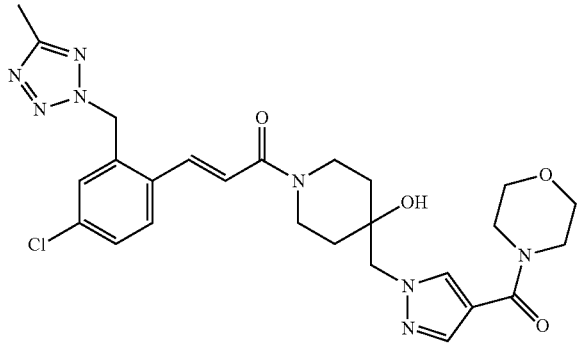 [SMILES: Cc1nnn(Cc2cc(Cl)ccc2/C=C/C(=O)N2CCC(O)(Cn3cc(C(=O)N4CCOCC4)cn3)CC2)n1]

Step 1: (E)-Ethyl 1-((1-(3-(4-chloro-2-((5-methyl-2H-tetrazol-2-yl)methyl)phenyl)acryloyl)-4-hydroxypiperidin-4-yl)methyl)-1H-pyrazole-4-carboxylate (E)-3-(4-Chloro-2-((5-methyl-2H-tetrazol-2-yl)methyl)phenyl)acrylic acid (Intermediate A) (500 mg, 1.79 mmol) and ethyl 1-((4-hydroxypiperidin-4-yl)methyl)-1H-pyrazole-4-carboxylate (Intermediate D) (572 mg, 1.97 mmol) were placed in a flask with dry DMF (10 mL). DIPEA (1.57 mL, 8.97 mmol) was added followed by the slow addition of T3P® (50% in DMF) (2.10 mL, 3.59 mmol). The reaction mixture was stirred at room temperature for 1 h and then partitioned between EtOAc (50 mL) and water (50 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.06 mins; [M+H]$^+$ 514.7; Method 2min-LowpHv03

Step 2: (E)-1-((1-(3-(4-Chloro-2-((5-methyl-2H-tetrazol-2-yl)methyl)phenyl)acryloyl)-4-hydroxypiperidin-4-yl)methyl)-1H-pyrazole-4-carboxylic acid (E)-Ethyl 1-((1-(3-(4-chloro-2-((5-methyl-2H-tetrazol-2-yl)methyl)phenyl)acryloyl)-4-hydroxypiperidin-4-yl)methyl)-1H-pyrazole-4-carboxylate (step 1) (600 mg, 1.167 mmol) was placed in a flask with EtOH (5 mL). 2M NaOH (2.92 mL, 5.84 mmol) was added and the reaction mixture was stirred at room temperature for 4 h. The EtOH was removed in vacuo and acidified with 2M HCl (4 mL). The resulting white solid was filtered off, washed with water and dried to afford the title compound;

LC-MS Rt=0.92 mins; [M+H]$^+$486.5; Method 2min-LowpHv03

Step 3: (E)-3-(4-Chloro-2-((5-methyl-2H-tetrazol-2-yl)methyl)phenyl)-1-(4-hydroxy-4-((4-(morpholine-4-carbonyl)-1H-pyrazol-1-yl)methyl)piperidin-1-yl)prop-2-en-1-one (E)-1-((1-(3-(4-Chloro-2-((5-methyl-2H-tetrazol-2-yl)methyl)phenyl)acryloyl)-4-hydroxypiperidin-4-yl)methyl)-1H-pyrazole-4-carboxylic acid (step 2) (100 mg, 0.206 mmol) and morpholine (53.8 mg, 0.617 mmol) were placed in a flask with dry DMF (2 mL). DIPEA (0.216 mL, 1.235 mmol) was added followed by the slow addition of T3P® (50% in DMF) (0.240 mL, 0.412 mmol). The reaction mixture was stirred at room temperature overnight and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=0.92 mins; [M+H]$^+$ 555.7; Method 2min-LowpHv03

Example 15

(E)-1-((1-(3-(4-Chloro-2-((5-methyl-2H-tetrazol-2-yl)methyl)phenyl)acryloyl)-4-hydroxypiperidin-4-yl)methyl)-N,N-dimethyl-1H-pyrazole-4-carboxamide

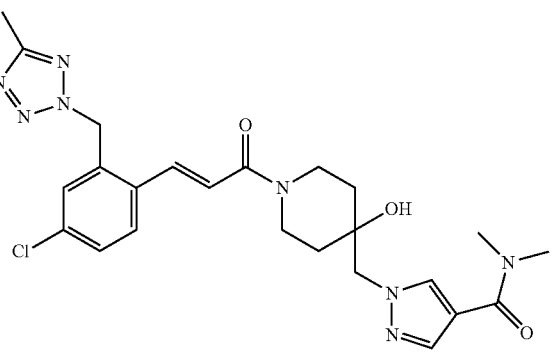

(E)-1-((1-(3-(4-Chloro-2-((5-methyl-2H-tetrazol-2-yl)methyl)phenyl)acryloyl)-4-hydroxypiperidin-4-yl)methyl)-1H-pyrazole-4-carboxylic acid (Example 14, step 2) (100 mg, 0.206 mmol) and dimethylamine hydrochloride (50.3 mg, 0.617 mmol) were placed in a flask with dry DMF (2 mL). DIPEA (0.216 mL, 1.235 mmol) was added followed by the slow addition of T3P® (50% in DMF) (0.240 mL, 0.412 mmol). The reaction mixture was stirred at room temperature overnight and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=0.92 mins; [M+H]$^+$ 513.4; Method 2min-LowpHv03

Example 16

(E)-3-(4-Chloro-2-((5-methyl-2H-tetrazol-2-yl)methyl)phenyl)-1-(4-hydroxy-4-((4-(piperidine-1-carbonyl)-1H-pyrazol-1-yl)methyl)piperidin-1-yl)prop-2-en-1-one

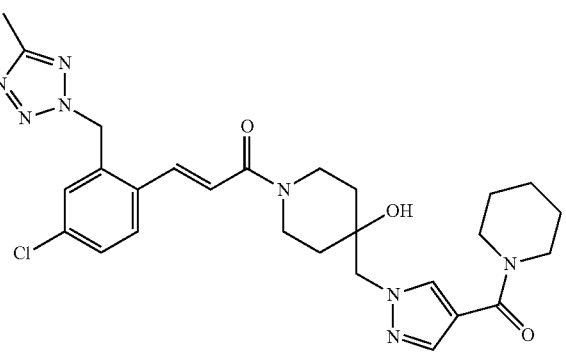

(E)-1-((1-(3-(4-Chloro-2-((5-methyl-2H-tetrazol-2-yl) methyl)phenyl)acryloyl)-4-hydroxypiperidin-4-yl)methyl)-1H-pyrazole-4-carboxylic acid (Example 14, step 2) (100 mg, 0.206 mmol) and piperidine (52.6 mg, 0.617 mmol) were placed in a flask with dry DMF (2 mL). DIPEA (0.216 mL, 1.235 mmol) was added followed by the slow addition of T3P® (50% in DMF) (0.240 mL, 0.412 mmol). The reaction mixture was stirred at room temperature overnight and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.02 mins; [M+H]$^+$ 553.6; Method 2min-LowpHv03

Example 17

(E)-3-(4-Chloro-2-((5-methyl-2H-tetrazol-2-yl) methyl)phenyl)-1-(4-(5-methyl-2H-tetrazol-2-yl) piperidin-1-yl)prop-2-en-1-one

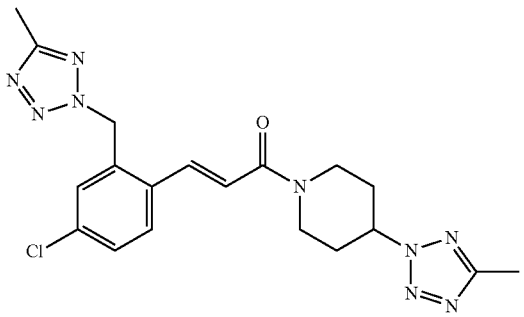 [SMILES: Cc1nnn(Cc2cc(Cl)ccc2/C=C/C(=O)N2CCC(n3nnc(C)n3)CC2)n1]

(E)-3-(4-Chloro-2-((5-methyl-2H-tetrazol-2-yl)methyl) phenyl)acrylic acid (Intermediate A) (100 mg, 0.359 mmol) and 4-(5-methyl-2H-tetrazol-2-yl)piperidine (Intermediate CD) (66 mg, 0.395 mmol) were placed in a flask with dry DMF (2 mL). DIPEA (0.31 mL, 1.79 mmol) was added followed by the slow addition of T3P® (50% in DMF) (0.42 mL, 0.718 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.16 mins; [M+H]$^+$428.4; Method 2min-LowpHv03

Example 18

(E)-3-(4-Chloro-2-((5-methyl-2H-tetrazol-2-yl) methyl)phenyl)-1-(4-hydroxy-4-((4-(trifluoromethyl)-1H-pyrazol-1-yl)methyl)piperidin-1-yl)prop-2-en-1-one

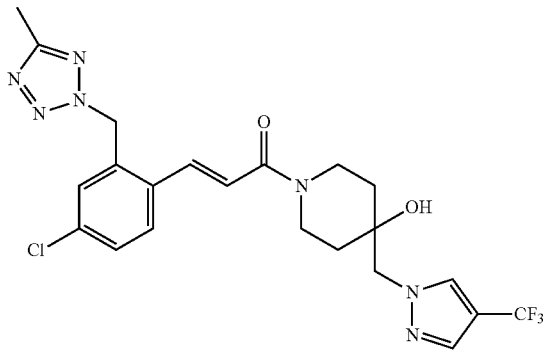 [SMILES: Cc1nnn(Cc2cc(Cl)ccc2/C=C/C(=O)N2CCC(O)(Cn3cc(C(F)(F)F)cn3)CC2)n1]

(E)-3-(4-Chloro-2-((5-methyl-2H-tetrazol-2-yl)methyl) phenyl)acrylic acid (Intermediate A) (150 mg, 0.538 mmol) and 4-((4-(trifluoromethyl)-1H-pyrazol-1-yl)methyl)piperidin-4-ol (Intermediate DA) (154 mg, 0.538 mmol) were placed in a flask with dry DMF (3 mL). DIPEA (0.47 mL, 2.69 mmol) was added followed by the slow addition of T3P® (50% in DMF) (0.63 mL, 1.08 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.14 mins; [M+H]$^+$510.6; Method 2min-LowpHv03

Example 19

(E)-3-(4-Chloro-2-((5-methyl-2H-tetrazol-2-yl) methyl)phenyl)-1-(4-(5-methyl-1,2,4-oxadiazol-3-yl) piperidin-1-yl)prop-2-en-1-one

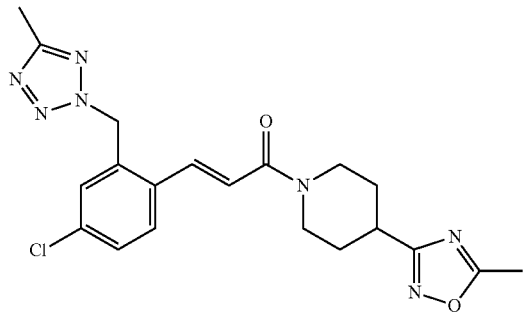 [SMILES: Cc1nnn(Cc2cc(Cl)ccc2/C=C/C(=O)N2CCC(c3noc(C)n3)CC2)n1]

(E)-3-(4-Chloro-2-((5-methyl-2H-tetrazol-2-yl)methyl) phenyl)acrylic acid (Intermediate A) (100 mg, 0.359 mmol) and 5-methyl-3-(piperidin-4-yl)-1,2,4-oxadiazole (Intermediate E) (66 mg, 0.395 mmol) were placed in a flask with dry DMF (2 mL). DIPEA (0.31 mL, 1.79 mmol) was added followed by the slow addition of T3P® (50% in DMF) (0.42 mL, 0.718 mmol). The reaction mixture was stirred at room temperature for 2 h and then partitioned between EtOAc (20 mL) and water (20 mL). The organic phase was washed with water and brine, dried over MgSO₄, filtered and the solvent was removed in vacuo. Purification of the crude product by chromatography on silica eluting with 0-100% (10% MeOH in EtOAc) in iso-hexane afforded the title compound;

LC-MS Rt=1.18 mins; [M+H]⁺428.5; Method 2min-LowpHv03

Example 20

(E)-3-(4-Chloro-2-((5-methyl-2H-tetrazol-2-yl)methyl)phenyl)-1-(4-(2-(5-methyl-1,3,4-oxadiazol-2-yl)ethyl)piperidin-1-yl)prop-2-en-1-one

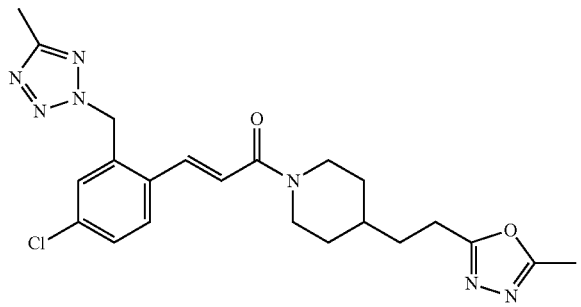 [SMILES: Cc1nnn(Cc2cc(Cl)ccc2/C=C/C(=O)N2CCC(CCc3nnc(C)o3)CC2)n1]

(E)-3-(4-Chloro-2-((5-methyl-2H-tetrazol-2-yl)methyl)phenyl)acrylic acid (Intermediate A) (100 mg, 0.359 mmol) and 2-methyl-5-(2-(piperidin-4-yl)ethyl)-1,3,4-oxadiazole (Intermediate BE) (105 mg, 0.538 mmol) were placed in a flask with dry DMF (2 mL). DIPEA (0.31 mL, 1.79 mmol) was added followed by the slow addition of T3P® (50% in DMF) (0.42 mL, 0.718 mmol). The reaction mixture was stirred at room temperature for 2 h and then partitioned between EtOAc (20 mL) and water (20 mL). The organic phase was washed with water and brine, dried over MgSO₄, filtered and the solvent was removed in vacuo. Purification of the crude product by chromatography on silica eluting with 0-100% (10% MeOH in EtOAc) in iso-hexane afforded the title compound;

LC-MS Rt=1.16 mins; [M+H]⁺456.5; Method 2min-LowpHv03

Example 21

(E)-3-(4-Chloro-2-((3-methyl-1,2,4-oxadiazol-5-yl)methyl)phenyl)-1-(4-((5-methyl-1,3,4-oxadiazol-2-yl)methyl)piperidin-1-yl)prop-2-en-1-one

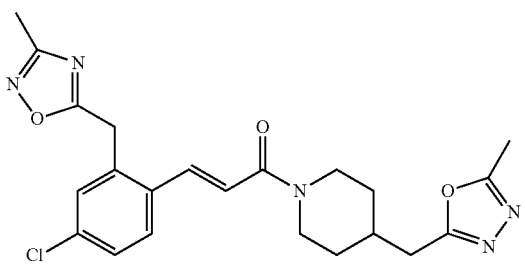 [SMILES: Cc1noc(Cc2cc(Cl)ccc2/C=C/C(=O)N2CCC(Cc3nnc(C)o3)CC2)n1]

(E)-3-(4-Chloro-2-((3-methyl-1,2,4-oxadiazol-5-yl)methyl)phenyl)acrylic acid (Intermediate AE) (100 mg, 0.359 mmol) and 2-methyl-5-(piperidin-4-ylmethyl)-1,3,4-oxadiazole (Intermediate BD) (147 mg, 0.359 mmol) were placed in a flask with dry DMF (2 mL). DIPEA (0.313 mL, 1.79 mmol) was added followed by the slow addition of T3P® (50% in DMF) (0.419 mL, 0.718 mmol). The reaction mixture was stirred at room temperature for 2 h and then partitioned between EtOAc (20 mL) and water (20 mL). The organic phase was washed with water and brine, dried over MgSO₄, filtered and the solvent was removed in vacuo. Purification of the crude product by chromatography on silica eluting with 0-100% (10% MeOH in EtOAc) in iso-hexane afforded the title compound;

LC-MS Rt=1.03 mins; [M+H]⁺ 442.3; Method 2min-LowpHv03

Example 22

(E)-1-(4-(2H-1,2,3-Triazol-2-yl)piperidin-1-yl)-3-(4-chloro-2-((5-methyl-2H-tetrazol-2-yl)methyl)phenyl)prop-2-en-1-one

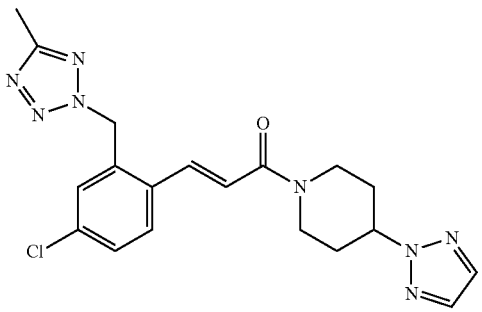 [SMILES: Cc1nnn(Cc2cc(Cl)ccc2/C=C/C(=O)N2CCC(n3nccn3)CC2)n1]

(E)-3-(4-Chloro-2-((5-methyl-2H-tetrazol-2-yl)methyl)phenyl)acrylic acid (Intermediate A) (100 mg, 0.359 mmol) and 4-(2H-1,2,3-triazol-2-yl)piperidine (Intermediate CE) (65 mg, 0.431 mmol) were placed in a flask with dry DMF (2 mL). DIPEA (0.31 mL, 1.79 mmol) was added followed by the slow addition of T3P® (50% in DMF) (0.42 mL, 0.718 mmol). The reaction mixture was stirred at room temperature for 2 h and then partitioned between EtOAc (20 mL) and water (20 mL). The organic phase was washed with water and brine, dried over MgSO₄, filtered and the solvent was removed in vacuo. Purification of the crude product by chromatography on silica eluting with 0-100% (10% MeOH in EtOAc) in iso-hexane afforded the title compound;

LC-MS Rt=1.23 mins; [M+H]⁺413.5; Method 2min-LowpHv03

Example 23

(rac)-(E)-3-(4-Chloro-2-((5-methyl-2H-tetrazol-2-yl)methyl)phenyl)-1-(2-(3-methyl-1,2,4-oxadiazol-5-yl)piperidin-1-yl)prop-2-en-1-one

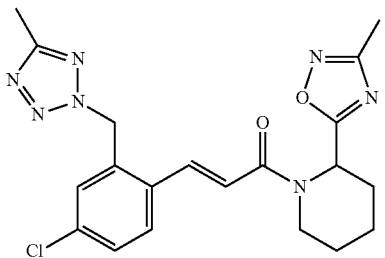 [SMILES: Cc1noc(C2CCCCN2C(=O)/C=C/c2ccc(Cl)cc2Cn2nnc(C)n2)n1]

(E)-3-(4-Chloro-2-((5-methyl-2H-tetrazol-2-yl)methyl)phenyl)acrylic acid (Intermediate A) (250 mg, 0.897 mmol) and 3-methyl-5-(piperidin-2-yl)-1,2,4-oxadiazole (165 mg, 0.987 mmol) were placed in a flask with dry DMF (5 mL). DIPEA (0.783 mL, 4.49 mmol) was added followed by the slow addition of T3P® (50% in DMF) (1.05 mL, 1.79 mmol). The reaction mixture was stirred at room temperature for 2 h and then partitioned between EtOAc (50 mL) and water (50 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.28 mins; [M+H]$^+$ 428.5; Method 2min-LowpHv03

Example 23a (R)- or (S)-(E)-3-(4-Chloro-2-((5-methyl-2H-tetrazol-2-yl)methyl)phenyl)-1-(2-(3-methyl-1,2,4-oxadiazol-5-yl)piperidin-1-yl)prop-2-en-1-one and

Example 23b (R)- or (S)-(E)-3-(4-Chloro-2-((5-methyl-2H-tetrazol-2-yl)methyl)phenyl)-1-(2-(3-methyl-1,2,4-oxadiazol-5-yl)piperidin-1-yl)prop-2-en-1-one

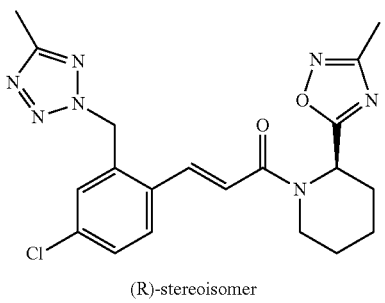

(R)-stereoisomer

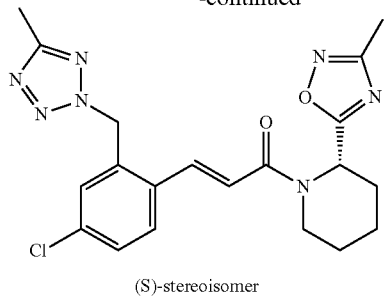

(S)-stereoisomer (rac)-(E)-3-(4-Chloro-2-((5-methyl-2H-tetrazol-2-yl)methyl)phenyl)-1-(2-(3-methyl-1,2,4-oxadiazol-5-yl)piperidin-1-yl)prop-2-en-1-one (Example 23) was separated by SFC chiral chromatography (CHIRALPAK IC 250×10 mm 5 um, 50% methanol in CO$_2$);

Example 23a (R)- or (S)-(E)-3-(4-Chloro-2-((5-methyl-2H-tetrazol-2-yl)methyl)phenyl)-1-(2-(3-methyl-1,2,4-oxadiazol-5-yl)piperidin-1-yl)prop-2-en-1-one First Eluted Peak:
SFC Rt=4.94 mins;
LC-MS Rt=1.28 mins; [M+H]$^+$ 428.5; Method 2min-LowpHv03

Example 23b (R)- or (S)-(E)-3-(4-Chloro-2-((5-methyl-2H-tetrazol-2-yl)methyl)phenyl)-1-(2-(3-methyl-1,2,4-oxadiazol-5-yl)piperidin-1-yl)prop-2-en-1-one Second Eluted Peak:
SFC Rt=6.67 mins;
LC-MS Rt=1.28 mins; [M+H]$^+$ 428.3; Method 2min-LowpHv03

Example 24

(E)-3-(4-Chloro-2-((5-methyl-2H-tetrazol-2-yl)methyl)phenyl)-1-(4-(5-methyloxazol-2-yl)piperidin-1-yl)prop-2-en-1-one

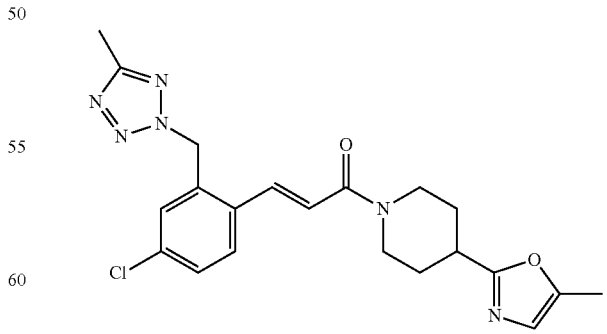

(E)-3-(4-Chloro-2-((5-methyl-2H-tetrazol-2-yl)methyl)phenyl)acrylic acid (Intermediate A) (150 mg, 0.538 mmol) and 5-methyl-2-(piperidin-4-yl)oxazole (Intermediate CI) (131 mg, 0.646 mmol) were placed in a flask with dry DMF (3 mL). DIPEA (0.47 mL, 2.69 mmol) was added followed by the slow addition of T3P® (50% in DMF) (0.63 mL, 1.08 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.10 mins; [M+H]$^+$427.2; Method 2min-LowpHv03

Example 25

(E)-3-(4-Chloro-2-((5-methyl-2H-tetrazol-2-yl)methyl)phenyl)-1-(4-(4-methyl-2H-1,2,3-triazol-2-yl)piperidin-1-yl)prop-2-en-1-one

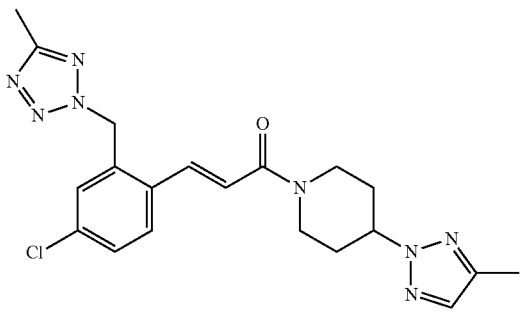 [SMILES: Cc1cnn(C2CCN(C(=O)/C=C/c3ccc(Cl)cc3Cn3nnc(C)n3)CC2)n1]

(E)-3-(4-Chloro-2-((5-methyl-2H-tetrazol-2-yl)methyl)phenyl)acrylic acid (Intermediate A) (100 mg, 0.359 mmol) and 4-(4-methyl-2H-1,2,3-triazol-2-yl)piperidine (Intermediate CJ) (66 mg, 0.395 mmol) were placed in a flask with dry DMF (2 mL). DIPEA (0.313 mL, 1.79 mmol) was added followed by the slow addition of T3P® (50% in DMF) (0.42 mL, 0.718 mmol). The reaction mixture was stirred at room temperature for 2 h and then partitioned between EtOAc (20 mL) and water (2 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.23 mins; [M+H]$^+$ 427.4; Method 2min-LowpHv03

Example 26

(E)-3-(4-Chloro-2-((5-methyl-2H-tetrazol-2-yl)methyl)phenyl)-1-(4-(3-(5-methyl-1,3,4-oxadiazol-2-yl)propyl)piperidin-1-yl)prop-2-en-1-one

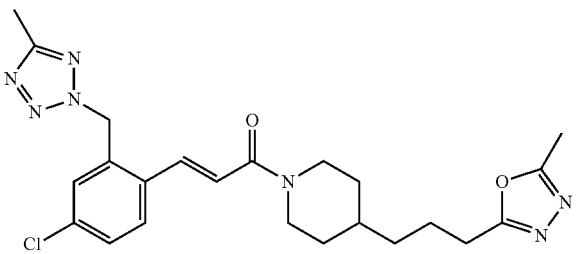 [SMILES: Cc1nnn(Cc2cc(Cl)ccc2/C=C/C(=O)N2CCC(CCCc3nnc(C)o3)CC2)n1]

(E)-3-(4-Chloro-2-((5-methyl-2H-tetrazol-2-yl)methyl)phenyl)acrylic acid (Intermediate A) (100 mg, 0.359 mmol) and 2-methyl-5-(3-(piperidin-4-yl)propyl)-1,3,4-oxadiazole (Intermediate BF) (113 mg, 0.538 mmol) were placed in a flask with dry DMF (2 mL). DIPEA (0.31 mL, 1.79 mmol) was added followed by the slow addition of T3P® (50% in DMF) (0.42 mL, 0.718 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.25 mins; [M+H]$^+$ 470.6; Method 2min-LowpHv03

Example 27

(E)-3-(4-Chloro-2-((5-methyl-2H-tetrazol-2-yl)methyl)phenyl)-1-(4-(2-methyloxazol-4-yl)piperidin-1-yl)prop-2-en-1-one

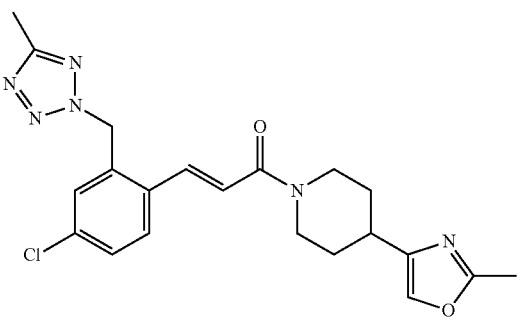

(E)-3-(4-Chloro-2-((5-methyl-2H-tetrazol-2-yl)methyl)phenyl)acrylic acid (Intermediate A) (100 mg, 0.359 mmol) and 2-methyl-4-(piperidin-4-yl)oxazole (Intermediate F) (98 mg, 0.395 mmol) were placed in a flask with dry DMF (2 mL). DIPEA (0.31 mL, 1.79 mmol) was added followed by the slow addition of T3P® (50% in DMF) (0.42 mL, 0.718 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.19 mins; [M+H]$^+$427.4; Method 2min-LowpHv03

Example 28

(E)-3-(4-Chloro-2-((5-methyl-2H-tetrazol-2-yl)methyl)phenyl)-1-(4-(4-methyl-1H-pyrazol-1-yl)piperidin-1-yl)prop-2-en-1-one

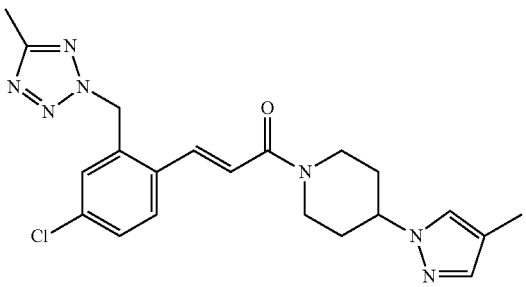

(E)-3-(4-Chloro-2-((5-methyl-2H-tetrazol-2-yl)methyl)phenyl)acrylic acid (Intermediate A) (150 mg, 0.538 mmol) and 4-(4-methyl-1H-pyrazol-1-yl)piperidine (Intermediate CH) (119 mg, 0.592 mmol) were placed in a flask with dry DMF (3 mL). DIPEA (0.47 mL, 2.69 mmol) was added followed by the slow addition of T3P® (50% in DMF) (0.63 mL, 1.08 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.09 mins; [M+H]$^+$ 426.3; Method 2min-LowpHv03

Example 29

(E)-Methyl 1-(3-(4-Chloro-2-((5-methyl-2H-tetrazol-2-yl)methyl)phenyl)acryloyl) piperidine-2-carboxylate

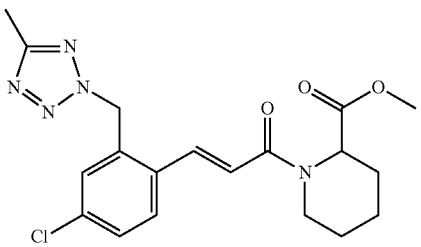

(E)-3-(4-Chloro-2-((5-methyl-2H-tetrazol-2-yl)methyl)phenyl)acrylic acid (Intermediate A) (500 mg, 1.79 mmol) and methyl piperidine-2-carboxylate (283 mg, 1.97 mmol) were placed in a flask with dry DMF (5 mL). DIPEA (1.57 mL, 8.97 mmol) was added followed by the slow addition of T3P® (50% in DMF) (2.09 mL, 3.59 mmol). The reaction mixture was stirred at room temperature for 2 h and then partitioned between EtOAc (50 mL) and water (50 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.27 mins; [M+H]$^+$ 404.5; Method 2min-LowpHv03

Example 30

(rac)-(E)-3-(4-Chloro-2-((5-methyl-2H-tetrazol-2-yl)methyl)phenyl)-1-(2-(3-isopropyl-1,2,4-oxadiazol-5-yl)piperidin-1-yl)prop-2-en-1-one

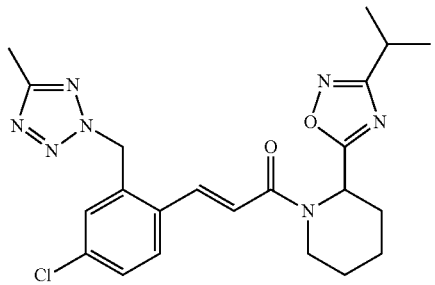 [SMILES: Cc1nnn(Cc2cc(Cl)ccc2/C=C/C(=O)N2CCCCC2c2nc(C(C)C)no2)n1]

(E)-3-(4-Chloro-2-((5-methyl-2H-tetrazol-2-yl)methyl)phenyl)acrylic acid (Intermediate A) (250 mg, 0.897 mmol) and 3-isopropyl-5-(piperidin-2-yl)-1,2,4-oxadiazole (193 mg, 0.987 mmol) were placed in a flask with dry DMF (5 mL). DIPEA (0.783 mL, 4.49 mmol) was added followed by the slow addition of T3P® (50% in DMF) (1.05 mL, 1.79 mmol). The reaction mixture was stirred at room temperature for 2 h and then partitioned between EtOAc (50 mL) and water (50 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.44 mins; [M+H]$^+$ 456.3; Method 2min-LowpHv03

Example 30a (R or S, E)-3-(4-Chloro-2-((5-methyl-2H-tetrazol-2-yl)methyl)phenyl)-1-(2-(3-isopropyl-1,2,4-oxadiazol-5-yl)piperidin-1-yl)prop-2-en-1-one

Example 30b (R or S, E)-3-(4-chloro-2-((5-methyl-2H-tetrazol-2-yl)methyl)phenyl)-1-(2-(3-isopropyl-1,2,4-oxadiazol-5-yl)piperidin-1-yl)prop-2-en-1-one

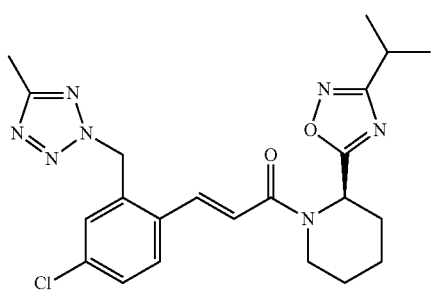

(R)-stereoisomer

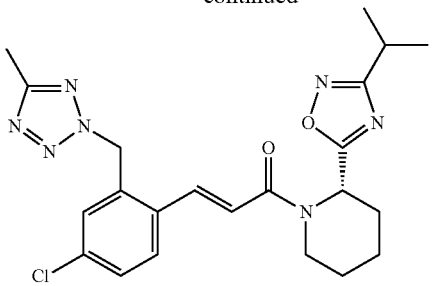

(S)-stereoisomer (rac)-(E)-3-(4-Chloro-2-((5-methyl-2H-tetrazol-2-yl)methyl)phenyl)-1-(2-(3-isopropyl-1,2,4-oxadiazol-5-yl)piperidin-1-yl)prop-2-en-1-one was separated by SFC chiral chromatography (CHIRALPAK IC 250×10 mm 5 um, 50% methanol in $CO_2$);

Example 30a (R or S, E)-3-(4-Chloro-2-((5-methyl-2H-tetrazol-2-yl)methyl)phenyl)-1-(2-(3-isopropyl-1,2,4-oxadiazol-5-yl)piperidin-1-yl)prop-2-en-1-one First Eluted Peak:
SFC Rt=4.30 mins; (CHIRALPAK IC 250×10 mm 5 um, 50% methanol in $CO_2$)
LC-MS Rt=1.44 mins; [M+H]$^+$ 456.5; Method 2min-LowpHv03

Example 30b (R or S, E)-3-(4-chloro-2-((5-methyl-2H-tetrazol-2-yl)methyl)phenyl)-1-(2-(3-isopropyl-1,2,4-oxadiazol-5-yl)piperidin-1-yl)prop-2-en-1-one Second Eluted Peak:
SFC Rt=5.35 mins; (CHIRALPAK IC 250×10 mm 5 um, 50% methanol in $CO_2$)
LC-MS Rt=1.43 mins; [M+H]$^+$456.5; Method 2min-LowpHv03

Example 31

(E)-3-(4-Chloro-2-((5-methyl-2H-tetrazol-2-yl)methyl)phenyl)-1-(4-((5-methyl oxazol-2-yl)methyl)piperidin-1-yl)prop-2-en-1-one

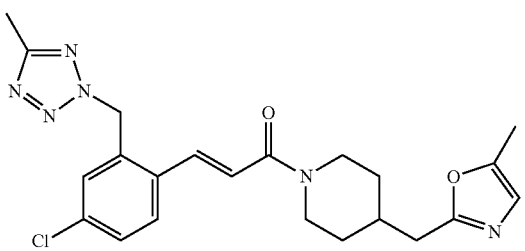 [SMILES: Cc1nnn(Cc2cc(Cl)ccc2/C=C/C(=O)N2CCC(Cc3ncc(C)o3)CC2)n1]

(E)-3-(4-Chloro-2-((5-methyl-2H-tetrazol-2-yl)methyl)phenyl)acrylic acid (Intermediate A) (200 mg, 0.718 mmol) and 5-methyl-2-(piperidin-4-ylmethyl)oxazole (Intermediate CG) (211 mg, 0.718 mmol) were placed in a flask with THF (5 mL). DIPEA (0.627 mL, 3.59 mmol) was added followed by HATU (327 mg, 0.861 mmol). The reaction mixture was stirred at 50° C. for 2 h and then partitioned between EtOAc (50 mL) and water (50 mL). The organic phase was washed with water and brine, dried over $MgSO_4$, filtered and the solvent was removed in vacuo. Purification of the crude product by chromatography on silica eluting with 0-100% (10% MeOH in EtOAc) in iso-hexane afforded the title compound;
LC-MS Rt=1.12 mins; [M+H]$^+$441.5; Method 2min-LowpHv03

Example 32

(E)-Ethyl 1-((1-(3-(4-chloro-2-((5-methyl-2H-tetrazol-2-yl)methyl)phenyl)acryloyl)-4-hydroxypiperidin-4-yl)methyl)-1H-pyrazole-4-carboxylate

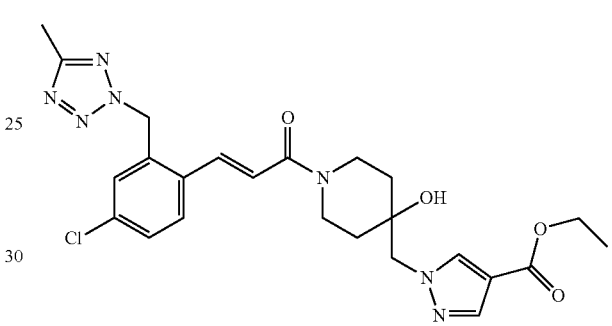

The preparation of the title compound is described in Example 14, step 1;
LC-MS Rt=1.06 mins; [M+H]$^+$ 514.7; Method 2min-LowpHv03

Example 33

(E)-3-(4-Chloro-2-((5-methyl-2H-tetrazol-2-yl)methyl)phenyl)-1-(4-(2-(4-methyl-1H-pyrazol-1-yl)ethyl)piperidin-1-yl)prop-2-en-1-one

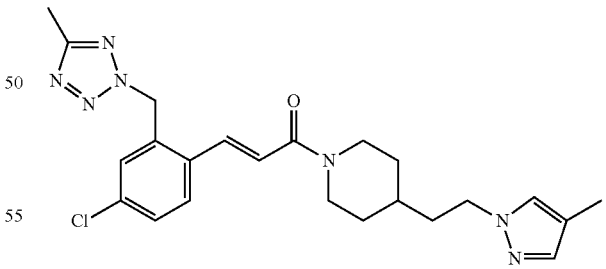

(E)-3-(4-Chloro-2-((5-methyl-2H-tetrazol-2-yl)methyl)phenyl)acrylic acid (Intermediate A) (133 mg, 0.479 mmol) and 4-(2-(4-Methyl-1H-pyrazol-1-yl)ethyl)piperidine (Intermediate CF) (110 mg, 0.479 mmol) were placed in a flask with dry DMF (2 mL). DIPEA (0.42 mL, 2.39 mmol) was added followed by the slow addition of T3P® (50% in DMF) (0.63 mL, 1.08 mmol). The reaction mixture was stirred at room temperature for 2 h and then partitioned between EtOAc (20 mL) and water (20 mL). The organic phase was washed with water and brine, dried over MgSO₄, filtered and the solvent was removed in vacuo. Purification of the crude product by chromatography on silica eluting with 0-100% (10% MeOH in EtOAc) in iso-hexane afforded the title compound;

LC-MS Rt=1.29 mins; [M+H]⁺ 454.3; Method 2min-LowpHv03

Example 34

(rac)-(E)-3-(4-Chloro-2-((5-methyl-2H-tetrazol-2-yl)methyl)phenyl)-1-(3-(3-isopropyl-1,2,4-oxadiazol-5-yl)piperidin-1-yl)prop-2-en-1-one

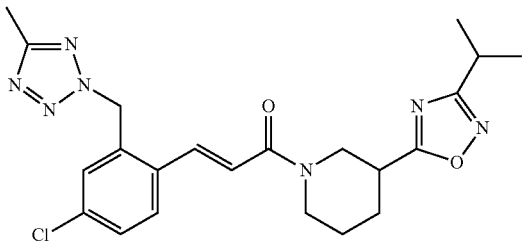 [SMILES: Cc1nnn(Cc2cc(Cl)ccc2/C=C/C(=O)N2CCCC(c3nc(C(C)C)no3)C2)n1]

(E)-3-(4-Chloro-2-((5-methyl-2H-tetrazol-2-yl)methyl)phenyl)acrylic acid (Intermediate A) (250 mg, 0.897 mmol) and 3-isopropyl-5-(piperidin-3-yl)-1,2,4-oxadiazole (193 mg, 0.987 mmol) were placed in a flask with dry DMF (5 mL). DIPEA (0.783 mL, 4.49 mmol) was added followed by the slow addition of T3P® (50% in DMF) (1.05 mL, 1.79 mmol). The reaction mixture was stirred at room temperature for 2 h and then partitioned between EtOAc (50 mL) and water (50 mL). The organic phase was washed with water and brine, dried over MgSO₄, filtered and the solvent was removed in vacuo. Purification of the crude product by chromatography on silica eluting with 0-100% (10% MeOH in EtOAc) in iso-hexane afforded the title compound;

LC-MS Rt=1.35 mins; [M+H]⁺ 456.5; Method 2min-LowpHv03

Example 34a (R or S, E)-3-(4-Chloro-2-((5-methyl-2H-tetrazol-2-yl)methyl)phenyl)-1-(3-(3-isopropyl-1,2,4-oxadiazol-5-yl)piperidin-1-yl)prop-2-en-1-one

Example 34b (R or S,E)-3-(4-chloro-2-((5-methyl-2H-tetrazol-2-yl)methyl)phenyl)-1-(3-(3-isopropyl-1,2,4-oxadiazol-5-yl)piperidin-1-yl)prop-2-en-1-one

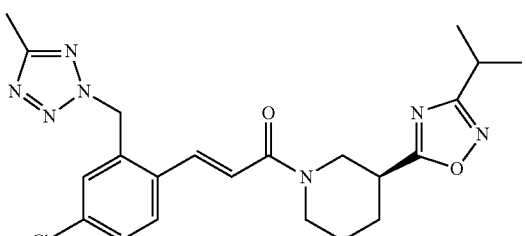

(S)-stereoisomer

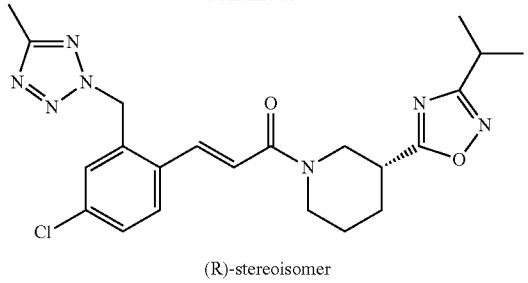

(R)-stereoisomer (rac)-(E)-3-(4-Chloro-2-((5-methyl-2H-tetrazol-2-yl)methyl)phenyl)-1-(3-(3-isopropyl-1,2,4-oxadiazol-5-yl)piperidin-1-yl)prop-2-en-1-one was separated by SFC chiral chromatography (CHIRALPAK IC 250×10 mm 5 um, 45% isopropanol in CO₂);

Example 34a (R or S, E)-3-(4-Chloro-2-((5-methyl-2H-tetrazol-2-yl)methyl)phenyl)-1-(3-(3-isopropyl-1,2,4-oxadiazol-5-yl)piperidin-1-yl)prop-2-en-1-one First Eluted Peak:
SFC Rt=7.46 mins; (CHIRALPAK IC 250×10 mm 5 um, 45% isopropanol in CO₂)
LC-MS Rt=1.35 mins; [M+H]⁺456.5; Method 2min-LowpHv03

Example 34b (R or S, E)-3-(4-chloro-2-((5-methyl-2H-tetrazol-2-yl)methyl)phenyl)-1-(3-(3-isopropyl-1,2,4-oxadiazol-5-yl)piperidin-1-yl)prop-2-en-1-one Second Eluted Peak:
SFC Rt=9.08 mins; (CHIRALPAK IC 250×10 mm 5 um, 45% isopropanol in CO₂)
LC-MS Rt=1.43 mins; [M+H]⁺ 456.5; Method 2min-LowpHv03

Example 35

(E)-1-((1-(3-(4-Chloro-2-((5-methyl-2H-tetrazol-2-yl)methyl)phenyl)acryloyl)-4-hydroxypiperidin-4-yl)methyl)-1H-pyrazole-4-carboxylic acid

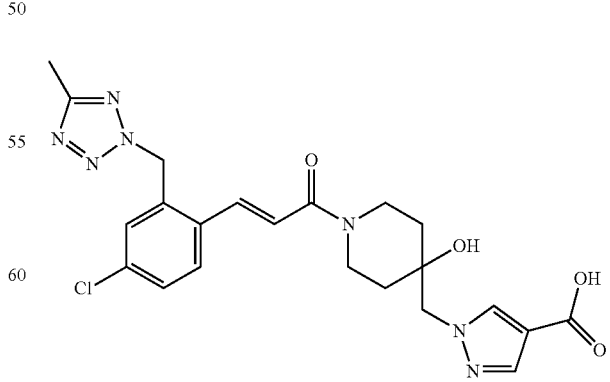

The preparation of the title compound is described in Example 14, step 2;

LC-MS Rt=0.92 mins; [M+H]+ 486.5; Method 2min-LowpHv03

Example 36

1-(4-(5-Methyl-1,2,4-oxadiazol-3-yl)piperidin-1-yl)-2-(2-((5-methyl-2H-tetrazol-2-yl)methyl)-4-(trifluoromethyl)phenoxy)ethanone

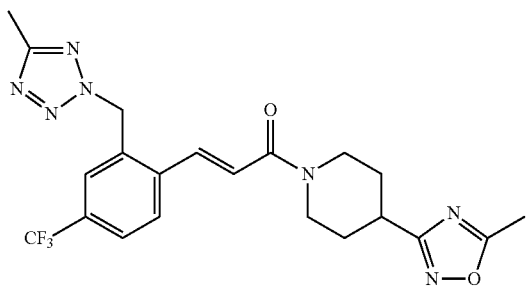

Step 1: 2-Hydroxy-5-(trifluoromethyl)benzoic acid

2-Methoxy-5-(trifluoromethyl)benzoic acid (5.00 g, 22.71 mmol) was placed in a flask with iodocyclohexane (29.4 mL, 227 mmol) and DMF (25 mL). The reaction mixture was refluxed for 4 h, cooled and the solvent was removed in vacuo. Purification of the crude product by chromatography on silica eluting with 0-100% EtOAc in iso-hexane afforded the title compound;

$^1$H NMR (400 MHz, CDCl$_3$) δ 10.70 (1H, s), 8.29 (1H, d), 7.80 (1H, d of d), 7.15 (1H, d).

Step 2: 2-(Hydroxymethyl)-4-(trifluoromethyl)phenol

2-Hydroxy-5-(trifluoromethyl)benzoic acid (6.50 g, 31.5 mmol) was placed in a flask with THF (50 mL) and cooled on ice. Borane tetrahydrofuran complex (47.3 mL, 47.3 mmol) was added and the reaction mixture was stirred at 50° C. for 6 h. The reaction mixture was quenched carefully with 1M HCl (50 mL) and partitioned between EtOAc and water. The organic phase was washed with water and brine, dried over MgSO$_4$, filtered and the solvent was removed in vacuo. Purification of the crude product by chromatography on silica eluting with 0-100% EtOAc in iso-hexane afforded the title compound;

$^1$H NMR (400 MHz, CDCl$_3$) δ 7.80 (1H, s), 7.50 (1H, d of d), 7.32 (1H, d), 7.00 (1H, d), 4.98 (2H, s), 2.23 (1H, br s).

Step 3: tert-Butyl 2-(2-(hydroxymethyl)-4-(trifluoromethyl)phenoxy)acetate 2-(Hydroxymethyl)-4-(trifluoromethyl)phenol (4.70 g, 24.46 mmol) was placed in a flask with dry MeCN (100 mL). tert-Butyl 2-bromoacetate (5.25 g, 26.9 mmol) was added followed by potassium carbonate (16.9 g, 122 mmol) and the reaction mixture was stirred at room temperature overnight. The K$_2$CO$_3$ was filtered off, washed with MeCN and the solvent was removed in vacuo. Purification of the crude product by chromatography on silica eluting with 0-100% EtOAc in iso-hexane afforded the title compound;

$^1$H NMR (400 MHz, DMSO-d6) δ 7.70 (1H, d), 7.58 (1H, d of d), 7.01 (1H, d), 5.30 (1H, t), 4.81 (2H, s), 4.60 (2H, d), 1.41 (9H, s).

Step 4: tert-Butyl 2-(2-(bromomethyl)-4-(trifluoromethyl)phenoxy)acetate tert-Butyl 2-(2-(hydroxymethyl)-4-(trifluoromethyl)phenoxy)acetate (1.00 g, 3.27 mmol) was placed in a flask with dry MeCN (25 mL). Triphenylphosphine (1.28 g, 4.90 mmol) was added followed by hexabromoacetone (0.868 g, 1.63 mmol) and the reaction mixture was stirred at 40° C. for 1 h. The solvent was removed in vacuo and purification of the crude product by chromatography on silica eluting with 0-40% EtOAc in iso-hexane afforded the title compound;

$^1$H NMR (400 MHz, DMSO-d6) δ 7.87 (1H, d), 7.69 (1H, d of d), 7.11 (1H, d), 4.91 (2H, s), 4.72 (2H, s), 1.43 (9H, s).

Step 5: tert-Butyl 2-(2-((5-methyl-2H-tetrazol-2-yl)methyl)-4-(trifluoromethyl)phenoxy)acetate tert-Butyl 2-(2-(bromomethyl)-4-(trifluoromethyl)phenoxy)acetate (1.20 g, 3.25 mmol) was placed in a flask with dry DMF (10 mL). 5-Methyl-2H-tetrazole (0.41 g, 4.88 mmol) was added followed by potassium carbonate (0.90 g, 6.50 mmol) and the reaction mixture was stirred at room temperature for 1 h. The reaction mixture was partitioned between EtOAc (100 mL) and water (100 mL). The organic phase was washed with water and brine, dried over MgSO$_4$, filtered and the solvent was removed in vacuo. Purification by chromatography on silica eluting with 0-100% EtOAc in iso-hexane afforded the title compound and a by-product tert-butyl 2-(2-((5-methyl-1H-tetrazol-1-yl)methyl)-4-(trifluoromethyl)phenoxy)acetate;

LC-MS Rt=1.42 mins; [M+H]+ 373.6; Method 2min-LowpHv03

Step 6: 2-(2-((5-Methyl-2H-tetrazol-2-yl)methyl)-4-(trifluoromethyl)phenoxy)acetic acid tert-Butyl 2-(2-((5-methyl-2H-tetrazol-2-yl)methyl)-4-(trifluoromethyl)phenoxy)acetate (260 mg, 0.70 mmol) was placed in a flask with dry DCM (2 mL). TFA (0.54 mL, 6.98 mmol) was added and the reaction mixture was stirred at room temperature for 2 h. The reaction mixture was partitioned between DCM (50 mL) and water (50 mL). The organic phase was washed with water and brine, dried over MgSO$_4$, filtered and the solvent was removed in vacuo to afford the title compound;

LC-MS Rt=1.10 mins; [M+H]+317.2; Method 2min-LowpHv03

Step 7: 1-(4-(5-Methyl-1,2,4-oxadiazol-3-yl)piperidin-1-yl)-2-(2-((5-methyl-2H-tetrazol-2-yl)methyl)-4-(trifluoromethyl)phenoxy)ethanone 2-(2-((5-Methyl-2H-tetrazol-2-yl)methyl)-4-(trifluoromethyl)phenoxy)acetic acid (50 mg, 0.158 mmol) and 5-methyl-3-(piperidin-4-yl)-1,2,4-oxadiazole (Intermediate E) (35.4 mg, 0.174 mmol) were placed in a flask with dry EtOAc (1 mL). DIPEA (0.138 mL, 0.79 mmol) was added to the suspension followed by the slow addition of T3P® (50% in EtOAc) (0.185 mL, 0.316 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.21 mins; [M+H]+ 466.3; Method 2min-LowpHv03

$^1$H NMR (400 MHz, DMSO-d6) δ 7.75 (1H, d), 7.70 (1H, d), 7.19 (1H, d), 5.91 (2H, s), 5.07 (2H, m), 4.21 (1H, m), 3.72 (1H, m), 3.18 (1H, m), 3.09 (1H, m), 2.82 (1H, m), 2.58 (3H, s), 2.42 (3H, s), 1.91 (2H, m), 1.68 (1H, m), 1.50 (1H, m).

Example 37

(E)-1-(4-(3-Methyl-1H-1,2,4-triazol-1-yl)piperidin-1-yl)-3-(2-((5-methyl-2H-tetrazol-2-yl)methyl)-4-(trifluoromethyl)phenyl)prop-2-en-1-one

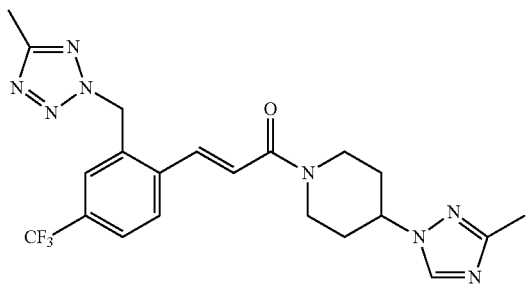

(E)-3-(2-((5-Methyl-2H-tetrazol-2-yl)methyl)-4-(trifluoromethyl)phenyl)acrylic acid (Intermediate AB) (180 mg, 0.576 mmol) and 4-(3-methyl-1H-1,2,4-triazol-1-yl)piperidine (Intermediate CA) (101 mg, 0.605 mmol) were placed in a flask with dry EtOAc (4 mL). DIPEA (0.503 mL, 2.88 mmol) was added to the suspension followed by the slow addition of T3P® (50% in EtOAc) (0.673 mL, 1.15 mmol). The reaction mixture was stirred at room temperature for 2 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=1.10 mins; [M+H]$^+$461.0; Method 2min-LowpHv03

$^1$H NMR (400 MHz, DMSO-d6) δ 8.41 (1H, s), 8.11 (1H, d), 7.90-7.73 (3H, m), 7.31 (1H, d), 6.11 (2H, s), 4.51 (2H, m), 4.30 (1H, m), 3.25 (1H, m), 2.89 (1H, m), 2.42 (3H, s), 2.23 (3H, s), 2.09 (2H, m), 1.70 (2H, m).

Example 38

(rac)-(E)-1-(2-(5-Methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one

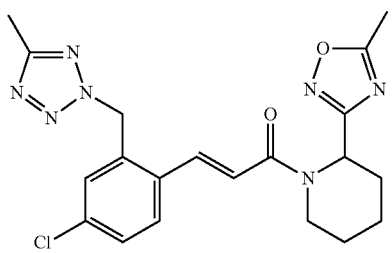

The title compound was prepared by a similar method to Example 36, step 7 from (E)-3-(2-((5-methyl-2H-tetrazol-2-yl)methyl)-4-(trifluoromethyl)phenyl)acrylic acid (Intermediate AB) and 5-methyl-3-(piperidin-2-yl)-1,2,4-oxadiazole hydrochloride.

Example 38a (R or S, E)-1-(2-(5-Methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one and

Example 38b (R or S, E)-1-(2-(5-methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one

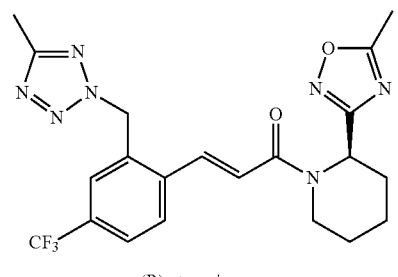

(R)-stereoisomer

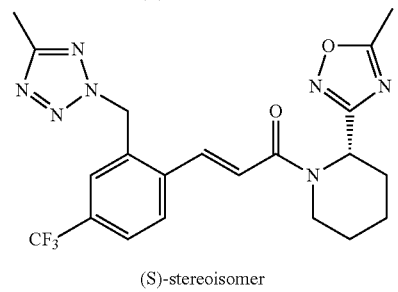

(S)-stereoisomer (rac)-(E)-1-(2-(5-Methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one was separated by SFC chiral chromatography (CHIRALPAK IC 250×10 mm 5 um, 45% isopropanol in CO$_2$);

Example 38a (R or S, E)-1-(2-(5-Methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one First Eluted Peak:
SFC Rt=3.61 mins;
LC-MS Rt=1.34 mins; [M+H]$^+$462.2; Method 2min-LowpHv03

Example 38b (R or S, E)-1-(2-(5-methyl-1,2,4-oxadiazol-3-yl)piperidin-1-yl)-3-(2-((5-methyl-2H-tetrazol-2-yl)methyl)-4-(trifluoromethyl)phenyl)prop-2-en-1-one Second Eluted Peak:
SFC Rt=6.34 mins; (CHIRALPAK IC 250×10 mm 5 um, 45% isopropanol in CO$_2$)
LC-MS Rt=1.32 mins; [M+H]$^+$ 462.2; Method 2min-LowpHv03

Example 39

(E)-3-(4-Chloro-2-((5-methyl-2H-tetrazol-2-yl)methyl)phenyl)-1-(4-(5-methyl-1,3,4-oxadiazol-2-yl)piperidin-1-yl)but-2-en-1-one

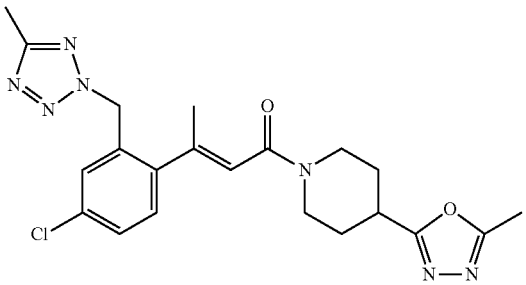

Step 1: 4-Chloro-N-methoxy-N-methyl-2-((5-methyl-2H-tetrazol-2-yl)methyl)benzamide 4-Chloro-2-((5-methyl-2H-tetrazol-2-yl)methyl)benzoic acid (Intermediate AG, step 4) (1.50 g, 5.94 mmol) was placed in a flask with THF (30 mL). HATU (2.48 g, 6.53 mmol) and N,O-dimethylhydroxylamine hydrochloride (0.724 g, 7.42 mmol) were then added followed by the slow addition of triethylamine (5.18 mL, 29.7 mmol) and the reaction mixture was stirred at room temperature for 2 h. The reaction mixture was partitioned between EtOAc and 1M NaOH. The organic phase was washed with water and brine, dried over $MgSO_4$, filtered and the solvent was removed in vacuo. Purification of the crude product by chromatography on silica eluting with 0-100% EtOAc in iso-hexane afforded the title compound;

LC-MS Rt=1.04 mins; $[M+H]^+$ 296.1; Method 2min-LowpHv03

Step 2: 1-(4-Chloro-2-((5-methyl-2H-tetrazol-2-yl)methyl)phenyl)ethanone

4-Chloro-N-methoxy-N-methyl-2-((5-methyl-2H-tetrazol-2-yl)methyl)benzamide (1.70 g, 5.75 mmol) was placed in a flask with THF (25 mL) and cooled to −78° C. Methylmagnesium bromide (3M in ether) (3.83 mL, 11.50 mmol) was then added and the reaction mixture was stirred at −78° C. for 30 minutes and then allowed to return to room temperature. The reaction mixture was quenched with water and partitioned between ether (200 mL) and 1M HCl (100 mL). The organic phase was washed with water and brine, dried over $MgSO_4$, filtered and the solvent was removed in vacuo. Purification of the crude product by chromatography on silica eluting with 0-100% EtOAc in iso-hexane afforded the title compound;

Step 3: (E)-Ethyl-3-(4-chloro-2-((5-methyl-2H-tetrazol-2-yl)methyl)phenyl)but-2-enoate NaH (60% in oil) (299 mg, 7.48 mmol) was suspended in dry THF (15 mL) and cooled on an ice-bath. Triethyl phosphonoacetate (1.80 mL, 8.98 mmol) was added and the reaction mixture was stirred at 0° C. for 30 minutes. A solution of 1-(4-chloro-2-((5-methyl-2H-tetrazol-2-yl)methyl) phenyl)ethanone (750 mg, 2.99 mmol) in THF (5 mL) was slowly added and the reaction mixture was refluxed for 1 h. The reaction mixture was partitioned between EtOAc and water. The organic phase was washed with water and brine, dried over $MgSO_4$, filtered and the solvent was removed in vacuo. Purification of the crude product by chromatography on silica eluting with 0-10% EtOAc in iso-hexane afforded the title compound;

LC-MS Rt=1.40 mins; $[M+H]^+$ 321.5; Method 2min-LowpHv03

Step 4: (E)-3-(4-Chloro-2-((5-methyl-2H-tetrazol-2-yl)methyl)phenyl)but-2-enoic acid (E)-Ethyl 3-(4-chloro-2-((5-methyl-2H-tetrazol-2-yl)methyl)phenyl)but-2-enoate (250 mg, 0.78 mmol) was placed in a flask with EtOH (4 mL). 2M NaOH (1.95 mL, 3.90 mmol) was added and the reaction mixture was stirred at room temperature for 4 h. The EtOH was removed in vacuo, the reaction mixture was acidified with 2M HCl (3 mL) and partitioned between DCM (10 mL) and water (10 mL). The organic phase was passed through a phase separator and the solvent was removed in vacuo. Purification of the crude product by chromatography on silica eluting with 0-100% EtOAc in iso-hexane afforded the title compound;

LC-MS Rt=1.14 mins; $[M+H]^+$293.5; Method 2min-LowpHv03

Step 5: (E)-3-(4-Chloro-2-((5-methyl-2H-tetrazol-2-yl)methyl)phenyl)-1-(4-(5-methyl-1,3,4-oxadiazol-2-yl)piperidin-1-yl)but-2-en-1-one The title compound was prepared by a similar method to Example 36, step 7 from (E)-3-(4-chloro-2-((5-methyl-2H-tetrazol-2-yl)methyl)phenyl)but-2-enoic acid and 2-methyl-5-(piperidin-4-yl)-1,3,4-oxadiazole (Intermediate BG);

LC-MS Rt=1.13 mins; $[M+H]^+$ 444.1; Method 2min-LowpHv03

Example 40

1-(4-(5-Methyl-1,3,4-oxadiazol-2-yl)piperidin-1-yl)-3-(2-((5-methyl-2H-tetrazol-2-yl)methyl)-4-(trifluoromethyl)phenyl)propan-1-one

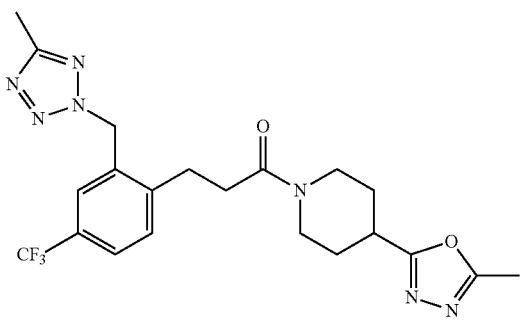 [SMILES: Cc1nnn(Cc2cc(C(F)(F)F)ccc2CCC(=O)N2CCC(c3nnc(C)o3)CC2)n1]

The title compound was prepared by a similar method to Example 36, step 7 from 3-(2-((5-methyl-2H-tetrazol-2-yl)methyl)-4-(trifluoromethyl)phenyl)propanoic acid (Intermediate AF) and 2-methyl-5-(piperidin-4-yl)-1,3,4-oxadiazole (Intermediate BG);

LC-MS Rt=1.16 mins; $[M+H]^+$464.6; Method 2min-LowpHv03

Example 41

(E)-3-(4-Fluoro-2-((5-methyl-2H-tetrazol-2-yl)methyl)phenyl)-1-(4-((5-methyl-1,3,4-oxadiazol-2-yl)methyl)piperidin-1-yl)prop-2-en-1-one

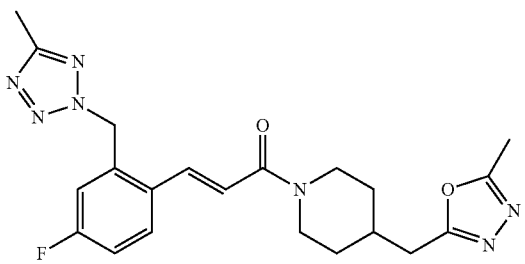 [SMILES: Cc1nnn(Cc2cc(F)ccc2/C=C/C(=O)N2CCC(Cc3nnc(C)o3)CC2)n1]

Step 1: 2-(2-Bromo-5-fluorobenzyl)-5-methyl-2H-tetrazole 2-(2-Bromo-5-fluorobenzyl)-5-methyl-2H-tetrazole was prepared by a similar method to Intermediate A, step 1 from 1-bromo-2-(bromomethyl)-4-fluorobenzene and 5-methyl-1H-tetrazole. Purification of the crude product by chromatography on silica eluting with 0-50% EtOAc in iso-hexane afforded the title compound.

Step 2: (E)-3-(4-Fluoro-2-((5-methyl-2H-tetrazol-2-yl)methyl)phenyl)-1-(4-((5-methyl-1,3,4-oxadiazol-2-yl)methyl)piperidin-1-yl)prop-2-en-1-one 2-(2-Bromo-5-fluorobenzyl)-5-methyl-2H-tetrazole (104 mg, 0.383 mmol), palladium diacetate (7.16 mg, 0.032 mmol) and tri-o-tolylphosphine (9.70 mg, 0.032 mmol) were placed in a flask. 1-(4-((5-Methyl-1,3,4-oxadiazol-2-yl)methyl)piperidin-1-yl)prop-2-en-1-one (Intermediate G) (75 mg, 0.319 mmol), dissolved in dry, degassed DMF (2 mL), was added followed by triethylamine (0.133 mL, 0.956 mmol) and the reaction mixture was stirred at 100° C. overnight. The reaction mixture was stirred at 100° C. for 18 h and then partitioned between EtOAc (20 mL) and water (20 mL). The organic phase was washed with water and brine, dried over MgSO$_4$, filtered and the solvent was removed in vacuo. Purification of the crude product by chromatography on silica eluting with 0-100% (10% MeOH in EtOAc) in iso-hexane afforded the title compound;

LC-MS Rt=0.95 mins; [M+H]$^+$ 426.3; Method 2min-LowpHv03

Example 42

(E)-3-(4,5-Difluoro-2-((5-methyl-2H-tetrazol-2-yl)methyl)phenyl)-1-(4-((5-methyl-1,3,4-oxadiazol-2-yl)methyl)piperidin-1-yl)prop-2-en-1-one

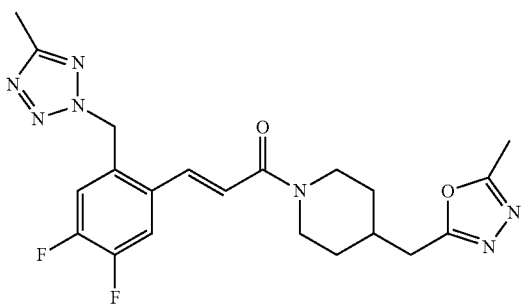 [SMILES: Cc1nnn(Cc2cc(F)c(F)cc2/C=C/C(=O)N2CCC(Cc3nnc(C)o3)CC2)n1]

Step 1: 1-Bromo-2-(bromomethyl)-4,5-difluorobenzene

1-Bromo-2-(bromomethyl)-4,5-difluorobenzene was prepared by a similar method to Intermediate AC, step 1 from 1-bromo-2-(bromomethyl)-4,5-difluorobenzene. The reaction mixture was filtered to remove the succinimide side product, the solvent was removed in vacuo and the product was used crude in the next step.

Step 2: 2-(2-Bromo-4,5-difluorobenzyl)-5-methyl-2H-tetrazole 2-(2-Bromo-4,5-difluorobenzyl)-5-methyl-2H-tetrazole was prepared by a similar method to Intermediate A, step 1 from 1-bromo-2-(bromomethyl)-4-fluorobenzene and 5-methyl-1H-tetrazole. Purification of the crude product by chromatography on silica eluting with 0-50% EtOAc in iso-hexane afforded the title compound.

Step 3: (E)-3-(4,5-Difluoro-2-((5-methyl-2H-tetrazol-2-yl)methyl)phenyl)-1-(4-((5-methyl-1,3,4-oxadiazol-2-yl)methyl)piperidin-1-yl)prop-2-en-1-one The title compound was prepared by a similar method to Example 41, step 2 from 2-methyl-5-(piperidin-4-ylmethyl)-1,3,4-oxadiazole (Intermediate G) and 2-(2-bromo-4,5-difluorobenzyl)-5-methyl-2H-tetrazole;

LC-MS Rt=0.98 mins; [M+H]$^+$ 444.3; Method 2min-LowpHv03

Example 43

(E)-3-(5-Chloro-2-((5-methyl-2H-tetrazol-2-yl)methyl)phenyl)-1-(4-((5-methyl-1,3,4-oxadiazol-2-yl)methyl)piperidin-1-yl)prop-2-en-1-one

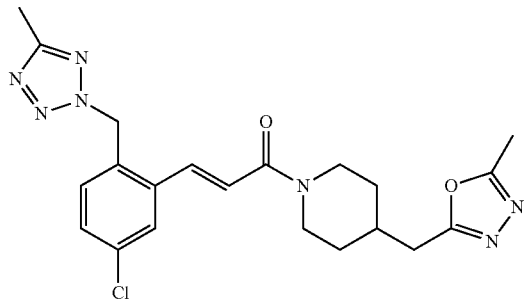 [SMILES: Cc1nnn(Cc2ccc(Cl)cc2/C=C/C(=O)N2CCC(Cc3nnc(C)o3)CC2)n1]

Step 1: 2-Bromo-1-(bromomethyl)-4-chlorobenzene

The title compound was prepared by a similar method to Intermediate AC, step 1 from 2-bromo-4-chloro-1-methylbenzene.

Step 2: 2-(2-Bromo-4-chlorobenzyl)-5-methyl-2H-tetrazole 2-(2-Bromo-4-chlorobenzyl)-5-methyl-2H-tetrazole was prepared by a similar method to Intermediate A, step 1 from 2-bromo-1-(bromomethyl)-4-chlorobenzene and 5-methyl-1H-tetrazole. Purification of the crude product by chromatography on silica eluting with 0-50% EtOAc in iso-hexane afforded the title compound.

Step 3: (E)-3-(5-Chloro-2-((5-methyl-2H-tetrazol-2-yl)methyl)phenyl)-1-(4-((5-methyl-1,3,4-oxadiazol-2-yl)methyl)piperidin-1-yl)prop-2-en-1-one The title compound was prepared by a similar method to Example 41, step 2 from 2-methyl-5-(piperidin-4-ylmethyl)-1,3,4-oxadiazole (Intermediate G) and 2-(2-bromo-4-chlorobenzyl)-5-methyl-2H-tetrazole;

LC-MS Rt=1.02 mins; [M+H]$^+$442.2; Method 2min-LowpHv03

Example 44

(E)-3-(2-Fluoro-6-((5-methyl-2H-tetrazol-2-yl)methyl)phenyl)-1-(4-((5-methyl-1,3,4-oxadiazol-2-yl)methyl)piperidin-1-yl)prop-2-en-1-one

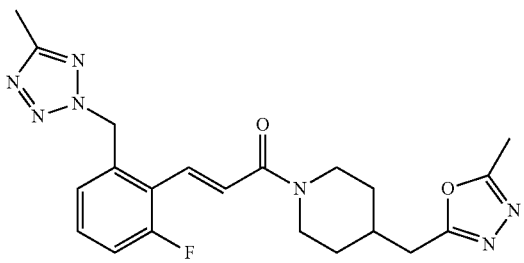

Step 1: 2-Bromo-1-(bromomethyl)-3-fluorobenzene

The title compound was prepared by a similar method to Intermediate AC, step 1 from 2-bromo-1-fluoro-3-methylbenzene.

Step 2: 2-(2-Bromo-3-fluorobenzyl)-5-methyl-2H-tetrazole, 2-(2-Bromo-3-fluorobenzyl)-5-methyl-2H-tetrazole was prepared by a similar method to Intermediate A, step 1 from 2-bromo-1-(bromomethyl)-3-fluorobenzene and 5-methyl-1H-tetrazole. Purification of the crude product by chromatography on silica eluting with 0-50% EtOAc in iso-hexane afforded the title compound.

Step 3: (E)-3-(2-Fluoro-6-((5-methyl-2H-tetrazol-2-yl)methyl)phenyl)-1-(4-((5-methyl-1,3,4-oxadiazol-2-yl)methyl)piperidin-1-yl)prop-2-en-1-one The title compound was prepared by a similar method to Example 41, step 2 from 2-methyl-5-(piperidin-4-ylmethyl)-1,3,4-oxadiazole (Intermediate G) and 2-(2-bromo-3-fluorobenzyl)-5-methyl-2H-tetrazole;

LC-MS Rt=0.94 mins; [M+H]$^+$ 426.3; Method 2min-LowpHv03

Example 45

(E)-3-(4-Chloro-2-((5-methyloxazol-2-yl)methyl)phenyl)-1-(4-((5-methyl-1,3,4-oxadiazol-2-yl)methyl)piperidin-1-yl)prop-2-en-1-one

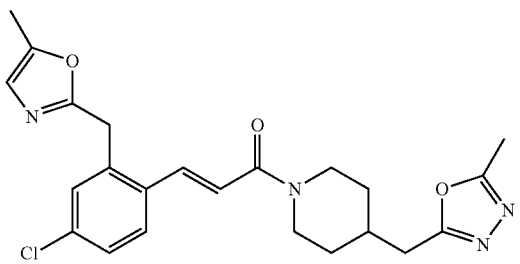 [SMILES: Cc1cnc(Cc2cc(Cl)ccc2/C=C/C(=O)N2CCC(Cc3nnc(C)o3)CC2)o1]

Step 1: 2-(2-Bromo-5-chlorophenyl)-N-(prop-2-yn-1-yl)acetamide

To a stirred solution of 2-(2-bromo-5-chlorophenyl)acetic acid (23 g, 92 mmol) in ethyl acetate (160 mL) under nitrogen was added DIPEA (40.3 mL, 230 mmol). The solution was cooled to 5° C. (ice-bath) and prop-2-yn-1-amine (7.09 mL, 111 mmol) was added. To this stirred suspension was added dropwise T3P® (50% in EtOAc) (81 mL, 138 mmol), maintaining the temperature below 20° C. during the addition. The reaction mixture was stirred at room temperature for 3 h and then quenched by addition of water, resulting in a thick off white precipitate. This was filtered off under vacuum, washing with water, followed by sat. NaHCO$_3$. The precipitate was suspended in diethyl ether (300 mL), filtered off under vacuum, washed with iso-hexane and then dried in a vacuum oven at 40° C. affording the title compound.

Step 2: 2-(2-Bromo-5-chlorobenzyl)-5-methyloxazole 2-(2-Bromo-5-chlorophenyl)-N-(prop-2-yn-1-yl)acetamide (22 g, 77 mmol) was dissolved in dioxane (256 mL). Triflic acid (6.82 mL, 77 mmol) was added and the reaction mixture was heated to 90° C. For 18 h. The reaction mixture was cooled and then neutralised with 2M NaOH. 50% of the dioxane was removed in vacuo and the aqueous emulsion was extracted with EtOAc (×2). The combined organic phases were washed with water (×2) and brine, dried over MgSO$_4$, filtered and the solvent was removed in vacuo. Purification of the crude product by chromatography on silica eluting with 10% EtOAc in iso-hexane afforded the title compound.

Step 3: (E)-3-(4-Chloro-2-((5-methyloxazol-2-yl)methyl)phenyl)-1-(4-((5-methyl-1,3,4-oxadiazol-2-yl)methyl)piperidin-1-yl)prop-2-en-1-one The title compound was prepared by a similar method to Example 41, step 2 from 2-methyl-5-(piperidin-4-ylmethyl)-1,3,4-oxadiazole (Intermediate G) and 2-(2-bromo-5-chlorobenzyl)-5-methyloxazole;

LC-MS Rt=1.18 mins; [M+H]$^+$ 441.2; Method 2min-LowpHv03

Example 46

(E)-3-(2-Chloro-6-((5-methyl-2H-tetrazol-2-yl)methyl)phenyl)-1-(4-((5-methyl-1,3,4-oxadiazol-2-yl)methyl)piperidin-1-yl)prop-2-en-1-one

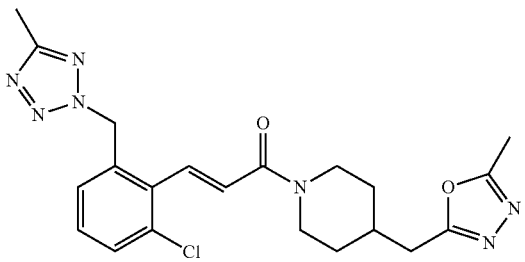 [SMILES: Cc1nnn(Cc2cccc(Cl)c2/C=C/C(=O)N2CCC(Cc3nnc(C)o3)CC2)n1]

Step 1: 2-Bromo-1-(bromomethyl)-3-chlorobenzene

The title compound was prepared by a similar method to Intermediate AC, step 1 from 2-bromo-1-chloro-3-methylbenzene.

Step 2: 2-(2-Bromo-3-chlorobenzyl)-5-methyl-2H-tetrazole, 2-(2-Bromo-3-chlorobenzyl)-5-methyl-2H-tetrazole was prepared by a similar method to Intermediate A, step 1 from 2-bromo-1-(bromomethyl)-3-chlorobenzene and 5-methyl-1H-tetrazole. Purification of the crude product by chromatography on silica eluting with 0-50% EtOAc in iso-hexane afforded the title compound.

Step 3: (E)-3-(2-Chloro-6-((5-methyl-2H-tetrazol-2-yl)methyl)phenyl)-1-(4-((5-methyl-1,3,4-oxadiazol-2-yl)methyl)piperidin-1-yl)prop-2-en-1-one The title compound was prepared by a similar method to Example 41, step 2 from 2-methyl-5-(piperidin-4-ylmethyl)-1,3,4-oxadiazole (Intermediate G) and 2-(2-bromo-3-chlorobenzyl)-5-methyl-2H-tetrazole;

LC-MS Rt=0.98 mins; [M+H]+ 442.3 Method 2min-LowpHv03

Example 47

4-Chloro-2-((5-methyl-2H-tetrazol-2-yl)methyl)benzyl 4-(5-methyl-1,3,4-oxadiazol-2-yl)piperidine-1-carboxylate

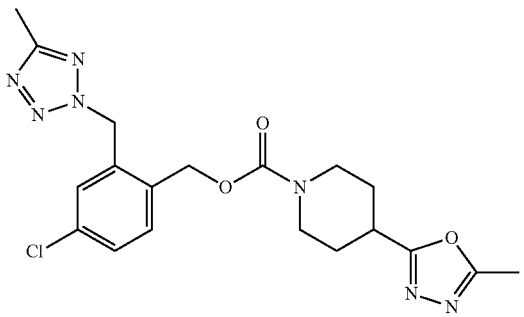 [SMILES: Cc1nnn(Cc2cc(Cl)ccc2COC(=O)N2CCC(c3nnc(C)o3)CC2)n1]

2-Methyl-5-(piperidin-4-yl)-1,3,4-oxadiazole (Intermediate BG) (77 mg, 0.463 mmol) was added to a solution of 4-chloro-2-((5-methyl-2H-tetrazol-2-yl)methyl)benzyl 1H-imidazole-1-carboxylate (Intermediate AG) (140 mg, 0.421 mmol) in DMF (2 mL). DIPEA (0.147 mL, 0.841 mmol) was added and the RM was stirred at 60° C. for 18 h. The reaction mixture was partitioned between EtOAc (20 mL) and water (20 mL). The organic phase was washed with water and brine, dried over MgSO4, filtered and the solvent was removed in vacuo. Purification of the crude product by chromatography on silica eluting with 0-100% (10% MeOH in EtOAc) in iso-hexane afforded the title compound;

LC-MS Rt=1.15 mins; [M+H]+432.2; Method 2min-LowpHv03

Example 48

4-Chloro-2-((5-methyl-2H-tetrazol-2-yl)methyl)benzyl 4-(5-methyloxazol-2-yl)piperidine-1-carboxylate

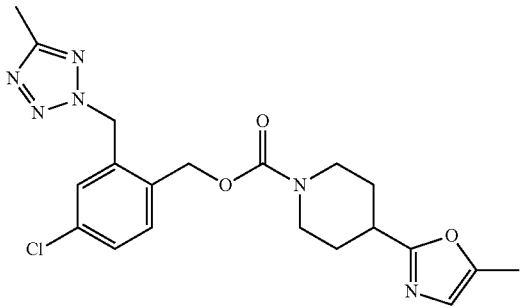 [SMILES: Cc1nnn(Cc2cc(Cl)ccc2COC(=O)N2CCC(c3ncc(C)o3)CC2)n1]

The title compound was prepared by a similar method to Example 47 from 5-methyl-2-(piperidin-4-yl)oxazole (Intermediate CI) and 4-chloro-2-((5-methyl-2H-tetrazol-2-yl)methyl)benzyl 1H-imidazole-1-carboxylate (Intermediate AG);

LC-MS Rt=1.29 mins; [M+H]+ 431.5; Method 2min-LowpHv03

Example 49.1

(E)-3-(4-Chloro-2-((5-methyl-2H-tetrazol-2-yl)methyl)phenyl)-1-(4-(pyrimidin-2-yl)piperazin-1-yl)prop-2-en-1-one

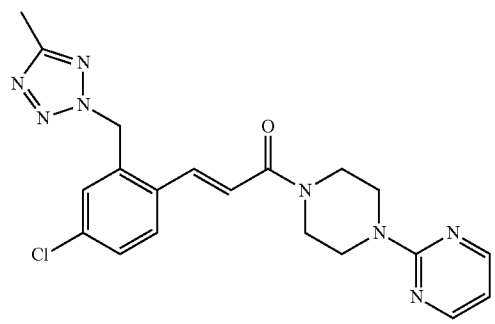 [SMILES: Cc1nnn(Cc2cc(Cl)ccc2/C=C/C(=O)N2CCN(c3ncccn3)CC2)n1]

(E)-3-(4-Chloro-2-((5-methyl-2H-tetrazol-2-yl)methyl)phenyl)acrylic acid (Intermediate A) (27.9 mg, 0.100 mmol) was dissolved in DMF (1 mL). This solution was added to HATU (46 mg, 0.120 mmol) and the reaction mixture was stirred at room temperature for 1 h. Triethylamine (1 mL) in DMF (1 mL) was added to a vial containing 2-(piperazin-1-yl)pyrimidine (16.4 mg, 0.100 mmol). The activated acid was added to the vial containing the amine and the reaction mixture was shaken at room temperature for 6 h. The crude sample was purified by reverse phase preparative HPLC to afford the title compound;

LC-MS Rt=1.23 mins; [M+H]+ 425.2; Method 2min-LowpHv03

Examples 49.2 to 49.20 and Examples 49.22 to 49.30 were prepared by a similar method to that of Example 49.1 from (E)-3-(4-Chloro-2-((5-methyl-2H-tetrazol-2-yl)methyl)phenyl)acrylic acid (Intermediate A) and the commercially available amine.

Example 49.2

(E)-3-(4-Chloro-2-((5-methyl-2H-tetrazol-2-yl)methyl)phenyl)-1-(3-(methylsulfonyl)azetidin-1-yl)prop-2-en-1-one

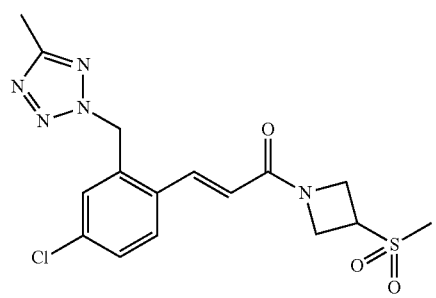 [SMILES: Cc1nnn(Cc2cc(Cl)ccc2/C=C/C(=O)N2CC(S(C)(=O)=O)C2)n1]

LC-MS Rt=1.21 mins; [M+H]+ 396.1; Method 2min-LowpHv03

Example 49.3

(E)-1-(1-(3-(4-Chloro-2-((5-methyl-2H-tetrazol-2-yl)methyl)phenyl)acryloyl)piperidin-4-yl)imidazolidin-2-one

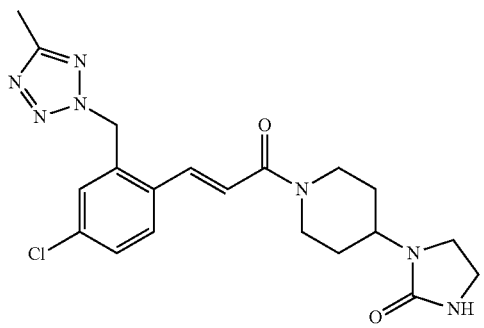 [SMILES: Cc1nnn(Cc2cc(Cl)ccc2/C=C/C(=O)N2CCC(N3CCNC3=O)CC2)n1]

LC-MS Rt=1.22 mins; [M+H]$^+$430.2; Method 2min-LowpHv03

Example 49.4

(E)-tert-Butyl ((1-(3-(4-chloro-2-((5-methyl-2H-tetrazol-2-yl)methyl)phenyl)acryloyl)azetidin-3-yl)methyl)carbamate

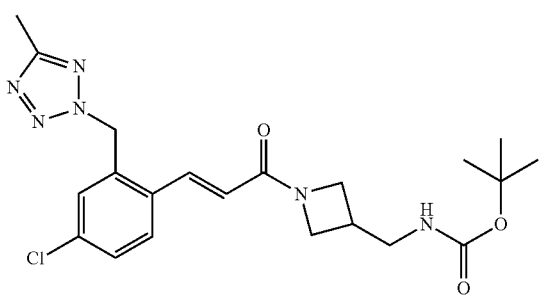 [SMILES: Cc1nnn(Cc2cc(Cl)ccc2/C=C/C(=O)N2CC(CNC(=O)OC(C)(C)C)C2)n1]

LC-MS Rt=1.12 mins; [M+H]$^+$ 391.4 (loss of t-butyl group in MS); Method 2minLowpHv03

Example 49.5

(E)-3-(4-Chloro-2-((5-methyl-2H-tetrazol-2-yl)methyl)phenyl)-1-(3-fluoropyrrolidin-1-yl)prop-2-en-1-one

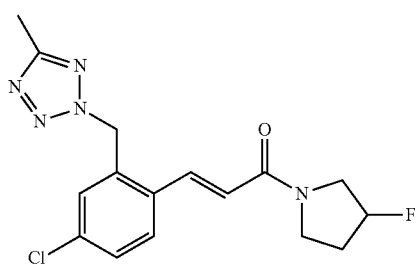 [SMILES: Cc1nnn(Cc2cc(Cl)ccc2/C=C/C(=O)N2CCC(F)C2)n1]

LC-MS Rt=1.01 mins; [M+H]$^+$ 350.1; Method 2min-LowpHv03

Example 49.6

(E)-3-(4-Chloro-2-((5-methyl-2H-tetrazol-2-yl)methyl)phenyl)-1-(4-(2-hydroxyethyl)piperidin-1-yl)prop-2-en-1-one

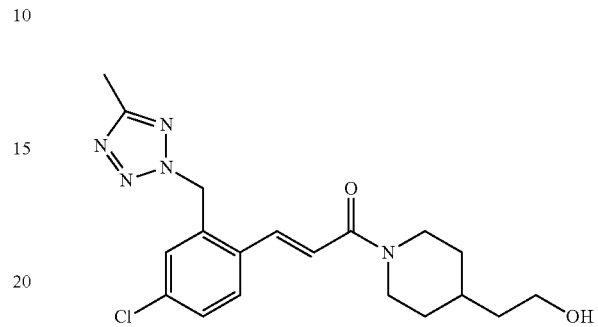

LC-MS Rt=1.20 mins; [M+H]$^+$390.2; Method 2min-LowpHv03

Example 49.7

(E)-3-(4-Chloro-2-((5-methyl-2H-tetrazol-2-yl)methyl)phenyl)-1-(3-hydroxypiperidin-1-yl)prop-2-en-1-one

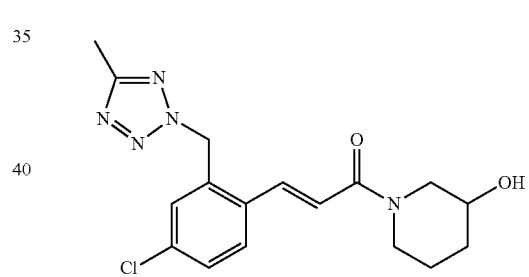

LC-MS Rt=1.17 mins; [M+H]$^+$ 362.1; Method 2min-LowpHv03

Example 49.8

(E)-1-(3-(4-Chloro-2-((5-methyl-2H-tetrazol-2-yl)methyl)phenyl)acryloyl)piperidine-3-carboxamide

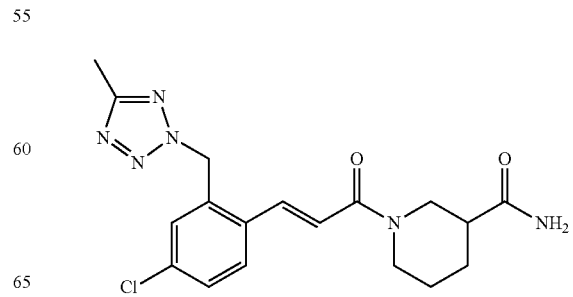

Example 49.9

(E)-ethyl 1-(3-(4-Chloro-2-((5-methyl-2H-tetrazol-2-yl)methyl)phenyl)acryloyl)piperidine-4-carboxylate

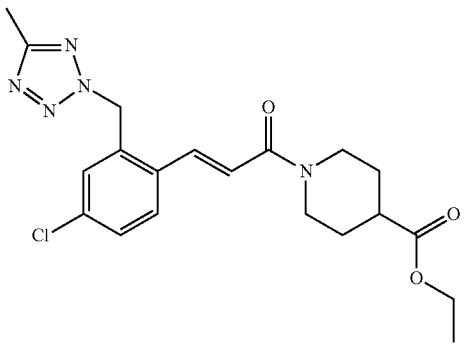 [SMILES: CCOC(=O)C1CCN(C(=O)/C=C/c2ccc(Cl)cc2Cn2nnc(C)n2)CC1]

LC-MS Rt=1.31 mins; [M+H]⁺418.2; Method 2min-LowpHv03

Example 49.10

(E)-3-(4-Chloro-2-((5-methyl-2H-tetrazol-2-yl)methyl)phenyl)-1-(4-(2-oxo-2-(piperidin-1-yl)ethoxy)piperidin-1-yl)prop-2-en-1-one

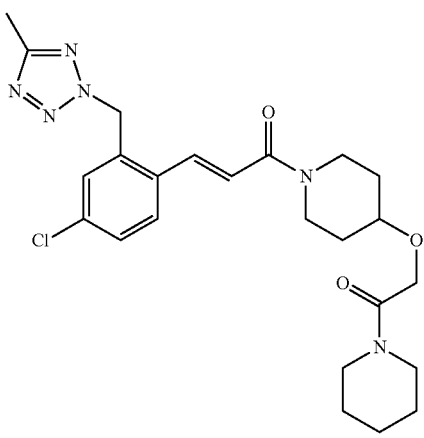 [SMILES: Cc1nnn(Cc2cc(Cl)ccc2/C=C/C(=O)N2CCC(OCC(=O)N3CCCCC3)CC2)n1]

LC-MS Rt=1.09 mins; [M+H]⁺ 487.3; Method 2min-LowpHv03

LC-MS Rt=1.14 mins; [M+H]⁺ 389.1; Method 2min-LowpHv03

Example 49.11

(E)-1-(4-((1H-Pyrazol-1-yl)methyl)piperidin-1-yl)-3-(4-chloro-2-((5-methyl-2H-tetrazol-2-yl)methyl)phenyl)prop-2-en-1-one

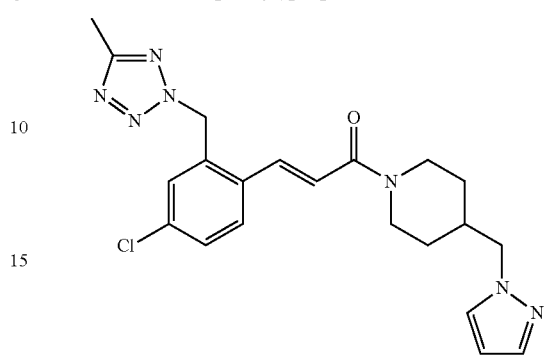

LC-MS Rt=1.06 mins; [M+H]⁺426.2; Method 2min-LowpHv03

Example 49.12

(E)-3-(4-Chloro-2-((5-methyl-2H-tetrazol-2-yl)methyl)phenyl)-1-(4-(trifluoromethyl)piperidin-1-yl)prop-2-en-1-one

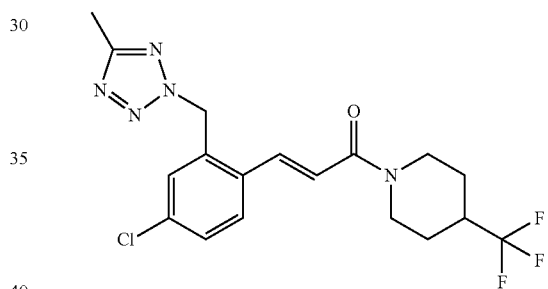

LC-MS Rt=1.19 mins; [M+H]⁺414.5; Method 2min-LowpHv03

Example 49.13

(E)-2-((1-(3-(4-Chloro-2-((5-methyl-2H-tetrazol-2-yl)methyl)phenyl)acryloyl)piperidin-4-yl)oxy)-N,N-dimethyl benzamide

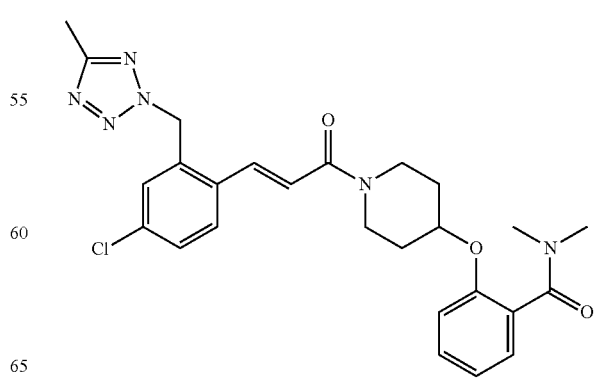

LC-MS Rt=1.11 mins; [M+H]⁺509.2; Method 2min-LowpHv03

Example 49.14

(R,E)-3-(4-Chloro-2-((5-methyl-2H-tetrazol-2-yl)methyl)phenyl)-1-(2-methylpiperidin-1-yl)prop-2-en-1-one

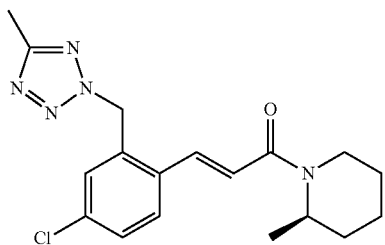 [SMILES: Cc1nnn(Cc2cc(Cl)ccc2/C=C/C(=O)N2CCCC[C@H]2C)n1]

LC-MS Rt=1.18 mins; [M+H]⁺360.5; Method 2min-LowpHv03

Example 49.15

(E)-1-(3-Acetylpiperidin-1-yl)-3-(4-chloro-2-((5-methyl-2H-tetrazol-2-yl)methyl)phenyl)prop-2-en-1-one

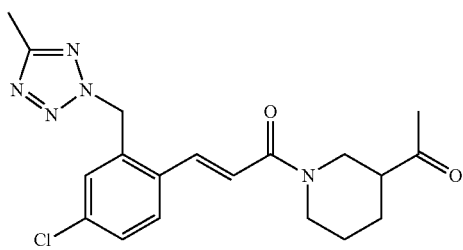 [SMILES: CC(=O)C1CCCN(C(=O)/C=C/c2ccc(Cl)cc2Cn2nnc(C)n2)C1]

LC-MS Rt=1.04 mins; [M+H]⁺388.2; Method 2min-LowpHv03

Example 49.16

(E)-3-(4-Chloro-2-((5-methyl-2H-tetrazol-2-yl)methyl)phenyl)-1-(3-(4-methyl-4H-1,2,4-triazol-3-yl)piperidin-1-yl)prop-2-en-1-one

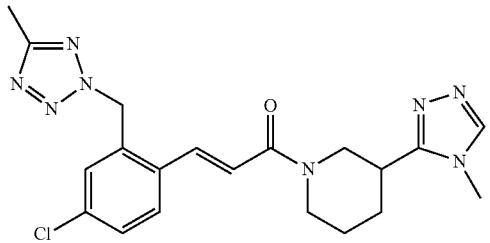 [SMILES: Cc1nnn(Cc2cc(Cl)ccc2/C=C/C(=O)N2CCCC(c3nncn3C)C2)n1]

LC-MS Rt=0.85 mins; [M+H]⁺ 427.2 Method 2min-LowpHv03

Example 49.17

(E)-3-(4-Chloro-2-((5-methyl-2H-tetrazol-2-yl)methyl)phenyl)-1-(3-(methoxymethyl)piperidin-1-yl)prop-2-en-1-one

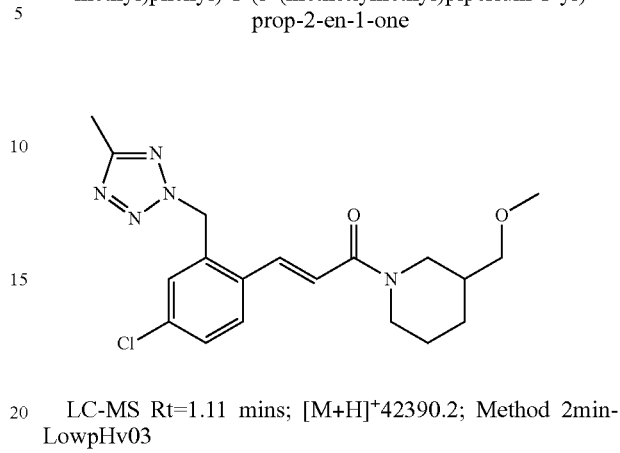

LC-MS Rt=1.11 mins; [M+H]⁺42390.2; Method 2min-LowpHv03

Example 49.18

(S,E)-N-(1-(3-(4-Chloro-2-((5-methyl-2H-tetrazol-2-yl)methyl)phenyl)acryloyl)pyrrolidin-3-yl)-2,2,2-trifluoroacetamide

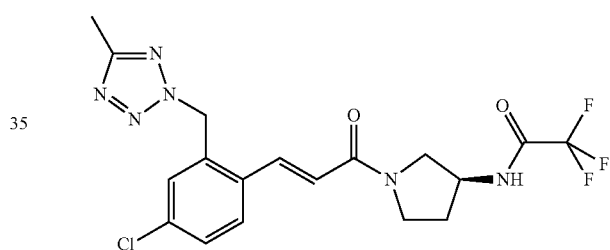

LC-MS Rt=1.05 mins; [M+H]⁺443.2; Method 2min-LowpHv03

Example 49.19

(E)-2-((1-(3-(4-Chloro-2-((5-methyl-2H-tetrazol-2-yl)methyl)phenyl)acryloyl)piperidin-4-yl)oxy)-N-methylacetamide

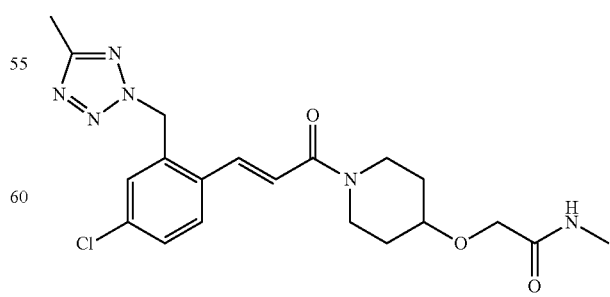

LC-MS Rt=0.96 mins; [M+H]⁺ 433.2; Method 2min-LowpHv03

Example 49.20

(E)-3-(4-Chloro-2-((5-methyl-2H-tetrazol-2-yl)methyl)phenyl)-1-(4-(furan-2-carbonyl)piperazin-1-yl)prop-2-en-1-one

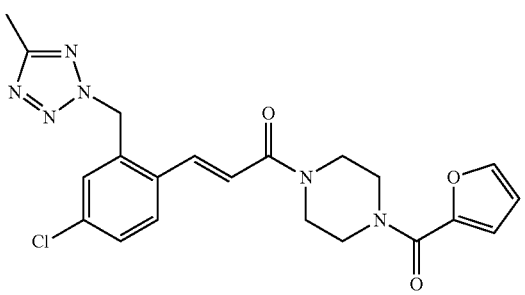 [SMILES: Cc1nnn(Cc2cc(Cl)ccc2/C=C/C(=O)N2CCN(C(=O)c3ccco3)CC2)n1]

LC-MS Rt=1.02 mins; [M+H]+441.2; Method 2min-LowpHv03

Example 49.21

(R,E)-3-(4-Chloro-2-((5-methyl-2H-tetrazol-2-yl)methyl)phenyl)-1-(2-methyl-4-(1-methyl-1H-pyrazol-3-yl)piperazin-1-yl)prop-2-en-1-one

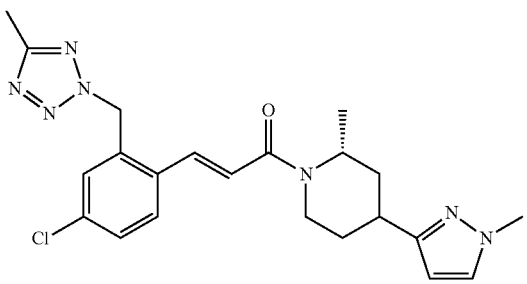

(E)-3-(4-Chloro-2-((5-methyl-2H-tetrazol-2-yl)methyl)phenyl)acrylic acid (Intermediate A) (49.5 mg, 0.178 mmol) and DIPEA (0.155 mL, 0.888 mmol) were placed in a flask with DMF (3 mL). HATU (81 mg, 0.213 mmol) was added and the reaction mixture was stirred at room temperature for 5 minutes. (R)-3-methyl-1-(1-methyl-1H-pyrazol-3-yl)piperazine (Intermediate H) (32 mg, 0.178 mmol) was then added. The reaction mixture was stirred at room temperature for 2 h and then partitioned between EtOAc (30 mL) and water (30 mL). The organic phase was washed with water and brine, dried over MgSO$_4$, filtered and the solvent was removed in vacuo. Purification of the crude product by chromatography on silica eluting with 0-100% EtOAc in iso-hexane afforded the title compound;

LC-MS Rt=1.17 mins; [M+H]+441.2; Method 2min-LowpHv03

Example 49.22

(E)-2-((1-(3-(4-Chloro-2-((5-methyl-2H-tetrazol-2-yl)methyl)phenyl)acryloyl)piperidin-3-yl)oxy)-N-ethylacetamide

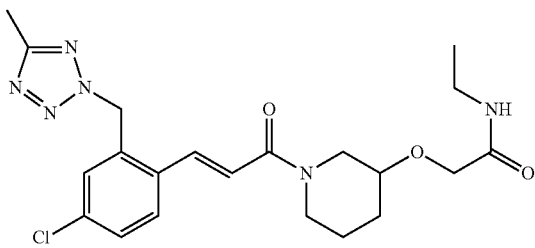 [SMILES: CCNC(=O)COC1CCCN(C(=O)/C=C/c2ccc(Cl)cc2Cn2nnc(C)n2)C1]

LC-MS Rt=1.02 mins; [M+H]+447.2; Method 2min-LowpHv03

Example 49.23

(E)-Methyl 4-(3-(4-Chloro-2-((5-methyl-2H-tetrazol-2-yl)methyl)phenyl)acryloyl)morpholine-3-carboxylate

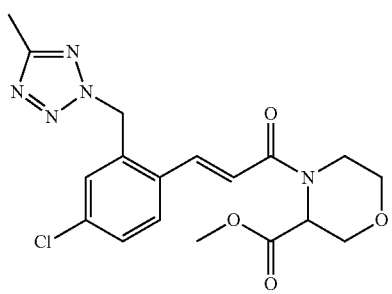 [SMILES: COC(=O)C1COCCN1C(=O)/C=C/c1ccc(Cl)cc1Cn1nnc(C)n1]

LC-MS Rt=1.02 mins; [M+H]+406.1; Method 2min-LowpHv03

Example 49.24

(E)-3-(4-Chloro-2-((5-methyl-2H-tetrazol-2-yl)methyl)phenyl)-1-(4-(methoxymethyl)piperidin-1-yl)prop-2-en-1-one

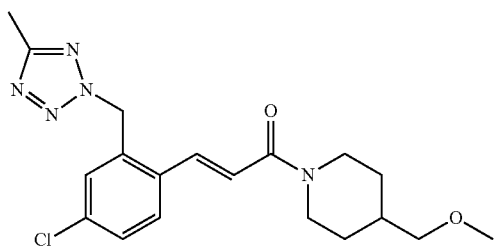

LC-MS Rt=1.11 mins; [M+H]+ 390.5; Method 2min-LowpHv03

Example 49.25

(E)-3-(4-Chloro-2-((5-methyl-2H-tetrazol-2-yl)methyl)phenyl)-1-(4-(pyrimidin-2-yl)-1,4-diazepan-1-yl)prop-2-en-1-one

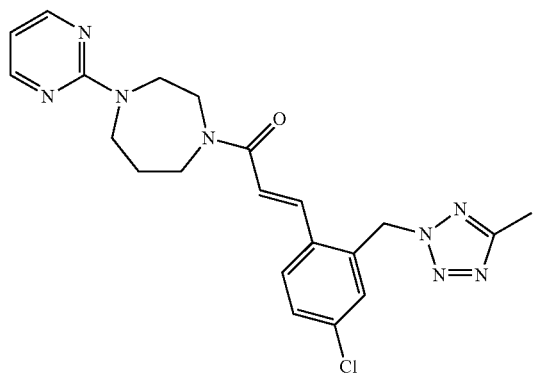 [SMILES: Cc1nnn(Cc2cc(Cl)ccc2/C=C/C(=O)N2CCCN(c3ncccn3)CC2)n1]

LC-MS Rt=0.95 mins; [M+H]$^+$ 439.2; Method 2min-LowpHv03

Example 49.26

(E)-1-(4-Acetyl-1,4-diazepan-1-yl)-3-(4-chloro-2-((5-methyl-2H-tetrazol-2-yl)methyl)phenyl)prop-2-en-1-one

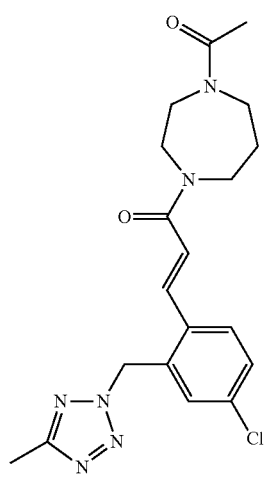 [SMILES: CC(=O)N1CCCN(C(=O)/C=C/c2ccc(Cl)cc2Cn2nnc(C)n2)CC1]

LC-MS Rt=0.94 mins; [M+H]$^+$ 403.2; Method 2min-LowpHv03

Example 49.27

(E)-Methyl 3-(3-(4-chloro-2-((5-methyl-2H-tetrazol-2-yl)methyl)phenyl)acryloyl)thiazolidine-2-carboxylate

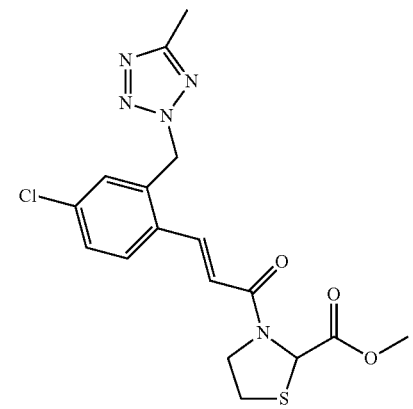 [SMILES: COC(=O)C1SCCN1C(=O)/C=C/c1ccc(Cl)cc1Cn1nnc(C)n1]

LC-MS Rt=1.09 mins; [M+H]$^+$408.1; Method 2min-LowpHv03

Example 49.28

(E)-2-(4-(3-(4-Chloro-2-((5-methyl-2H-tetrazol-2-yl)methyl)phenyl)acryloyl)piperazin-1-yl)nicotinonitrile LC-MS Rt=1.14 mins; [M+H]$^+$449.1; Method 2min-LowpHv03

Example 49.29

(E)-3-(4-Chloro-2-((5-methyl-2H-tetrazol-2-yl)methyl)phenyl)-1-(4-(3-(pyrrolidine-1-carbonyl)pyridin-2-yl)piperazin-1-yl)prop-2-en-1-one

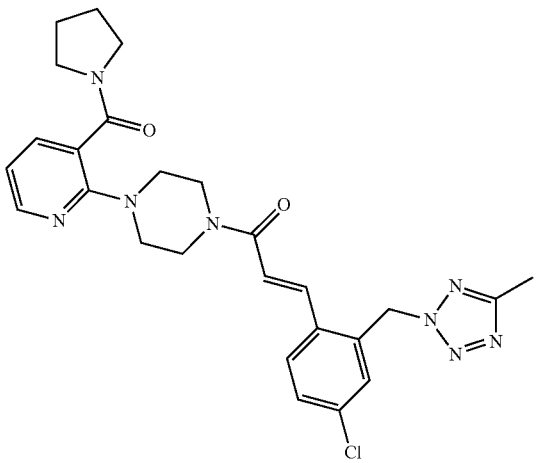 [SMILES: Cc1nnn(Cc2cc(Cl)ccc2/C=C/C(=O)N2CCN(c3ncccc3C(=O)N3CCCC3)CC2)n1]

LC-MS Rt=0.92 mins; [M+H]$^+$521.3; Method 2min-LowpHv03

Example 49.30

(E)-2-((1-(3-(4-Chloro-2-((5-methyl-2H-tetrazol-2-yl)methyl)phenyl)acryloyl)piperidin-4-yl)oxy)-N-propylacetamide

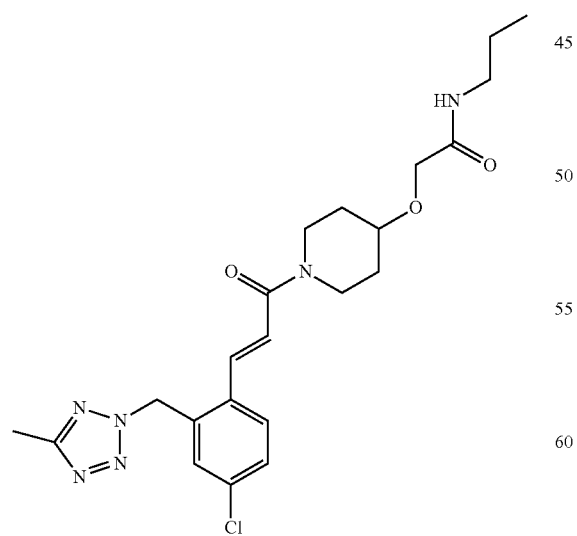

LC-MS Rt=1.07 mins; [M+H]$^+$461.3; Method 2min-LowpHv03

Example 50a (E)-3-(4-chloro-2-((5-methyl-2H-tetrazol-2-yl)methyl)phenyl)-1-((2S, 4R or 4S)-4-hydroxy-2-methylpiperidin-1-yl)prop-2-en-1-one and

Example 50b (E)-3-(4-chloro-2-((5-methyl-2H-tetrazol-2-yl)methyl)phenyl)-1-((2R, 4R or 4S)-4-hydroxy-2-methylpiperidin-1-yl)prop-2-en-1-one

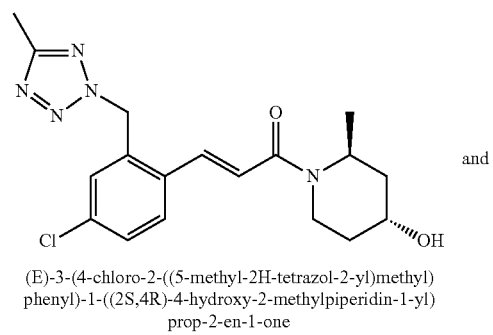 and (E)-3-(4-chloro-2-((5-methyl-2H-tetrazol-2-yl)methyl)phenyl)-1-((2S,4R)-4-hydroxy-2-methylpiperidin-1-yl)prop-2-en-1-one

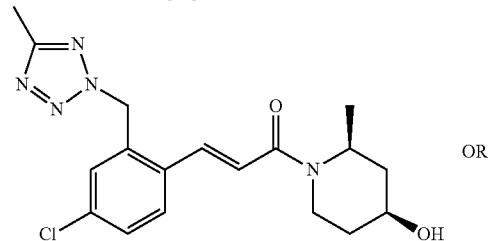 OR (E)-3-(4-chloro-2-((5-methyl-2H-tetrazol-2-yl)methyl)phenyl)-1-((2S,4R)-4-hydroxy-2-methylpiperidin-1-yl)prop-2-en-1-one

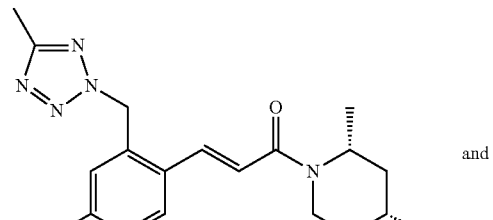 and (E)-3-(4-chloro-2-((5-methyl-2H-tetrazol-2-yl)methyl)phenyl)-1-((2S,4R)-4-hydroxy-2-methylpiperidin-1-yl)prop-2-en-1-one

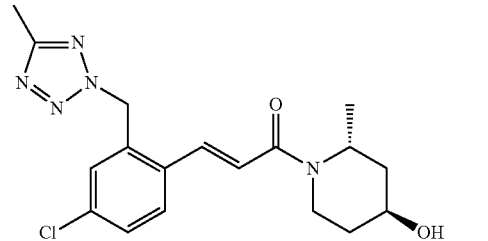

(E)-3-(4-chloro-2-((5-methyl-2H-tetrazol-2-yl)methyl)phenyl)-1-((2S,4R)-4-hydroxy-2-methylpiperidin-1-yl)prop-2-en-1-one Step 1: ((R or S),E)-1-(3-(4-Chloro-2-((5-methyl-2H-tetrazol-2-yl)methyl)phenyl)acryloyl)-2-methylpiperidin-4-one, ((R or S), E)-1-(3-(4-chloro-2-((5-methyl-2H-tetrazol-2-yl)methyl)phenyl)acryloyl)-2-methylpiperidin-4-one rac-(E)-1-(3-(4-chloro-2-((5-methyl-2H-tetrazol-2-yl)methyl)phenyl)acryloyl)-2-methylpiperidin-4-one was prepared analogously to Example 49.21 from (E)-3-(4-chloro-2-((5-methyl-2H-tetrazol-2-yl)methyl)phenyl)acrylic acid (Intermediate A) and 2 methylpiperidin-4-one. The racemate was separated by SFC chiral chromatography (CHIRALPAK AD-H 250×10 mm 5 um, 40% methanol in $CO_2$) to afford the individual enantiomers:

First eluted peak: ((R or S),E)-1-(3-(4-Chloro-2-((5-methyl-2H-tetrazol-2-yl)methyl)phenyl)acryloyl)-2-methylpiperidin-4-one:

SFC Rt=4.29 mins; (CHIRALPAK AD-H 250×10 mm 5 um, 40% methanol in $CO_2$)

LC-MS Rt=1.02 mins; $[M+H]^+$ 374.2; Method 2min-LowpHv03

Second eluted peak: ((R or S),E)-1-(3-(4-Chloro-2-((5-methyl-2H-tetrazol-2-yl)methyl)phenyl)acryloyl)-2-methylpiperidin-4-one:

SFC Rt=5.62 mins; (CHIRALPAK AD-H 250×10 mm 5 um, 40% methanol in $CO_2$)

LC-MS Rt=1.02 mins; $[M+H]^+$ 374.1; Method 2min-LowpHv03

Step 2: (E)-3-(4-Chloro-2-((5-methyl-2H-tetrazol-2-yl)methyl)phenyl)-1-((2S, 4R or 4S)-4-hydroxy-2-methylpiperidin-1-yl)prop-2-en-1-one and Example 50b: (E)-3-(4-chloro-2-((5-methyl-2H-tetrazol-2-yl)methyl)phenyl)-1-((2R, 4R or 4S)-4-hydroxy-2-methylpiperidin-1-yl)prop-2-en-1-one ((R or S),E)-1-(3-(4-Chloro-2-((5-methyl-2H-tetrazol-2-yl)methyl)phenyl)acryloyl)-2-methylpiperidin-4-one (second eluted peak from step 1) (199 mg, 0.532 mmol) was placed in a flask with methanol (10 mL) and the reaction mixture was cooled on an ice-bath. Sodium borohydride (40.3 mg, 1.065 mmol) was added and the reaction mixture was allowed to warm to room temperature. The solvent was removed in vacuo and the resulting residue partitioned between EtOAc (40 mL) and saturated sodium bicarbonate solution (40 mL). The organic phase was washed with water and brine, dried over $MgSO_4$, filtered and the solvent was removed in vacuo. The diastereomeric mixture was separated by SFC chiral chromatography (CHIRALPAK ID 250×10 mm 5 um, 30% isopropanol in $CO_2$) to afford the following diastereomers of the title compounds:

Peak 3:

SFC Rt=11.66 mins; (CHIRALPAK ID 250×10 mm 5 um, 30% isopropanol in $CO_2$)

LC-MS Rt=1.06 mins; $[M+H]^+$ 376.3; Method 2min-LowpHv03

Peak 4:

SFC Rt=16.47 mins; (CHIRALPAK ID 250×10 mm 5 um, 30% isopropanol in $CO_2$)

LC-MS Rt=1.07 mins; $[M+H]^+$ 376.3; Method 2min-LowpHv03

Example 51

(E)-1-(3-(2-((5-Methyl-2H-tetrazol-2-yl)methyl)-4-(trifluoromethyl)phenyl)acryloyl)piperidine-4-carboxylic acid

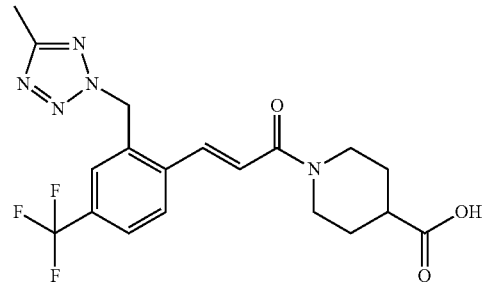 [SMILES: Cc1nnn(Cc2cc(C(F)(F)F)ccc2/C=C/C(=O)N2CCC(C(=O)O)CC2)n1]

Step 1: (E)-Methyl 1-(3-(2-((5-methyl-2H-tetrazol-2-yl)methyl)-4-(trifluoromethyl)phenyl)acryloyl)piperidine-4-carboxylate T3P® 50% in ethyl acetate (0.679 mL, 1.153 mmol) was added to a solution of (E)-3-(2-((5-methyl-2H-tetrazol-2-yl)methyl)-4-(trifluoromethyl)phenyl)acrylic acid (Intermediate AB) (300 mg, 0.961 mmol), methyl piperidine-4-carboxylate (138 mg, 0.961 mmol) and TEA (0.536 mL, 3.84 mmol) in DCM (3 mL) and the resulting mixture stirred for 1 h The reaction mixture was poured into saturated sodium bicarbonate solution (1 mL). The aqueous layer was extracted with DCM (3×5 mL). The organic solutions were combined, washed with brine (5 mL), dried over sodium sulphate, filtered and concentrated in vacuo. Purification was by silica gel column chromatography eluting with a gradient of iso-hexane to ethyl acetate. The product fractions were combined and evaporated in vacuo to give the title compound as a clear oil;

LC MS Rt 1.27 min; $[M-100+H]^+$ 438.3, Method 2min-LowpHv03

Step 2: (E)-1-(3-(2-((5-Methyl-2H-tetrazol-2-yl)methyl)-4-(trifluoromethyl)phenyl)acryloyl)piperidine-4-carboxylic acid A solution of lithium hydroxide (61.3 mg, 2.56 mmol) in water (2.00 mL) was added to a solution of (E)-Methyl 1-(3-(2-((5-methyl-2H-tetrazol-2-yl)methyl)-4-(trifluoromethyl)phenyl)acryloyl)piperidine-4-carboxylate (step 1) (280 mg, 0.640 mmol) in THF (2 mL) and the resulting mixture stirred overnight at room temperature. The reaction was concentrated to 2 mL and the pH adjusted to 1 with 2M hydrochloric acid. The resulting mixture was extracted with ethyl acetate (3×20 mL). The combined organic solutions were washed with brine (20 mL), dried over sodium sulphate, filtered and concentrated in vacuo to give the title compound as a white foam;

LC MS Rt 1.12 min; $[M+H]^+$ 424.3, Method 2min-LowpHv03

$^1$H NMR (400 MHz, DMSO-d6) δ 12.29 (1H, s), 8.08 (1H, d), 7.85 (1H, s), 7.81 (1H, d), 7.41 (1H, d), 7.26 (1H, d), 6.11 (2H, d), 4.28 (1H, m), 4.09 (1H, m), 3.18 (1H, m), 2.86 (1H, m), 2.55 (1H, m), 2.14 (3H, s), 1.87 (2H, m), 1.46 (2H, m).

Example 52

(E)-3-(4-(Difluoromethyl)-2-((5-methyl-2H-tetrazol-2-yl)methy)phenyl)-1-(4-(5-methyl-1,3,4-oxadiazol-2-yl)piperidin-1-yl)prop-2-en-1-one

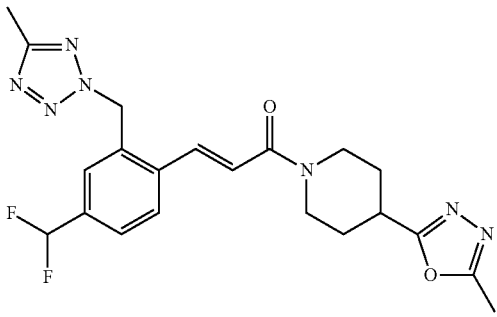

T3P® 50% in ethyl acetate (240 μl, 0.408 mmol) was added to a solution of (E)-3-(4-(difluoromethyl)-2-((5-methyl-2H-tetrazol-2-yl)methyl)phenyl)acrylic acid (Intermediate AH) (100 mg, 0.340 mmol), 2-methyl-5-(piperidin-4-yl)-1,3,4-oxadiazole (Intermediate BG) (96 mg, 0.340 mmol) and TEA (189 μl, 1.359 mmol) in DCM (1 mL) and the resulting mixture stirred for 18 h at room temperature. The reaction mixture was diluted with saturated sodium bicarbonate solution (5 mL) The aqueous solution was extracted with ethyl acetate (3×10 mL). The combined organic solutions were washed with, brine (10 mL), dried over sodium sulphate, filtered and concentrated in vacuo. Purification was by silica gel column chromatography eluting with a gradient of iso-hexane to 10% MeOH in ethyl acetate. The product fractions were combined and evaporated in vacuo to give a clear gum. The gum was triturated with MTBE to give the title compound as a white solid;

LC MS Rt 1.05 min; [M+H]$^+$ 444.3, Method 2min-LowpHv03

$^1$H NMR (400 MHz, DMSO-d6) δ 8.01 (1H, m), 7.80 (1H, d), 7.68-7.57 (2H, m), 7.25 (1H, d), 7.09 (1H, t), 6.07 (2H, s), 4.35 (1H, m), 4.19 (1H, m), 3.28 (2H, m), 3.00 (1H, m), 2.47 (3H, s), 2.41 (3H, s), 2.05 (2H, m), 1.64 (2H, m).

Example 53

(E)-1-(4-((1-Methyl-1H-pyrazol-4-yl)methyl)piperazin-1-yl)-3-(2-((5-methyl-2H-tetrazol-2-yl)methyl)-4-(trifluoromethyl)phenyl)prop-2-en-1-one

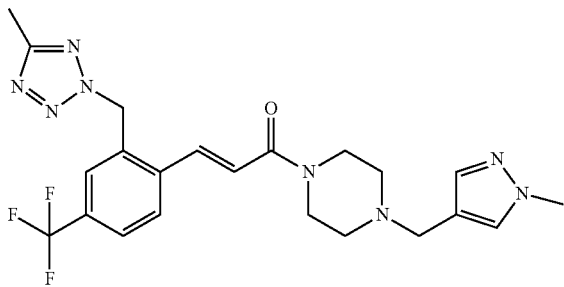

Step 1: (E)-tert-Butyl 4-(3-(2-((5-methyl-2H-tetrazol-2-yl)methyl)-4-(trifluoromethyl)phenyl)acryloyl)piperazine-1-carboxylate T3P® 50% in ethyl acetate (2.94 mL, 5.00 mmol) was added to a solution of (E)-3-(2-((5-methyl-2H-tetrazol-2-yl)methyl)-4-(trifluoromethyl)phenyl)acrylic acid (Intermediate AB) (1.3 g, 4.16 mmol), tert-butyl piperazine-1-carboxylate (0.775 g, 4.16 mmol) and TEA (2.321 mL, 16.65 mmol) in DCM (10 mL) and the resulting mixture stirred at room temperature for 5 h then stood at room temperature for 4 days. The reaction mixture was poured into saturated sodium bicarbonate (100 mL) The aqueous layer was extracted with ethyl acetate (3×100 mL). The organic solutions were combined washed with water (50 mL), brine (50 mL), dried over sodium sulphate, filtered and concentrated in vacuo. Purification was by silica gel column chromatography eluting with a gradient of iso-hexane to ethyl acetate in iso-hexane. The product fractions were combined and concentrated in vacuo to give the title compound as a white solid;

LC MS Rt 1.36 min; [M+H]$^+$ 481.7, Method 2min-LowpHv03

Step 2: (E)-3-(2-((5-Methyl-2H-tetrazol-2-yl)methyl)-4-(trifluoromethyl)phenyl)-1-(piperazin-1-yl)prop-2-en-1-one TFA (20 mL) was added dropwise to a solution of (E)-tert-Butyl 4-(3-(2-((5-methyl-2H-tetrazol-2-yl)methyl)-4-(trifluoromethyl)phenyl)acryloyl)piperazine-1-carboxylate (step 1) (1.82 g, 3.79 mmol) in DCM (20 mL) and the resulting mixture stirred at room temperature for 2 h.

Toluene (50 mL) was added and the reaction concentrated in vacuo. The residue was triturated with ether to give the title compound as a white solid;

LC MS Rt 0.73 min; [M+H]$^+$ 381.8, Method 2min-LowpHv03

Step 3: (E)-1-(4-((1-Methyl-1H-pyrazol-4-yl)methyl)piperazin-1-yl)-3-(2-((5-methyl-2H-tetrazol-2-yl)methyl)-4-(trifluoromethyl)phenyl)prop-2-en-1-one 2-Picoline borane complex (34.6 mg, 0.324 mmol) was added to a solution of 1-methyl-1H-pyrazole-4-carbaldehyde (33.4 mg, 0.303 mmol), (E)-3-(2-((5-Methyl-2H-tetrazol-2-yl)methyl)-4-(trifluoromethyl)phenyl)-1-(piperazin-1-yl)prop-2-en-1-one (step 2) (100 mg, 0.202 mmol) and Acetic Acid (0.1 mL) in MeOH (1 mL) and the resulting mixture was stirred at room temperature for 18 h. The reaction was concentrated in vacuo. Purification was carried out by silica gel column chromatography eluting with a gradient of iso-hexane to 10% MeOH in ethyl acetate. The product fractions were combined and evaporated in vacuo to give a colourless gum. The gum was dissolved in ether (5 mL) and 1M HCl in ether solution (2 mL) was added. The resulting suspension was concentrated in vacuo to give the title compound as a hydrochloride salt as a yellow solid.

LC MS Rt 0.76 min; [M+H]$^+$ 475.4 Method 2min-LowpHv03

1H NMR (400 MHz, 403K, DMSO-d6) δ 7.95 (1H, d), 7.85 (1H, s), 7.81-7.74 (m, 3H), 7.59 (1H, s), 7.09 (1H, d), 6.04 (2H, s), 4.18 (2H, s), 4.12-3.77 (5H, m), 3.42-2.70 (6H, m), 2.43 (3H, s). (1 exchangeable proton not observed at this temperature)

Example 54

(E)-1-(4-(5-Methyl-1,3,4-oxadiazol-2-yl)piperidin-1-yl)-3-(2-((5-methyl-2H-tetrazol-2-yl)methyl)-4-(trifluoromethoxy)phenyl)prop-2-en-1-one

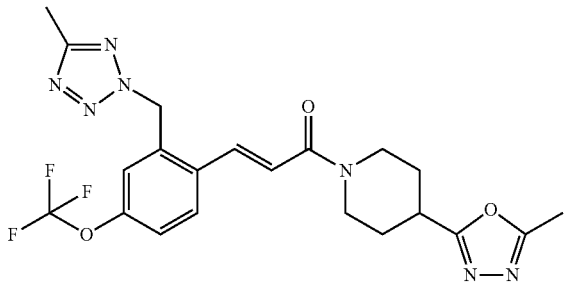 [SMILES: Cc1nnn(Cc2cc(OC(F)(F)F)ccc2/C=C/C(=O)N2CCC(c3nnc(C)o3)CC2)n1]

T3P® 50% in ethyl acetate (0.215 mL, 0.366 mmol) was added to a solution of (E)-3-(2-((5-methyl-2H-tetrazol-2-yl)methyl)-4-(trifluoromethoxy)phenyl)acrylic acid (Intermediate AC)(100 mg, 0.305 mmol), 2-methyl-5-(piperidin-4-yl)-1,3,4-oxadiazole (Intermediate BG)(50.9 mg, 0.305 mmol) and TEA (0.170 mL, 1.219 mmol) in DCM (1 mL) and the resulting mixture stirred at room temperature for 2 h. The reaction mixture was poured into saturated sodium bicarbonate solution (1 mL). The aqueous layer was extracted with ethyl acetate (3×5 mL). The organic solutions were combined washed with brine (5 mL), dried over sodium sulphate, filtered and concentrated in vacuo. Purification was carried out by silica gel column chromatography eluting with a gradient of iso-hexane to 10% MeOH in ethyl acetate. The product fractions were combined and evaporated in vacuo to give the title compound as a white solid;

LC MS Rt 1.20 min; [M+H]$^+$ 478.3, Method 2min-LowpHv03

$^1$H NMR (400 MHz, DMSO-d6) δ 8.00 (1H, d), 7.74 (1H, d), 7.48-7.41 (2H, m), 7.20 (1H, s), 6.07 (2H, s), 4.35 (1H, m), 4.18 (1H, m), 3.27 (2H, m), 2.99 (1H, m), 2.47 (3H, s), 2.42 (3H, s), 2.04 (2H, m), 1.63 (2H, m)

Example 55

(E)-3-(4-(Difluoromethyl)-2-((5-methyl-2H-tetrazol-2-yl)methy)phenyl)-1-(4-(5-methyl-1,2,4-oxadiazol-3-yl)piperidin-1-yl)prop-2-en-1-one

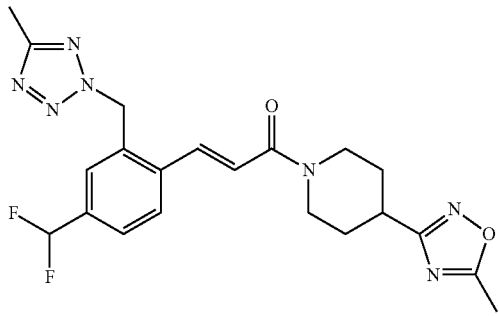

T3P® 50% in ethyl acetate (240 μl, 0.408 mmol) was added to a solution of (E)-3-(4-(difluoromethyl)-2-((5-methyl-2H-tetrazol-2-yl)methyl)phenyl)acrylic acid (Intermediate AH) (100 mg, 0.340 mmol), 5-methyl-3-(piperidin-4-yl)-1,2,4-oxadiazole hydrochloride (69.2 mg, 0.340 mmol) and TEA (189 μl, 1.359 mmol) in DCM (1 mL) and the resulting mixture stirred at room temperature for 2 h. The reaction mixture was poured into saturated sodium bicarbonate (55 mL) The aqueous layer was extracted with ethyl acetate (3×10 mL). The organic solutions were combined washed with, brine (10 mL), dried over sodium sulphate, filtered and concentrated in vacuo. Purification was carried out by silica gel column chromatography eluting with a gradient of iso-hexane to 10% MeOH in ethyl acetate. The product fractions were combined and evaporated in vacuo to give a clear gum. The gum was triturated with MTBE and the resulting white solid dried in a vacuum oven to give the title compound as a white solid;

LC MS Rt 1.14 min; [M+H]$^+$ 444.3, Method 2min-LowpHv03

$^1$H NMR (400 MHz, DMSO-d6) δ 8.02 (1H, d), 7.81 (1H, d), 7.66-7.58 (2H, m), 7.25 (1H, d), 7.09 1H, t), 6.08 (2H, s), 4.41 (1H, m), 4.21 (1H, m), 3.29 (1H, m), 3.12 (1H, m), 2.94 (1H, m), 2.57 (3H, s), 2.42 (3H, s), 2.00 (2H, m), 1.60 (2H, m).

Example 56

(E)-1-(4-((5-Methyl-1,3,4-oxadiazol-2-yl)methyl)piperidin-1-yl)-3-(2-((5-methyl-2H-tetrazol-2-yl)methyl)-4-(trifluoromethoxy)phenyl)prop-2-en-1-one

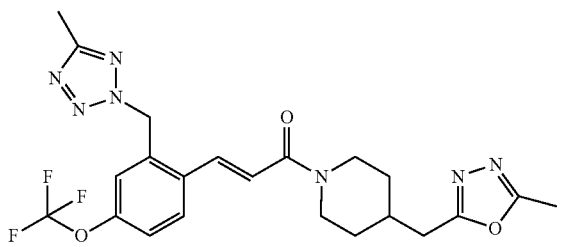 [SMILES: Cc1nnn(Cc2cc(OC(F)(F)F)ccc2/C=C/C(=O)N2CCC(Cc3nnc(C)o3)CC2)n1]

A solution of 1-(4-((5-methyl-1,3,4-oxadiazol-2-yl)methyl)piperidin-1-yl)prop-2-en-1-one (Intermediate G)(75 mg, 0.319 mmol) in degassed DMF (2 mL) was added to a mixture of 2-(2-bromo-5-(trifluoromethoxy)benzyl)-5-methyl-2H-tetrazole (Intermediate AB step 2)(129 mg, 0.383 mmol), palladium diacetate (7.16 mg, 0.032 mmol) and tri(o-tolyl) phosphine (9.70 mg, 0.032 mmol). The mixture was stirred briefly, TEA (0.133 mL, 0.956 mmol) was added and the mixture heated at 10° C. for 18 h. Water (20 mL) was added and the mixture extracted with ethyl acetate (3×20 mL). The combined organic extracts were washed with water (20 mL), brine (20 mL), dried over sodium sulphate, filtered and concentrated in vacuo. Purification was carried out by silica gel column chromatography eluting with a gradient of iso-hexane to 10% MeOH in ethyl acetate. The product fractions were combined and evaporated in vacuo and the residue was crystallised from ethyl acetate\iso-hexane to give the title compound as a white solid;

LC MS Rt 1.07 min; [M+H]$^+$ 492.3, Method 2min-LowpHv01

$^1$H NMR (400 MHz, DMSO-d6) δ 7.99 (1H, d), 7.71 (1H, d) 7.47-7.42 (2H, m), 7.17 (1H, d), 6.05 (2H, s), 4.45 (1H, m), 4.19 (1H, m), 3.06 (1H, m), 2.79 (2H, m), 2.67 (1H, m), 2.46 (3H, s), 2.42 (3H, s), 2.03 (1H, m), 1.73 (2H, m), 1.16 (2H, m).

Example 57

(E)-1-(4-(5-Methyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one

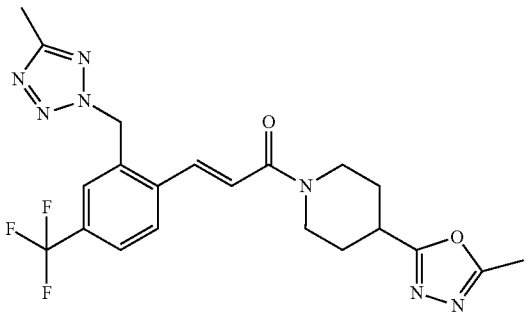 [SMILES: Cc1nnn(Cc2cc(C(F)(F)F)ccc2/C=C/C(=O)N2CCC(c3nnc(C)o3)CC2)n1]

T3P® 50% solution in ethyl acetate (0.765 mL, 1.299 mmol) was added to a solution of (E)-3-(2-((5-methyl-2H-tetrazol-2-yl)methyl)-4-(trifluoromethyl)phenyl)acrylic acid (Intermediate AB) (338 mg, 1.082 mmol), 2-methyl-5-(piperidin-4-yl)-1,3,4-oxadiazole (Intermediate BG)(181 mg, 1.082 mmol) and TEA (0.604 mL, 4.33 mmol) in DCM (5 mL) and the resulting mixture stirred for 1 h. The reaction mixture was poured into saturated sodium bicarbonate solution (25 mL). The organic portion was separated and the aqueous layer was extracted with ethyl acetate (3×25 mL). The organic portions were combined washed with water (25 mL), brine (25 mL), dried over sodium sulphate, filtered and concentrated in vacuo. Purification was carried out by chromatography on silica eluting with a gradient of iso-hexane/10% MeOH in ethyl acetate. The product fractions were combined and evaporated in vacuo. The resulting gum was dissolved in hot TBME and seeded. The precipitate was aged for 2 h, collected by filtration, washed with TBME and dried in a vacuum oven to give the title compound as a white solid;

LC MS: Rt 1.13 min; [M+H]⁺ 462.3, Method 2min-LowpHv01

¹H NMR (400 MHz, DMSO-d6) δ 8.09 (1H, d), 7.86 (1H, d), 7.82 (1H, dd), 7.77 (1H, d), 7.29 (1H, d), 6.12 (2H, s), 4.35 (1H, m), 4.18 (1H, m), 3.28 (2H, m), 2.99 (1H, t), 2.48 (3H, s), 2.41 (3H, s), 2.05 (2H, m), 1.64 (2H, m).

Example 58

(E)-3-(4-(Difluoromethoxy)-2-((5-methyl-2H-tetrazol-2-yl)methyl)phenyl)-1-(4-((5-methyl-1,3,4-oxadiazol-2-yl)methyl)piperidin-1-yl)prop-2-en-1-one

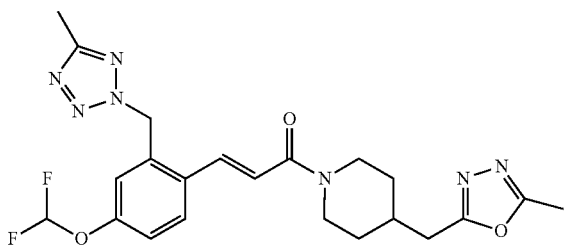 [SMILES: Cc1nnn(Cc2cc(OC(F)F)ccc2/C=C/C(=O)N2CCC(Cc3nnc(C)o3)CC2)n1]

The title compound was prepared by a similar method to Example 52 from (E)-3-(4-(difluoromethoxy)-2-((5-methyl-2H-tetrazol-2-yl)methyl)phenyl)acrylic acid (Intermediate AI) and 2-methyl-5-(piperidin-4-ylmethyl)-1,3,4-oxadiazole (Intermediate BD);

LC MS:Rt 1.13 min; [M+H]⁺ 474.3, Method 2min-LowpHv03

Example 59

(E)-3-(4-(Difluoromethyl)-2-((5-methyl-2H-tetrazol-2-yl)methyl)phenyl)-1-(4-((5-methyl-1,3,4-oxadiazol-2-yl)methyl)piperidin-1-yl)prop-2-en-1-one

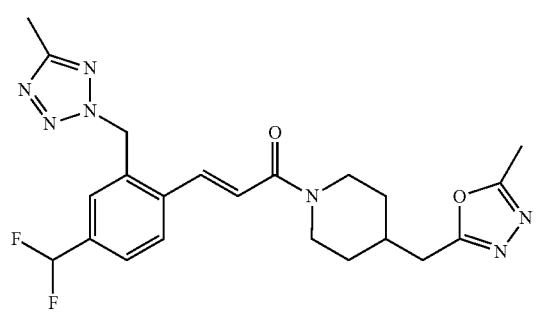 [SMILES: Cc1nnn(Cc2cc(C(F)F)ccc2/C=C/C(=O)N2CCC(Cc3nnc(C)o3)CC2)n1]

The title compound was prepared by a similar method to Example 52 from (E)-3-(4-(difluoromethyl)-2-((5-methyl-2H-tetrazol-2-yl)methyl)phenyl)acrylic acid (Intermediate AH) and 2-methyl-5-(piperidin-4-ylmethyl)-1,3,4-oxadiazole (Intermediate BD);

LC MS:Rt 1.08 min; [M+H]⁺ 458.3, Method 2min-LowpHv03

Example 60

(E)-1-(4-((3-Methyl-1,2,4-oxadiazol-5-yl)methyl)piperidin-1-yl)-3-(2-((5-methyl-2H-tetrazol-2-yl)methyl)-4-(trifluoromethyl)phenyl)prop-2-en-1-one

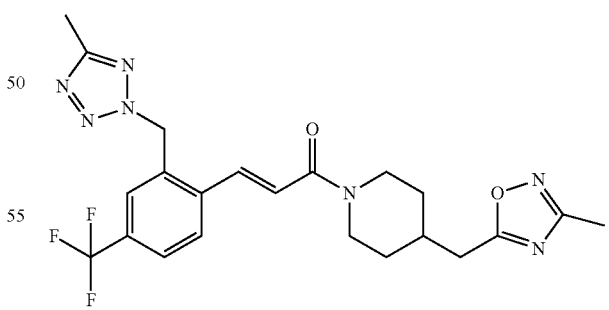

The title compound was prepared by a similar method to Example 52 from (E)-3-(2-((5-methyl-2H-tetrazol-2-yl)methyl)-4-(trifluoromethyl)phenyl)acrylic acid (Intermediate AB) (150 mg, 0.480 mmol) and 3-methyl-5-(piperidin-4-ylmethyl)-1,2,4-oxadiazole (Intermediate BH);

LC MS:Rt 1.27 min; [M+H]⁺ 476.2, Method 2min-LowpHv03

Example 61

(E)-3-(4-Chloro-2-((5-methyl-2H-tetrazol-2-yl)methyl)phenyl)-1-(5-((2-methyl oxazol-4-yl)methyl)-2,5-diazabicyclo[2.2.2]octan-2-yl)prop-2-en-1-one

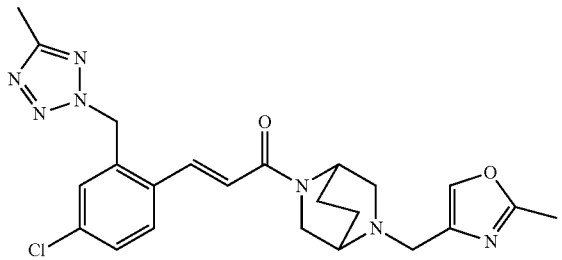 [SMILES: Cc1nnn(Cc2cc(Cl)ccc2/C=C/C(=O)N2CC3CCC2CN3Cc2coc(C)n2)n1]

Step 1: 2,5-Diazabicyclo[2.2.2]octane

A suspension of 2,5-diazabicyclo[2.2.2]octane-3,6-dione (100 mg, 0.714 mmol) in THF (20 mL) was added dropwise to 1M LiAlH4 in THF (3.57 mL, 3.57 mmol) at reflux The resulting mixture was stirred at reflux overnight. The reaction was cooled to 0° C. in an ice bath. Water (0.2 mL) was added followed by 1M NaOH solution (1.2 mL) and the mixture stirred for 10 min. Sodium sulphate was added and the mixture stirred for 10 min. The reaction mixture was filtered through Celite® (filter material) and the filter pad washed with THF (3×50 mL). The filtrate and washings were combined and concentrated in vacuo to give the title compound as a yellow gum which was used directly without further purification.

Step 2: (E)-1-(2,5-Diazabicyclo[2.2.2]octan-2-yl)-3-(4-chloro-2-((5-methyl-2H-tetrazol-2-yl)methyl)phenyl)prop-2-en-1-one The title compound were prepared by a similar method to Example 52 from (E)-3-(4-Chloro-2-((5-methyl-2H-tetrazol-2-yl)methyl)phenyl)acrylic acid (Intermediate A) and 2,5-diazabicyclo[2.2.2]octane (step 1);

LC MS: Rt 0.68 min [M+H]+ 373.6, 375.6 Method 2minLowpHv01.

Step 3: (E)-3-(4-Chloro-2-((5-methyl-2H-tetrazol-2-yl)methyl)phenyl)-1-(5-((2-methyloxazol-4-yl)methyl)-2,5-diazabicyclo[2.2.2]octan-2-yl)prop-2-en-1-one The title compound was prepared by a similar method to Example 53 step 3 from (E)-1-(2, 5-diazabicyclo[2.2.2]octan-2-yl)-3-(4-chloro-2-((5-methyl-2H-tetrazol-2-yl)methyl)phenyl)prop-2-en-1-one (Step 2) and 2-methyloxazole-4-carbaldehyde; LC MS: Rt 0.74 min; [M+H]+ 468.6, 470.6, Method 2minLowpHv01

Example 62

(R,E)-3-(4-Chloro-2-((5-methyl-2H-tetrazol-2-yl)methyl)phenyl)-1-(2-methyl-4-((2-methyloxazol-4-yl)methyl)piperazin-1-yl)prop-2-en-1-one

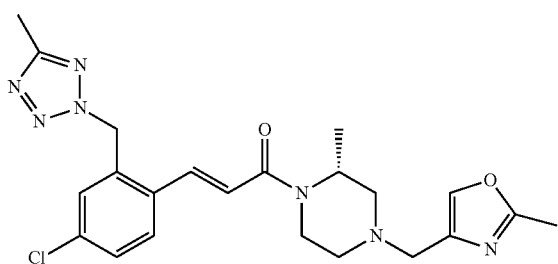 [SMILES: Cc1nnn(Cc2cc(Cl)ccc2/C=C/C(=O)N2CCN(Cc3coc(C)n3)C[C@H]2C)n1]

The title compound was prepared by a similar method to Example 53 (steps 1-3) from (E)-3-(4-chloro-2-((5-methyl-2H-tetrazol-2-yl)methyl)phenyl)acrylic acid (Intermediate A) and (R)-tert-butyl 3-methylpiperazine-1-carboxylate;

LC MS: Rt 0.79 min [M+H]+ 456.5, 458.4, Method 2minLowpHv03

Example 63

(E)-3-(4-Chloro-2-((5-methyl-2H-tetrazol-2-yl)methyl)phenyl)-1-(4-(hydroxy(4-methylthiazol-2-yl)methyl)piperidin-1-yl)prop-2-en-1-one

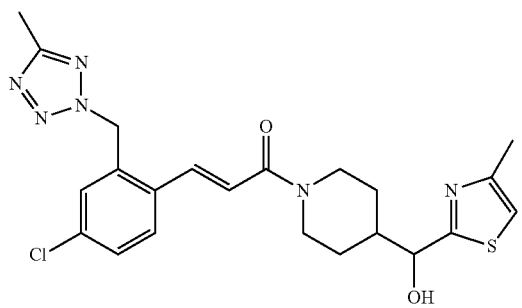 [SMILES: Cc1csc(C(O)C2CCN(C(=O)/C=C/c3ccc(Cl)cc3Cn3nnc(C)n3)CC2)n1]

Step 1: (E)-3-(4-Chloro-2-((5-methyl-2H-tetrazol-2-yl)methyl)phenyl)-1-(4-(hydroxymethyl)piperidin-1-yl)prop-2-en-1-one The title compound was prepared by a similar method to Example 52 from (E)-3-(4-chloro-2-((5-methyl-2H-tetrazol-2-yl)methyl)phenyl)acrylic acid (Intermediate A) and piperidin-4-ylmethanol;

LC MS Rt 0.96 min [M+H]+ 376.6, 378.6, Method 2minLowpHv01

Step 2: (E)-1-(3-(4-Chloro-2-((5-methyl-2H-tetrazol-2-yl)methyl)phenyl)acryloyl)piperidine-4-carbaldehyde A solution of pyridine sulfur trioxide (1.46 g, 9.15 mmol) in DMSO (2 mL) was added to a solution of (E)-3-(4-chloro-2-((5-methyl-2H-tetrazol-2-yl)methyl)phenyl)-1-(4-(hydroxymethyl)piperidin-1-yl)prop-2-en-1-one (step 1) (860 mg, 2.29 mmol) and DIPEA (1.60 mL, 9.15 mmol) in DCM (20 mL) and stirred at 0° C. for 1 hour. The reaction mixture was partitioned between DCM and 1M HCl. The organic phase was washed with water and brine, dried over magnesium sulphate, filtered and concentrated in vacuo. Purification was by silica gel column chromatography eluting with a gradient of iso-hexane to 10% methanol in ethyl acetate. The product fractions were combined and evaporated in vacuo to give the title compound as a white foam;

LC MS Rt 1.01 min [M+H]+ 374.5, 376.5, Method 2minLowpHv01

Step 3: (E)-3-(4-Chloro-2-((5-methyl-2H-tetrazol-2-yl)methyl)phenyl)-1-(4-(hydroxy(4-methylthiazol-2-yl)methyl)piperidin-1-yl)prop-2-en-1-one Butyl lithium 2.5M solution in hexanes (0.120 mL, 0.300 mmol) was added dropwise to a solution of 2-bromo-4-methylthiazole (44.5 mg, 0.250 mmol) in THF (2 mL) at <−70° C. and the resulting mixture stirred for 30 min. Lathanum chloride lithium chloride solution (0.6M in THF, 0.417 mL, 0.250 mmol) was added dropwise and the resulting mixture was stirred for 30 min. A solution of: (E)-1-(3-(4-Chloro-2-((5-methyl-2H-tetrazol-2-yl)methyl)phenyl)acryloyl)piperidine-4-carbaldehyde (step 2) (93 mg, 0.25 mmol) in THF (1 mL) was added dropwise and the mixture was stirred at −70° C. for 30 min then allowed to warm to RT. The reaction was quenched with saturated ammonium chloride solution (5 mL) and extracted with ethyl acetate (3×10 mL). The combined organic solutions were washed with brine (20 mL), dried over sodium sulphate, filtered and concentrated in vacuo. Purification was carried out by silica gel column chromatography eluting with a gradient of iso-hexane to ethyl acetate. The product fractions were combined and concentrated in vacuo to give the title compound as a white solid;

LC MS Rt 1.07 min [M+H]$^+$ 473.6, 475.6, Method 2minLowpHv01

Example 64

(E)-3-(4-Chloro-2-((5-methyl-2H-tetrazol-2-yl)methyl)phenyl)-1-(4-(4-fluorophenyl)piperidin-1-yl)prop-2-en-1-one

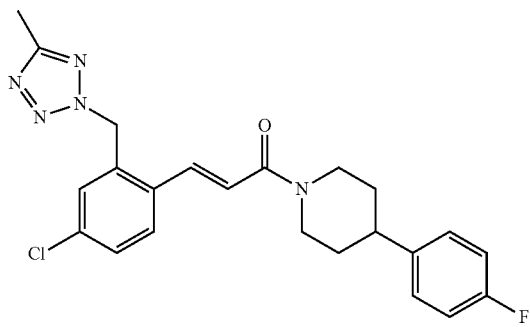 [SMILES: Cc1nnn(Cc2cc(Cl)ccc2/C=C/C(=O)N2CCC(c3ccc(F)cc3)CC2)n1]

The title compound was prepared by a similar method to Example 52 from (E)-3-(4-chloro-2-((5-methyl-2H-tetrazol-2-yl)methyl)phenyl)acrylic acid (Intermediate A) and 4-(4-fluorophenyl)piperidine (commercially available);

LC MS: Rt 1.32 min [M+H]$^+$ 440.2, 442.2 Method 2minLowpHv01

Example 65

(R,E)-tert-Butyl 2-(3-methyl-4-(3-(2-((5-methyl-2H-tetrazol-2-yl)methyl)-4-(trifluoromethyl)phenyl)acryloyl)piperazin-1-yl)acetate

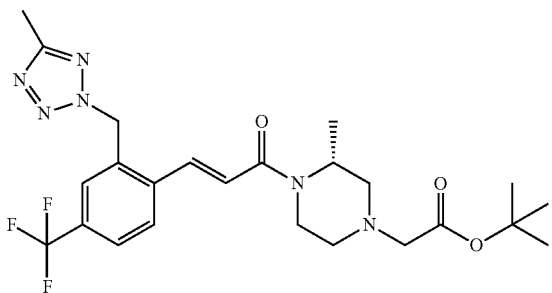 [SMILES: Cc1nnn(Cc2cc(C(F)(F)F)ccc2/C=C/C(=O)N2CCN(CC(=O)OC(C)(C)C)C[C@H]2C)n1]

Step 1: (R,E)-tert-Butyl 3-methyl-4-(3-(2-((5-methyl-2H-tetrazol-2-yl)methyl)-4-(trifluoromethyl)phenyl)acryloyl)piperazine-1-carboxylate The title compound was prepared by a similar method to Example 52 from (E)-3-(2-((5-methyl-2H-tetrazol-2-yl)methyl)-4-(trifluoromethyl)phenyl)acrylic acid (Intermediate AB) (2 g, 6.41 mmol) and (R)-tert-butyl 3-methylpiperazine-1-carboxylate;

LC MS:Rt 1.39 min; [M−100+H]$^+$395.3, Method 2minLowpHv03

Step 2: (R,E)-3-(2-((5-Methyl-2H-tetrazol-2-yl)methyl)-4-(trifluoromethyl)phenyl)-1-(2-methylpiperazin-1-yl)prop-2-en-1-one TFA (10 mL) was added to a solution of (R,E)-tert-Butyl 2-(3-methyl-4-(3-(2-((5-methyl-2H-tetrazol-2-yl)methyl)-4-(trifluoromethyl)phenyl)acryloyl)piperazin-1-yl)acetate (step 1) (2.7 g, 5.46 mmol) in DCM (10 mL) and the resulting mixture stirred for 1 h. Toluene (100 mL) was added and the reaction concentrated in vacuo. The resulting gum was stirred in diethyl ether (250 mL), water (1 mL) was added and the resulting solid was collected by filtration, washed with ether and dried under vacuum to give the title compound as a trifluoroacetate salt;

LC MS Rt 0.74 min; [M+H]$^+$ 395.0, 397.5, Method 2minLowpHv03

Step 3: (R,E)-tert-Butyl 2-(3-methyl-4-(3-(2-((5-methyl-2H-tetrazol-2-yl)methyl)-4-(trifluoromethyl)phenyl)acryloyl)piperazin-1-yl)acetate tert-Butyl bromoacetate (0.512 mL, 3.46 mmol) was added dropwise to a mixture of (R,E)-3-(2-((5-methyl-2H-tetrazol-2-yl)methyl)-4-(trifluoromethyl)phenyl)-1-(2-methylpiperazin-1-yl)prop-2-en-1-one trifluroacetate salt (step 2) (1.6 g, 3.15 mmol) and potassium carbonate (0.957 g, 6.92 mmol) in DMF (12 mL) and the resulting mixture was stirred overnight at room temperature. The reaction was poured into water (120 mL) and extracted with ethyl acetate (3×50 mL). The combined organic extracts were washed with water (50 mL), brine (50 mL), dried over sodium sulphate, filtered and concentrated in vacuo. Purification was by silica gel column chromatography eluting with a gradient of iso-hexane to 10% MeOH in ethyl acetate. The product fractions were combined and evaporated in vacuo to give the title compound as a yellow foam;

LC MS Rt 1.09 min; [M+H]$^+$; 509.6, Method 2minLowpHv03

Example 66 rac-(E)-3-(4-Chloro-2-((5-methyl-2H-tetrazol-2-yl)methyl)phenyl)-1-(4-((4-chlorophenyl)(hydroxy)methyl)piperidin-1-yl)prop-2-en-1-one

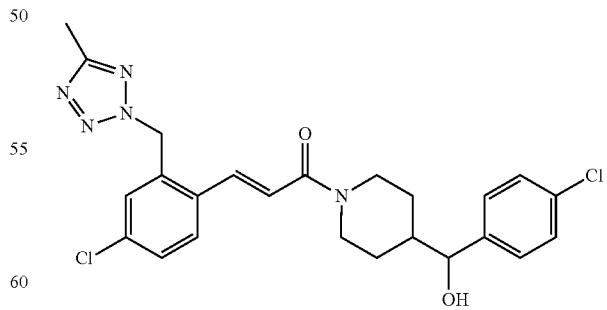

The title compound was prepared by a similar method to Example 52 from (E)-3-(4-Chloro-2-((5-methyl-2H-tetrazol-2-yl)methyl)phenyl)acrylic acid (Intermediate A) and (4-chlorophenyl)(piperidin-4-yl)methanol (commercially available);

LC MS: Rt 1.25 min; [M+H]+; 486.2, 488.2, 490.2, Method 2minLowpHv01

Example 66a ((R or S), E)-3-(4-Chloro-2-((5-methyl-2H-tetrazol-2-yl)methyl)phenyl)-1-(4-((4-chlorophenyl)(hydroxy)methyl)piperidin-1-yl)prop-2-en-1-one and

Example 66b ((R or S), E)-3-(4-Chloro-2-((5-methyl-2H-tetrazol-2-yl)methyl)phenyl)-1-(4-((4-chlorophenyl)(hydroxy)methyl)piperidin-1-yl)prop-2-en-1-one

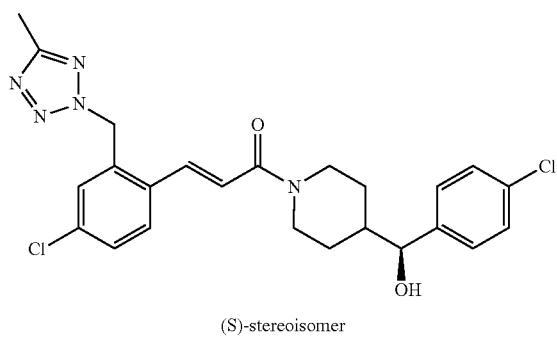
(S)-stereoisomer

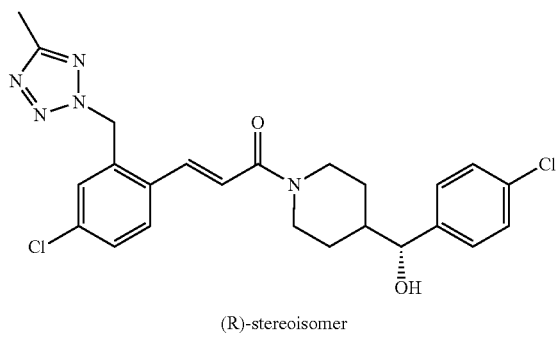
(R)-stereoisomer

Racemic (E)-3-(4-chloro-2-((5-methyl-2H-tetrazol-2-yl)methyl)phenyl)-1-(4-((4-chlorophenyl)(hydroxy)methyl)piperidin-1-yl)prop-2-en-1-one (Example 66) was separated by SFC chiral chromatography (Method: CHIRALPAK AD-H 250×10 mm 5 um, 40% methanol in CO₂);

Example 66a ((R or S), E)-3-(4-Chloro-2-((5-methyl-2H-tetrazol-2-yl)methyl)phenyl)-1-(4-((4-chlorophenyl)(hydroxy)methyl)piperidin-1-yl)prop-2-en-1-one First Eluted Peak:
SFC Rt=4.96 mins; (LUX A2, 250×10 mm, 5 um, 35° C., 10 mL/min 50% methanol in CO₂)
LCMS Rt=1.25 mins; [M+H]+ 486.2, 488.2, 490.2; Method 2minLowpHv03

Example 66b ((R or S), E)-3-(4-Chloro-2-((5-methyl-2H-tetrazol-2-yl)methyl)phenyl)-1-(4-((4-chlorophenyl)(hydroxy)methyl)piperidin-1-yl)prop-2-en-1-one Second Eluted Peak:
SFC Rt=7.74 mins; (LUX A2, 250×10 mm, 5 um, 35° C., 10 mL/min, 50% methanol in CO₂)
LCMS Rt=1.24 mins; [M+H]+ 486.3, 488.3, 490.3; Method 2minLowpHv03

Example 67

(E)-Methyl 1-(3-(2-((5-methyl-2H-tetrazol-2-yl)methyl)-4-(trifluoromethyl)phenyl)acryloyl)piperidine-4-carboxylate

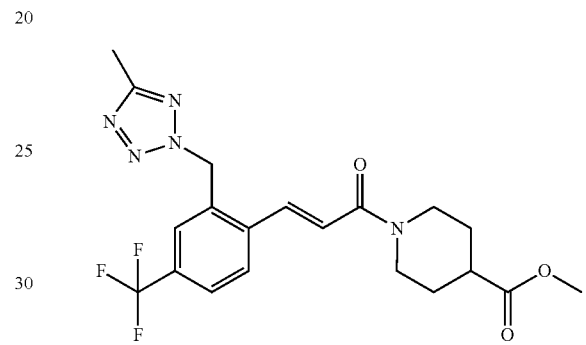

The title compound was prepared by a similar method to Example 52 from (E)-3-(2-((5-methyl-2H-tetrazol-2-yl)methyl)-4-(trifluoromethyl)phenyl)acrylic acid (Intermediate AB) and methyl piperidine-4-carboxylate;
LCMS: Rt 1.27 min; [M+H]+ 438.3 Method 2minLowpHv03

Example 68

(E)-tert-Butyl-4-(3-(2-((5-methyl-2H-tetrazol-2-yl)methyl)-4-(trifluoromethyl)phenyl)acryloyl)piperazine-1-carboxylate

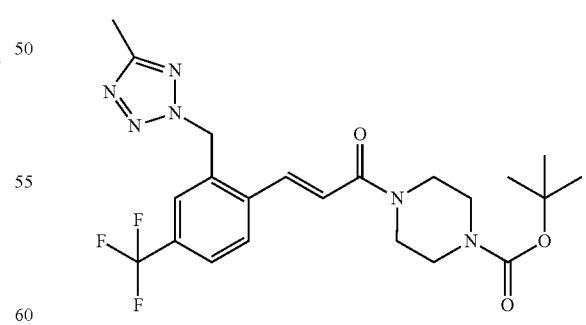

The title compound was prepared by a similar method to Example 52 from (E)-3-(2-((5-methyl-2H-tetrazol-2-yl)methyl)-4-(trifluoromethyl)phenyl)acrylic acid (Intermediate AB) and tert-butyl piperazine-1-carboxylate;
LCMS: Rt 1.38 min; [M−100+H]+; 381.3 Method 2minLowpHv03

Example 69

(R,E)-3-(2-((5-Methyl-2H-tetrazol-2-yl)methyl)-4-(trifluoromethyl)phenyl)-1-(2-methyl-4-((2-methyloxazol-4-yl)methyl)piperazin-1-yl)prop-2-en-1-one

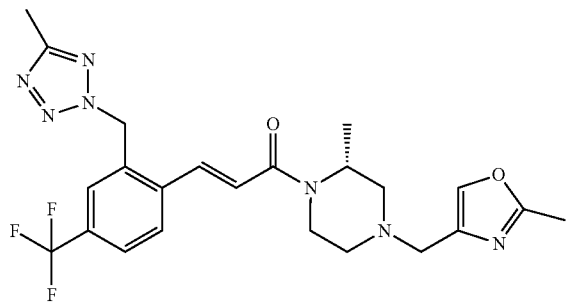 [SMILES: Cc1nnn(Cc2cc(C(F)(F)F)ccc2/C=C/C(=O)N2CCN(Cc3coc(C)n3)C[C@H]2C)n1]

The title compound was prepared by a similar method to Example 53 by replacing tert-butyl piperazine-1-carboxylate (step 1) with (R)-tert-butyl 3-methylpiperazine-1-carboxylate and by replacing 1-methyl-1H-pyrazole-4-carbaldehyde (step 3) with 2-methyloxazole-4-carbaldehyde. The compound was isolated as a hydrochloride salt;

LCMS: Rt 0.82 min; [M+H]$^+$ 490.5, Method 2min-LowpHv03

Example 70

(R,E)-3-(2-((5-Methyl-2H-tetrazol-2-yl)methyl)-4-(trifluoromethyl)phenyl)-1-(2-methyl-4-((1-methyl-1H-pyrazol-4-yl)methyl)piperazin-1-yl)prop-2-en-1-one

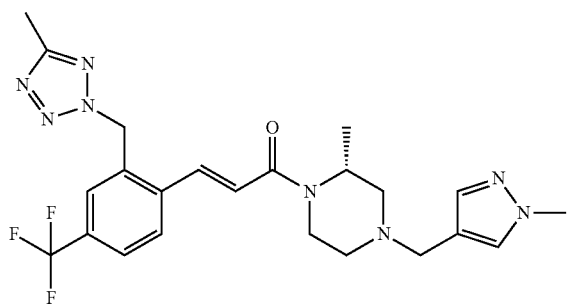 [SMILES: Cc1nnn(Cc2cc(C(F)(F)F)ccc2/C=C/C(=O)N2CCN(Cc3cnn(C)c3)C[C@H]2C)n1]

The title compound was prepared by a similar method to Example 53 by replacing tert-butyl piperazine-1-carboxylate (step 1) with (R)-tert-butyl 3-methylpiperazine-1-carboxylate. The compound was isolated as a hydrochloride salt;

LC MS Rt 0.76 min; [M+H]$^+$ 489.3, Method 2min-LowpHv03

Example 71

(E)-1-(4-((5-Methyl-1,2,4-oxadiazol-3-yl)methyl)piperidin-1-yl)-3-(2-((5-methyl-2H-tetrazol-2-yl)methyl)-4-(trifluoromethyl)phenyl)prop-2-en-1-one

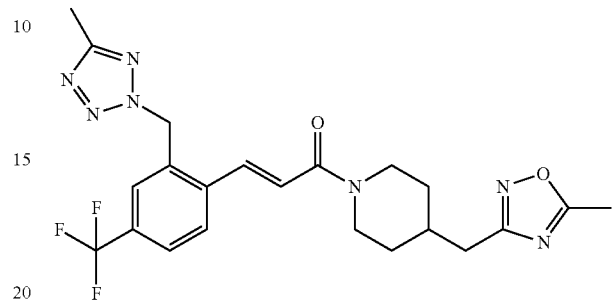

The title compound was prepared by a similar method to Example 52 from (E)-3-(2-((5-methyl-2H-tetrazol-2-yl)methyl)-4-(trifluoromethyl)phenyl)acrylic acid (Intermediate AB) and 5-methyl-3-(piperidin-4-ylmethyl)-1,2,4-oxadiazole hydrochloride;

LC MS; Rt 1.26 min; [M+H]$^+$ 476.4, Method 2min-LowpHv03

Example 72

(E)-1-(4-((5-Methyl-1,3,4-oxadiazol-2-yl)methyl)piperidin-1-yl)-3-(4-methyl-2-((5-methyl-2H-tetrazol-2-yl)methyl)phenyl)prop-2-en-1-one

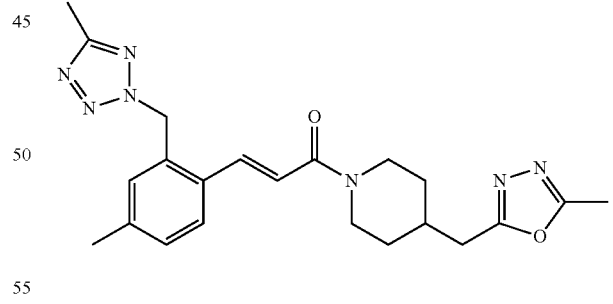

The title compound was prepared by a similar method to Example 52 from (E)-3-(4-methyl-2-((5-methyl-2H-tetrazol-2-yl)methyl)phenyl)acrylic acid (Intermediate AJ) and 2-methyl-5-(piperidin-4-ylmethyl)-1,3,4-oxadiazole (Intermediate BD);

LC MS: Rt 1.13 min; [M+H]$^+$ 422.3, Method 2min-LowpHv03

Example 73

(R,E)-3-(4-Chloro-2-((5-methyl-2H-tetrazol-2-yl)methyl)phenyl)-1-(2-methyl-4-((1-methyl-1H-pyrazol-4-yl)methyl)piperazin-1-yl)prop-2-en-1-one

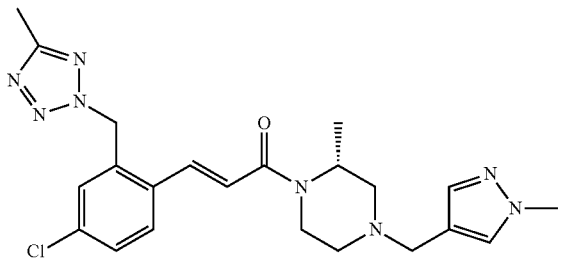 [SMILES: Cc1nnn(Cc2cc(Cl)ccc2/C=C/C(=O)N2CCN(Cc3cnn(C)c3)C[C@H]2C)n1]

The title compound was prepared by a similar method to Example 53 (steps 1-3) from (E)-3-(4-chloro-2-((5-methyl-2H-tetrazol-2-yl)methyl)phenyl)acrylic acid (Intermediate A) and (R)-tert-butyl 3-methylpiperazine-1-carboxylate and by using the appropriate carbaldehyde in step 3. The compound was isolated as a hydrochloride salt;

LC MS:Rt 0.71 min; [M+H]$^+$ 455.3, 457.3, Method 2minLowpHv03

Example 74

(E)-3-(2-((5-Methyl-2H-tetrazol-2-yl)methyl)-4-(trifluoromethyl)phenyl)-1-(4-((2-methyloxazol-4-yl)methyl)piperazin-1-yl)prop-2-en-1-one

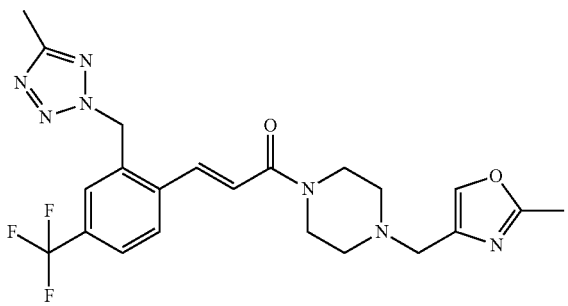 [SMILES: Cc1nnn(Cc2cc(C(F)(F)F)ccc2/C=C/C(=O)N2CCN(Cc3coc(C)n3)CC2)n1]

The title compound was prepared by a similar method to Example 53 from (E)-3-(2-((5-methyl-2H-tetrazol-2-yl)methyl)-4-(trifluoromethyl)phenyl)acrylic acid (Intermediate AB) and tert-butyl piperazine-1-carboxylate and by using the appropriate carbaldehyde in step 3. The compound was isolated as a hydrochloride salt;

LC MS:Rt 0.84 min; MS m/z 476.5 [M+H]+; Method 2minLowpHv03

Example 75

(E)-3-(2-((2H-1,2,3-Triazol-2-yl)methyl)-4-chlorophenyl)-1-(4-((5-methyl-1,3,4-oxadiazol-2-yl)methyl)piperidin-1-yl)prop-2-en-1-one

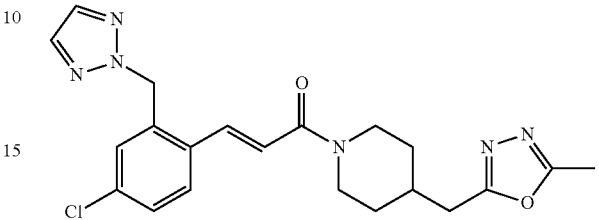

Step 1: 2-(2-Bromo-5-chlorobenzyl)-2H-1,2,3-triazole 2H-1,2,3-Triazole (0.486 g, 7.03 mmol) was added to a suspension of potassium carbonate (1.166 g, 8.44 mmol) and 1-bromo-2-(bromomethyl)-4-chlorobenzene (2 g, 7.03 mmol) in DMF (15 mL) and the resulting mixture stirred at room temperature for 60 h. The reaction was poured into water (150 mL) and extracted with ethyl acetate (3×100 mL). The combined organics were washed with water (100 mL), dried over sodium sulphate, filtered and concentrated in vacuo. Purification was carried out by silica gel column chromatography eluting with a gradient of iso-hexane to 75% ethyl acetate in iso-hexane. The product fractions were combined and evaporated in vacuo to give the title compound as a white solid;

$^1$H NMR (400 MHz, CDCl$_3$) δ 7.73 (2H, s), 7.55 (1H, d), 7.19, (1H, dd), 6.87 (1H, m), 5.74 (2H, s).

Step 2: (E)-3-(2-((2H-1,2,3-Triazol-2-yl)methyl)-4-chlorophenyl)-1-(4-((5-methyl-1,3,4-oxadiazol-2-yl)methyl)piperidin-1-yl)prop-2-en-1-one A solution of 2-methyl-5-(piperidin-4-ylmethyl)-1,3,4-oxadiazole (Intermediate G) (75 mg, 0.319 mmol) in degassed DMF (2 mL) was added to a mixture of 2-(2-bromo-5-chlorobenzyl)-2H-1,2,3-triazole (step 1)(104 mg, 0.383 mmol), palladium acetate (7.16 mg, 0.032 mmol) and tri(o-tolyl)phosphine (9.70 mg, 0.032 mmol). The mixture was stirred briefly and TEA (0.133 mL, 0.956 mmol) was added and the mixture heated at 100° C. for 18 h. Water (20 mL) was added and the mixture extracted with ethyl acetate (3×20 mL). The combined organics were washed with water (20 mL), brine (20 mL), dried over sodium sulphate, filtered and concentrated in vacuo to a gum. Purification was carried out by silica gel column chromatography eluting with a gradient of iso-hexane to 10% MeOH in ethyl acetate. The product fractions were combined and concentrated in vacuo and the residue was crystallised from ether to give the title compound as a white solid;

LC MS Rt 1.02 min; [M+H]$^+$ 427.2, 429.2, Method 2minLowpHv01

Example 76

(E)-3-(4-Chloro-2-((3-methyl-1,2,4-oxadiazol-5-yl)methyl)phenyl)-1-(4-((2-methyloxazol-4-yl)methyl)piperazin-1-yl)prop-2-en-1-one

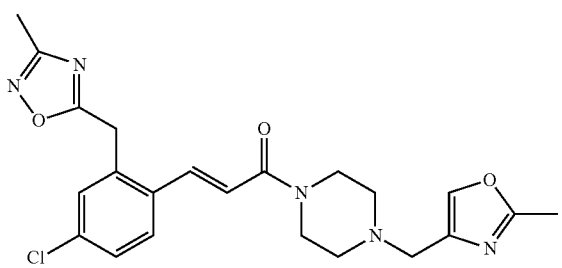 [SMILES: Cc1noc(Cc2cc(Cl)ccc2/C=C/C(=O)N2CCN(Cc3coc(C)n3)CC2)n1]

Step 1: 5-(2-Bromo-5-chlorobenzyl)-3-methyl-1,2,4-oxadiazole

TEA (0.833 mL, 6.01 mmol) was added to a solution of 2-bromo-5-chlorophenylacetic acid (500 mg, 2.004 mmol) and acetamide oxime (163 mg, 2.205 mmol) in a mixture of ethyl acetate (4 mL,) and DMF (1 mL). T3P® (50% in EtOAc) (2.952 mL, 5.01 mmol) was then added dropwise over 10 mins and the resulting mixture stirred at room temperature for 60 h then at reflux for 72 h. The mixture was partitioned between ethyl acetate (10 mL) and water (10 mL). The layers were separated and the organic solution washed with saturated sodium bicarbonate solution (10 mL), water (10 mL), brine (10 mL), dried over magnesium sulphate, filtered and concentrated in vacuo. Purification was carried out by silica gel column chromatography eluting with a gradient of iso-hexane to 20% ethyl acetate in iso-hexane. The product fractions were combined and concentrated in vacuo to give the title compound as a yellow oil;

LCMS-Method: Rt 1.22 min [M+H]$^+$ 289.4 Method 2minLowpHv01

Step 2: (E)-3-(4-Chloro-2-((3-methyl-1,2,4-oxadiazol-5-yl)methyl)phenyl)-1-(4-((2-methyloxazol-4-yl)methyl)piperazin-1-yl)prop-2-en-1-one The title compound was prepared by a similar method to Example 56 from 1-(4-((2-methyloxazol-4-yl)methyl)piperazin-1-yl)prop-2-en-1-one (Intermediate IA) and 5-(2-bromo-5-chlorobenzyl)-3-methyl-1,2,4-oxadiazole (step 1);

LC MS: Rt 0.73 min; [M+H]$^+$ 442.4, 444.4, Method 2minLowpHv01

Examples 77-80

These examples were prepared by a similar method to Example 75 from the appropriate commercially available starting compounds in step 1. The resulting product is coupled with Intermediate G in step 2;

Example 77

(E)-3-(2-((2H-Tetrazol-2-yl)methyl)-4-chlorophenyl)-1-(4-((5-methyl-1,3,4-oxadiazol-2-yl)methyl)piperidin-1-yl)prop-2-en-1-one

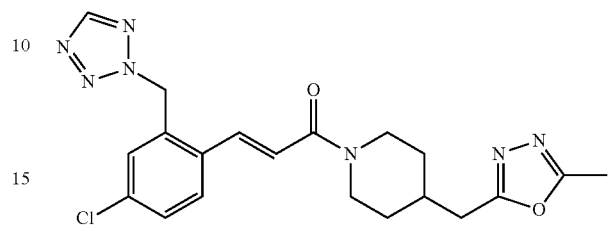

LC MS:Rt 0.99 min; [M+H]$^+$ 428.2, 430.2, Method 2minLowpHv01

Example 78

(E)-3-(3-Fluoro-2-((5-methyl-2H-tetrazol-2-yl)methyl)phenyl)-1-(4-((5-methyl-1,3,4-oxadiazol-2-yl)methyl)piperidin-1-yl)prop-2-en-1-one LC MS: Rt 0.94 min; [M+H]$^+$ 426.3, Method 2minLowpHv01

Example 79

(E)-3-(5-Fluoro-2-((5-methyl-2H-tetrazol-2-yl)methyl)phenyl)-1-(4-((5-methyl-1,3,4-oxadiazol-2-yl)methyl)piperidin-1-yl)prop-2-en-1-one

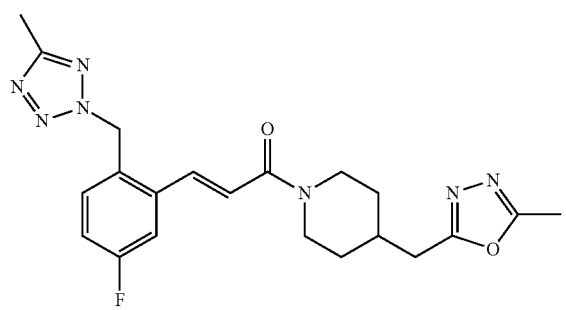 [SMILES: Cc1nnn(Cc2ccc(F)cc2/C=C/C(=O)N2CCC(Cc3nnc(C)o3)CC2)n1]

LC MS:Rt 0.96 min; [M+H]$^+$ 426.3, Method 2minLowpHv01

Example 80

(E)-3-(4-Chloro-2-((4-methyl-2H-1,2,3-triazol-2-yl)methyl)phenyl)-1-(4-((5-methyl-1,3,4-oxadiazol-2-yl)methyl)piperidin-1-yl)prop-2-en-1-one

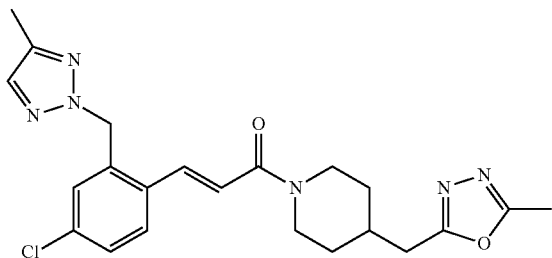 [SMILES: Cc1cnn(Cc2cc(Cl)ccc2/C=C/C(=O)N2CCC(Cc3nnc(C)o3)CC2)n1]

LC MS: Rt 1.07 min; [M+H]+ 441.2, 443.2, Method 2minLowpHv01

Example 81

(E)-1-(4-((5-Methyl-1,3,4-oxadiazol-2-yl)methyl)piperidin-1-yl)-3-(2-((5-methyl-2H-tetrazol-2-yl)methyl)-4-(trifluoromethyl)phenyl)prop-2-en-1-one

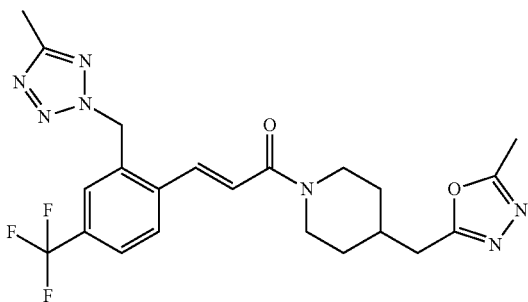 [SMILES: Cc1nnn(Cc2cc(C(F)(F)F)ccc2/C=C/C(=O)N2CCC(Cc3nnc(C)o3)CC2)n1]

T3P® 50% in ethyl acetate (1.132 mL, 1.922 mmol) was added to a solution of (E)-3-(2-((5-methyl-2H-tetrazol-2-yl)methyl)-4-(trifluoromethyl)phenyl)acrylic acid (Intermediate AB) (0.5 g, 1.601 mmol), 2-methyl-5-(piperidin-4-ylmethyl)-1,3,4-oxadiazole (Intermediate BD) and TEA (0.893 mL, 6.41 mmol) in DCM (10 mL) and the resulting mixture stirred at room temperature for 2 h. The reaction mixture was poured into saturated sodium bicarbonate solution (50 mL). The aqueous layer was extracted with ethyl acetate (3×50 mL). The organic solutions were combined washed with, brine (50 mL), dried over sodium sulphate, filtered and concentrated in vacuo. Purification was carried out by silica gel column chromatography eluting with a gradient of iso-hexane to 10% MeOH in ethyl acetate. The product fractions were combined and evaporated in vacuo the residue was crystallised from hot MTBE, the precipitate was aged for 3 h, collected by filtration, washed with a small amount of MTBE and dried to give the title compound as a white solid;

LC MS Rt 1.21 min; [M+H]+ 476.4, Method 2min-LowpHv03

1H NMR (400 MHz, DMSO-D6) δ 8.06 (1H, d), 7.84 (1H, d), 7.79 (1H, dd), 7.73 (1H, d), 7.25 (1H, d), 6.09 (2H, s), 4.43 (1H, m), 4.17 (1H, m), 3.07 (1H, m), 2.79 (2H, d), 2.67 (1H, m), 2.45 (3H, s), 2.40 (3H, s), 2.02 (1H, m), 1.72 (2H, m), 1.15 (2H, m).

Example 82

(E)-4-(3-(4-((5-Methyl-1,3,4-oxadiazol-2-yl)methyl)piperidin-1-yl)-3-oxoprop-1-en-1-yl)-3-((5-methyl-2H-tetrazol-2-yl)methyl)benzonitrile

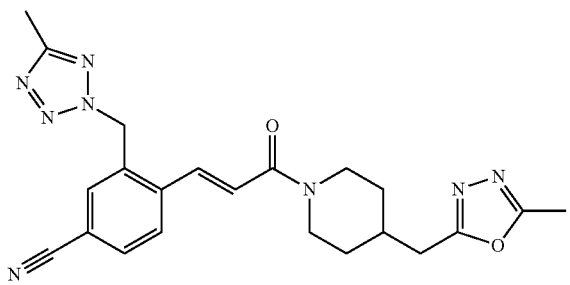 [SMILES: Cc1nnn(Cc2cc(C#N)ccc2/C=C/C(=O)N2CCC(Cc3nnc(C)o3)CC2)n1]

Step 1: 4-Bromo-3-(bromomethyl)benzonitrile

NBS (1.482 g, 8.32 mmol), AIBN (0.057 g, 0.347 mmol) and 4-bromo-3-methylbenzonitrile (1.36 g, 6.94 mmol) were combined in t-butyl acetate (20 mL) and heated at 90° C. for 1 h. The reaction was filtered and the filtrate concentrated in vacuo to give the title compound as as a yellow solid;

1H NMR (400 MHz, CDCl3) δ 7.77) 1H, s), 7.74 (1H, d), 7.46 (1H, s), 4.60 (2H, s).

Step 2: 4-Bromo-3-((5-methyl-2H-tetrazol-2-yl)methyl)benzonitrile

5-Methyl-2H-tetrazole (0.872 g, 10.37 mmol) was added to a mixture of 4-bromo-3-(bromomethyl)benzonitrile (step 1) (1.9 g, 6.91 mmol) and potassium carbonate (1.910 g, 13.82). The reaction was poured into water (100 mL) and extracted with ethyl acetate (3×100 mL). The combined organics were washed with water (100 mL), brine (100 mL), dried over sodium sulphate, filtered and concentrated in vacuo. Purification was carried out by silica gel column chromatography eluting with a gradient of iso-hexane to ethyl acetate The product fractions were combined and concentrated in vacuo to give the title compound as a clear oil;

LC MS Rt 0.96 min; [M+H]+ 278.1, 280.1 Method 2minLowpHv01

Step 3: (E)-4-(3-(4-((5-Methyl-1,3,4-oxadiazol-2-yl)methyl)piperidin-1-yl)-3-oxoprop-1-en-1-yl)-3-((5-methyl-2H-tetrazol-2-yl)methyl)benzonitrile Palladium acetate (6.68 mg, 0.030 mmol) was added to a solution of 4-bromo-3-((5-methyl-2H-tetrazol-2-yl)methyl)benzonitrile (step 2) (99 mg, 0.357 mmol), 2-methyl-5-(piperidin-4-ylmethyl)-1,3,4-oxadiazole (Intermediate G) (70 mg, 0.298 mmol), tri(o-tolyl)phosphine (9.70 mg, 0.032 mmol). in TEA (0.124 mL, 0.893 mmol), DMF (2 mL) and the resulting mixture stirred at 100° C. for 18 h. The reaction was partitioned between water (20 mL) and ethyl acetate (20 mL). The mixture was filtered and the phases separated. The aqueous was extracted with ethyl acetate (2×20 mL). The organic solutions were combined, washed with brine (20 mL), dried over sodium sulphate, filtered and concentrated in vacuo. Purification was carried out by silica gel column chromatography eluting with a gradient of iso-hexane to 10% MeOH in ethyl acetate. The product fractions were combined and evaporated in vacuo to give the title compound as a white foam;

LC MS Rt 0.89 min; [M+H]+ 433.5, Method 2min-LowpHv01

Example 83

(E)-3-(4-Methoxy-2-((5-methyl-2H-tetrazol-2-yl)methyl)phenyl)-1-(4-((5-methyl-1,3,4-oxadiazol-2-yl)methyl)piperidin-1-yl)prop-2-en-1-one

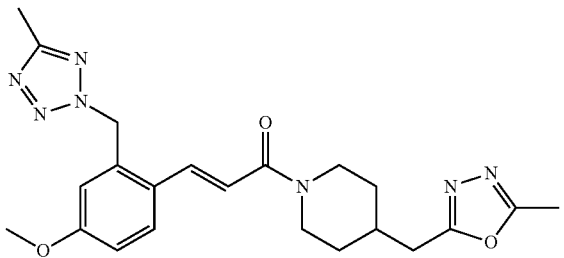

The title compound was prepared by a similar method to Example 75 from the appropriate commercially available starting compounds in step 1. The resulting product is coupled with Intermediate G in step 2;

LC MS: Rt 0.94 min; [M+H]+ 438.4, Method 2min-LowpHv01

Example 84

(E)-2-Methoxy-N-methyl-N-(1-(3-(2-((5-methyl-2H-tetrazol-2-yl)methyl)-4-(trifluoromethyl)phenyl)acryloyl)piperidin-4-yl)acetamide

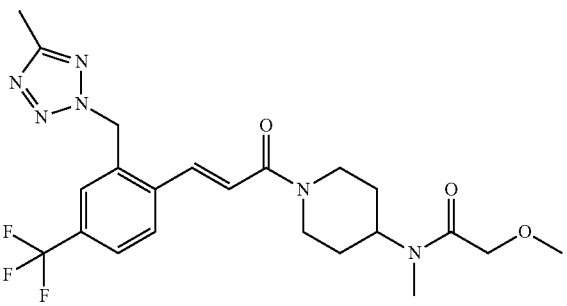 [SMILES: COCC(=O)N(C)C1CCN(C(=O)/C=C/c2ccc(C(F)(F)F)cc2Cn2nnc(C)n2)CC1]

Step 1: (E)-tert-Butyl methyl(1-(3-(2-((5-methyl-2H-tetrazol-2-yl)methyl)-4-(trifluoromethyl)phenyl)acryloyl)piperidin-4-yl)carbamate To (E)-3-(2-((5-methyl-2H-tetrazol-2-yl)methyl)-4-(trifluoromethyl)phenyl)acrylic acid (Intermediate AB)(1 g, 3.20 mmol) and tert-butyl methyl(piperidin-4-yl)carbamate (0.686 g, 3.20 mmol) in DCM (10 mL) was added triethylamine (2.232 mL, 16.01 mmol) followed by T3P® (50% in DMF) (2.244 mL, 3.84 mmol) dropwise and the mixture was stirred at room temperature for 2 h. The resulting mixture was partitioned between EtOAc and water and the aqueous layer was removed. The organic layer was washed with saturated sodium bicarbonate solution, water, brine and dried using a phase separating column. The solvent was removed under reduced pressure. Purification of the crude product by chromatography on silica using a gradient from 0-100% EtOAc in iso-hexane afforded the title compound;

LC-MS: Rt=1.42 mins; [M+H]+ 509.3, Method 2min-LowpHv03

Step 2: (E)-3-(2-((5-Methyl-2H-tetrazol-2-yl)methyl)-4-(trifluoromethyl)phenyl)-1-(4-(methylamino)piperidin-1-yl)prop-2-en-1-one To (E)-tert-butyl methyl(1-(3-(2-((5-methyl-2H-tetrazol-2-yl)methyl)-4-(trifluoromethyl)phenyl)acryloyl)piperidin-4-yl)carbamate (1.6 g, 3.15 mmol) in DCM (12 mL) was added TFA (2.91 mL, 37.8 mmol) and the mixture was stirred at room temperature for 4 h. The organic solvent was removed under reduced pressure. The resulting residue was loaded onto an Isolute® SCX-2 cartridge eluting with MeOH followed by 2M NH3 in MeOH. The methanolic ammonia fractions were concentrated under reduced pressure. To the product was added excess diethyl ether followed by HCl (2M in diethyl ether, 6.3 mmol) and solvent removed under reduced pressure to afford the title compound as a hydrochloride salt;

LC-MS: Rt=0.80 mins; [M+H]+ 408.9, Method 2min-LowpHv03

Step 3: (E)-2-Methoxy-N-methyl-N-(1-(3-(2-((5-methyl-2H-tetrazol-2-yl)methyl)-4-(trifluoromethyl)phenyl)acryloyl)piperidin-4-yl)acetamide To 2-methoxyacetic acid (commercially available) in DCM (2 mL) was added (E)-3-(2-((5-methyl-2H-tetrazol-2-yl)methyl)-4-(trifluoromethyl)phenyl)-1-(4-(methylamino)piperidin-1-yl)prop-2-en-1-one (Example 84, step 2)(100 mg, 0.245 mmol) and triethylamine (0.171 mL, 1.224 mmol). T3P® (50% in DMF) (0.171 mL, 0.294 mmol) was added and the reaction was left to stir at room temperature for 2 h. The resulting mixture was partitioned between EtOAc and water and the aqueous layer was removed. The organic layer was washed with saturated sodium bicarbonate solution, water, brine and dried using a phase separating column. The solvent was removed under reduced pressure. Purification of the crude product by chromatography on silica using a gradient from 0-100% EtOAc in iso-hexane followed by methanol in EtOAc (10%) afforded the title compound;

LC-MS: Rt=1.13 mins; [M+H]+481.3, Method 2min-LowpHv03

1H NMR (400 MHz, DMSO-d6) δ 8.09 (1H, d), 7.86 (1H, s), 7.83-7.70 (2H, mult), 7.28 (1H, d), 6.11 (2H, s), 4.62-3.76 (5H, mult), 3.29 (3H, s), 3.12 (1H, t), 2.77-2.64 (4H, mult), 2.42 (3H, s), 1.72-1.52 (4H, mult).

Example 85

(E)-3-(4-Chloro-2-((5-methyl-2H-tetrazol-2-yl)methyl)phenyl)-1-(3-(5-methyl-1,3,4-oxadiazol-2-yl)azetidin-1-yl)prop-2-en-1-one

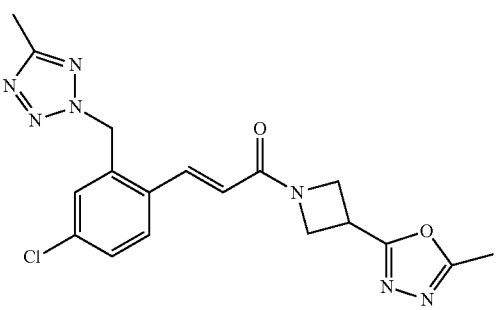 [SMILES: Cc1nnn(Cc2cc(Cl)ccc2/C=C/C(=O)N2CC(c3nnc(C)o3)C2)n1]

The title compound was prepared by a similar method to Example 84, step 1 from (E)-3-(4-chloro-2-((5-methyl-2H-tetrazol-2-yl)methyl)phenyl)acrylic acid (Intermediate A) and 2-(azetidin-3-yl)-5-methyl-1,3,4-oxadiazole (Intermediate BI);

LC-MS: Rt=1.03 mins; [M+H]+ 400.3, Method 2min-LowpHv03.

Example 86

(E)-1-(4-(5-Cyclopropyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one

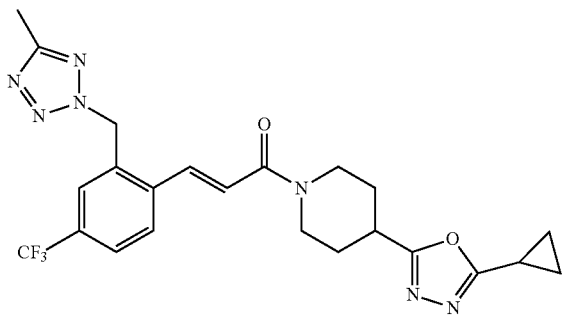 [SMILES: Cc1nnn(Cc2cc(C(F)(F)F)ccc2/C=C/C(=O)N2CCC(c3nnc(C4CC4)o3)CC2)n1]

To (E)-3-(2-((5-methyl-2H-tetrazol-2-yl)methyl)-4-(trifluoromethyl)phenyl)acrylic acid (Intermediate AB) (191 mg, 0.611 mmol) and 2-cyclopropyl-5-(piperidin-4-yl)-1,3,4-oxadiazole (Intermediate IB)(118 mg, 0.611 mmol) in DCM (3 mL) was added triethylamine (0.426 mL, 3.05 mmol) followed by T3P® (50% in DMF) (0.428 mL, 0.733 mmol) dropwise. The mixture was stirred at room temperature for 18 h. The solvent was removed under reduced pressure. The resulting mixture was partitioned between EtOAc and water and the aqueous layer was removed. The organic layer was washed with saturated sodium bicarbonate solution, water, brine and dried using a phase separating column. The solvent was removed under reduced pressure. Purification of the crude product by chromatography on silica using a gradient from 0-100% EtOAc in iso-hexane followed by methanol in EtOAc (10%) afforded the title compound;

LC-MS: Rt=3.82 mins; [M+H]+ 488.5, Method 8min-LowpHv01

1H NMR (400 MHz, DMSO-d6) δ 8.09 (1H, d), 7.86 (1H, s), 7.81 (1H, d), 7.76 (1H, d), 7.28 (1H, d), 6.12 (2H, s), 4.38-4.12 (2H, mult), 3.31-3.19 (2H, mult), 2.97 (1H, t), 2.41 (3H, s), 2.20 (1H, mult), 2.07-2.00 (2H, mult), 1.71-1.51 (2H, mult), 1.15-1.06 (2H, mult), 1.02-0.94 (2H, mult).

Example 87

(R)-4-Fluoro-N-methyl-N-(1-(3-(2-((5-methyl-2H-tetrazol-2-yl)methyl)-4-(trifluoromethyl)phenyl)acryloyl)piperidin-4-yl)benzamide

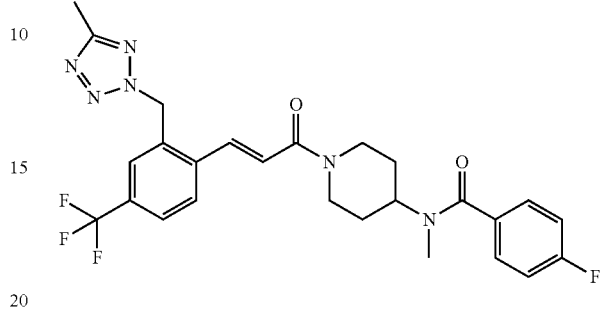

To 4-fluorobenzoic acid (commercially available) in DCM was added (E)-3-(2-((5-methyl-2H-tetrazol-2-yl)methyl)-4-(trifluoromethyl)phenyl)-1-(4-(methylamino)piperidin-1-yl)prop-2-en-1-one (Example 84, step 2) (100 mg, 0.245 mmol) followed by triethylamine (0.171 mL, 1.224 mmol). T3P® (50% in DMF) (0.171 mL, 0.294 mmol) was added and the reaction stirred at room temperature for 2 h. The reaction mixture was partitioned between EtOAc and water and the aqueous layer was removed. The organic layer was washed with saturated sodium bicarbonate solution, water, brine and dried using a phase separating column. The solvent was removed under reduced pressure. Purification of the crude product by chromatography on silica using a gradient from 0-100% EtOAc in iso-hexane afforded the title compound;

LC-MS: Rt=1.30 mins; [M+H]+ 531.3, Method 2min-LowpHv03

1H NMR (400 MHz, DMSO-d6) δ 8.09 (1H, d), 7.86 (1H, s), 7.84-7.71 (2H, mult), 7.48 (2H, mult), 7.28 (3H, mult), 6.11 (2H, s), 4.71-4.12 (2H, mult), 3.17 (1H, broad), 2.92-2.64 (5H, broad mult), 2.41 (3H, s), 1.72 (4H, broad).

Example 88

(E)-1-(4-((3-Methyl-1,2,4-oxadiazol-5-yl)methyl)piperazin-1-yl)-3-(2-((5-methyl-2H-tetrazol-2-yl)methyl)-4-(trifluoromethyl)phenyl)prop-2-en-1-one

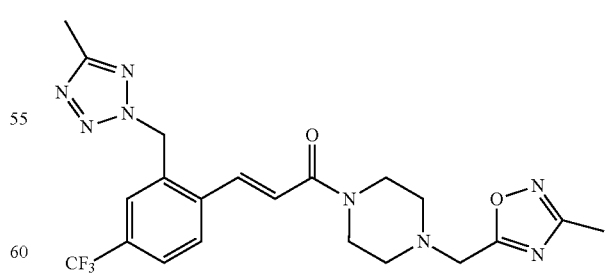

Step 1: (E)-tert-Butyl 4-(3-(2-((5-methyl-2H-tetrazol-2-yl)methyl)-4-(trifluoromethyl)phenyl)acryloyl)piperazine-1-carboxylate T3P® 50% in EtOAc (2.94 mL, 5.00 mmol) was added to a solution of (E)-3-(2-((5-methyl-2H-tetrazol-2-yl)methyl)-

4-(trifluoromethyl)phenyl)acrylic acid (Intermediate AB) (1.3 g, 4.16 mmol), tert-butyl piperazine-1-carboxylate (0.775 g, 4.16 mmol) and triethylamine (2.321 mL, 16.65 mmol) in DCM (10 mL) and the resulting mixture stirred for 5 h at room temperature. The reaction mixture was poured into saturated sodium bicarbonate (100 mL) and the aqueous layer was extracted with ethyl acetate (3×100 mL). The organic solutions were combined and washed with water (50 mL), brine (50 mL), dried over sodium sulphate, filtered and concentrated under reduced pressure. Purification of the crude product by chromatography on silica using a gradient from 0-100% EtOAc in iso-hexane afforded the title compound.

Step 2: (E)-3-(2-((5-Methyl-2H-tetrazol-2-yl)methyl)-4-(trifluoromethyl)phenyl)-1-(piperazin-1-yl)prop-2-en-1-one TFA (20 mL) was added to a solution of (E)-tert-butyl 4-(3-(2-((5-methyl-2H-tetrazol-2-yl)methyl)-4-(trifluoromethyl)phenyl)acryloyl)piperazine-1-carboxylate (1.82 g, 3.79 mmol) in DCM (20 mL) and the resulting mixture stirred for 2 h. Toluene (50 mL) was added and the mixture was concentrated under reduced pressure. The residue was triturated with ether to afford the title compound as a TFA salt;

LC-MS: Rt 0.73 min; [M+H]$^+$ 381.8, Method 2min-LowpHv03

Step: (E)-1-(4-((3-Methyl-1,2,4-oxadiazol-5-yl)methyl)piperazin-1-yl)-3-(2-((5-methyl-2H-tetrazol-2-yl)methyl)-4-(trifluoromethyl)phenyl)prop-2-en-1-one To (E)-3-(2-((5-methyl-2H-tetrazol-2-yl)methyl)-4-(trifluoromethyl)phenyl)-1-(piperazin-1-yl)prop-2-en-1-one (350 mg, 0.708 mmol) and 5-(chloromethyl)-3-methyl-1,2,4-oxadiazole (commercially available) (103 mg, 0.779 mmol) in DCM (5 mL) was added triethylamine (0.395 mL, 2.83 mmol) and the mixture was stirred at room temperature for 18 h. Additional 5-(chloromethyl)-3-methyl-1,2,4-oxadiazole (103 mg, 0.779 mmol) was added and stirring continued for 18 h at room temperature. The reaction mixture was diluted with DCM and washed with water. The organic portion was dried over a phase separating column and solvent concentrated under reduced pressure. Purification of the crude product by chromatography on silica using a gradient from 0-100% EtOAc in iso-hexane afforded the title compound;

LC-MS: Rt=3.51 mins; [M+H]$^+$ 477.4, Method 8min-LowpHv01.

Example 89

(E)-1-(4-((1-Methyl-1H-pyrazol-3-yl)methyl)piperazin-1-yl)-3-(2-((5-methyl-2H-tetrazol-2-yl)methyl)-4-(trifluoromethyl)phenyl)prop-2-en-1-one

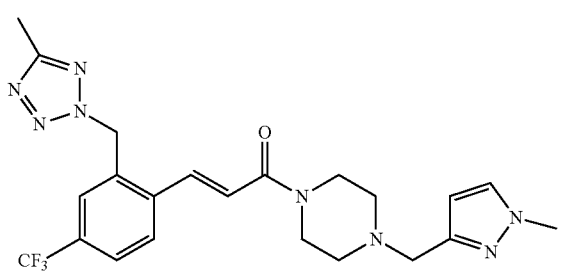 [SMILES: Cc1nnn(Cc2cc(C(F)(F)F)ccc2/C=C/C(=O)N2CCN(Cc3ccn(C)n3)CC2)n1]

To (E)-3-(2-((5-methyl-2H-tetrazol-2-yl)methyl)-4-(trifluoromethyl)phenyl)-1-(piperazin-1-yl)prop-2-en-1-one (Example 88, step 2) (110 mg, 0.289 mmol) in methanol (2.621 mL) was added acetic acid (0.262 mL) and 1-methyl-1H-pyrazole-3-carbaldehyde (commercially available) (47.8 mg, 0.434 mmol) and the mixture was stirred for 5 minutes. 2-Picoline borane (49.0 mg, 0.463 mmol) was added and the mixture was stirred at room temperature for 18 h. The solvent was removed under reduced pressure. Purification of the crude product by chromatography on silica using a gradient from 0-100% EtOAc in iso-hexane followed by methanol in EtOAc (10%) afforded the title compound;

LC-MS: Rt=2.16 mins; [M+H]$^+$475.4, Method 8min-LowpHv01.

$^1$H NMR (400 MHz, DMSO-d6) δ 8.07 (1H, d), 7.85 (1H, s), 7.80 (1H, d), 7.75 (1H, d), 7.6 (1H, s), 7.24 (1H, s), 6.15-6.07 (3H, mult), 3.79 (3H, s), 3.67-3.50 (4H, mult), 3.48-3.28 (4H, mult), 2.44-2.32 (7H, mult).

Example 90

(S,E)-N-Methyl-1-(3-(2-((5-methyl-2H-tetrazol-2-yl)methyl)-4-(trifluoromethyl)phenyl)acryloyl)pyrrolidine-2-carboxamide

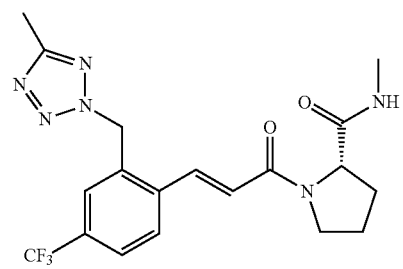 [SMILES: CNC(=O)[C@@H]1CCCN1C(=O)/C=C/c1ccc(C(F)(F)F)cc1Cn1nnc(C)n1]

The title compound was prepared by a similar method to Example 86 from (E)-3-(2-((5-methyl-2H-tetrazol-2-yl)methyl)-4-(trifluoromethyl)phenyl)acrylic acid (Intermediate AB) and (S)-N-methylpyrrolidine-2-carboxamide (commercially available);

LC-MS: Rt=1.12 mins; [M+H]$^+$423.3, Method 2min-LowpHv03

Example 91

(S,E)-4,4-Difluoro-N-methyl-1-(3-(2-((5-methyl-2H-tetrazol-2-yl)methyl)-4-(trifluoromethyl)phenyl)acryloyl)pyrrolidine-2-carboxamide

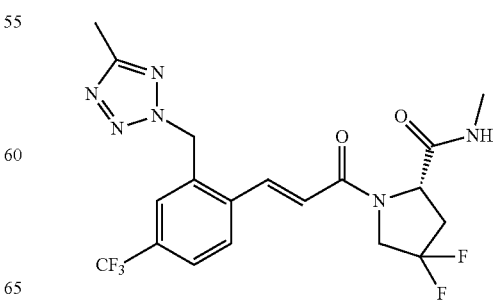

Step 1: (S)-tert-Butyl 4,4-difluoro-2-(methylcarbamoyl)pyrrolidine-1-carboxylate To (S)-1-(tert-butoxycarbonyl)-4,4-difluoropyrrolidine-2-carboxylic acid (commercially available) (442 mg, 1.759 mmol) and methylamine hydrochloride (commercially available) (1188 mg, 17.59 mmol) in DCM (3 mL) was added triethylamine (1.226 mL, 8.80 mmol) followed by T3P® (50% in DMF) (2.054 mL, 3.52 mmol) dropwise. The reaction was stirred at room temperature for 3 h. EtOAc and water was added to the reaction mixture and the aqueous layer was removed. The organic layer was washed with saturated sodium bicarbonate solution, water, brine and dried over a phase separating cartridge. Solvent was removed under reduced pressure to afford the title compound which was taken to the next step without further purification.

Step 2: (S)-4,4-Difluoro-N-methylpyrrolidine-2-carboxamide

To (S)-tert-butyl 4,4-difluoro-2-(methylcarbamoyl)pyrrolidine-1-carboxylate (446 mg, 1.688 mmol) in DCM (5 mL) was added TFA (1.560 mL, 20.25 mmol) and the mixture was stirred at room temperature for 4 h. The solvent was removed under reduced pressure. The resulting residue was loaded onto an Isolute® SCX-2 cartridge eluting with MeOH followed by 2M NH$_3$ in MeOH. The methanolic ammonia fractions were concentrated under reduced pressure. The crude product was used in next step without further purification.

Step 3: (S,E)-4,4-Difluoro-N-methyl-1-(3-(2-((5-methyl-2H-tetrazol-2-yl)methyl)-4-(trifluoromethyl)phenyl)acryloyl)pyrrolidine-2-carboxamide The title compound was prepared by a similar method to Example 86 from (E)-3-(2-((5-methyl-2H-tetrazol-2-yl)methyl)-4-(trifluoromethyl)phenyl)acrylic acid (Intermediate AB) and (S)-4,4-difluoro-N-methylpyrrolidine-2-carboxamide (step 2);

LC-MS: Rt=1.14 mins; [M+H]$^+$459.3, Method 2min-LowpHv03

Example 92

(E)-1-(4-(5-Ethyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one

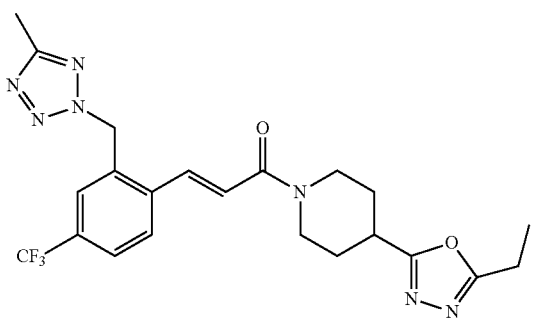 [SMILES: CCc1nnc(C2CCN(C(=O)/C=C/c3ccc(C(F)(F)F)cc3Cn3nnc(C)n3)CC2)o1]

The title compound was prepared by a similar method to Example 86 from (E)-3-(2-((5-methyl-2H-tetrazol-2-yl)methyl)-4-(trifluoromethyl)phenyl)acrylic acid (Intermediate AB) and 2-ethyl-5-(piperidin-4-yl)-1,3,4-oxadiazole (Intermediate IC);

LC-MS: Rt=3.77 mins; [M+H]$^+$ 476.4, Method 8min-LowpHv01.

Example 93

(E)-1-(4-((5-Methyl-1,2,4-oxadiazol-3-yl)methyl)piperazin-1-yl)-3-(2-((5-methyl-2H-tetrazol-2-yl)methyl)-4-(trifluoromethyl)phenyl)prop-2-en-1-one

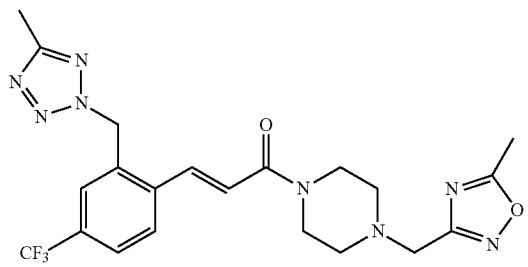 [SMILES: Cc1nnn(Cc2cc(C(F)(F)F)ccc2/C=C/C(=O)N2CCN(Cc3noc(C)n3)CC2)n1]

The title compound was prepared by a similar method to Example 86 from (E)-3-(2-((5-methyl-2H-tetrazol-2-yl)methyl)-4-(trifluoromethyl)phenyl)acrylic acid (Intermediate AB) and 5-methyl-3-(piperazin-1-ylmethyl)-1,2,4-oxadiazole (commercially available);

LC-MS: Rt=1.05 mins; [M+H]$^+$ 476.9, Method 2min-LowpHv03.

Example 94

(E)-3-(4-Chloro-2-((5-methyl-2H-tetrazol-2-yl)methyl)phenyl)-1-(4-(5-ethyl-1,3,4-oxadiazol-2-yl)piperidin-1-yl)prop-2-en-1-one

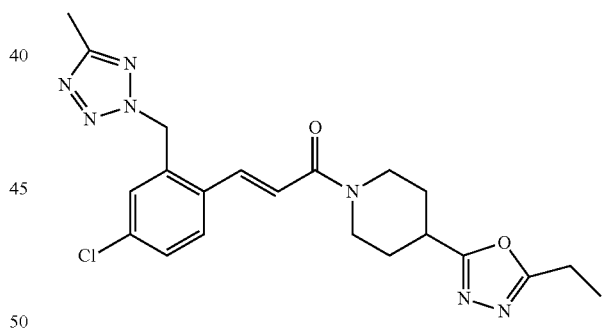

Step 1: (E)-Methyl 1-(3-(4-chloro-2-((5-methyl-2H-tetrazol-2-yl)methyl)phenyl)acryloyl)piperidine-4-carboxylate T3P® (50% in DMF) (1.760 mL, 3.01 mmol) was added dropwise to a solution of (E)-3-(4-chloro-2-((5-methyl-2H-tetrazol-2-yl)methyl)phenyl)acrylic acid (Intermediate A) (700 mg, 2.51 mmol), methyl piperidine-4-carboxylate (commercially available) (451 mg, 2.51 mmol) and triethylamine (1.400 mL, 10.05 mmol) in DCM (7 mL) and the resulting mixture stirred at room temperature for 2 h. The solvent was removed under reduced pressure and the residue was diluted with EtOAc, washed with saturated sodium bicarbonate solution, water, brine and dried over a phase separating column. The solvent was removed under reduced pressure. Purification of the crude product by chromatography on silica using a gradient from 0-100% EtOAc in iso-hexane afforded the title compound;

LC-MS: Rt=1.19 mins; [M+H]⁺404.4, Method 2min-LowpHv03.

Step 2: (E)-1-(3-(4-Chloro-2-((5-methyl-2H-tetrazol-2-yl)methyl)phenyl)acryloyl)piperidine-4-carboxylic acid To (E)-methyl 1-(3-(4-chloro-2-((5-methyl-2H-tetrazol-2-yl)methyl)phenyl)acryloyl)piperidine-4-carboxylate (829 mg, 2.053 mmol) in THF (8 mL) was added 2M sodium hydroxide (3.08 mL, 6.16 mmol) and the mixture was stirred at room temperature for 18 h. The solvent was removed under reduced pressure leaving aqueous residue. The residue was diluted with a minimal volume of EtOAc and the aqueous was acidifed to pH1 using 1M HCl (aq). The product was extracted using DCM and dried using a phase separating column. The solvent was removed under reduced pressure to afford the title compound;

LC-MS: Rt=1.06 mins; [M+H]⁺ 390.4, Method 2min-LowpHv03.

Step 3: (E)-tert-Butyl 2-(1-(3-(4-chloro-2-((5-methyl-2H-tetrazol-2-yl)methyl)phenyl)acryloyl)piperidine-4-carbonyl)hydrazinecarboxylate T3P® (50% in DMF) (1.321 mL, 2.262 mmol) was added dropwise to a solution of (E)-1-(3-(4-chloro-2-((5-methyl-2H-tetrazol-2-yl)methyl)phenyl)acryloyl)piperidine-4-carboxylic acid (735 mg, 1.885 mmol), tert-butyl hydrazinecarboxylate (commercially available) (249 mg, 1.885 mmol) and triethylamine (1.051 mL, 7.54 mmol) in DCM (10 mL) and the resulting mixture was stirred at room temperature for 1 h. The solvent was removed under reduced pressure and the resulting residue was poured into water followed by extraction with EtOAc. The organic extracts were washed with water, saturated sodium bicarbonate solution, water, brine and dried using a phase separating column. The solvent was removed under reduced pressure. Purification of the crude product by chromatography on silica using a gradient from 0-100% EtOAc in iso-hexane afforded the title compound;

LC-MS: Rt=1.14 mins; [M+H]⁺504.5, Method 2min-LowpHv03.

Step 4: (E)-1-(3-(4-Chloro-2-((5-methyl-2H-tetrazol-2-yl)methyl)phenyl)acryloyl)piperidine-4-carbohydrazide To (E)-tert-butyl 2-(1-(3-(4-chloro-2-((5-methyl-2H-tetrazol-2-yl)methyl)phenyl)acryloyl) piperidine-4-carbonyl) hydrazinecarboxylate (685 mg, 1.359 mmol) in DCM (12 mL) was added TFA (1.257 mL, 16.31 mmol) and the mixture was stirred at room temperature for 1 h. The resulting residue was loaded onto an Isolute® SCX-2 cartridge eluting with MeOH followed by 2M NH₃ in MeOH. The methanolic ammonia fractions were concentrated under reduced pressure to afford the title compound as a TFA salt;

LC-MS: Rt=0.89 mins; [M+H]⁺ 405.5, Method 2min-LowpHv03.

Step 5: (E)-1-(3-(4-Chloro-2-((5-methyl-2H-tetrazol-2-yl)methyl)phenyl)acryloyl)-N'-propionylpiperidine-4-carbohydrazide T3P® (50% in DMF) (0.260 mL, 0.446 mmol) was added dropwise to a solution of (E)-1-(3-(4-chloro-2-((5-methyl-2H-tetrazol-2-yl)methyl)phenyl)acryloyl)piperidine-4-carbohydrazide (150 mg, 0.371 mmol), propanoic acid (0.028 mL, 0.371 mmol) and triethylamine (0.259 mL, 1.857 mmol) in DCM (4 mL) and the resulting mixture stirred at room temperature for 2 h. EtOAc was added forming a white suspension. The solution was filtered under vacuum to afford the title compound;

LC-MS: Rt=0.98 mins; [M+H]⁺ 460.5, Method 2min-LowpHv03.

Step 6: (E)-3-(4-Chloro-2-((5-methyl-2H-tetrazol-2-yl)methyl)phenyl)-1-(4-(5-ethyl-1,3,4-oxadiazol-2-yl)piperidin-1-yl)prop-2-en-1-one To (E)-1-(3-(4-Chloro-2-((5-methyl-2H-tetrazol-2-yl)methyl)phenyl)acryloyl)-N'-propionyl piperidine-4-carbohydrazide (80 mg, 0.174 mmol) in DCM (5 mL) was added DIPEA (0.182 mL, 1.044 mmol), polymer bound triphenylphosphine (3 mmol/g loading) (124 mg, 0.261 mmol) and hexachloroethane (124 mg, 0.522 mmol) and the reaction mixture was heated to 45° C. for 4 h. The reaction mixture was filtered under vacuum and the solvent was removed under reduced pressure. Purification of the crude product by chromatography on silica using a gradient from 0-100% EtOAc in iso-hexane followed by methanol in EtOAc (10%) afforded the title compound;

LC-MS: Rt=1.15 mins; [M+H]⁺442.4, Method 2min-LowpHv03.

Example 95

(E)-N-Methyl-N-(1-(3-(2-((5-methyl-2H-tetrazol-2-yl)methyl)-4-(trifluoromethyl)phenyl)acryloyl)piperidin-4-yl)-2-(3-methylisoxazol-5-yl)acetamide

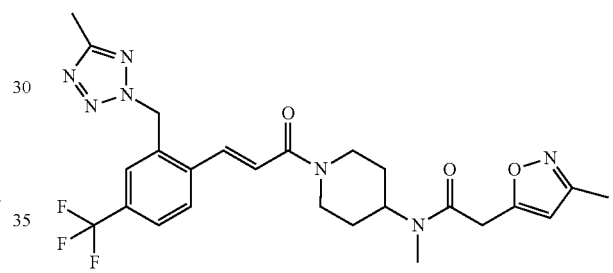

The title compound was prepared by a similar method to Example 86 from (E)-3-(2-((5-methyl-2H-tetrazol-2-yl)methyl)-4-(trifluoromethyl)phenyl)-1-(4-(methylamino)piperidin-1-yl)prop-2-en-1-one (Example 84, step 2) and 2-(3-methylisoxazol-5-yl)acetic acid (commercially available);

LC-MS: Rt=1.20 mins; [M+H]⁺ 532.4, Method 2min-LowpHv03.

Example 96

(E)-3-(4-Chloro-2-((5-methyl-2H-tetrazol-2-yl)methyl)phenyl)-1-(4-(5-cyclopropyl-1,3,4-oxadiazol-2-yl)piperidin-1-yl)prop-2-en-1-one

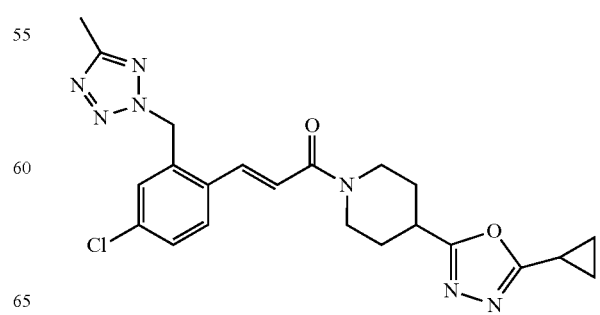

The title compound was prepared by a similar method to Example 84 from (E)-3-(4-chloro-2-((5-methyl-2H-tetrazol-2-yl)methyl)phenyl)acrylic acid (Intermediate A) and 2-cyclopropyl-5-(piperidin-4-yl)-1,3,4-oxadiazole (Intermediate IB);

LC-MS: Rt=3.67 mins; [M+H]+ 454.4, Method 8min-LowpHv01.

Example 97

(E)-1'-(3-(2-((5-Methyl-2H-tetrazol-2-yl)methyl)-4-(trifluoromethyl)phenyl)acryloyl)-[1,4'-bipiperidin]-2-one

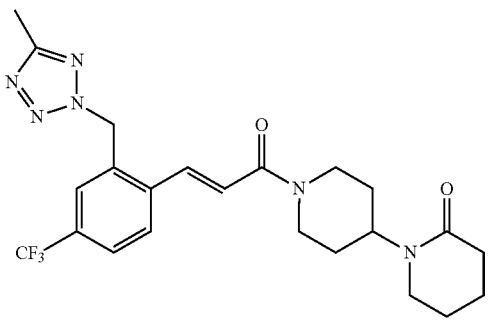 [SMILES: Cc1nnn(Cc2cc(C(F)(F)F)ccc2/C=C/C(=O)N2CCC(N3CCCCC3=O)CC2)n1]

The title compound was prepared by a similar method to Example 86 from (E)-3-(2-((5-methyl-2H-tetrazol-2-yl)methyl)-4-(trifluoromethyl)phenyl)acrylic acid and [1,4'-bipiperidin]-2-one (commercially available);

LC-MS: Rt=3.66 mins; [M+H]+ 477.5, Method 8min-LowpHv01.

Example 98

(E)-3-(4-Chloro-2-((5-methyl-2H-tetrazol-2-yl)methyl)phenyl)-1-((2R,4R)-2-methyl-4-(5-methyl-1,3,4-oxadiazol-2-yl)piperidin-1-yl)prop-2-en-1-one

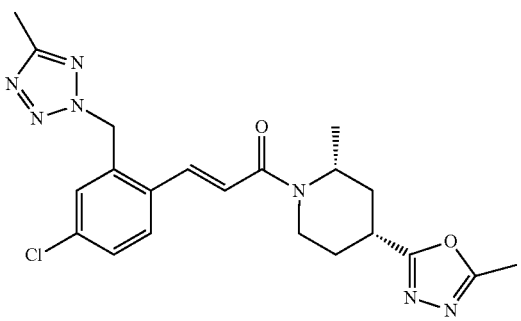 [SMILES: Cc1nnn(Cc2cc(Cl)ccc2/C=C/C(=O)N2CC[C@@H](c3nnc(C)o3)C[C@H]2C)n1]

A diastereomeric mixture of the title compound was prepared by a similar method to Example 84 from (E)-3-(4-chloro-2-((5-methyl-2H-tetrazol-2-yl)methyl)phenyl)acrylic acid (Intermediate A) and 2-methyl-5-(2-methylpiperidin-4-yl)-1,3,4-oxadiazole (Intermediate J). Chiral separation under the following conditions afforded the title compound:

Method Details:
Column: Chiralpak IC, 250×10 mm, 5 um @35 deg C.
Mobile phase: 50% Isopropanol/50% CO2
Flow: 10 mL/min
Detection: UV @220 nm
System: Berger Minigram SFC1
Second eluted peak: SFC retention time=23.52 min
LC-MS: Rt=3.48 mins; [M+H]+ 442.3, Method 8min-LowpHv01.

Example 99

(E)-1-(4-(Methoxymethyl)piperidin-1-yl)-3-(2-((5-methyl-2H-tetrazol-2-yl)methyl)-4-(trifluoromethyl)phenyl)prop-2-en-1-one

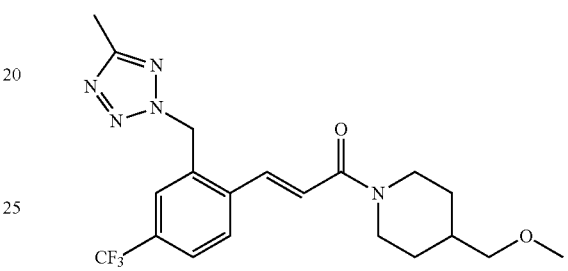

The title compound was prepared by a similar method to Example 86 from (E)-3-(2-((5-methyl-2H-tetrazol-2-yl)methyl)-4-(trifluoromethyl)phenyl)acrylic acid and 4-(methoxymethyl)piperidine (commercially available);

LC-MS: Rt=4.01 mins; [M+H]+ 424.3, Method 8min-LowpHv01.

Example 100

(E)-3-(4-Chloro-2-((5-methyl-2H-tetrazol-2-yl)methyl)phenyl)-1-(4-(5-isopropyl-1,3,4-oxadiazol-2-yl)piperidin-1-yl)prop-2-en-1-one

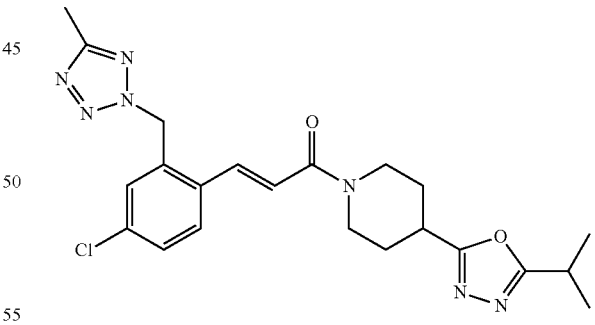

Step 1: (E)-1-(3-(4-Chloro-2-((5-methyl-2H-tetrazol-2-yl)methyl)phenyl)acryloyl)-N'-isobutyryl piperidine-4-carbohydrazide T3P® (50% in DMF) (0.260 mL, 0.446 mmol) was added dropwise to a solution of (E)-1-(3-(4-chloro-2-((5-methyl-2H-tetrazol-2-yl)methyl)phenyl)acryloyl)piperidine-4-carbohydrazide (Example 94, step 4) (150 mg, 0.371 mmol), isobutyric acid (0.034 mL, 0.371 mmol) and triethylamine (0.259 mL, 1.857 mmol) in DCM (4 mL) and the resulting mixture was stirred at room temperature for 2 h. The reaction mixture was diluted with EtOAc and washed with water. The organic solvent was removed under reduced pressure. The crude product was used in the next step without further purification.

Step 2: (E)-3-(4-Chloro-2-((5-methyl-2H-tetrazol-2-yl)methyl)phenyl)-1-(4-(5-isopropyl-1,3,4-oxadiazol-2-yl)piperidin-1-yl)prop-2-en-1-one To (E)-1-(3-(4-chloro-2-((5-methyl-2H-tetrazol-2-yl)methyl)phenyl)acryloyl)-N'-isobutyryl piperidine-4-carbohydrazide (176 mg, 0.371 mmol) in THF (6 mL) was added Burgess reagent (221 mg, 0.928 mmol) and was stirred at reflux for 3 h followed by additional Burgess reagent (221 mg, 0.928 mmol) and was stirred at reflux for a further 3 h. The reaction mixture was left to cool to room temperature and filtered under vacuum. The solvent was removed under reduced pressure. Purification of the crude product by chromatography on silica using a gradient from 0-100% EtOAc in iso-hexane followed by methanol in EtOAc (10%) afforded the title compound. The crude product was then dissolved in EtOAc and washed with water, brine and dried over a phase separating column. The solvent was removed under reduced pressure to afford the title compound;

LC-MS: Rt=1.21 mins; [M+H]+ 456.5, Method 2min-LowpHv03.

Example 101

(E)-3-(2-((5-Methyl-2H-tetrazol-2-yl)methyl)-4-(trifluoromethyl)phenyl)-1-(4-((3-methylisoxazol-5-yl)methyl)piperazin-1-yl)prop-2-en-1-one

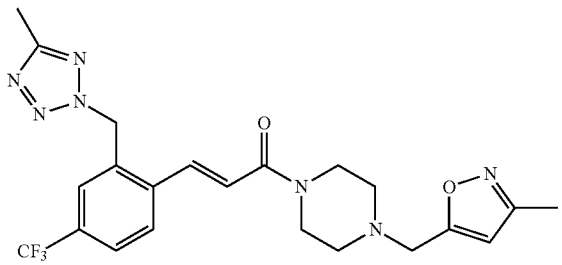 [SMILES: Cc1cc(CN2CCN(C(=O)/C=C/c3ccc(C(F)(F)F)cc3Cn3nnc(C)n3)CC2)on1]

The title compound was prepared by a similar method to Example 89 from (E)-3-(2-((5-methyl-2H-tetrazol-2-yl)methyl)-4-(trifluoromethyl)phenyl)-1-(piperazin-1-yl)prop-2-en-1-one (Example 88, step 2) and 3-methylisoxazole-5-carbaldehyde (commercially available);

LC-MS: Rt=1.01 mins; [M+H]+ 476.3, Method 2min-LowpHv03.

Example 102

(E)-1-(4-(Ethylsulfonyl)piperazin-1-yl)-3-(2-((5-methyl-2H-tetrazol-2-yl)methyl)-4-(trifluoromethyl)phenyl)prop-2-en-1-one

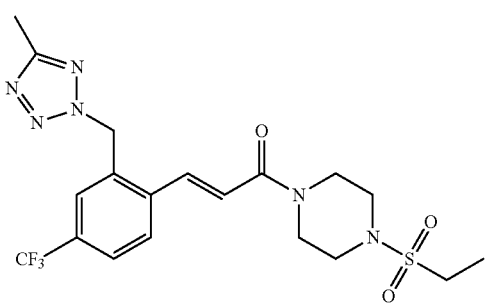 [SMILES: CCS(=O)(=O)N1CCN(C(=O)/C=C/c2ccc(C(F)(F)F)cc2Cn2nnc(C)n2)CC1]

The title compound was prepared by a similar method to Example 86 from (E)-3-(2-((5-methyl-2H-tetrazol-2-yl)methyl)-4-(trifluoromethyl)phenyl)acrylic acid (Intermediate AB) and 1-(ethylsulfonyl)piperazine;

LC-MS: Rt=1.24 mins; [M+H]+ 473.3, Method 2min-LowpHv03.

Example 103

(E)-1-(4-(5-Cyclobutyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one

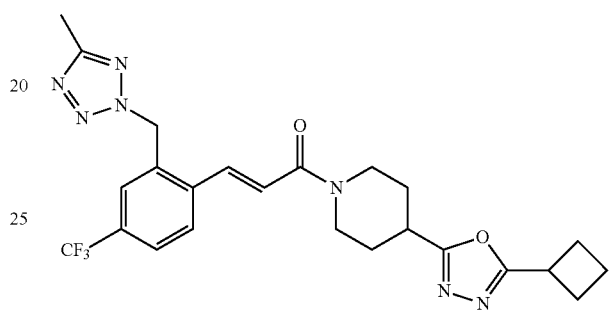

The title compound was prepared by a similar method to Example 86 from (E)-3-(2-((5-methyl-2H-tetrazol-2-yl)methyl)-4-(trifluoromethyl)phenyl)acrylic acid (Intermediate AB) and 2-cyclobutyl-5-(piperidin-4-yl)-1,3,4-oxadiazole (Intermediate ID);

LC-MS: Rt=4.03 mins; [M+H]+ 502.4, Method 8min-LowpHv01.

Example 104

(R,E)-3-(4-Chloro-2-((5-methyl-2H-tetrazol-2-yl)methyl)phenyl)-1-(2-methyl-4-((5-methyl-1,2,4-oxadiazol-3-yl)methyl)piperazin-1-yl)prop-2-en-1-one

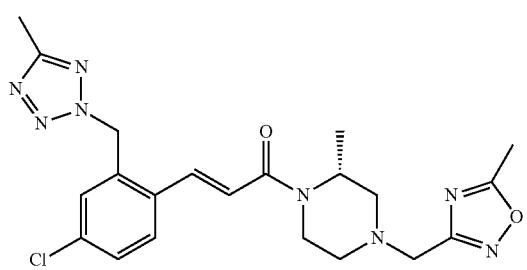 [SMILES: Cc1nnn(Cc2cc(Cl)ccc2/C=C/C(=O)N2CCN(Cc3noc(C)n3)C[C@H]2C)n1]

The title compound was prepared by a similar method to Example 86 from (E)-3-(4-chloro-2-((5-methyl-2H-tetrazol-2-yl)methyl)phenyl)acrylic acid (Intermediate A) and (R)-5-methyl-3-((3-methylpiperazin-1-yl)methyl)-1,2,4-oxadiazole (Intermediate K);

LC-MS: Rt=1.09 mins; [M+H]+ 457.5, Method 2min-LowpHv03

Example 105

(E)-3-(2-((5-Methyl-2H-tetrazol-2-yl)methyl)-4-(trifluoromethyl)phenyl)-1-(4-((5-methylisoxazol-3-yl)methyl)piperazin-1-yl)prop-2-en-1-one

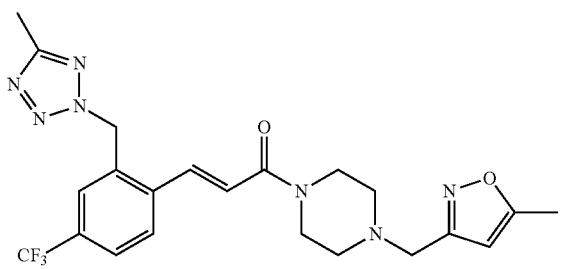 [SMILES: Cc1nnn(Cc2cc(C(F)(F)F)ccc2/C=C/C(=O)N2CCN(Cc3cc(C)on3)CC2)n1]

The title compound was prepared by a similar method to Example 89 from (E)-3-(2-((5-methyl-2H-tetrazol-2-yl)methyl)-4-(trifluoromethyl)phenyl)-1-(piperazin-1-yl)prop-2-en-1-one (Example 88, step 2) and 5-methylisoxazole-3-carbaldehyde (commercially available);

LC-MS: Rt=2.84 mins; [M+H]$^+$ 576.6, Method 8min-LowpHv01

Example 106

(S,E)-1-(2-(Methoxymethyl)-4-((2-methyloxazol-4-yl)methyl)piperazin-1-yl)-3-(2-((5-methyl-2H-tetrazol-2-yl)methyl)-4-(trifluoromethyl)phenyl)prop-2-en-1-one

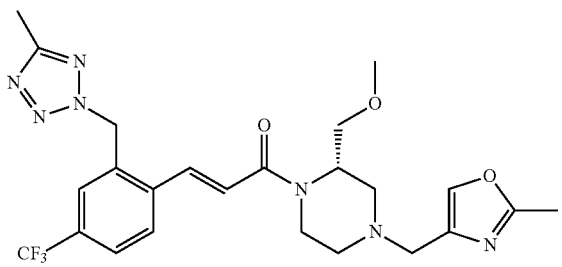 [SMILES: COC[C@@H]1CN(Cc2coc(C)n2)CCN1C(=O)/C=C/c1ccc(C(F)(F)F)cc1Cn1nnc(C)n1]

The title compound was prepared by a similar method to Example 86 from (E)-3-(2-((5-methyl-2H-tetrazol-2-yl)methyl)-4-(trifluoromethyl)phenyl)acrylic acid (Intermediate AB) and (S)-4-((3-(methoxymethyl)piperazin-1-yl)methyl)-2-methyloxazole (Intermediate L);

LC-MS: Rt=2.58 mins; [M+H]$^+$ 521.3, Method 8min-LowpHv01.

Example 107 rac-(E)-1-(3-Methoxypiperidin-1-yl)-3-(2-((5-methyl-2H-tetrazol-2-yl)methyl)-4-(trifluoromethyl)phenyl)prop-2-en-1-one

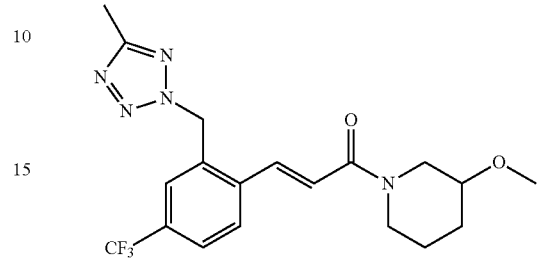

The title compound was prepared by a similar method to Example 86 from (E)-3-(2-((5-methyl-2H-tetrazol-2-yl)methyl)-4-(trifluoromethyl)phenyl)acrylic acid (Intermediate AB) and 3-methoxypiperidine (commercially available);

LC-MS: Rt=1.23 mins; [M+H]$^+$410.6, Method 2min-LowpHv03.

Example 108a ((R or S), E)-1-(3-Methoxypiperidin-1-yl)-3-(2-((5-methyl-2H-tetrazol-2-yl)methyl)-4-(trifluoromethyl)phenyl)prop-2-en-1-one and Example 108b: ((R or S), E)-1-(3-Methoxypiperidin-1-yl)-3-(2-((5-methyl-2H-tetrazol-2-yl)methyl)-4-(trifluoromethyl)phenyl)prop-2-en-1-one

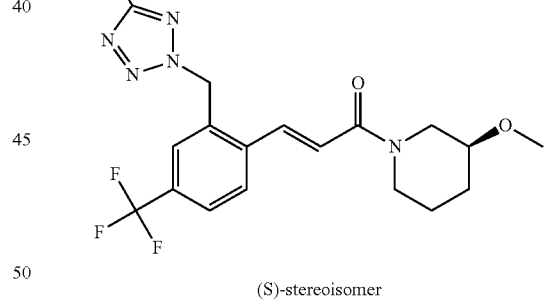

(S)-stereoisomer

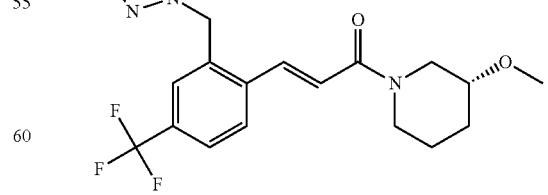

(R)-stereoisomer rac-(E)-1-(3-Methoxypiperidin-1-yl)-3-(2-((5-methyl-2H-tetrazol-2-yl)methyl)-4-(trifluoromethyl)phenyl)prop-2- en-1-one (Example 107) was purified by chiral separation by SFC using the following conditions:
Method Details:
Column: Chiralpak AD-H 250×10 mm, 5 um @35 deg C.
Mobile phase: 25% Methanol/75% CO2
Flow: 10 ml/min
Detection: UV @220 nm
Instrument: Berger Minigram SFC2

Example 108b ((R or S), E)-1-(3-Methoxypiperidin-1-yl)-3-(2-((5-methyl-2H-tetrazol-2-yl)methyl)-4-(trifluoromethyl)phenyl)prop-2-en-1-one First Eluted Peak:
SFC retention time 2.87 min
LC-MS: Rt=1.24 mins; [M+H]$^+$ 409.8, Method 2min-LowpHv03.

Example 108a ((R or S), E)-1-(3-Methoxypiperidin-1-yl)-3-(2-((5-methyl-2H-tetrazol-2-yl)methyl)-4-(trifluoromethyl)phenyl)prop-2-en-1-one Second Eluted Peak:
SFC retention time=3.68 min
LC-MS: Rt=1.24 mins; [M+H]$^+$ 409.8, Method 2min-LowpHv03.

Example 109

(E)-3-(4-Chloro-2-((5-methyl-2H-tetrazol-2-yl)methyl)phenyl)-1-(4-((5-methyl-2H-tetrazol-2-yl)methyl)piperidin-1-yl)prop-2-en-1-one

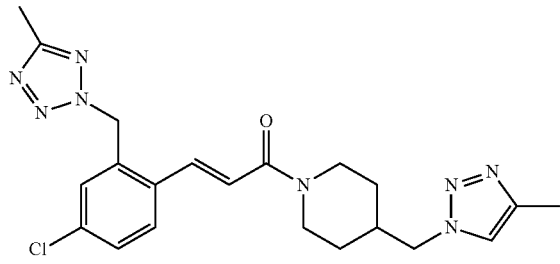 [SMILES: Cc1cn(CC2CCN(C(=O)/C=C/c3ccc(Cl)cc3Cn3nnc(C)n3)CC2)nn1]

Step 1: (E)-3-(4-Chloro-2-((5-methyl-2H-tetrazol-2-yl)methyl)phenyl)-1-(4-(hydroxymethyl)piperidin-1-yl)prop-2-en-1-one T3P® (50% in DMF) (0.503 mL, 0.861 mmol) was added dropwise to a solution of (E)-3-(4-chloro-2-((5-methyl-2H-tetrazol-2-yl)methyl)phenyl)acrylic acid (Intermediate A) (200 mg, 0.718 mmol), piperidin-4-ylmethanol (commercially available) (83 mg, 0.718 mmol) and triethylamine (0.400 mL, 2.87 mmol) in DCM (3 mL). The resulting mixture was stirred at room temperature for 2 h. The reaction mixture was partitioned between a mixture of brine and saturated sodium bicarbonate (1:1, 50 mL) and EtOAc (50 mL). The layers were separated and the aqueous extracted with EtOAc (2×50 mL). The combined organic extracts were washed with brine (50 mL), dried over a phase separating column and solvent removed under reduced pressure. The solvent was removed under reduced pressure. Purification of the crude product by chromatography on silica using a gradient from 0-100% EtOAc in iso-hexane afforded the title compound;
LC-MS: Rt=0.94 mins; [M+H]$^+$ 376.4, Method 2min-LowpHv03.

Step 2: (E)-(1-(3-(4-Chloro-2-((5-methyl-2H-tetrazol-2-yl)methyl)phenyl)acryloyl)piperidin-4-yl)methyl methanesulfonate (E)-3-(4-Chloro-2-((5-methyl-2H-tetrazol-2-yl)methyl)phenyl)-1-(4-(hydroxymethyl)piperidin-1-yl)prop-2-en-1-one (1 g, 2.66 mmol) in DCM (10 mL) was cooled to 0° C. Triethylamine (0.445 mL, 3.19 mmol) was added followed by dropwise addition of methanesulfonyl chloride (0.249 mL, 3.19 mmol). The reaction was stirred at 0° C. for 3 h. Saturated sodium bicarbonate solution was added to the reaction mixture and organic extracts were dried over a phase separating column. The resulting residue was loaded onto an Isolute® SCX-2 cartridge eluting with MeOH followed by 2M NH$_3$ in MeOH. The methanolic ammonia fractions were concentrated under reduced pressure to afford the title compound;
LC-MS: Rt=1.17 mins; [M+H]$^+$454.2, Method 2min-LowpHv03.

Step 3: (E)-3-(4-Chloro-2-((5-methyl-2H-tetrazol-2-yl)methyl)phenyl)-1-(4-((5-methyl-2H-tetrazol-2-yl)methyl)piperidin-1-yl)prop-2-en-1-one To 5-methyl-2H-tetrazole (commercially available) (148 mg, 1.762 mmol) in DMF (4 mL) was added cesium carbonate (574 mg, 1.762 mmol) and the mixture was stirred at 0° C. for 5 minutes. (E)-(1-(3-(4-Chloro-2-((5-methyl-2H-tetrazol-2-yl)methyl)phenyl)acryloyl)piperidin-4-yl)methyl methanesulfonate (400 mg, 0.881 mmol) in DMF (2 mL) was added and the reaction mixture was heated at 120° C. for 3 h. The reaction mixture was left to cool to room temperature and was then poured into water and extracted into EtOAc. The aqueous portion was back extracted with EtOAc and the organic extracts were combined. The combined organic extracts were dried over a phase separating column and the solvent was removed under reduced pressure. Purification of the crude product by chromatography on silica using a gradient from 0-100% EtOAc in iso-hexane followed by methanol in EtOAc (10%) afforded the title compound;
LC-MS: Rt=1.19 mins; [M+H]$^+$442.3, Method 2min-LowpHv03.

Example 110

(E)-3-(4-Chloro-2-((5-methyl-2H-tetrazol-2-yl)methyl)phenyl)-1-(4-(5-((tetrahydro-2H-pyran-4-yl)methyl)-1,3,4-oxadiazol-2-yl)piperidin-1-yl)prop-2-en-1-one

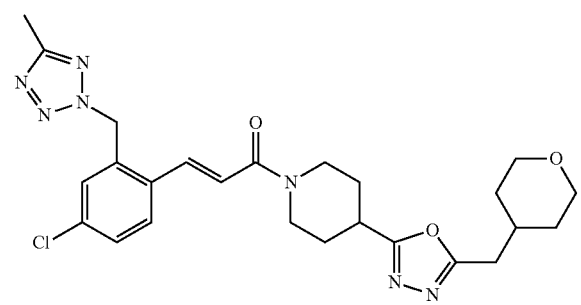 [SMILES: Cc1nnn(Cc2cc(Cl)ccc2/C=C/C(=O)N2CCC(c3nnc(CC4CCOCC4)o3)CC2)n1]

The title compound was prepared by a similar method to Example 100 (steps 1 and 2) from (E)-1-(3-(4-chloro-2-((5-methyl-2H-tetrazol-2-yl)methyl)phenyl)acryloyl)piperidine-4-carbohydrazide (Example 94, step 4) and 2-(tetrahydro-2H-pyran-4-yl)acetic acid (commercially available);

LC-MS: Rt=1.15 mins; [M+H]⁺512.6, Method 2min-LowpHv03.

Example 111

(S,E)-1-(2-(Methoxymethyl)pyrrolidin-1-yl)-3-(2-((5-methyl-2H-tetrazol-2-yl)methyl)-4-(trifluoromethyl)phenyl)prop-2-en-1-one

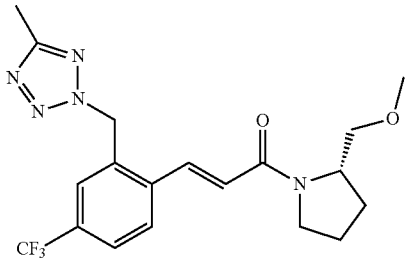 [SMILES: COC[C@@H]1CCCN1C(=O)/C=C/c1ccc(C(F)(F)F)cc1Cn1nnc(C)n1]

The title compound was prepared by a similar method to Example 86 from (E)-3-(2-((5-methyl-2H-tetrazol-2-yl)methyl)-4-(trifluoromethyl)phenyl)acrylic acid (Intermediate AB) and (S)-2-(methoxymethyl)pyrrolidine (commercially available);

LC-MS: Rt=1.29 mins; [M+H]⁺410.3, Method 2min-LowpHv03.

Example 112

(E)-N-Methyl-N-(1-(3-(2-((5-methyl-2H-tetrazol-2-yl)methyl)-4-(trifluoromethyl)phenyl)acryloyl)piperidin-4-yl)cyclopropanesulfonamide

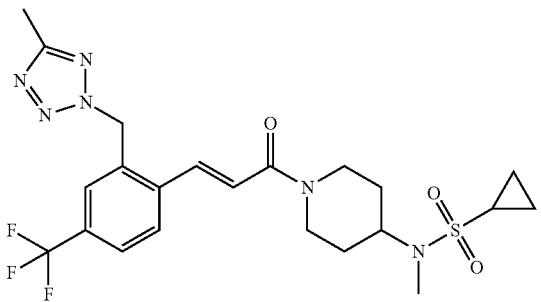 [SMILES: Cc1nnn(Cc2cc(C(F)(F)F)ccc2/C=C/C(=O)N2CCC(N(C)S(=O)(=O)C3CC3)CC2)n1]

To (E)-3-(2-((5-methyl-2H-tetrazol-2-yl)methyl)-4-(trifluoromethyl)phenyl)-1-(4-(methylamino) piperidin-1-yl)prop-2-en-1-one hydrochloride (Example 84, step 2) (131 mg, 0.294 mmol) in DCM (2 mL) was added triethylamine (0.123 mL, 0.883 mmol) followed by cyclopropanesulfonyl chloride (commercially available) (0.060 mL, 0.589 mmol) and the reaction mixture was stirred at room temperature for 2 h. The reaction mixture was diluted with DCM and washed with water. The organic extracts were dried over a phase separating column and solvent removed under reduced pressure. Purification of the crude product by chromatography on silica using a gradient from 0-100% EtOAc in iso-hexane afforded the title compound;

LC-MS: Rt=1.24 mins; [M+H]⁺ 513.6, Method 2min-LowpHv03.

Example 114

(R,E)-3-(4-Chloro-2-((5-methyl-2H-tetrazol-2-yl)methyl)phenyl)-1-(2-methyl-4-((3-methyl-1,2,4-oxadiazol-5-yl)methyl)piperazin-1-yl)prop-2-en-1-one

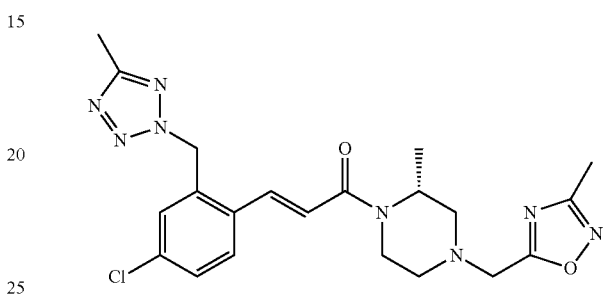

Step 1: (R,E)-tert-Butyl 4-(3-(4-chloro-2-((5-methyl-2H-tetrazol-2-yl)methyl)phenyl)acryloyl)-3-methyl piperazine-1-carboxylate T3P® (50% in DMF) (12.57 mL, 21.53 mmol) was added to a solution of (E)-3-(4-chloro-2-((5-methyl-2H-tetrazol-2-yl)methyl)phenyl)acrylic acid (Intermediate A) (5 g, 17.94 mmol), (R)-tert-butyl 3-methylpiperazine-1-carboxylate (5.64 g, 17.94 mmol) and triethylamine (10.00 mL, 71.8 mmol) in DCM (50 mL) and the resulting mixture stirred at room temperature for 1 h. The reaction mixture was poured into saturated sodium bicarbonate (100 mL) and the aqueous layer was extracted with EtOAc. The organic solutions were combined and washed with water, brine, dried over sodium sulphate, filtered and concentrated under reduced pressure. Purification of the crude product by chromatography on silica using a gradient from 0-75% EtOAc in iso-hexane afforded the title compound;

LC-MS: Rt 1.36 min; [M−100+H]⁺361.4, Method 2min-LowpHv03.

Step 2: (R,E)-3-(4-Chloro-2-((5-methyl-2H-tetrazol-2-yl)methyl)phenyl)-1-(2-methylpiperazin-1-yl)prop-2-en-1-one TFA (40 mL) was added cautiously to a solution of (R,E)-tert-butyl 4-(3-(4-chloro-2-((5-methyl-2H-tetrazol-2-yl)methyl)phenyl)acryloyl)-3-methylpiperazine-1-carboxylate (7.2 g, 15.62 mmol) in DCM (40 mL) and the resulting mixture stirred at room temperature for 1 h. Toluene was added and the mixture was concentrated under reduced pressure. The resulting gum was stirred vigorously in diethyl ether and a white solid formed. The solid was collected by filtration, washed with diethyl ether and dried in the vacuum oven for 18 h to afford the title compound;

LC-MS: Rt 0.70 min; [M+H]⁺ 361.3, Method 2min-LowpHv03.

Step 3: (R,E)-tert-Butyl 2-(4-(3-(4-chloro-2-((5-methyl-2H-tetrazol-2-yl)methyl)phenyl)acryloyl)-3-methylpiperazin-1-yl)acetate tert-Butyl bromoacetate (0.685 mL, 4.63 mmol) was added dropwise to a mixture of (R,E)-3-(4-chloro-2-((5-methyl-2H-tetrazol-2-yl)methyl)phenyl)-1-(2-methylpiperazin-1-yl)prop-2-en-1-one (2 g, 4.21 mmol) and potassium carbonate (1.281 g, 9.27 mmol) in DMF (12 mL). The resulting mixture was stirred at room temperature for 18 h. The reaction was poured into water and extracted with EtOAc. The organic extracts were combined and washed with water, brine, dried over sodium sulphate, filtered and concentrated under reduced pressure to afford the title compound;

LC-MS: Rt 1.05 min; [M+H]⁺ 475.5, Method 2min-LowpHv03

Step 4: (R,E)-2-(4-(3-(4-Chloro-2-((5-methyl-2H-tetrazol-2-yl)methyl)phenyl)acryloyl)-3-methylpiperazin-1-yl)acetic acid TFA (25 mL) was added to a solution of (R,E)-tert-butyl 2-(4-(3-(4-chloro-2-((5-methyl-2H-tetrazol-2-yl)methyl)phenyl)acryloyl)-3-methylpiperazin-1-yl)acetate (1.4 g, 2.95 mmol) in DCM (25 mL) and the resulting mixture was stirred at room temperature for 4 h. The mixture was concentrated under reduced pressure and triturated with diethyl ether to afford the title compound;

LC-MS: Rt 0.85 min; [M+H]⁺419.4, Method 2min-LowpHv03.

Step 5: (Z)—N'-(2-((R)-4-((E)-3-(4-Chloro-2-((5-methyl-2H-tetrazol-2-yl)methyl)phenyl)acryloyl)-3-methylpiperazin-1-yl)acetoxy)acetimidamide T3P® (50% in DMF) (0.418 mL, 0.716 mmol) was added dropwise to a solution of (R,E)-2-(4-(3-(4-chloro-2-((5-methyl-2H-tetrazol-2-yl)methyl)phenyl)acryloyl)-3-methylpiperazin-1-yl)acetic acid (250 mg, 0.597 mmol), N-hydroxyacetimidamide (commercially available) (44.2 mg, 0.597 mmol) and triethylamine (0.333 mL, 2.387 mmol) in DCM (5 mL) and the resulting mixture stirred at room temperature for 1 h. The solvent was removed under reduced pressure. The residue was poured into water and extracted with EtOAc and was washed with water, saturated sodium bicarbonate solution, water, brine and dried using a phase separating column. The solvent was removed under reduced pressure. Purification of the crude product by chromatography on silica using a gradient from 0-100% EtOAc in iso-hexane followed by methanol in EtOAc (10%) afforded the title compound;

LC-MS: Rt=0.84 mins; [M+H]⁺ 475.6, Method 2min-LowpHv03.

Step 6: (R,E)-3-(4-Chloro-2-((5-methyl-2H-tetrazol-2-yl)methyl)phenyl)-1-(2-methyl-4-((3-methyl-1,2,4-oxadiazol-5-yl)methyl)piperazin-1-yl)prop-2-en-1-one To (Z)-N'-(2-((R)-4-((E)-3-(4-chloro-2-((5-methyl-2H-tetrazol-2-yl)methyl)phenyl)acryloyl)-3-methylpiperazin-1-yl)acetoxy)acetimidamide (140 mg, 0.295 mmol) in toluene (5 mL) was added a spatula of molecular sieves and the mixture was heated to reflux for 5 h. The reaction mixture was filtered under vacuum and the solvent was removed under reduced pressure. Purification of the crude product by chromatography on silica using a gradient from 0-100% EtOAc in iso-hexane followed by methanol in EtOAc (10%) afforded the title compound;

LC-MS: Rt=1.14 mins; [M+H]⁺457.3, Method 2min-LowpHv03.

Example 115 rac-(E)-1-(3-Fluoropiperidin-1-yl)-3-(2-((5-methyl-2H-tetrazol-2-yl)methyl)-4-(trifluoromethyl)phenyl)prop-2-en-1-one

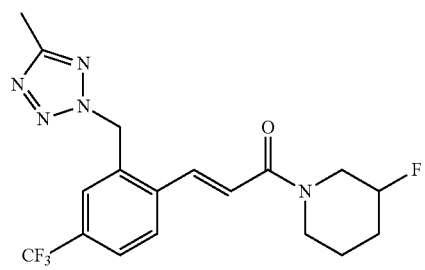 [SMILES: Cc1nnn(Cc2cc(C(F)(F)F)ccc2/C=C/C(=O)N2CCCC(F)C2)n1]

A racemic mixture of the title compound was prepared by a similar method to Example 86 from (E)-3-(2-((5-methyl-2H-tetrazol-2-yl)methyl)-4-(trifluoromethyl)phenyl)acrylic acid (Intermediate AB) and 3-fluoropiperidine (commercially available);

LC-MS: Rt=1.26 mins; [M+H]⁺ 398.3, Method 2min-LowpHv03.

Example 115a ((R or S), E)-1-(3-Fluoropiperidin-1-yl)-3-(2-((5-methyl-2H-tetrazol-2-yl)methyl)-4-(trifluoromethyl)phenyl)prop-2-en-1-one and Example 115b ((R or S), E)-1-(3-Fluoropiperidin-1-yl)-3-(2-((5-methyl-2H-tetrazol-2-yl)methyl)-4-(trifluoromethyl)phenyl)prop-2-en-1-one

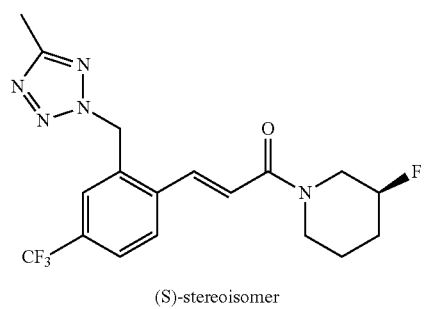

(S)-stereoisomer

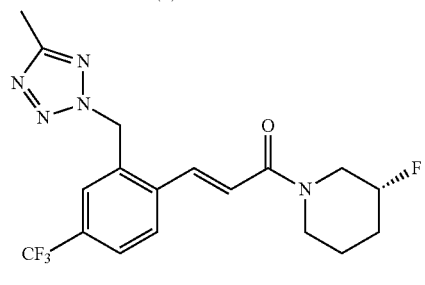

(R)-stereoisomer

Racemic (E)-1-(3-Fluoropiperidin-1-yl)-3-(2-((5-methyl-2H-tetrazol-2-yl)methyl)-4-(trifluoromethyl)phenyl)prop-2- en-1-one (Example 115) (219 mg, 0.551 mmol) was purified by SFC under the following conditions:

Method Details:
Column: Chiralpak IC, 250×10 mm, 5 um @35 deg C.
Mobile phase: 50% Isopropanol/50% CO2
Flow: 10 mL/min
Detection: UV @220 nm
System: Berger Minigram SFC1

Example 115a ((R or S), E)-1-(3-Fluoropiperidin-1-yl)-3-(2-((5-methyl-2H-tetrazol-2-yl)methyl)-4-(trifluoromethyl)phenyl)prop-2-en-1-one Second Eluted Peak:
SFC retention time=3.16 min
LC-MS: Rt=1.26 mins; [M+H]$^+$398.5, Method 2min-LowpHv03.

Example 115b ((R or S), E)-1-(3-Fluoropiperidin-1-yl)-3-(2-((5-methyl-2H-tetrazol-2-yl)methyl)-4-(trifluoromethyl)phenyl)prop-2-en-1-one First Eluted Peak:
SFC retention time=3.04 min
Peak 1=103 mg (3.04 minutes)
LC-MS: Rt=1.26 mins; [M+H]$^+$ 398.6, Method 2min-LowpHv03.

Example 116

(E)-1-(4-((4-Methyl-1,2,5-oxadiazol-3-yl)methyl)piperazin-1-yl)-3-(2-((5-methyl-2H-tetrazol-2-yl)methyl)-4-(trifluoromethyl)phenyl)prop-2-en-1-one

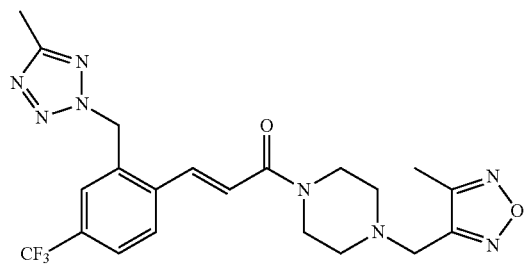 [SMILES: Cc1nnn(Cc2cc(C(F)(F)F)ccc2/C=C/C(=O)N2CCN(Cc3nonc3C)CC2)n1]

The title compound was prepared by a similar method to Example 86 from (E)-3-(2-((5-methyl-2H-tetrazol-2-yl)methyl)-4-(trifluoromethyl)phenyl)acrylic acid (Intermediate AB) and 3-methyl-4-(piperazin-1-ylmethyl)-1,2,5-oxadiazole (commercially available);

LC-MS: Rt=3.79 mins; [M+H]$^+$ 477.3, Method 8min-LowpHv01.

Example 117

(R,E)-3-(2-((5-Methyl-2H-tetrazol-2-yl)methyl)-4-(trifluoromethyl)phenyl)-1-(2-methylpyrrolidin-1-yl)prop-2-en-1-one

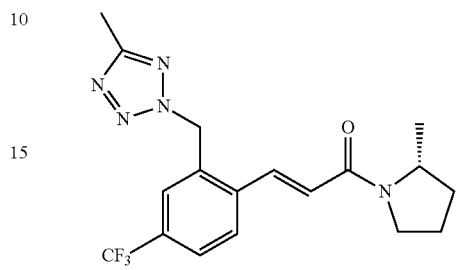

The title compound was prepared by a similar method to Example 86 from (E)-3-(2-((5-methyl-2H-tetrazol-2-yl)methyl)-4-(trifluoromethyl)phenyl)acrylic acid (Intermediate AB) and (R)-2-methylpyrrolidine (commercially available);

LC-MS: Rt=1.29 mins [M+H]$^+$ 379.8, Method 2min-LowpHv03.

Example 118

(E)-4-Fluoro-N-methyl-N-(1-(3-(2-((5-methyl-2H-tetrazol-2-yl)methyl)-4-(trifluoromethyl)phenyl)acryloyl)piperidin-4-yl)benzenesulfonamide

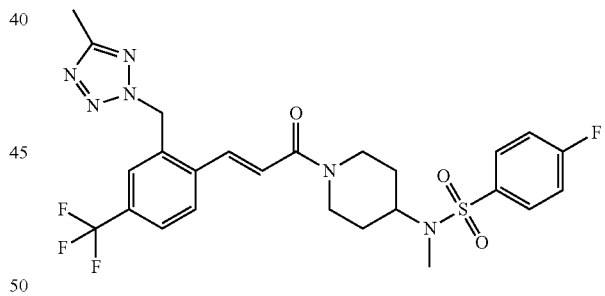

To (E)-3-(2-((5-methyl-2H-tetrazol-2-yl)methyl)-4-(trifluoromethyl)phenyl)-1-(4-(methylamino)piperidin-1-yl)prop-2-en-1-one (Example 84, step 2) (131 mg, 0.294 mmol) in DCM (2 mL) was added triethylamine (0.123 mL, 0.883 mmol) followed by 4-fluorobenzene-1-sulfonyl chloride (commercially available) (115 mg, 0.589 mmol). The reaction mixture was stirred at room temperature for 2 h. The resulting mixture was diluted with DCM and washed with water and the organic portion was dried over a phase separating column. The solvent was removed under reduced pressure. Purification of the crude product by chromatography on silica using a gradient from 0-100% EtOAc in iso-hexane afforded the title compound;

LC-MS: Rt=1.38 mins; [M+H]$^+$ 567.3, Method 2min-LowpHv03.

Example 119

(E)-1-(4-((4-Methoxybenzyl)(methyl)amino)piperidin-1-yl)-3-(2-((5-methyl-2H-tetrazol-2-yl)methyl)-4-(trifluoromethyl)phenyl)prop-2-en-1-one

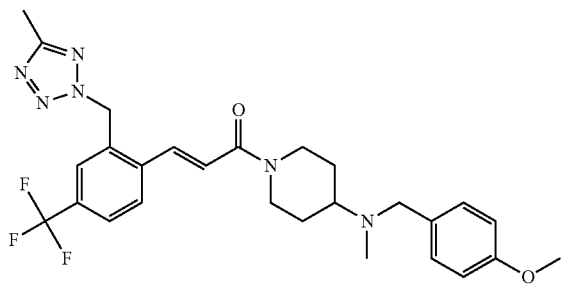 [SMILES: COc1ccc(CN(C)C2CCN(C(=O)/C=C/c3ccc(C(F)(F)F)cc3Cn3nnc(C)n3)CC2)cc1]

The title compound was prepared by a similar method to Example 89 from (E)-3-(2-((5-methyl-2H-tetrazol-2-yl)methyl)-4-(trifluoromethyl)phenyl)-1-(4-(methylamino)piperidin-1-yl)prop-2-en-1-one (Example 84, step 2) and 4-methoxybenzaldehyde (commercially available);

LC-MS: Rt=0.91 mins; [M+H]$^+$ 529.5, Method 2min-LowpHv03.

Example 120

(E)-3-(4-Chloro-2-((5-methyl-2H-tetrazol-2-yl)methyl)phenyl)-1-(4-((4-methyl-2H-1,2,3-triazol-2-yl)methyl)piperidin-1-yl)prop-2-en-1-one

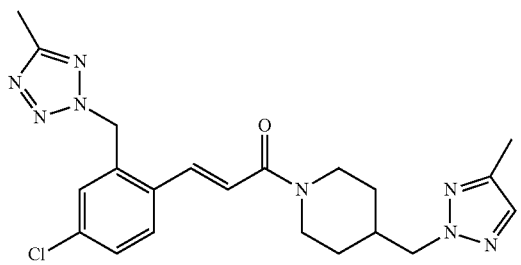 [SMILES: Cc1cnn(CC2CCN(C(=O)/C=C/c3ccc(Cl)cc3Cn3nnc(C)n3)CC2)n1]

To 4-methyl-1H-1,2,3-triazole (commercially available) (128 mg, 1.536 mmol) in DMF (5 mL) was added sodium hydride (60% in mineral oil) (66.5 mg, 1.664 mmol) and the resulting mixture was stirred for 5 minutes. (E)-(1-(3-(4-chloro-2-((5-methyl-2H-tetrazol-2-yl)methyl)phenyl)acryloyl)piperidin-4-yl)methyl methanesulfonate (Example 109, step 2) (581 mg, 1.280 mmol) was added and the mixture was heated to 120° C. for 3 h. The reaction mixture was left to cool and was poured into EtOAc and washed with excess water, brine and dried over a phase separator. The solvent was removed under reduced pressure. Purification of the crude product by chromatography on silica using a gradient from 0-100% EtOAc in iso-hexane followed by 10% methanol in EtOAc afforded the title compound;

LCMS: Rt=1.23 mins; [M+H]$^+$441.5, Method 2min-LowpHv03.

Example 121

(S,E)-3-(2-((5-Methyl-2H-tetrazol-2-yl)methyl)-4-(trifluoromethyl)phenyl)-1-(2-(trifluoromethyl)piperidin-1-yl)prop-2-en-1-one

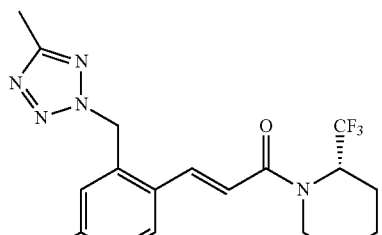

The title compound was prepared by a similar method to Example 86 from (E)-3-(2-((5-methyl-2H-tetrazol-2-yl)methyl)-4-(trifluoromethyl)acrylic acid (Intermediate AB) and (S)-2-(trifluoromethyl)piperidine (commercially available);

LC-MS: Rt=1.45 mins; [M+H]$^+$448.2, Method 2min-LowpHv03.

Example 122

(E)-3-(4-Chloro-2-((5-methyl-2H-tetrazol-2-yl)methyl)phenyl)-1-(4-(5-(piperidin-1-ylmethyl)-1,3,4-oxadiazol-2-yl)piperidin-1-yl)prop-2-en-1-one

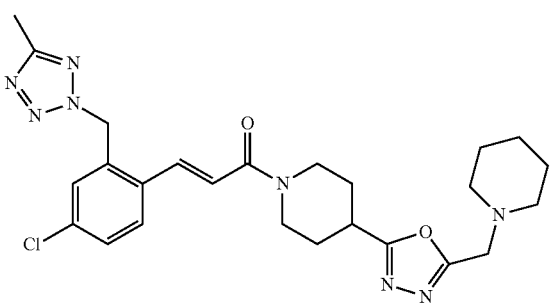

The title compound was prepared by a similar method to Example 100 (steps 1 and 2) from (E)-1-(3-(4-chloro-2-((5-methyl-2H-tetrazol-2-yl)methyl)phenyl)acryloyl)piperidine-4-carbohydrazide (Example 94, step 4) and 2-(piperidin-1-yl)acetic acid (commercially available);

LC-MS: Rt=0.78 mins; [M+H]$^+$ 511.4, Method 2min-LowpHv03.

Example 123

(R,E)-3-(4-Chloro-2-((5-methyl-2H-tetrazol-2-yl)methyl)phenyl)-1-(4-((5-methoxypyridin-2-yl)methyl)-2-methylpiperazin-1-yl)prop-2-en-1-one

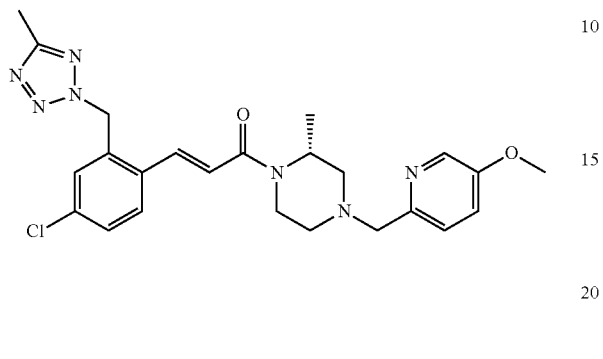

Step 1: (R,E)-tert-Butyl 4-(3-(4-chloro-2-((5-methyl-2H-tetrazol-2-yl)methyl)phenyl)acryloyl)-3-methyl piperazine-1-carboxylate To (E)-3-(4-chloro-2-((5-methyl-2H-tetrazol-2-yl)methyl)phenyl)acrylic acid (Intermediate A) (1.29 g, 4.63 mmol) in NMP (15 mL) was added HATU (2.112 g, 5.55 mmol) and the mixture was stirred at room temperature for 5 minutes. (R)-tert-Butyl 3-methylpiperazine-1-carboxylate (0.927 g, 4.63 mmol) was added followed by DIPEA (1.617 mL, 9.26 mmol) and the reaction was stirred at room temperature for 2 h. The reaction mixture was poured into water and extracted with EtOAc. The organic portion was washed with water, saturated sodium bicarbonate solution, water, brine and dried over a phase separating column. The solvent was removed under reduced pressure. Purification of the crude product by chromatography on silica using a gradient from 0-100% EtOAc in iso-hexane afforded the title compound;

LC-MS: Rt=1.23 mins; [M+H]$^+$ 461.3, Method 2min-LowpH.

Step 2: (R,E)-3-(4-Chloro-2-((5-methyl-2H-tetrazol-2-yl)methyl)phenyl)-1-(2-methylpiperazin-1-yl)prop-2-en-1-one To (R,E)-tert-butyl 4-(3-(4-chloro-2-((5-methyl-2H-tetrazol-2-yl)methyl)phenyl)acryloyl)-3-methylpiperazine-1-carboxylate (2.1 g, 4.56 mmol) in DCM (22 mL) was added TFA (4.21 mL, 54.7 mmol) and the mixture was stirred at room temperature for 4 h. The solvent was removed under reduced pressure. The resulting residue was loaded onto an Isolute® SCX-2 cartridge eluting with MeOH followed by 2M NH$_3$ in MeOH. The methanolic ammonia fractions were concentrated under reduced pressure to afford the title compound;

LC-MS: Rt=2.40 mins; [M+H]$^+$=361.6, Method 10min-LowpH.

Step 3: (R,E)-3-(4-Chloro-2-((5-methyl-2H-tetrazol-2-yl)methyl)phenyl)-1-(4-((5-methoxypyridin-2-yl)methyl)-2-methylpiperazin-1-yl)prop-2-en-1-one The title compound was prepared using a similar method to Example 89 from (R,E)-3-(4-chloro-2-((5-methyl-2H-tetrazol-2-yl)methyl)phenyl)-1-(2-methylpiperazin-1-yl)prop-2-en-1-one (step 2) and 5-methoxypicolinaldehyde (commercially available);

LC-MS: Rt=3.04 mins; [M+H]$^+$482.6, Method 10min-LowpH.

Example 124

(E)-3-(2-((5-Methyl-2H-tetrazol-2-yl)methyl)-4-(trifluoromethyl)phenyl)-1-(2-(trifluoromethyl)piperidin-1-yl)prop-2-en-1-one

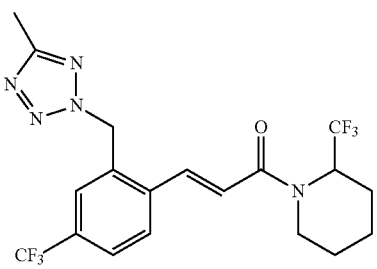 [SMILES: Cc1nnn(Cc2cc(C(F)(F)F)ccc2/C=C/C(=O)N2CCCC[C@H]2C(F)(F)F)n1]

The title compound was prepared by a similar method to Example 86 from (E)-3-(2-((5-methyl-2H-tetrazol-2-yl)methyl)-4-(trifluoromethyl)phenyl)acrylic acid (Intermediate AB) and 2-(trifluoromethyl)piperidine (commercially available);

LC-MS: Rt=1.47 mins; [M+H]$^+$ 448.2, Method 2min-LowpHv03.

Example 125

(E)-N-(1-(3-(4-Chloro-2-((5-methyl-2H-tetrazol-2-yl)methyl)phenyl)acryloyl)piperidin-4-yl)acetamide

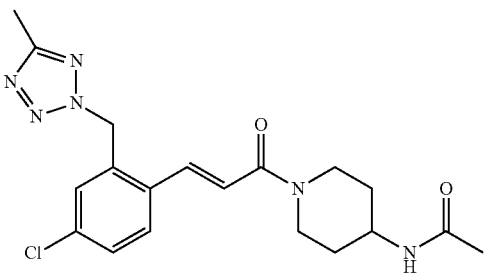 [SMILES: CC(=O)NC1CCN(C(=O)/C=C/c2ccc(Cl)cc2Cn2nnc(C)n2)CC1]

The title compound was prepared by a similar method to Example 86 from (E)-3-(4-chloro-2-((5-methyl-2H-tetrazol-2-yl)methyl)phenyl)acrylic acid (Intermediate A) and N-(piperidin-4-yl)acetamide (commercially available);

LC-MS: Rt=0.97 mins; [M+H]$^+$ 403.3, Method 2min-LowpH.

Example 126

(E)-1-(1-(3-(2-((5-Methyl-2H-tetrazol-2-yl)methyl)-4-(trifluoromethyl)phenyl)acryloyl)piperidin-4-yl)pyrrolidin-2-one

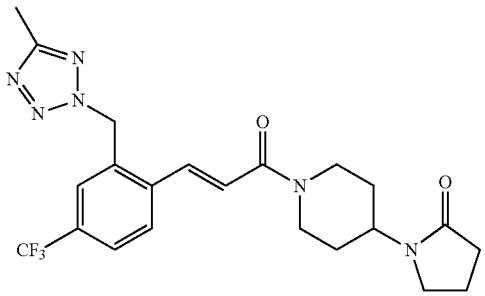 [SMILES: Cc1nnn(Cc2cc(C(F)(F)F)ccc2/C=C/C(=O)N2CCC(N3CCCC3=O)CC2)n1]

The title compound was prepared by a similar method to Example 86 from (E)-3-(2-((5-methyl-2H-tetrazol-2-yl)methyl)-4-(trifluoromethyl)phenyl)acrylic acid (Intermediate AB) and 1-(piperidin-4-yl)pyrrolidin-2-one (commercially available);

LC-MS: Rt=3.55 mins; [M+H]$^+$ 463.4, Method 8min-LowpHv01.

Example 127

(E)-3-(4-Chloro-2-((5-methyl-2H-tetrazol-2-yl)methyl)phenyl)-1-(4-((5-methyl-1,3,4-oxadiazol-2-yl)methyl)piperidin-1-yl)prop-2-en-1-one

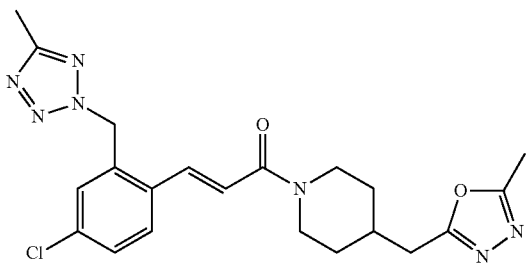 [SMILES: Cc1nnn(Cc2cc(Cl)ccc2/C=C/C(=O)N2CCC(Cc3nnc(C)o3)CC2)n1]

Step 1: (E)-Ethyl 2-(1-(3-(4-chloro-2-((5-methyl-2H-tetrazol-2-yl)methyl)phenyl)acryloyl)piperidin-4-yl)acetate To (E)-3-(4-chloro-2-((5-methyl-2H-tetrazol-2-yl)methyl)phenyl)acrylic acid (Intermediate A) (700 mg, 2.51 mmol) in NMP (10 mL) was added HATU (1146 mg, 3.01 mmol) and the mixture was stirred for 5 minutes. Ethyl 2-(piperidin-4-yl)acetate (commercially available) (430 mg, 2.51 mmol) was added followed by DIPEA (1.316 mL, 7.54 mmol) and stirring continued at room temperature for 18 h. The reaction mixture was poured into water and extracted with EtOAc. The organic extracts were washed with water, saturated sodium bicarbonate solution, water, brine and dried over a phase separating column. The solvent was removed under reduced pressure. Purification of the crude product by chromatography on silica using a gradient from 0-100% EtOAc in iso-hexane afforded the title compound;

LC-MS: Rt=1.19 mins; [M+H]$^+$432.6, Method 2min-LowpH.

Step 2: (E)-2-(1-(3-(4-Chloro-2-((5-methyl-2H-tetrazol-2-yl)methyl)phenyl)acryloyl)piperidin-4-yl)acetic acid To (E)-ethyl 2-(1-(3-(4-chloro-2-((5-methyl-2H-tetrazol-2-yl)methyl)phenyl)acryloyl)piperidin-4-yl)acetate (813 mg, 1.882 mmol) in THF (9 mL) was added 2M sodium hydroxide (2.82 mL, 5.65 mmol) and stirred at room temperature for 18 h. The solvent was removed under reduced pressure. The residue was basified to pH 14 using 2M sodium hydroxide and the resulting aqueous solution washed with EtOAc. The aqueous portion was acidified to pH 1 using 1M HCl and the resulting solid was extracted into DCM. The combined organic extracts were dried over a phase separating column and the solvent was removed under reduced pressure to afford the title compound;

LC-MS: Rt=0.99 mins; [M+H]$^+$ 404.4, Method 2min-LowpH.

Step 3: (E)-N'-Acetyl-2-(1-(3-(4-chloro-2-((5-methyl-2H-tetrazol-2-yl)methyl)phenyl)acryloyl)piperidin-4-yl)acetohydrazide To (E)-2-(1-(3-(4-chloro-2-((5-methyl-2H-tetrazol-2-yl)methyl)phenyl)acryloyl)piperidin-4-yl)acetic acid (200 mg, 0.495 mmol) in NMP (3 mL) was added HATU (226 mg, 0.594 mmol) and the mixture was stirred for 5 minutes at room temperature. Acetohydrazide (36.7 mg, 0.495 mmol) was added followed by DIPEA (0.259 mL, 1.486 mmol) and the reaction mixture was stirred at room temperature for 18 h. The resulting mixture was poured into water followed by addition of EtOAc at which point a product precipitated. The solid was collected by filtration under vacuum to afford the title compound;

LC-MS: Rt=0.89 mins; [M+H]$^+$ 460.6, Method 2min-LowpH.

Step 4: (E)-3-(4-Chloro-2-((5-methyl-2H-tetrazol-2-yl)methyl)phenyl)-1-(4-((5-methyl-1,3,4-oxadiazol-2-yl)methyl)piperidin-1-yl)prop-2-en-1-one To (E)-N'-acetyl-2-(1-(3-(4-chloro-2-((5-methyl-2H-tetrazol-2-yl)methyl)phenyl)acryloyl)piperidin-4-yl)acetohydrazide (150 mg, 0.326 mmol) in DCM (10 mL) was added DIPEA (0.342 mL, 1.957 mmol), polymer bound triphenylphosphine (233 mg, 0.489 mmol) and hexachloroethane (232 mg, 0.978 mmol). The reaction mixture was heated to 45° C. for 4 h. After cooling to room temperature, the mixture was filtered and the filtrate was concentrated under reduced pressure. Purification of the crude product by chromatography on silica using a gradient from 0-100% EtOAc in iso-hexane followed by 10% methanol in EtOAc afforded the title compound;

LC-MS: Rt=1.02 mins; [M+H]$^+$ 442.6, Method 2min-LowpH.

Example 128

(E)-Methyl 1-(3-(4-chloro-2-((5-methyl-2H-tetrazol-2-yl)methyl)phenyl)acryloyl)piperidine-4-carboxylate

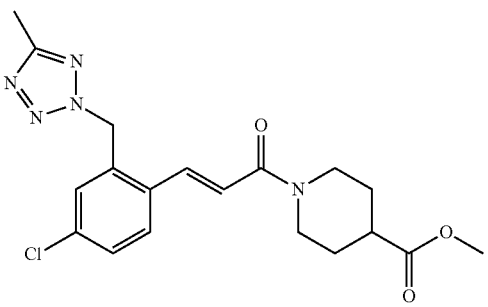 [SMILES: COC(=O)C1CCN(C(=O)/C=C/c2ccc(Cl)cc2Cn2nnc(C)n2)CC1]

The title compound was prepared according to the protocol for Example 123, step 1;

LC-MS: Rt=1.08 mins; [M+H]+ 404.6, Method 2min-LowpH.

Example 129

(E)-3-(4-Chloro-2-((5-methyl-2H-tetrazol-2-yl)methyl)phenyl)-1-(4-(2-morpholino-2-oxoethyl)piperidin-1-yl)prop-2-en-1-one

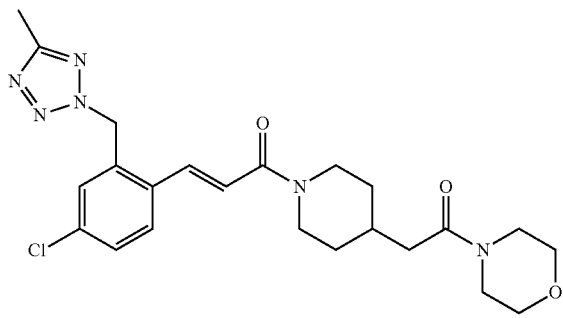 [SMILES: Cc1nnn(Cc2cc(Cl)ccc2/C=C/C(=O)N2CCC(CC(=O)N3CCOCC3)CC2)n1]

To (E)-2-(1-(3-(4-chloro-2-((5-methyl-2H-tetrazol-2-yl)methyl)phenyl)acryloyl)piperidin-4-yl)acetic acid (Example 127 step 2)(100 mg, 0.248 mmol) in NMP (2 mL) was added HATU (113 mg, 0.297 mmol) and the mixture was stirred for 5 minutes at room temperature. Morpholine (0.022 mL, 0.248 mmol) was added followed by DIPEA (0.130 mL, 0.743 mmol) and the reaction mixture was stirred at room temperature for 18 h. The resulting mixture was poured into water and extracted with EtOAc. The organic extracts were washed with water, saturated sodium bicarbonate solution, water, brine and dried over a phase separating column. The solvent was removed under reduced pressure. Purification of the crude product by chromatography on silica using a gradient from 0-100% EtOAc in iso-hexane followed by 10% methanol in EtOAc afforded the title compound;

LC-MS: Rt=3.99 mins; [M+H]+473.7, Method 10min-LowpH.

Example 130

(E)-3-(4-Chloro-2-((5-methyl-2H-tetrazol-2-yl)methyl)phenyl)-1-(3-(4-fluorophenoxy)azetidin-1-yl)prop-2-en-1-one

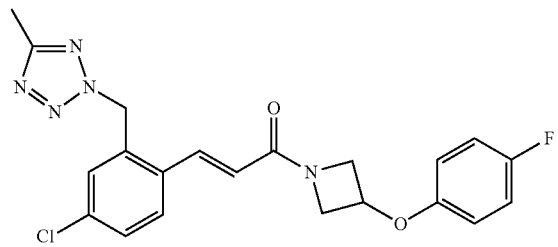 [SMILES: Cc1nnn(Cc2cc(Cl)ccc2/C=C/C(=O)N2CC(Oc3ccc(F)cc3)C2)n1]

The title compound was prepared by a similar method to Example 123 step 1 from (E)-3-(4-chloro-2-((5-methyl-2H-tetrazol-2-yl)methyl)phenyl)acrylic acid (Intermediate A) and (commercially available);

LC-MS: Rt=1.21 mins; [M+H]+428.1, Method 2min-LowpH.

Example 131

(E)-1-((2S,4S)-4-Fluoro-2-(hydroxymethyl)pyrrolidin-1-yl)-3-(2-((5-methyl-2H-tetrazol-2-yl)methyl)-4-(trifluoromethyl)phenyl)prop-2-en-1-one

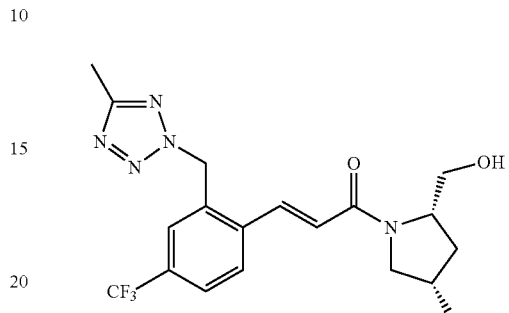

To (E)-3-(2-((5-methyl-2H-tetrazol-2-yl)methyl)-4-(trifluoromethyl)phenyl)acrylic acid (Intermediate AB)(250 mg, 0.801 mmol) in NMP (2 mL) was added HATU (365 mg, 0.961 mmol) and the resulting mixture was stirred at room temperature for 5 minutes. ((2S,4S)-4-fluoropyrrolidin-2-yl)methanol (commercially available) (95 mg, 0.801 mmol) was added followed by DIPEA (0.420 mL, 2.402 mmol) and stirring continued at room temperature for 2 h. The reaction mixture was poured into water and extracted with EtOAc. The organic extracts were washed with water, saturated sodium bicarbonate solution, water, brine and dried using a phase separating column. The solvent was removed under reduced pressure. Purification of the crude product by chromatography on silica using a gradient from 0-100% EtOAc in iso-hexane afforded the title compound;

LC-MS: Rt=1.11 mins; [M+H]+ 414.2, Method 2min-LowpHv03.

1H NMR (400 MHz, DMSO-d6) δ 8.11-7.94 (1H, mult), 7.91-7.75 (3H, mult), 7.17-6.91 (1H, mult), 6.11 (2H, s), 5.49-5.23 (1H, mult), 5.10-4.85 (1H, mult), 4.38-4.18 (1H, mult), 4.00-3.73 (2H, mult), 3.53-3.36 (2H, mult), 2.42 (3H, s), 2.36-2.12 (2H, mult).

Example 132

(S,E)-1-(2-(Hydroxymethyl)-4-((2-methyloxazol-4-yl)methyl)piperazin-1-yl)-3-(2-((5-methyl-2H-tetrazol-2-yl)methyl)-4-(trifluoromethyl)phenyl)prop-2-en-1-one

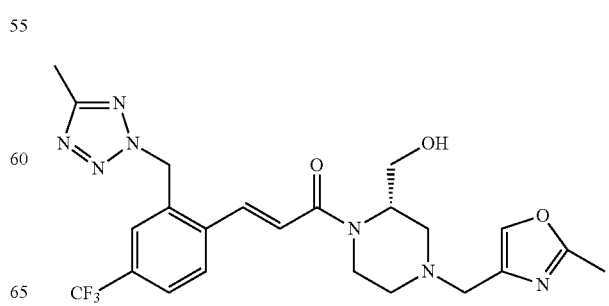

Step 1: (S,E)-tert-Butyl 3-(hydroxymethyl)-4-(3-(2-((5-methyl-2H-tetrazol-2-yl)methyl)-4-(trifluoromethyl)phenyl)acryloyl)piperazine-1-carboxylate, To (E)-3-(2-((5-methyl-2H-tetrazol-2-yl)methyl)-4-(trifluoromethyl)phenyl)acrylic acid (Intermediate AB) (100 mg, 0.320 mmol) in NMP (1.5 mL) was added HATU (146 mg, 0.384 mmol) and the mixture was stirred for 5 minutes. (S)-tert-Butyl 3-(hydroxymethyl) piperazine-1-carboxylate (69.3 mg, 0.320 mmol) was added followed by DIPEA (0.168 mL, 0.961 mmol) and the reaction mixture was stirred at room temperature for 2 h. The resulting mixture was poured into water and extracted with EtOAc. The organics were washed with water, saturated sodium bicarbonate solution, water, brine and dried using a phase separating column. The solvent was removed under reduced pressure. Purification of the crude product by chromatography on silica using a gradient from 0-100% EtOAc in iso-hexane afforded the title compound;

LC-MS: Rt=1.30 mins; [M+H]$^+$ 511.3, Method 2min-HighpHv03.

$^1$H NMR (400 MHz, DMSO-d6) δ 8.12-7.98 (1H, mult), 7.90-7.72 (3H, mult), 7.22 (1H, d), 6.11 (2H, s), 4.90 (1H, br), 4.56-3.74 (4H, mult), 3.45 (2H, br), 3.06-2.74 (3H mult), 2.42 (3H, s), 1.42 (9H, s).

Step 2: (S,E)-1-(2-(Hydroxymethyl)piperazin-1-yl)-3-(2-((5-methyl-2H-tetrazol-2-yl)methyl)-4-(trifluoromethyl) phenyl)prop-2-en-1-one To (S,E)-tert-butyl 3-(hydroxymethyl)-4-(3-(2-((5-methyl-2H-tetrazol-2-yl)methyl)-4-(trifluoromethyl)phenyl)acryloyl)piperazine-1-carboxylate (383 mg, 0.750 mmol) in DCM (4 mL) was added TFA (0.694 mL, 9.00 mmol) and the mixture was stirred at room temperature for 4 h. The solvent was removed under reduced pressure. The resulting residue was loaded onto an Isolute® SCX-2 cartridge eluting with MeOH followed by 2M NH$_3$ in MeOH. The methanolic ammonia fractions were concentrated under reduced pressure to afford the title compound;

LC-MS: Rt=0.75 mins; [M+H]$^+$ 411.0, Method 2min-LowpHv03.

Step 3: (S,E)-1-(2-(Hydroxymethyl)-4-((2-methyloxazol-4-yl)methyl)piperazin-1-yl)-3-(2-((5-methyl-2H-tetrazol-2-yl)methyl)-4-(trifluoromethyl)phenyl)prop-2-en-1-one To (S,E)-1-(2-(hydroxymethyl) piperazin-1-yl)-3-(2-((5-methyl-2H-tetrazol-2-yl)methyl)-4-(trifluoromethyl)phenyl)prop-2-en-1-one (487 μl, 0.244 mmol) in methanol (443 μl) was added acetic acid (44.3 μl) and 2-methyloxazole-4-carbaldehyde (commercially available) (27.1 mg, 0.244 mmol) and the mixture was stirred for 5 minutes. 2-Picoline borane (41.3 mg, 0.390 mmol) was added and the mixture was stirred at room temperature for 18 h. The solvent was removed under reduced pressure. Purification of the crude product by chromatography on silica using a gradient from 0-100% EtOAc in iso-hexane afforded the title compound;

LC-MS 2: Rt=0.85 mins; [M+H]$^+$ 506.4, Method 2min-LowpHv03.

$^1$H NMR (400 MHz, DMSO-d6) δ 8.11-7.96 (1H mult), 7.88-7.66 (4H, mult), 7.21 (1H, d), 6.1-(2H, s), 4.86-4.66 (1H, mult), 4.54-3.90 (2H, mult), 3.77-3.49 (2H, mult), 3.45-3.44 (2H, br), 3.00-2.73 (2H, mult), 2.41 (3H, s), 2.37 (3H, s), 2.10-1.86 (3H, mult).

Example 133

(S,E)-1-(2-(Hydroxymethyl)pyrrolidin-1-yl)-3-(2-((5-methyl-2H-tetrazol-2-yl)methyl)-4-(trifluoromethyl)phenyl)prop-2-en-1-one

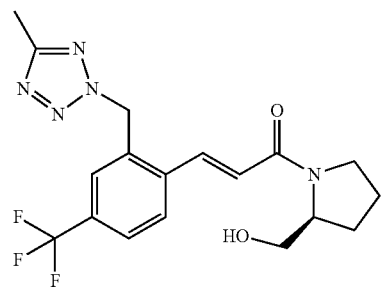 [SMILES: Cc1nnn(Cc2cc(C(F)(F)F)ccc2/C=C/C(=O)N2CCC[C@H]2CO)n1]

The title compound was prepared by a similar method to Example 129 from (E)-3-(2-((5-methyl-2H-tetrazol-2-yl)methyl)-4-(trifluoromethyl)phenyl)acrylic acid (Intermediate AB) and (S)-pyrrolidin-2-ylmethanol (commercially available);

LC-MS: Rt=1.15 mins; [M+H]$^+$396.5, Method 2min-LowpHv03.

Example 134

(E)-3-(4-Chloro-2-((5-methyl-2H-tetrazol-2-yl)methyl)phenyl)-1-(4-(5-(morpholinomethyl)-1,3,4-oxadiazol-2-yl)piperidin-1-yl)prop-2-en-1-one

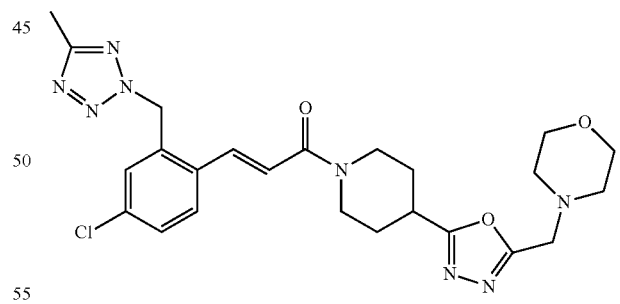

The title compound was prepared by a similar method to Example 127 steps 1-4 from (E)-3-(4-chloro-2-((5-methyl-2H-tetrazol-2-yl)methyl)phenyl)acrylic acid (Intermediate A) and methyl piperidine-4-carboxylate;

LC-MS: Rt=0.86 mins; [M+H]$^+$ 513.5, Method 2min-LowpH.

Example 135

(E)-3-(4-Chloro-2-((5-methyl-2H-tetrazol-2-yl)methyl)phenyl)-1-(4-((5-(trifluoromethyl)pyridin-2-yl)oxy)piperidin-1-yl)prop-2-en-1-one

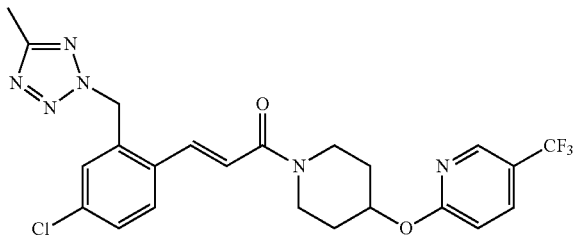 [SMILES: Cc1nnn(Cc2cc(Cl)ccc2/C=C/C(=O)N2CCC(Oc3ccc(C(F)(F)F)cn3)CC2)n1]

Step 1: (E)-3-(4-Chloro-2-((5-methyl-2H-tetrazol-2-yl)methyl)phenyl)-1-(4-hydroxypiperidin-1-yl)prop-2-en-1-one To (E)-3-(4-chloro-2-((5-methyl-2H-tetrazol-2-yl)methyl)phenyl)acrylic acid (Intermediate A) (1 g, 3.59 mmol) in NMP (16 mL) was added HATU (1.637 g, 4.31 mmol) and the mixture was stirred for 5 minutes. Piperidin-4-ol (commercially available) (0.363 g, 3.59 mmol) was added followed by DIPEA (1.253 mL, 7.18 mmol) and the mixture was stirred at room temperature for 2 h. The reaction mixture was poured into water and extracted with EtOAc. The organic extracts were washed with water, saturated sodium bicarbonate solution, water, brine and dried over a phase separating column. The solvent was removed under reduced pressure. Purification of the crude product by chromatography on silica using a gradient from 0-100% EtOAc in iso-hexane followed by methanol in EtOAc (10%) afforded the title compound;

LC-MS: Rt=0.92 mins; [M+H]+ 362.2, Method 2min-LowpH.

Step 2: (E)-3-(4-Chloro-2-((5-methyl-2H-tetrazol-2-yl)methyl)phenyl)-1-(4-((5-(trifluoromethyl)pyridin-2-yl)oxy)piperidin-1-yl) prop-2-en-1-one To polymer bound triphenylphosphine (461 mg, 1.382 mmol) in DCM (5528 µl) at 0° C. was added di-tert-butyl azodicarboxylate (255 mg, 1.106 mmol) followed by 5-(trifluoromethyl) pyridin-2-ol (commercially available) (45.1 mg, 0.276 mmol) and (E)-3-(4-Chloro-2-((5-methyl-2H-tetrazol-2-yl)methyl)phenyl)-1-(4-hydroxypiperidin-1-yl) prop-2-en-1-one (100 mg, 0.276 mmol). The reaction was stirred at room temperature for 18 h. The reaction mixture was filtered under vacuum and the solvent was removed under reduced pressure. TFA (1 mL) was added to the filtrate and the mixture was stirred for 10 minutes. The solvent was removed under reduced pressure. The residue was diluted in DCM and washed with HCl (1M). The organic portion was dried over a phase separating column and the solvent removed under reduced pressure. The crude material was purified by preparative HPLC under the following conditions:
Prep Run 50-98% Gradient low pH 8.5 min UV only trigger
Waters Sunfire C18, 150×30 mm, 5 mic
A=0.1% TFA in Water, B=0.1% TFA in MeCN
0.0-0.5 min 50% B 30 mL/min
0.5-1.0 min 50% B 30-50 mL/min
1.0-7.25 min 50-98% B, 7.25-8.3 min 98% B, 8.3-8.5 min 98-50% B 50 mL/min The product fractions were concentrated under high vacuum to afford the title compound;

LC-MS: Rt=5.85 mins; [M+H]+507.6, Method 10min-LowpH.

Example 136

(E)-3-(4-Chloro-2-((5-methyl-2H-tetrazol-2-yl)methyl)phenyl)-1-(4-((5-(morpholinomethyl)-1,3,4-oxadiazol-2-yl)methyl)piperidin-1-yl)prop-2-en-1-one

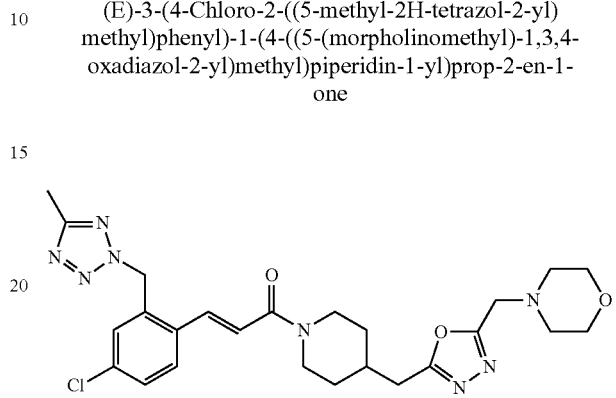

The title compound was prepared by a similar method to Example 127 (steps 3 and 4) from (E)-2-(1-(3-(4-chloro-2-((5-methyl-2H-tetrazol-2-yl)methyl)phenyl)acryloyl)piperidin-4-yl)acetic acid (Example 127, step 2) and 2-morpholinoacetohydrazide (commercially available);

LC-MS: Rt=3.5 mins; [M+H]+ 527.3, Method 10min-LowpH.

Example 137

(S,E)-3-(2-((5-Methyl-2H-tetrazol-2-yl)methyl)-4-(trifluoromethyl)phenyl)-1-(2-(trifluoromethyl)pyrrolidin-1-yl)prop-2-en-1-one

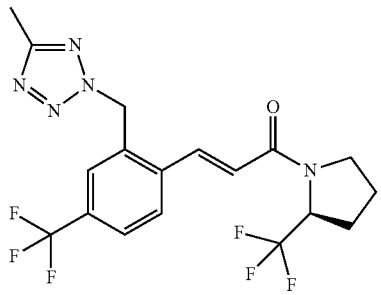 [SMILES: Cc1nnn(Cc2cc(C(F)(F)F)ccc2/C=C/C(=O)N2CCC[C@H]2C(F)(F)F)n1]

The title compound was prepared by a similar method to Example 123, step 1 from (E)-3-(2-((5-methyl-2H-tetrazol-2-yl)methyl)-4-(trifluoromethyl)phenyl)acrylic acid (Intermediate AB) and (S)-2-(trifluoromethyl)pyrrolidine (commercially available);

LC-MS: Rt=1.15 mins; [M+H]+396.5, Method 2min-LowpHv03.

Example 138

(E)-1-(4-Benzyl-4-hydroxypiperidin-1-yl)-3-(4-chloro-2-((5-methyl-2H-tetrazol-2-yl)methyl)phenyl)prop-2-en-1-one-N

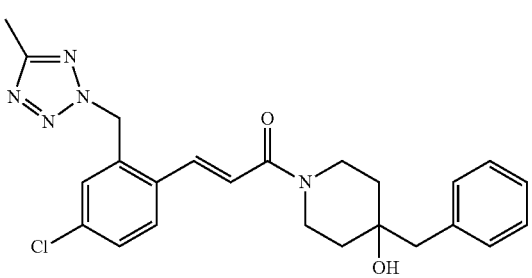 [SMILES: Cc1nnn(Cc2cc(Cl)ccc2/C=C/C(=O)N2CCC(O)(Cc3ccccc3)CC2)n1]

To 4-benzylpiperidin-4-ol in DMA (1 mL) was added triethylamine (30 μl, 0.200 mmol) followed by a pre-stirred solution of (E)-3-(4-chloro-2-((5-methyl-2H-tetrazol-2-yl)methyl)phenyl)acrylic acid (0.1 mmol) and HATU (0.120 mmol) in DMA (1 mL). The reaction mixture was stirred at room temperature for 18 h. The reaction mixture was dried under high vacuum. DMSO (1 mL) was added to the residue and purification of the crude product by preparative HPLC afforded the title compound;

LC-MS: Rt=1.19 mins; [M+H]$^+$452.18, Method 2min-LowpHv01

Example 139

(E)-1-(4-Benzylpiperidin-1-yl)-3-(4-chloro-2-((5-methyl-2H-tetrazol-2-yl)methyl)phenyl)prop-2-en-1-one

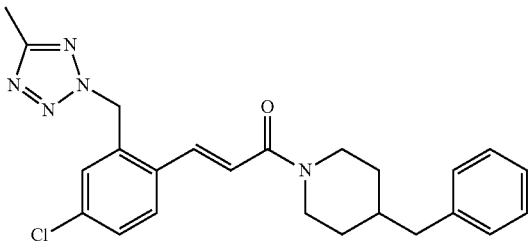 [SMILES: Cc1nnn(Cc2cc(Cl)ccc2/C=C/C(=O)N2CCC(Cc3ccccc3)CC2)n1]

The title compound was prepared analogously to Example 138 from (E)-3-(4-chloro-2-((5-methyl-2H-tetrazol-2-yl)methyl)phenyl)acrylic acid (Intermediate A) and 4-benzylpiperidine (commercially available);

LC-MS: Rt=1.37 mins; [M+H]$^+$ 436.2, Method 2min-LowpH.

Example 140.1

(E)-3-(4-Chloro-2-((5-methyl-2H-tetrazol-2-yl)methyl)phenyl)-1-(4-((5-methoxypyridin-2-yl)methyl)piperazin-1-yl)prop-2-en-1-one

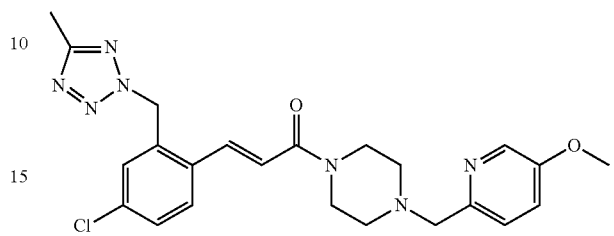

Step 1: tert-Butyl 4-acryloylpiperazine-1-carboxylate

To tert-butyl piperazine-1-carboxylate (1 g, 5.37 mmol) in DCM (10 mL) was added acryloyl chloride (0.512 mL, 6.44 mmol) and DIPEA (1.875 mL, 10.74 mmol) and the resulting mixture was stirred at room temperature. After 18 h, the reaction mixture was diluted with saturated ammonium chloride solution and the product was extracted with DCM. The organic extracts were dried over a phase separating column and the solvent was removed under reduced pressure. Purification of the crude product by chromatography on silica using a gradient from 0-100% EtOAc in iso-hexane afforded the title compound. The crude product was used in the next step without further purification.

Step 2: (E)-tert-Butyl 4-(3-(4-chloro-2-((5-methyl-2H-tetrazol-2-yl)methyl)phenyl)acryloyl)piperazine-1-carboxylate To 2-(2-bromo-5-chlorobenzyl)-5-methyl-2H-tetrazole (Intermediate A, step 1) (1 g, 3.48 mmol) and tert-butyl 4-acryloylpiperazine-1-carboxylate (0.836 g, 3.48 mmol) in DMF (10 mL) under nitrogen was added bis(tri-tert-butylphosphine)palladium(0) (0.177 g, 0.348 mmol) and triethylamine (0.969 mL, 6.96 mmol). The reaction mixture was heated to 80° C. for 2 h and then allowed to cool to room temperature. The mixture was added into water and extracted with EtOAc:Et$_2$O (400 mL:100 mL). The organic extracts were washed with brine and dried over magnesium sulfate and concentrated under reduced pressure. Purification of the crude product by chromatography on silica using a gradient from 0-100% EtOAc in iso-hexane afforded the title compound;

LC-MS: Rt=1.22 mins; [M+H]$^+$447.3, Method 2min-LowpH.

Step 3: (E)-3-(4-Chloro-2-((5-methyl-2H-tetrazol-2-yl)methyl)phenyl)-1-(piperazin-1-yl)prop-2-en-1-one To (E)-tert-butyl 4-(3-(4-chloro-2-((5-methyl-2H-tetrazol-2-yl)methyl)phenyl)acryloyl)piperazine-1-carboxylate (477 mg, 1.067 mmol) in DCM (5 mL) was added TFA (0.493 mL, 6.40 mmol) and the reaction mixture was stirred at room temperature for 3 h. A further portion of TFA (0.493 mL, 6.40 mmol) was added and stirring continued at room temperature for 48 h. The solvent was removed under reduced pressure. The resulting residue was loaded onto an Isolute® SCX-2 cartridge eluting with MeOH followed by 2M NH$_3$ in MeOH. The methanolic ammonia fractions were concentrated under reduced pressure to afford the title compound;

LC-MS: Rt=0.94 mins; [M+H]$^+$ 347.2, Method 2min-LowpH.

Step 4: (E)-3-(4-Chloro-2-((5-methyl-2H-tetrazol-2-yl)methyl)phenyl)-1-(4-((5-methoxypyridin-2-yl)methyl)piperazin-1-yl)prop-2-en-1-one To (E)-3-(4-chloro-2-((5-methyl-2H-tetrazol-2-yl)methyl)phenyl)-1-(piperazin-1-yl)prop-2-en-1-one (750 mg, 2.163 mmol) in methanol (19.700 mL) was added acetic acid (1.970 mL) and 5-methoxypicolinaldehyde (commercially available) (445 mg, 3.24 mmol) and the mixture was stirred for 5 minutes. 2-Picoline borane (367 mg, 3.46 mmol) was added and stirring continued at room temperature for 18 h. The solvent was removed under reduced pressure. Purification of the crude product by chromatography on silica using a gradient from 0-100% EtOAc in iso-hexane followed by methanol in EtOAc (10%) afforded the title compound;

LC-MS: Rt=2.84 mins; [M+H]$^+$468.6, Method 10min-LowpH.

Example 140.2-140.9

The following examples were prepared by a similar method to Example 140.1 from (E)-3-(4-chloro-2-((5-methyl-2H-tetrazol-2-yl)methyl)phenyl)-1-(piperazin-1-yl)prop-2-en-1-one (Example 140.1 step 3) and the appropriate commercially available aldehyde:

Example 140.2

(E)-3-(4-Chloro-2-((5-methyl-2H-tetrazol-2-yl)methyl)phenyl)-1-(4-((3-methylisoxazol-5-yl)methyl)piperazin-1-yl)prop-2-en-1-one

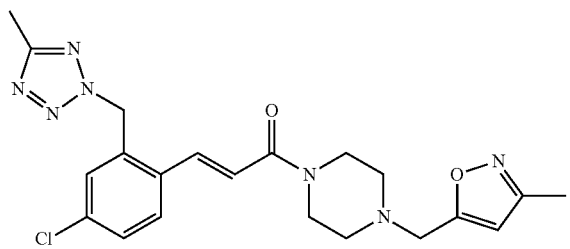

LC-MS: Rt=1.06 mins; [M+H]$^+$ 442.3, Method 2min-LowpHv01.

Example 140.3

(E)-3-(4-Chloro-2-((5-methyl-2H-tetrazol-2-yl)methyl)phenyl)-1-(4-((2-methyloxazol-4-yl)methyl)piperazin-1-yl)prop-2-en-1-one

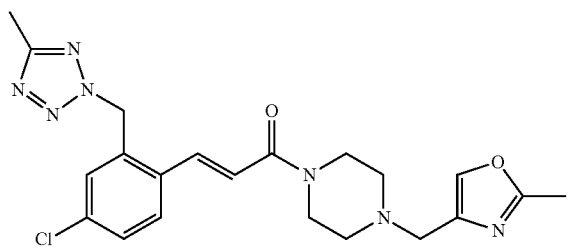

LC-MS: Rt=0.71 mins; [M+H]$^+$ 442.5, Method 2min-LowpHv01.

Example 140.4

(E)-3-(4-Chloro-2-((5-methyl-2H-tetrazol-2-yl)methyl)phenyl)-1-(4-((1-methyl-1H-benzo[d]imidazol-2-yl)methyl)piperazin-1-yl)prop-2-en-1-one

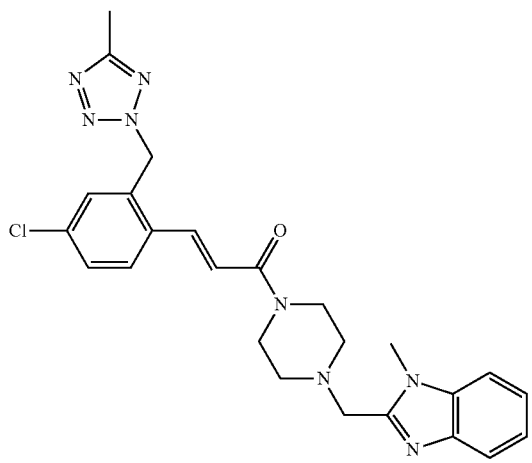 [SMILES: Cc1nnn(Cc2cc(Cl)ccc2/C=C/C(=O)N2CCN(Cc3nc4ccccc4n3C)CC2)n1]

LC-MS: Rt=1.13 mins; [M+H]$^+$ 491.3, Method 2min-LowpHv01.

Example 140.5

(E)-3-(4-Chloro-2-((5-methyl-2H-tetrazol-2-yl)methyl)phenyl)-1-(4-((1-methyl-5-phenyl-1 H-pyrazol-3-yl)methyl)piperazin-1-yl)prop-2-en-1-one

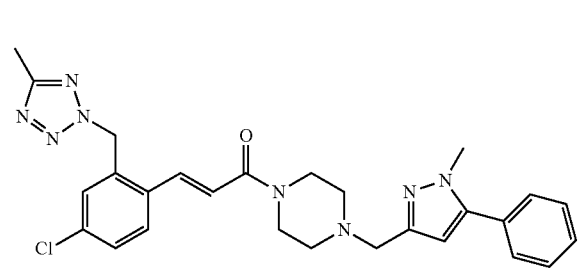 [SMILES: Cc1nnn(Cc2cc(Cl)ccc2/C=C/C(=O)N2CCN(Cc3cc(-c4ccccc4)n(C)n3)CC2)n1]

LC-MS: Rt=1.20 mins; [M+H]$^+$ 516.22, Method 2min-LowpHv01.

Example 140.6

(E)-3-(4-Chloro-2-((5-methyl-2H-tetrazol-2-yl)methyl)phenyl)-1-(4-((1-methyl-3-phenyl-1H-pyrazol-5-yl)methyl)piperazin-1-yl)prop-2-en-1-one

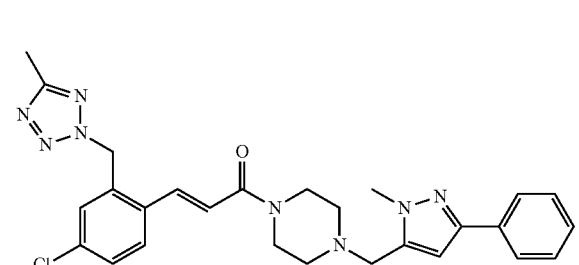

LC-MS: Rt=1.24 mins; [M+H]⁺ 517.3, Method 2min-LowpHv01.

Example 140.7

(E)-3-(4-Chloro-2-((5-methyl-2H-tetrazol-2-yl)methyl)phenyl)-1-(4-((5-methoxypyrazin-2-yl)methyl)piperazin-1-yl)prop-2-en-1-one

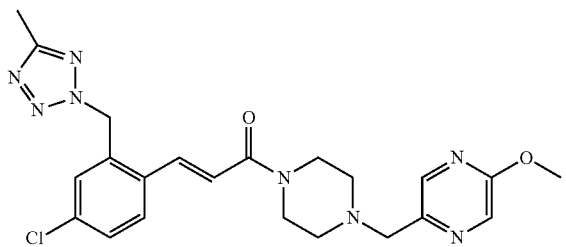 [SMILES: COc1cnc(CN2CCN(C(=O)/C=C/c3ccc(Cl)cc3Cn3nnc(C)n3)CC2)cn1]

LC-MS: Rt=1.09 mins; [M+H]⁺468.18, Method 2min-LowpHv01.

Example 140.8

(E)-3-(4-Chloro-2-((5-methyl-2H-tetrazol-2-yl)methyl)phenyl)-1-(4-((2-morpholinopyrimidin-5-yl)methyl)piperazin-1-yl)prop-2-en-1-one

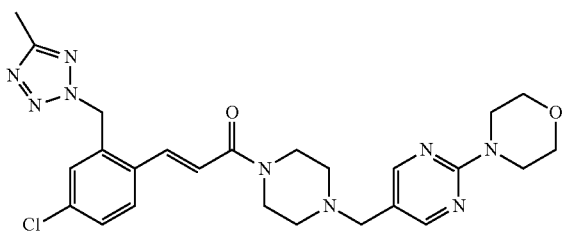 [SMILES: Cc1nnn(Cc2cc(Cl)ccc2/C=C/C(=O)N2CCN(Cc3cnc(N4CCOCC4)nc3)CC2)n1]

LC-MS: Rt=1.10 mins; [M+H]⁺ 524.3, Method 2min-LowpHv01.

Example 140.9

(E)-3-(4-Chloro-2-((5-methyl-2H-tetrazol-2-yl)methyl)phenyl)-1-(4-((1-methyl-1H-pyrazol-4-yl)methyl)piperazin-1-yl)prop-2-en-1-one

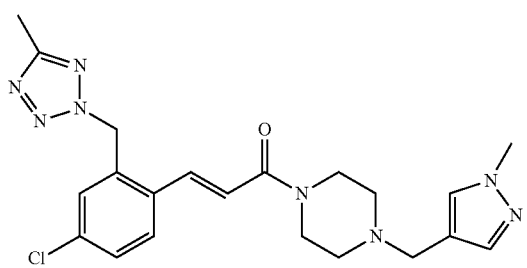 [SMILES: Cc1nnn(Cc2cc(Cl)ccc2/C=C/C(=O)N2CCN(Cc3cnn(C)c3)CC2)n1]

LC-MS: Rt=0.69 mins; [M+H]⁺ 441.5, Method 2min-LowpHv01.

Example 141

(E)-3-(4-Chloro-2-((5-methyl-2H-tetrazol-2-yl)methyl)phenyl)-1-(4-(5-(2,2,2-trifluoroethyl)-1,3,4-oxadiazol-2-yl)piperidin-1-yl)prop-2-en-1-one

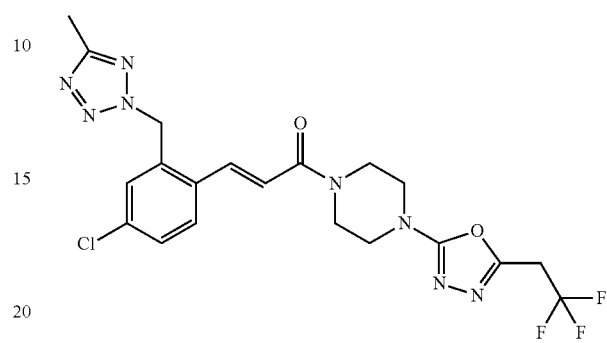

The title compound was prepared by a similar method to Example 100 (steps 1 and 2) from (E)-1-(3-(4-chloro-2-((5-methyl-2H-tetrazol-2-yl)methyl)phenyl)acryloyl)piperidine-4-carbohydrazide (Example 94, step 4) and 3,3,3-trifluoropropanoic acid (commercially available);

LC-MS: Rt=1.22 mins; [M+H]⁺ 496.3, Method 2min-LowpHv03.

Example 142

(E)-3-(2-((5-Methyl-2H-tetrazol-2-yl)methyl)-4-(trifluoromethyl)phenyl)-1-(3-(trifluoromethyl)morpholino)prop-2-en-1-one

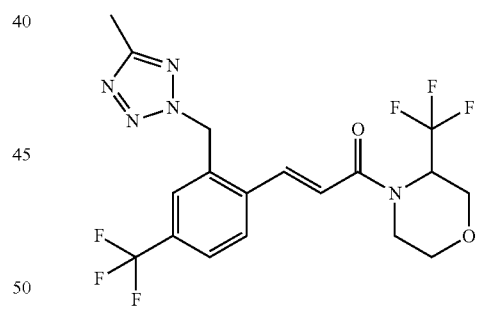

To (E)-3-(2-((5-methyl-2H-tetrazol-2-yl)methyl)-4-(trifluoromethyl)phenyl)acrylic acid (Intermediate AB) (200 mg, 0.641 mmol) in DCM (4 mL) was added 1 drop of DMF followed by oxalyl chloride (0.067 mL, 0.769 mmol) dropwise. The solution was stirred for 15 minutes. The solvent was removed under reduced pressure. The resulting residue was diluted with DCM (4 mL) and excess triethylamine was added dropwise followed by 3-(trifluoromethyl)morpholine (123 mg, 0.641 mmol). The reaction was stirred at room temperature for 2 h. The reaction mixture was washed with water and the organics were dried over a phase separating column. The solvent was removed under reduced pressure. Purification of the crude product by chromatography on silica using a gradient from 0-100% EtOAc in iso-hexane afforded the title compound;

LC-MS: Rt=1.30 mins; [M+H]+ 450.5, Method 2min-LowpHv03.

Example 143

(R,E)-3-(4-Chloro-2-((2-methyl-2H-tetrazol-5-yl)methyl)phenyl)-1-(4-(4-fluorobenzyl)-2-methylpiperazin-1-yl)prop-2-en-1-one

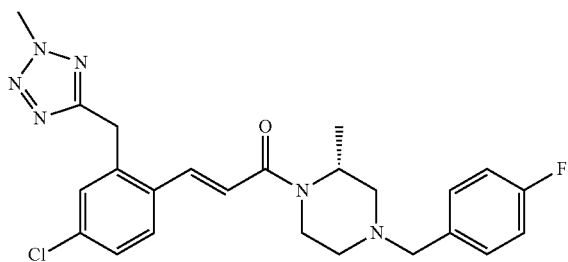 [SMILES: C[C@@H]1CN(Cc2ccc(F)cc2)CCN1C(=O)/C=C/c1ccc(Cl)cc1Cc1nnn(C)n1]

The title compound was prepared by a similar method to Example 41, step 2 from (R)-1-(4-(4-Fluorobenzyl)-2-methylpiperazin-1-yl)prop-2-en-1-one (Intermediate GA) and 5-(2-bromo-5-chlorobenzyl)-2-methyl-2H-tetrazole (Intermediate M);

LC MS: Rt 0.88 min; MS m/z 469.5, 471.6 [M+H]+; Method 2minLowpHv01

Example 144

(R,E)-3-(4-Chloro-2-((5-methyl-1,2,4-oxadiazol-3-yl)methyl)phenyl)-1-(4-(4-fluorobenzyl)-2-methylpiperazin-1-yl)prop-2-en-1-one

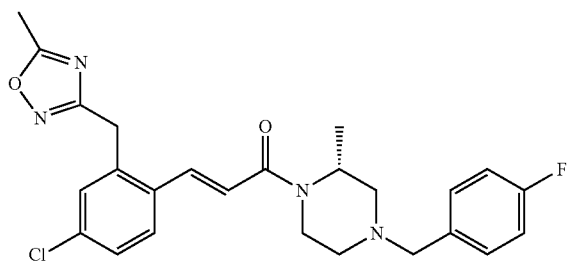 [SMILES: Cc1nc(Cc2cc(Cl)ccc2/C=C/C(=O)N2CCN(Cc3ccc(F)cc3)C[C@H]2C)no1]

The title compound was prepared by a similar method to Example 41, step 2 from 3-(2-bromo-5-chlorobenzyl)-5-methyl-1,2,4-oxadiazole (Intermediate N) and (R)-1-(4-(4-Fluorobenzyl)-2-methylpiperazin-1-yl)prop-2-en-1-one (Intermediate GA);

LCMS: Rt 0.90 min; MS m/z 469.5, 471.5 [M+H]+; Method 2minLowpHv01

Example 145

(E)-N-(2-(1-(3-(4-Chloro-2-((5-methyl-2H-tetrazol-2-yl)methyl)phenyl)acryloyl)piperidin-4-yl)ethyl)-1H-1,2,3-triazole-4-carboxamide

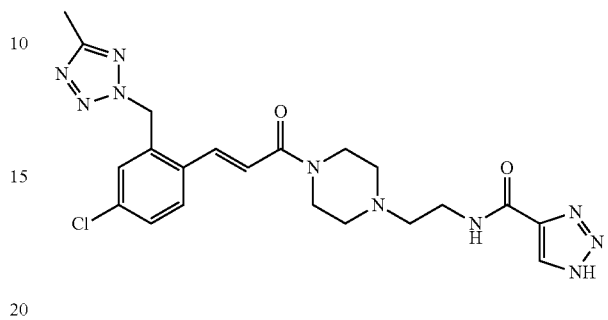

Step 1: (E)-tert-Butyl (2-(1-(3-(4-chloro-2-((5-methyl-2H-tetrazol-2-yl)methyl)phenyl)acryloyl)piperidin-4-yl)ethyl)carbamate To a solution of tert-butyl 2-(piperidin-4-yl)ethylcarbamate (500 mg, 2.190 mmol), ((E)-3-(4-chloro-2-((5-methyl-2H-tetrazol-2-yl)methyl)phenyl)acrylic acid (Intermediate A) (600 mg, 2.2 mmol) and DIPEA (1.5 ml, 8.6 mmol) in DCM (20 ml) was added T3P®, 50% solution in EtOAc (2.5 ml, 4.3 mmol) and the mixture was stirred at room temperature overnight. Further T3P®, 50% solution in EtOAc (0.25 ml, 0.43 mmol) was added and the mixture stirred for 1 hour at room temperature. The mixture was diluted with DCM and washed with 2M NaOH aqueous solution. The DCM layer was separated, dried (MgSO4) and concentrated in vacuo. The residue was purified by chromatography on silica gel, eluting with 25-100% EtOAc in iso-hexanes to afford the title compound (1.03 g).

LC-MS: Rt=1.23 mins; [M+H]+489.3 and 491.5 Method 2minLowpHv01

Step 2: (E)-1-(4-(2-Aminoethyl)piperidin-1-yl)-3-(4-chloro-2-((5-methyl-2H-tetrazol-2-yl)methyl)phenyl)prop-2-en-1-one A solution of (E)-tert-butyl (2-(1-(3-(4-chloro-2-((5-methyl-2H-tetrazol-2-yl)methyl)phenyl)acryloyl)piperidin-4-yl)ethyl)carbamate (Example 145, step 1)(550 mg, 1.13 mmol) in TFA (5 ml, 65 mmol) in DCM (5 ml) was stirred at room temperature for 1 hour. The solvent was removed in vacuo. The residue was re-dissolved in DCM and washed with 2M NaOH solution. The DCM layer was separated, dried (MgSO4) and concentrated in vacuo to afford the title compound (428 mg).

LC-MS: Rt=0.70 mins; [M+H]+389.3 and 391.3; Method 2minLowpHv01

Step 3: (E)-N-(2-(1-(3-(4-Chloro-2-((5-methyl-2H-tetrazol-2-yl)methyl)phenyl)acryloyl)piperidin-4-yl)ethyl)-1H-1,2,3-triazole-4-carboxamide To a solution of (E)-1-(4-(2-aminoethyl)piperidin-1-yl)-3-(4-chloro-2-((5-methyl-2H-tetrazol-2-yl)methyl)phenyl)prop-2-en-1-one (Example 145, step 2)(53 mg, 0.136 mmol), DIPEA (0.095 ml, 0.545 mmol) and 1H-1,2,3-triazole-4-carboxylic acid (17 mg, 0.150 mmol) in DMF (2 ml) was added T3P®, 50% solution in EtOAc (0.159 ml, 0.273 mmol). The resultant mixture was stirred at room temperature for 5 hours. Water (0.5 ml) was added and the mixture was concentrated in vacuo. The residue was purified by reverse phase preparative HPLC to afford the title compound.

Example 146

(E)-N-(2-(1-(3-(4-Chloro-2-((5-methyl-2H-tetrazol-2-yl)methyl)phenyl)acryloyl)piperidin-4-yl)ethyl)-3-(trifluoromethyl)-1H-pyrazole-4-carboxamide

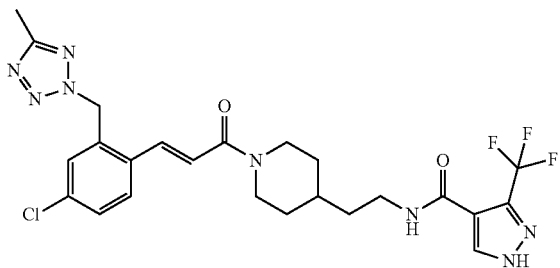 [SMILES: Cc1nnn(Cc2cc(Cl)ccc2/C=C/C(=O)N2CCC(CCNC(=O)c3c[nH]nc3C(F)(F)F)CC2)n1]

Example 146 was prepared by a similar method to that of Example 145 from (E)-1-(4-(2-aminoethyl)piperidin-1-yl)-3-(4-chloro-2-((5-methyl-2H-tetrazol-2-yl)methyl)phenyl)prop-2-en-1-one (Example 145, step 2) and the commercially available acid.

LC-MS: Rt 1.10 mins; MS m/z 551.6 (M+H)+; Method 2minLowpHv01

Example 147

(E)-N-((1-(3-(4-Chloro-2-((5-methyl-2H-tetrazol-2-yl)methyl)phenyl)acryloyl)piperidin-4-yl)methyl)-3-(3-hydroxyisoxazol-5-yl)propanamide

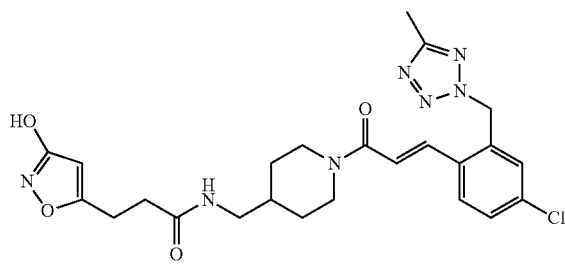 [SMILES: Cc1nnn(Cc2cc(Cl)ccc2/C=C/C(=O)N2CCC(CNC(=O)CCc3cc(O)no3)CC2)n1]

Step 1: tert-Butyl 4-((3-(3-hydroxyisoxazol-5-yl)propanamido)methyl)piperidine-1-carboxylate To a solution of 3-(3-hydroxyisoxazol-5-yl)propanoic acid (300 mg, 1.9 mmol) in DMF (7 mL) was added DIPEA (0.667 mL, 3.8 mmol) followed by COMU (1-[(1-(cyano-2-ethoxy-2-oxoethylideneaminooxy)dimethylaminomorpholino)]uronium hexafluorophosphate) (981 mg, 2.3 mmol) and the resulting mixture stirred 5 mins, then 1-BOC-4-(aminomethyl)piperidine (409 mg, 1.9 mmol) was added. The mixture was stirred at room temperature for 2 hrs. The solution was concentrated in vacuo and the residue suspended in 0.2M aqueous HCl (200 ml). This was extracted with EtOAc (2×100 ml). The extracts were dried (MgSO4) and concentrated. The residue was dissolved in DCM (100 ml) and treated with 2M NaOH (50 ml). The mixture was stirred vigorously overnight. The mixture was acidified with citric acid and the organics removed, dried (MgSO4) and concentrated. The residue was purified by chromatography on silica gel, eluting with 25-100% EtOAc in iso-hexane to afford the title compound;

LCMS Rt=0.91 mins; [M+H]+354.5 Method 2minLowpHv01

Step 2: 3-(3-Hydroxyisoxazol-5-yl)-N-(piperidin-4-ylmethyl)propanamide

To a solution of tert-butyl 4-((3-(3-hydroxyisoxazol-5-yl)propanamido)methyl)piperidine-1-carboxylate (Example 147, step 1)(539 mg, 1.525 mmol) in EtOAc (15 mL) was added 4N HCl in dioxane (15 ml, 60.0 mmol) and the resulting mixture stirred at room temperature for 2 hrs. The mixture was concentrated in vacuo to afford the title compound;

LC-MS: Rt=0.58 mins; [M+H]+254.5; Method 2minLowpHv01

Step 3: (E)-N-((1-(3-(4-Chloro-2-((5-methyl-2H-tetrazol-2-yl)methyl)phenyl)acryloyl)piperidin-4-yl)methyl)-3-(3-hydroxyisoxazol-5-yl)propanamide To a solution of (E)-3-(4-chloro-2-((5-methyl-2H-tetrazol-2-yl)methyl)phenyl)acrylic acid (Intermediate A) (96 mg, 0.345 mmol) and 3-(3-hydroxyisoxazol-5-yl)-N-(piperidin-4-ylmethyl)propanamide (Example 147, step 2)(100 mg, 0.345 mmol) in DMF (2 mL) was added DIPEA (0.241 mL, 1.380 mmol) and 50% T3P® in DMF (0.403 mL, 0.690 mmol). The mixture was stirred at room temperature overnight. DIPEA (0.241 mL, 1.380 mmol) and 50% T3P® in DMF (0.403 mL, 0.690 mmol) were added. The solution was stirred at room temperature for 7 hrs, The solution was concentrated in vacuo and diluted with water (10 ml). This was extracted with EtOAc (2×50 ml). The extracts were dried (MgSO4) and concentrated. The residue was purified by chromatography on silica gel, eluting with [1% AcOH in EtOAc]/iso-hexanes to afford the title compound.

LCMS; Rt=0.96 mins; [M+H]+514.5 and 516.4; Method 2minLowpHv01

Example 148

(E)-N-(2-(1-(3-(4-Chloro-2-((5-methyl-2H-tetrazol-2-yl)methyl)phenyl)acryloyl)piperidin-4-yl)ethyl)-N-methyl-2-oxo-2,3-dihydrooxazole-5-carboxamide

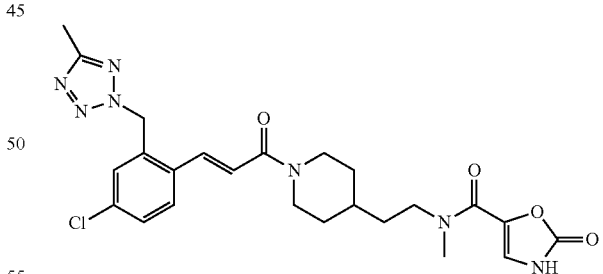

Step 1: 2-Oxo-2,3-dihydrooxazole-5-carboxylic acid

To a solution of ethyl 2-oxo-2,3-dihydrooxazole-5-carboxylate (300 mg, 1.91 mmol) in THF (5 ml,) was added a solution of LiOH.H2O (176 mg, 4.2 mmol) in water (5 ml). The mixture was stirred at room temperature for 2 hours. A solution of LiOH.H2O (88 mg, 2.1 mmol) in water (1 ml) was added and the mixture was stirred at room temperature for an additional 90 mins. A further portion of LiOH.H2O (88 mg, 2.1 mmol) in water (1 ml) was added and the mixture was stirred at room temperature overnight. The solvent was removed in vacuo. To the residue was added 4M HCl in dioxane (6 ml, 24 mmol). The solvent was removed in vacuo to afford the title compound.

LC-MS: Rt=0.26 mins; [M−H]−128.4; Method 2min-LowpHv01

Step 2: Benzyl 4-(2-((tert-butoxycarbonyl)amino)ethyl)piperidine-1-carboxylate

To a solution of tert-butyl 2-(piperidin-4-yl)ethylcarbamate (2.965 g, 12.99 mmol) and DIPEA (9.07 ml, 51.9 mmol) in DCM (60 ml) was added a solution of benzyl chloroformate (2.326 g, 13.63 mmol) in DCM (15 ml). The resultant solution was stirred at room temperature overnight. The mixture was partitioned between water and diluted with DCM. The DCM layer was separated and concentrated in vacuo to afford the title compound;

LC-MS: Rt 1.32 mins; [M+H]+363.7; Method 2min-LowpHv01

Step 3: Benzyl 4-(2-((tert-butoxycarbonyl)(methyl)amino)ethyl)piperidine-1-carboxylate To a suspension of sodium hydride, 60% dispersion in mineral oil (0.225 g, 5.62 mmol) in DMF (10 ml) at 0° C. was added benzyl 4-(2-((tert-butoxycarbonyl)amino)ethyl)piperidine-1-carboxylate (Example 148, step 2)(1.018 g, 2.81 mmol) as a solution in DMF (12 ml). The mixture was stirred at 0° C. for 20 minutes and the resulting mixture was treated with a solution of methyl iodide (0.439 mL, 7.02 mmol) in DMF (3 ml). The resultant mixture was stirred at 0° C. and then allowed to gradually warm overnight to room temperature. Water was added and the resulting mixture extracted with DCM. The DCM extracts were washed 3 times with water and concentrated in vacuo to afford the title compound;

LC-MS: Rt 1.32 mins; [M+H]$^+$ 363.7; Method 2min-LowpHv01

Step 4: tert-Butyl methyl(2-(piperidin-4-yl)ethyl)carbamate

To a solution of benzyl 4-(2-((tert-butoxycarbonyl)(methyl)amino)ethyl)piperidine-1-carboxylate (Example 148, step 3) (1.08 g, 2.87 mmol) in EtOH (25 mL) was added Pearlman's catalyst (palladium hydroxide, Pd 20% on carbon, nominally 50% water, 0.242 g, 0.861 mmol) and ammonium formate (1.809 g, 28.7 mmol). The resultant mixture was heated at reflux for 1 hour. The mixture was cooled to room temperature, filtered through Celite® and the filter pad washed with DCM. The filtrate was concentrated in vacuo. The residue was partitioned between 1M K$_2$CO$_3$ solution and DCM, the DCM layer separated and concentrated in vacuo to afford the title compound.

Step 5: (E)-tert-butyl (2-(1-(3-(4-chloro-2-((5-methyl-2H-tetrazol-2-yl)methyl)phenyl)acryloyl)piperidin-4-yl)ethyl)(methyl)carbamate To a solution of (E)-3-(4-chloro-2-((5-methyl-2H-tetrazol-2-yl)methyl)phenyl)acrylic acid (Intermediate A) (0.854 g, 3.07 mmol), tert-butyl methyl(2-(piperidin-4-yl)ethyl)carbamate (tert-butyl methyl(2-(piperidin-4-yl)ethyl)carbamate (Example 148, step 4) (0.743 g, 3.07 mmol) and DIPEA (2.142 mL, 12.26 mmol) in DMF (30 ml) was added T3P®, 50% solution in EtOAc (3.58 mL, 6.13 mmol). The resultant mixture was stirred at room temperature for 2.5 hours. The mixture was partitioned between DCM and 1M sodium carbonate solution. The DCM layer was separated and washed with twice with water. The DCM extracts were concentrated in vacuo. The residue was purified by chromatography on silica gel, eluting with EtOAc/iso-hexanes to afford the title compound.

LC-MS: Rt=1.36 mins; [M+H]+503.4; Method 2min-LowpHv01

Step 6: (E)-3-(4-Chloro-2-((5-methyl-2H-tetrazol-2-yl)methyl)phenyl)-1-(4-(2-(methylamino)ethyl)piperidin-1-yl)prop-2-en-1-one 4M HCl in dioxane (20 ml, 80 mmol) was added to (E)-tert-butyl (2-(1-(3-(4-chloro-2-((5-methyl-2H-tetrazol-2-yl)methyl)phenyl)acryloyl)piperidin-4-yl)ethyl)(methyl)carbamate (0.754 g, 1.499 mmol) in methanol (10 ml) and the mixture stirred at room temperature overnight.

The solvent was removed in vacuo. The residue was redissolved in DCM and washed with 1M sodium carbonate solution. The DCM layer was separated and the aqueous layer extracted with DCM. The combined DCM extracts were concentrated in vacuo to afford the title compound;

LC-MS Rt=0.73 mins; [M+H]+; 403.2 and 405.3 Method 2minLowpHv01

Step 7: (E)-N-(2-(1-(3-(4-Chloro-2-((5-methyl-2H-tetrazol-2-yl)methyl)phenyl)acryloyl)piperidin-4-yl)ethyl)-N-methyl-2-oxo-2,3-dihydrooxazole-5-carboxamide To a mixture of (E)-3-(4-chloro-2-((5-methyl-2H-tetrazol-2-yl)methyl)phenyl)-1-(4-(2-(methylamino)ethyl)piperidin-1-yl)prop-2-en-1-one (Example 148, step 6) (74 mg, 0.184 mmol), DIPEA (0.257 mL, 1.469 mmol) and 2-oxo-2,3-dihydrooxazole-5-carboxylic acid (Example 148, step 1), (0.2 M solution in DMF 2.75 mL, 0.551 mmol) in DMF (2 ml) was added T3P®, 50% solution in EtOAc (0.429 mL, 0.735 mmol). The resultant mixture was stirred at room temperature overnight. T3P®, 50% solution in EtOAc (0.429 mL, 0.735 mmol) and DIPEA (0.257 mL, 1.469 mmol) were added to the mixture, as well as further DMF (5 ml). The mixture was stirred at room temperature for 4 hours. 50% solution in EtOAc (0.429 mL, 0.735 mmol), DIPEA (0.257 mL, 1.469 mmol) and DMF (2 ml) were added to the mixture and stirred overnight. Water (1 ml) was added and solvent was removed in vacuo. The residue was partitioned between DCM and water and the DCM layer was separated. The aqueous layer was further extracted with DCM and the combined organic extracts were concentrated in vacuo. The residue was purified by reverse phase preparative HPLC to afford the title compound;

LC-MS Rt 1.01 mins; [M+H]+514.3; Method 2min-LowpHv01

Example 149

(E)-1-(4-(1-(1H-1,2,3-Triazole-4-carbonyl)piperidin-4-yl)piperazin-1-yl)-3-(4-chloro-2-((5-methyl-2H-tetrazol-2-yl)methyl)phenyl)prop-2-en-1-one

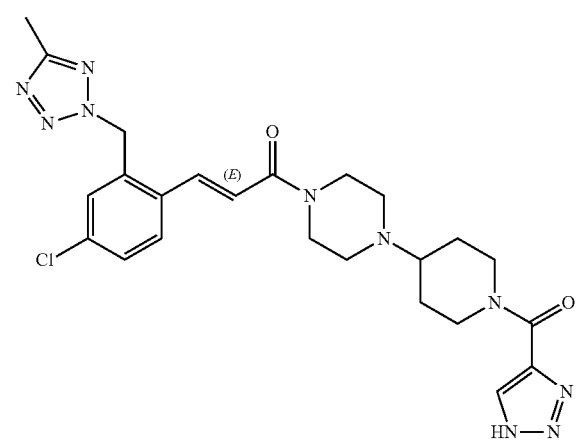 [SMILES: Cc1nnn(Cc2cc(Cl)ccc2/C=C/C(=O)N2CCN(C3CCN(C(=O)c4c[nH]nn4)CC3)CC2)n1]

Step 1: (E)-tert-butyl 4-(4-(3-(4-chloro-2-((5-methyl-2H-tetrazol-2-yl)methyl) phenyl)acryloyl) piperazin-1-yl)piperidine-1-carboxylate To a solution of tert-butyl 4-(piperazin-1-yl)piperidine-1-carboxylate (2.954 g, 10.97 mmol), DIPEA ((7.66 ml, 43.9 mmol) and (E)-3-(4-chloro-2-((5-methyl-2H-tetrazol-2-yl)methyl)phenyl) acrylic acid (Intermediate A) (3.21 g, 11.51 mmol) in DMF (60 ml) was added T3P®, 50% solution in EtOAc (12.80 ml, 21.93 mmol). The resultant mixture was stirred at room temperature overnight. The mixture was partitioned between 1M sodium carbonate solution and DCM, the DCM layer separated. The DCM layer was washed with water (3×) and concentrated in vacuo to afford the title compound;

LC-MS: Rt 0.84 mins; [M+H]+530.3; Method 2min-LowpHv01

Step 2: (E)-3-(4-Chloro-2-((5-methyl-2H-tetrazol-2-yl)methyl)phenyl)-1-(4-(piperidin-4-yl)piperazin-1-yl)prop-2-en-1-one dihydrochloride 4M HCl in dioxane (40 ml, 160 mmol) was added to (E)-tert-butyl 4-(4-(3-(4-chloro-2-((5-methyl-2H-tetrazol-2-yl)methyl)phenyl)acryloyl)piperazin-1-yl)piperidine-1-carboxylate (Example 149, step 1) The resulting mixture was stirred at room temperature for 2 hours and the solvent was removed in vacuo to afford the title compound as a dihydrochloride salt;

LC-MS: Rt 0.54 mins; [M+H]+; 430.2 Method 2min-LowpHv01

Step 3: (E)-1-(4-(1-(1H-1,2,3-Triazole-4-carbonyl)piperidin-4-yl)piperazin-1-yl)-3-(4-chloro-2-((5-methyl-2H-tetrazol-2-yl)methyl)phenyl)prop-2-en-1-one trifluoroacetate To a mixture of (E)-3-(4-chloro-2-((5-methyl-2H-tetrazol-2-yl)methyl)phenyl)-1-(4-(piperidin-4-yl)piperazin-1-yl)prop-2-en-1-one, dihydrochloride salt (Example 149, step 2)(130 mg, 0.259 mmol), DIPEA (0.316 ml, 1.810 mmol) and 1H-1,2,3-triazole-4-carboxylic acid (38.0 mg, 0.336 mmol) in DMF (1.5 ml) was added T3P®, 50% solution in EtOAc (0.302 ml, 0.517 mmol). The resultant mixture was stirred at room temperature over the weekend. Water (0.5 ml) was added and the solvent removed in vacuo. The residue was purified by reverse phase preparative HPLC to afford the title compound as the trifluoroacetate salt;

LC-MS: Rt 0.87 mins; MS m/z 525.3 (M+H)+; Method 2minLowpHv02

Example 150

(E)-3-((2-(4-(3-(4-Chloro-2-((5-methyl-2H-tetrazol-2-yl)methyl)phenyl)acryloyl)morpholin-2-yl)ethyl)amino)-4-ethoxycyclobut-3-ene-1,2-dione

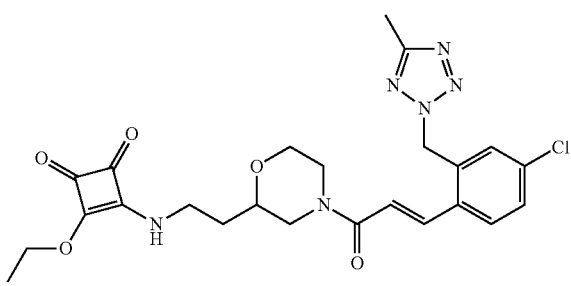 [SMILES: CCOc1c(NCCC2CN(C(=O)/C=C/c3ccc(Cl)cc3Cn3nnc(C)n3)CCO2)c(=O)c1=O]

Step 1: (E)-tert-Butyl (2-(4-(3-(4-chloro-2-((5-methyl-2H-tetrazol-2-yl)methyl)phenyl)acryloyl) morpholin-2-yl)ethyl)carbamate To ((E)-3-(4-chloro-2-((5-methyl-2H-tetrazol-2-yl)methyl)phenyl)acrylic acid (Intermediate A) (968 mg, 3.47 mmol) in DMF (20 ml) was added t-butyl (2-morpholin-2-ylethyl)carbamate (800 mg, 3.47 mmol) and DIPEA (1.820 ml, 10.42 mmol) followed by 50% T3P® in DMF (4.06 ml, 6.95 mmol). The yellow solution that formed immediately was stirred at room temperature overnight. The resulting mixture was concentrated in vacuo and the residue diluted with water (50 ml). This was extracted with EtOAc (2×100 ml). The extracts were treated with MgSO4 and ~5 g silica. After filtration, the filtrate was concentrated to give an orange gum. This was dried at 50° C. under vacuum for 2 hrs to give (E)-tert-butyl (2-(4-(3-(4-chloro-2-((5-methyl-2H-tetrazol-2-yl)methyl)phenyl)acryloyl) morpholin-2-yl)ethyl)carbamate (1.46 g).

LC-MS: Rt=1.22 mins; m/z 491.3 and 493.3 [M+H]+ for Cl isotopes; Method 2minLowpHv01.

Step 2: (E)-1-(2-(2-Aminoethyl)morpholino)-3-(4-chloro-2-((5-methyl-2H-tetrazol-2-yl)methyl)phenyl)prop-2-en-1-one (E)-tert-butyl (2-(4-(3-(4-chloro-2-((5-methyl-2H-tetrazol-2-yl)methyl)phenyl)acryloyl) morpholin-2-yl)ethyl)carbamate (0.73 g, 1.487 mmol) and TFA (4.6 ml, 60 mmol) in DCM (5 ml) were stirred at ambient temperature for 1 hr. The reaction mixture was diluted with DCM (5 ml) and washed with water, then sat. NaHCO3. The organic layer was dried (MgSO4) and concentrated to give (E)-1-(2-(2-aminoethyl)morpholino)-3-(4-chloro-2-((5-methyl-2H-tetrazol-2-yl)methyl)phenyl)prop-2-en-1-one (517 mg).

LC-MS: Rt: 0.69 mins; MS m/z 390 [M+H]+; Method 2minLowpH_v01.

Step 3: (E)-3-((2-(4-(3-(4-Chloro-2-((5-methyl-2H-tetrazol-2-yl)methyl)phenyl)acryloyl) morpholin-2-yl)ethyl)amino)-4-ethoxycyclobut-3-ene-1,2-dione 3,4-Diethoxycyclobut-3-ene-1,2-dione (196 µl, 1.3 mmol) and triethylamine (737 µl, 5.3 mmol) in ethanol (5 ml) was stirred at 40° C. for 20 minutes. The reaction mixture was cooled to room temperature and (E)-1-(2-(2-aminoethyl)morpholino)-3-(4-chloro-2-((5-methyl-2H-tetrazol-2-yl)methyl)phenyl)prop-2-en-1-one (517 mg, 1.323 mmol) was added and stirred at ambient temperature overnight. The mixture was concentrated under pressure and then diluted with EtOAc. The organic layer was washed with water and then dried (MgSO4) and concentrated. The residue was purified by silica chromatography, eluting with 10% EtOH/EtOAc. The product fractions were combined and concentrated to give (E)-3-((2-(4-(3-(4-chloro-2-((5-methyl-2H-tetrazol-2-yl)methyl)phenyl)acryloyl)morpholin-2-yl) ethyl)amino)-4-ethoxycyclobut-3-ene-1,2-dione (10 mg).

LC-MS: Rt: 1.01 mins; MS m/z 515 [M+H]+; Method 2minLowpH_v01.

Example 151

(E)-N-(1-(3-(4-Chloro-2-((5-methyl-2H-tetrazol-2-yl)methyl)phenyl)acryloyl)piperidin-4-yl)-4-(1H-1,2,3-triazol-4-yl)butanamide

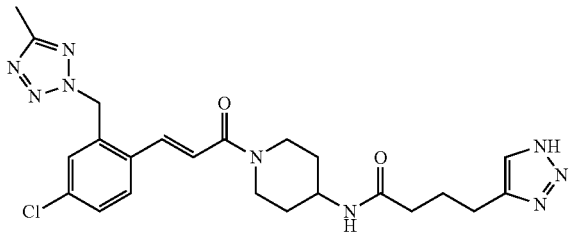 [SMILES: Cc1nnn(Cc2cc(Cl)ccc2/C=C/C(=O)N2CCC(NC(=O)CCCc3c[nH]nn3)CC2)n1]

Step 1: 4-(1-Benzyl-1H-1,2,3-triazol-4-yl)butanoic acid

Copper (II) acetate (385 mg, 2.118 mmol) and sodium L-ascorbate (837 mg, 4.24 mmol) were added to a solution of benzyl azide (2.82 ml, 21.18 mmol) in a mixture of t-butanol (212 ml) and water (212 ml). Hex-5-ynoic acid (2.337 ml, 21.18 mmol) was added and the reaction stirred over the weekend. Sodium chloride and EtOAc (~100 ml) were added. The phases were separated and the aqueous extracted with ethyl acetate. The organic portion was combined, dried over MgSO4, filtered and concentrated in vacuo to afford the title compound;

LCMS Rt=0.81 mins [M+H]+246.5; Method 2min-lowpHv01

Step 2: 4-(1H-1,2,3-triazol-4-yl)Butanoic acid

A solution of 4-(1-benzyl-1H-1,2,3-triazol-4-yl)butanoic acid (Example 151, step 1) (5.3396 g, 21.77 mmol) in EtOH (435 ml) was hydrogenated using the H-Cube at 60° C., 30 bar pressure. The reaction was concentrated in vacuo to afford the title compound;

LCMS Rt=0.33 mins [M+H]+156.2; Method 2min-LowpHv01

Step 3: (E)-tert-Butyl (1-(3-(4-chloro-2-((5-methyl-2H-tetrazol-2-yl)methyl)phenyl)acryloyl) piperidin-4-yl)carbamate (E)-3-(4-Chloro-2-((5-methyl-2H-tetrazol-2-yl)methyl)phenyl)acrylic acid (Intermediate A) (500 mg, 1.794 mmol) and tert-butyl piperidin-4-ylcarbamate (359 mg, 1.794 mmol) were combined in DMF (9 ml). DIPEA (1.253 ml, 7.18 mmol) was added followed by 50% T3P® solution in DMF (2.095 ml, 3.59 mmol) and the resulting mixture stirred at room temperature overnight. The reaction was diluted with EtOAc (100 mL) and the resulting solution washed with 10% citric acid solution, bicarbonate solution and brine. The solution was dried (MgSO4) filtered and concentrated in vacuo to afford the title compound;

LCMS Rt=1.15 mins; [M+H−100]+; Method 2min-LowpHv01

Step 4: (E)-1-(4-Aminopiperidin-1-yl)-3-(4-chloro-2-((5-methyl-2H-tetrazol-2-yl)methyl)phenyl)prop-2-en-1-one 4M HCl in dioxane (4.46 ml, 17.83 mmol) was added to a solution of (E)-tert-butyl (1-(3-(4-chloro-2-((5-methyl-2H-tetrazol-2-yl)methyl)phenyl)acryloyl)piperidin-4-yl)carbamate (Example 151, step 3) (822 mg, 1.783 mmol) in DCM (5 ml) and the reaction mixture stirred for 3 hr. The reaction was concentrated in vacuo and the residue solubilised in a minimal volume of MeOH and applied to 10 g Isolute®SCX-2 cartridge pre-wetted with MeOH. The cartridge was washed with MeOH and eluted with 7M ammonia in MeOH. The eluent was concentrated in vacuo to afford the title compound;

LCMS Rt=0.65 mins [M+H]+361.4; Method 2min-LowpHv01

Step 5: (E)-N-(1-(3-(4-Chloro-2-((5-methyl-2H-tetrazol-2-yl)methyl)phenyl)acryloyl)piperidin-4-yl)-4-(1H-1,2,3-triazol-4-yl)butanamide (E)-1-(4-Aminopiperidin-1-yl)-3-(4-chloro-2-((5-methyl-2H-tetrazol-2-yl)methyl)phenyl)prop-2-en-1-one (Example 151, step 4) (100 mg, 0.227 mmol) and 4-(1H-1,2,3-triazol-4-yl)butanoic acid (Example 151, step 2) (43 mg, 0.277 mmol) were dissolved in DMF (1.5 ml). DIPEA (194 µl, 1.109 mmol) was added followed by 50% T3P® in DMF (324 µl, 0.554 mmol) and the resulting mixture stirred for 2 days. The reaction mixture was diluted with EtOAc and washed with 10% citric acid, dried (MgSO4), filtered and concentrated in vacuo. The residue was purified by reverse phase preparative HPLC to afford the title compound;

LCMS Rt=0.97 mins [M+H]+; 498.4; Method 2min-lowpHv01

Example 152

(E)-N-(1-(3-(2-((5-Methyl-2H-tetrazol-2-yl)methyl)-4-(trifluoromethyl)phenyl)acryloyl) piperidin-4-yl)-4-(1H-1,2,3-triazol-4-yl)butanamide

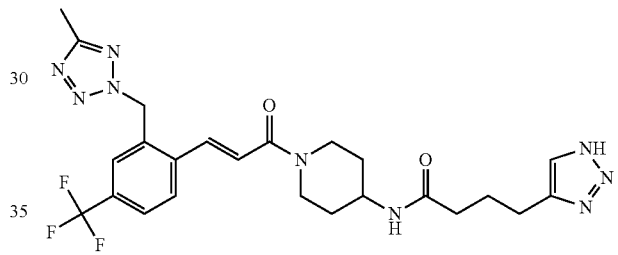

Step 1: (E)-N-(1-(3-(2-((5-Methyl-2H-tetrazol-2-yl)methyl)-4-(trifluoromethyl)phenyl)acryloyl) piperidin-4-yl)-4-(1H-1,2,3-triazol-4-yl)butanamide The title compound was prepared using a similar method to Example 151, step 5 using (E)-3-(2-((5-methyl-2H-tetrazol-2-yl)methyl)-4-(trifluoromethyl)phenyl)acrylic acid (Intermediate AB) and 4-(1H-1,2,3-triazol-4-yl)butanoic acid (Example 151, step 2)

LCMS Rt=1.06 mins; [M+H]+532.4; Method 2min-LowpHv03

Example 153

1-(4-(5-(1H-1,2,3-Triazol-4-yl)pentyl)piperidin-1-yl)-3-(2-((5-methyl-2H-tetrazol-2-yl)methyl)-4-(trifluoromethyl)phenyl)propan-1-one

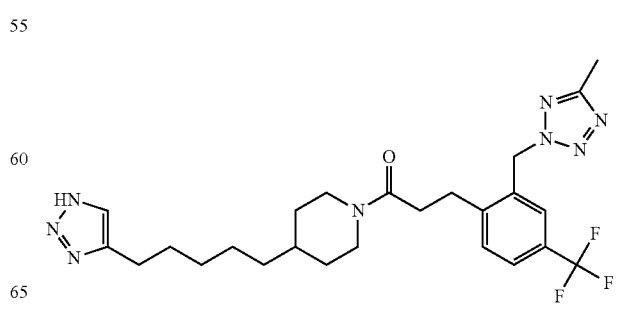

Step 1: tert-Butyl 4-(((methylsulfonyl)oxy)methyl)piperidine-1-carboxylate

To N-BOC-4-piperidinemethanol (2 g, 9.29 mmol) in DCM (10 mL) at 0° C. (ice-bath) was added triethylamine (1.424 mL, 10.22 mmol) followed by methanesulfonyl chloride (0.8 mL, 10.2 mmol). The ice bath was removed and the resulting suspension was stirred and allowed to warm to room temperature over 1 hr. The suspension was diluted with DCM (50 ml) and washed with water (20 ml). The organic portion was dried (MgSO4), treated with 10 g silica and filtered. The filtrate was concentrated under reduced pressure to give the title compound as a tan oil (2.57 g);

1H NMR (400 MHz, CDCl$_3$) δ 1.24 (2H, dq), 1.48 (9H, s), 1.72-1.80 (2H, m), 1.88-2.0 (1H, m), 2.73 (2H, t), 3.04 (3H, s), 4.10 (2H, d), 4.14-4.23 (2H, m).

Step 2: tert-Butyl 4-(iodomethyl)piperidine-1-carboxylate

To tert-butyl 4-(((methylsulfonyl)oxy)methyl)piperidine-1-carboxylate (2.57 g, 8.8 mmol) in acetone (60 mL) was added sodium iodide (2.63 g, 17.5 mmol). The yellow solution formed was heated at reflux overnight. The resulting orange suspension formed was cooled to room temperature and filtered. The filtrate was concentrated in vacuo and the residue partitioned between DCM (100 ml) and water (20 ml). The organic portion was dried (MgSO4) and treated with silica (10 g). This was filtered and the filtrate concentrated to give the title compound as an orange oil (2.19 g);

1H NMR (400 MHz, CDCl$_3$) δ 1.14 (2H, dq), 1.48 (9H, s), 1.57-1.70 (1H, m), 1.82-1.90 (2H, m), 2.73 (2H, t), 3.12 (2H, d), 4.10-4.20 (2H, m).

Step 3: ((1-(tert-Butoxycarbonyl)piperidin-4-yl)methyl) triphenylphosphonium

To tert-butyl 4-(iodomethyl)piperidine-1-carboxylate (3.44 g, 10.58 mmol) in DMF (20 mL) was added triphenylphosphine (4.16 g, 15.9 mmol) and the mixture heated at 90° C. overnight. The resulting mixture was cooled and the solvent removed in vacuo to give a viscous oil. This was dissolved in DCM (20 ml) and applied to a 125 g silica cartridge, which was eluted with 0-10% MeOH/DCM. The product fractions were combined and concentrated to give 4.7 g of crystalline material. The material was stirred with diethyl ether overnight, then filtered and dried under vacuum at 40° C. to afford the title compound as a yellow white solid (3.6 g);

LCMS: Rt=1.04 mins; MS m/z 460.4 [M]+; Method 2minLowpHv03

Step 4: 4-(1-Benzyl-1H-1,2,3-triazol-4-yl)butan-1-ol

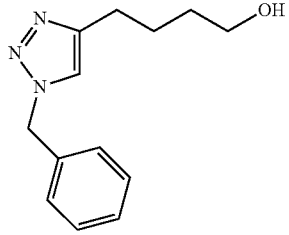 [SMILES: OCCCCc1cn(Cc2ccccc2)nn1]

To 5-hexyn-1-ol (1.47 g, 15 mmol) in t-BuOH (150 ml) and water (150 ml) was added benzyl azide (2 g, 15 mmol) and copper (II) acetate (0.273 g, 1.5 mmol). Sodium L-ascorbate (0.60 g, 3.00 mmol) was added and the resulting suspension was stirred at room temperature overnight. The mixture was concentrated to half volume in vacuo, then treated with solid NaCl and extracted with EtOAc (2×200 ml). The organic extracts were dried (MgSO4) and concentrated to give a gum. This was dissolved in MeOH (100 ml) and treated with activated charcoal (5 g). The suspension was warmed to 50° C. and then cooled, before being filtered through Celite® (filter material). The filtrate was concentrated to give the title compound (2.86 g) as a solid.

LCMS: Rt=0.88 mins; MS m/z 233.1 [M+2H]+; Method 2minLowpHv03

Step 5: 4-(1-Benzyl-1H-1,2,3-triazol-4-yl)butanal

To 4-(1-benzyl-1H-1,2,3-triazol-4-yl)butan-1-ol (2.6 g, 11.2 mmol) dissolved in DCM (80 ml) was added Dess-Martin periodane (4.77 g, 11.2 mmol). The reaction mixture was stirred at room temperature for 5 hours then quenched with 2.0 M NaOH (100 ml). The organic portion was removed in vacuo. The aqueous phase was washed with DCM (2×50 ml) and the combined organic portion was dried (MgSO4) and concentrated. Purification by chromatography on silica using a 40 g cartridge and 0-100% iso-hexanes/EtOAc gradient as eluent gave the titled compound (1.65 g);

LCMS: Rt=0.86 mins; MS m/z 230.2 [M+H]+; Method 2minLowpHv03

Step 6: (E)-tert-Butyl 4-(5-(1-benzyl-1H-1,2,3-triazol-4-yl)pent-1-en-1-yl)piperidine-1-carboxylate To ((1-(tert-butoxycarbonyl)piperidin-4-yl)methyl)triphenylphosphonium iodide (1.8 g, 3.1 mmol) in THF (10 ml) was added 1.6 M n-butyllithium in hexanes (3.83 mL, 6.1 mmol) dropwise at −78° C. The resulting solution was stirred at room temperature for 30 mins, then re-cooled to −78° C. and 4-(1-benzyl-1H-1,2,3-triazol-4-yl)butanal (0.703 g, 3.06 mmol) in THF (5 ml) was added. The yellow solution formed was allowed to stir at room temperature for 6 hrs. The suspension was quenched with NH4Cl solution (100 ml) and extracted with EtOAc (2×100 ml). The combined organic extracts were dried (MgSO4) and concentrated. The residue was purified on silica eluting with 0-100% EtOAc/iso-hexanes to give the title compound (854 mg).

LC-MS: Rt 1.63 mins; MS m/z 411.4 [M+H]+; Method 2minLowpHv03

Step 7: tert-Butyl 4-(5-(1H-1,2,3-triazol-4-yl)pentyl)piperidine-1-carboxylate (E)-tert-Butyl 4-(5-(1-benzyl-1H-1,2,3-triazol-4-yl)pent-1-en-1-yl)piperidine-1-carboxylate (854 mg, 2.080 mmol) was dissolved in EtOH (40 ml) and flow-hydrogenated using an H-Cube® using 10% Pd on carbon at 30 bar and 70° C., for 2 hrs. The reaction mixture was concentrated under reduced pressure to afford the title compound as a colourless oil (635 mg);

LC-MS Rt 1.37 mins; MS m/z 323.6 [M+H]+; Method 2minLowPHv03

Step 8: 4-(5-(1H-1,2,3-Triazol-4-yl)pentyl)piperidine

To tert-butyl 4-(5-(1H-1,2,3-triazol-4-yl)pentyl)piperidine-1-carboxylate (635 mg, 1.9 mmol) in EtOAc (10 ml) was added 4N HCl in dioxane (7.4 ml, 29.5 mmol) and the solution stirred at room temperature for 1.5 hrs. The reaction mixture was concentrated in vacuo to give the title compound as white gum (510 mg);

LC-MS: Rt 0.59 mins; MS m/z 223.3 [M+H]+; Method 2minLowPHv03

Step 9: 1-(4-(5-(1H-1,2,3-Triazol-4-yl)pentyl)piperidin-1-yl)-3-(2-((5-methyl-2H-tetrazol-2-yl)methyl)-4-(trifluoromethyl)phenyl)propan-1-one To 4-(5-(1H-1,2,3-triazol-4-yl)pentyl)piperidine (100 mg, 0.386 mmol) and 3-(2-((5-methyl-2H-tetrazol-2-yl)methyl)-4-(trifluoromethyl)phenyl) propanoic acid (Intermediate AF)(121 mg, 0.386 mmol) suspended in EtOAc (10 ml) was added triethylamine (0.215 ml, 1.546 mmol) with stirring. After 5 minutes T3P® 50% in EtOAc (0.299 ml, 0.502 mmol) was added and the reaction mixture stirred at ambient temperature for 5 hrs. The resulting mixture was diluted with EtOAc (100 ml) and washed with 10% citric acid solution (100 ml), brine (100 ml) and saturated solution of sodium bicarbonate (100 ml). The organic portion was dried (MgSO4), filtered and concentrated in vacuo. The crude material was purified by chromatography on silica eluting with 0-100% [10% MeOH-EtOAc]/iso-hexanes to give the title compound (110 mg);

LC-MS: Rt 1.36 mins; MS m/z 519.5 [M+H]+; Method 2minLowPHv03

Example 154

1-(4-(5-(1H-1,2,3-Triazol-4-yl)pentyl)piperidin-1-yl)-2-(2-((5-methyl-2H-tetrazol-2-yl)methyl)-4-(trifluoromethyl)phenoxy)ethanone

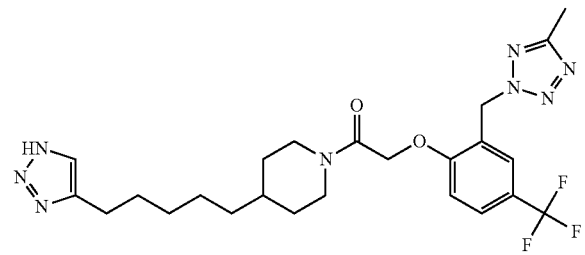 [SMILES: Cc1nnn(Cc2cc(C(F)(F)F)ccc2OCC(=O)N2CCC(CCCCCc3c[nH]nn3)CC2)n1]

Step 1: 1-(4-(5-(1H-1,2,3-Triazol-4-yl)pentyl)piperidin-1-yl)-2-(2-((5-methyl-2H-tetrazol-2-yl)methyl)-4-(trifluoromethyl)phenoxy)ethanone To 4-(5-(1H-1,2,3-triazol-4-yl)pentyl)piperidine (Example 153 step 8) (100 mg, 0.386 mmol) and 2-(2-((5-methyl-2H-tetrazol-2-yl)methyl)-4-(trifluoromethyl)phenoxy)acetic acid (Example 36 step 6) (122 mg, 0.386 mmol) suspended in EtOAc (10 ml) was added triethylamine (0.215 ml, 1.546 mmol) with stirring. DMF (3 ml) was added to aid solubility. After 5 minutes T3P® 50% in EtOAc (0.299 ml, 0.502 mmol) was added and the reaction mixture stirred for 4 hours. The resulting mixture was diluted with EtOAc (50 ml) and washed with a 10% citric acid solution (30 ml), brine (30 ml), a saturated solution of sodium bicarbonate and then dried (MgSO4) before being concentrated in vacuo. The crude material was purified by chromatography on silica eluting with 0-100% [10% MeOH-EtOAc]/iso-hexanes to afford the title compound (160 mg);

LC-MS: Rt 1.30 mins; MS m/z 521.6 [M+H]+; Method 2minLowpHv03

Example 155

(E)-1-(4-((4-(1H-1,2,3-Triazol-4-yl)butyl)amino)piperidin-1-yl)-3-(2-((5-methyl-2H-tetrazol-2-yl)methyl)-4-(trifluoromethyl)phenyl)prop-2-en-1-one

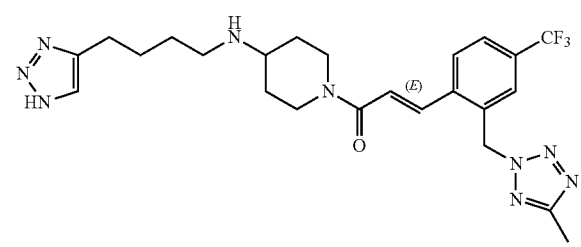 [SMILES: Cc1nnn(Cc2cc(C(F)(F)F)ccc2/C=C/C(=O)N2CCC(NCCCCc3c[nH]nn3)CC2)n1]

Step 1: (E)-tert-Butyl (1-(3-(2-((5-methyl-2H-tetrazol-2-yl)methyl)-4-(trifluoromethyl) phenyl)acryloyl)piperidin-4-yl)carbamate To 4-(BOC-amino)piperidine (257 mg, 1.3 mmol) and (E)-3-(2-((5-methyl-2H-tetrazol-2-yl)methyl)-4-(trifluoromethyl)phenyl)acrylic acid (Intermediate AB) (400 mg, 1.3 mmol) in DMF (7 ml) was added DIPEA (0.67 ml, 3.84 mmol) and 50% T3P® in EtOAc (1.53 ml, 2.56 mmol). The solution was stirred at room temperature for 2 hrs, then concentrated in vacuo. The crude residue was dissolved in diethyl ether (200 ml) and washed with water (2×50 ml) and brine (20 ml). The organic extracts were dried (MgSO4) and concentrated in vacuo to give the title compound as a yellow/white solid (536 mg);

LC-MS: Rt=1.44 mins; MS m/z 395.4 [M+H−BOC]+; Method 2minLowpHv03

Step 2: (E)-1-(4-Aminopiperidin-1-yl)-3-(2-((5-methyl-2H-tetrazol-2-yl)methyl)-4-(trifluoromethyl)phenyl)prop-2-en-1-one To (E)-tert-butyl (1-(3-(2-((5-methyl-2H-tetrazol-2-yl)methyl)-4-(trifluoromethyl)phenyl) acryloyl) piperidin-4-yl) carbamate (536 mg, 1.1 mmol) in EtOAc (10 ml) was added 4N HCl in dioxane (8.1 mL, 32.5 mmol) and the resulting solution was stirred at room temperature for 3 hrs. The mixture was concentrated in vacuo and the residue was partitioned between EtOAc (100 ml) and 1N NaOH (50 ml). The organic portion was dried (MgSO4) and concentrated to give a gum. The residue was suspended in MeOH/DCM and dry loaded onto silica (10 g). This was applied to a 20 g silica cartridge which was eluted with 0-10% MeOH/DCM containing 1% aqueous 880 ammonia. The product fractions were combined and concentrated to give the title compound as a gum (314 mg).

LC-MS: Rt=0.77 mins; MS m/z 395.5 [M+H]+; Method 2minLowpHv03

Step 3: 1-(Azidomethyl)-4-methoxybenzene

To 4-methoxybenzyl chloride (8.5 mL, 62.8 mmol) in DMF (40 ml) was added sodium azide. The reaction mixture was diluted with ether (400 ml) and washed with water (2×200 mL) and brine (20 ml). The organic layers were dried (MgSO4) and then carefully concentrated (water bath temp 20° C.) behind a blast shield. The title compound was obtained as a clear oil (11 g).

NMR (400 MHz, d6-DMSO): δ 4.36 (2H, s), 6.96 (2H, d), 7.32 (2H, d).

Step 4: 4-(1-(4-Methoxybenzyl)-1H-1,2,3-triazol-4-yl)butan-1-ol

To 5-hexynol (1.2 g, 12.3 mmol) in t-BuOH (120 ml) and water (150 ml) was added 1-(azidomethyl)-4-methoxybenzene (2 g, 12.3 mmol) and copper (II) acetate (0.223 g, 1.23 mmol). Sodium L-ascorbate (0.486 g, 2.5 mmol) was added and the white suspension was stirred at room temperature for 3 hrs, then concentrated to half volume. NaCl was added and the precipitate formed was extracted with EtOAc (2×100 ml). The organic portion was dried (MgSO4) and concentrated. The solid was triturated with iso-hexanes, then filtered and dried. The title compound was isolated as a tan solid (3.10 g);

LC-MS: Rt=0.90 mins; MS m/z 262.5 [M+H]+; Method 2minLowpHv03

Step 5: 4-(1-(4-Methoxybenzyl)-1H-1,2,3-triazol-4-yl)butanal

To 4-(1-(4-methoxybenzyl)-1H-1,2,3-triazol-4-yl)butan-1-ol (1 g, 3.8 mmol) in DCM (40 ml) was added Dess-Martin periodinane (1.62 g, 3.8 mmol). The pale blue/green solution formed was stirred at room temperature for 2 hrs when quenched with 1N NaOH solution (40 ml) and extracted with DCM (2×50 ml). The extracts were dried (MgSO4) and concentrated to give the title compound as a white solid (775 mg).

LC-MS: Rt=0.84 mins; MS m/z 260.2 [M+H]+; Method 2minLowpHv03

Step 6: (E)-1-(4-((4-(1-(4-Methoxybenzyl)-1H-1,2,3-triazol-4-yl)butyl)amino)piperidin-1-yl)-3-(2-((5-methyl-2H-tetrazol-2-yl)methyl)-4-(trifluoromethyl)phenyl)prop-2-en-1-one To 4-(1-(4-methoxybenzyl)-1H-1,2,3-triazol-4-yl)butanal (206 mg, 0.8 mmol) and (E)-1-(4-aminopiperidin-1-yl)-3-(2-((5-methyl-2H-tetrazol-2-yl)methyl)-4-(trifluoromethyl) phenyl)prop-2-en-1-one (314 mg, 0.8 mmol) in DCM (10 ml) was added sodium triacetoxyborohydride (337 mg, 1.59 mmol). The mixture was stirred at room temperature overnight. The reaction was quenched with 1N NaOH (30 ml) and extracted with DCM (2×50 ml). The extracts were dried (MgSO4) and concentrated.

The residue was loaded onto a 24 g silica cartridge in DCM and eluted with 0-20% MeOH containing 1% aqueous 880 NH₃/DCM. The product fractions were combined and concentrated to give the title compound as a gum (283 mg);

LC-MS: Rt=0.98 mins; MS m/z 638.6 [M+H]+; Method 2minLowpHv03

Step 7: (E)-1-(4-((4-(1H-1,2,3-Triazol-4-yl)butyl)amino) piperidin-1-yl)-3-(2-((5-methyl-2H-tetrazol-2-yl)methyl)-4-(trifluoromethyl)phenyl)prop-2-en-1-one To (E)-1-(4-((4-(1-(4-methoxybenzyl)-1H-1,2,3-triazol-4-yl)butyl)amino)piperidin-1-yl)-3-(2-((5-methyl-2H-tetrazol-2-yl)methyl)-4-(trifluoromethyl)phenyl)prop-2-en-1-one (280 mg, 0.44 mmol) in MeCN (5 ml) and water (0.5 ml) was added ceric ammonium nitrate (963 mg, 1.76 mmol). The orange solution formed was stirred at room temperature for 3 hrs. The solution was quenched with NaHCO₃ solution (50 ml) and the resulting suspension extracted with EtOAc (2×100 ml), dried (MgSO4) and concentrated. The residue was dissolved in MeCN (3 ml) and water (300 µl) then ceric ammonium nitrate (963 mg, 1.756 mmol) was added. The orange solution was stirred at room temperature overnight. The solution was diluted with saturated sodium bicarbonate solution (50 ml) and extracted with EtOAc (2×100 ml) then dried (MgSO4) and concentrated. The residue was dissolved in DCM. This was applied to a 12 g silica cartridge which was eluted with 0-20% MeOH containing 1% aqueous 880 NH3/DCM. The product fractions were combined and concentrated to give a gum. This was dissolved in MeOH and treated with 2N HCl in ether (1 ml). After concentration, the residue was suspended in ether and this stirred at room temperature overnight. The resulting solid was collected by filtration and dried at 40° C. under vacuum overnight. The title compound was isolated as the hydrochloride salt (82 mg);

LC-MS: Rt=0.84 mins; MS m/z 518.5 [M+H]+; Method 2minLowpHv03

Example 156

(E)-N-(1-(3-(2-((5-Methyl-2H-tetrazol-2-yl)methyl)-4-(trifluoromethyl)phenyl) acryloyl) piperidin-4-yl)-6-(1H-1,2,3-triazol-5-yl)hexanamide

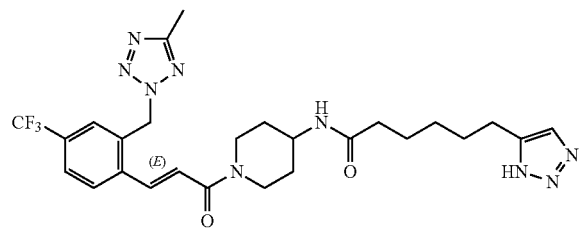 [SMILES: Cc1nnn(Cc2cc(C(F)(F)F)ccc2/C=C/C(=O)N2CCC(NC(=O)CCCCCc3cnn[nH]3)CC2)n1]

Step 1: 6-(1-Benzyl-1H-1,2,3-triazol-4-yl)hexan-1-ol

To 7-octyn-1-ol (2.75 g, 21.6 mmol) in t-BuOH (150 ml) and water (150 mL) was added (azidomethyl)benzene, (2.88 g, 21.6 mmol) followed by copper (II) acetate, (0.39 g, 2.2 mmol). Sodium L-ascorbate, (0.858 g, 4.3 mmol) was then added. The mixture was stirred at ambient temperature overnight. The t-BuOH solvent was removed under vacuum and solid sodium chloride was then added followed by EtOAc (100 ml). The layers were separated and the aqueous washed with a further portion of EtOAc (100 ml). The organic portions were combined, dried (MgSO4) and concentrated to give the title compound as a solid (5.58 g);

LC-MS: Rt 1.04 mins; MS m/z 260.2 [M+H]+; Method 2minLowPHv03

Step 2: 6-(1-Benzyl-1H-1,2,3-triazol-4-yl)hexanoic acid 6-(1-Benzyl-1H-1,2,3-triazol-4-yl)hexan-1-ol (1 g, 3.86 mmol), sodium periodate (3.30 g, 15.4 mmol) and ruthenium trichloride (0.016 g, 0.077 mmol) were mixed in water (4.3 ml), ethyl acetate (4.3 ml) and acetonitrile (4.3 ml) to give a green suspension. The reaction was stirred at room temperature overnight. The reaction was filtered through Celite® and the filtrate concentrated. This was applied to an Isolute® Si-TMT resin cartridge and washed through with EtOAc and concentrated under reduced pressure to give the title compound (729 mg).

Step 3: 6-(1H-1,2,3-Triazol-4-yl)hexanoic acid 6-(1-Benzyl-1H-1,2,3-triazol-4-yl)hexanoic acid (300 mg, 1.1 mmol) and 10% Pd/C (117 mg) was suspended acetic acid (20 mL) and hydrogenated at a pressure of 30 bar at 70° C. overnight. The reaction mixture was diluted with water and filtered. The filter cake was washed with EtOAc and the combined filtrates concentrated under vacuum to give the title compound;

LC-MS: Rt 0.73 mins; m/z 183 [M]+; Method 2min-LowpH_v01.

Step 4: (E)-N-(1-(3-(2-((5-Methyl-2H-tetrazol-2-yl) methyl)-4-(trifluoromethyl)phenyl) acryloyl)piperidin-4-yl)-6-(1H-1,2,3-triazol-5-yl)hexanamide To (E)-1-(4-aminopiperidin-1-yl)-3-(2-((5-methyl-2H-tetrazol-2-yl)methyl)-4-(trifluoromethyl) phenyl)prop-2-en-1-one (Example 155, step 2) (108 mg, 0.27 mmol) and 6-(1H-1,2,3-triazol-5-yl)hexanoic acid (50 mg, 0.27 mmol) in EtOAc (1 ml) was added triethylamine (114 µl, 0.82 mmol) and T3P® (376 µl, 0.41 mmol). The mixture was stirred at ambient temperature overnight. The reaction mixture was diluted with NaHCO₃ solution (20 ml) and extracted with EtOAc (2×50 ml). The extracts were dried (MgSO4) and concentrated. The residue was dissolved in DMSO at a concentration of 100 mg/ml. This was purified using mass directed HPLC, using an XSelect CSH Prep C18 column, 30×100 mm, 5 um and 30-70% MeCN/0.1% aqueous TFA as eluent. The product fractions were collected and concentrated to give the title compound (6.8 mg).

LC-MS: Rt 1.12 mins, m/z 560.6 [M+H]+; Method 2min-LowpHv03

Example 157

(E)-1-(4-(2-(2-(1H-1,2,3-Triazol-5-yl)ethoxy)ethyl)
piperidin-1-yl)-3-(2-((5-methyl-2H-tetrazol-2-yl)
methyl)-4-(trifluoromethyl)phenyl)prop-2-en-1-one

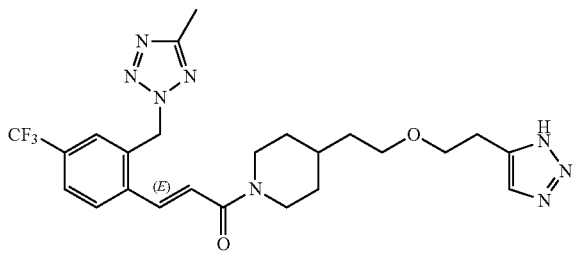 [SMILES: Cc1nnn(Cc2cc(C(F)(F)F)ccc2/C=C/C(=O)N2CCC(CCOCCc3cnn[nH]3)CC2)n1]

Step 1: tert-Butyl 4-(2-(but-3-yn-1-yloxy)ethyl)piperidine-1-carboxylate

But-3-yn-1-ol (72 mg, 1.03 mmol) was dissolved in THF (3.5 ml). Sodium hydride (61.6 mg, 1.54 mmol) was added to the reaction and this was stirred for 30 mins. tert-Butyl 4-(2-bromoethyl)piperidine-1-carboxylate (300 mg, 1.03 mmol) was added and stirred at room temperature for 18 hours. The reaction mixture was quenched with methanol and water, then concentrated under reduced pressure. The aqueous solution remaining was extracted with DCM (2×20 ml) and the combined organics dried (MgSO4) and concentrated to give the title compound (182 mg);

LC-MS: Rt 1.12 mins, m/z 560.6 [M+H]$^+$; Method 2minLowpHv03

Step 2: (4-(2-(2-(Piperidin-4-yl)ethoxy)ethyl)-1H-1,2,3-triazol-1-yl)methyl pivalate To chloromethyl pivalate (18.22 g, 121 mmol) suspended in water (25 ml) was added sodium azide (11.8 g, 182 mmol) and the mixture stirred at 90° C. overnight. The reaction was cooled and the organic layer was separated and filtered through a pad of MgSO4 to yield crude azidomethyl pivalate as a clear liquid (15.9 g). This was used without further purification. Tert-butyl 4-(2-(but-3-yn-1-yloxy)ethyl)piperidine-1-carboxylate (182 mg, 0.65 mmol), azidomethyl pivalate (102 mg, 0.65 mmol) and copper (II) acetate (2.4 mg, 0.013 mmol) were dissolved in in tert-butanol (1 ml) and water (1 ml) to give a solution. This was treated with sodium L-ascorbate (26 mg, 0.13 mmol) and the mixture was stirred at ambient temperature overnight. The reaction mixture was concentrated to remove the t-BuOH, saturated with NaCl and extracted with EtOAc (2×20 ml). The extracts were dried (MgSO4) and concentrated. The residue (54 mg) was dissolved in 1,4-dioxane (0.5 ml). 4N HCl in dioxane (31 µl, 0.12 mmol) was added and the mixture was stirred at room temperature for an hour. The mixture was concentrated to give the title compound as the hydrochloride salt (42 mg);

LC-MS: Rt 0.78 mins; MS m/z 338 [M+H]+; Method 2minLowpHv03

Step 3: (E)-(5-(2-(2-(1-(3-(2-((5-M ethyl-2H-tetrazol-2-yl)methyl)-4-(trifluoromethyl)phenyl) acryloyl)piperidin-4-yl)ethoxy)ethyl)-1H-1,2,3-triazol-1-yl)methyl pivalate (5-(2-(2-(Piperidin-4-yl)ethoxy)ethyl)-1H-1,2,3-triazol-1-yl)methyl pivalate hydrochloride (42 mg, 0.13 mmol) and (E)-3-(2-((5-methyl-2H-tetrazol-2-yl)methyl)-4-(trifluoromethyl)phenyl) acrylic acid (Intermediate AB) (39 mg, 0.13 mmol) in EtOAc (0.5 ml) were treated with 50% T3P® in ethyl acetate (110 µl, 0.19 mmol) and triethylamine (35 µl, 0.25 mmol). The reaction mixture was stirred for 1 hour at room temperature. The reaction mixture was diluted with NaHCO$_3$ solution (10 ml) and extracted with ethyl acetate (2×20 ml). The organic portion was dried (MgSO4) and concentrated. The residue was dissolved in DMSO at a concentration of 100 mg/ml. This was purified using mass directed HPLC, using an XSelect CSH Prep C18 column, 30×100 mm, 5 um and 40-80% MeCN/0.1% aqueous TFA as eluent. The product fractions were collected and concentrated to give the title compound (35 mg);

LC-MS: Rt 1.46 mins, MS m/z 633.5 [M+H]+, Method 2minLowpHv03

Step 4: (E)-1-(4-(2-(2-(1H-1,2,3-Triazol-5-yl)ethoxy)ethyl)piperidin-1-yl)-3-(2-((5-methyl-2H-tetrazol-2-yl)methyl)-4-(trifluoromethyl)phenyl)prop-2-en-1-one (E)-(5-(2-(2-(1-(3-(2-((5-Methyl-2H-tetrazol-2-yl)methyl)-4-(trifluoromethyl)phenyl)acryloyl) piperidin-4-yl)ethoxy)ethyl)-1H-1,2,3-triazol-1-yl)methyl pivalate (35 mg, 0.06 mmol) in EtOH (200 µl) was treated with sodium hydroxide (83 µl, 0.17 mmol) to give a yellow solution. The reaction was stirred for 4 hrs at room temperature. The reaction mixture was concentrated and diluted with ethyl acetate (10 ml) and water (1 ml). The organic portion was dried (MgSO4) and concentrated to give the title compound as a gum (3.4 mg).

LC-MS: Rt 1.48 mins, MS m/z 517.4 [M−H], Method 2minLowpHv03.

Preparation of Intermediates

Intermediate A (E)-3-(4-Chloro-2-((5-methyl-2H-tetrazol-2-yl)methyl)phenyl)acrylic acid

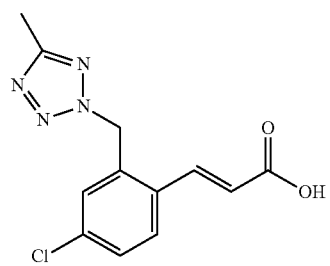 [SMILES: Cc1nnn(Cc2cc(Cl)ccc2/C=C/C(=O)O)n1]

Step 1: 2-(2-Bromo-5-chlorobenzyl)-5-methyl-2H-tetrazole

5-Methyl-2H-tetrazole (77 g, 913 mmol) was placed in a flask with dry DMF (400 mL) at 0° C. using an ice bath. Potassium carbonate (168 g, 1217 mmol) was added portionwise followed by dropwise addition of 1-bromo-2-(bromomethyl)-4-chlorobenzene (173 g, 608 mmol) in DMF (400 mL) and the resulting mixture was stirred at room temperature for 2 h. The mixture was poured into water and the resulting suspension was collected by filtration. The solid was triturated with iso-hexane and the undissolved solid was removed by filtration. The filtrate was concentrated under reduced pressure giving a white solid which was suspended in water and stirred overnight. The product was filtered and washed with water to afford the title compound;

LCMS: Rt 1.15 mins; MS m/z 289.0 [M+H]+; 2minLowpHv01

Step 2: (E)-Ethyl 3-(4-chloro-2-((5-methyl-2H-tetrazol-2-yl)methyl)phenyl)acrylate 2-(2-Bromo-5-chlorobenzyl)-5-methyl-2H-tetrazole (step 1) (15 g, 52.2 mmol), tri-o-tolylphosphine (0.794 g, 2.61 mmol) and triethylamine (10.56 g, 104 mmol) were placed in a flask with dry, degassed DMF (80 mL). Ethyl acrylate (7.83 g, 78 mmol) was added followed by palladium diacetate (0.586 g, 2.61 mmol) and the reaction mixture was stirred at 100° C. overnight. The mixture was allowed to cool and diluted with EtOAc (150 mL) and filtered to remove any precipitated palladium (also some insoluble salts). The reaction mixture was partitioned between EtOAc and water. The organic phase was washed with water and brine, dried over MgSO4, filtered and the solvent was removed in vacuo. When ~75% of the solvent was removed, a solid precipitated out which was filtered collected by filtration and dried to afford the title compound as a white solid;

$^1$H NMR (400 MHz, DMSO-d6) δ 7.92 (1H, d), 7.89 (1H, d), 7.59 (1H, d), 7.51 (1H, d of d), 6.59 (1H, d), 6.09 (2H, s), 4.20 (2H, q), 2.41 (3H, s), 1.26 (3H, t),

Step 3: (E)-3-(4-Chloro-2-((5-methyl-2H-tetrazol-2-yl)methyl)phenyl)acrylic acid (E)-Ethyl 3-(4-chloro-2-((5-methyl-2H-tetrazol-2-yl)methyl)phenyl)acrylate (8.75 g, 28.5 mmol) was placed in a flask with EtOH (100 mL). 2M NaOH (57.1 mL, 114 mmol) was added and the reaction mixture was stirred at room temperature overnight. The ethanol was removed in vacuo and the reaction mixture was acidified with 2M HCl. The resulting precipitate was collected by filtration, washed with water and dried to afford the title compound as a white solid;

LCMS: Rt 0.99 mins; MS m/z 279.2 [M+H]+; Method 2minLowpHv01

Intermediate AB (E)-3-(2-((5-Methyl-2H-tetrazol-2-yl)methyl)-4-(trifluoromethyl)phenyl)acrylic acid

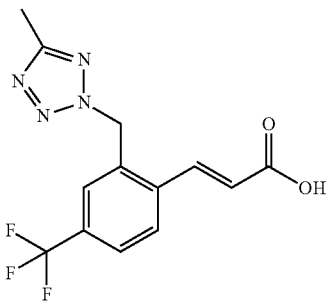 [SMILES: Cc1nnn(Cc2cc(C(F)(F)F)ccc2/C=C/C(=O)O)n1]

Step 1: 2-(2-Bromo-5-(trifluoromethyl)benzyl)-5-methyl-2H-tetrazole

To a stirred solution of 5-methyl-2H-tetrazole (19.44 g, 231 mmol) in DMF (154 mL) at 10° C. under N$_2$ was added K$_2$CO$_3$ (42.6 g, 308 mmol). The resulting suspension was cooled to −2° C. (ice salt bath) and a solution of 1-bromo-2-(bromomethyl)-4-(trifluoromethyl)benzene (49 g, 154 mmol) in DMF (66 mL) was added dropwise over 30 mins keeping the internal T below 5° C. On complete addition, the mixture was allowed to warm to room temperature and the resulting white suspension stirred overnight. Water (400 mL) was added slowly to the mixture which was then extracted with EtOAc (2×500 mL). The combined organic extracts were washed with brine (500 mL), dried (MgSO4) and concentrated in vacuo to yield a colourless oil. On standing a white crystalline solid formed which was suspended in a colourless oil. Iso-hexane (150 mL) was added and the resulting slurry was filtered and washed with iso-hexane (2×50 mL). The filtrate was concentrated in vacuo to yield a colourless oil. Purification of the oil by chromatography on silica eluting with 0-50% EtOAc in iso-hexane afforded the title compound;

LCMS: Rt 1.30 mins; MS m/z 321.3 [M+H]+; Method 2minLowpHv03

Step 2: (E)-Ethyl 3-(2-((5-methyl-2H-tetrazol-2-yl)methyl)-4-(trifluoromethyl)phenyl)acrylate To a stirred solution of 2-(2-bromo-5-(trifluoromethyl)benzyl)-5-methyl-2H-tetrazole (step 1) (17 g, 52.9 mmol) in DMF (76 mL) was added tri-o-tolylphosphine (0.806 g, 2.65 mmol) and triethylamine (14.76 mL, 106 mmol). The solution was de-gassed by bubbling N$_2$ through for 20 mins. Pd(OAc)$_2$ (0.594 g, 2.65 mmol) and ethyl acrylate (8.66 mL, 79 mmol) were added and the reaction mixture heated to 90° C. under N$_2$. After cooling to room temperature, the mixture was partitioned between water (150 mL) and EtOAc (250 mL). The phases were separated and the aqueous phase extracted with more EtOAc (250 mL). The combined organic layers were washed with brine (2×250 mL), dried (MgSO4) and concentrated in vacuo to yield the title compound as an orange oil;

LCMS: Rt 1.36 mins; MS m/z 341.5 [M+H]+; Method 2minLowpHv03

Step 3: (E)-3-(2-((5-Methyl-2H-tetrazol-2-yl)methyl)-4-(trifluoromethyl)phenyl)acrylic acid To a stirred solution of crude (E)-ethyl 3-(2-((5-methyl-2H-tetrazol-2-yl)methyl)-4-(trifluoromethyl)phenyl)acrylate (step 2) (18.02 g, assume 53.0 mmol) in EtOH (212 mL) was added 2M NaOH (79 mL, 159 mmol) slowly. The resulting orange solution stirred at room temperature overnight. The resulting mixture was concentrated in vacuo to a volume of 100 ml and then filtered. 5M HCl (38 mL) was added slowly to adjust the pH to 2 whereupon a solid started to crystallise out of solution. The mixture was stirred at room temperature for 2 h to allow full crystallisation. The resulting slurry was filtered, washing the filter cake with 50% aq. EtOH (2×20 mL). The solid was dried in vacuo at 40° C. overnight to afford the title compound;

LCMS: Rt 1.14 mins; MS m/z 313.4[M+H]+; Method 2minLowpHv03

Intermediate AC (E)-3-(2-((5-Methyl-2H-tetrazol-2-yl)methyl)-4-(trifluoromethoxy)phenyl)acrylic acid

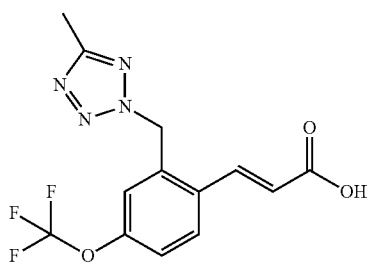 [SMILES: Cc1nnn(Cc2cc(OC(F)(F)F)ccc2/C=C/C(=O)O)n1]

Step 1: 1-Bromo-2-(bromomethyl)-4-(trifluoromethoxy) benzene

To a stirred solution of 1-bromo-2-methyl-4-(trifluoromethoxy)benzene (commercially available) (0.125 mL, 0.784 mmol) in t-butyl acetate (3.921 mL) was added NBS (147 mg, 0.823 mmol) and the suspension was stirred at room temperature for 5 min. To the suspension was added 2,2'-azobis(2-methylpropionitrile) (6.44 mg, 0.039 mmol) and the reaction mixture was heated to 80° C. for 1 hour, then was cooled to 70° C. and left overnight. The reaction was quenched by addition of sat. NaHCO$_3$ (2 mL) and EtOAc (1 mL). The organic layer was separated, washed with sat. NaHCO$_3$, dried over MgSO$_4$, filtered and concentrated to give the title compound which was used in the next step without further purification.

Step 2: 2-(2-Bromo-5-(trifluoromethoxy)benzyl)-5-methyl-2H-tetrazole

The title compound was prepared by a similar method to Intermediate AB step 1 by replacing 1-bromo-2-(bromomethyl)-4-(trifluoromethyl)benzene with 1-bromo-2-(bromomethyl)-4-(trifluoro methoxy)benzene;

LCMS: Rt 1.33 mins; MS m/z 339.1[M+H]+; Method 2minLowpHv03

Step 3: (E)-Ethyl 3-(2-((5-methyl-2H-tetrazol-2-yl) methyl)-4-(trifluoromethoxy)phenyl)acrylate The title compound was prepared by a similar method to Intermediate AB step 2 by replacing 2-(2-bromo-5-(trifluoromethyl)benzyl)-5-methyl-2H-tetrazole with 2-(2-bromo-5-(trifluoromethoxy) benzyl)-5-methyl-2H-tetrazole (step 2);

LCMS: Rt 1.43 mins; MS m/z 357.3 [M+H]+; Method 2minLowpHv03

Step 4: (E)-3-(2-((5-Methyl-2H-tetrazol-2-yl)methyl)-4-(trifluoromethoxy)phenyl)acrylic acid The title compound was prepared by a similar method to Intermediate AB step 3 by replacing (E)-ethyl 3-(2-((5-methyl-2H-tetrazol-2-yl)methyl)-4-(trifluoromethyl)phenyl)acrylate with (E)-ethyl 3-(2-((5-methyl-2H-tetrazol-2-yl)methyl)-4-(trifluoromethoxy)phenyl)acrylate (step 3);

LCMS: Rt 1.20 mins; MS m/z 327.1[M+H]+; Method 2minLowpHv03

Intermediate AD (E)-3-(4-Chloro-2-((5-methyl-1,3,4-oxadiazol-2-yl) methyl)phenyl)acrylic acid

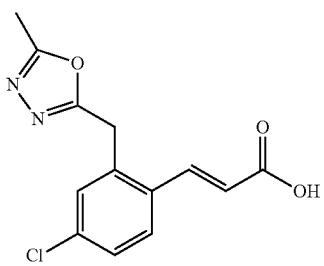 [SMILES: Cc1nnc(Cc2cc(Cl)ccc2/C=C/C(=O)O)o1]

Step 1: 2-(2-Bromo-5-chlorobenzyl)-5-methyl-1,3,4-oxadiazole

This following procedure was carried out according to Augustine et. al., Tetrahedron, 2009, 9989-9996.

To a stirred solution of 2-bromo-5-chlorophenylacetic acid (commercially available) (500 mg, 2.004 mmol) and acetohydrazide (148 mg, 2.004 mmol) in EtOAc (4 mL) under N$_2$ was added Et$_3$N (0.556 mL, 4.01 mmol). The resulting mixture was cooled to 10° C. and T3P® (50% in EtOAc) (1.535 mL, 2.61 mmol) was added dropwise over 10 mins keeping internal T below 15° C. The reaction mixture was allowed to warm to room temperature. After stirring for 1 h, the mixture was diluted with water (2 mL) and filtered, washing with water (2 mL) and EtOAc (2×2 mL). The resulting solid was dried in vacuo at 40° C. for 2 h and then slurried in EtOAc (4 mL). Et3N (0.556 mL, 4.01 mmol) was added followed by T3P® (1.76 mL, 1.5 eq.) and the mixture was heated to reflux overnight. Further triethylamine (0.28 mL, 1 eq.) and T3P® (1.18 mL, 1 eq.) were added and heating at reflux continued for a total of 40 h. After cooling to room temperature, EtOAc (10 mL) was added and the mixture washed with water (10 mL), sat. NaHCO$_3$ (10 mL), water (10 mL) and brine (10 mL), dried (MgSO4) and concentrated in vacuo to yield the title compound as a white solid;

LCMS: Rt 1.05 mins; MS m/z 289.3 [M+H]+; Method 2minLowpHv03

Step 2: (E)-Ethyl 3-(4-chloro-2-((5-methyl-1,3,4-oxadiazol-2-yl)methyl)phenyl)acrylate A solution of 2-(2-bromo-5-chlorobenzyl)-5-methyl-1,3,4-oxadiazole (5 g, 17.39 mmol), tri-o-tolylphosphine (0.265 g, 0.869 mmol) and triethylamine (4.85 mL, 34.8 mmol) in DMF (25 mL) was de-gassed by bubbling N$_2$ through the solution for 20 minutes. Ethyl acrylate (2.84 mL, 26.1 mmol) and Pd(OAc)$_2$ (0.195 g, 0.869 mmol) were added and the mixture was heated under N$_2$ to 100° C. After 1 h, the mixture was cooled to room temperature and water (50 mL) was added slowly causing a brown slurry to form. The further cooling overnight, the resulting solid was collected by filtration, washing the solid with (3×20 mL) and drying in vacuo at 40° C. for 2 h to afford the title compound;

LCMS: Rt 1.14 mins; MS m/z 307.5/309.5 [M+H]+; Method 2minLowpHv01

Step 3: (E)-3-(4-Chloro-2-((5-methyl-1,3,4-oxadiazol-2-yl)methyl)phenyl)acrylic acid To a stirred suspension of (E)-ethyl 3-(4-chloro-2-((5-methyl-1,3,4-oxadiazol-2-yl)methyl)phenyl) acrylate (step 2) (5.34 g, 17.4 mmol) in EtOH (69.6 mL) was added 2M NaOH (43.5 mL, 87 mmol) and the mixture was stirred at room temperature for 1.5 h. The EtOH was removed under reduced pressure and the aqueous slurry was extracted with TBME (2×40 mL) and then acidified by addition of 2M HCl (42 mL) to pH 3. The aqueous phase was extracted with EtOAc (2×50 mL) and the combined organic extracts were washed with brine (50 mL), dried (MgSO4) and concentrated in vacuo to yield the title compound as a pale yellow solid;

LCMS: Rt 0.91 mins; MS m/z 377.5[M–H]–: Method 2minLowpHv01

Intermediate AE (E)-3-(4-Chloro-2-((3-methyl-1,2,4-oxadiazol-5-yl) methyl)phenyl)acrylic acid

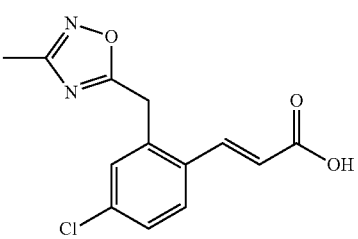 [SMILES: Cc1noc(Cc2cc(Cl)ccc2/C=C/C(=O)O)n1]

The title compound was prepared by a similar method to Intermediate AD by replacing acetohydrazide (step 1) with acetamide oxime;

LCMS: Rt 1.00 mins; MS m/z 277.1 [M–H]–: Method 2minLowpHv01

Intermediate AF 3-(2-((5-Methyl-2H-tetrazol-2-yl)methyl)-4-(trifluoromethyl)phenyl)propanoic acid

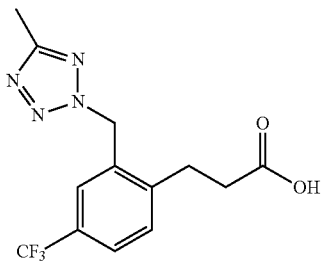

The title compound was prepared by a similar method to Intermediate A by replacing ethyl acrylate (step 2) with acrolein diethylacetal (Aldrich);

LCMS: Rt 1.12 mins; MS m/z 315.5 [M–H]–: Method 2minLowpHv01

Intermediate AG

4-Chloro-2-((5-methyl-2H-tetrazol-2-yl)methyl)benzyl 1H-imidazole-1-carboxylate

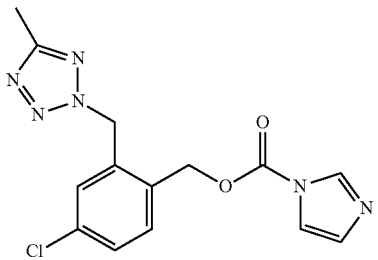 [SMILES: Cc1nnn(Cc2cc(Cl)ccc2COC(=O)n2ccnc2)n1]

Step 1: Methyl 4-chloro-2-methylbenzoate

4-Chloro-2-methylbenzoic acid (25 g, 147 mmol) was placed in a flask with dry MeOH (250 mL). Concentrated sulfuric acid (15.62 mL, 293 mmol) was added slowly to the suspension and the mixture was heated at reflux overnight. The solvent was removed in vacuo and the mixture was partitioned between EtOAc and 1M NaOH. The organic phase was washed with water and brine, dried over MgSO4, filtered and the solvent was removed in vacuo to give the title compound as a light golden oil;

$^1$H NMR (400 MHz, DMSO-d6) δ 7.82 (1H, d), 7.46 (1H, d), 7.39 (1H, d of d), 3.82 (3H, s), 2.50 (3H, s).

Step 2: Methyl 2-(bromomethyl)-4-chlorobenzoate

Methyl 4-chloro-2-methylbenzoate (25.7 g, 139 mmol) was placed in a flask with t-butyl acetate (400 mL). NBS (32.2 g, 181 mmol) was added followed by AIBN (1.14 g, 6.96 mmol) and the mixture was stirred at 90° C. overnight. The mixture was partitioned between EtOAc and water. The organic phase was washed with water and brine, dried over MgSO4, filtered and the solvent was removed in vacuo. The product was purified by chromatography on silica eluting with 19:1 iso-hexane: EtOAc. The resulting material was triturated in a minimal volume of ice cold iso-hexane and filtered to afford the title compound;

$^1$H NMR (400 MHz, DMSO-d6) δ 7.90 (1H, d), 7.78 (1H, d), 7.57 (1H, d of d), 5.01 (2H, s), 3.89 (3H, s).

Step 3: Methyl 4-chloro-2-((5-methyl-2H-tetrazol-2-yl)methyl)benzoate

Methyl 2-(bromomethyl)-4-chlorobenzoate (step 2)(15 g, 56.9 mmol) was placed in a flask with dry DMF (100 mL) and cooled (ice-bath). 5-Methyl-2H-tetrazole (7.18 g, 85 mmol) was added followed by potassium carbonate (15.73 g, 114 mmol) and the mixture was stirred at room temperature overnight. The mixture was partitioned between EtOAc and water. The organic phase was washed with water and brine, dried over MgSO4, filtered and the solvent was removed in vacuo. The product was purified by chromatography on silica eluting with iso-hexane: EtOAc afforded the title compound;

$^1$H NMR (400 MHz, DMSO-d6) δ 7.99 (1H, d), 7.63 (1H, d of d), 7.43 (1H, d), 6.18 (2H, s), 3.80 (3H, s), 2.43 (3H, s).

Step 4: 4-Chloro-2-((5-methyl-2H-tetrazol-2-yl)methyl)benzoic acid

Methyl 4-chloro-2-((5-methyl-2H-tetrazol-2-yl)methyl)benzoate (step 3) (5.50 g, 20.62 mmol) was placed in a flask with MeOH (100 mL). 2M NaOH (51.6 mL, 103 mmol) was added and the mixture was stirred at room temperature overnight. The MeOH was removed in vacuo and the mixture was acidified with 2M HCl. The resulting solid was filtered, washed with water and dried to give the title compound as a white solid;

LCMS: Rt 0.95 mins; MS m/z 253.4 [M+H]+; 2minLowpHv01

Step 5: (4-Chloro-2-((5-methyl-2H-tetrazol-2-yl)methyl)phenyl)methanol

4-Chloro-2-((5-methyl-2H-tetrazol-2-yl)methyl)benzoic acid (step 4)(3.00 g, 11.87 mmol) was placed in a flask with THF (50 mL). Borane tetrahydrofuran complex (1M in THF) (29.7 mL, 29.7 mmol) was added slowly and the reaction mixture was stirred at 50° C. for 2 hours. The reaction was quenched carefully with 2M HCl and stirred for 30 minutes The resulting mixture was partitioned between EtOAc and water. The organic phase was washed with water and brine, dried over MgSO4, filtered and the solvent was removed in vacuo. The product was purified by chromatography on silica eluting with iso-hexane/EtOAc to afford the title compound;

LCMS: Rt 0.88 mins; MS m/z 239.4 [M+H]+; Method 2minLowpHv01

Step 6: 4-Chloro-2-((5-methyl-2H-tetrazol-2-yl)methyl)benzyl 1H-imidazole-1-carboxylate (4-Chloro-2-((5-methyl-2H-tetrazol-2-yl)methyl)phenyl)methanol (step 5)(200 mg, 0.838 mmol) was placed in a flask with DMF (4 mL). CDI (204 mg, 1.26 mmol) was added and the reaction mixture was stirred at room temperature for 2 hours. The resulting mixture was used as a stock solution of 4-chloro-2-((5-methyl-2H-tetrazol-2-yl)methyl)benzyl 1H-imidazole-1-carboxylate in DMF and no further analysis was carried out.

Intermediate AH (E)-3-(4-(Difluoromethyl)-2-((5-methyl-2H-tetrazol-2-yl)methyl)phenyl)acrylic acid

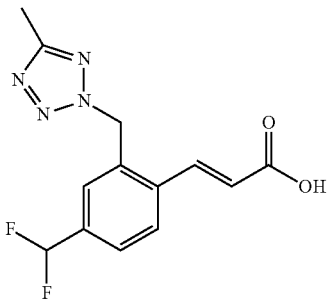 [SMILES: Cc1nnn(Cc2cc(C(F)F)ccc2/C=C/C(=O)O)n1]

Step 1: 1-Bromo-4-(difluoromethyl)-2-methylbenzene

DeoxoFluor® (bis(2-methoxyethyl)aminosulfur trifluoride) (12.60 mL, 34.2 mmol) was added to a solution of 4-bromo-3-methylbenzaldehyde (4 g, 20.10 mmol) in DCM (12 mL) and the resulting mixture was stirred for 18 h at room temperature. The reaction was quenched with water and the pH adjusted to 8-9 with saturated sodium bicarbonate solution. The mixture was extracted with DCM (3×20 mL). The combined organic extracts were washed with water (20 mL), brine (20 mL), dried over magnesium sulfate, filtered and concentrated in vacuo. Purification was by silica gel column chromatography eluting with a gradient of iso-hexane to 50% ethyl acetate in iso-hexane. The product fractions were combined and evaporated in vacuo to give the title compound as a colourless oil;

$^1$H NMR (400 MHz, CDCl3) δ 7.63 (1H, d), 7.39 (1H, d), 7.20 (1H, d of d), 6.60 (1H, t), 2.49 (3H, s).

Step 2: 1-Bromo-2-(bromomethyl)-4-(difluoromethyl)benzene

A degassed solution of 1-bromo-2-(bromomethyl)-4-(difluoromethyl)benzene (step 1) (4 g, 18.10 mmol) and NBS (3.86 g, 21.72 mmol) in a mixture of acetonitrile (81 mL) and acetic acid (34.6 mL) was pumped though a photochemical flow reactor and irradiated with a 125 W medium pressure mercury lamp. The resulting solution was concentrated in vacuo and dissolved in DCM (500 mL). The solution was washed with saturated sodium bicarbonate solution (200 mL), saturated sodium thiosulfate solution (100 mL), dried over magnesium sulfate, filtered and concentrated in vacuo to give a the title compound as a brown oil;

LC MS Rt 1.45 mins; MS m/z [M−H]⁻ 296.8, Method 2minLowpH

Step 3: 2-(2-Bromo-5-(difluoromethyl)benzyl)-5-methyl-2H-tetrazole

5-Methyl-2H-tetrazole (2.060 g, 24.51 mmol) was added to a mixture of 1-bromo-2-(bromomethyl)-4-(difluoromethyl)benzene (step 2) (4.9 g, 16.34 mmol) and potassium carbonate (4.52 g, 32.7 mmol) in DMF (50 mL) and the resulting mixture stirred for 18 h at room temperature. The reaction was poured into water (500 mL) and extracted with ether (3×250 mL). The combined organic solutions were washed with water (100 mL), brine (100 mL), dried over magnesium sulfate, filtered and concentrated in vacuo. Purification was carried out by silica gel column chromatography eluting with a gradient of iso-hexane to ethyl acetate. The product fractions were combined and concentrated in vacuo to give the title compound as a clear oil;

LC MS Rt 1.24 min; MS m/z [M+H]⁺ 303.1, 305.1, Method 2minLowpHv03

Step 4: (E)-Ethyl 3-(4-(difluoromethyl)-2-((5-methyl-2H-tetrazol-2-yl)methyl)phenyl)acrylate Degassed DMF (5 mL) was added to a mixture of 2-(2-bromo-5-(difluoromethyl)benzyl)-5-methyl-2H-tetrazole (step 3) (500 mg, 1.650 mmol), palladium acetate (9.26 mg, 0.041 mmol) and tri(o-tolyl)phosphine (25.1 mg, 0.082 mmol). Ethyl acrylate (0.270 mL, 2.474 mmol) was then added followed by triethylamine (0.460 mL, 3.30 mmol) and the resulting mixture heated at 90° C. for 18 h. The reaction was diluted with water (30 mL) and extracted with diethyl ether (3×25 mL). The combined organic solutions were washed with water (2×20 mL), brine (20 mL), dried over sodium sulfate, filtered and concentrated in vacuo. Purification was carried out by silica gel column chromatography eluting with a gradient of iso-hexane to ethyl acetate. The product fractions were combined and evaporated in vacuo to give the title compound as a white solid;

LC MS Rt 1.30 min; MS m/z [M+H]⁺ 323.3, Method 2minLowpHv03

Step 5: (E)-3-(4-(Difluoromethyl)-2-((5-methyl-2H-tetrazol-2-yl)methyl)phenyl)acrylic acid A solution of lithium hydroxide (149 mg, 6.21 mmol) in water (5.00 mL) was added to a solution of (E)-ethyl 3-(4-(difluoromethyl)-2-((5-methyl-2H-tetrazol-2-yl)methyl)phenyl)acrylate (step 4) (500 mg, 1.551 mmol) in THF (5 mL) and the resulting mixture stirred for 18 h at room temperature. The reaction was concentrated to 5 mL and the pH adjusted to pH1 with 2M hydrochloric acid. The resulting mixture was extracted with ethyl acetate (3×20 mL). The combined organic extracts were washed with brine (20 mL), dried over sodium sulfate, filtered and concentrated in vacuo to give the title compound as a light yellow solid;

LC MS Rt 1.03 min; MS m/z [M+H]⁺ 295.2, Method 2minLowpHv03

Intermediate AI (E)-3-(4-(Difluoromethoxy)-2-((5-methyl-2H-tetrazol-2-yl)methyl)phenyl)acrylic acid

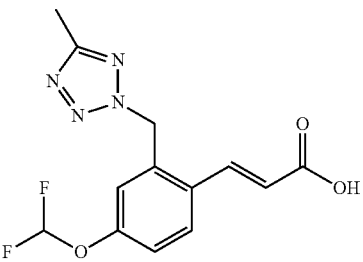 [SMILES: Cc1nnn(Cc2cc(OC(F)F)ccc2/C=C/C(=O)O)n1]

Step 1: 1-Bromo-4-(difluoromethoxy)-2-methylbenzene

Potassium hydroxide (9.00 g, 160 mmol) was added to a solution of 4-bromo-3-methylphenol (1.5 g, 8.02 mmol) in acetonitrile (40 mL) and water (40.0 mL) and the solution cooled to −78° C. The mixture was warmed to 0° C. and diethyl (bromodifluoromethyl)phosphonate (2.85 mL, 16.04 mmol) was added dropwise. The mixture was stirred at 0° C. for 30 min then allowed to warm to room temperature and stirred for a further 1 h. The reaction was diluted with ethyl acetate (5 mL) and the aqueous layer was separated. The organic solution was washed with water (5 mL), dried over magnesium sulfate, filtered and concentrated in vacuo to give the title compound as a clear oil;

$^1$H NMR (400 MHz, CDCl$_3$) δ 7.52 (1H, d), 7.04 (1H, d), 6.86 (1H, dd), 6.50 (1H, t), 2.42 (3H, s)

Step 2: 1-Bromo-2-(bromomethyl)-4-(difluoromethoxy) benzene

A degassed solution of 1-bromo-4-(difluoromethoxy)-2-methylbenzene (step 1) (4 g, 18.10 mmol) and NBS (1.279 g, 7.19 mmol) in a mixture of acetonitrile (26.7 mL) and acetic acid (11.46 mL) was pumped though a photochemical flow reactor and irradiated with a 125 W medium pressure mercury lamp. The resulting solution was concentrated in vacuo and dissolved in ethyl acetate (500 mL). The solution was washed with saturated sodium bicarbonate solution (200 mL), saturated sodium thiosulfate solution (100 mL), dried over magnesium sulfate, filtered and concentrated in vacuo to give a the title compound as a brown oil;

LC-MS: RT 1.41 mins; [M+H]$^+$ 314, 316 Method 2minLowpH

Step 3: 2-(2-Bromo-5-(difluoromethoxy)benzyl)-5-methyl-2H-tetrazole

5-Methyl-1H-tetrazole (0.373 g, 4.43 mmol) and potassium carbonate (0.612 g, 4.43 mmol) were added to a solution of 1-bromo-2-(bromomethyl)-4-(difluoromethoxy) benzene (step 2) (1.4 g, 4.43 mmol) in DMF (10 mL). The suspension was stirred at room temperature for 2 h and left standing over the weekend. The reaction mixture was concentrated in vacuo. The residue was dissolved in ethyl acetate and washed once with water and once with brine. The organic layer was dried over magnesium sulfate, filtered and concentrated in vacuo. Purification was carried out by silica gel column chromatography eluting with a gradient of iso-hexane to ethyl acetate. The product fractions were combined and evaporated in vacuo to give the title compound as a yellow oil;

LC MS Rt 1.26 mins; [M+H]$^+$ 319.1 321.1: Method 2minLowpHv03

Step 4: (E)-Ethyl 3-(4-(difluoromethoxy)-2-((5-methyl-2H-tetrazol-2-yl)methyl)phenyl)acrylate Ethyl acrylate (0.179 mL, 1.645 mmol) and palladium acetate (12.31 mg, 0.055 mmol) were added to a degassed solution of 2-(2-bromo-5-(difluoromethoxy)benzyl)-5-methyl-2H-tetrazole (step 3) (350 mg, 1.097 mmol), tri-o-tolylphosphine (16.69 mg, 0.055 mmol) and triethylamine (0.306 mL, 2.194 mmol) in DMF (3 mL) and the resulting mixture heated to 100° C. for 4 h. The reaction mixture was poured into water (20 mL). The mixture was extracted with ethyl acetate. The organic layer was washed with brine, dried over magnesium sulfate and filtered through 2 g of 2,4,6-trimercaptotriazine silica. The filtrate was concentrated in vacuo. Purification was carried out by silica gel column chromatography eluting with a gradient of iso-hexane to ethyl acetate. The product fractions were combined and evaporated in vacuo to give the title compound as a colourless oil;

$^1$H NMR (400 MHz, DMSO-d6) δ 7.95 (1H, d), 7.92 (1H, s), 7.34 (1H, t), 7.27 (1H, s), 7.26 (1H, d), 6.54 (1H, d), 6.07 (2H, s), 4.95 (2H, q), 2.42 (3H, s), 1.26 (3H, t).

Step 5: (E)-3-(4-(Difluoromethoxy)-2-((5-methyl-2H-tetrazol-2-yl)methyl)phenyl)acrylic acid 2M Sodium hydroxide solution (1.005 mL, 2.010 mmol) was added to a solution of (E)-ethyl 3-(4-(difluoromethoxy)-2-((5-methyl-2H-tetrazol-2-yl) methyl)phenyl)acrylate in ethanol (3 mL). The mixture was briefly warmed and stirred at room temperature for 3 h. The reaction mixture was concentrated in vacuo. The residue was dissolved in water (5 mL) and acidified with 2M hydrochloric acid. Ethyl acetate (10 mL) was added and the layers were separated. The organic solution was dried over magnesium sulfate, filtered and concentrated in vacuo to give the title compound as a white solid;

LC MS Rt 1.10 mins; [M+H]$^+$ 311.2 2minLowpHv03

Intermediate AJ (E)-3-(4-Methyl-2-((5-methyl-2H-tetrazol-2-yl)methyl)phenyl)acrylic acid

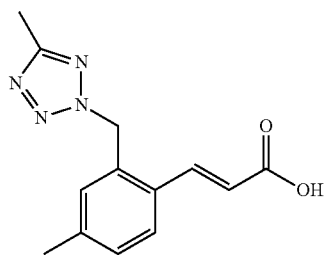 [SMILES: Cc1ccc(/C=C/C(=O)O)c(Cn2nnc(C)n2)c1]

Step 1: (2-Bromo-5-methylphenyl)methanol

A solution of borane THF complex 1M in THF (13.95 mL, 13.95 mmol) was added dropwise to a solution of 2-bromo-5-methylbenzoic acid (1 g, 4.65 mmol) in THF (20 mL) at 0° C. The resulting mixture was stirred for 30 min at 0° C. then allowed to warm to room temperature and stirred for 18 h. The reaction was quenched with methanol followed by 2M hydrochloric acid. The resulting mixture was stirred for 30 min and extracted with ethyl acetate (3×25 mL). The combined organic solutions were washed with water (25 mL), brine (25 mL), dried over magnesium sulfate, filtered and concentrated in vacuo to the title compound as a white solid;

LC MS Rt 1.13 min; MS m/z [M−18+H]$^+$183.1, 185.1, Method 2minLowpHv03.

Step 2: 1-Bromo-2-(bromomethyl)-4-methylbenzene

Triphenylphosphine (1565 mg, 5.97 mmol) was added to a solution of (2-bromo-5-methylphenyl)methanol (step 1) (800 mg, 3.98 mmol) and hexabromoacetone (1057 mg, 1.989 mmol) in MeCN (20 mL) and the mixture stirred for 2 h at room temperature. The reaction was concentrated in vacuo. Purification was carried out by silica gel column chromatography eluting with a gradient of iso-hexane to 20% ethyl acetate in iso-hexane. The product fractions were combined and evaporated in vacuo to give the title compound as a colourless oil;

$^1$H NMR (400 MHz, CDCl$_3$) δ 7.47 (1H, d), 7.29 (1H, s), 7.00 (1H, d), 4.59 (2H, s), 2.34 (3H, s)

Step 3: 2-(2-Bromo-5-methylbenzyl)-5-methyl-2H-tetrazole

5-Methyl-2H-tetrazole (430 mg, 5.11 mmol) was added to a mixture of 1-bromo-2-(bromomethyl)-4-methylbenzene (step 2) (900 mg, 3.41 mmol) and potassium carbonate (942 mg, 6.82 mmol) in DMF (10 mL) and the resulting mixture stirred at room temperature for 18 h. The reaction was poured into water (100 mL) and extracted with ether (3×50 mL). The combined organic solutions were washed with water (50 mL), brine (50 mL), dried over magnesium sulfate, filtered and concentrated in vacuo. Purification was carried out by silica gel column chromatography eluting with a gradient of iso-hexane to ethyl acetate. The product fractions were combined and evaporated in vacuo to give the title compound as a colourless oil;

LC MS Rt 1.28 min; MS m/z [M+H]+267.1, 269.1, Method 2minLowpHv03

Step 4: (E)-Ethyl 3-(4-methyl-2-((5-methyl-2H-tetrazol-2-yl)methyl)phenyl)acrylate DMF (3 mL) was added to a mixture of 2-(2-bromo-5-methylbenzyl)-5-methyl-2H-tetrazole (step 3) (250 mg, 0.936 mmol), palladium acetate (5.25 mg, 0.023 mmol) and tri(o-tolyl)phosphine (14.24 mg, 0.047 mmol). Ethyl acrylate (0.153 mL, 1.404 mmol) was then added followed by triethylamine (0.261 mL, 1.872 mmol) and the resulting mixture heated at 90° C. for 18 h. The reaction was diluted with water (30 mL) and extracted with ether (3×25 mL). The combined organic solutions were washed with water (2×20 mL), brine (20 mL), dried over sodium sulfate, filtered and concentrated in vacuo. Purification was carried out by silica gel column chromatography eluting with a gradient of iso-hexane to ethyl acetate. The product fractions were combined and evaporated in vacuo to give the title compound as a white solid;

LC MS Rt 1.33 min; MS m/z [M+H]+287.2, Method 2minLowpHv03

Step 5: (E)-3-(4-Methyl-2-((5-methyl-2H-tetrazol-2-yl)methyl)phenyl)acrylic acid 1M Sodium hydroxide solution (0.880 mL, 0.880 mmol) was added to a solution of (E)-ethyl 3-(4-methyl-2-((5-methyl-2H-tetrazol-2-yl)methyl)phenyl)acrylate (step 4) (63 mg, 0.220 mmol) in THF (1 mL) and the resulting mixture stirred at room temperature for 18 h. The reaction was concentrated to 1 mL and acidified with 1M hydrochloric acid. The resulting mixture was extracted with ethyl acetate (3×10 mL). The combined organic solutions were washed with brine (10 mL), dried over sodium sulfate, filtered and concentrated in vacuo to give the title compound as a colourless gum;

LC MS 1.03 min; MS m/z [M+H]+ 259.5, Method 2minLowpHv03

Intermediate B (S)-2-Methyl-5-(piperidin-2-yl)-1,3,4-oxadiazole

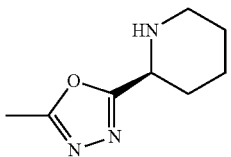

Step 1: (S)-tert-Butyl 2-(2-acetylhydrazinecarbonyl)piperidine-1-carboxylate (S)-1-(tert-Butoxycarbonyl)piperidine-2-carboxylic acid (2.00 g, 7.53 mmol) and acetohydrazide (0.681 g, 8.28 mmol) were placed in a flask with EtOAc (10 mL). DIPEA (3.94 mL, 22.58 mmol) was added followed by the slow addition of T3P® (50% in EtOAc) (6.59 mL, 11.29 mmol) and the reaction mixture was stirred at room temperature for 2 h. The solvent was removed in vacuo and the crude residue was purified by chromatography on silica eluting with iso-hexane/EtOAc to afford the title compound;

¹H NMR (400 MHz, DMSO-d6) δ 9.70 (2H, d), 4.59 (1H, m), 3.80 (1H, m), 3.10 (1H, m), 2.08 (1H, m), 1.88 (3H, s), 1.58 (3H, m), 1.39 (9H, 2), 1.30 (2H, m).

Step 2: (S)-tert-Butyl 2-(5-methyl-1,3,4-oxadiazol-2-yl)piperidine-1-carboxylate (S)-tert-Butyl 2-(2-acetylhydrazinecarbonyl)piperidine-1-carboxylate (step 1) (2.00 g, 7.01 mmol) was placed in a flask with DCM (75 mL). DIPEA (7.35 mL, 42.1 mmol) was added followed by PS—PPh₃ (5.13 g, 10.51 mmol) and hexachloroethane (4.98 g, 21.03 mmol). After stirring at at 45° C. for 4 hours, the PS—PPh₃ was removed by filtration and washed with DCM. The filtrate was partitioned between DCM and water. The organic phase was washed with 1M HCl, water and brine, dried over MgSO4, filtered and the solvent was removed in vacuo. The product was purified by chromatography on silica eluting with iso-hexane/(EtOAc: MeOH 10:1). The product fractions were combined and the solvent was removed in vacuo to give a colourless oil which slowly crystallised to afford the title compound;

¹H NMR (400 MHz, DMSO-d6) δ 5.42 (1H, m), 3.89 (1H, m), 2.80 (1H, m), 2.48 (3H, s), 2.12 (1H, m), 1.80 (1H, m), 1.61 (2H, m), 1.41 (9H, 2), 1.38 (2H, m).

Step 3: (S)-2-Methyl-5-(piperidin-2-yl)-1,3,4-oxadiazole (S)-tert-Butyl 2-(5-methyl-1,3,4-oxadiazol-2-yl)piperidine-1-carboxylate (step 2) (500 mg, 1.87 mmol) was placed in a flask with DCM (2 mL). TFA (1.44 mL, 18.7 mmol) was added and the reaction mixture was stirred at room temperature for 2 h. The solvent was removed in vacuo and the residue was dissolved in acetonitrile (10 mL) and treated with MP-carbonate (2 g, ~2.5 mmol/g loading, macroporous polymer supported hydrogen carbonate). After swirling for 10 minutes the pH was tested to ensure all the TFA had been neutralised. The resin was filtered off and the solvent was removed in vacuo to afford the title compound. No further purification.

Intermediate BA (R)-2-Methyl-5-(pyrrolidin-3-yl)-1,3,4-oxadiazole

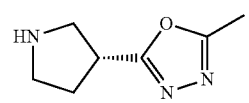

The title compound was prepared by a similar method to Intermediate B steps 1-3 from (R)-1-(tert-butoxycarbonyl)pyrrolidine-3-carboxylic acid and acetohydrazide.

Intermediate BB (S)-2-Methyl-5-(pyrrolidin-2-yl)-1,3,4-oxadiazole

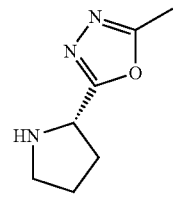

The title compound was prepared by a similar method to Intermediate B steps 1-3 from Boc-L-Pro-OH and acetohydrazide.

Intermediate BC

(S)—N-Methylpiperidine-2-carboxamide

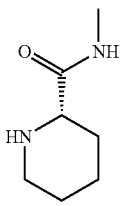

Step 1: (S)-tert-Butyl 2-(methylcarbamoyl)piperidine-1-carboxylate (S)-1-(tert-Butoxycarbonyl)piperidine-2-carboxylic acid (1.00 g, 4.36 mmol) and methylamine hydrochloride (2.94 g, 43.6 mmol) were placed in a flask with dry DMF (3 mL). DIPEA (3.81 mL, 21.81 mmol) was added followed by the slow addition of T3P® (50% in DMF) (5.09 mL, 8.72 mmol) and the mixture was stirred at room temperature for 2 h. The mixture was partitioned between EtOAc and water. The organic phase was washed with water and brine, dried over MgSO4, filtered and the solvent was removed in vacuo to afford the title compound;

$^1$H NMR (400 MHz, DMSO-d6) δ 7.69 (1H, s), 4.48 (1H, m), 3.80 (1H, m), 3.00 (1H, m), 2.60 (3H, d), 2.03 (1H, m), 1.51 (3H, m), 1.39 (9H, s), 1.22 (2H, m).

Step 2: (S)—N-Methylpiperidine-2-carboxamide (S)-tert-Butyl 2-(methylcarbamoyl)piperidine-1-carboxylate (step 1)(700 mg, 2.89 mmol) was dissolved in DCM (2 mL). TFA (1.11 mL, 14.44 mmol) was added and the reaction mixture was stirred at room temperature for 2 h. The solvent was removed in vacuo to give a colourless oil.

The residue was dissolved in acetonitrile (10 mL) and treated with MP-carbonate (5 g, ~2.5 mmol/g loading, macroporous polymer supported hydrogen carbonate). After swirling for 10 minutes the pH was tested to ensure all the TFA had been neutralised. The resin was filtered off and the solvent was removed in vacuo to give the title compound as a white solid. No further purification.

Intermediate BD

2-Methyl-5-(piperidin-4-yl methyl)-1,3,4-oxadiazole

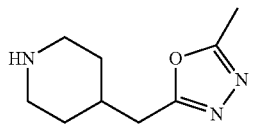

The title compound was prepared by a similar method to Intermediate B steps 1-3 from 2-(1-(tert-butoxycarbonyl)piperidin-4-yl)acetic acid and acetohydrazide;

$^1$H NMR (400 MHz, DMSO-d6) δ 8.63 (1H, br s), 8.32 (1H, br s), 3.28 (2H, m), 2.90 (2H, m), 2.80 (2H, d), 2.43 (3H, s), 2.03 (1H, m), 1.81 (2H, m), 1.40 (2H, m).

Intermediate BE

2-Methyl-5-(2-(piperidin-4-yl)ethyl)-1,3,4-oxadiazole

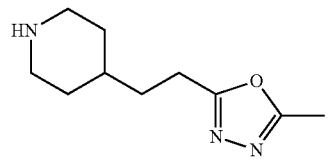

The title compound was prepared by a similar method to Intermediate B steps 1-3 from 3-(1-(tert-butoxycarbonyl)piperidin-4-yl)propanoic acid and acetohydrazide;

$^1$H NMR (400 MHz, DMSO-d6) δ 3.10 (2H, m), 2.80 (2H, t), 2.63 (2H, m), 2.45 (3H, s), 1.72 (2H, m), 1.61 (2H, m), 1.47 (1H, m), 1.15 (2H, m).

Intermediate BF

2-Methyl-5-(3-(piperidin-4-yl)propyl)-1,3,4-oxadiazole

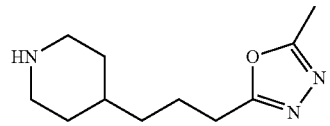

Step 1: tert-Butyl 4-(4-(2-acetylhydrazinyl)-4-oxobutyl)piperidine-1-carboxylate 4-(1-(tert-Butoxycarbonyl)piperidin-4-yl)butanoic acid (commercially available) (2.00 g, 6.50 mmol) and acetohydrazide (0.588 g, 7.15 mmol) were placed in a flask with EtOAc (10 mL). DIPEA (3.40 mL, 19.49 mmol) was added followed by the slow addition of T3P® (50% in EtOAc) (5.69 mL, 9.75 mmol). The reaction mixture was stirred at room temperature for 2 hours. The solvent was removed in vacuo and the crude product was purified by chromatography on silica eluting with iso-hexane/(EtOAc:MeOH-10:1) to afford the title compound.

Step 2: tert-Butyl 4-(3-(5-methyl-1,3,4-oxadiazol-2-yl)propyl)piperidine-1-carboxylate tert-Butyl 4-(4-(2-acetylhydrazinyl)-4-oxobutyl)piperidine-1-carboxylate (step 1)(2.00 g, 6.11 mmol) was placed in a flask with DCM (75 mL). DIPEA (6.40 mL, 36.7 mmol) was added followed by PS—PPh$_3$ (4.36 g, 9.16 mmol) and hexachloroethane (4.34 g, 18.33 mmol). After stirring at at 45° C. for 4 hours, the PS—PPh$_3$ was removed by filtration and washed with DCM. The filtrate was partitioned between DCM and water. The organic phase was washed with 1M HCl, water and brine, dried over MgSO4, filtered and the solvent was removed in vacuo. The product was purified by chromatography on silica eluting with iso-hexane/(EtOAc:MeOH 10:1). The product fractions were combined and the solvent was removed in vacuo to give the title compound;

Step 3: 2-Methyl-5-(3-(piperidin-4-yl)propyl)-1,3,4-oxadiazole tert-Butyl 4-(3-(5-methyl-1,3,4-oxadiazol-2-yl)propyl)piperidine-1-carboxylate (step 2) (530 mg, 1.71 mmol) was placed in a flask with DCM (2 mL). TFA (1.32 mL, 17.13 mmol) was added and the resulting mixture was stirred at room temperature for 2 hours. The solvent was removed in vacuo and the residue was dissolved in acetonitrile (10 mL) and treated with MP-carbonate (2 g, ~2.5 mmol/g loading, macroporous polymer supported hydrogen carbonate). After swirling for 10 minutes the pH was tested to ensure all the TFA had been neutralised. The resin was filtered off and the solvent was removed in vacuo to afford the title compound. No further purification.

$^1$H NMR (400 MHz, DMSO-d6) δ 7.15 (very broad s), 3.12 (2H, m), 2.80 (2H, t), 2.70 (2H, m), 2.42 (3H, s), 1.70 (4H, m), 1.45 (1H, m), 1.28 (2H, m), 1.12 (2H, m).

Intermediate BG

2-Methyl-5-(piperidin-4-yl)-1,3,4-oxadiazole

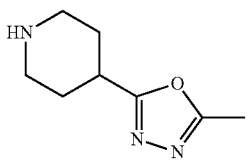

Step 1: tert-Butyl 4-(2-acetylhydrazinecarbonyl)piperidine-1-carboxylate

T3P® (50% in ethyl acetate) (73.2 ml, 124 mmol) was added dropwise to a solution of 1-(tert-butoxycarbonyl)piperidine-4-carboxylic acid (commercially available) (30 g, 113 mmol), acetohydrazide (9.20 g, 124 mmol) and DIPEA (59.2 ml, 339 mmol) in EtOAc (500 ml) at 0° C. The resulting mixture was allowed to warm to room temperature and stirred for overnight. The solvent was removed in vacuo and the crude product was purified by chromatography on silica eluting with iso-hexane/(EtOAc:MeOH-10:1) to afford the title compound.

LCMS: Rt 0.84 min; MS m/z 284 [M−H]−; Method 2minLowpHv03

Step 2: tert-Butyl 4-(5-methyl-1,3,4-oxadiazol-2-yl)piperidine-1-carboxylate

SMOPEX®-PPh$_3$, 1 mmol/g (19.3 g, 19.28 mmol) was added to a solution of tert-Butyl 4-(2-acetylhydrazinecarbonyl)piperidine-1-carboxylate (step 1) (5 g, 17.52 mmol), hexachloroethane (12.45 g, 52.6 mmol) and DIPEA (3.06 mL, 17.52 mmol) in DCM (50 mL) and the resulting mixture stirred overnight. The mixture was filtered and the resin washed with DCM (3×100 mL). The combined filtrate and washings were concentrated in vacuo. The residue was purified by chromatography on silica eluting with iso-hexane/EtOAc. The product fractions were combined and the solvent was removed in vacuo to give the title compound;

LC MS: Rt 1.03 min; MS m/z 268.5 [M+H]+; Method 2minLowpHv03

Step 3: 2-Methyl-5-(piperidin-4-yl)-1,3,4-oxadiazole

TFA (15 mL) was cautiously added to a solution of tert-butyl 4-(5-methyl-1,3,4-oxadiazol-2-yl)piperidine-1-carboxylate (step 2)(2.3 g, 8.60 mmol) in DCM (15 mL) and the resulting mixture stirred at room temperature for 2 h. Toluene (30 mL) was added and the mixture was concentrated in vacuo to a form a gum. Ether (100 mL) was added and the mixture stirred rapidly for 1 h. The resulting white solid was collected by filtration, washed with ether (2×50 mL) and dried to give the title compound as a white solid;

$^1$H NMR (400 MHz, DMSO-d6) δ 8.89 (1H, br s), 8.62 (1H, br s), 3.30 (3H, m), 3.07 (2H, m), 2.47 (3H, s), 2.12 (2H, m), 1.89 (2H, m).

Intermediate BH

3-Methyl-5-(piperidin-4-yl methyl)-1,2,4-oxadiazole

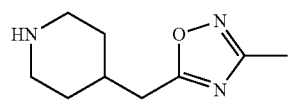

The title compound was prepared by a similar method to Intermediate B steps 1-3 from 2-(1-(tert-butoxycarbonyl)piperidin-4-yl)acetic acid and (Z)—N'-hydroxyacetimidamide;

$^1$H NMR (400 MHz, DMSO-d6) δ 8.62 (1H, br s), 8.31 (1H, br s), 3.28 (2H, m), 2.90 (4H, m), 2.32 (3H, s), 2.11 (1H, m), 1.82 (2H, m), 1.41 (2H, m).

Intermediate BI 2-(Azetidin-3-yl)-5-methyl-1,3,4-oxadiazole

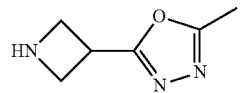

Step 1: N'-Acetyl-1-benzhydrylazetidine-3-carbohydrazide

To 1-benzhydrylazetidine-3-carboxylic acid (prepared according to patent US2008/214815 A1, page 73 example 83) in DCM (10 mL) was added acetohydrazide (commercially available) and triethylamine (2.321 mL, 16.65 mmol) followed by T3P® 50% in DMF (2.92 mL, 5.00 mmol) dropwise and the mixture was stirred at room temperature for 2 h. T3P® (50% in DMF) (2.92 mL, 5.00 mmol), was added and the mixture was stirred for a further 1 h. The resulting mixture was partitioned between EtOAc and water and the aqueous layer was removed. The organic layer was washed with saturated sodium bicarbonate solution, water, brine and dried using a phase separating column. The solvent was removed under reduced pressure. Purification of the crude product by chromatography on silica using a gradient from 0-100% EtOAc in iso-hexane followed by methanol in EtOAc (10%) afforded the title compound as a yellow oil that solidified. The crude product was used in the next step without further purification.

Step 2: 2-(1-Benzhydrylazetidin-3-yl)-5-methyl-1,3,4-oxadiazole

To N'-acetyl-1-benzhydrylazetidine-3-carbohydrazide (554 mg, 1.713 mmol) in DCM (8 mL) was added DIPEA (1.795 mL, 10.28 mmol), polymer bound triphenylphosphine (3 mmol/g loading) (1224 mg, 2.57 mmol) and hexachloroethane (1217 mg, 5.14 mmol). The reaction mixture was heated to 45° C. for 4 h. The mixture was left to cool to room temperature and the solution was filtered under vacuum and solvent removed under reduced pressure. Purification of the crude product by chromatography on silica using a gradient from 0-100% EtOAc in iso-hexane followed by methanol in EtOAc (10%) afforded the title compound as a yellow oil;

LC-MS: Rt=0.77 mins; [M+H]+ 306.2, Method 2min-LowpH

Step 3: 2-(Azetidin-3-yl)-5-methyl-1,3,4-oxadiazole

To 2-(1-benzhydrylazetidin-3-yl)-5-methyl-1,3,4-oxadiazole (186 mg, 0.609 mmol) in ethanol (5 mL) was added Pd(OH)$_2$/C (10%) (77 mg, 0.055 mmol) and was stirred under a hydrogen atmosphere (4 bar) at room temperature for 18 h. The reaction was filtered through a Celite® cartridge (2.5 g) followed by an Isolute® SCX-2 cartridge eluting with MeOH followed by 2M NH$_3$ in MeOH. The methanolic ammonia fractions were concentrated under reduced pressure to afford the title compound. The crude product was used in the next step without further purification.

Intermediate C 4-(4-Methyl-1H-1,2,3-triazol-1-yl)piperidine

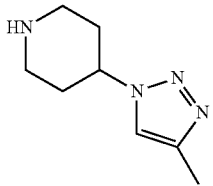

Step 1: tert-Butyl 4-((methylsulfonyl)oxy)piperidine-1-carboxylate tert-Butyl 4-hydroxypiperidine-1-carboxylate (2.50 g, 12.42 mmol) was placed in a flask with dry THF (25 mL) and cooled using an ice-bath. Triethylamine (2.60 mL, 18.63 mmol) was added followed by the dropwise addition of mesyl chloride (1.16 mL, 14.91 mmol). The reaction mixture was stirred at 0° C. for 3 hours and then partitioned between EtOAc and water. The organic phase was washed with 1M HCl, sat. NaHCO$_3$, brine, dried over MgSO4, filtered and the solvent was removed in vacuo to give the title compound as an off-white crystalline solid;

$^1$H NMR (400 MHz, DMSO-d6) δ 4.81 (1H, m), 3.60 (2H, m), 3.20 (3H, s), 3.18 (2H, m), 1.90 (2H, m), 1.60 (2H, m), 1.40 (9H, s).

Step 2: tert-Butyl 4-(4-methyl-2H-1,2,3-triazol-2-yl)piperidine-1-carboxylate, tert-Butyl 4-(4-methyl-1H-1,2,3-triazol-1-yl)piperidine-1-carboxylate, tert-Butyl 4-(5-methyl-1H-1,2,3-triazol-1-yl)piperidine-1-carboxylate 4-Methyl-1H-1,2,3-triazole (357 mg, 4.30 mmol) was placed in a flask with dry DMF (5 mL). Sodium hydride (186 mg, 4.65 mmol) was added and the reaction mixture was stirred at room temperature for 15 minutes. tert-Butyl 4-((methylsulfonyl)oxy)piperidine-1-carboxylate (step 1) (1.00 g, 3.58 mmol) was added and the reaction mixture was stirred at 100° C. for 4 hours. The resulting mixture was partitioned between EtOAc and water. The organic phase was washed with water and brine, dried over MgSO$_4$, filtered and the solvent was removed in vacuo. The product was purified by chromatography on silica eluting with iso-hexane/(EtOAc:MeOH-10:1) to afford:

Product Step 2a: tert-Butyl 4-(4-methyl-2H-1,2,3-triazol-2-yl)piperidine-1-carboxylate $^1$H NMR (400 MHz, DMSO-d6) δ 7.52 (1H, s), 4.60 (1H, m), 3.93 (2H, m), 2.98 (2H, m), 2.21 (3H, s), 2.03 (2H, m), 1.80 (2H, m), 1.40 (9H, s).

Product Step 2b: tert-Butyl 4-(4-methyl-1H-1,2,3-triazol-1-yl)piperidine-1-carboxylate $^1$H NMR (400 MHz, DMSO-d6) δ 7.91 (1H, s), 4.62 (1H, m), 4.02 (2H, m), 2.92 (2H, m), 2.21 (3H, s), 2.01 (2H, m), 1.80 (2H, m), 1.42 (9H, s).

Product Step 2c: tert-Butyl 4-(5-methyl-1H-1,2,3-triazol-1-yl)piperidine-1-carboxylate $^1$H NMR (400 MHz, DMSO-d6) δ 7.49 (1H, s), 4.51 (1H, m), 4.08 (2H, m), 2.97 (2H, m), 2.31 (3H, s), 1.95 (2H, m), 1.87 (2H, m), 1.42 (9H, s).

Step 3: 4-(4-Methyl-1H-1,2,3-triazol-1-yl)piperidine tert-Butyl 4-(4-methyl-1H-1,2,3-triazol-1-yl)piperidine-1-carboxylate (Product step 2b) (120 mg, 0.45 mmol) was placed in a flask with DCM (0.5 mL). TFA (0.347 mL, 4.51 mmol) was added and the reaction mixture was stirred at room temperature for 2 hours. The solvent was removed in vacuo. The residue was dissolved in acetonitrile (5 mL) and treated with MP-carbonate (1 g, ~2.5 mmol/g loading, macroporous polymer supported hydrogen carbonate). After swirling for 10 minutes the pH was tested to ensure all the TFA had been neutralised. The resin was filtered off and the solvent was removed in vacuo to afford the title compound. No further purification.

Intermediate CA 4-(3-Methyl-1H-1,2,4-triazol-1-yl)piperidine

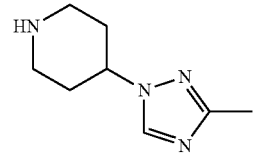

Step 1: tert-Butyl 4-(3-methyl-1H-1,2,4-triazol-1-yl)piperidine-1-carboxylate and tert-butyl 4-(5-methyl-1H-1,2,4-triazol-1-yl)piperidine-1-carboxylate 3-Methyl-1H-1,2,4-triazole (375 mg, 4.51 mmol) was placed in a flask with dry DMF (5 mL). Sodium hydride (195 mg, 4.89 mmol) was added and the RM was stirred at room temperature for 15 minutes. tert-Butyl 4-((methylsulfonyl)oxy)piperidine-1-carboxylate (Intermediate C, step 1) (1.00 g, 3.58 mmol) was then added and the RM was stirred at 100° C. for 4 hours. The resulting mixture was partitioned between EtOAc and water. The organic phase was washed with water and brine, dried over MgSO$_4$, filtered and the solvent was removed in vacuo. The product was purified by chromatography on silica eluting with iso-hexane/(EtOAc:MeOH-10:1) to afford:

Product Step 1a: tert-Butyl 4-(3-methyl-1H-1,2,4-triazol-1-yl)piperidine-1-carboxylate $^1$H NMR (400 MHz, DMSO-d6) δ 8.40 (1H, s), 4.48 (1H, m), 4.01 (2H, m), 2.90 (2H, m), 2.22 (3H, s), 1.99 (2H, m), 1.72 (2H, m), 1.40 (9H, s).

Product Step 1b: tert-Butyl 4-(5-methyl-1H-1,2,4-triazol-1-yl)piperidine-1-carboxylate $^1$H NMR (400 MHz, DMSO-d6) δ 7.79 (1H, s), 4.45 (1H, m), 4.02 (2H, m), 2.90 (2H, m), 2.41 (3H, s), 1.82 (2H, m), 1.75 (2H, m), 1.41 (9H, s).

Step 2: 4-(3-Methyl-1H-1,2,4-triazol-1-yl)piperidine

The title compound was prepared by a similar method to Intermediate C step 3 using tert-butyl 4-(3-methyl-1H-1,2,4-triazol-1-yl)piperidine-1-carboxylate to afford the title compound.

Intermediate CB 4-(5-Methyl-1H-1,2,4-triazol-1-yl)piperidine

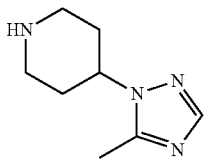

Step 1: tert-Butyl 4-(3-methyl-1H-1,2,4-triazol-1-yl)piperidine-1-carboxylate and tert-butyl 4-(5-methyl-1H-1,2,4-triazol-1-yl)piperidine-1-carboxylate
See Intermediate CA (step 2)
Step 2: 4-(5-Methyl-1H-1,2,4-triazol-1-yl)piperidine The title compound was prepared by a similar method to Intermediate C step 3 using tert-butyl 4-(5-methyl-1H-1,2,4-triazol-1-yl)piperidine-1-carboxylate to afford the title compound.

Intermediate CC 4-(5-Methyl-1H-tetrazol-1-yl)piperidine

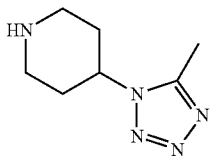

Step 1: tert-Butyl 4-(5-methyl-2H-tetrazol-2-yl)piperidine-1-carboxylate and tert-butyl 4-(5-methyl-1H-tetrazol-1-yl)piperidine-1-carboxylate 5-Methyl-2H-tetrazole (181 mg, 2.15 mmol) was placed in a flask with dry DMF (5 mL). Sodium hydride (93 mg, 2.33 mmol) was added and the reaction mixture was stirred at room temperature for 15 minutes. tert-Butyl 4-((methylsulfonyl)oxy)piperidine-1-carboxylate (Intermediate C, step 1) (500 mg, 1.79 mmol) was then added and the reaction mixture was stirred at 100° C. for 4 hours. The resulting mixture was partitioned between EtOAc and water. The organic phase was washed with water and brine, dried over MgSO$_4$, filtered and the solvent was removed in vacuo. The product was purified by chromatography on silica eluting with iso-hexane/(EtOAc:MeOH-10:1) to afford:

Product Step 1a: tert-Butyl 4-(5-methyl-2H-tetrazol-2-yl)piperidine-1-carboxylate
$^1$H NMR (400 MHz, DMSO-d6) δ 4.50 (1H, m), 3.98 (2H, m), 3.03 (2H, m), 2.45 (3H, s), 2.18 (2H, m), 1.88 (2H, m), 1.41 (9H, s).

Product Step 1b: tert-Butyl 4-(5-methyl-1H-tetrazol-1-yl)piperidine-1-carboxylate
$^1$H NMR (400 MHz, DMSO-d6) δ 4.65 (1H, m), 4.08 (2H, m), 2.93 (2H, m), 2.59 (3H, s), 2.01 (2H, m), 1.80 (2H, m), 1.43 (9H, s).

Step 2: 4-(5-Methyl-1H-tetrazol-1-yl)piperidine

The title compound was prepared by a similar method to Intermediate C step 3 using tert-butyl 4-(5-methyl-1H-tetrazol-1-yl)piperidine-1-carboxylate to afford the title compound.

Intermediate CD 4-(5-Methyl-2H-tetrazol-2-yl)piperidine

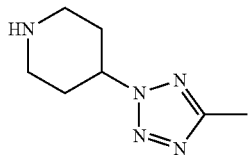

The title compound was prepared by a similar method to Intermediate C by replacing 4-methyl-1H-1,2,3-triazole (step 2) with 5-methyl-2H-tetrazole. Two products were isolated in this step; tert-butyl 4-(5-methyl-2H-tetrazol-2-yl)piperidine-1-carboxylate and tert-butyl 4-(5-methyl-1H-tetrazol-1-yl)piperidine-1-carboxylate. Tert-butyl 4-(5-methyl-2H-tetrazol-2-yl)piperidine-1-carboxylate was taken forward to step 3.

Intermediate CE 4-(2H-1,2,3-Triazol-2-yl)piperidine

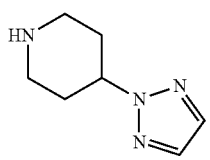 [SMILES: c1cnn(C2CCNCC2)n1]

Step 1: tert-Butyl 4-(2H-1,2,3-triazol-2-yl)piperidine-1-carboxylate and tert-butyl 4-(1H-1,2,3-triazol-1-yl)piperidine-1-carboxylate 1,2,3-triazole (148 mg, 2.15 mmol) was placed in a flask with dry DMF (5 mL). Sodium hydride (93 mg, 2.33 mmol) was added and the RM was stirred at room temperature for 15 minutes. tert-Butyl 4-((methylsulfonyl)oxy)piperidine-1-carboxylate (Intermediate C, step 1) (500 mg, 1.79 mmol) was then added and the RM was stirred at 100° C. for 4 hours. The resulting mixture was partitioned between EtOAc and water. The organic phase was washed with water and brine, dried over MgSO$_4$, filtered and the solvent was removed in vacuo. The product was purified by chromatography on silica eluting with iso-hexane/(EtOAc:MeOH-10:1) to afford:

Product Step 1a: tert-Butyl 4-(2H-1,2,3-triazol-2-yl)piperidine-1-carboxylate
$^1$H NMR (400 MHz, DMSO-d6) δ 7.80 (1H, s), 4.73 (1H, m), 3.97 (2H, m), 3.00 (2H, m), 2.08 (2H, m), 1.81 (2H, m), 1.41 (9H, s).

Product Step 1b: tert-Butyl 4-(1H-1,2,3-triazol-1-yl)piperidine-1-carboxylate
$^1$H NMR (400 MHz, DMSO-d6) δ 8.23 (1H, s), 7.73 (1H, s), 4.73 (1H, m), 4.07 (2H, m), 2.93 (2H, m), 2.06 (2H, m), 1.82 (2H, m), 1.41 (9H, s).

Step 2: 4-(2H-1,2,3-Triazol-2-yl)piperidine

The title compound was prepared by a similar method to Intermediate C step 3 using tert-butyl 4-(2H-1,2,3-triazol-2-yl)piperidine-1-carboxylate to afford the title compound.

Intermediate CF 4-(2-(4-Methyl-1H-pyrazol-1-yl)ethyl)piperidine

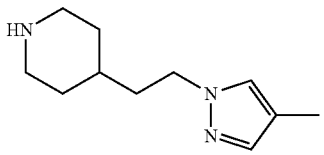

Step 1: tert-Butyl 4-(2-((methylsulfonyl)oxy)ethyl)piperidine-1-carboxylate tert-Butyl 4-(hydroxyethyl)piperidine-1-carboxylate (commercially available) (1.00 g, 4.36 mmol) was placed in a flask with dry THF (10 mL) and cooled using an ice-bath. Triethylamine (0.53 g, 5.23 mmol) was added followed by the dropwise addition of mesyl chloride (0.60 g, 5.23 mmol). After stirring at 0° C. for 3 hours, the reaction mixture was partitioned between EtOAc and sat. NaHCO₃. The organic phase was washed with water and brine, dried over MgSO4, filtered and the solvent was removed in vacuo to afford the title compound;

¹H NMR (400 MHz, DMSO-d6) δ 4.23 (2H, t), 4.02 (1H, m), 3.91 (2H, m), 3.18 (3H, s), 2.69 (2H, m), 1.66 (2H, m), 1.60 (2H, t), 1.40 (9H, s), 1.00 (2H, m).

Step 2. tert-Butyl 4-(2-(4-methyl-1H-pyrazol-1-yl)ethyl)piperidine-1-carboxylate tert-Butyl 4-(2-((methylsulfonyl)oxy)ethyl)piperidine-1-carboxylate (step 1) (500 mg, 1.70 mmol) and 4-methyl-1H-pyrazole (168 mg, 2.04 mmol) were placed in a flask with dry DMF (5 mL). Potassium carbonate (471 mg, 3.41 mmol) was added and the reaction mixture was stirred at 100° C. overnight. The resulting mixture was partitioned between EtOAc and water. The organic phase was washed with water and brine, dried over MgSO4, filtered and the solvent was removed in vacuo. The product was purified by chromatography on silica eluting with-iso-hexane/(EtOAc:MeOH-10:1) to afford the title compound;

¹H NMR (400 MHz, DMSO-d6) δ 7.49 (1H, s), 7.20 (1H, s), 4.05 (2H, t), 3.90 (2H, m), 2.65 (2H, m), 2.00 (3H, s), 1.69 (2H, t), 1.62 (2H, m), 1.40 (9H, s), 1.31 (1H, m), 1.00 (2H, m).

Step 3: 4-(2-(4-Methyl-1H-pyrazol-1-yl)ethyl)piperidine tert-Butyl 4-(2-(4-methyl-1H-pyrazol-1-yl)ethyl)piperidine-1-carboxylate (280 mg, 0.954 mmol) was placed in a flask with dry MeOH (1 mL). 4M HCl/dioxan (1.19 mL, 4.77 mmol) was added and the reaction mixture was stirred at room temperature for 4 hours. The solvent was removed in vacuo to afford the title compound.

Intermediate CG

5-Methyl-2-(piperidin-4-yl methyl)oxazole

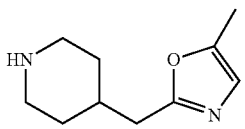

Step 1: tert-Butyl 4-(2-oxo-2-(prop-2-yn-1-ylamino)ethyl)piperidine-1-carboxylate 2-(1-(tert-Butoxycarbonyl)piperidin-4-yl)acetic acid (2.00 g, 8.22 mmol) and 2-aminopropan-1-ol (3.09 g, 41.1 mmol) were placed in a flask with dry DMF (10 mL). T3P® (50% in DMF) (9.60 mL, 16.44 mmol) was added dropwise and the reaction mixture was stirred at room temperature for 3 hours. The resulting mixture was partitioned between EtOAc and sat. NaHCO₃. The organic phase was washed with water and brine, dried over MgSO4, filtered and the solvent was removed in vacuo to afford the title compound which slowly crystallised;

¹H NMR (400 MHz, DMSO-d6) δ 8.28 (1H, t), 3.90 (2H, m), 3.84 (2H, d), 3.10 (1H, m), 2.70 (2H, m), 2.02 (2H, d), 1.82 (1H, m), 1.59 (2H, m), 1.40 (9H, s), 1.00 (2H, m).

Step 2: tert-Butyl 4-((5-methyloxazol-2-yl)methyl)piperidine-1-carboxylate tert-Butyl 4-(2-oxo-2-(prop-2-yn-1-ylamino)ethyl)piperidine-1-carboxylate (1.50 g, 5.35 mmol) was placed in a flask with dry DCM (50 mL). Gold(III) chloride (0.325 g, 1.07 mmol) was added and the reaction mixture was stirred at room temperature for 24 hours. The resulting mixture was partitioned between DCM and sat. NaHCO₃. The organic phase was washed with water and brine, dried over MgSO4, filtered and the solvent was removed in vacuo. The product was purified by chromatography on silica eluting with iso-hexane/EtOAc to afford the title compound;

¹H NMR (400 MHz, DMSO-d6) δ 6.70 (1H, s), 3.90 (2H, m), 2.70 (2H, m), 2.60 (2H, d), 2.28 (3H, s), 1.88 (1H, m), 1.60 (2H, m), 1.40 (9H, s), 1.09 (2H, m).

Step 3: 5-Methyl-2-(piperidin-4-ylmethyl)oxazole

Tert-Butyl 4-((5-methyloxazol-2-yl)methyl)piperidine-1-carboxylate (step 2) (400 mg, 1.43 mmol) was placed in a flask with dry DCM (5 mL). TFA (1.00 mL, 12.98 mmol) was added and the reaction mixture was stirred at room temperature for 2 hours. The solvent was removed in vacuo to give the title compound;

¹H NMR (400 MHz, DMSO-d6) δ 8.60 (1H, broad s), 8.23 (1H, broad s), 6.72 (1H, s), 3.28 (2H, m), 2.88 (2H, m), 2.69 (2H, d), 2.25 (3H, s), 2.00 (1H, m), 1.80 (2H, m), 1.38 (2H, m).

Intermediate CH 4-(4-Methyl-1H-pyrazol-1-yl)piperidine

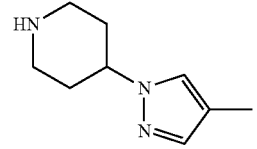

The title compound was prepared by a similar method to Intermediate CF from tert-butyl 4-hydroxypiperidine-1-carboxylate;

Intermediate CI

5-Methyl-2-(piperidin-4-yl)oxazole

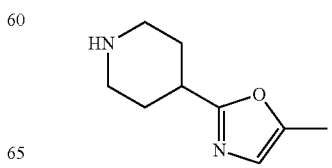

The title compound was prepared by a similar method to Intermediate CG from 1-(tert-butoxycarbonyl)piperidine-4-carboxylic acid and prop-2-yn-1-amine;

Intermediate CJ 4-(4-Methyl-2H-1,2,3-triazol-2-yl)piperidine

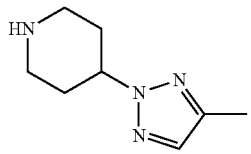

The title compound was prepared from tert-butyl 4-(4-methyl-2H-1,2,3-triazol-2-yl)piperidine-1-carboxylate (Intermediate C step 2) by a similar method to Intermediate C step 3;

Intermediate D

Ethyl 1-((4-hydroxypiperidin-4-yl)methyl)-1H-pyrazole-4-carboxylate

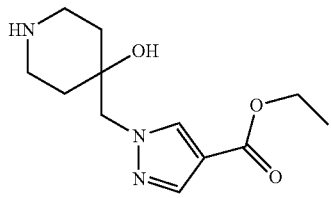 [SMILES: CCOC(=O)c1cnn(CC2(O)CCNCC2)c1]

Step 1: tert-Butyl 4-((4-(ethoxycarbonyl)-1H-pyrazol-1-yl)methyl)-4-hydroxypiperidine-1-carboxylate tert-Butyl 1-oxa-6-azaspiro[2.5]octane-6-carboxylate (1.00 g, 4.69 mmol) and ethyl 1H-pyrazole-4-carboxylate (0.789 g, 5.63 mmol) were placed in a flask with dry DMF (10 mL). Potassium carbonate (1.296 g, 9.38 mmol) was added and the reaction mixture was stirred at 100° C. overnight. The resulting mixture was partitioned between EtOAc and water. The organic phase was washed with water and brine, dried over MgSO4, filtered and the solvent was removed in vacuo to afford the title compound;

LC-MS Rt=1.02 mins; [M+H]$^+$ 354.5; Method 2min-LowpHv03

Step 2: Ethyl 1-((4-hydroxypiperidin-4-yl)methyl)-1H-pyrazole-4-carboxylate tert-Butyl 4-((4-(ethoxycarbonyl)-1H-pyrazol-1-yl)methyl)-4-hydroxypiperidine-1-carboxylate (step 1) (1.50 g, 4.24 mmol) was placed in a flask with dry EtOH (5 mL). 4 M HCl in dioxan (5.31 mL, 21.22 mmol) was added and the reaction mixture was stirred at room temperature for 2 hours. The solvent was removed in vacuo to afford the title compound;

$^1$H NMR (400 MHz, DMSO-d6) δ 8.90 (1H, broad s), 8.58 (1H, broad s), 8.28 (1H, s), 7.89 (1H, s), 4.22 (2H, q), 4.18 (2H, s), 3.58 (1H, s), 3.10 (2H, m), 2.99 (2H, m), 1.70 (2H, m), 1.51 (2H, m), 1.25 (3H, t).

Intermediate DA 4-((4-(Trifluoromethyl)-1H-pyrazol-1-yl)methyl)piperidin-4-ol

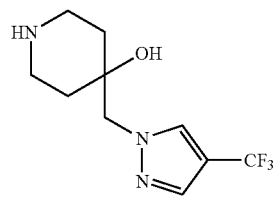 [SMILES: OC1(Cn2cc(C(F)(F)F)cn2)CCNCC1]

The title compound was prepared by a similar method to Intermediate D by replacing ethyl 1H-pyrazole-4-carboxylate (step 1) with 4-(trifluoromethyl)-1H-pyrazole;

$^1$H NMR (400 MHz, DMSO-d6) δ 8.93 (1H, broad s), 8.62 (1H, broad s), 8.31 (1H, s), 7.92 (1H, s), 4.22 (2H, s), 3.59 (1H, s), 3.11 (2H, m), 2.99 (2H, m), 1.71 (2H, m), 1.52 (2H, m).

Intermediate E

5-Methyl-3-(piperidin-4-yl)-1,2,4-oxadiazole

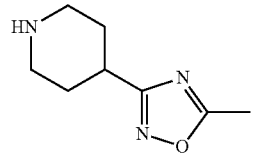

The title compound is available commercially as the hydrochloride salt.

Intermediate F

2-Methyl-4-(piperidin-4-yl)oxazole

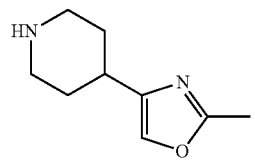

Step 1: Tert-butyl 4-(2-bromoacetyl)piperidine-1-carboxylate

Tert-butyl 4-acetylpiperidine-1-carboxylate (2.00 g, 8.80 mmol) was placed in a flask with dry THF (20 mL) under an atmosphere of nitrogen. The mixture was cooled to −78° C. and lithium bis(trimethylsilyl)amide (1M in toluene) (9.24 mL, 9.24 mmol) was slowly added over 10 minutes. The resulting mixture was stirred at −78° C. for 1 hour. Trimethylsilylchloride (1.24 mL, 9.68 mmol) was added dropwise and the mixture was stirred at 0° C. for 30 minutes and re-cooled to −78° C. Bromine (0.453 mL, 8.80 mmol) was added dropwise and the mixture was allowed to return to room temperature. The mixture was diluted with EtOAc and washed with a mixture of 10% sodium thiosulfate (20 mL)

and sat. ammonium chloride (20 mL). The resulting mixture was partitioned between EtOAc and water. The organic phase was separated, washed with water and brine, dried over MgSO4, filtered and the solvent was removed in vacuo. The product was purified by chromatography on silica eluting with iso-hexane/EtOAc to afford the title compound as a light brown crystalline solid;

$^1$H NMR (400 MHz, DMSO-d6) δ 4.42 (2H, s), 3.82 (2H, m), 2.70 (3H, m), 1.72 (2H, m), 1.30 (9H, s), 1.22 (2H, m).

Step 2: 2-Methyl-4-(piperidin-4-yl)oxazole tert-Butyl 4-(2-bromoacetyl)piperidine-1-carboxylate (step 1) (500 mg, 1.63 mmol) and acetamide (1929 mg, 32.7 mmol) were placed in a flask and heated to 130° C. for 2 hours. The mixture was poured into EtOAc (50 mL) and the resulting suspension was collected by filtration and dried to afford the title compound;

$^1$H NMR (400 MHz, DMSO-d6) δ 8.63 (1H, broad s), 8.39 (1H, broad s), 7.78 (1H, s), 3.30 (2H, m), 3.00 (2H, m), 2.78 (1H, m), 2.39 (3H, s), 2.02 (2H, m), 1.69 (2H, m).

Intermediate G 1-(4-((5-Methyl-1,3,4-oxadiazol-2-yl)methyl)piperidin-1-yl)prop-2-en-1-one

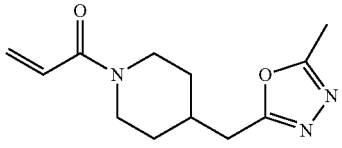 [SMILES: C=CC(=O)N1CCC(Cc2nnc(C)o2)CC1]

2-Methyl-5-(piperidin-4-ylmethyl)-1,3,4-oxadiazole (Intermediate BD) (6.00 g, 14.66 mmol) and triethylamine (7.42 g, 73.3 mmol) were placed in a flask with dry DCM (100 mL) and cooled using an ice-bath. Acryloyl chloride (1.59 g, 17.59 mmol) was added dropwise and the reaction mixture was stirred at room temperature for 1 hour. The resulting mixture was partitioned between DCM and water. The organic phase was washed with water and brine, dried over MgSO4, filtered and the solvent was removed in vacuo to give an orange oil. Purification by chromatography on silica eluting with iso-hexane/(EtOAc:MeOH-10:1) afford the title compound as a golden oil;

LC-MS Rt=0.73 mins; [M+H]$^+$ 236.2; Method 2min-LowpHv03

Intermediate GA (R)-1-(4-(4-Fluorobenzyl)-2-methylpiperazin-1-yl)prop-2-en-1-one

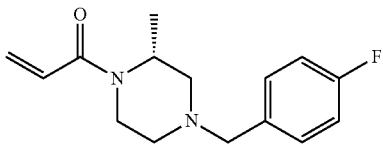 [SMILES: C=CC(=O)N1CCN(Cc2ccc(F)cc2)C[C@H]1C]

Step 1: (R)-1-(4-Fluorobenzyl)-3-methylpiperazine (R)-2-Methylpiperazine (15.5 g, 155 mmol) and 1-(chloromethyl)-4-fluorobenzene (23.49 g, 162 mmol) were placed in a flask with dry MeOH (250 mL). Sodium bicarbonate (39 g, 464 mmol) was added and the reaction mixture was heated at reflux overnight. After cooling to room temperature, the salts were filtered off. The solvent was removed in vacuo and the resulting solid was heated at reflux in EtOAc. The hot solution/suspension was filtered hot to remove more salts and the solvent was removed in vacuo. The residue was triturated in iso-hexane and the solid was removed by filtration. The mother liquor was concentrated in vacuo and the resulting crude product was purified by chromatography on silica eluting with 0-10% MeOH in DCM to afford the title compound.

Step 2: (R)-1-(4-(4-Fluorobenzyl)-2-methylpiperazin-1-yl)prop-2-en-1-one

The title compound was prepared from (R)-1-(4-gluorobenzyl)-3-mthylpiperazine (step 1) and acryloyl chloride using a similar method to Intermediate G.

Intermediate H (R)-3-Methyl-1-(1-methyl-1H-pyrazol-3-yl)piperazine

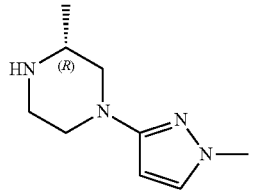

Step 1: (R)-tert-Butyl 2-methyl-4-(1-methyl-1H-pyrazol-3-yl)piperazine-1-carboxylate Dicyclohexylphosphino2'4'6'triisopropyl biphenyl (11.46 mg, 0.024 mmol) and tris(dibenzylideneacetone)dipalladium(0) (22.01 mg, 0.024 mmol) in DME (1 mL) was stirred for 3 mins. In a separate 10 mL round-bottomed flask, sodium tert-butoxide (64.7 mg, 0.673 mmol) and 3-iodo-1-methyl-1H-pyrazole (0.052 mL, 0.481 mmol) were mixed in DME (1 mL) to give a white suspension. To this mixture was added the catalyst suspension followed by sodium tert-butoxide (64.7 mg, 0.673 mmol). The reaction mixture was heated to 85° C. overnight. The reaction mixture was diluted with ethyl acetate (20 mL) and washed with water (30 mL) and saturated brine (30 mL). The organic phase was passed through a phase separator and evaporated in vacuo to afford the title compound as a dark orange oil.

Step 2: (R)-3-Methyl-1-(1-methyl-1H-pyrazol-3-yl)piperazine (R)-tert-Butyl 2-methyl-4-(1-methyl-1H-pyrazol-3-yl)piperazine-1-carboxylate (73 mg, 0.260 mmol) in DCM (3 mL) was treated with TFA (1 mL, 12.98 mmol) and the reaction mixture stirred at room temperature for 20 min. The solvent was evaporated under reduced pressure and the mixture was applied to an Isolute® SCX-2 column eluting with MeOH to afford the title compound;

$^1$H NMR (400 MHz, CDCl3) δ 7.15 (1H, s), 5.62 (1H, s), 3.76 (3H, s), 3.59 (1H, m), 3.51 (1H, m), 2.90-3.10 (3H, m), 2.70 (1H, m), 2.32 (1H, m), 1.90 (2H, m), 1.10 (3H, d).

Intermediate IA 1-(4-((2-Methyloxazol-4-yl)methyl)piperazin-1-yl)prop-2-en-1-one

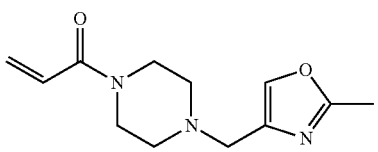 [SMILES: C=CC(=O)N1CCN(Cc2coc(C)n2)CC1]

Step 1: tert-Butyl 4-((2-methyloxazol-4-yl)methyl)piperazine-1-carboxylate

Sodium triacetoxyborohydride (2.29 g, 10.80 mmol) was added to a solution of tert-butyl piperazine-1-carboxylate (1.68 g, 9.00 mmol) and 2-methyloxazole-4-carbaldehyde (1.00 g, 9.00 mmol) in 1,2-dichloroethane (25 mL) and the mixture was stirred at room temperature for 18 h. The reaction was concentrated in vacuo to 5 mL and partitioned between EtOAc and water. The organic phase was washed with water and brine, dried over magnesium sulfate, filtered and concentrated in vacuo. Purification of the crude product by chromatography on silica eluting with 0-100% (10% MeOH in EtOAc) in iso-hexane afforded the title compound;

$^1$H NMR (400 MHz, DMSO-d6) δ 7.80 (1H, s), 3.35 (2H, s), 3.28 (4H, m), 2.38 (3H, s), 2.32 (4H, m), 1.40 (9H, s).

Step 2: 2-Methyl-4-(piperazin-1-ylmethyl)oxazole

TFA (2 mL) was added to a solution tert-butyl 4-((2-methyloxazol-4-yl)methyl)piperazine-1-carboxylate (step 1) (850 mg, 3.02 mmol) in DCM (20 mL) and the mixture stirred for 4 h at room temperature. Toluene (100 mL) was added and the mixture concentrated in vacuo. The residue was dissolved in toluene and concentrated in vacuo, The residue was dissolved in DCM and concentrated in vacuo and triturated with ether to give the title compound as a ditrifluoroacetate salt.

Step 3: 1-(4-((2-Methyloxazol-4-yl)methyl)piperazin-1-yl)prop-2-en-1-one

Acryloyl chloride (0.262 mL, 3.23 mmol) was added dropwise to a solution of 2-methyl-4-(piperazin-1-ylmethyl)oxazole (step 2) (1.1 g, 2.69 mmol) and TEA (1.873 mL, 13.44 mmol) in DCM (10 mL) at 0° C. The reaction was allowed to warm to room temperature and stirred for 1 h. The reaction was quenched with saturated sodium bicarbonate solution (20 mL) and extracted with ethyl acetate (3×50 mL). The aqueous solutions were combined, saturated with sodium chloride and extracted with ethyl acetate (3×50 mL). The combined organic solutions were washed with brine, dried over sodium sulfate, filtered and concentrated in vacuo. Purification was carried out by silica gel column chromatography eluting with a gradient of DCM to 10% MeOH in DCM using the instrument's default settings. The product fractions were combined and concentrated in vacuo to give the title compound as a yellow oil;

$^1$H NMR (400 MHz, CDCl$_3$) δ 7.44 (1H, s), 6.47 (1H, dd), 6.29 (1H, dd), 5.70 (1H, dd), 3.75 (2H, m), 3.62 (1H, m), 3.47 (2H, s), 2.53 (4H, m), 2.47 (3H, s)

Intermediate IB

2-Cyclopropyl-5-(piperidin-4-yl)-1,3,4-oxadiazole

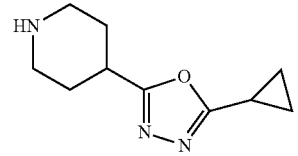 [SMILES: C1CC(c2nnc(C3CC3)o2)CCN1]

Step 1: tert-Butyl 4-(2-(cyclopropanecarbonyl)hydrazinecarbonyl)piperidine-1-carboxylate To cyclopropanecarboxylic acid (commercially available) (0.164 mL, 2.055 mmol) and tert-butyl 4-(hydrazinecarbonyl)piperidine-1-carboxylate (commercially available) (500 mg, 2.055 mmol) in DCM (10 mL) was added triethylamine (1.432 mL, 10.28 mmol) followed by T3P® (50% in DMF) (1.440 mL, 2.466 mmol) dropwise. The mixture was stirred at room temperature for 2 h. The solvent was removed under reduced pressure. The resulting mixture was partitioned between EtOAc and water and the aqueous layer was removed. The organic layer was washed with saturated sodium bicarbonate solution, water, brine and dried using a phase separating column. The solvent was removed under reduced pressure. The crude product was used in the next step without further purification.

Step 2: tert-Butyl 4-(5-cyclopropyl-1,3,4-oxadiazol-2-yl)piperidine-1-carboxylate To tert-butyl 4-(2-(cyclopropanecarbonyl)hydrazinecarbonyl)piperidine-1-carboxylate (593 mg, 1.904 mmol) in THF (10 mL) was added Burgess reagent (1135 mg, 4.76 mmol) and the mixture was stirred at reflux for 5 h. The solvent was removed under reduced pressure. The resulting mixture was partitioned between EtOAc and water and the aqueous layer was removed. The organic layer was washed with saturated sodium bicarbonate solution, water, brine and dried using a phase separating column. The solvent was removed under reduced pressure and crude product was used in the next step without further purification.

Step 3: 2-Cyclopropyl-5-(piperidin-4-yl)-1,3,4-oxadiazole

To tert-butyl 4-(5-cyclopropyl-1,3,4-oxadiazol-2-yl)piperidine-1-carboxylate (593 mg, 2.021 mmol) in DCM (7 mL) was added TFA (1.869 mL, 24.26 mmol) and the mixture was stirred at room temperature for 1 h. The solvent was removed under reduced pressure. The resulting residue was loaded onto an Isolute® SCX-2 cartridge eluting with MeOH followed by 2M NH$_3$ in MeOH. The methanolic ammonia fractions were concentrated under reduced pressure. The crude product was used in next step without further purification.

Intermediate IC

2-Ethyl-5-(piperidin-4-yl)-1,3,4-oxadiazole

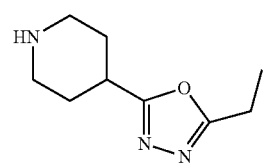

The title compound was prepared by a similar method to Intermediate IB from propionic acid and tert-butyl 4-(hydrazinecarbonyl)piperidine-1-carboxylate (commercially available);

$^1$H NMR (400 MHz, DMSO-d6) δ 3.59 (1H, br), 3.00-2.91 (3H, mult), 2.81 (2H, q), 2.58 (2H, t), 1.88 (2H, br d), 1.57 (2H, q), 1.24 (3H, t).

Intermediate ID

2-Cyclobutyl-5-(piperidin-4-yl)-1,3,4-oxadiazole

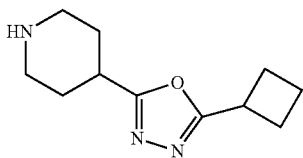 [SMILES: C1CC(c2nnc(C3CCNCC3)o2)C1]

The title compound was prepared by a similar method to Intermediate IB from cyclobutanecarboxylic acid and tert-butyl 4-(hydrazinecarbonyl)piperidine-1-carboxylate.

Intermediate J

2-Methyl-5-(2-methylpiperidin-4-yl)-1,3,4-oxadiazole

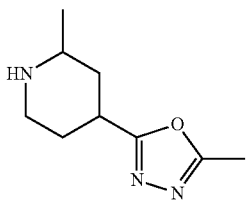

Step 1: Methyl 2-methylpiperidine-4-carboxylate

To methyl 2-chloro-6-methylisonicotinate (1 g, 5.39 mmol) in ethanol (10.78 mL) was added Nishimura catalyst (0.052 g, 0.108 mmol) and the mixture was stirred under a hydrogen atmosphere (3 bar) for 18 h. Additional Nishimura catalyst (100 mg) was added and the mixture was stirred under a hydrogen atmosphere (3 bar) for a further 5 hours. The reaction mixture was filtered over a Celite® cartridge (10 g) and the solvent was removed under reduced pressure to afford the title compound as a hydrochloride salt.

$^1$H NMR (400 MHz, DMSO-d6) δ 8.87 (1H, br), 3.63 (3H, s), 3.25 (1H, br d), 3.1 (1H, br mult), 2.86 (1H, t), 2.68 (1H, t), 1.99 (2H, t), 1.67 (2H, t), 1.67 (1H, q), 1.47 (1H, q), 1.24 (3H, d).

Step 2: 1-tert-Butyl 4-methyl 2-methylpiperidine-1,4-dicarboxylate

To methyl 2-methylpiperidine-4-carboxylate (8.7 g, 44.9 mmol) in DCM (96 mL) and methanol (16.04 mL) was added triethylamine (8.14 mL, 58.4 mmol) and the reaction mixture was cooled to 0° C. in an ice bath. Di-tert-butyl dicarbonate (14.60 mL, 62.9 mmol) was added followed by triethylamine (8.14 mL, 58.4 mmol) and the reaction was stirred to room temperature for 18 h.

To the reaction mixture was added 0.1 M HCl and the aqueous portion was back extracted with DCM. The combined organic extracts were dried over a phase separating column and the solvent was removed under reduced pressure. The residue was diluted with EtOAc and the organic portion were washed with excess water, brine, dried over a phase separating column and solvent removed under reduced pressure to afford the title compound.

Step 3: 1-(tert-Butoxycarbonyl)-2-methylpiperidine-4-carboxylic acid

To 1-tert-butyl 4-methyl 2-methylpiperidine-1,4-dicarboxylate (12.28 g, 47.7 mmol) in THF (250 mL) was added 2M lithium hydroxide (71.6 mL, 143 mmol) and the mixture was stirred at room temperature for 18 h. The solvent was removed under reduced pressure. The residue was washed with DCM and the aqueous was acidified to pH 4 using 1M HCl. The product was extracted using DCM and the organic extracts were dried over a phase separating column. The solvent was removed under reduced pressure to afford the title compound.

Step 4: tert-Butyl 4-(2-acetylhydrazinecarbonyl)-2-methylpiperidine-1-carboxylate T3P® 50% in DMF (2.504 mL, 4.29 mmol) was added dropwise to a solution of 1-(tert-butoxycarbonyl)-2-methylpiperidine-4-carboxylic acid (1 g, 3.57 mmol), acetohydrazide (commercially available) (0.265 g, 3.57 mmol) and triethylamine (1.993 mL, 14.30 mmol) in DCM (15 mL) and the resulting mixture was stirred at room temperature for 2 h. The solvent was removed under reduced pressure. Purification of the crude product by chromatography on silica using a gradient from 0-100% EtOAc in iso-hexane followed by methanol in EtOAc (10%) afforded the title compound.

Step 5: tert-Butyl 2-methyl-4-(5-methyl-1,3,4-oxadiazol-2-yl)piperidine-1-carboxylate To tert-butyl 4-(2-acetylhydrazinecarbonyl)-2-methylpiperidine-1-carboxylate (780 mg, 2.61 mmol) in DCM (10 mL) was added DIPEA (2.73 mL, 15.63 mmol), polymer bound triphenylphosphine (3 mmol/g loading) (1861 mg, 3.91 mmol) and hexachloroethane (1850 mg, 7.82 mmol). The reaction was heated to 45° C. for 4 h and was then left to cool to room temperature and filtered under vacuum. The solvent was removed under reduced pressure. To the residue was added DCM and the organic portion was washed with 1M HCl, dried over a phase separating column and the solvent was removed under reduced pressure. Purification of the crude product by chromatography on silica using a gradient from 0-100% EtOAc in iso-hexane afforded the title compound.

Step 6: 2-Methyl-5-(2-methylpiperidin-4-yl)-1,3,4-oxadiazole

To tert-butyl 2-methyl-4-(5-methyl-1,3,4-oxadiazol-2-yl)piperidine-1-carboxylate (620 mg, 2.204 mmol) in DCM (10 mL) was added TFA (2.037 mL, 26.4 mmol) and was stirred at room temperature for 3 h. The solvent was removed under reduced pressure. The resulting residue was loaded onto an Isolute® SCX-2 cartridge eluting with MeOH followed by 2M NH$_3$ in MeOH. The methanolic ammonia fractions were concentrated under reduced pressure. The crude product was used in next step without further purification.

Intermediate K

(R)-5-Methyl-3-((3-methylpiperazin-1-yl)methyl)-1,2,4-oxadiazole

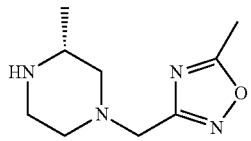

Step 1: (R)-tert-Butyl 4-(cyanomethyl)-2-methylpiperazine-1-carboxylate

To (R)-tert-butyl 2-methylpiperazine-1-carboxylate (500 mg, 2.497 mmol) in THF (10 mL) was added tetramethylguanidine (0.458 mL, 3.62 mmol) and the mixture was cooled to 0° C. using an ice bath. Bromoacetonitrile (0.209 mL, 3.00 mmol) was added and the mixture was stirred at room temperature for 18 h. To the reaction mixture was added EtOAc and water. The organic portion was washed with excess water, brine, dried over a phase separating column and solvent removed under reduced pressure. The crude product was used in the next step without further purification.

Step 2: (R)-tert-Butyl 4-(2-(hydroxyamino)-2-iminoethyl)-2-methylpiperazine-1-carboxylate To (R)-tert-butyl 4-(cyanomethyl)-2-methylpiperazine-1-carboxylate (250 mg, 1.045 mmol) in methanol (10 mL) was added hydroxylamine hydrochloride (123 mg, 1.776 mmol) followed by tetramethylguanidine (0.225 mL, 1.776 mmol) and the resulting mixture was heated at 70° C. for 4 h. Additional hydroxylamine hydrochloride (123 mg, 1.776 mmol) and tetramethylguanidine (0.225 mL, 1.776 mmol) was added and heating continued at 70° C. for a further 18 h. The mixture was cooled to room temperature and EtOAc was added. The organic portion was washed with water, brine, dried over a phase separating column and the the solvent was removed under reduced pressure. The crude product was used without further purification.

Step 3: (R,Z)-tert-Butyl 4-(2-(acetoxyimino)-2-aminoethyl)-2-methylpiperazine-1-carboxylate T3P® (50% in DMF) (0.617 mL, 1.057 mmol) was added dropwise to a solution of (R)-tert-butyl 4-(2-(hydroxyamino)-2-iminoethyl)-2-methylpiperazine-1-carboxylate (240 mg, 0.881 mmol), acetic acid (0.050 mL, 0.881 mmol) and triethylamine (0.614 mL, 4.41 mmol) in DCM (4 mL) and the resulting mixture stirred at room temperature for 2 h. The reaction was poured into EtOAc and washed with water, saturated sodium bicarbonate solution, water, brine and dried over a phase separating column. The solvent was removed under reduced pressure and the crude product was used without further purification.

Step 4: (R)-tert-Butyl 2-methyl-4-((5-methyl-1,2,4-oxadiazol-3-yl)methyl)piperazine-1-carboxylate To (R,Z)-tert-butyl 4-(2-(acetoxyimino)-2-aminoethyl)-2-methylpiperazine-1-carboxylate (277 mg, 0.881 mmol) in toluene (5 mL) was added a spatula of molecular sieves and the resulting mixture was heated using microwave radiation at 120° C. for 4 h. The molecular sieves were removed by filtering under vacuum and the solvent was removed under reduced pressure. The crude product was used without further purification.

Step 5: (R)-5-Methyl-3-((3-methylpiperazin-1-yl)methyl)-1,2,4-oxadiazole

To (R)-tert-butyl 2-methyl-4-((5-methyl-1,2,4-oxadiazol-3-yl)methyl)piperazine-1-carboxylate (119 mg, 0.402 mmol) in DCM (1 mL) was added TFA (0.371 mL, 4.82 mmol) and the mixture was stirred at room temperature for 1 h. The resulting mixture was loaded onto an Isolute® SCX-2 cartridge eluting with MeOH followed by 2M $NH_3$ in MeOH. The methanolic ammonia fractions were concentrated under reduced pressure and the crude product used without further purification.

Intermediate L

(S)-4-((3-(Methoxymethyl)piperazin-1-yl)methyl)-2-methyloxazole

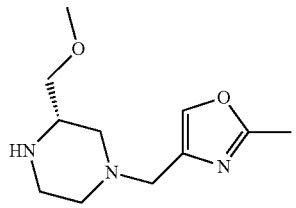 [SMILES: COC[C@@H]1CN(Cc2coc(C)n2)CCN1]

Step 1: (S)-tert-Butyl 2-(hydroxymethyl)-4-((2-methyloxazol-4-yl)methyl)piperazine-1-carboxylate To (S)-tert-butyl 2-(hydroxymethyl)piperazine-1-carboxylate (100 mg, 0.462 mmol) in MeOH (3 mL) and acetic acid (0.300 mL) was added 2-methyloxazole-4-carbaldehyde (commercially available) (77 mg, 0.694 mmol) and the mixture was stirred for 5 minutes. 2-Picoline borane (78 mg, 0.740 mmol) was then added and the mixture was stirred at room temperature for 18 h. The solvent was removed under reduced pressure. Purification of the crude product by chromatography on silica using a gradient from 0-100% EtOAc in iso-hexane afforded the title compound. The crude product was used without further purification.

Step 2: (S)-tert-Butyl 2-(methoxymethyl)-4-((2-methyloxazol-4-yl)methyl)piperazine-1-carboxylate To (S)-tert-butyl 2-(hydroxymethyl)-4-((2-methyloxazol-4-yl)methyl)piperazine-1-carboxylate (111 mg, 0.356 mmol) at 0° C. under nitrogen was added sodium hydride (17.11 mg, 0.428 mmol) and the mixture was left to stir for 15 minutes. Iodomethane (0.027 mL, 0.428 mmol) was added and stirring continued at room temperature for 72 h. EtOAc was added to the reaction mixture and the organic portion was washed with water, saturated sodium bicarbonate solution, water, brine and dried over a phase separating column. The solvent was removed under reduced pressure. The crude product was used in next step without further purification.

Step 3: (S)-4-((3-(Methoxymethyl)piperazin-1-yl)methyl)-2-methyloxazole

To (S)-tert-butyl 2-(methoxymethyl)-4-((2-methyloxazol-4-yl)methyl)piperazine-1-carboxylate (90 mg, 0.277 mmol) in DCM (3 mL) was added TFA (0.256 mL, 3.32 mmol) and the mixture was stirred at room temperature for 18 h. The solvent was removed under reduced pressure. The resulting residue was loaded onto an Isolute® SCX-2 cartridge eluting with MeOH followed by 2M $NH_3$ in MeOH. The methanolic ammonia fractions were concentrated under reduced pressure. The crude product was used in the next step without further purification.

Intermediate M 5-(2-Bromo-5-chlorobenzyl)-2-methyl-2H-tetrazole

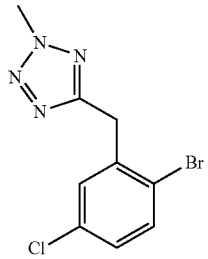

Step 1: 2-(2-Bromo-5-chlorophenyl)acetonitrile

KCN (0.275 g, 4.22 mmol) was added to a mixture of 1-bromo-2-(bromomethyl)-4-chlorobenzene (1 g, 3.52 mmol) in DMF (4 ml) and water (4.00 mL) and the resulting mixture stirred overnight. The resulting mixture was diluted with water (50 mL) and extracted with ethyl acetate (3×50 mL). The combined organic extracts were washed with water (2×30 mL), dried over magnesium sulphate, filtered and concentrated in vacuo. Purification was carried out chromatography on silica eluting with 0-50% EtOAc in iso-hexane to give the title product as a white solid.

Step 2: 5-(2-Bromo-5-chlorobenzyl)-2H-tetrazole 2-(2-Bromo-5-chlorophenyl)acetonitrile (step 1)(100 mg, 0.434 mmol), triethylamine hydrochloride (71.7 mg, 0.521 mmol) and NaN$_3$ (33.8 mg, 0.521 mmol) were combined in toluene (2 mL) and the resulting mixture heated at 100° C. overnight. After cooling to room temperature, 1M HCl (10 mL) and ethyl acetate (10 mL) were added and stirring continued for 30 min. The resulting layers were separated and the aqueous portion was extracted with ethyl acetate (2×10 mL). The combined organic extracts were washed with brine (10 mL) and concentrated in vacuo. 2M NaOH (20 mL) was added and the resulting suspension stirred vigorously for 30 min. The mixture was filtered and the filtrate acidified with conc HCl. The resulting solid was isolated by filtration, washed with water (2×10 mL) and dried in the vacuum oven to give the title compound;

LC MS: Rt 0.93 min; MS m/z 273.0, 275.0, 277.1 [M+H]+; Method 2minLowpHv01 LISTEAN1-007-EXP026-2 was registered as NVP-AFQ926-NX-3.

Step 3: 5-(2-Bromo-5-chlorobenzyl)-2-methyl-2H-tetrazole

The following procedure was carried out according to Bioorganic and medicinal chemistry 19, 19, 2011, 5749:

MeI (0.022 ml, 0.358 mmol) was cautiously added to a solution of 5-(2-bromo-5-chlorobenzyl)-2H-tetrazole (89 mg, 0.325 mmol) and triethylamine (0.054 ml, 0.390 mmol) in acetonitrile (2 ml) and the resulting mixture was heated at reflux overnight. The reaction mixture was concentrated in vacuo. Purification was carried out chromatography on silica eluting with EtOAc in iso-hexane to give the title product as a white solid.

LC MS; Rt 1.18 min; MS m/z 287.4, 289.4, 291.4 [M+H]+; Method 2minLowpHv01

A second regioisomer was also isolated:

5-(2-Bromo-5-chlorobenzyl)-1-methyl-2H-tetrazole

LC MS: Rt 1.00 min; MS m/z 287.3, 289.3, 291.3 [M+H]+; Method 2minLowpHv01

Intermediate N 3-(2-Bromo-5-chlorobenzyl)-5-methyl-1,2,4-oxadiazole

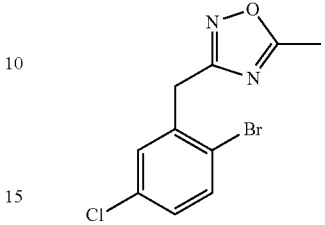

Step 1: (Z)-2-(2-Bromo-5-chlorophenyl)-N'-hydroxyacetimidamide (Prepared according to J. Med. Chem. 2008, 51 (11), 3182-3193):

NH$_2$OH.HCl (102 mg, 1.464 mmol) was added to a mixture comprising 2-(2-bromo-5-chlorophenyl)acetonitrile (Intermediate M, step 1) (250 mg, 1.085 mmol) and K$_2$CO$_3$ (150 mg, 1.085 mmol) in EtOH (5 mL) and the mixture heated at reflux overnight. The reaction was quenched with 1M HCl solution (10 mL) and extracted with ethyl acetate (3×25 ml). The combined organics were washed with water (10 mL), brine (10 mL), dried over sodium sulphate, filtered and concentrated in vacuo to give a the title compound as a yellow oil which was used directly in the next stage without further purification;

LC MS: Rt 0.51 min; MS m/z 263.1, 265.1, 267.1 [M+H]+; Method 2minLowpHv01

Step 2: (Z)—N'-Acetoxy-2-(2-bromo-5-chlorophenyl)acetimidamide

Acetyl chloride (0.026 mL, 0.361 mmol) was added dropwise to a solution of (Z)-2-(2-bromo-5-chlorophenyl)-N'-hydroxyacetimidamide (95 mg, 0.361 mmol) and TEA (0.050 mL, 0.361 mmol) in DCM (2 mL) and the resulting mixture stirred for at room temperature overnight. The reaction was quenched with water (5 mL) and extracted with ethyl acetate (3×15 mL). The combined organic extracts were washed with brine (10 mL), dried over sodium sulphate, filtered and concentrated in vacuo to give a gum. Purification by chromatography on silica eluting with ethyl acetate in iso-hexane afforded the title compound as a yellow solid;

LCMS: Rt 0.96 min; MS m/z 305.1, 307.0, 309.0 [M+H]+; Method 2minLowpHv01

Step 3: 3-(2-Bromo-5-chlorobenzyl)-5-methyl-1,2,4-oxadiazole

A mixture comprising (Z)—N'-acetoxy-2-(2-bromo-5-chlorophenyl)acetimidamide (step 2)(56 mg, 0.183 mmol) and hexachloroethane (130 mg, 0.550 mmol) in AcOH (2 mL) was stirred briefly and heated in using microwave radiation for 1 h at 100° C. A further portion of hexachloroethane (43 mg, 0.183 mmol) was added and the reaction mixture was heated in the microwave for a further 1 h at 100° C. Toluene (20 mL) was added and the mixture was concentrated in vacuo. Purification by chromatography on silica eluting with ethyl acetate in iso-hexane afforded the title compound as a yellow oil;

LC MS: Rt 1.20 min; MS m/z 287.3, 289.3, 291.3 [M+H]+; Method 2minLowpHv01

Biological Data:

The compounds of the invention are suitable as ATX inhibitors and may be tested in the following assays.

Reagents—LPC (oleoyl (18:1)) was purchased from Avanti Polar Lipids (Alabaster, Ala.) and solubilized in methanol to 20 mM. Amplex Red was obtained from Invitrogen Life Technologies (Paisley, UK) and dissolved in DMSO to 10 mM. Choline oxidase and horseradish peroxidase (HRP) were obtained from Sigma Aldrich (Dorset, UK) and dissolved in HBSS to 20 U/ml and 200 U/ml respectively. All reagents were stored at −20° C. in single use aliquots. All experimental measurements were performed in assay buffer made up immediately prior to use (HBSS, 0.01% BSA essentially fatty acid free).

Protein—Recombinant human ATX was prepared at Novartis (Basel, CH) in a human embryonic kidney (HEK) cell preparation, and stored in single use aliquots of 26 mg/ml (26 µM) stocks stored at −80° C.

Method—All experimental measurements were performed in black 384 well polystyrene (low volume, round bottom, Corning (3676)) plates. PerkinElmer EnVision (Fluorescence Intensity/Absorbance Monochromator) or Tecan Infinite 200 PRO series plate reader was used to detect change in fluorescent intensity.

Assessing ATX inhibition—ATX activity was determined by measurement of released choline in reactions containing ATX (10 nM), choline oxidase (0.1 U/ml), HRP (100 U/ml), amplex red (50 µM) and LPC 18:1 (10 µM). Compounds of the invention were prepared as 10 point serial dilutions from 1 µM in duplicate and pre-incubated with ATX at 37° C. for 20 minutes prior to the addition of remaining reagents. The liberated choline was measured from changes in fluorescence intensity ($\lambda$ex 530 nm, $\lambda$em 590 nm) of the product resurofin at 37° C. every 2 minutes over a 40-minute period. ATX activity was measured as a slope of the linear portion of the progress curve, typically between 14 to 24 minutes.

Data analysis—Slope data was exported to Graphpad prism (Graphpad software, San Diego, Calif.) where data was fitted to equation 1.

$$Y = \text{Bottom} + (\text{Top} - \text{Bottom})/(1 + 10\char`\^((\text{Log } IC50 - X)*\text{HillSlope}))$$
Equation 1:

$IC_{50}$ values are determined from the concentration of compound that reduced the total activity by 50% and represent the mean of $n \geq 2$.

Table 1: The following table gives the $IC_{50}$ values for the exemplified compounds as measured in the above assay

TABLE 1

| Example no. | $IC_{50}$ (µM) |
|---|---|
| 1 | 0.0088 |
| 2 | 0.0095 |
| 3 | 0.012 |
| 4 | 0.0058 |
| 5 | — |
| 5a | 0.0035 |
| 5b | 0.12 |
| 6 | 0.018 |
| 7 | 0.14 |
| 8 | 0.378 |
| 9 | 0.1 |
| 10 | 0.04 |
| 11 | 0.073 |
| 12 | 0.157 |
| 13 | 2.359 |
| 14 | 0.012 |
| 15 | 0.062 |
| 16 | 0.011 |

TABLE 1-continued

| Example no. | $IC_{50}$ (µM) |
|---|---|
| 17 | 0.024 |
| 18 | 0.037 |
| 19 | 0.031 |
| 20 | 0.163 |
| 21 | 0.208 |
| 22 | 0.026 |
| 23 | 0.028 |
| 23a | 0.0095 |
| 24 | 0.004 |
| 25 | 0.0085 |
| 26 | 0.031 |
| 27 | 0.059 |
| 28 | 0.0063 |
| 29 | 0.032 |
| 30 | 0.011 |
| 30a | 0.0049 |
| 30b | 0.1 |
| 31 | 0.0079 |
| 32 | 0.0035 |
| 33 | 0.053 |
| 34 | 0.029 |
| 34a | 0.018 |
| 34b | 0.149 |
| 35 | 0.924 |
| 36 | 0.171 |
| 37 | 0.017 |
| 38 | — |
| 38a | 0.02 |
| 38b | 0.41 |
| 39 | 0.075 |
| 40 | 0.042 |
| 41 | 0.654 |
| 42 | 0.436 |
| 43 | 2.372 |
| 44 | 0.535 |
| 45 | 0.644 |
| 46 | 0.204 |
| 47 | 0.442 |
| 48 | 0.07 |
| 49.1 | 0.02 |
| 49.2 | 0.477 |
| 49.3 | 0.129 |
| 49.4 | 0.12 |
| 49.5 | 0.32 |
| 49.6 | 0.11 |
| 49.7 | 0.151 |
| 49.8 | 0.354 |
| 49.9 | 0.0059 |
| 49.10 | 0.024 |
| 49.11 | 0.014 |
| 49.12 | 0.049 |
| 49.13 | 0.017 |
| 49.14 | 0.085 |
| 49.15 | 0.127 |
| 49.16 | 1.06 |
| 49.17 | 0.222 |
| 49.18 | 0.13 |
| 49.19 | 0.176 |
| 49.20 | 0.11 |
| 50a | 0.07 |
| 50b | 0.079 |
| 49.21 | 0.016 |
| 51 | 0.077 |
| 52 | 0.017 |
| 53 | 0.002 |
| 54 | 0.0089 |
| 55 | 0.008 |
| 56 | 0.012 |
| 57 | 0.008 |
| 58 | 0.053 |
| 59 | 0.021 |
| 60 | 0.0088 |
| 61 | 0.045 |
| 62 | 0.0042 |
| 63 | 0.0055 |
| 64 | 0.031 |
| 65 | 0.0055 |
| 66 | 0.006 |

TABLE 1-continued

| Example no. | IC$_{50}$ (μM) |
|---|---|
| 66a | 0.0042 |
| 66b | 0.0046 |
| 67 | 0.0088 |
| 68 | 0.0045 |
| 69 | 0.002 |
| 70 | 0.0042 |
| 71 | 0.006 |
| 72 | 0.29 |
| 73 | 0.0042 |
| 74 | 0.0055 |
| 75 | 1.439 |
| 76 | 0.073 |
| 77 | 1.993 |
| 78 | 1.456 |
| 79 | 3.145 |
| 80 | 0.454 |
| 81 | 0.013 |
| 82 | 0.785 |
| 83 | 0.846 |
| 49.22 | 0.11 |
| 49.23 | 0.078 |
| 49.24 | 0.045 |
| 49.25 | 0.01 |
| 49.26 | 0.16 |
| 49.27 | 0.11 |
| 49.28 | 0.01 |
| 49.29 | 0.078 |
| 49.30 | 0.052 |
| 84 | 0.0081 |
| 85 | 0.289 |
| 86 | 0.0048 |
| 87 | 0.019 |
| 88 | 0.016 |
| 89 | 0.0035 |
| 90 | 0.049 |
| 91 | 0.16 |
| 92 | 0.0036 |
| 93 | 0.01 |
| 94 | 0.01 |
| 95 | 0.025 |
| 96 | 0.0083 |
| 97 | 0.023 |
| 98 | 0.066 |
| 99 | 0.025 |
| 100 | 0.0039 |
| 101 | 0.005 |
| 102 | 0.053 |
| 103 | 0.0053 |
| 104 | 0.0039 |
| 105 | 0.0066 |
| 106 | 0.028 |
| 107 | 0.046 |
| 108a | 0.058 |
| 108b | 0.061 |
| 109 | 0.016 |
| 110 | 0.0052 |
| 111 | 0.047 |
| 112 | 0.014 |
| 115 | 0.012 |
| 114 | 0.0039 |
| 115a | 0.018 |
| 115b | 0.14 |
| 116 | 0.033 |
| 117 | 0.263 |
| 118 | 0.024 |
| 119 | 0.047 |
| 120 | 0.0081 |
| 121 | 0.0069 |
| 122 | 0.058 |
| 123 | 0.0035 |
| 124 | 0.035 |
| 125 | 0.11 |
| 126 | 0.022 |
| 127 | 0.06 |
| 128 | 0.028 |
| 129 | 0.049 |
| 130 | 0.17 |
| 131 | 0.023 |
| 132 | 0.014 |
| 133 | 0.081 |
| 134 | 0.012 |
| 135 | 0.327 |
| 136 | 0.032 |
| 137 | 0.0075 |
| 138 | 0.0063 |
| 139 | 0.067 |
| 140.1 | 0.0059 |
| 140.2 | 0.064 |
| 140.3 | 0.03 |
| 140.4 | 0.043 |
| 140.5 | 0.025 |
| 140.6 | 0.042 |
| 140.7 | 0.042 |
| 140.8 | 0.0088 |
| 140.9 | 0.034 |
| 141 | 0.011 |
| 142 | 0.012 |
| 143 | 0.031 |
| 144 | 0.014 |
| 145 | 0.013 |
| 146 | 0.017 |
| 147 | 0.013 |
| 148 | 0.0089 |
| 149 | 0.0049 |
| 150 | 0.0069 |
| 151 | 0.0031 |
| 152 | 0.0039 |
| 153 | 0.002 |
| 154 | 0.0024 |
| 155 | 0.013 |
| 156 | 0.0053 |
| 157 | 0.0092 |

The invention claimed is:

1. A compound which is selected from the group consisting of:
   (E)-1-(4-(5-methyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one;
   (E)-1-(4-(3-methyl-1H-1,2,4-triazol-1-yl)piperidin-1-yl)-3-(2-((5-methyl-2H-tetrazol-2-yl)methyl)-4-(trifluoromethyl)phenyl)prop-2-en-1-one;
   1-(4-(5-Methyl-1,3,4-oxadiazol-2-yl)piperidin-1-yl)-3-(2-((5-methyl-2H-tetrazol-2-yl)methyl)-4-(trifluoromethyl)phenyl)propan-1-one;
   or a pharmaceutically acceptable salt thereof.

2. The compound which is (E)-1-(4-(5-methyl-1,3,4-oxadiazol-2-yl)piperidin-1-yl)-3-(2-((5-methyl-2H-tetrazol-2-yl)methyl)-4-(trifluoromethyl)phenyl)prop-2-en-1-one; or a pharmaceutically acceptable salt thereof.

3. The compound which is (E)-1-(4-(3-methyl-1H-1,2,4-triazol-1-yl)piperidin-1-yl)-3-(2-((5-methyl-2H-tetrazol-2-yl)methyl)-4-(trifluoromethyl)phenyl)prop-2-en-1-one; or a pharmaceutically acceptable salt thereof.

4. The compound which is 1-(4-(5-Methyl-1,3,4-oxadiazol-2-yl)piperidin-1-yl)-3-(2-((5-methyl-2H-tetrazol-2-yl)methyl)-4-(trifluoromethyl)phenyl)propan-1-one; or a pharmaceutically acceptable salt thereof.

5. A pharmaceutical composition comprising a compound according to claim 1, or a pharmaceutically acceptable salt thereof, and a pharmaceutically acceptable carrier.

6. A pharmaceutical combination comprising a therapeutically effective amount of a compound according to claim 1, or a pharmaceutically acceptable salt thereof, and one or more therapeutically active co-agent.

7. A method of treating an autotaxin dependent or an autotaxin mediated disease or condition, wherein the disease or condition is idiopathic pulmonary fibrosis, comprising administering to a subject a therapeutically effective amount of a compound according to claim 1.

* * * * *